United States Patent
Barbero Calzado et al.

(10) Patent No.: US 11,951,163 B2
(45) Date of Patent: Apr. 9, 2024

(54) ZIKA VIRUS VACCINE

(71) Applicant: Valneva Austria GmbH, Vienna (AT)

(72) Inventors: Jana Barbero Calzado, Vienna (AT); Mario Nebenführ, Vienna (AT); Robert Schlegl, Siegenfeld (AT); Michael Weber, Vienna (AT); Jürgen Heindl-Wruss, Vienna (AT)

(73) Assignee: Valneva Austria GMBH, Vienna (AT)

( * ) Notice: Subject to any disclaimer, the term of this patent is extended or adjusted under 35 U.S.C. 154(b) by 0 days.

(21) Appl. No.: 18/178,638

(22) Filed: Mar. 6, 2023

(65) Prior Publication Data

US 2023/0226165 A1    Jul. 20, 2023

Related U.S. Application Data

(63) Continuation of application No. 17/548,721, filed on Dec. 13, 2021, which is a continuation of application No. 16/813,862, filed on Mar. 10, 2020, now Pat. No. 11,219,681, which is a continuation of application No. 16/063,007, filed as application No. PCT/EP2016/082664 on Dec. 23, 2016, now Pat. No. 10,639,365.

(30) Foreign Application Priority Data

| Dec. 23, 2015 | (EP) | ................................. 15202585 |
| Mar. 18, 2016 | (EP) | ................................. 16161068 |
| Jun. 23, 2016 | (EP) | ................................. 16176025 |
| Jun. 23, 2016 | (EP) | ................................. 16176049 |
| Aug. 4, 2016 | (EP) | ................................. 16182845 |

(51) Int. Cl.
| A61K 39/12 | (2006.01) |
| A61K 9/00 | (2006.01) |
| A61K 39/00 | (2006.01) |
| A61K 39/39 | (2006.01) |
| A61P 31/14 | (2006.01) |
| C07K 14/18 | (2006.01) |
| C12N 7/00 | (2006.01) |
| C12N 7/02 | (2006.01) |
| C12N 7/06 | (2006.01) |

(52) U.S. Cl.
CPC .............. *A61K 39/12* (2013.01); *A61K 39/39* (2013.01); *A61P 31/14* (2018.01); *C07K 14/18* (2013.01); *C07K 14/1825* (2013.01); *C12N 7/00* (2013.01); *C12N 7/02* (2013.01); *C12N 7/06* (2013.01); *A61K 2039/5252* (2013.01); *A61K 2039/5254* (2013.01); *A61K 2039/5258* (2013.01); *A61K 2039/55505* (2013.01); *C12N 2770/24134* (2013.01); *C12N 2770/24151* (2013.01); *C12N 2770/24163* (2013.01); *Y02A 50/30* (2018.01)

(58) Field of Classification Search
CPC ............ A61K 2039/5252; A61K 39/12; A61K 39/39; A61K 2039/5254; A61P 31/14
See application file for complete search history.

(56) References Cited

U.S. PATENT DOCUMENTS

| 6,309,650 B1 | 10/2001 | Kim et al. |
| 8,765,148 B2 | 7/2014 | Wizel et al. |
| 10,086,061 B2 | 10/2018 | Thomas et al. |
| 10,537,630 B2 | 1/2020 | Barbero Calzado et al. |
| 10,639,365 B2 | 5/2020 | Barbero Calzado et al. |
| 10,744,194 B2 | 8/2020 | Barbero Calzado et al. |
| 11,219,681 B2 | 1/2022 | Barbero Calzado et al. |
| 11,331,382 B2 | 5/2022 | Barbero Calzado et al. |
| 11,524,064 B2 | 12/2022 | Barbero Calzado et al. |
| 2013/0280295 A1 | 10/2013 | Schlegl et al. |
| 2018/0362936 A1 | 12/2018 | Barbero Calzado et al. |
| 2018/0362937 A1 | 12/2018 | Barbero Calzado et al. |
| 2018/0369359 A1 | 12/2018 | Barbero Calzado et al. |
| 2018/0371027 A1 | 12/2018 | Barbero Calzado et al. |
| 2019/0008945 A1 | 1/2019 | Barbero Calzado et al. |
| 2020/0017555 A9 | 1/2020 | Barbero Calzado et al. |
| 2020/0384099 A1 | 12/2020 | Barbero Calzado et al. |
| 2021/0093707 A1 | 4/2021 | Barbero Calzado et al. |
| 2022/0273786 A1 | 9/2022 | Barbero Calzado et al. |

FOREIGN PATENT DOCUMENTS

| CN | 105749268 A | 7/2016 |
| WO | WO 1999/011762 A1 | 3/1999 |
| WO | WO 2001/092552 A2 | 12/2001 |
| WO | WO 2013/083726 A1 | 6/2013 |
| WO | WO 2016/145149 A1 | 9/2016 |
| WO | WO 2017/009873 A1 | 1/2017 |
| WO | WO 2017/109225 A1 | 6/2017 |

OTHER PUBLICATIONS

[No Author Listed], Centers for Disease Control and Prevention Ingredients of vaccines fact sheet. Retrieved from https://www.cdc.gov/vaccines/vac-gen/additives.htm.
[No Author Listed], Centers for Disease Control and Prevention. 2016. Japanese Encephalitis Vaccine. Retrieved from https://www.cdc.gov/japaneseencephalitis/vaccine/ on Jun. 16, 2016.
[No Author Listed], Genbank Accession No. ABI54475. polyprotein [Zika virus]. Dec. 24, 2009. 4 pages.
[No Author Listed], Genbank Accession No. AY632535. Zika virus strain MR 766, complete genome. Nov. 23, 2010. 4 pages.
[No Author Listed], Genbank Accession No. KJ776791.2. Zika virus strain H/PF/2013, complete genome. Aug. 31, 2016. 5 pages.
[No Author Listed], Media centre. Zika virus. World Health Organization, 2016. Zika Virus Fact Sheet. Downloaded Mar. 11, 2016 from http://www.who.int/en/news-room/fact-sheets/detail/zika-virus.
[No Author Listed], Pan-American Health Organization. 2015. Number of Reported Cases of Chikungunya Fever in the Americas, by Country or Territory 2013-2014, Cumulative Cases (Updated Oct. 23, 2015).

(Continued)

*Primary Examiner* — Barry A Chestnut
(74) *Attorney, Agent, or Firm* — Banner & Witcoff, Ltd.

(57) ABSTRACT

Described herein are Zika virus vaccines and compositions and methods of producing and administering said vaccines to subjects in need thereof.

58 Claims, 23 Drawing Sheets

Specification includes a Sequence Listing.

(56) References Cited

OTHER PUBLICATIONS

[No Author Listed], Valneva Announces Successful Generation of a Highly-purified Zika Vaccine Candidate Using its FDA-EMA Approved Japanese Encephalitis Platform. Press release Jul. 7, 2016.
[No Author Listed], Wikimedia Foundation, Inc., 2015. https://en.wikipedia.org/wiki/Protamine_sulfate; updated Sep. 30, 2015; downloaded Nov. 26, 2015.
[No Author Listed], World Health Organization, 2016. Zika Situation Report Feb. 5, 2016.
[No Author Listed], Zika virus, strain H/PF/2013. Nov. 28, 2013. European Virus Archive retrieved on Dec. 22, 2016 from http://www.who.int/mediacentre/factsheets/zika/en.
Abbink et al, Durability and correlates of vaccine protection against Zika virus in rhesus monkeys. Sci. Transl. Med. 2017;9:eaao4163.
Altschul et al., Basic Local Alignment Search Tool. J. Mol. Biol. 1990;215:403-410.
Altschul et al., Gapped BLAST and PSI-BLAST: a new generation of protein database search programs. Nuc. Acids Res. 1997;25:3389-3402.
Athmaram et al., A two step purification strategy for Chikungunya virions purification using sucrose buoyant density gradient separation. J Virology Res. 2013;2(1):18-21.
Aubry et al., Inactivation of Zika virus in plasma with amotosalen and ultraviolet A illumination. Transfusion. Jan. 2016;56(1):33-40. doi: 10.1111/trf.13271. Epub Aug. 18, 2015.
Baronti et al., Complete Coding Sequence of Zika Virus from a French Polynesia Outbreak in 2013. Genome Announc. May-Jun. 2014; 2(3):e00500-14. Abstract.
Bender et al., Zika Virus Vaccine Candidate VLA1601: Cooperation Valneva & Emergent, Presentation at World Vaccine Congress Apr. 4, 2018.
Cohen, Infectious Disease. The race for a Zika vaccine is on. Science. Feb. 5, 2016;351(6273):543-4. doi: 10.1126/science.351.6273.543.
Cox et al., Predicting Zika virus structural biology:Challenges and opportunities for intervention. Antivir Chem Chemother. Aug. 2015;24(3-4):118-26. doi: 10.1177/2040206616653873. Epub Jun. 13, 2016.
Dowall et al., A susceptible mouse model for Zika virus infection. PLOS Neglected Tropical Diseases; DOI:10.1371/journal.pntd.0004658. May 5, 2016.
Fritsche et al., Vaccine hypersensitivity—update and overview. Swiss Med Wkly. 2010;140(17-18):238-246.
Gardner et al., Deliberate Attenuation of Chikungunya Virus by Adaptation to Heparan Sulfate-Dependent Infectivity: A Model of Rational Arboviral Vaccine Design. PLOS Neglected Tropical Diseases. 2014;8(2):e2719.
Geradin et al., Chikungunya virus-associated encephalitis: A cohort study on La Réunion Island, 2005-2009. Neurology. 2016;86(1):94-102.
Haddow et al., Genetic Characterization of Zika Virus Strains: Geographic Expansion of the Asian Lineage. PLoS Negl Trop Dis. 2012;6(2): e1477. doi:10.1371/journal.pntd.0001477.
Hallengärd et al., Prime-Boost Immunization Strategies against Chikungunya Virus. J Virology. 2014;88(22):13333-13343.
Hallengärd et al., Novel Attenuated Chikungunya Vaccine Candidates Elicit Protective Immunity in C57BL/6 mice. J Virology. 2014;88(5):2858-2866.
Hombach et al., Report on a WHO consultation on immunological endpoints for evaluation of new Japanese encephalitis vaccines, WHO, Geneva, Sep. 2-3, 2004. Vaccine. 2005; 23(45):5205-5211.
Hutornojs et al., Comparison of ultracentrifugation methods for concentration of recombinant alphaviruses: sucrose and iodixanol cushions, Environmental and Experimental Biology. 2012; 10:117-123.
Katoh et al., Recent developments in the MAFFT multiple sequence alignment program. Briefings in Bioinformatics. 2008;9(4):286-298.
Kofler et al., Capsid protein C of tick-borne encephalitis virus tolerates large internal deletions and is a favorable target for attenuation of virulence. J Virol. Apr. 2002;76(7):3534-43.
Konishi et al., Studies on structural proteins of Chikungunya Virus. I. Separation of three species of proteins and their preliminary characterization. Microbiol Immunol. 1980;24(5):419-28. doi: 10.1111/j.1348-0421.1980.tb02846.x.
Kuno et al., Full-length sequencing and genomic characterization of Bagaza, Kedougou, and Zika viruses. Arch Virol. 2007;152(4):687-696. doi:10.1007/s00705-006-0903-z.
Larkin et al., Clustal W and Clustal X version 2.0. Bioinformatics. 2007;23(21):2947-2948.
Larocca et al., Vaccine protection against Zika virus from Brazil. Nature. 2016;536:474-478. doi:10.1038/nature18952. Methods.
Malone et al., Zika Virus: Medical Countermeasure Development Challenges. PLoS Negl Trop Dis. 2016;10(3):e0004530. doi:10.1371/journal.pntd.0004530.
Modjarrad et al., Preliminary aggregate safety and immunogenicity results from three trials of a purified inactivated Zika virus vaccine candidate: phase 1, randomised, double-blind, placebo-controlled clinical trials. www.thelancet.com Published online Dec. 4, 2017 http://dx.doi.org/10.1016/S0140-6736(17)33106-9.
Needleman et al., A general method applicable to the search for similarities in the amino acid sequence of two proteins. J. Mol. Biol. 1970;48(3):443-453.
Pearson et al., Improved tools for biological sequence comparison. Proc. Natl. Acad. Sci. USA. 1988;85(8):2444-8.
Pellerin, Walter Reed Scientists Test Zika Vaccine Candidate, U.S. Department of Defense News. Jun. 9, 2016.
Pinto et al., A Temporal Role Of Type I Interferon Signaling in CD8+ T Cell Maturation during Acute West Nile Virus Infection. PLoS Pathog. 2011;7(12): e1002407. https://doi.org/10.1371/journal.ppat.1002407.
Plevka et al., Maturation of flaviviruses starts from one or more icosahedrally independent nucleation centres EMBO reports. 2011;12(6):602-606.
Putnak et al., Development of a purified, inactivated, dengue-2 virus vaccine prototype in Vero cells: immunogenicity and protection in mice and rhesus monkeys. J Infect Dis. Dec. 1996;174(6):1176-84.
Reed et al., A simple method of estimating fifty percent endpoints. American J Hygiene. 1938;27:493-497.
Rocha et al., Microcephaly: normality parameters and its determinants in northeastern Brazil: a multicentre prospective cohort study. Bull World Health Organ, E-pub: Feb. 8, 2016. doi:http://dx.doi.org/10.2471/BLT.16.171215.
Schlegl, Influence of elemental impurities in aluminum hydroxide adjuvant on the stability of inactivated Japanese Encephalitis vaccine, IXIARO®. Vaccine. 2015;33(44):5989-5996.
Smith et al., Comparison of Biosequences. Adv Appl Math. 1981;2:482-489.
Srivastava et al., A purified inactivated Japanese encephalitis virus vaccine made in vero cells. Vaccine. 2001;19:4557-4565.
Third Party Observations filed in Opposition to EP 16828746.4, filed on Oct. 13, 2021. 6 pages.
Tiwari et al., Assessment of immunogenic potential of Vero adapted formalin inactivated vaccine derived from novel ECSA genotype of Chikungunya virus. Vaccine. Apr. 21, 2009;27(18):2513-22. doi: 10.1016/j.vaccine.2009.02.062. Epub Feb. 27, 2009.
Vega-Rua et al., Chikungunya Virus Transmission Potential by Local Aedes Mosquitoes in the Americas and Europe. PLOS Neglected Tropical Diseases. 2015;9(5): e0003780.
Waterhouse et al., Jalview Version 2—a multiple sequence alignment editor and analysis workbench. Bioinformatics. 2009;25(9):1189-1191.
Way et al., Comparative studies of some African arboviruses in cell culture and in mice. J Gen Virol. Jan. 1976;30(1):123-30.
Weaver, Arrival of Chikungunya Virus in the New World: Prospects for Spread and Impact on Public Health. PLoS Negl Trop Dis. 2014;8(6):e2921. doi:10.1371/journal.pntd.0002921.
Petition for Inter Partes Review of U.S. Pat. No. 11,219,681. *Takeda Vaccines, Inc.* vs *Valneva Austria GmbH*. 96 pages. Paper No. 2, submitted in PTAB Case No. IPR2023-00354, Dec. 27, 2022.
Declaration of Dan H. Barouch, M.D., Ph.D., submitted to United States Patent and Trademark Office Patent Trial and Appeal Board

(56) References Cited

OTHER PUBLICATIONS (PTAB); Case No. IPR2023-00354, U.S. Pat. No. 11,219,681. Dec. 15, 2022. 223 pages. Ex. 1002 submitted in PTAB Case No. IPR2023-00354, Dec. 27, 2022.
Curriculum Vitae for Dan H. Barouch. Dec. 14, 2022. 133 pages. Ex. 1003 submitted in PTAB Case No. IPR2023-00354, Dec. 27, 2022.
United States Patent and Trademark Office File History for U.S. Pat. No. 11,219,681. 1023 pages. Ex. 1004, submitted in PTAB Case No. IPR2023-00354, Dec. 27, 2022.
Yoshii et al., A conserved region in the prM protein is a critical determinant in the assembly of flavivirus particles. J Gen Virol. Jan. 2012;93(Pt 1):27-38. doi: 10.1099/vir.0.035964-0. Epub Sep. 28, 2011. Ex. 1005 submitted in PTAB Case No. IPR2023-00354, Dec. 27, 2022.
Larocca et al., Vaccine protection against Zika virus from Brazil. Nature. Aug. 25, 2016;536(7617):474-8. doi: 10.1038/nature18952. Epub Jun. 28, 2016. Ex. 1006 submitted in PTAB Case No. IPR2023-00354, Dec. 27, 2022.
Holloway, Wrair Technology helps create Japanese Encephalitis Vaccine. The United States Army. Retrieved from The Wayback Machine—www.army.mil on Sep. 27, 2022. 2 pages. Ex. 1007 submitted in PTAB Case No. IPR2023-00354, Dec. 27, 2022.
[No Author Listed], Blast Global Alignment results for RID-UNWF87RP114. Retrieved on Dec. 27, 2022. 11 pages. Ex. 1009 submitted in PTAB Case No. IPR2023-00354, Dec. 27, 2022.
[No Author Listed], Certified copy of priority document for Application No. EP15202585.4, filed Dec. 23, 2015. 37 pages. Ex. 1014 submitted in PTAB Case No. IPR2023-00354, Dec. 27, 2022.
[No Author Listed], Certified copy of priority document for Application No. EP 16161068.8, filed Mar. 18, 2016. 79 pages. Ex. 1015 submitted in PTAB Case No. IPR2023-00354, Dec. 27, 2022.
[No Author Listed], Certified copy of priority document for Application No. EP 16176025.1, filed Jun. 23, 2016. 134 pages. Ex. 1016 submitted in PTAB Case No. IPR2023-00354, Dec. 27, 2022.
[No Author Listed], Certified copy of priority document for Application No. EP 16176049.1, filed Jun. 23, 2016. 92 pages. Ex. 1017 submitted in PTAB Case No. IPR2023-00354, Dec. 27, 2022.
[No Author Listed], Certified copy of priority document for Application No. EP 16182845.4, filed Aug. 4, 2016. 137 pages. Ex. 1018 submitted in PTAB Case No. IPR2023-00354, Dec. 27, 2022.
[No Author Listed], Zika virus strain H/PF/2013 polyprotein gene, complete cds. GenBank Acc. No. KJ776791.1. Jun. 13, 2014. Retrieved on Sep. 16, 2022. 5 pages. Ex. 1019 submitted in PTAB Case No. IPR2023-00354, Dec. 27, 2022.
[No Author Listed], Blast Global Alignment results for RID-PKE92BN8114. Retrieved on Nov. 7, 2022. 18 pages. Ex. 1020 submitted in PTAB Case No. IPR2023-00354, Dec. 27, 2022.
Watanaveeradej et al., Safety and immunogenicity of a rederived, live-attenuated dengue virus vaccine in healthy adults living in Thailand: a randomized trial. Am J Trop Med Hyg. Jul. 2014;91(1):119-28. doi: 10.4269/ajtmh.13-0452. Epub May 27, 2014. Ex. 1021 submitted in PTAB Case No. IPR2023-00354, Dec. 27, 2022.
Orenstein et al., Global vaccination recommendations and thimerosal. Pediatrics. Jan. 2013;131(1):149-51. doi: 10.1542/peds.2012-1760. Epub Dec. 17, 2012. Ex. 1022 submitted in PTAB Case No. IPR2023-00354, Dec. 27, 2022.
Eckels et al., Japanese encephalitis virus live-attenuated vaccine, Chinese strain SA14-14-2; adaptation to primary canine kidney cell cultures and preparation of a vaccine for human use. Vaccine. Dec. 1988;6(6):513-8. doi: 10.1016/0264-410x(88)90103-x. Ex. 1023 submitted in PTAB Case No. IPR2023-00354, Dec. 27, 2022.
Martinez et al., Safety and Immunogenicity of a Dengue Virus Serotype-1 Purified-Inactivated Vaccine: Results of a Phase 1 Clinical Trial. Am J Trop Med Hyg. Sep. 2015;93(3):454-460. doi: 10.4269/ajtmh.14-0819. Epub Jul. 6, 2015. Ex. 1024 submitted in PTAB Case No. IPR2023-00354, Dec. 27, 2022.
World Health Organization, WHO Director-General summarizes the outcome of the Emergency Committee regarding clusters of microcephaly and Guillain-Barré syndrome. WHO Media Centre. Retrieved from The Wayback Machine—http://www.who.int on Sep. 22, 2022. 2 pages. Ex. 1025 submitted in PTAB Case No. IPR2023-00354, Dec. 27, 2022.
Li et al., Complete genome sequence of a chikungunya virus isolated in Guangdong, China. J Virol. Aug. 2012;86(16):8904-5. doi: 10.1128/JVI.01289-12. Ex. 1027 submitted in PTAB Case No. IPR2023-00354, Dec. 27, 2022.
Putnak et al., Development of a purified, inactivated, dengue-2 virus vaccine prototype in Vero cells: immunogenicity and protection in mice and rhesus monkeys. J Infect Dis. Dec. 1996;174(6):1176-84. doi: 10.1093/infdis/174.6.1176. Ex. 1028 submitted in PTAB Case No. IPR2023-00354, Dec. 27, 2022.
Musso et al., Potential sexual transmission of Zika virus. Emerg Infect Dis. Feb. 2015;21(2):359-61. doi: 10.3201/eid2102.141363. Erratum in: Emerg Infect Dis. Mar. 2015;21(3):552. Ex. 1029 submitted in PTAB Case No. IPR2023-00354, Dec. 27, 2022.
Cox et al., Predicting Zika virus structural biology: Challenges and opportunities for intervention. Antivir Chem Chemother. Aug. 2015;24(3-4):118-26. doi: 10.1177/2040206616653873. Epub Jun. 13, 2016. Ex. 1030 submitted in PTAB Case No. IPR2023-00354, Dec. 27, 2022.
Duffy et al., Zika virus outbreak on Yap Island, Federated States of Micronesia. N Engl J Med. Jun. 11, 2009;360(24):2536-43. doi: 10.1056/NEJMoa0805715. Ex. 1031 submitted in PTAB Case No. IPR2023-00354, Dec. 27, 2022.
Cao-Lormeau et al., Emerging arboviruses in the Pacific. Lancet. Nov. 1, 2014;384(9954):1571-2. doi: 10.1016/S0140-6736(14)61977-2. Epub Oct. 31, 2014. Ex. 1032 submitted in PTAB Case No. IPR2023-00354, Dec. 27, 2022.
World Health Organization, Zika Virus Microcephaly and Guillain-Barre Syndrome. Situation Report. Mar. 17, 2016. 13 pages. Ex. 1033 submitted in PTAB Case No. IPR2023-00354, Dec. 27, 2022.
Maurice, WHO reveals its shopping list for weapons against Zika. Lancet. Feb. 20, 2016;387(10020):733. doi: 10.1016/s0140-6736(16)00390-1. Ex. 1034 submitted in PTAB Case No. IPR2023-00354, Dec. 27, 2022.
Besnard et al., Evidence of perinatal transmission of Zika virus, French Polynesia, Dec. 2013 and Feb. 2014. Euro Surveill. Apr. 3, 2014;19(13):20751. Ex. 1035 submitted in PTAB Case No. IPR2023-00354, Dec. 27, 2022.
Monath et al., Inactivated yellow fever 17D vaccine: development and nonclinical safety, immunogenicity and protective activity. Vaccine. May 14, 2010;28(22):3827-40. doi: 10.1016/j.vaccine.2010.03.023. Epub Mar. 26, 2010. Ex. 1036 submitted in PTAB Case No. IPR2023-00354, Dec. 27, 2022.
Rasmussen et al., Vaccines and pregnancy: past, present, and future. Semin Fetal Neonatal Med. Jun. 2014;19(3):161-9. doi: 10.1016/j.siny.2013.11.014. Epub Dec. 17, 2013. Ex. 1037 submitted in PTAB Case No. IPR2023-00354, Dec. 27, 2022.
Plotkin et al., The development of vaccines: how the past led to the future. Nat Rev Microbiol. Oct. 3, 2011;9(12):889-93. doi: 10.1038/nrmicro2668. Ex. 1038 submitted in PTAB Case No. IPR2023-00354, Dec. 27, 2022.
Heinz et al., Flaviviruses and flavivirus vaccines. Vaccine. Jun. 19, 2012;30(29):4301-6. doi: 10.1016/j.vaccine.2011.09.114. Ex. 1039 submitted in PTAB Case No. IPR2023-00354, Dec. 27, 2022.
Shan et al., Zika Virus: Diagnosis, Therapeutics, and Vaccine. ACS Infect Dis. Mar. 11, 2016;2(3):170-2. doi: 10.1021/acsinfecdis.6b00030. Epub Mar. 3, 2016. Ex. 1040 submitted in PTAB Case No. IPR2023-00354, Dec. 27, 2022.
Ishikawa et al., A review of successful flavivirus vaccines and the problems with those flaviviruses for which vaccines are not yet available. Vaccine. Mar. 10, 2014;32(12):1326-37. doi: 10.1016/j.vaccine.2014.01.040. Epub Jan. 29, 2014. Ex. 1041 submitted in PTAB Case No. IPR2023-00354, Dec. 27, 2022.
Burton, Antibodies, viruses and vaccines. Nat Rev Immunol. Sep. 2002;2(9):706-13. doi: 10.1038/nri891. Ex. 1042 submitted in PTAB Case No. IPR2023-00354, Dec. 27, 2022.
Roehrig et al., Guidelines for Plaque-Reduction Neutralization Testing of Human Antibodies to Dengue Viruses. Viral Immunol. Jun. 2008;21(2):123-32. doi: 10.1089/vim.2008.0007. Ex. 1043 submitted in PTAB Case No. IPR2023-00354, Dec. 27, 2022.

(56) References Cited

OTHER PUBLICATIONS

Laurie et al., International Laboratory Comparison of Influenza Microneutralization Assays for A(H1N1)pdm09, A(H3N2), and A(H5N1) Influenza Viruses by CONSISE. Clin Vaccine Immunol. Aug. 2015;22(8):957-64. doi: 10.1128/CVI.00278-15. Epub Jun. 24, 2015. Ex. 1044 submitted in PTAB Case No. IPR2023-00354, Dec. 27, 2022.

Klasse, Neutralization of Virus Infectivity by Antibodies: Old Problems in New Perspectives. Adv Biol. 2014;2014:157895. doi: 10.1155/2014/157895. Epub Sep. 9, 2014. Ex. 1045 submitted in PTAB Case No. IPR2023-00354, Dec. 27, 2022.

Bauer et al., A Phase II, Randomized, Safety and Immunogenicity Trial of a Re-Derived, Live-Attenuated Dengue Virus Vaccine in Healthy Children and Adults Living in Puerto Rico. Am J Trop Med Hyg. Sep. 2015;93(3):441-453. doi: 10.4269/ajtmh.14-0625. Epub Jul. 14, 2015. Ex. 1046 submitted in PTAB Case No. IPR2023-00354, Dec. 27, 2022.

Hombach et al., Report on a WHO consultation on immunological endpoints for evaluation of new Japanese encephalitis vaccines, WHO, Geneva, Sep. 2-3, 2004. Vaccine. Nov. 1, 2005;23(45):5205-11. doi: 10.1016/j.vaccine.2005.07.002. Epub Jul. 18, 2005. Ex. 1047 submitted in PTAB Case No. IPR2023-00354, Dec. 27, 2022.

Lindenbach et al., Molecular biology of flaviviruses. Adv Virus Res. 2003;59:23-61. doi: 10.1016/s0065-3527(03)59002-9. Ex. 1048 submitted in PTAB Case No. IPR2023-00354, Dec. 27, 2022.

Tauber et al., Safety and immunogenicity of a Vero-cell-derived, inactivated Japanese encephalitis vaccine: a non-inferiority, phase III, randomised controlled trial. Lancet. Dec. 1, 2007;370(9602):1847-53. doi: 10.1016/S0140-6736(07)61780-2. Ex. 1049 submitted in PTAB Case No. IPR2023-00354, Dec. 27, 2022.

Brinton et al., Functions of the 3' and 5' genome RNA regions of members of the genus Flavivirus. Virus Res. Aug. 3, 2015;206:108-19. doi: 10.1016/j.virusres.2015.02.006. Epub Feb. 13, 2015. Ex. 1050 submitted in PTAB Case No. IPR2023-00354, Dec. 27, 2022.

Okada et al., Safety and immunogenicity of a freeze-dried, cell culture-derived Japanese encephalitis vaccine (Inactivated) (JEBIK®)V) in children. Vaccine. Sep. 7, 2012;30(41):5967-72. doi: 10.1016/j.vaccine.2012.07.034. Epub Jul. 25, 2012. Ex. 1051 submitted in PTAB Case No. IPR2023-00354, Dec. 27, 2022.

Cohen, Infectious Disease. The race for a Zika vaccine is on. Science. Feb. 5, 2016;351(6273):543-4. doi: 10.1126/science.351.6273.543. Ex. 1052 submitted in PTAB Case No. IPR2023-00354, Dec. 27, 2022.

[No Author Listed], Zika virus strain MR 766, complete genome. GenBank Acc. No. AY632535.2. Nov. 23, 2010. Retrieved on Sep. 24, 2022. 5 pages. Ex. 1053 submitted in PTAB Case No. IPR2023-00354, Dec. 27, 2022.

[No Author Listed], Zika virus strain PRVABC59, complete genome. GenBank Acc. No. KU501215.1. Feb. 1, 2016. Retrieved on Sep. 24, 2022. 4 pages. Ex. 1054 submitted in PTAB Case No. IPR2023-00354, Dec. 27, 2022.

[No Author Listed], Zika virus isolate Brazil-ZKV2015, complete genome. GenBank Acc. No. KU497555.1. Feb. 18, 2016. Retrieved on Sep. 24, 2022. 5 pages. Ex. 1055 submitted in PTAB Case No. IPR2023-00354, Dec. 27, 2022.

Zhang et al., Genetic and biochemical characterizations of Zika virus NS2A protein. Emerg Microbes Infect. 2019;8(1):585-602. doi: 10.1080/22221751.2019.1598291. Ex. 1056 submitted in PTAB Case No. IPR2023-00354, Dec. 27, 2022.

[No Author Listed], Sample GenBank Record. GenBank. Public nucleic acid sequence repository. Accessible at https://www.ncbi.nlm.nih.gov/genbank/samplerecord/#ModificationDateB. Retrieved on Oct. 2, 2022. 15 pages. Ex. 1057 submitted in PTAB Case No. IPR2023-00354, Dec. 27, 2022.

Musso, Zika Virus Transmission from French Polynesia to Brazil. Emerg Infect Dis. Oct. 2015;21(10):1887. doi: 10.3201/eid2110.151125. Ex. 1058 submitted in PTAB Case No. IPR2023-00354, Dec. 27, 2022.

Schuller et al., Comparison of a single, high-dose vaccination regimen to the standard regimen for the investigational Japanese encephalitis vaccine, IC51: a randomized, observer-blind, controlled Phase 3 study. Vaccine. Mar. 26, 2009;27(15):2188-93. doi: 10.1016/j.vaccine.2008.12.062. Epub Feb. 4, 2009. Ex. 1059 submitted in PTAB Case No. IPR2023-00354, Dec. 27, 2022.

Schuller et al., Long-term immunogenicity of the new Vero cell-derived, inactivated Japanese encephalitis virus vaccine IC51 Six and 12 month results of a multicenter follow-up phase 3 study. Vaccine. Aug. 12, 2008;26(34):4382-6. doi: 10.1016/j.vaccine.2008.05.081. Epub Jun. 17, 2008. Ex. 1060 submitted in PTAB Case No. IPR2023-00354, Dec. 27, 2022.

European Medicines Agency, Assessment Report for Ixiaro. 2009. 50 pages. Ex. 1061 submitted in PTAB Case No. IPR2023-00354, Dec. 27, 2022.

Abbink et al., Protective efficacy of multiple vaccine platforms against Zika virus challenge in rhesus monkeys. Science. Sep. 9, 2016;353(6304):1129-32. doi: 10.1126/science.aah6157. Epub Aug. 4, 2016. Ex. 1062 submitted in PTAB Case No. IPR2023-00354, Dec. 27, 2022.

Schlegl et al., Influence of elemental impurities in aluminum hydroxide adjuvant on the stability of inactivated Japanese Encephalitis vaccine, IXIARO®. Vaccine. Nov. 4, 2015;33(44):5989-96. doi: 10.1016/j.vaccine.2015.05.103. Epub Jun. 19, 2015. Ex. 1063 submitted in PTAB Case No. IPR2023-00354, Dec. 27, 2022.

[No Author Listed], Ixiaro—Summary Basis for Regulatory Action. Vaccines, Blood & Biologics. Retrieved from The Wayback Machine—http://www.fda on Sep. 27, 2022. 17 pages. Ex. 1064 submitted in PTAB Case No. IPR2023-00354, Dec. 27, 2022.

Duggan et al., Japanese encephalitis vaccine (inactivated, adsorbed) [IXIARO]. Drugs. 2009;69(1):115-22. doi: 10.2165/00003495-200969010-00008. Ex. 1065 submitted in PTAB Case No. IPR2023-00354, Dec. 27, 2022.

Schellack et al., IC31, a novel adjuvant signaling via TLR9, induces potent cellular and humoral immune responses. Vaccine. Jun. 29, 2006;24(26):5461-72. doi: 10.1016/j.vaccine.2006.03.071. Epub Apr. 7, 2006. Ex. 1066 submitted in PTAB Case No. IPR2023-00354, Dec. 27, 2022.

Annunziato et al., The 3 major types of innate and adaptive cell-mediated effector immunity. J Allergy Clin Immunol. Mar. 2015;135(3):626-35. doi: 10.1016/j.jaci.2014.11.001. Epub Dec. 18, 2014. Ex. 1067 submitted in PTAB Case No. IPR2023-00354, Dec. 27, 2022.

Smith et al., Zika virus and Guillain-Barré syndrome: another viral cause to add to the list. Lancet. Apr. 9, 2016;387(10027):1486-1488. doi: 10.1016/S0140-6736(16)00564-X. Epub Mar. 2, 2016. Ex. 1068 submitted in PTAB Case No. IPR2023-00354, Dec. 27, 2022.

Benson et al., GenBank. Nucleic Acids Res. Jan. 2013;41(Database issue):D36-42. doi: 10.1093/nar/gks1195. Epub Nov. 27, 2012. Ex. 1069 submitted in PTAB Case No. IPR2023-00354, Dec. 27, 2022.

Samarasekera et al., Concern over Zika virus grips the world. Lancet. Feb. 6, 2016;387(10018):521-524. doi: 10.1016/S0140-6736(16)00257-9. Ex. 1070 submitted in PTAB Case No. IPR2023-00354, Dec. 27, 2022.

[No Author Listed], Blast Global Alignment results for RID-PKEBSNWN114. Retrieved on Nov. 7, 2022. 12 pages. Ex. 1071 submitted in PTAB Case No. IPR2023-00354, Dec. 27, 2022.

Fox, Could We Have a Zika Vaccine Soon? NBC News. Retrieved from The Wayback Machine—http://www.nbcnews.com/storyl on Oct. 1, 2022. 5 pages. Ex. 1072 submitted in PTAB Case No. IPR2023-00354, Dec. 27, 2022.

Fauci et al., Zika Virus in the Americas—Yet Another Arbovirus Threat. N Engl J Med. Feb. 18, 2016;374(7):601-4. doi: 10.1056/NEJMp1600297. Epub Jan. 13, 2016. Ex. 1073 submitted in PTAB Case No. IPR2023-00354, Dec. 27, 2022.

Dyer, Zika vaccine could be in production by year's end, says maker. BMJ. Feb. 1, 2016;352:i630. doi: 10.1136/bmj.i630. Ex. 1074 submitted in PTAB Case No. IPR2023-00354, Dec. 27, 2022.

[No Author Listed], Blast Global Alignment results for RID-PKEFKXBV114. Retrieved on Nov. 7, 2022. 18 pages. Ex. 1075 submitted in PTAB Case No. IPR2023-00354, Dec. 27, 2022.

[No Author Listed], Blast Global Alignment results for RID-PKEJEXRF114. Retrieved on Nov. 7, 2022. 12 pages. Ex. 1076. submitted in PTAB Case No. IPR2023-00354, Dec. 27, 2022.

(56) References Cited

OTHER PUBLICATIONS

Kumar et al., Metal ion leachates and the physico-chemical stability of biotherapeutic drug products. Curr Pharm Des. 2014;20(8):1173-81. doi: 10.2174/13816128113199990063. Ex. 1077 submitted in PTAB Case No. IPR2023-00354, Dec. 27, 2022.

Declaration of Scott Bailey, Ph.D., submitted to United States Patent and Trademark Office Patent Trial and Appeal Board; Case No. IPR2023-00354, U.S. Pat. No. 11,219,681. Dec. 14, 2022. 39 pages. Ex. 1078 submitted Dec. 27, 2022.

Curriculum Vitae for Scott Bailey. Nov. 1, 2022. 12 pages. Ex. 1079 submitted in PTAB Case No. IPR2023-00354, Dec. 27, 2022.

Luca et al., Crystal structure of the Japanese encephalitis virus envelope protein. J Virol. Feb. 2012;86(4):2337-46. doi: 10.1128/JVI.06072-11. Epub Dec. 7, 2011. Ex. 1080 submitted in PTAB Case No. IPR2023-00354, Dec. 27, 2022.

Klema et al., Dengue Virus Nonstructural Protein 5 (NS5) Assembles into a Dimer with a Unique Methyltransferase and Polymerase Interface. PLoS Pathog. Feb. 19, 2016;12(2):e1005451. doi: 10.1371/journal.ppat.1005451. Ex. 1081 submitted in PTAB Case No. IPR2023-00354, Dec. 27, 2022.

Mukhopadhyay et al., A structural perspective of the flavivirus life cycle. Nat Rev Microbiol. Jan. 2005;3(1):13-22. doi: 10.1038/nrmicro1067. Ex. 1082 submitted in PTAB Case No. IPR2023-00354, Dec. 27, 2022.

[No Author Listed], Zika virus strain H/PF/2013, complete genome. GenBank Acc. No. KJ776791.2. Aug. 31, 2016. Retrieved on Oct. 8, 2022. 5 pages. Ex. 1084 submitted in PTAB Case No. IPR2023-00354, Dec. 27, 2022.

Ledgerwood et al., A West Nile virus DNA vaccine utilizing a modified promoter induces neutralizing antibody in younger and older healthy adults in a phase I clinical trial. J Infect Dis. May 15, 2011;203(10):1396-404. doi: 10.1093/infdis/jir054. Epub Mar. 11, 2011. Ex. 1085 submitted in PTAB Case No. IPR2023-00354, Dec. 27, 2022.

International Preliminary Report on Patentability for International Application No. PCT/EP2016/082664, dated Jul. 5, 2018. 15 pages. Ex. 1086 submitted in PTAB Case No. IPR2023-00354, Dec. 27, 2022.

Delrue et al., Inactivated virus vaccines from chemistry to prophylaxis: merits, risks and challenges. Expert Rev Vaccines. Jun. 2012;11(6):695-719. doi: 10.1586/erv.12.38. Ex. 1087 submitted in PTAB Case No. IPR2023-00354, Dec. 27, 2022.

Stephenson et al., Safety and immunogenicity of a Zika purified inactivated virus vaccine given via standard, accelerated, or shortened schedules: a single-centre, double-blind, sequential-group, randomised, placebo-controlled, phase 1 trial. Lancet Infect Dis. Sep. 2020;20(9):1061-1070. doi: 10.1016/S1473-3099(20)30085-2. Epub May 6, 2020. Ex. 1088 submitted in PTAB Case No. IPR2023-00354, Dec. 27, 2022.

Collette et al., Single Amino Acid Mutations Affect Zika Virus Replication In Vitro and Virulence In Vivo. Viruses. Nov. 12, 2020;12(11):1295. doi: 10.3390/v12111295. Ex. 1089 submitted in PTAB Case No. IPR2023-00354, Dec. 27, 2022.

Dinunno et al., Identification of a pocket factor that is critical to Zika virus assembly. Nat Commun. Oct. 2, 2020;11(1):4953. doi: 10.1038/s41467-020-18747-4. Ex. 1091 submitted in PTAB Case No. IPR2023-00354, Dec. 27, 2022.

Barnard et al., Molecular Determinants of Flavivirus Virion Assembly. Trends Biochem Sci. May 2021;46(5):378-390. doi: 10.1016/j.tibs.2020.12.007. Epub Jan. 7, 2021. Ex. 1092 submitted in PTAB Case No. IPR2023-00354, Dec. 27, 2022.

Tan et al., Capsid protein structure in Zika virus reveals the flavivirus assembly process. Nat Commun. Feb. 1, 20204;11(1):895. doi: 10.1038/s41467-020-14647-9. Ex. 1093 submitted in PTAB Case No. IPR2023-00354, Dec. 27, 2022.

Ma et al., Identification and characterization of key residues in Zika virus envelope protein for virus assembly and entry. Emerg Microbes Infect. Dec. 2022;11(1):1604-1620. doi: 10.1080/22221751.2022.2082888. 18 pages. Ex. 1094 submitted in PTAB Case No. IPR2023-00354, Dec. 27, 2022.
Pierson et al., Degrees of maturity: the complex structure and biology of flaviviruses. Curr Opin Virol. Apr. 2012;2(2):168-75. doi: 10.1016/j.coviro.2012.02.011. Epub Mar. 23, 2012. Ex. 1095 submitted in PTAB Case No. IPR2023-00354, Dec. 27, 2022.
Barzon et al., Zika virus: from pathogenesis to disease control. FEMS Microbiol Lett. Sep. 2016;363(18):fnw202. doi: 10.1093/femsle/fnw202. Epub Aug. 21, 2016. Ex. 1096 submitted in PTAB Case No. IPR2023-00354, Dec. 27, 2022.
Declaration of Ingrid Hsieh-Yee, Ph.D. in Support of Petition for Inter Partes Review of U.S. Pat. No. 11,219,681, submitted under United States Patent and Trademark Office Patent Trial and Appeal Board; Case No. IPR2023-00354, U.S. Pat. No. 11,219,681. Dec. 19, 2022. 65 pages. Ex. 1097 submitted in PTAB Case No. IPR2023-00354, Dec. 27, 2022.
[No Author Listed], Blast Global Alignment results for RID-U7BP1US5114. Retrieved on Dec. 21, 2022. 17 pages. Ex. 1098 submitted in PTAB Case No. IPR2023-00354, Dec. 27, 2022.
Poland et al., Zika Vaccine Development: Current Status. Mayo Clin Proc. Dec. 2019;94(12):2572-2586. doi: 10.1016/j.mayocp.2019.05.016. Ex. 1099 submitted in PTAB Case No. IPR2023-00354, Dec. 27, 2022.
Aubry et al., Flavivirus reverse genetic systems, construction techniques and applications: a historical perspective. Antiviral Res. Feb. 2015;114:67-85. doi: 10.1016/j.antiviral.2014.12.007. Epub Dec. 12, 2014. Ex. 1100 submitted in PTAB Case No. IPR2023-00354, Dec. 27, 2022.
Shan et al., An Infectious cDNA Clone of Zika Virus to Study Viral Virulence, Mosquito Transmission, and Antiviral Inhibitors. Cell Host Microbe. Jun. 8, 2016;19(6):891-900. doi: 10.1016/j.chom.2016.05.004. Epub May 16, 2016. 11 pages. Ex. 1101 submitted in PTAB Case No. IPR2023-00354, Dec. 27, 2022.
Singh et al., orfipy: a fast and flexible tool for extracting ORFs. Bioinformatics. Sep. 29, 2021;37(18):3019-3020. doi: 10.1093/bioinformatics/btab090. Ex. 1102 submitted in PTAB Case No. IPR2023-00354, Dec. 27, 2022.
Bennett, How Many Particles Are in the Observable Universe? Popular Mechanics. Jul. 11, 2017. Retrieved from https://www.popularmechanics.com/space/a27259/how-many-particles-are-in-the-entire-universe/ on Dec. 14, 2022. 4 pages. Ex. 1103 submitted in PTAB Case No. IPR2023-00354, Dec. 27, 2022.
[No Author Listed], File History for U.S. Appl. No. 16/063,007. Application filed Jun. 15, 2018. 1449 pages. Ex. 1104 submitted in PTAB Case No. IPR2023-00354, Dec. 27, 2022.
[No Author Listed], Blast Global Alignment results for RID-PKD4DBPR114. Retrieved on Nov. 7, 2022. 18 pages. Ex. 1105 submitted in PTAB Case No. IPR2023-00354, Dec. 27, 2022.
[No Author Listed], Blast Global Alignment results for RID-PKD84V7U114. Retrieved on Nov. 7, 2022. 18 pages. Ex. 1106 submitted in PTAB Case No. IPR2023-00354, Dec. 27, 2022.
[No Author Listed], Blast Global Alignment results for RID-PKDAOFNF114. Retrieved on Nov. 7, 2022. 18 pages. Ex. 1107 submitted in PTAB Case No. IPR2023-00354, Dec. 27, 2022.
[No Author Listed], Blast Global Alignment results for RID-PKDBBE56114. Retrieved on Nov. 7, 2022. 18 pages. Ex. 1108 submitted in PTAB Case No. IPR2023-00354, Dec. 27, 2022.
[No Author Listed], Blast Global Alignment results for RID-PKDCZZDV114. Retrieved on Nov. 7, 2022. 18 pages. Ex. 1109 submitted in PTAB Case No. IPR2023-00354, Dec. 27, 2022.
[No Author Listed], Blast Global Alignment results for RID-PCDE772T114. Retrieved on Nov. 7, 2022. 18 pages. Ex. 1110 submitted in PTAB Case No. IPR2023-00354, Dec. 27, 2022.
[No Author Listed], Blast Global Alignment results for RID-PKDFM82R114. Retrieved on Nov. 7, 2022. 18 pages. Ex. 1111 submitted in PTAB Case No. IPR2023-00354, Dec. 27, 2022.
[No Author Listed], Blast Global Alignment results for RID-PKDHCCHB114. Retrieved on Nov. 7, 2022. 18 pages. Ex. 1112 submitted in PTAB Case No. IPR2023-00354, Dec. 27, 2022.
[No Author Listed], Blast Global Alignment results for RID-PKDMJ7XV114. Retrieved on Nov. 7, 2022. 18 pages. Ex. 1113 submitted in PTAB Case No. IPR2023-00354, Dec. 27, 2022.
[No Author Listed], Blast Global Alignment results for RID-PKDNW6MB114. Retrieved on Nov. 7, 2022. 18 pages. Ex. 1114 submitted in PTAB Case No. IPR2023-00354, Dec. 27, 2022.

(56) References Cited

OTHER PUBLICATIONS

[No Author Listed], Blast Global Alignment results for RID-PKDR1EU6114. Retrieved on Nov. 7, 2022. 18 pages. Ex. 1115 submitted in PTAB Case No. IPR2023-00354, Dec. 27, 2022.

[No Author Listed], Blast Global Alignment results for RID-PKDSNN5B114. Retrieved on Nov. 7, 2022. 18 pages. Ex. 1116 submitted in PTAB Case No. IPR2023-00354, Dec. 27, 2022.

[No Author Listed], Blast Global Alignment results for RID-PKDUZMG3114. Retrieved on Nov. 7, 2022. 18 pages. Ex. 1117 submitted in PTAB Case No. IPR2023-00354, Dec. 27, 2022.

Nema et al., Excipients and their role in approved injectable products: current usage and future directions. PDA J Pharm Sci Technol. May-Jun. 2011;65(3):287-332. doi: 10.5731/pdajpst.2011.00634. Downloaded on Mar. 23, 2022. Ex. 1118 submitted in PTAB Case No. IPR2023-00354, Dec. 27, 2022.

Chen et al., Dengue—quo tu et quo vadis? Viruses. Sep. 2011;3(9):1562-608. doi: 10.3390/v3091562. Epub Sep. 1, 2011. Ex. 1119 submitted in PTAB Case No. IPR2023-00354, Dec. 27, 2022.

Manikandan, Measures of central tendency: The mean. J Pharmacol Pharmacother. Apr. 2011;2(2):140-2. doi: 10.4103/0976-500X.81920. Ex. 1120 submitted in PTAB Case No. IPR2023-00354, Dec. 27, 2022.

Miller, Jr. College Physics. Harcourt Brace Jovanovich, Inc. 4th Ed. 1977:790. 4 pages. Ex. 1121 submitted in PTAB Case No. IPR2023-00354, Dec. 27, 2022.

Bayat, Science, medicine, and the future: Bioinformatics. BMJ. Apr. 27, 2002;324(7344):1018-22. doi: 10.1136/bmj.324.7344.1018. Ex. 1122 submitted in PTAB Case No. IPR2023-00354, Dec. 27, 2022.

Ekmekci et al., An Introduction to Programming for Bioscientists: A Python-Based Primer. PLoS Comput Biol. Jun. 7, 2016;12(6):e1004867. doi: 10.1371/journal.pcbi.1004867. Ex. 1123 submitted in PTAB Case No. IPR2023-00354, Dec. 27, 2022.

Sauter et al., New Python-based methods for data processing. Acta Crystallogr D Biol Crystallogr. Jul. 2013;69(Pt 7):1274-82. doi: 10.1107/S0907444913000863. Epub Jun. 18, 2013. Ex. 1124 submitted in PTAB Case No. IPR2023-00354, Dec. 27, 2022.

Venners, The Making of Python: A Conversation with Guido van Rossum, Part I. Jan. 13, 2003. 3 pages. Accessible at https://www.artima.com/articles/the-making-of-python. Retrieved on Nov. 10, 2022. 3 pages. Ex. 1125 submitted in PTAB Case No. IPR2023-00354, Dec. 27, 2022.

Adams et al., PHENIX: a comprehensive Python-based system for macromolecular structure solution. Acta Crystallogr D Biol Crystallogr. Feb. 2010;66(Pt 2):213-21. doi: 10.1107/S0907444909052925. Epub Jan. 22, 2010. Ex. 1126 submitted in PTAB Case No. IPR2023-00354, Dec. 27, 2022.

Hayes et al., Structural basis for promiscuous PAM recognition in type I-E Cascade from E. coli. Nature. Feb. 25, 2016;530(7591):499-503. doi: 10.1038/nature16995. Epub Feb. 10, 2016. Author Manuscript. 23 pages. Ex. 1127 submitted in PTAB Case No. IPR2023-00354, Dec. 27, 2022.

[No Author Listed], BLAST+ 2.13.0 is here! BLAST® Basic Local Alignment Search Tool. Mar. 17, 2022. Retrieved on Nov. 10, 2022. 10 pages. Ex. 1128 submitted in PTAB Case No. IPR2023-00354, Dec. 27, 2022.

Mount, Using the Basic Local Alignment Search Tool (BLAST). CSH Protoc. Jul. 1, 2007;2007:pdb.top17. doi: 10.1101/pdb.top17. 6 pages. Ex. 1129 submitted in PTAB Case No. IPR2023-00354, Dec. 27, 2022.

Chen et al., Cut site selection by the two nuclease domains of the Cas9 RNA-guided endonuclease. J Biol Chem. May 9, 2014;289(19):13284-94. doi: 10.1074/jbc.M113.539726. Epub Mar. 14, 2014. Ex. 1130 submitted in PTAB Case No. IPR2023-00354, Dec. 27, 2022.

Mann, Introductory Statistics. 7th Ed. John Wiley & Sons, Inc. 2010. 750 pages. Ex. 1131 submitted in PTAB Case No. IPR2023-00354, Dec. 27, 2022.

[No Author Listed], Summation Notation. Retrieved from www.columbia.edu/itc/sipa/math/summation.html on Nov. 10, 2022. 4 pages. Ex. 1132 submitted in PTAB Case No. IPR2023-00354, Dec. 27, 2022.

Harvey et al., How many stars are in the universe? Space. Feb. 11, 2022. Retrieved from https://www.space.com/26078-how-many-stars-are-there.html on Nov. 10, 2022. 18 pages. Ex. 1133 submitted in PTAB Case No. IPR2023-00354, Dec. 27, 2022.

Lopez et al., Biochemistry, Essential Amino Acids. Mar. 18, 2022. In: StatPearls [Internet]. Treasure Island (FL): StatPearls Publishing; Jan. 2022—. Retrieved from https://www.ncbi.nlm.nih.gov/books/NBK557845/?report=printable on Nov. 10, 2022. 5 pages. Ex. 1134 submitted in PTAB Case No. IPR2023-00354, Dec. 27, 2022.

Shchelochkov, Open Reading Frame. Updated Dec. 8, 2022. Retrieved from https://www.genome.gov/genetics-glossary/open-reading-frame on Dec. 14, 2022. 4 pages. Ex. 1135 submitted in PTAB Case No. IPR2023-00354, Dec. 27, 2022.

[No Author Listed], Read. Definition. NHS Health Education England. Retrieved from https://www.genomicseducation.hee.nhs.uk/glossary/read/ on Nov. 10, 2022. 4 pages. Ex. 1136 submitted in PTAB Case No. IPR2023-00354, Dec. 27, 2022.

Kurnaz et al., A statistical analysis of the robustness of alternate genetic coding tables. Int J Mol Sci. May 2008;9(5):679-697. doi: 10.3390/ijms9050679. Epub May 2, 2008. 20 pages. Ex. 1137 submitted in PTAB Case No. IPR2023-00354, Dec. 27, 2022.

Enfissi et al., Zika virus genome from the Americas. Lancet. Jan. 16, 2016;387(10015):227-8. doi: 10.1016/S0140-6736(16)00003-9. Epub Jan. 8, 2016. Ex. 1138 submitted in PTAB Case No. IPR2023-00354, Dec. 27, 2022.

Baronti et al., Complete coding sequence of zika virus from a French polynesia outbreak in 2013. Genome Announc. Jun. 5, 2014;2(3):e00500-14. doi: 10.1128/genomeA.00500-14. Ex. 1139 submitted in PTAB Case No. IPR2023-00354, Dec. 27, 2022.

[No Author Listed], The Wayback Machine page for http://www.who.int/entity/csr/research-and-developmen. 1 page. Ex. 1140 submitted in PTAB Case No. IPR2023-00354, Dec. 27, 2022.

[No Author Listed], Table of Contents. Genome Announcements. American Society for Microbiology. May/Jun. 2014. Retrieved from The Wayback Machine—http://genomea.asm.org:80/content/2/3.toc on Nov. 11, 2022. 16 pages. Ex. 1141 submitted in PTAB Case No. IPR2023-00354, Dec. 27, 2022.

[No Author Listed], Complete coding sequence of zika virus from a French Polynesia outbreak in 2013. Google Scholar Search Results. 2 pages. Ex. 1142 submitted in PTAB Case No. IPR2023-00354, Dec. 27, 2022.

[No Author Listed], Current Zika Product Pipeline. World Health Organization. Retrieved from The Wayback Machine—http://www.who.int/csr/research-and-dev on Nov. 10, 2022. 18 pages. Ex. 1143 submitted in PTAB Case No. IPR2023-00354, Dec. 27, 2022.

[No Author Listed], WHO and experts prioritize vaccines, diagnostics and innovative vector control tools for Zika R&D. World Health Organization. Mar. 9, 2016. Retrieved from The Wayback Machine—http://www.who.int/mediacentre/news/notes/2016/research-development-zika/en/ on Dec. 5, 2022. 4 pages. Ex. 1144 submitted in PTAB Case No. IPR2023-00354, Dec. 27, 2022.

Sifferlin, U.S. Launches 'Full-court Press' for a Zika Vaccine. Time—Health. Jan. 21, 2016. Retrieved from The Wayback Machine—http://time.com/4188973/zika-virus-vaccine-nih/ on Dec. 5, 2022. 3 pages. Ex. 1145. submitted in PTAB Case No. IPR2023-00354, Dec. 27, 2022.

Srivastava et al., A purified inactivated Japanese encephalitis virus vaccine made in Vero cells. Vaccine. Aug. 14, 2001;19(31):4557-65. doi: 10.1016/s0264-410x(01)00208-0. 13 pages. Ex. 1146 submitted in PTAB Case No. IPR2023-00354, Dec. 27, 2022.

[No Author Listed], Vaccine. UW-Madison Libraries Catalog Search Results. Retrieved from https://search.library.wisc.edu/catalog/999552122802121 on Nov. 11, 2022. 6 pages. Ex. 1147 submitted in PTAB Case No. IPR2023-00354, Dec. 27, 2022.

Srivastava et al., A purified inactivated Japanese encephalitis virus vaccine made in Vero cells. Vaccine. Aug. 14, 2001;19(31):4557-65. doi: 10.1016/s0264-410x(01)00208-0. Abstract only. 3 pages. Ex. 1148 submitted in PTAB Case No. IPR2023-00354, Dec. 27, 2022.

(56) References Cited

OTHER PUBLICATIONS

[No Author Listed], Vaccine. Elsevier Science. 1999-2002. Cover page. Retrieved from The Wayback Machine—http://www.elsevier.com/locate/vaccine on Nov. 26, 2022. 2 pages. Ex. 1149 submitted in PTAB Case No. IPR2023-00354, Dec. 27, 2022.

[No Author Listed], A purified inactivated Japanese encephalitis virus vaccine made in Vero cells. Google Scholar Search Results. 2 pages. Ex. 1150 submitted in PTAB Case No. IPR2023-00354, Dec. 27, 2022.

Thomas et al., A phase II, randomized, safety and immunogenicity study of a re-derived, live-attenuated dengue virus vaccine in healthy adults. Am J Trop Med Hyg. Jan. 2013;88(1):73-88. doi: 10.4269/ajtmh.2012.12-0361. Epub Dec. 3, 2012. 20 pages. Ex. 1151 submitted in PTAB Case No. IPR2023-00354, Dec. 27, 2022.

[No Author Listed], The American journal of tropical medicine and hygiene. PubMed Central Journal Page Search Results. https://catalog.nlm.nih.gov/permalink/01NLM_INST/1o1phhn/alma991179293406676. Retrieved on Nov. 15, 2022. 9 pages. Ex. 1152 submitted in PTAB Case No. IPR2023-00354, Dec. 27, 2022.

Thomas et al., A phase II, randomized, safety and immunogenicity study of a re-derived, live-attenuated dengue virus vaccine in healthy adults. Am J Trop Med Hyg. Jan. 2013;88(1):73-88. doi: 10.4269/ajtmh.2012.12-0361. Epub Dec. 3, 2012. Abstract only. 4 pages. Ex. 1153 submitted in PTAB Case No. IPR2023-00354, Dec. 27, 2022.

[No Author Listed], A phase II, randomized, safety and immunogenicity study of a re-derived, live-attenuated . . . Google Scholar Search Results. 2 pages. Ex. 1154 submitted in PTAB Case No. IPR2023-00354, Dec. 27, 2022.

Baronti et al., Complete coding sequence of Zika virus from a French polynesia outbreak in 2013. Genome Announc. Jun. 5, 2014;2(3):e00500-14. doi: 10.1128/genomeA.00500-14. Ex. 1160 submitted in PTAB Case No. IPR2023-00354, Dec. 27, 2022.

[No Author Listed] World Health Organization: Current Zika Product Pipeline. Mar. 3, 2016. 16 pages. Ex. 1161 submitted in PTAB Case No. IPR2023-00354, Dec. 27, 2022.

Sifferlin, U.S. Launches 'Full-Court Press' for a Zika Vaccine. Time. Jan. 21, 2016, Retrieved from https://time.com/4188973/zika-virus-vaccine-nih/ on Nov. 11, 2022. 2 pages. Ex. 1162 submitted in PTAB Case No. IPR2023-00354, Dec. 27, 2022.

Srivastava et al., A purified inactivated Japanese encephalitis virus vaccine made in Vero cells. Vaccine. Aug. 14, 2001;19(31):4557-65. doi: 10.1016/s0264-410x(01)00208-0. Ex. 1163 submitted in PTAB Case No. IPR2023-00354, Dec. 27, 2022.

Thomas et al., A phase II, randomized, safety and immunogenicity study of a re-derived, live-attenuated dengue virus vaccine in healthy adults. Am J Trop Med Hyg. Jan. 2013;88(1):73-88. doi: 10.4269/ajtmh.2012.12-0361. Epub Dec. 3, 2012. Ex.1164 submitted in PTAB Case No. IPR2023-00354, Dec. 27, 2022.

Declaration of Nathaniel E. Frank-White, Nov. 16, 2022, archive.org, 42 pages. Ex. 1166 submitted in PTAB Case No. IPR2023-00354, Dec. 27, 2022.

Hsieh-Yee, Curriculum Vitae, 21 pages. Ex. 1167 submitted in PTAB Case No. IPR2023-00354, Dec. 27, 2022.

[No Author Listed] Part VII: A Summary of Commonly Used MARC 21 Fields. MARC 21 Reference Materials. Retrieved from https://www.loc.gov/marc/umb/um07to10.html on Dec. 5, 2022. 17 pages. Ex. 1168 submitted in PTAB Case No. IPR2023-00354, Dec. 27, 2022.

[No Author Listed] Stop Codon. ScienceDirect Topics. Retrieved from https://www.sciencedirect.com/topics/neuroscience/stop-codon# :~: text=Premature stop codons are those,as truncated) protein is formed on Dec. 6, 2022. 10 pages. Ex. 1169 submitted in PTAB Case No. IPR2023-00354, Dec. 27, 2022.

Shiver, et al. Scientific Notation and Order of Magnitude, Visionlearning, 2016. Retrieved from https://www.visionlearning.com/en/library/Math-in-Science/62/Scientific-Notation-and-Order-of-Magnitude/250#top on Dec. 6, 2022. 16 pages. Ex. 1170 submitted in PTAB Case No. IPR2023-00354, Dec. 27, 2022.

[No Author Listed] Python Code as Ran. Sequence Length 5, Identity 60. 1 page. Ex. 1171 submitted in PTAB Case No. IPR2023-00354, Dec. 27, 2022.

[No Author Listed] Python Code as Ran. Sequence Length 500, Identity 95. 1 page. Ex. 1172 submitted in PTAB Case No. IPR2023-00354, Dec. 27, 2022.

[No Author Listed] Python (Calculate Number of AA Sequences). Sequence Length 500, Identity 95. 1 page. Ex. 1173 submitted in PTAB Case No. IPR2023-00354, Dec. 27, 2022.

[No Author Listed] Python (Calculate Number of DNA Sequences). Sequence Length 10272, Identity 99.99.1 page. Ex. 1174 submitted in PTAB Case No. IPR2023-00354, Dec. 27, 2022.

[No Author Listed] Python (Calculate Number of Protein Sequences without Internal Stops). 3 pages. Ex. 1175 submitted in PTAB Case No. IPR2023-00354, Dec. 27, 2022.

Ramachandran et al., Processing and integration of functionally oriented prespacers in the *Escherichia coli* CRISPR system depends on bacterial host exonucleases. J Biol Chem. Mar. 13, 2020;295(11):3403-3414. doi: 10.1074/jbc.RA119.012196. Epub Dec. 30, 2019. Ex. 1176 submitted in PTAB Case No. IPR2023-00354, Dec. 27, 2022.

Plevka et al., Maturation of flaviviruses starts from one or more icosahedrally independent nucleation centres. EMBO Rep. Jun. 2011;12(6):602-6. doi: 10.1038/embor.2011.75. Epub May 13, 2011. Ex. 1177 submitted in PTAB Case No. IPR2023-00354, Dec. 27, 2022.

Rodrigues et al., Viral vaccines and their manufacturing cell substrates: New trends and designs in modern vaccinology. Biotechnol J. Sep. 2015;10(9):1329-44. doi: 10.1002/biot.201400387. Epub Jul. 24, 2015. Ex. 1178 submitted in PTAB Case No. IPR2023-00354, Dec. 27, 2022.

Souza et al., Production of yellow fever virus in microcarrier-based Vero cell cultures. Vaccine. Oct. 30, 2009;27(46):6420-3. doi: 10.1016/j.vaccine.2009.06.023. Epub Jun. 24, 2009. Ex. 1179 submitted in PTAB Case No. IPR2023-00354, Dec. 27, 2022.

Pereira et al., An inactivated yellow fever 17DD vaccine cultivated in Vero cell cultures. Vaccine. Aug. 20, 2015;33(35):4261-8. doi: 10.1016/j.vaccine.2015.03.077. Epub Apr. 7, 2015. Ex. 1180 submitted in PTAB Case No. IPR2023-00354, Dec. 27, 2022.

[No Author Listed], Amended Articles of Incorporation of OCLC, Inc. Revised Jun. 23, 2017. 2 pages. Ex. 1181 submitted in PTAB Case No. IPR2023-00354, Dec. 27, 2022.

[No Author Listed], Discussion Paper No. 2020-DP16. MARC Standards. Retrieved from https://www.loc.gov/marc/mac/2020/2020-dp16.html on Dec. 13, 2022. 12 pages. Ex. 1183 submitted in PTAB Case No. IPR2023-00354, Dec. 27, 2022.

Baronti et al., Complete Coding Sequence of Zika Virus from a French Polynesia Outbreak in 2013. ASM Journals. Genome Announcements. Jun. 5, 2014;2(3). Partial abstract only. 1 page. Ex. 1185 submitted in PTAB Case No. IPR2023-00354, Dec. 27, 2022.

[No Author Listed], Trending Articles. PubMed records with recent increases in activity. 2 pages. Ex. 1186 submitted in PTAB Case No. IPR2023-00354, Dec. 27, 2022.

[No Author Listed], Early Citations to Baronti from 2015. 1 page. Ex. 1187 submitted in PTAB Case No. IPR2023-00354, Dec. 27, 2022.

[No Author Listed], Current Zika Product Pipeline. World Health Organization. Mar. 3, 2016. Retrieved from who.int/publications/m/item/current-zika-product-pipeline. 1 page. Ex. 1188 submitted in PTAB Case No. IPR2023-00354, Dec. 27, 2022.

[No Author Listed], Library Search Page. WorldCat.Org. Retrieved from https://www.worldcat.org on Dec. 13, 2022. 5 pages. Ex. 1189 submitted in PTAB Case No. IPR2023-00354, Dec. 27, 2022.

[No Author Listed], Blast Global Alignment results for RID-THJEH558114. Retrieved on Dec. 13, 2022. 17 pages. Ex. 1190 submitted in PTAB Case No. IPR2023-00354, Dec. 27, 2022.

[No Author Listed], Blast Global Alignment results for RID-THT9HZ7G114. Retrieved on Dec. 13, 2022. 17 pages. Ex. 1191 submitted in PTAB Case No. IPR2023-00354, Dec. 27, 2022.

[No Author Listed], Blast Global Alignment results for RID-THTJHT47114. Retrieved on Dec. 13, 2022. 11 pages. Ex. 1192 submitted in PTAB Case No. IPR2023-00354, Dec. 27, 2022.

(56) References Cited

OTHER PUBLICATIONS

[No Author Listed], Python Code as Ran. 6 pages. Ex. 1193 submitted in PTAB Case No. IPR2023-00354, Dec. 27, 2022.
Srivastava et al., A purified inactivated Japanese encephalitis virus vaccine made in Vero cells. Vaccine. Aug. 14, 2001;19(31):4557-65. doi: 10.1016/s0264-410x(01)00208-0. Journal Article Home Page. Retrieved from sciencedirect.com/science/article/pii/S0264410X01002080?via%3Dihub. 1 page. Ex. 1195 submitted in PTAB Case No. IPR2023-00354, Dec. 27, 2022.
[No Author Listed], ScienceDirect Webpage. Elsevier. 2022. Retrieved from https://www.elsevier.com/. 9 pages. Ex. 1197 submitted in PTAB Case No. IPR2023-00354, Dec. 27, 2022.
[No Author Listed], Vaccine. WorldCat.org. Retrieved from https://worldcat.org/title/10399916 on Dec. 13, 2022. 5 pages. Ex. 1198 submitted in PTAB Case No. IPR2023-00354, Dec. 27, 2022.
[No Author Listed], Vaccine Journal Home Page. ScienceDirect. Retrieved from https://www.sciencedirect.com/journal/vaccine on Dec. 13, 2022. 9 pages. Ex. 1199 submitted in PTAB Case No. IPR2023-00354, Dec. 27, 2022.
[No Author Listed], Directory of OCLC Members: gzm. Retrieved from https://www.oclc.org/en/contacts/libraries.html on Dec. 13, 2022. 2 pages. Ex. 1200 submitted in PTAB Case No. IPR2023-00354, Dec. 27, 2022.
[No Author Listed], W: General Medicine. Health Professions. NIH National Library Classification 2022 Summer Edition. Retrieved from https://classification.nlm.nih.gov/schedules/w on Dec. 13, 2022. 9 pages. Ex. 1202 submitted in PTAB Case No. IPR2023-00354, Dec. 27, 2022.
Thomas et al., A phase II, randomized, safety and immunogenicity study of a re-derived, live-attenuated dengue virus vaccine in healthy adults. Am J Trop Med Hyg. Jan. 2013;88(1):73-88. doi: 10.4269/ajtmh.2012.12-0361. Epub Dec. 3, 2012. Introduction. Retrieved from ajtmh.org/view/journals/tpmd/88/1/article-p73.xml. 25 pages. Ex. 1204 submitted in PTAB Case No. IPR2023-00354, Dec. 27, 2022.
[No Author Listed], The American Journal of Tropical Medicine and Hygiene. WorldCat.org Search Page. Retrieved from https://worldcat.org/title/1724826 on Dec. 13, 2022. 5 pages. Ex. 1205 submitted in PTAB Case No. IPR2023-00354, Dec. 27, 2022.
[No Author Listed], DNLM Search Results from MARC Code List for Organizations. Retrieved from https://www.loc.gov/marc/organizations/org-search.php on Dec. 13, 2022. 1 page. Ex. 1206 submitted in PTAB Case No. IPR2023-00354, Dec. 27, 2022.
[No Author Listed], MEDLINE/PubMed Data Element (Field) Descriptions. PubMed Resources. Retrieved from https://www.nlm.nih.gov/bsd/mms/medlineelements.html on Dec. 13, 2022. 35 pages. Ex. 1207 submitted in PTAB Case No. IPR2023-00354, Dec. 27, 2022.
[No Author Listed], Early Citations to Thomas from Jun. 2013-Mar. 2014. 1 page. Ex. 1208 submitted in PTAB Case No. IPR2023-00354, Dec. 27, 2022.
[No Author Listed], Early Citations to Srivastava from 2002-2003. 1 page. Ex. 1209 submitted in PTAB Case No. IPR2023-00354, Dec. 27, 2022.
Email Regarding Statutory Disclaimer Filing in U.S. Pat. No. 11,219,681. Submitted in Inter Partes Review of *Takeda Vaccines, Inc.* vs *Valneva Austria GmbH*. 1 page. Ex. 3001 in PTAB Case No. IPR2023-00354, Mar. 22, 2023.
Statutory Disclaimer, Form PTO-SB-43 submitted in U.S. Pat. No. 11,219,681. Submitted in Inter Partes Review of *Takeda Vaccines, Inc.* vs *Valneva Austria GmbH*. 1 page. Ex. 3002 in PTAB Case No. IPR2023-00354, Mar. 21, 2023.
Petitioner's Email Response to Email Regarding Statutory Disclaimer Filing in U.S. Pat. No. 11,219,681. Submitted in Inter Partes Review of *Takeda Vaccines, Inc.* vs *Valneva Austria GmbH*. 2 pages. Ex. 3003 in PTAB Case No. IPR2023-00354, Mar. 24, 2023.
Confirmation Email from The PTAB Confirming Understanding of Parties Positions on Statutory Disclaimer in U.S. Pat. No. 11,219,681. Submitted in Inter Partes Review of *Takeda Vaccines, Inc.* vs *Valneva Austria GmbH*. 4 pages. Ex. 3004 in PTAB Case No. IPR2023-00354, Mar. 28, 2023.
Petitioner's Updated Exhibit List in Inter Partes Review of U.S. Pat. No. 11,219,681. *Takeda Vaccines, Inc.* vs *Valneva Austria GmbH*. 19 pages. Paper No. 5, submitted in PTAB Case No. IPR2023-00354, Apr. 20, 2023.
Telephonic Conference Transcript of Conference Taking Place Apr. 19, 2023 in Inter Partes Review of U.S. Pat. No. 11,219,681. *Takeda Vaccines, Inc.* vs *Valneva Austria GmbH*. 38 pages. Ex. 1210 submitted in PTAB Case No. IPR2023-00354, Apr. 20, 2023.
Order Denying Authorization of Motion in Inter Partes Review of U.S. Pat. No. 11,219,681. *Takeda Vaccines, Inc.* vs *Valneva Austria GMBH*. 5 pages. Paper No. 6, issued in PTAB Case No. IPR2023-00354, Jun. 6, 2023.
Decision for Inter Partes Review of U.S. Pat. No. 11,219,681. *Takeda Vaccines, Inc.* vs *Valneva Austria GmbH*. 6 pages. Paper No. 7, issued in PTAB Case No. IPR2023-00354, Jun. 9, 2023.
U.S. Appl. No. 17/548,721, filed Dec. 13, 2021, Barbero Calzado et al.
PCT/EP2016/082664, dated Apr. 10, 2017, *International Search Report and Written Opinion.
PCT/EP2016/082664, dated Jun. 26, 2018, *International Preliminary Report on Patentability.

TEV_virus.NC_001672.1
YFV_ASIBI.AY640589.1
YFV_17D_vaccine_strain.NC_002031.1
YFV_virus_isol-Pasteur_17D-204_yellow_fever_vaccine.X15062.1
YFV_vaccine_strain_17D-213.U17067.1
JEV_SA14.D90194.1
JEV_virus.M55506.1
JEV_SA14-14-2.AF315119.1
JEV_SA14-14-2.D90195.1
JEV_virus.NC_001437.1
WNV_956.NC_001563.2
WNV_NY99_isol-385-99.NC_009942.1
WNV_Chin-01.AY490240.2
ZVV_MR766-NIID.LC002520.1
ZVV_MR_766.NC_012532.1
ZVV_MR_766.AY632535.2
ZVV_ZikaSPH2015.KU321639.1
DVV_1.NC_001477.1
DVV_3_isol-D3%H%IMTSSA-SRI%2000%1266.NC_001475.2
DVV_16681.NC_001474.2
DVV_4.NC_002640.1

000
ZIKA VIRUS VACCINE

RELATED APPLICATIONS

This Application is a continuation of U.S. application Ser. No. 17/548,721, filed Dec. 13, 2021, which is a continuation of U.S. application Ser. No. 16/813,862, now U.S. Pat. No. 11,219,681, filed Mar. 10, 2020, which is a continuation of U.S. application Ser. No. 16/063,007, now U.S. Pat. No. 10,639,365, filed Jun. 15, 2018, which is a national stage filing under 35 U.S.C. § 371 of International Patent Application Serial No. PCT/EP2016/082664, filed Dec. 23, 2016, the contents of each of which is herein incorporated by reference in its entirety.

REFERENCE TO AN ELECTRONIC SEQUENCE LISTING

The contents of the electronic sequence listing (I042270125US03-SEQ-JRV.xml; Size: 280,804 bytes; and Date of Creation: Mar. 3, 2023) is herein incorporated by reference in its entirety.

FIELD OF INVENTION

The disclosure relates to methods for the purification of Zika viruses for use in vaccines and in particular relates to an improved sucrose gradient process step allowing the separation of impurities such as protamine sulphate. The disclosure also relates to Zika virus vaccines and compositions and methods for producing said vaccines and administering the vaccines to subjects for the generation of an anti-Zika virus immune response.

BACKGROUND OF THE INVENTION

Adverse responses to protamine sulfate have been known for many years. Previous exposure to protamine can induce a humoral immune response and predispose susceptible individuals to the development of untoward reactions from the subsequent use of this drug. Patients exposed to protamine through the use of protamine-containing insulin or during heparin neutralization may experience life-threatening reactions and fatal anaphylaxis upon receiving large doses of protamine intravenously. Severe reactions to intravenous protamine can occur in the absence of local or systemic allergic reactions to subcutaneous injection of protamine-containing insulin. Although there is no clear evidence for hypersensitivity reactions of protamine sulphate linked to vaccination, vaccines containing protamine impurities have a precaution and contraindication warning in their labels stating that a serious allergic reaction after a previous dose of such a protamine containing vaccine (e.g. IXIARO®, see CDC site www.cdc.gov/japaneseencephalitis/vaccine/) is a contraindication to further doses. Thus elimination of said impurity is a medical request for an improved safety profile. On the other hand protamine sulphate is an excellent tool (and often better than other tools such as benzonase) to purify crude harvests of viruses grown on cell substrates.

In 2007, Zika virus was detected for the first time outside of the endemic regions of Asia and Africa since its discovery in a Rhesus monkey in Uganda in 1947. Since then, the virus has caused a large epidemic in French Polynesia, spreading through islands in the Pacific and into South and Central America by 2015 (WHO "Zika Situation Report" Feb. 5, 2016). Evidence suggests that in addition to being transmitted by *Aedes* species mosquitos, other vectors may exist, and the virus may be transmitted by blood transfusion, transplacentally, and through sexual transmission (WHO Zika Virus Fact Sheet, February 2016). Though the symptoms of Zika virus infection include mild fever, rash, and conjunctivitis, there is a likely correlation between infection and neurological disorders, including Guillain-Barre syndrome and microcephaly in fetuses/neonates subsequent to infection during pregnancy. There is currently no specific treatment or vaccine for Zika virus and the only preventative measures involve control of the mosquito vector. Zika virus presents a substantial public health threat due to the wide circulation of the *Aedes* mosquito, multiple routes of transmission, and potentially severe neurological effects of infection.

A preventative vaccine against Zika virus is a pressing medical need in endemic areas and in geographical areas where the vector is spreading. Furthermore, as Zika infection has dire consequences on embryonic and fetal development, a safe and effective vaccine for women of child-bearing potential or pregnant women is needed. Vaccines administered during pregnancy must be very safe for both the mother and the developing fetus. While live attenuated viral vaccines are highly effective, they are often not considered safe enough for administration to pregnant women. In this regard, inactivated viral vaccines, which lack the ability to propagate in the vaccinated subject, are considered much safer. Development of an inactivated Zika virus vaccine for administration to at-risk patients would fill this need.

SUMMARY OF THE INVENTION

During the course of virus purification, it was observed that addition of protamine sulfate to a virus harvest produced on a cell substrate removed not only contaminating DNA derived from host cells, as expected, but surprisingly also virtually eliminated immature and otherwise non-infectious virus particles from the preparation. This finding provided a streamlined, gentle, reproducible and broadly-applicable process for obtaining highly-purified infectious virus particles for applications such as vaccine preparation. In addition, it was surprisingly found that said protamine sulfate can be very efficiently separated from the virus fraction allowing for a safer vaccine produced at high yields.

Disclosed herein are virus vaccines and compositions comprising an inactivated Zika virus, and related methods of producing said vaccines and compositions. Also provided are methods of administering said Zika virus vaccines for the prevention of Zika virus infection and/or for the production of an anti-virus immune response in subjects, for example subjects at risk of being exposed to Zika virus. In particular, the invention is directed to a virus vaccine comprising an optimally inactivated Zika virus particle, wherein the Zika virus particle in an appropriate dose is able to seroconvert a subject that is administered the virus vaccine with at least a 70% probability, preferably an 80% probability. Another advantage of the invention is that related methods of producing said vaccines and compositions are very efficient and provide pure compositions largely devoid of impurities, in particular protamine sulphate, allowing for high volume production of vaccines. Detail experimental examples to the above are provided for Zika virus.

The herein disclosed in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was unexpectedly higher than the recently reported inactivated Zika virus vaccine candidate (Larocca, et. al, 2016, Nature doi:10.1038/nature18952.). Inactivated viruses are among the safest vaccines and especially preferred for delivery to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing, alignments were performed with the multi alignment package Jalview (Waterhouse et al., 2009, Bioinformatics 25 (9) 1189-1191). In the drawings:

FIG. 1: Average distance tree (by % identity, nt), complete genomes.

Figure 2:
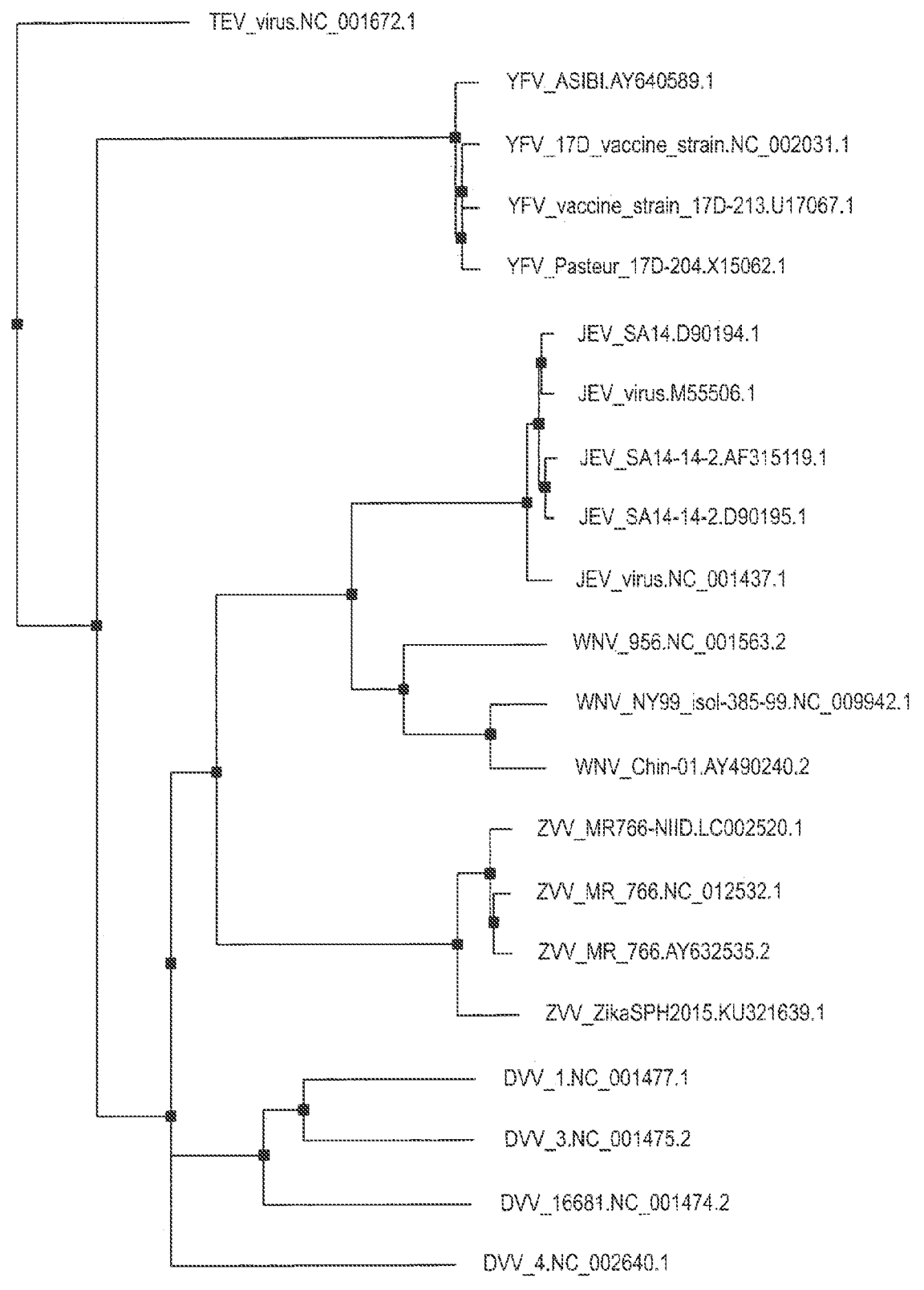

FIG. 2: Neighbor joining tree (by % identity, nt), complete genomes.

Figure 5:
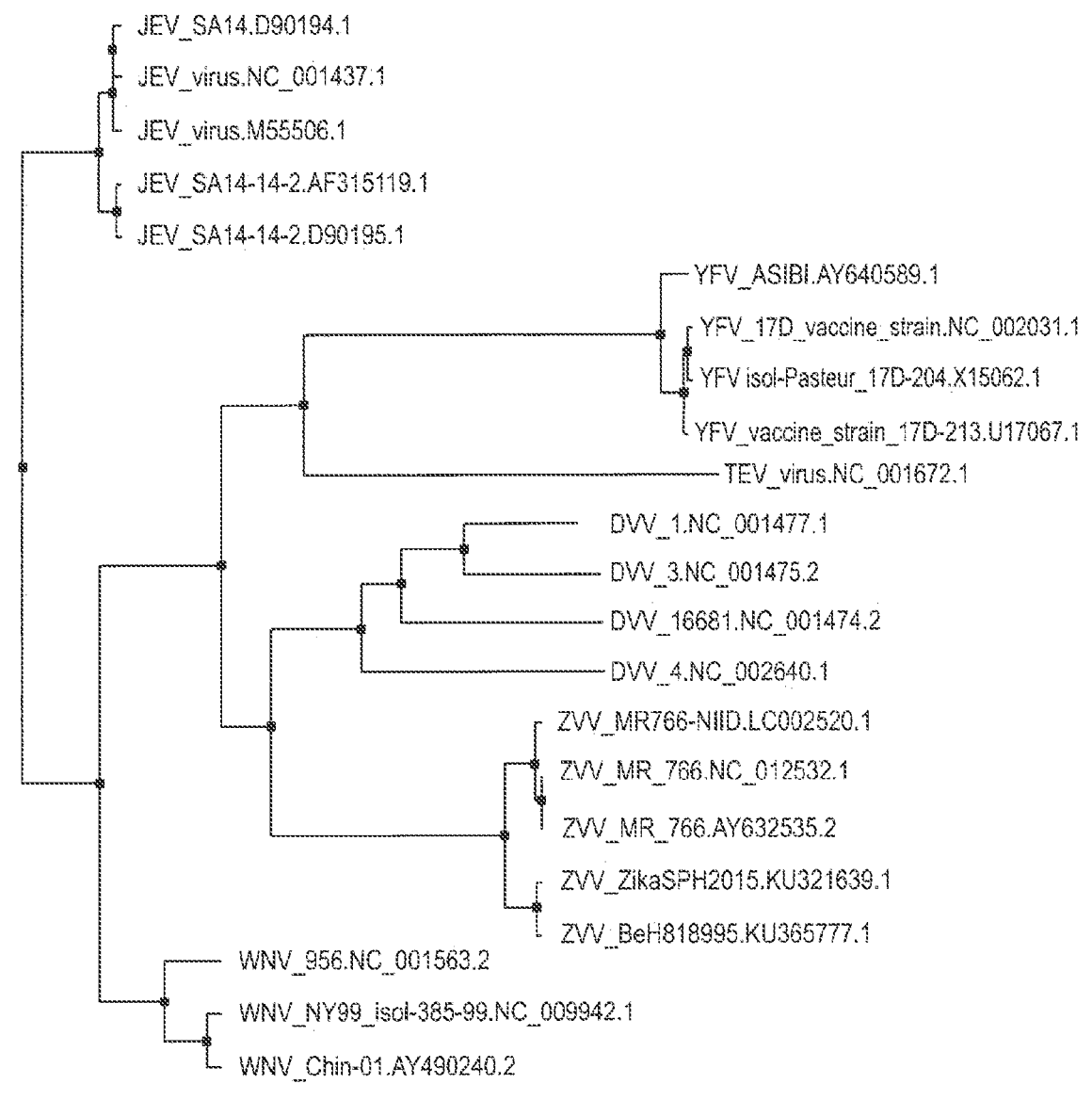

FIG. 5: Neighbor joining tree (by % identity. aa), E-protein.

Figure 6:
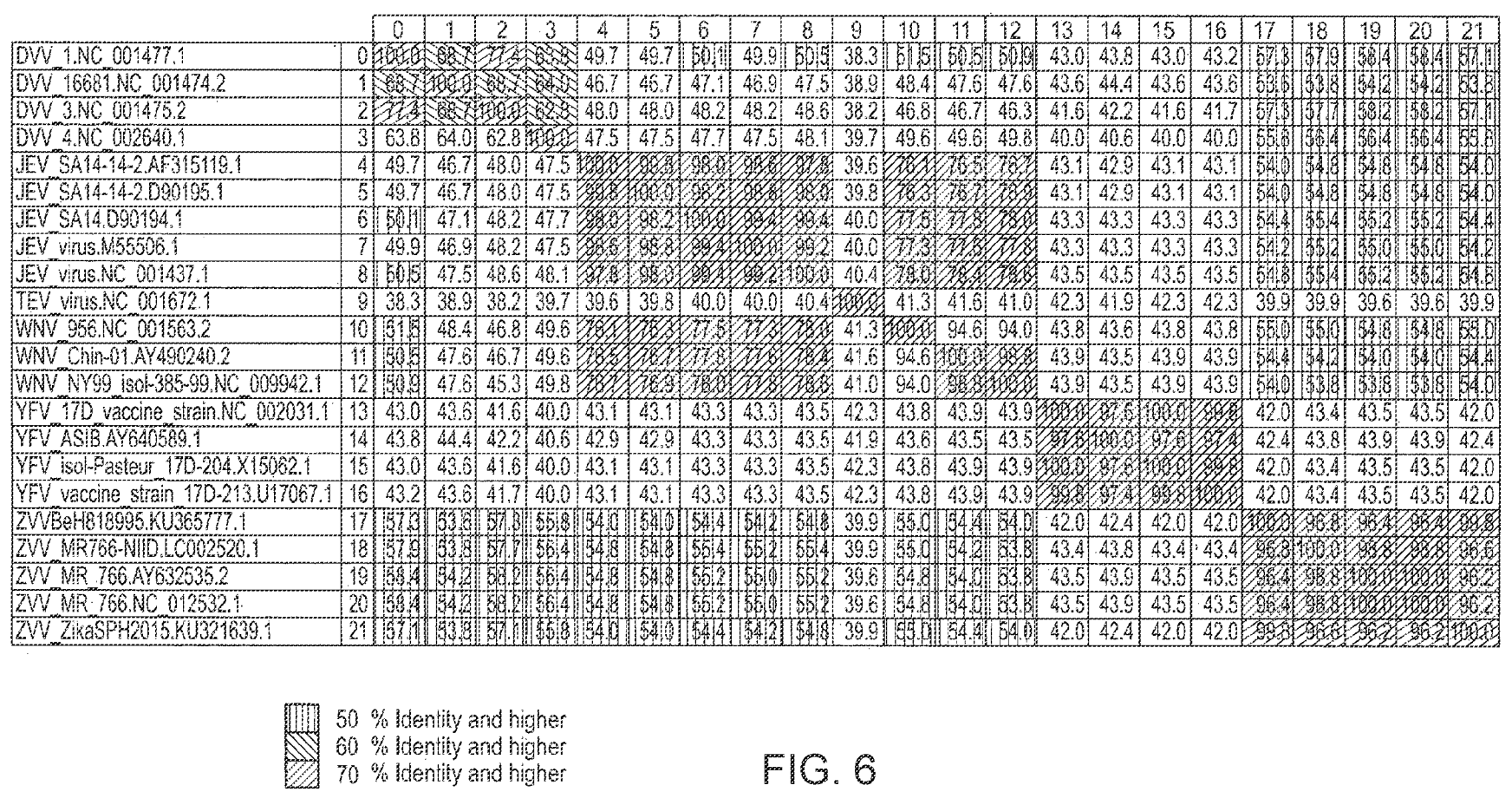

FIG. 6: Pairwise alignment-Jalview (% identity, aa), E-protein.

Figure 7B:
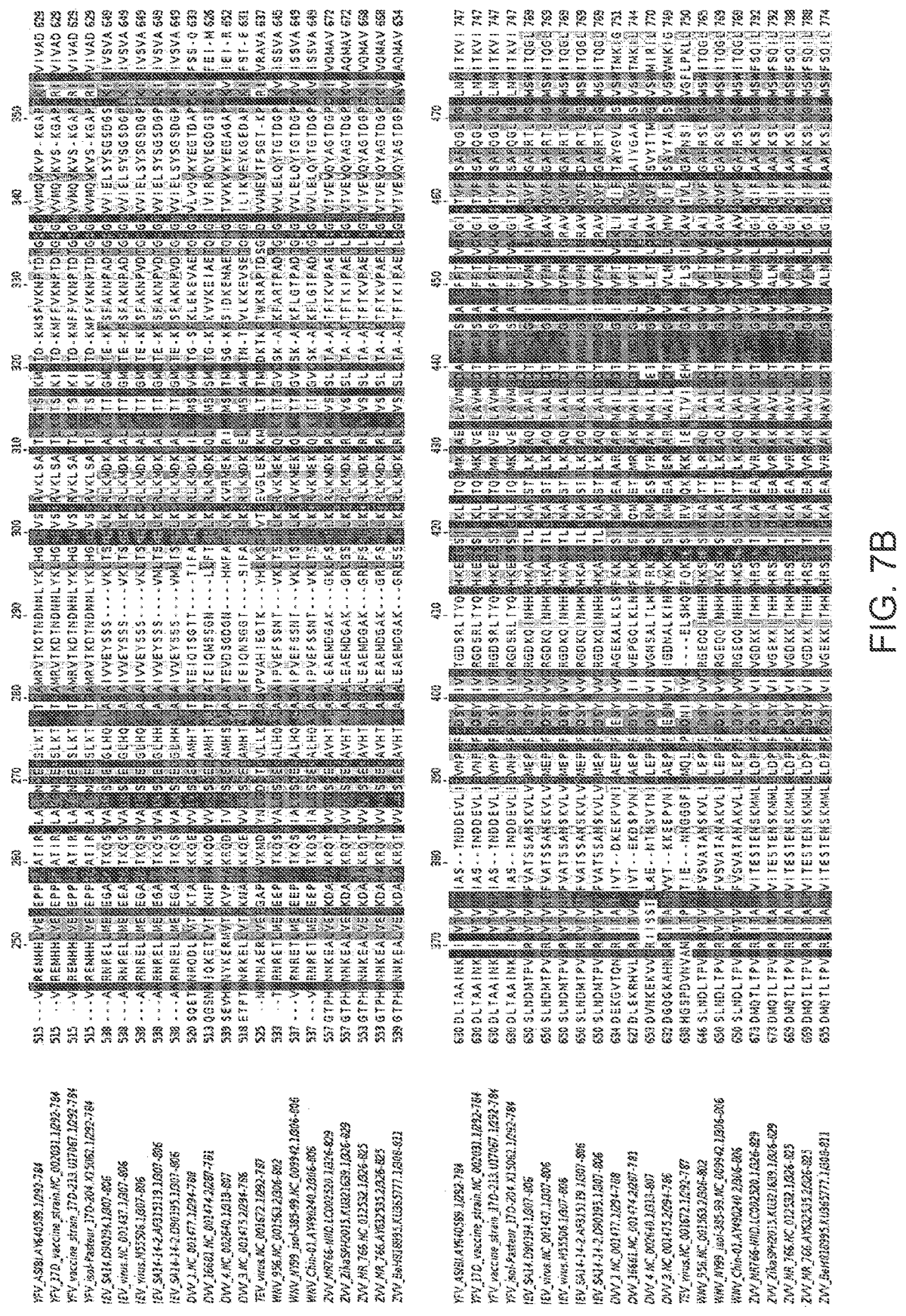
Figure 7C:
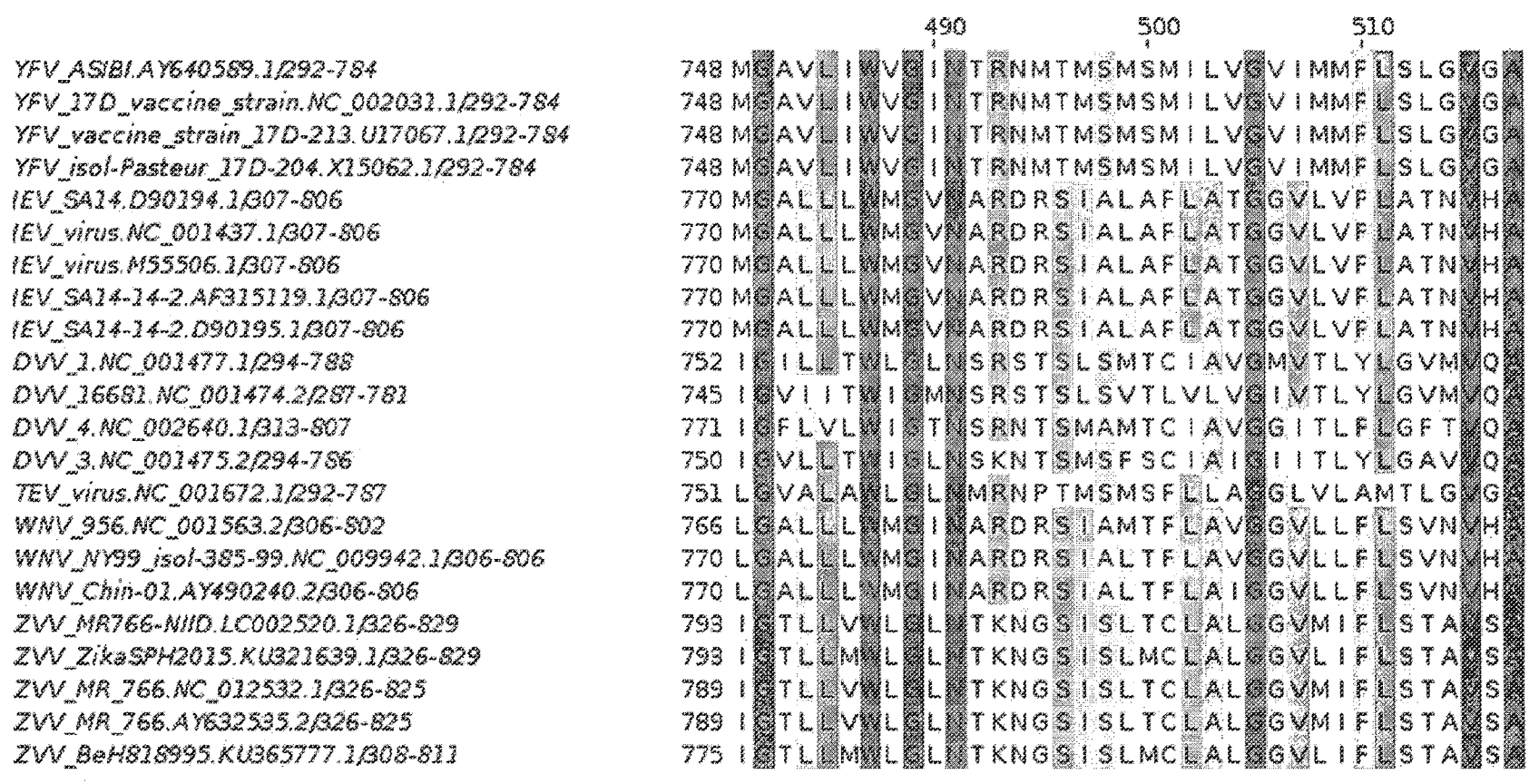

FIGS. 7A-7C: Alignment (shading: % identity, aa), E-protein.

DETAILED DESCRIPTION OF THE INVENTION

Figure 3:
FIG. 3: Pairwise alignment-Jalview (% identity, nt), complete genomes.
Figure 4:
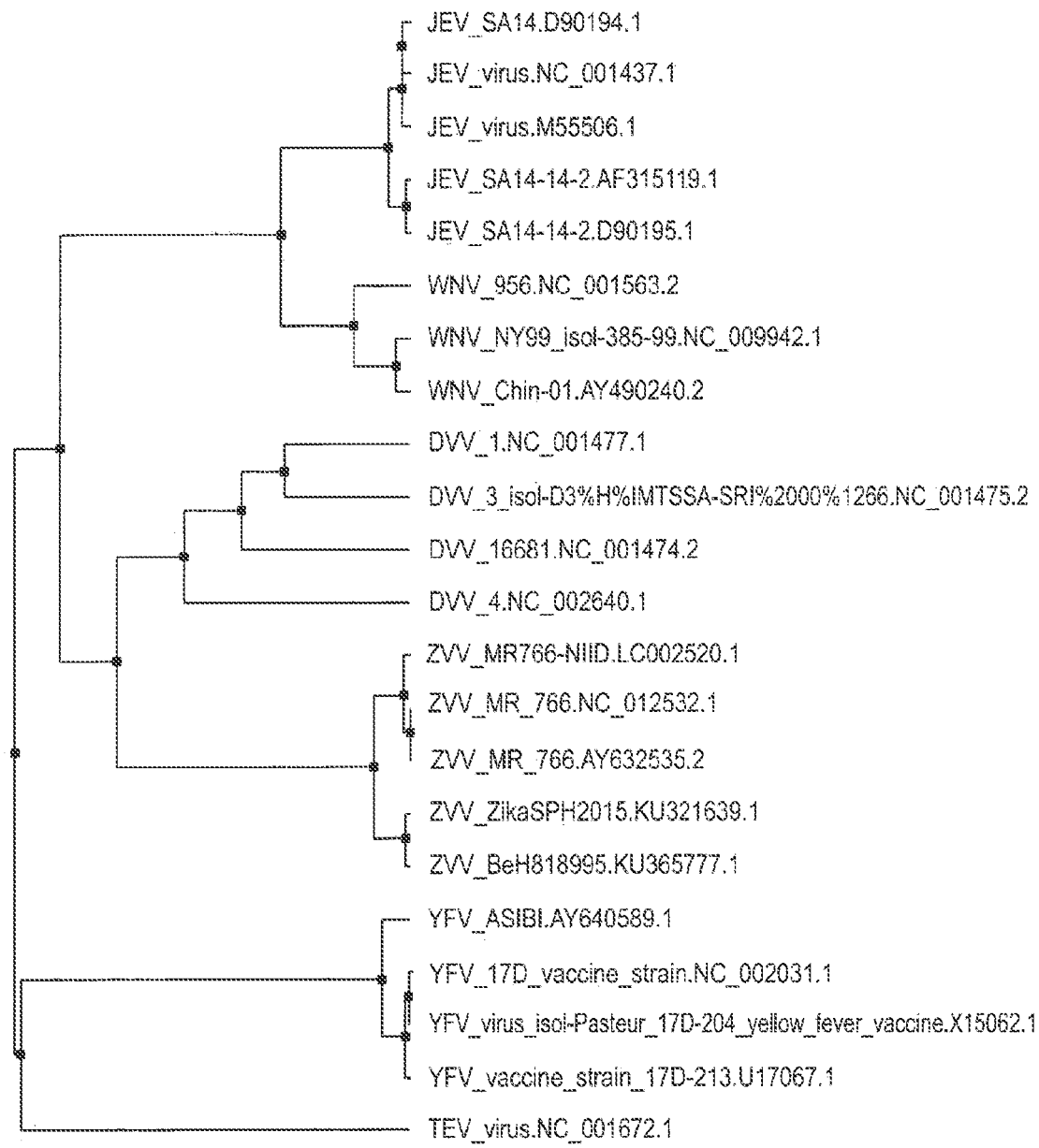
FIG. 4: Average distance tree (by % identity, aa), E-protein.
Figure 7A:
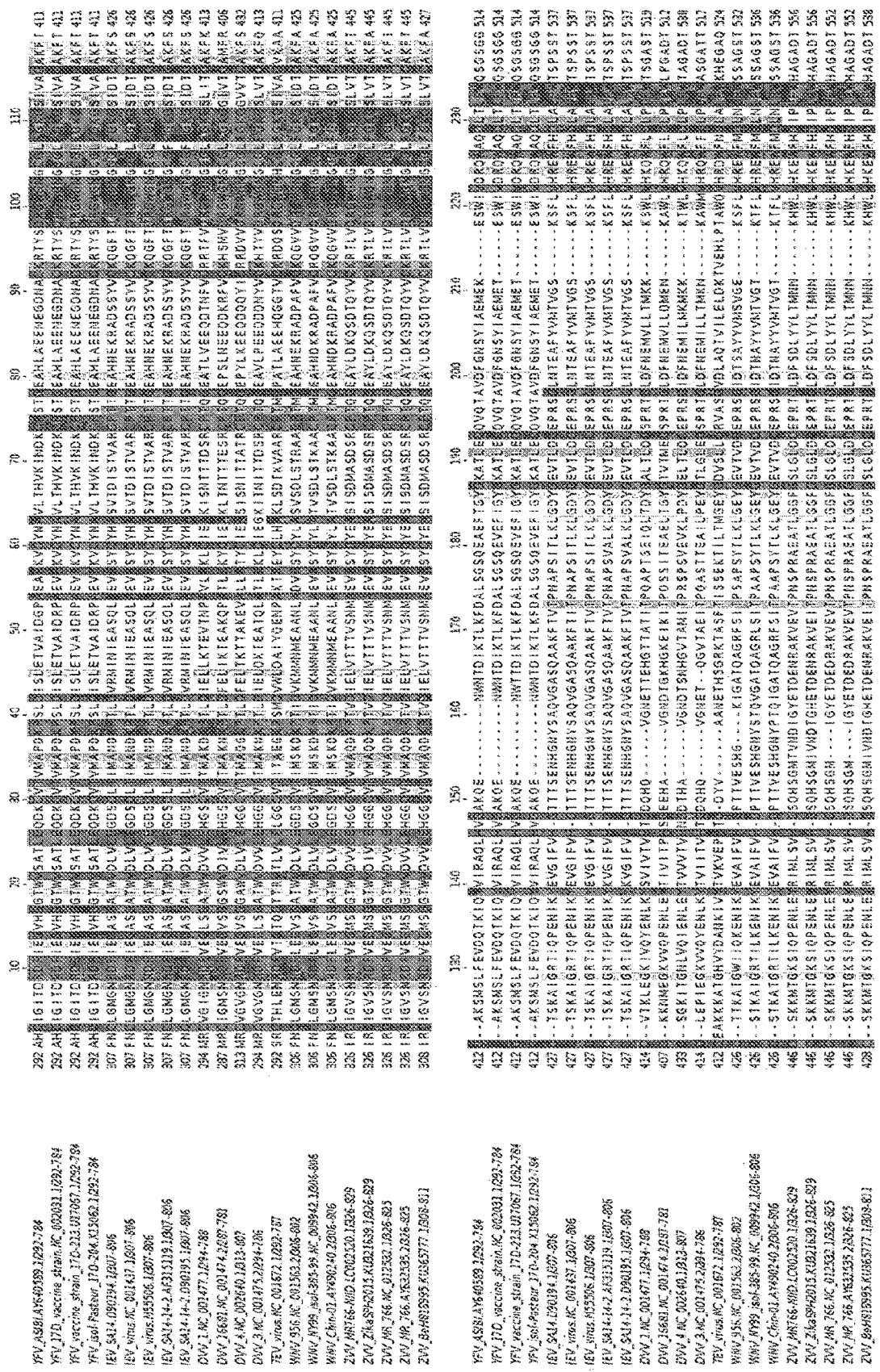
Figure 8:
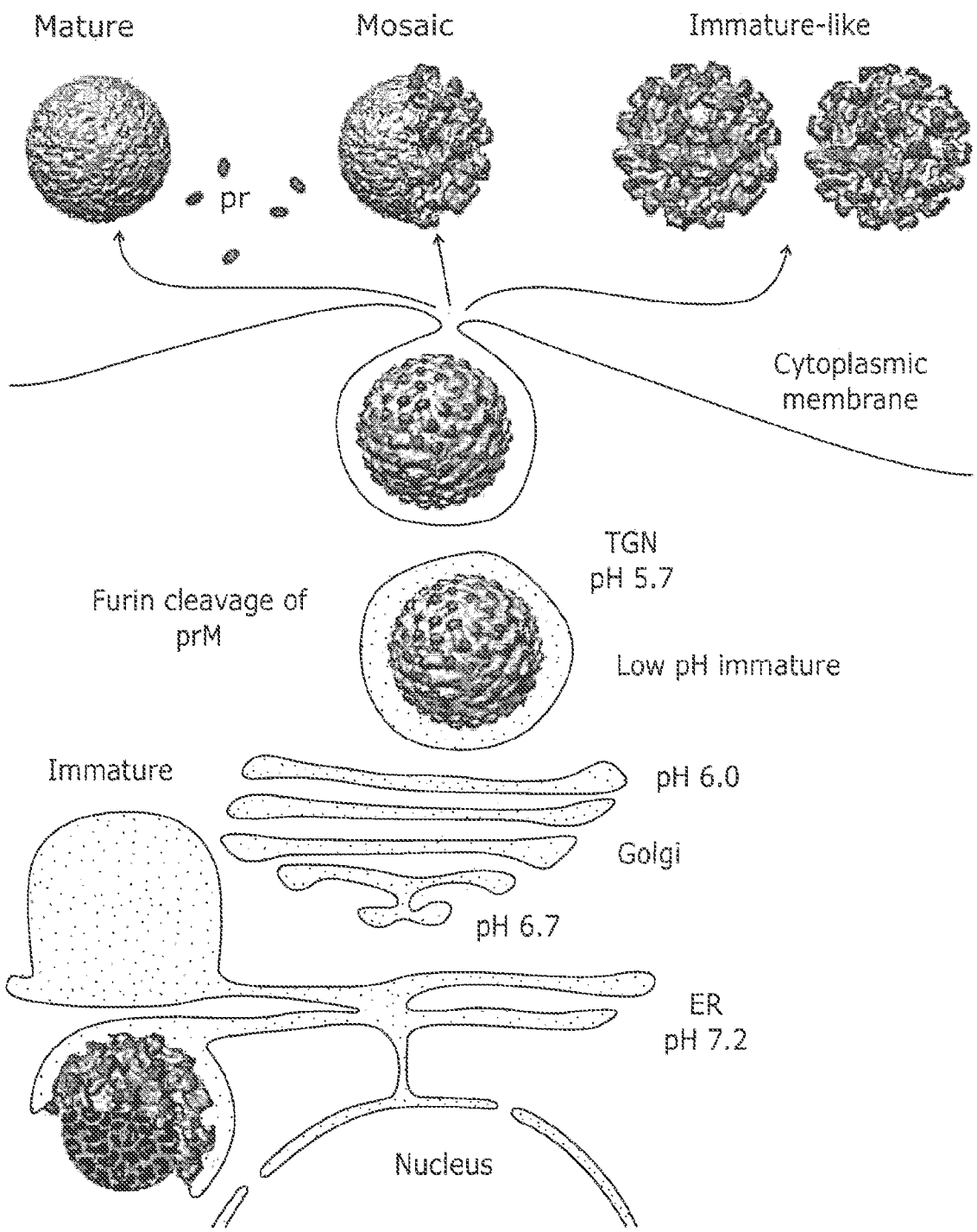
FIG. 8: An example of virus particle maturation in the host cell. As observed in flaviviruses, full maturation of the particles requires proteolytic cleavage of the precursor membrane glycoprotein (prM) by the host protease furin. Not all prM molecules are cleaved, resulting in the release of mature, mosaic or immature-like conformations from the cells. Mosaic and immature forms are generally not infectious—only mature virions are infective and have hemagglutinin (HA)/TCID50 activity. (Figure adapted from Plevka, et al., Maturation of flaviviruses starts from one or more icosahedrally independent nucleation centres, EMBO reports (2011) 12, 602-606).

Disclosed herein are Zika virus vaccines and compositions comprising an inactivated Zika virus, and related methods of producing said vaccines and compositions. Also provided are methods of administering said virus vaccines for the prevention of virus infection and/or for the production of an anti-virus immune response in subjects, for example subjects at risk of being exposed to virus. In particular, the invention is directed to a virus vaccine comprising an optimally inactivated virus particle, wherein the virus particle in an appropriate dose is able to seroconvert a subject that is administered the virus vaccine with at least a 70% probability, preferably an 80% probability. Another advantage of the invention is that related methods of producing said vaccines and compositions are very efficient and provide pure compositions largely devoid of impurities, in particular protamine sulphate, allowing for high volume production of vaccines. Examples to the above are provided for Zika virus.

Disclosed herein are downstream processes for purifying Zika virus particles from a crude preparation. The downstream process can be applied to either a virus which has not adapted for propagation on a particular cell substrate or for a partially/fully cell substrate adapted Zika virus particle.

Aspects of the invention provide processes for the purification of infectious Zika virus particles comprising the steps of (a) providing a crude harvest (a) comprising virus particles and impurities, wherein the impurities are generated from growing said virus particles on a cell substrate; (b) reducing impurities from the crude harvest (a) by precipitation with an agent comprising a protamine salt, preferably a protamine sulphate, to obtain a virus preparation (b); and further purifying the virus preparation (b) by an optimized sucrose density gradient centrifugation to obtain a virus preparation (c) comprising the infectious virus particles.

In some embodiments, the concentration of protamine sulphate in step (b) is about 1 to 10 mg/ml, more preferably about 1 to 5 mg/ml, more preferably about 1 to 2 mg/ml. In one embodiment, the concentration of protamine sulphate in step (b) is about 2 mg/mL. In one embodiment, the concentration of protamine sulphate is 1.2 to 1.8 mg/ml, more preferably 1.4 to 1.6 mg/ml. In a preferred embodiment, the concentration of protamine sulphate in step (b) is about 2 mg/ml.

In some embodiments, the residual host cell DNA of the virus preparation (c) is less than 1 µg/mL, especially less than 900, 800, 700, 600, 500, 400, 300 or 200 ng/mL, preferably less than 100 ng/mL.

In a preferred embodiment, the residual host cell DNA of the virus preparation (c) is less than 10 ng/mL. In some embodiments, the residual host cell protein of the final virus preparation (c) is less than 10 µg/mL, especially less than 9, 8, 7, 6, 5, 4, 3 or 2 µg/mL, preferably less than 1 µg/mL. In a preferred embodiment, the residual host cell protein of the virus preparation (c) is less than 100 ng/mL. In some embodiments, the residual non-infectious virus particles of the final virus preparation (c) is less than 10 µg/mL, especially less than 9, 8, 7, 6, 5, 4, 3 or 2 µg/mL, preferably less than 1 µg/mL. In a preferred embodiment, the content of residual non-infectious virus particles of the virus preparation (c) is less than 100 ng/mL.

In some embodiments, the residual protamine is less than 1 µg/mL, especially less than 900, 800, 700, 600, 500, 400, 300 or 200 ng/mL, preferably less than 100 ng/mL, more preferably is below the detection limit of HPLC, in particular below the detection limit in the final drug substance. In some embodiments, the PS content is tested by HPLC or size exclusion chromatography (SEC). For example, HPLC is validated for PS determination in JEV sucrose gradient pool samples as a routine release assay and is very sensitive (i.e., LOQ 3 µg/mL; LOD 1 µg/mL). In the current invention, PS content in in Zika virus DS samples was <LOD. In one embodiment, the HPLC assessment of PS content can be performed on a Superdex Peptide 10/300GL column (GE: 17-5176-01) using 30% Acetonitrile, 0.1% Trifluoroacetic acid as solvent with a flow rate of 0.6 ml/min at 25° C. and detection at 214 nm. A more sensitive method of measurement for residual protamine in a purified virus preparation is mass spectrometry (MS). In some embodiments, the residual PS levels in a Zika virus preparation are tested by MS or other such highly sensitive method, e.g. nuclear magnetic resonance (NMR). With this method, residual PS, as well as fragments and/or break-down products of PS, can be detected at trace amounts, such as levels as low as, for example, $10^6$, $10^7$ or $10^8$ molecules per typical sample load. In some embodiments, the PS levels are tested in the sucrose gradient pool. In some embodiments, the PS levels are tested in the drug product. In some embodiments, the PS levels are tested in the drug substance.

In some embodiments, the crude harvest (a) comprising the virus particles and impurities is subjected to one or more pre-purification step(s) prior to step (b). In some embodiments, the one or more pre-purification step(s) comprises digesting host cell genomic DNA in the crude harvest (a) comprising the virus particles and impurities by enzymatic treatment. In some embodiments, the one or more pre-purification step(s) comprises filtration, ultrafiltration, concentration, buffer exchange and/or diafiltration. In some embodiments, the one or more pre-purification steps is filtration using a filter having a pore size equal to or less than 1 µm. In some embodiments, the filter has a pore size equal to or less than 0.2 µm. In a preferred embodiment, the filter has a pore size of 0.2 µm. In some embodiments, the concentration and/or ultra/diafiltration and/or buffer exchange is performed by tangential flow filtration (TFF). In some embodiments, ultra/diafiltration of the crude harvest (a) comprising the virus particles and impurities is performed using a hollow fiber membrane having a cut-off of equal to or less than 300 kDa. In a preferred embodiment, the hollow fiber membrane has a cut-off of about 100 kDa.

The process according to the current invention may also comprise the use of a sucrose gradient, preferably an optimized sucrose gradient. The sucrose gradient is preferably optimized for the removal of protamine sulfate, also for the removal of immature viral particles or other viral particles which are non-infectious or host cell proteins or nucleic acids (DNA, RNA, mRNA, etc) or other host cell debris. In the current invention the optimized sucrose gradient comprises at least two, at least three, at least four layers of sucrose solutions with different densities. In one embodiment, the virus preparation to be purified is provided in a sucrose solution which has a density of about 8%, about 9%, about 10%, about 11%, about 12% sucrose (w/w), preferably about 10%. In one embodiment, one sucrose solution in the gradient has a density of about 45%, about 46%, about 47%, about 48%, about 49%, about 50%, about 51%, about 52%, about 53%, about 54%, about 55% sucrose (w/w), preferably about 50%. In one embodiment, one sucrose solution in the gradient has a density of about 30%, about 31%, about 32%, about 33%, about 34%, about 35%, about 36%, about 37%, about 38%, about 39%, about 40% sucrose (w/w), preferably about 35%. In one embodiment, one sucrose solution in the gradient has a density of about 10%, about 11%, about 12%, about 13%, about 14%, about 15%, about 16%, about 17%, about 18%, about 19%, about 20% sucrose (w/w), preferably about 15% sucrose. In a preferred embodiment, the sucrose gradient comprises three layers of sucrose solutions of about 50%, about 35% and about 15% (w/w) sucrose and the virus composition to be purified is contained in about 10% (w/w) sucrose. Because the invention provided for means to not only test for host cell DNA but also immature viral particles, the skilled person in the art is able to more precisely optimize the sucrose gradient for most efficient purification and include additional tools such as PRNT assay to monitor purification success.

In some embodiments, the virus particle is a live virus, a chimeric virus, an attenuated live virus, a modified live virus, or a recombinant live virus. In a further step, the virus particles of the invention may be optionally inactivated. In some embodiments, the virus particle is an attenuated form of the virus particle. For example, the virus may have reduced infectivity, virulence, and/or replication in a host, as compared to a wild-type virus. In some embodiments, the virus is a mutated or modified virus, for example the nucleic acid of the virus may contain at least one mutation relative to the wild-type virus. In some embodiments, the virus is a recombinant live virus, meaning a virus that is generated recombinantly and may contain nucleic acid from different sources.

In some embodiments, the Zika virus particle is a live virus, an attenuated live virus, a modified live virus, or a recombinant live virus. In preferred embodiments, the Zika virus is a Zika virus from the Asian lineage.

In some embodiments, the relative reduction of impurity of the final virus preparation relative to the liquid medium (a) comprising the virus particles and impurities is in a range from 60 to 95%. In some embodiments, the residual impurity of the final virus preparation is less than 1%.

In some embodiments, the Zika virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line. In some embodiments, said cell line is a duck cell line. In some embodiments, said cell line is a diploid avian cell line. In some embodiments, said cell line is an EB66 cell line. In a preferred embodiment, said cell line is a Vero cell line.

Aspects of the invention provide a use of any of the processes described herein for manufacturing a composition for immunization against a viral infection. In a preferred embodiment, the composition or vaccine is directed against Zika virus such as e.g. a Zika virus of the Asian lineage.

Other aspects provide compositions comprising the Zika virus particles obtainable by any of the processes described herein for treating and/or preventing (i.e. protecting from) a viral infection. In a preferred embodiment, the viral infection is caused by Zika virus such as e.g. a Zika virus of the Asian lineage.

Furthermore, disclosed herein are Zika virus vaccines and compositions comprising an inactivated Zika virus, and related methods of producing said vaccines and compositions. Also provided are methods of administering the Zika virus vaccines for the prevention of Zika virus infection and/or for the production of an anti-Zika virus immune response in subjects, for example subjects at risk of being exposed to Zika virus.

Zika virus is a flavivirus closely related to Dengue virus and is similarly transmitted by the *Aedes* species mosquito, although other arthropod vectors for Zika virus are possible. Since it was first isolated from a Rhesus monkey in the Zika forest of Uganda in 1947, there were very few reported incidents of human infection, especially outside of the endemic regions of Africa and Asia until a large outbreak in French Polynesia in 2007 (Haddow et al. *PLoS Neglected Tropical Diseases* (2012) 6(2), Malone et al. *PLoS Neglected Tropical Diseases* (2016) 10(3),). The virus has since spread through islands of the Pacific, including Oceania, and into South and Central America (WHO "Zika Situation Report" Feb. 5, 2016).

In addition to being spread by the bite of an infected mosquito, evidence also suggests transmission may occur between individuals, such as from the blood of an infected individual, in utero/transplacental transmission from an infected mother to the fetus, sexual transmission between sexual partners, and possibly by other local transmission routes. There is a possible association between Zika virus infection during pregnancy and microcephaly in the fetus/neonate. Microcephaly is a rare condition in which a baby's head circumference is significantly less than expected based on the average for their age, sex, and ethnicity. This is a result of the brain failing to undergo proper embryonic development, and in 90% of cases is associated with mental retardation (Rocha et al. (2016) *Bull World Health Organ* 8 Feb. 2016).

There is a probable association between individuals having had a prior Zika virus infection and the incidence of Guillain-Barré syndrome, a neurological disorder in which the individual's immune system destroys the myelin sheath surrounding axons of the peripheral nervous system (WHO "Zika Situation Report" Feb. 5, 2016).

No specific treatments or vaccines for Zika virus currently exist, and the only measures at this time to prevent infection are through vector control and avoiding travel to regions experiencing outbreaks.

Described herein are Zika virus vaccines and compositions comprising inactivated Zika virus that provide a safe method for generating an immune response to Zika virus, including virus-neutralizing antibodies, that may help prevent against Zika virus infection.

Any strain of Zika virus may be used in the methods and compositions described herein. In some embodiments, the Zika virus is an isolate from an infected subject during a Zika virus outbreak. In some embodiments, the Zika virus is a strain isolated from Africa or from the African virus lineage. In some embodiments, the Zika virus is a strain isolated from Asia or from the Asian lineage (includes also strains from French Polynesia). In some embodiments, the Zika virus is a strain isolated from the Americas (South America, Central America, or North America), such as a Suriname Zika virus strain. In some embodiments, the Zika virus has an RNA genome corresponding (but not limited) to the DNA sequence provided by GenBank Accession No. AY632535.2, KU321639.1, KU497555.1, KU501215.1, KU509998.1, KU527068.1, KU681081.3, KU681082.3, KU707826.1, KU744693.1, or LC002520.1 or RNA genome disclosed partially or fully herein (SEQ ID NO: 2 to 69).

In some embodiments, the process of the invention results in an enrichment of infectious Zika virus particles from the crude harvest comprising infectious Zika virus particles and non-infectious virus particles and other virus products such that the enrichment of the infectious virus particles is at least 50%, at least 60%, at least 70%, at least 80%, at least 90%, at least 95%, preferably at least 80%, especially at least 85% relative to the total virus particle content of the crude harvest (a) comprising the virus particles and impurities.

In some embodiments, the residual impurity of the final virus preparation with respect to all impurities in the crude harvest is less than 10%, 9%, 8%, 7%, 6%, 5%, 4%, 3%, 2%, 1%, preferably less than 5% as determined by SEC-HPLC (Size Exclusion Chromatography—HPLC).

A unique aspect of the current invention is the realization that know-how related to the vaccine design and purification approach used for the Japanese Encephalitis Vaccine (JEV) IXIARO® (see Srivastava A. K. et al., 2001, Vaccine 19, 4557-4565, WO99/11762) may be employed and improved upon in order to expedite the development of a Zika virus vaccine and provide it to the subjects in need as soon as possible. The industrial process as disclosed for IXIARO®, providing a very effective vaccine against JEV, was complemented by further significant improvements disclosed herein in order to provide a more efficient (higher yield) and safer (less or no protamine sulphate with its allergic potential) Zika vaccine compared to the available JEV vaccine. A particular innovation of the herein disclosed vaccines is their greatly reduced protamine salt (SEQ ID NO: 1) content in the final drug substance facilitated by the development of an improved sucrose gradient. Said sucrose gradient not only allowed the separation of protamine sulphate but also allowed for a very effective inactivation by formaldehyde and resulted in the case of Zika with over 90% yield with the improved process disclosed herein vs about 35% yield with the published JEV process, see experimental part for comparison).

Aspects of the disclosure relate to methods of producing a virus in Vero tissue culture cells. Vero cells are a commonly used tissue culture cell line derived from the kidney of an African green monkey. The Vero cells used in the methods described herein are the Vero (WHO) cell line, obtained from the Health Protection Agency general cell collection under catalogue number 88020401.

Vero cells can be grown to confluent monolayers, for example in tissue culture flasks; in suspension (on microcarriers), for example in roller bottles; or in any other cell culture system for viral production. In some embodiments, the Vero cells are grown in a bioreactor for viral production. For plaque assays or the plaque reduction neutralization test (PRNT), Vero cells are grown in monolayers in tissue culture flasks, dishes, or wells of a plate. To infect the Vero cells with the virus, the culture medium is inoculated with virus and the cells are incubated with the virus for a period of time. The cells may be washed after inoculation to remove any virus that did not adsorb to the cells in a given amount of time.

The methods provided herein involve passaging the virus in Vero cells. As used herein, the terms "passage" or "passaging" refer to infecting a population of Vero cells with virus and subsequently inoculating a second population of Vero cells with virus produced by infection of the first Vero cell population. In some embodiments, a portion of the culture medium from the infected Vero cells (containing virus that was released from the infected cells) is used to inoculate a second population of Vero cells. This is referred to as one passage or one round of passaging. The passaging may be performed serially, for example, a portion of the culture medium from the infected second population of Vero cells is used to inoculate a third population of Vero cells, and so on. In some embodiments, virus obtained from a single plaque is used to inoculate another population of cells.

In some embodiments, the virus is passaged in Vero cells several times, such as at least 4, 5, 6, 7, 8, 9, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 times. In some embodiments, the virus is passaged in Vero cells at least 4 times or 5 times. In some embodiments, the virus is passaged in Vero cells at least 30 times. It is important that the virus population, i.e. the virus sequences, stays as much as possible constant over said passaging. If adaption of the virus occurs (i.e. appearance of mutated viruses in the original virus population), it is preferred that said passages are not used in the context of manufacturing of said virus, e.g. for Zika it was found that up to passage 3 and culturing to day 7 can be used without major shifts in virus population, i.e. introduction of virus population with mutations. However this observation needs to be done for each virus strain and may be different.

In some embodiments, the Vero cells are incubated for at least 2 days after inoculation with the virus at e.g. a typical 0.01 MOI (multiplicity of infection) to allow for viral production prior to passaging. In some embodiments, the Vero cells are incubated for at least 3, 4, 5, 6, 7, 8, 9, 10 or more than 10 days e.g. at least 7 days after inoculation with the virus prior to passaging. The number of days the Vero cells are incubated after viral inoculation may depend on factors such as the multiplicity of infection used to inoculate the cells and the viral titer desired in the culture medium. Serial passaging of the virus in Vero cells may result in generation of a Vero cell adapted virus strain.

The culture medium from the infected Vero cells may be harvested (collected) to obtain the virus. In some embodiments, the culture medium is harvested from infected Vero cells and is replaced with fresh culture medium, which is then harvested after another period of time. In some embodiments, the culture medium harvested from infected Vero cells is pooled from independent Vero cell cultures and/or from independent days. Harvesting can be repeated up to 4 times by 7 or 9 days post infection, for example, and result in a high yield of virus per unit cell culture. In order to minimize the adaption of Zika virus strain to Vero cells, it was found that Vero cells could be incubated for at least 7 days, more preferably 5 days, prior to passaging and subsequently supernatants could be harvested at days 2, 3, 5 and 7 or 2, 3, and 5 (see also experimental part). The harvested culture medium can be stored at +4° C. prior to purification of the virus from the culture medium up to 2 weeks.

In some embodiments, debris from infected and lysed Vero cells may be removed from the harvested culture medium, referred to as a "clarification" of the culture medium. The harvested culture medium may be clarified by common methods known in the art, such as low-speed centrifugation, for example, at 1500 g for 10 min, and/or by filtration through a filter of pore size of 0.45 μm. The harvested culture medium can be stored at +4° C. prior to concentration.

To concentrate the titer of the Zika virus in the harvested culture medium, it may be subjected to concentration by any method known in the art. For example, the harvested culture medium may be concentrated by methods including, without limitation, ultrafiltration, ultracentrifugation, centrifugal concentrator, vacuum centrifugation, and lyophilization. In some embodiments, the harvested culture medium is concentrated by ultrafiltration and the retentate containing the Zika virus is collected. In some embodiments, the harvested culture medium is concentrated by precipitation in which polyethylene glycol (PEG) 8000 is dissolved in the culture medium (up to 10%) and the precipitate is dissolved in a buffer, for example phosphate-buffered saline (PBS, pH 7.0).

The harvested culture medium may be precipitated to produce a virus supernatant. In some embodiments, the harvested culture medium is precipitated to remove Vero cell DNA and other undesired material, such as Vero cell debris, from the harvested culture medium. In some embodiments, the harvested culture medium is concentrated prior to precipitation. In some embodiments, the harvested culture medium is precipitated by adding protamine sulfate (e.g. SEQ ID NO: 1) to the harvested culture medium and incubating the mixture, for example at +4° C. or on ice. In some embodiments, the harvested culture medium is treated with benzonase to remove Vero cell DNA and other undesired material, such as Vero cell debris, from the harvested culture medium. However, it was found that the treatment with protamine sulfate is preferred (see experimental part). In some embodiments, the precipitated culture medium is centrifuged to collect precipitated material and the supernatant containing the virus, referred to as a "virus supernatant", is collected.

The virus supernatant may be further purified after precipitation, for example density gradient ultracentrifugation. In some embodiments, the virus supernatant is further purified by sucrose gradient. Fractions may be collected from the sucrose gradients and assayed for presence of the virus. Methods for assaying for virus positive fractions include plaque assay, hemagglutination assay, polyacrylamide gel electrophoresis, and antigen assays such as Western blotting and ELISA. The fractions containing virus may be pooled based on titer of the virus and level of other impurities. The level or amount of impurities present in the virus supernatant can be estimated by testing for Vero cell DNA, virus aggregates and/or Vero cell protein (see experimental part). A particular embodiment of the invention is the improved sucrose gradient that allows for an efficient protamine separation as shown in the experimental part. It was surprisingly found that the addition of a virus-containing fraction with 10% (w/w) sucrose to a simple three layer sucrose density gradient (e.g. a gradient comprising a 15% (w/w) sucrose solution, a 35% (w/w) sucrose solution, and a 50% (w/w) sucrose solution) resulted in efficient separation of protamine sulphate without much loss of virus. Thus a particularly preferred embodiment of the invention is the use of a sucrose density gradient that is able to efficiently separate protamine sulphate, wherein said sucrose density gradient is used in the purification of virus such as the viruses described herein, i.e. a Zika virus.

To achieve a safe vaccine or composition for the administration to subjects, the virus supernatant may be inactivated (see experimental part for Zika virus). As used herein, the terms "inactivated" and "optimally inactivated" may be used interchangeably and refer to a process (or its result) by which the virus is rendered unable to infect a host cell (non-infectious), but that does not affect or substantially affect the antigenicity of the virus, for example, the immunogenic antigens exposed on the surface of the virus are able to stimulate an immune response in a subject (e.g., antigen-specific antibodies). By "does not affect or substantially affect the antigenicity of the virus" is meant that the inactivated virus retains at least 50%, at least 55%, at least 60%, at least 65%, at least 70%, at least 75%, at least 80%, at least 85%, at least 90%, at least 95%, at least 96%, at least 97%, at least 98%, at least 99%, or even essentially 100% of the antigenicity of a virus that is not subjected to inactivation.

A variety of methods are known in the art for inactivating viruses. In some embodiments, the virus is inactivated by chemical inactivation, thermal inactivation, pH inactivation, or UV inactivation.

In some embodiments, the inactivating is by chemical inactivation and involves contacting the virus with one or more chemical inactivation agents for a period of time under conditions such that the virus is inactivated but the antigenic epitopes are substantially intact. In some embodiments, the virus is inactivated for a period of time that is longer than is required to completely inactivate the virus. In some embodiments, the virus supernatant is inactivated for the number of days required to inactivate the virus plus at least one additional day. Samples of the virus supernatant may be taken at one or more times throughout the inactivation process and assessed for viral viability (infectivity) by any method known in the art, such as by infecting a monolayer of host cells (i.e., plaque assay). Using such a procedure, the period of time that is required to completely inactivate the virus can be determined, and a longer period of time is selected to ensure complete inactivation.

In some embodiments, the virus is contacted with a chemical inactivation agent for between 1 day and days, between 2 days and 40 days, between 2 days and 30 days, between 2 days and 20 days, between 2 days and 10 days, between 3 days and 9 days, between 4 days and 8 days, between 5 days and 7 days, between 2 days and 5 days, or between 5 and 10 days. In some embodiments, the virus is contacted with one or more chemical inactivation agents for at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, or at least 50 days.

In some embodiments, the chemical inactivation is performed at about +5° C., +10° C., +15° C., +20° C., +25° C., +30° C., +35° C., +40° C., or about +45° C. In some embodiments, the chemical inactivation is performed at about +4° C. In some embodiments, the chemical inactivation is performed at about +22° C.

Any chemical inactivation agent known in the art may be suitable for inactivating the virus in the methods described herein. It will be appreciated by one of skill in the art that factors such as the chemical inactivation agent and the temperature at which inactivation is performed may affect the length of time (number of days) required to completely inactivate the virus. Examples of chemical inactivation agents include, without limitation, formaldehyde, enzymes, β-propiolactone, ethanol, trifluroacetic acid, acetonitrile, bleach, urea, guanidine hydrochloride, tri-n-butyl phosphate, ethylene-imine or a derivatives thereof, and organic solvents such as Tween, Triton, sodium deoxycholate, and sulphobetaine. A preferred inactivation is inactivation with formaldehyde at 22° C.+/−2° C. for about 10 days.

In some embodiments, the inactivating agent is neutralized after chemical inactivation of the virus. In some embodiments, the inactivating agent is formaldehyde and is neutralized after chemical inactivation using sodium thiosulphate or sodium metabisulfite.

In some embodiments, the virus is inactivated by thermal inactivation. In some embodiments, the thermal inactivation involves exposing the virus to heat, such as dry heat or vapor heat, for a period of time. In some embodiments, the thermal inactivation involves exposing the virus to temperatures of about +40° C., +45° C., +50° C., +55° C., +60° C., +65° C., +70° C., +75° C., +80° C., +85° C., +90° C., +95° C., or about +100° C. In some embodiments, the virus is exposed to heat for at least 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, about 96 hours, or longer. A preferred thermal inactivation involves exposing the virus to temperatures of about +56° C. for 60 minutes.

In some embodiments, the virus is inactivated by exposing the virus to acidic or alkaline conditions for a period of time such that the virus is completely inactivated. The pH of a virus preparation may be adjusted to a desired pH, for example by the addition of an acid, a base, or a buffer with a particular pH to the virus preparation. In some embodiments, the virus is inactivated at an acidic pH of about 2, 2.5, 3, 3.5, 4, 4.5, 5 or about 5.5. In other embodiments, the virus is inactivated at an alkaline pH of about 8, 8.5, 9, 9.5, 10, or about 10.5.

In some embodiments, the virus is inactivated using UV inactivation. UV inactivation involves exposing the virus to energy-rich radiation, such as UV-A, UV-B, or UV-C light for a period of time. It will be appreciated that any two or more methods of inactivation may be combined and performed concurrently or serially.

The inactivated virus may be subsequently dialyzed to remove any undesired material, including the inactivating agent and any neutralizing agent, and/or to replace the buffer with a buffer that is pharmaceutically acceptable for administration to subjects. In some embodiments, the inactivated virus is dialyzed with PBS. In addition or alternatively, the inactivated virus may be filtered, such as sterile filtered, through a 0.22 μm filter.

Any of the methods or uses described herein may be for the prevention of a Zika virus infection in a subject. As used herein, the terms "prevent," "preventing" and "protection from" include the administration of a virus vaccine or composition to a subject to reduce, or delay the onset of the manifestation of clinical or subclinical symptoms, complications, pathologies or biochemical indicia of a disease or infection, or to reduce or inhibit the spread/transmission of the Zika virus. As used herein, antigen(s), such as an inactivated Zika virus, that is administered to a subject prophylactically (e.g., prior to infection) may be referred to as a vaccine.

Zika Vaccine

As described herein Zika virus may cause any of a variety of symptoms upon infection of a subject, and is generally characterized by mild fever; rash (exanthema) on face, neck, trunk, upper arms; headache; sensitivity to light; non-inflammatory joint pain; conjunctivitis; lack of appetite; diarrhea; abdominal pain; and/or dizziness. Zika virus infection during pregnancy is associated with microcephaly in the fetus/neonate. There is also a probable association between the onset of Guillain-Barré syndrome or symptoms thereof. Diagnosis of Zika virus infection in subjects exposed to Zika virus or suspected of being exposed to Zika virus involves detecting the presence of virus-specific antibodies and/or molecular testing, such as PCR or real-time PCR detection of Zika virus.

Provided herein are methods for administering a dose of a therapeutically effective amount of a Zika virus vaccine to a subject in need thereof. In some embodiments, the subject is a mammalian subject, such as a human, non-human primate, rodent, rabbit, sheep, dog, cat, horse, or cow. In some embodiments, the subject is a mouse. In some embodiments, the subject is a human subject, such as a child, an adult, or an elderly adult. In some embodiments, the subject is a female subject. In some embodiments, the subject is pregnant or planning on becoming pregnant. In some embodiments, the subject is at risk of being exposed to Zika virus. In some embodiments, the subject is living in or traveling to an area where Zika virus is present or is thought to be present. In some embodiments, the subject has been previously infected with or vaccinated against Dengue virus; i.e., at risk for antibody-dependent enhancement of disease. In some embodiments, the subject is living in or traveling to an area that is experiencing a Zika virus infection outbreak. In some embodiments, the subject is living in or traveling to an area where an arthropod vector capable of transmitting the Zika virus vector is present or is thought to be present.

Any of the Zika virus vaccines or compositions described herein may be administered to a subject in a therapeutically effective amount or a dose of a therapeutically effective amount. As used herein, a "therapeutically effective amount" of vaccine is any amount that results in a desired response or outcome in a subject, such as those described herein, including but not limited to prevention of infection, an immune response or an enhanced immune response to Zika virus, or prevention or reduction of symptoms associated with Zika disease.

In some embodiments, the therapeutically effective amount of a Zika virus vaccine or composition described herein is an amount sufficient to generate antigen-specific antibodies (e.g., anti-Zika virus antibodies). In some embodiments, the therapeutically effective amount is sufficient to provide seroprotection in a subject; i.e., to generate sufficient antigen-specific antibodies to prevent/protect from infection. In some embodiments, seroprotection is conferred on at least 75%, 80%, 90%, 95%, 96%, 97%, 98%, or at least 99% of vaccinated subjects. In some embodiments, seroprotection is defined by a reduction in the number of Zika virus plaques by 50% or more in a plaque reduction neutralization test (PRNT) by a 1:10 or higher dilution of sera from a vaccinated subject. In some embodiments, an effective amount of the Zika vaccine is sufficient to seroconvert a subject with at least 70% probability. In some embodiments, the therapeutically effective amount is sufficient to seroconvert a subject with at least 75%, 80%, 85% 90%, 95%, 96%, 97%, 98%, or at least 99% probability. Whether a subject has been seroconverted can be assessed by any method known in the art, such as obtaining a serum sample from the subject and performing an assay to detect anti-Zika virus antibodies. In some embodiments, a subject is seroconverted if a serum sample from the subject contains an amount of anti-Zika virus antibodies that surpasses a threshold or predetermined baseline. A subject is generally considered seroconverted if there is at least a 4-fold increase in anti-Zika virus antibodies (i.e., anti-Zika E protein IgG antibodies) in a serum sample from the subject as compared to a serum sample previously taken from the same subject.

In some embodiments, seroconversion of a subject is assessed by performing a plaque reduction neutralization test (PRNT). Briefly, PRNT is used to determine the serum titer required to reduce the number of Zika virus plaques by 50% (PRNT50) as compared to a control serum/antibody. The PRNT50 may be carried out using monolayers of Vero cells or any other cell type/line that can be infected with Zika virus. Sera from subjects are diluted and incubated with live, non-inactivated Zika virus. The serum/virus mixture may be applied to the Vero cells and incubated for a period of time. Plaques formed on the Vero cell monolayers are counted and compared to the number of plaques formed by the Zika virus in the absence of serum or a control antibody. A threshold of neutralizing antibodies of 1:10 dilution of serum in a PRNT50 is generally accepted as evidence of protection (Hombach et. al. Vaccine (2005) 23:5205-5211).

In some embodiments, the Zika virus may be formulated for administration in a composition, such as a pharmaceutical composition. The term "pharmaceutical composition" as used herein means a product that results from the mixing or combining of at least one active ingredient, such as an inactivated Zika virus, and one or more inactive ingredients, which may include one or more pharmaceutically acceptable excipient.

Pharmaceutical compositions of the invention, including vaccines, can be prepared in accordance with methods well known and routinely practiced in the art (see e.g., Remington: The Science and Practice of Pharmacy, Mack Publishing Co. 20th ed. 2000; and Ingredients of Vaccines—Fact Sheet from the Centers for Disease Control and Prevention, e.g., adjuvants and enhancers such as alum to help the vaccine improve its work, preservatives and stabilizers to help the vaccine remain unchanged (e.g., albumin, phenols, glycine)). Pharmaceutical compositions are preferably manufactured under GMP conditions. Typically a therapeutically effective dose of the inactivated Zika virus preparation is employed in the pharmaceutical composition of the invention. The inactivated Zika virus is formulated into pharmaceutically acceptable dosage forms by conventional methods known to those of skill in the art. Dosage regimens are adjusted to provide the optimum desired response (e.g., the prophylactic response).

Dosages of the active ingredients in the pharmaceutical compositions of the present invention can be varied so as to obtain an amount of the active ingredient which is effective to achieve the desired pharmaceutical response for a particular subject, composition, and mode of administration, without being toxic to the subject. The selected dosage level depends upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the inactivated Zika virus vaccine employed in the pharmaceutical composition at levels lower than that required to achieve the desired therapeutic effect and gradually increase the dosage until the desired effect (e.g., production of anti-Zika virus antibodies) is achieved. In general, effective doses of the compositions of the present invention, for the prophylactic treatment of groups of people as described herein vary depending upon many different factors, including means of administration, target site, physiological state of the patient, whether the patient is human or an animal, other medications administered, and the titer of anti-Zika virus antibodies desired. Dosages need to be titrated to optimize safety and efficacy. In some embodiments, the dosing regimen entails subcutaneous or intramuscular administration of a dose of inactivated Zika virus twice, once at day 0 and once at about day 7. In some embodiments, the dosing regimen entails subcutaneous administration of a dose of inactivated Zika virus twice, once at day 0 and once at about day 14. In some embodiments, the dosing regimen entails subcutaneous administration of a dose of inactivated Zika virus twice, once at day 0 and once at about day 28. In some embodiments, the inactivated Zika virus is administered to the subject once.

Any of the Zika virus vaccines or compositions described herein may be administered to a subject with, prior to, or after administration of one or more adjuvants. An adjuvant is a molecule that enhances a response in a subject, such as an immune response, to an antigen or other molecule. In some embodiments, an adjuvant may stabilize an antigen or other molecule. Determining whether a Zika virus vaccine or compositions thereof are administered with an adjuvant depends on various factors (e.g., type and extent of response desired) and will be evident to one of skill in the art. In some embodiments, administering any of the Zika virus vaccines or compositions described herein with, prior to, or after administration of an adjuvant may enhance the production of virus neutralizing (anti-Zika virus) antibodies. In some embodiments, a subject that is administered any of the Zika virus vaccines or compositions described herein with, prior to, or after administration of an adjuvant may only require a single administration of the Zika virus vaccine or composition to be seroconverted (produce a level of anti-Zika virus antibodies). Examples of adjuvants may include, without limitation, aluminium salt (aluminium hydroxide or aluminium phosphate), calcium phosphate hydroxide, paraffin oil, killed bacteria, bacterial toxins, toxoids, subunits of bacteria, squalene, thimerosal, detergents, IL-1, IL-2, IL-12, 2-component adjuvants, such as 2-component adjuvants containing an antibacterial peptide and a TLR9 agonist (e.g., IC31®), and combinations such as Freund's complete adjuvant and Freund's incomplete adjuvant. In some embodiments, the Zika virus vaccines or compositions is administered with aluminium hydroxide. In some embodiments, the inactivated Zika virus vaccine or composition is administered with aluminium phosphate salt. A preferred aluminium salt is the aluminium hydroxide with reduced Cu content, e.g. lower than 1.25 ppb based on the weight of the Zika composition, an adjuvant described in detail in WO 2013/083726 or Schlegl et al., Vaccine 33 (2015) 5989-5996.

In some embodiments, the adjuvant is comprised of two components. In some embodiments, the 2-component adjuvant comprises an antibacterial peptide and a TLR9 agonist. In some embodiments, the antibacterial peptide is provided by the amino acid sequence KLKL$_5$KLK (SEQ ID NO: 71). In some embodiments, the TLR9 agonist is a deoxyinosine-containing immunostimulatory oligodeoxynucleic acid molecule (I-ODN). In some embodiments, the I-ODN comprises the nucleic acid sequence (dIdC)$_{13}$ (SEQ ID NO: 70). In some embodiments, the adjuvant is IC31®. In some embodiments, the adjuvant is in nanoparticle form (See, e.g., U.S. Pat. No. 8,765,148 B2, incorporated by reference in its entirety). In some embodiments, the adjuvant is IC31®, i.e. KLKL$_5$KLK (SEQ ID NO: 71) and the nucleic acid sequence (dIdC)$_{13}$ (SEQ ID NO: 70), in combination with an aluminium salt such as aluminium hydroxide.

The Zika virus vaccines or compositions described herein may be administered to a subject concomitantly with one or more vaccines to another infectious agent, such as another infectious agent is that present or thought to be present in the same geographic area as Zika virus. In some embodiments, the other infectious agent is one that the subject is also at risk of being in contact with. In some embodiments, the other infectious agent is transmitted by the same arthropod vector as Zika virus. In some embodiments, the other infectious agent is Japanese Encephalitis virus, Yellow Fever virus, Dengue virus and/or Chikungunya virus.

Also within the scope of the present disclosure are kits for use in prophylactically administering to a subject, for example to prevent or reduce the severity of Zika virus infection. Such kits can include one or more containers comprising a composition containing inactivated Zika virus, such as an inactivated Zika virus vaccine. In some embodiments, the kit may further include one or more additional containing comprising a second composition, such as a second vaccine. In some embodiments, the second vaccine is a vaccine for another arbovirus. In some embodiments, the second vaccine is a Dengue virus vaccine and/or a Chikungunya virus vaccine.

In some embodiments, the kit can comprise instructions for use in accordance with any of the methods described herein. The included instructions can comprise a description of administration of the composition containing inactivated Zika virus to prevent, delay the onset, or reduce the severity of Zika virus infection. The kit may further comprise a description of selecting a subject suitable for administration based on identifying whether that subject is at risk for exposure to Zika virus or contracting a Zika virus infection. In still other embodiments, the instructions comprise a description of administering a composition containing inactivated Zika virus to a subject at risk of exposure to Zika virus or contracting Zika virus infection.

The instructions relating to the use of the composition containing inactivated Zika virus generally include information as to the dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine readable instructions are also acceptable.

The kits of the present disclosure are in suitable packaging. Suitable packaging includes, but is not limited to, vials, bottles, jars, flexible packaging, and the like. Also contemplated are packages for use in combination with a specific device, such as a syringe or an infusion device. The container may have a sterile access port, for example the container may be a vial having a stopper pierceable by a hypodermic injection needle. At least one active agent in the composition is an inactivated Zika virus, as described herein.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having, ", "containing", "involving", and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

TABLE 1

Overview of process buffers and stock solutions.

| Buffer | Composition | Final pH | Final conductivity [mS/cm] |
|---|---|---|---|
| A | 0.5M NaOH | | n.a. |
| B | 0.1M NaOH | | n.a. |
| C | 25 mM Tris, 150 mM NaCl | 7.4 ± 0.2 | 16.5 |
| D | 1M Tris | 7.4 ± 0.2 | n.a. |
| E | 4.5M NaCl | n.a. | n.a. |
| F | 1M NaCl | n.a. | n.a. |
| G | 1% SDS | n.a. | n.a. |
| H | 50% (w/w) Sucrose in 25 mM Tris, 150 mM NaCl | 7.4 ± 0.2 | n.a. |
| I | 35% (w/w) Sucrose in 25 mM Tris, 150 mM NaCl | 7.4 ± 0.2 | n.a. |
| J | 15% (w/w) Sucrose in 25 mM Tris, 150 mM NaCl | 7.4 ± 0.2 | n.a. |

TABLE 1-continued

Overview of process buffers and stock solutions.

| Buffer | Composition | Final pH | Final conductivity [mS/cm] |
|---|---|---|---|
| K | 10× PBS | 7.4 ± 0.2 | n.a. |
| L | 50 mg/mL Protamine sulphate | 7.4 ± 0.2 | n.a. |
| M | Drug substance formulation buffer (10 mM Tris(hydroxymethyl)-aminomethan, 5% Sucrose, 1% (10 mg/mL) rHSA) | 7.4 ± 0.2 | 1.3 |

TABLE 2

Abbreviations.

| | |
|---|---|
| ° Bx | Degrees Brix = sugar content (w/w) of an aqueous solution* |
| BSA | Bovine serum albumin |
| CC700 | Capto ™ Core 700 |
| CPE | Cytopathic effect |
| EtOH | Ethanol |
| EU | Endotoxin units |
| DS | Drug Substance |
| DP | Drug Product |
| DSP | Downstream Process |
| HCP | Host cell protein |
| hcDNA | Host cell DNA |
| hpi | Hours post infection |
| HPLC | High Performance Liquid Chromatography |
| ID | Inner diameter |
| JEV | Japanese Encephalitis virus |
| LAL | Limulus amebocyte lysate |
| LDS buffer | Lithium dodecyl sulfate sample loading buffer |
| LOD | Limit of detection |
| LOQ | Limit of quantitation |
| MALLS | Multiangle light scattering |
| mAU | Milli absorbance units |
| MS | Mass spectroscopy |
| NIV | Neutralized inactivated virus |
| PBS | Phosphate buffered saline |
| PD | Process development |
| PFU | Plaque forming units |
| p.i. | Post-infection |
| PS | Protamine sulphate or protamine sulfate |
| rcf | Relative centrifugal force |
| rHSA | Recombinant human serum albumin |
| Rms radius | Root mean square radius |
| rMSB | Research master seed bank |
| RSD | Relative standard deviation |
| SEC | Size exclusion chromatography |
| SGC | Sucrose gradient centrifugation |
| SGP | Sucrose gradient purified |
| SDS | Sodium dodecyl sulphate |
| TBS | Tris buffered saline |
| TFF | Tangential flow filtration |
| TCID50 | Tissue culture infectious dose 50% |
| UF/DF | Ultrafiltration/diafiltration |
| WFI | Water for injection |
| ZikaV | Zika virus |

*Degrees Brix (° Bx) is the sugar content of an aqueous solution. One degree Brix is 1 gram of sucrose in 100 grams of solution and represents the strength of the solution as percentage by mass. ° Bx corresponds to the sucrose content in percent (w/w), e.g., 45° Bx equals 45% (w/w) sucrose.

TABLE A

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 1 | 9320_Zika_PF_1F | SEQ ID NO: 74<br>ttaggatccGTTGTTGATCTGTGTGAAT | 69.9 | 74.6 | 707 |
|   | 9321_Zika_PF_1R | SEQ ID NO: 75<br>taactcgagCGTACACAACCCAAGTT | 69.3 | 75.6 |   |
| 2 | 9322_Zika_PF_2F | SEQ ID NO: 76<br>ttaggatccTCACTAGACGTGGGAGTG | 70 | 73.9 | 704 |
|   | 9323_Zika_PF_2R | SEQ ID NO: 77<br>taactcgagAAGCCATGTCYGATATTGAT | 69.8 | 73.7 |   |
| 3 | 9324_Zika_PF_3F | SEQ ID NO: 78<br>ttaggatccGCATACAGCATCAGGTG | 72.3 | 74.5 | 712 |
|   | 9325_Zika_PF_3R | SEQ ID NO: 79<br>taactcgagTGTGGAGTTCCGGTGTCT | 72 | 76.4 |   |
| 4 | 9326_Zika_PF_4F | SEQ ID NO: 80<br>ttaggatccGAATAGAGCGAARGTTGAGATA | 70.9 | 74 | 712 |
|   | 9327_Zika_PF_4R | SEQ ID NO: 81<br>taactcgAGTGGTGGGTGATCTTCTTCT | 70.5 | 73.7 |   |
| 5 | 9328_Zika_PF_5F | SEQ ID NO: 82<br>ttaggatccCAGTCACAGTGGAGGTACAGTAC | 70.3 | 75 | 704 |
|   | 9329_Zika_PF_5R | SEQ ID NO: 83<br>taactcgagCRCAGATACCATCTTCCC | 71.5 | 77.3 |   |
| 6 | 9330_Zika_PF_6F | SEQ ID NO: 84<br>ttaggatCCCTTATGTGCTTGGCCTTAG | 70.7 | 72.7 | 698 |
|   | 9331_Zika_PF_6R | SEQ ID NO: 85<br>taactcgagTCTTCAGCCTCCATGTG | 70.4 | 76.9 |   |
| 7 | 9332_Zika_PF_7F | SEQ ID NO: 86<br>ttaggatccAATGCCCACTCAAACATAGA | 71.9 | 75 | 716 |
|   | 9333_Zika_PF_7R | SEQ ID NO: 87<br>taactcgagTCATTCTCTTCTTCAGCCCTT | 71 | 74 |   |
| 8 | 9334_Zika_PF_8F | SEQ ID NO: 88<br>ttaggatccAAGGGTGATCGAGGAAT | 70.9 | 75.2 | 703 |
|   | 9335_Zika_PF_8R | SEQ ID NO: 89<br>taactcgagTTCCCTTCAGAGAGAGGAGC | 71.9 | 73.4 |   |
| 9 | 9336_Zika_PF_9F | SEQ ID NO: 90<br>ttaggatccTCTTTTGCAAACTGCGATC | 71.9 | 75 | 699 |
|   | 9337_Zika_PF_9R | SEQ ID NO: 91<br>taactcgagTCCAGCTGCAAAGGGTAT | 71 | 74.9 |   |
| 10 | 9338_Zika_PF_10F | SEQ ID NO: 92<br>ttaggatccGTGTGGACATGTACATTGA | 71.4 | 75.8 | 706 |
|   | 9339_Zika_PF_10R | SEQ ID NO: 93<br>taactcgagCCCATTGCCATAAAGTC | 70.4 | 75.8 |   |
| 11 | 9340_Zika_PF_11F | SEQ ID NO: 94<br>ttaggatccTCATACTGTGGTCCATGGA | 71.6 | 78.1 | 692 |
|   | 9341_Zika_PF_11R | SEQ ID NO: 95<br>taactcgagGCCCATCTCAACCCTTG | 74 | 78 |   |
| 12 | 9342_Zika_PF_12F | SEQ ID NO: 96<br>ttaggatccTAGAGGGCTTCCAGTGC | 70.9 | 74 | 707 |
|   | 9343_Zika_PF_12R | SEQ ID NO: 97<br>taactcgAGATACTCATCTCCAGGTTTGTTG | 70.2 | 72.2 |   |
| 13 | 9344_Zika_PF_13F | SEQ ID NO: 98<br>ttaggatccGAAAACAAAACATCAAGAGTG | 70.6 | 75.4 | 726 |
|   | 9345_Zika_PF_13R | SEQ ID NO: 99<br>taactcgagGAATCTCTCTGTCATGTGTCCT | 71.9 | 75.6 |   |
| 14 | 9346_Zika_PF_14F | SEQ ID NO: 100<br>ttaggatccTTGATGGCACGACCAAC | 73.1 | 75.6 | 715 |
|   | 9347_Zika_PF_14R | SEQ ID NO: 101<br>ttaggatccGTTGTTGATCTGTGTGAAT | 70.8 | 77.9 |   |
| 15 | 9348_Zika_PF_15F | SEQ ID NO: 102<br>taactcgagCAGGTCAATGTCCATTG | 71.9 | 75.4 | 719 |
|   | 9349_Zika_PF_15R | SEQ ID NO: 103<br>ttaggatccTGTTGTGTTCCTATTGCTGGT | 73.9 | 77.2 |   |
| 16 | 9350_Zika_PF_16F | SEQ ID NO: 104<br>taactcgaGTGATCAGRGCCCCAGC | 72.3 | 75.4 | 703 |
|   | 9351_Zika_PF_16R | SEQ ID NO: 105<br>ttaggatccTGCTGCCCAGAAGAGAA | 72 | 76.3 |   |
| 17 | 9352_Zika_PF_17F | SEQ ID NO: 106<br>taactcgaGCACCAACAYGGGTTCTT | 73.6 | 76 | 705 |
|   | 9353_Zika_PF_17R | SEQ ID NO: 107<br>ttaggatcCTCAAGGACGGTGTGGC | 72 | 75.5 |   |
| 18 | 9354_Zika_PF_18F | SEQ ID NO: 108<br>taactcgagCAATGATCTTCATGTTGGG | 71.7 | 75.8 | 699 |
|   | 9355_Zika_PF_18R | SEQ ID NO: 109<br>ttaggatccTATGGGGGAGGACTGGT | 71 | 74.1 |   |

TABLE A-continued

Primers for_Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 19 | 9356_Zika_PF_19F | SEQ ID NO: 110 taactcGAGCCCAGAACCTTGGATC | 73.3 | 75.5 | 711 |
|  | 9357_Zika_PF_19R | SEQ ID NO: 111 ttaggatcCAGACCCCCAAGAAGGC | 71.3 | 76.9 |  |
| 20 | 9358_Zika_PF_20F | SEQ ID NO: 112 taactcgagCCCCTTTGGTCTTGTCT | 71.7 | 75 | 706 |
|  | 9359_Zika_PF_20R | SEQ ID NO: 113 ttaggatccAGGAAGGATGTATGCAGATG | 71.9 | 73.9 |  |
| 21 | 9360_Zika_PF_21F | SEQ ID NO: 114 taactcgagACATTTGCGCATATGATTTTG | 70.4 | 75.7 | 709 |
|  | 9361_Zika_PF_21R | SEQ ID NO: 115 ttaggatccAGGAAGGACACACAAGAGT | 71.8 | 75 |  |
| 22 | 9362_Zika_PF_22F | SEQ ID NO: 116 taactcgagACAGGCTGCACAGCTTT | 70 | 79.1 | 581 |
|  | 9363_Zika_PF_22R | SEQ ID NO: 117 ttaggatccTCTCTCATAGGGCACAGAC | 74.8 | 81.1 |  |

SEQUENCES

25

```
A typical form of protamine
                              SEQ ID NO: 1
    PRRRRSSSRP VRRRRRPRVS RRRRRRGGRR RR
```

Provided below are examples of nucleic acid sequences of the genomes of Zika viruses that may be used in the methods, compositions, and/or vaccines described herein.

```
KU321639.1 Zika virus strain ZikaSPH2015, Brazil, complete genome
                                                          SEQ ID NO: 2
GTTGTTACTGTTGCTGACTCAGACTGCGACAGTTCGAGTTTGAAGCGAAAGCTAGCAACAGTATCAACAGGTTTTATTTGG

ATTTGGAAACGAGAGTTTCTGGTCATGAAAAACCCAAAAAAGAAATCCGGAGGATTCCGGATTGTCAATATGCTAAAACG

CGGAGTAGCCCGTGTGAGCCCCTTTGGGGGCTTGAAGAGGCTGCCAGCCGGACTTCTGCTGGGTCATGGGCCCATCAGG

ATGGTCTTGGCAATTCTAGCCTTTTTGAGATTCACGGCAATCAAGCCATCACTGGGTCTCATCAATAGATGGGGTTCAGTG

GGGAAAAAAGAGGCTATGGAAATAATAAAGAAGTTCAAGAAAGATCTGGCTGCCATGCTGAGAATAATCAATGCTAGGA

AGGAGAAGAAGAGACGGGGCGCAGATACTAGTGTCGGAATTGTTGGCCTCCTGCTGACCACAGCTATGGCAGCGGAGG

TCACTAGACGTGGGAGTGCATACTATATGTACTTGGACAGAAACGATGCTGGGGAGGCCATATCTTTTCCAACCACATTG

GGGATGAATAAGTGTTATATACAGATCATGGATCTTGGACACATGTGTGATGCCACCATGAGCTATGAATGCCCTATGCT

GGATGAGGGGGTGGAACCAGATGACGTCGATTGTTGGTGCAACACGACGTCAACTTGGGTTGTGTACGGAACCTGCCAT

CACAAAAAAGGTGAAGCACGGAGATCTAGAAGAGCTGTGACGCTCCCCTCCCATTCCACTAGGAAGCTGCAAACGCGGT

CGCAAACCTGGTTGGAATCAAGAGAATACACAAAGCACTTGATTAGAGTCGAAAATTGGATATTCAGGAACCCTGGCTTC

GCGTTAGCAGCAGCTGCCATCGCTTGGCTTTTGGGAAGCTCAACGAGCCAAAAAGTCATATACTTGGTCATGATACTGCT

GATTGCCCCGGCATACAGCATCAGGTGCATAGGAGTCAGCAATAGGGACTTTGTGGAAGGTATGTCAGGTGGGACTTGG

GTTGATATTGTCTTGGAACATGGAGGTTGTGTCACCGTAATGGCACAGGACAAACCGACTGTCGACATAGAGCTGGTTAC

AACAACAGTCAGCAACATGGCGGAGGTAAGATCCTACTGCTATGAGGCATCAATATCAGACATGGCTTCGGACAGCCGCT

GCCCAACACAAGGTGAAGCCTACCTTGACAAGCAATCAGACACTCAATATGTCTGCAAAAGAACGTTAGTGGACAGAGGC

TGGGGAAATGGATGTGGACTTTTTGGCAAAGGGAGTCTGGTGACATGCGCTAAGTTTGCATGCTCCAAGAAAATGACCG

GGAAGAGCATCCAGCCAGAGAATCTGGAGTACCGGATAATGCTGTCAGTTCATGGCTCCCAGCACAGTGGGATGATCGT

TAATGACACAGGACATGAAACTGATGAGAATAGAGCGAAGGTTGAGATAACGCCCAATTCACCAAGAGCCGAAGCCACC
```

```
CTGGGGGGTTTTGGAAGCCTAGGACTTGATTGTGAACCGAGGACAGGCCTTGACTTTTCAGATTTGTATTACTTGACTATG

AATAACAAGCACTGGTTGGTTCACAAGGAGTGGTTCCACGACATTCCATTACCTTGGCACGCTGGGGCAGACACCGGAAC

TCCACACTGGAACAACAAAGAAGCACTGGTAGAGTTCAAGGACGCACATGCCAAAAGGCAAACTGTCGTGGTTCTAGGG

AGTCAAGAAGGAGCAGTTCACACGGCCCTTGCTGGAGCTCTGGAGGCTGAGATGGATGGTGCAAAGGGAAGGCTGTCCT

CTGGCCACTTGAAATGTCGCCTGAAAATGGATAAACTTAGATTGAAGGGCGTGTCATACTCCTTGTGTACCGCAGCGTTCA

CATTCACCAAGATCCCGGCTGAAACACTGCACGGGACAGTCACAGTGGAGGTACAGTACGCAGGGACAGATGGACCTTG

CAAGGTTCCAGCTCAGATGGCGGTGGACATGCAAACTCTGACCCCAGTTGGGAGGTTGATAACCGCTAACCCCGTAATCA

CTGAAAGCACTGAGAACTCTAAGATGATGCTGGAACTTGATCCACCATTTGGGGACTCTTACATTGTCATAGGAGTCGGG

GAGAAGAAGATCACCCACCACTGGCACAGGAGTGGCAGCACCATTGGAAAAGCATTTGAAGCCACTGTGAGAGGTGCCA

AGAGAATGGCAGTCTTGGGAGACACAGCCTGGGACTTTGGATCAGTTGGAGGCGCTCTCAACTCATTGGGCAAGGGCAT

CCATCAAATTTTTGGAGCAGCTTTCAAATCATTGTTTGGAGGAATGTCCTGGTTCTCACAAATTCTCATTGGAACGTTGCTG

ATGTGGTTGGGTCTGAACACAAAGAATGGATCTATTTCCCTTATGTGCTTGGCCTTAGGGGAGTGTTGATCTTCTTATCC

ACAGCCGTCTCTGCTGATGTGGGGTGCTCGGTGGACTTCTCAAAGAAGGAGACGAGATGCGGTACAGGGGTGTTCGTCT

ATAACGACGTTGAAGCCTGGAGGGACAGGTACAAGTACCATCCTGACTCCCCCCGTAGATTGGCAGCAGCAGTCAAGCA

AGCCTGGGAAGATGGTATCTGCGGGATCTCCTCTGTTTCAAGAATGGAAAACATCATGTGGAGATCAGTAGAAGGGGAG

CTCAACGCAATCCTGGAAGAGAATGGAGTTCAACTGACGGTCGTTGTGGGATCTGTAAAAAACCCCATGTGGAGAGGTC

CACAGAGATTGCCCGTGCCTGTGAACGAGCTGCCCCACGGCTGGAAGGCTTGGGGGAAATCGCACTTCGTCAGAGCAGC

AAAGACAAATAACAGCTTTGTCGTGGATGGTGACACACTGAAGGAATGCCCACTCAAACATAGAGCATGGAACAGCTTTC

TTGTGGAGGATCATGGGTTCGGGGTATTTCACACTAGTGTCTGGCTCAAGGTTAGAGAAGATTATTCATTAGAGTGTGAT

CCAGCCGTTATTGGAACAGCTGTTAAGGGAAAGGAGGCTGTACACAGTGATCTAGGCTACTGGATTGAGAGTGAGAAGA

ATGACACATGGAGGCTGAAGAGGGCCCATCTGATCGAGATGAAAACATGTGAATGGCCAAAGTCCCACACATTGTGGAC

AGATGGAATAGAAGAGAGTGATCTGATCATACCCAAGTCTTTAGCTGGGCCACTCAGCCATCACAATACCAGAGAGGGCT

ACAGGACCCAAATGAAAGGGCCATGGCACAGTGAAGAGCTTGAAATTCGGTTTGAGGAATGCCCAGGCACTAAGGTCCA

CGTGGAGGAAACATGTGGAACAAGAGGACCATCTCTGAGATCAACCACTGCAAGCGGAAGGGTGATCGAGGAATGGTG

CTGCAGGGAGTGCACAATGCCCCCACTGTCGTTCCGGGCTAAAGATGGCTGTTGGTATGGAATGGAGATAAGGCCCAGG

AAAGAACCAGAAAGCAACTTAGTAAGGTCAATGGTGACTGCAGGATCAACTGATCACATGGATCACTTCTCCCTTGGAGT

GCTTGTGATTCTGCTCATGGTGCAGGAAGGGCTGAAGAAGAGAATGACCACAAAGATCATCATAAGCACATCAATGGCA

GTGCTGGTAGCTATGATCCTGGGAGGATTTTCAATGAGTGACCTGGCTAAGCTTGCAATTTTGATGGGTGCCACCTTCGC

GGAAATGAACACTGGAGGAGATGTAGCTCATCGGCGCTGATAGCGGCATTCAAAGTCAGACCAGCGTTGCTGGTATCTT

TCATCTTCAGAGCTAATTGGACACCCCGTGAAAGCATGCTGCTGGCCTTGGCCTCGTGTCTTTTGCAAACTGCGATCTCCG

CCTTGGAAGGCGACCTGATGGTTCTCATCAATGGTTTTGCTTTGGCCTGGTTGGCAATACGAGCGATGGTTGTTCCACGCA

CTGATAACATCACCTTGGCAATCCTGGCTGCTCTGACACCACTGGCCCGGGGCACACTGCTTGTGGCGTGGAGAGCAGGC

CTTGCTACTTGCGGGGGGTTTATGCTCCTCTCTCTGAAGGGAAAAGGCAGTGTGAAGAAGAACTTACCATTTGTCATGGC

CCTGGGACTAACCGCTGTGAGGCTGGTCGACCCCATCAACGTGGTGGGGCTGCTGTTGCTCACAAGGAGTGGGAAGCGG

AGCTGGCCCCCTAGCGAAGTACTCACAGCTGTTGGCCTGATATGCGCATTGGCTGGAGGGTTCGCCAAGGCAGATATAGA

GATGGCTGGGCCCATGGCCGCGGTCGGTCGCTAATTGTCAGTTACGTGGTCTCAGGAAAGAGTGTGGACATGTACATTG

AAAGAGCAGGTGACATCACATGGGAAAAAGATGCGGAAGTCACTGGAAACAGTCCCCGGCTCGATGTGGCGCTAGATG

AGAGTGGTGATTTCTCCCTGGTGGAGGATGACGGTCCCCCCATGAGAGAGATCATACTCAAGGTGGTCCTGATGACCATC

TGTGGCATGAACCCAATAGCCATACCCTTTGCAGCTGGAGCGTGGTACGTATACGTGAAGACTGGAAAAAGGAGTGGTG

CTCTATGGGATGTGCCTGCTCCCAAGGAAGTAAAAAAGGGGGAGACCACAGATGGAGTGTACAGAGTAATGACTCGTAG
```

```
ACTGCTAGGTTCAACACAAGTTGGAGTGGGAGTTATGCAAGAGGGGGTCTTTCACACTATGTGGCACGTCACAAAAGGA
TCCGCGCTGAGAAGCGGTGAAGGGAGACTTGATCCATACTGGGGAGATGTCAAGCAGGATCTGGTGTCATACTGTGGTC
CATGGAAGCTAGATGCCGCCTGGGACGGGCACAGCGAGGTGCAGCTCTTGGCCGTGCCCCCCGGAGAGAGAGCGAGGA
ACATCCAGACTCTGCCCGGAATATTTAAGACAAAGGATGGGGACATTGGAGCGGTTGCGCTGGATTACCCAGCAGGAAC
TTCAGGATCTCCAATCCTAGACAAGTGTGGGAGAGTGATAGGACTTTATGGCAATGGGGTCGTGATCAAAAATGGGAGT
TATGTTAGTGCCATCACCCAAGGGAGGAGGGAGGAAGAGACTCCTGTTGAGTGCTTCGAGCCTTCGATGCTGAAGAAGA
AGCAGCTAACTGTCTTAGACTTGCATCCTGGAGCTGGGAAAACCAGGAGAGTTCTTCCTGAAATAGTCCGTGAAGCCATA
AAAACAAGACTCCGTACTGTGATCTTAGCTCCAACCAGGGTTGTCGCTGCTGAAATGGAGGAAGCCCTTAGAGGGCTTCC
AGTGCGTTATATGACAACAGCAGTCAATGTCACCCACTCTGGAACAGAAATCGTCGACTTAATGTGCCATGCCACCTTCAC
TTCACGTCTACTACAGCCAATCAGAGTCCCCAACTATAATCTGTATATTATGGATGAGGCCCACTTCACAGATCCCTCAAGT
ATAGCAGCAAGAGGATACATTTCAACAAGGGTTGAGATGGGCGAGGCGGCTGCCATCTTCATGACCGCCACGCCACCAG
GAACCCGTGACGCATTTCCGGACTCCAACTCACCAATTATGGACACCGAAGTGGAAGTCCCAGAGAGAGCCTGGAGCTCA
GGCTTTGATTGGGTGACGGATTATTCTGGAAAAACAGTTTGGTTTGTTCCAAGCGTGAGGAACGGCAATGAGATCGCAGC
TTGTCTGACAAAGGCTGGAAAACGGGTCATACAGCTCAGCAGAAAGACTTTTGAGACAGAGTTCCAGAAAACAAAACATC
AAGAGTGGGACTTTGTCGTGACAACTGACATTTCAGAGATGGGCGCCAACTTTAAAGCTGACCGTGTCATAGATTCCAGG
AGATGCCTAAAGCCGGTCATACTTGATGGCGAGAGAGTCATTCTGGCTGGACCCATGCCTGTCACACATGCCAGCGCTGC
CCAGAGGAGGGGCGCATAGGCAGGAATCCCAACAAACCTGGAGATGAGTATCTGTATGGAGGTGGGTGCGCAGAGAC
TGACGAAGACCATGCACACTGGCTTGAAGCAAGAATGCTCCTTGACAATATTTACCTCCAAGATGGCCTCATAGCCTCGCT
CTATCGACCTGAGGCCGACAAAGTAGCAGCCATTGAGGGAGAGTTCAAGCTTAGGACGGAGCAAAGGAAGACCTTTGTG
GAACTCATGAAAAGAGGAGATCTTCCTGTTTGGCTGGCCTATCAGGTTGCATCTGCCGGAATAACCTACACAGATAGAAG
ATGGTGCTTTGATGGCACGACCAACAACACCATAATGGAAGACAGTGTGCCGGCAGAGGTGTGGACCAGACACGGAGA
GAAAAGAGTGCTCAAACCGAGGTGGATGGACGCCAGAGTTTGTTCAGATCATGCGGCCCTGAAGTCATTCAAGGAGTTT
GCCGCTGGGAAAAGAGGAGCGGCTTTTGGAGTGATGGAAGCCCTGGGAACACTGCCAGGACACATGACAGAGAGATTC
CAGGAAGCCATTGACAACCTCGCTGTGCTCATGCGGGCAGAGACTGGAAGCAGGCCTTACAAAGCCGCGGCGGCCCAAT
TGCCGGAGACCCTAGAGACCATTATGCTTTTGGGGTTGCTGGGAACAGTCTCGCTGGGAATCTTTTTCGTCTTGATGAGG
AACAAGGGCATAGGGAAGATGGGCTTTGGAATGGTGACTCTTGGGGCCAGCGCATGGCTCATGTGGCTCTCGGAAATTG
AGCCAGCCAGAATTGCATGTGTCCTCATTGTTGTGTTCCTATTGCTGGTGGTGCTCATACCTGAGCCAGAAAAGCAAAGAT
CTCCCCAGGACAACCAAATGGCAATCATCATCATGGTAGCAGTAGGTCTTCTGGGCTTGATTACCGCCAATGAACTCGGAT
GGTTGGAGAGAACAAAGAGTGACCTAAGCCATCTAATGGGAAGGAGAGAGGAGGGGGCAACCATGGGATTCTCAATGG
ACATTGACCTGCGGCCAGCCTCAGCTTGGGCCATCTATGCTGCCTTGACAACTTTCATTACCCCAGCCGTCCAACATGCAGT
GACCACTTCATACAACAACTACTCCTTAATGGCGATGGCCACGCAAGCTGGAGTGTTGTTTGGTATGGGCAAAGGGATGC
CATTCTACGCATGGGACTTTGGAGTCCCGCTGCTAATGATAGGTTGCTACTCACAATTAACGCCCCTGACCCTAATAGTGG
CCATCATTTTGCTCGTGGCGCACTACATGTACTTGATCCCAGGGCTGCAGGCAGCAGCTGCGCGTGCTGCCCAGAAGAGA
ACGGCAGCTGGCATCATGAAGAACCCTGTTGTGGATGGAATAGTGGTGACTGACATTGACACAATGACAATTGACCCCCA
AGTGGAGAAAAGATGGGACAGGTGCTACTCATGGCAGTAGCCGTCTCCAGCGCCATACTGTCGCGGACCGCCTGGGGG
TGGGGGGAGGCTGGGCCCTGATCACAGCCGCAACTTCCACTTTGTGGGAAGGCTCTCCGAACAAGTACTGGAACTCCTC
TACAGCCACTTCACTGTGTAACATTTTTAGGGGAAGTTACTTGGCTGGAGCTTCTCTAATCTACACAGTAACAAGAAACGC
TGGCTTGGTCAAGAGACGTGGGGGTGGAACAGGAGAGACCCTGGGAGAGAAATGGAAGGCCCGCTTGAACCAGATGTC
GGCCCTGGAGTTCTACTCCTACAAAAAGTCAGGCATCACCGAGGTGTGCAGAGAAGAGGCCCGCCGCGCCCTCAAGGAC
GGTGTGGCAACGGGAGGCCATGCTGTGTCCCGAGGAAGTGCAAAGCTGAGATGGTTGGTGGAGCGGGGATACCTGCAG
```

-continued

```
CCCTATGGAAAGGTCATTGATCTTGGATGTGGCAGAGGGGGCTGGAGTTACTACGCCGCCACCATCCGCAAAGTTCAAGA

AGTGAAAGGATACACAAAAGGAGGCCCTGGTCATGAAGAACCCGTGTTGGTGCAAAGCTATGGGTGGAACATAGTCCGT

CTTAAGAGTGGGGTGGACGTCTTTCATATGGCGGCTGAGCCGTGTGACACGTTGCTGTGTGACATAGGTGAGTCATCATC

TAGTCCTGAAGTGGAAGAAGCACGGACGCTCAGAGTCCTCTCCATGGTGGGGGATTGGCTTGAAAAAAGACCAGGAGCC

TTTTGTATAAAAGTGTTGTGCCCATACACCAGCACTATGATGGAAACCCTGGAGCGACTGCAGCGTAGGTATGGGGGAG

GACTGGTCAGAGTGCCACTCTCCCGCAACTCTACACATGAGATGTACTGGGTCTCTGGAGCGAAAAGCAACACCATAAAA

AGTGTGTCCACCACGAGCCAGCTCCTCTTGGGGCGCATGGACGGGCCTAGGAGGCCAGTGAAATATGAGGAGGATGTGA

ATCTCGGCTCTGGCACGCGGGCTGTGGTAAGCTGCGCTGAAGCTCCCAACATGAAGATCATTGGTAACCGCATTGAAAGG

ATCCGCAGTGAGCACGCGGAAACGTGGTTCTTTGACGAGAACCACCCATATAGGACATGGGCTTACCATGGAAGCTATGA

GGCCCCCACACAAGGGTCAGCGTCCTCTCTAATAAACGGGGTTGTCAGGCTCCTGTCAAAACCCTGGGATGTGGTGACTG

GAGTCACAGGAATAGCCATGACCGACACCACACCGTATGGTCAGCAAAGAGTTTTCAAGGAAAAAGTGGACACTAGGGT

GCCAGACCCCCAAGAAGGTACTCGTCAGGTTATGAGCATGGTCTCTTCCTGGTTGTGGAAAGAGCTAGGCAAACACAAAC

GGCCACGAGTCTGTACCAAAGAAGAGTTCATCAACAAGGTTCGTAGCAATGCAGCATTAGGGGCAATATTTGAAGAGGA

AAAAGAGTGGAAGACTGCAGTGGAAGCTGTGAACGATCCAAGGTTCTGGGCTCTAGTGGACAAGGAAAGAGAGCACCA

CCTGAGAGGAGAGTGCCAGAGTTGTGTGTACAACATGATGGGAAAAAGAGAAAAGAAACAAGGGGAATTTGGAAAGGC

CAAGGGCAGCCGCGCCATCTGGTATATGTGGCTAGGGGCTAGATTTCTAGAGTTCGAAGCCCTTGGATTCTTGAACGAGG

ATCACTGGATGGGGAGAGAGAACTCAGGAGGTGGTGTTGAAGGGCTGGGATTACAAAGACTCGGATATGTCCTAGAAG

AGATGAGTCGCATACCAGGAGGAAGGATGTATGCAGATGACACTGCTGGCTGGGACACCCGCATCAGCAGGTTTGATCT

GGAGAATGAAGCTCTAATCACCAACCAAATGGAGAAAGGGCACAGGGCCTTGGCATTGGCCATAATCAAGTACACATAC

CAAAACAAAGTGGTAAAGGTCCTTAGACCAGCTGAAAAAGGGAAAACAGTTATGGACATTATTTCGAGACAAGACCAAA

GGGGGAGCGGACAAGTTGTCACTTACGCTCTTAACACATTTACCAACCTAGTGGTGCAACTCATTCGGAATATGGAGGCT

GAGGAAGTCCTAGAGATGCAAGACTTGTGGCTGCTGCGGAGGTCAGAGAAAGTGACCAACTGGTTGCAGAGCAACGGA

TGGGATAGGCTCAAACGAATGGCAGTCAGTGGAGATGATTGCGTTGTGAAGCCAATTGATGATAGGTTTGCACATGCCCT

CAGGTTCTTGAATGATATGGGAAAAGTTAGGAAGGACACACAAGAGTGGAAACCCTCAACTGGATGGGACAACTGGGAA

GAAGTTCCGTTTTGCTCCCACCACTTCAACAAGCTCCATCTCAAGGACGGGAGGTCCATTGTGGTTCCCTGCCGCCACCAA

GATGAACTGATTGGCCGGGCCCGCGTCTCTCCAGGGGGGGATGGAGCATCCGGGAGACTGCTTGCCTAGCAAAATCAT

ATGCGCAAATGTGGCAGCTCCTTTATTTCCACAGAAGGGACCTCCGACTGATGGCCAATGCCATTTGTTCATCTGTGCCAG

TTGACTGGGTTCCAACTGGGAGAACTACCTGGTCAATCCATGGAAAGGGAGAATGGATGACCACTGAAGACATGCTTGT

GGTGTGGAACAGAGTGTGGATTGAGGAGAACGACCACATGGAAGACAAGACCCCAGTTACGAAATGGACAGACATTCCC

TATTTGGGAAAAAGGGAAGACTTGTGGTGTGGATCTCTCATAGGGCACAGACCGCGCACCACCTGGGCTGAGAACATTA

AAAACACAGTCAACATGGTGCGCAGGATCATAGGTGATGAAGAAAGTACATGGACTACCTATCCACCCAAGTTCGCTAC

TTGGGTGAAGAAGGGTCTACACCTGGAGTGCTGTAAGCACCAATCTTAATGTTGTCAGGCCTGCTAGTCAGCCACAGCTT

GGGGAAAGCTGTGCAGCCTGTGACCCCCCAGGAGAAGCTGGGAAACCAAGCCTATAGTCAGGCCGAGAACGCCATGG

CACGGAAGAAGCCATGCTGCCTGTGAGCCCCTCAGAGGACACTGAGTCAAAAAACCCCACGCGCTTGGAGGCGCAGGAT

GGGAAAAGAAGGTGGCGACCTTCCCCACCCTTCAATCTGGGGCCTGAACTGGAGATCAGCTGTGGATCTCCAGAAGAGG

GACTAGTGGTTAGAGGAGA
```

KU497555.1 Zika virus isolate Brazil-ZKV2015, Brazil, complete genome

SEQ ID NO: 3

CCAATCTGTGAATCAGACTGCGACAGTTCGAGTTTGAAGCGAAAGCTAGCAACAGTATCAACAGGTTTTATTTTGGATTTG
GAAACGAGAGTTTCTGGTCATGAAAAACCCAAAAAAGAAATCCGGAGGATTCCGGATTGTCAATATGCTAAAACGCGGA
GTAGCCCGTGTGAGCCCCTTTGGGGGCTTGAAGAGGCTGCCAGCCGGACTTCTGCTGGGTCATGGGCCCATCAGGATGG
TCTTGGCGATTCTAGCCTTTTTGAGATTCACGGCAATCAAGCCATCACTGGGTCTCATCAATAGATGGGGTTCAGTGGGA
AAAAAGAGGCTATGGAAATAATAAAGAAGTTCAAGAAAGATCTGGCTGCCATGCTGAGAATAATCAATGCCAGGAAGGA
GAAGAAGAGACGAGGCGCAGATACTAGTGTCGGAATCGTTGGCCTCCTGCTGACCACAGCTATGGCAGCGGAGGTCACT
AGACGTGGGAGTGCATACTATATGTACTTGGACAGAAACGATGCTGGGGAGGCCATATCTTTTCCAACCACATTGGGGAT
GAATAAGTGTTATATACAGATCATGGATCTTGGACACATGTGTGATGCCACCATGAGCTATGAATGCCCTATGCTGGATG
AGGGGGTGGAACCAGATGACGTCGATTGTTGGTGCAACACGACGTCAACTTGGGTTGTGTACGGAACCTGCCATCACAA
AAAAGGTGAAGCACGGAGATCTAGAAGAGCTGTGACGCTCCCCTCCCATTCCACTAGGAAGCTGCAAACGCGGTCGCAA
ACCTGGTTGGAATCAAGAGAATACACAAAGCACTTGATTAGAGTCGAAAATTGGATATTCAGGAACCCTGGCTTCGCGTT
AGCAGCAGCTGCCATCGCTTGGCTTTTGGGAAGCTCAACGAGCCAAAAAGTCATATACTTGGTCATGATACTGCTGATTGC
CCCGGCATACAGCATCAGGTGCATAGGAGTCAGCAATAGGGACTTTGTGGAAGGTATGTCAGGTGGGACTTGGGTTGAT
GTTGTCTTGGAACATGGGGGTTGTGTCACCGTAATGGCACAGGACAAACCGACTGTCGACATAGAGCTGGTTACAACAAC
AGTCAGCAACATGGCGGAGGTAAGATCCTACTGCTATGAGGCATCAATATCAGACATGGCTTCGGACAGCCGCTGCCCAA
CACAAGGTGAAGCCTACCTTGACAAGCAATCAGACACTCAATATGTCTGCAAAGAACGTTAGTGGACAGAGGCTGGGG
AAATGGATGTGGACTTTTTGGCAAAGGGAGCCTGGTGACATGCGCTAAGTTTGCATGCTCCAAGAAAATGACCGGGAAG
AGCATCCAGCCAGAGAATCTGGAGTACCGGATAATGCTGTCAGTTCATGGCTCCCAGCACAGTGGGATGATCGTTAATGA
CACAGGACATGAAACTGATGAGAATAGAGCGAAGGTTGAGATAACGCCCAATTCACCAAGAGCCGAAGCCACCCTGGGG
GGTTTTGGAAGCTTAGGACTTGATTGTGAACCGAGGACAGGCCTTGACTTTTCAGATTTGTATTACTTGACTATGAATAAC
AAGCACTGGTTGGTTCACAAGGAGTGGTTCCACGACATTCCATTACCTTGGCACGCTGGGGCAGACACCGGAACTCCACA
CTGGAACAACAAAGAAGCACTGGTAGAGTTCAAGGACGCACATGCCAAAAGGCAAACTGTCGTGGTTCTAGGGACTCAA
GAAGGAGCAGTTCACACGGCCCTTGCTGGAGCTCTGGAGGCTGAGATGGATGGTGCAAAGGGAAGGCTGTCCTCTGGCC
ACTTGAAATGTCGCCTGAAAATGGATAAACTTAGATTGAAGGGCGTGTCATACTCCTTGTGTACCGCAGCGTTCACATTCA
CCAAGATCCCGGCTGAAACACTGCACGGGACAGTCACAGTGGAGGTACAGTACGCAGGGACAGATGGACCTTGCAAGGT
TCCAGCTCAGATGGCGGTGGACATGCAAACTCTGACCCCAGTTGGGAGGTTGATAACCGCTAACCCCGTAATCACTGAAA
GCACTGAGAACTCTAAGATGATGCTGGAACTTGATCCACCATTTGGGGACTCTTACATTGTCATAGGAGTCGGGGAGAAG
AAGATCACCCACCACTGGCACAGGAGTGGCAGCACCATTGGAAAAGCATTTGAAGCCACTGTGAGAGGTGCCAAGAGAA
TGGCAGTCTTGGGAGACACAGCCTGGGACTTTGGATCAGTTGGAGGCGCTCTCAACTCATTGGGCAAGGGCATCCATCAA
ATTTTTGGAGCAGCTTTCAAATCATTGTTTGGAGGAATGTCCTGGTTCTCACAAATTCTCATTGGAACGTTGCTGATGTGGT
TGGGTCTGAACACAAAGAATGGATCTATTTCCCTTATGTGCTTGGCCTTAGGGGGAGTGTTGATCTTCTTATCCACAGCCG
TCTCTGCTGATGTGGGGTGCTCGGTGGACTTCTCAAAGAAGGAGACGAGATGTGGTACAGGGGTGTTCGTCTATAACGA
CGTTGAAGCCTGGAGGGACAGGTACAAGTACCATCCTGACTCTCCCCGTAGATTGGCAGCAGCAGTCAAGCAAGCCTGG
GAAGATGGTATCTGCGGGATCTCCTCTGTTTCAAGAATGGAAAACATCATGTGGAGATCAGTAGAAGGGGAGCTTAACG
CAATCCTGGAAGAGAATGGAGTTCAACTGACGGTCGTTGTGGGATCTGTAAAAAACCCCATGTGGAGAGGTCCACAGAG
ATTGCCCGTGCCTGTGAACGAGCTGCCCCACGGCTGGAAGGCTTGGGGGAAATCGTACTTCGTCAGAGCAGCAAAGACA
AATAACAGCTTTGTCGTGGATGGTGACACACTGAAGGAATGCCCACTCAAACATAGAGCATGGAACAGCTTTCTTGTGGA
GGATCATGGGTTCGGGGTATTTCACACTAGTGTCTGGCTCAAGGTTAGAGAAGATTATTCATTAGAGTGTGATCCAGCCG
TTATTGGAACAGCTGTTAAGGGAAGGAGGCTGTACACAGTGATCTAGGCTACTGGATTGAGAGTGAGAAGAATGACAC
ATGGAGGCTGAAGAGGGCCCATCTGATCGAGATGAAAACATGTGAATGGCCAAAGTCCCACACATTGTGGACAGATGGA

-continued

```
ATAGAAGAGAGTGATCTGATCATACCCAAGTCTTTAGCTGGGCCACTCAGCCATCACAATACCAGAGAGGGCTACAGGAC

CCAAATGAAAGGGCCATGGCACAGTGAAGAGCTTGAAATTCGGTTTGAGGAATGCCCAGGCACTAAGGTCCACGTGGAG

GAAACATGTGGAACAAGAGGACCATCTCTGAGATCAACCACTGCAAGCGGAAGGGTGATCGAGGAATGGTGCTGCAGG

GAGTGCACAATGCCCCCACTGTCGTTCCGGGCTAAAGATGGCTGTTGGTATGGAATGGAGATAAGGCCCAGGAAAGAAC

CAGAAAGCAACTTAGTAAGGTCAATGGTGACTGCAGGATCAACTGATCACATGGATCACTTCTCCCTTGGAGTGCTTGTG

ATTCTGCTCATGGTGCAGGAAGGGCTGAAGAAGAGAATGACCACAAAGATCATCATAAGCACATCAATGGCAGTGCTGG

TAGCTATGATCCTGGGAGGATTTTCAATGAGTGACCTGGCTAAGCTTGCAATTTTGATGGGTGCCACCTTCGCGGAAATG

AACACTGGAGGAGATGTAGCTCATCTGGCGCTGATAGCGGCATTCAAAGTCAGACCAGCGTTGCTGGTATCTTTCATCTTC

AGAGCTAATTGGACACCCCGTGAAAGCATGCTGCTGGCCTTGGCCTCGTGTTTTTTGCAAACTGCGATCTCCGCCTTGGAA

GGCGACCTGATGGTTCTCATCAATGGTTTTGCTTTGGCCTGGTTGGCAATACGAGCGATGGTTGTTCCACGCACTGACAAC

ATCACCTTGGCAATCCTGGCTGCTCTGACACCACTGGCCCGGGGCACACTGCTTGTGGCGTGGAGAGCAGGCCTTGCTAC

TTGCGGGGGTTTATGCTCCTCTCTCTGAAGGGAAAAGGCAGTGTGAAGAAGAACTTACCATTTGTCATGGCCCTGGGAC

TAACCGCTGTGAGGCTGGTCGACCCCATCAACGTGGTGGGACTGCTGTTGCTCACAAGGAGTGGGAAGCGGAGCTGGCC

CCCTAGCGAAGTACTCACAGCTGTTGGCCTGATATGCGCATTGGCTGGAGGGTTCGCCAAGGCAGATATAGAGATGGCT

GGGCCCATGGCCGCGGTCGGTCTGCTAATTGTCAGTTACGTGGTCTCAGGAAAGAGTGTGGACATGTACATTGAAAGAG

CAGGTGACATCACATGGGAAAAAGATGCGGAAGTCACTGGAAACAGTCCCCGGCTCGATGTGGCGCTAGATGAGAGTG

GTGACTTCTCCCTGGTGGAGGATGACGGTCCCCCCATGAGAGAGATCATACTCAAGGTGGTCCTGATGACCATCTGTGGC

ATGAACCCAATAGCCATACCCTTTGCAGCTGGAGCGTGGTACGTATACGTGAAGACTGGAAAAAGGAGTGGTGCTCTATG

GGATGTGCCTGCTCCCAAGGAAGTAAAAAAGGGGGAGACCACAGATGGAGTGTACAGAGTAATGACTCGTAGACTGCTA

GGTTCAACACAAGTTGGAGTGGGAGTTATGCAAGAGGGGGTCTTTCACACTATGTGGCACGTCACAAAAGGATCCGCGC

TGAGAAGCGGTGAAGGGAGACTTGATCCATACTGGGGAGATGTCAAGCAGGATCTGGTGTCATACTGTGGTCCATGGAA

GCTAGATGCCGCCTGGGACGGGCACAGCGAGGTGCAGCTCTTGGCCGTGCCCCCCGGAGAGAGAGCGAGGAACATCCA

GACTCTGCCCGGAATATTTAAGACAAAGGATGGGGACATTGGAGCGGTTGCGCTGGATTACCCAGCAGGAACTTCAGGA

TCTCCAATCCTAGACAAGTGTGGGAGAGTGATAGGACTTTATGGCAATGGGGTCGTGATAAAAAATGGGAGTTATGTTA

GTGCCATCACCCAAGGGAGGAGGGAGGAAGAGACTCCTGTTGAGTGCTTCGAGCCTTCGATGCTGAAGAAGAAGCAGCT

AACTGTCTTAGACTTGCATCCTGGAGCTGGGAAACCAGGAGAGTTCTTCCTGAAATAGTCCGTGAAGCCATAAAAACAA

GACTCCGTACTGTGATCTTAGCTCCAACCAGGGTTGTCGCTGCTGAAATGGAGGAAGCCCTTAGAGGGCTTCCAGTGCGT

TATATGACAACAGCAGTCAATGTCACCCACTCTGGAACAGAAATCGTCGACTTAATGTGCCATGCCACCTTCACTTCACGT

CTACTACAGCCAATCAGAGTCCCCAACTATAATCTGTATATTATGGATGAGGCCCACTTCACAGATCCCTCAAGCATAGCA

GCAAGAGGATACATTTCAACAAGGGTTGAGATGGGCGAGGCGGCTGCCATCTTCATGACCGCCACGCCACCAGGAACCC

GTGACGCATTTCCGGACTCCAACTCACCAATTATGGACACCGAAGTGGAAGTCCCAGAGAGAGCCTGGAGCTCAGGCTTT

GATTGGGTGACGGATCATTCTGGAAAAACAGTTTGGTTTGTTCCAAGCGTGAGGAACGGCAATGAGATCGCAGCTTGTCT

GACAAAGGCTGGAAAACGGGTCATACAGCTCAGCAGAAAGACTTTTGAGACAGAGTTCCAGAAAACAAAACATCAAGAG

TGGGACTTTGTCGTGACAACTGACATTTCAGAGATGGGCGCCAACTTTAAAGCTGACCGTGTCATAGATTCCAGGAGATG

CCTAAAGCCGGTCATACTTGATGGCGAGAGAGTCATTCTGGCTGGACCCATGCCTGTCACACATGCCAGCGCTGCCCAGA

GGAGGGGGCGCATAGGCAGGAATCCCAACAAACCTGGAGATGAGTACCTGTATGGAGGTGGGTGCGCAGAGACTGACG

AAGACCATGCACACTGGCTTGAAGCAAGAATGCTCCTTGACAATATTTACCTCCAAGATGGCCTCATAGCCTCGCTCTATC

GACCTGAGGCCGACAAAGTAGCAGCCATTGAGGGAGAGTTCAAGCTTAGGACGGAGCAAAGGAAGACCTTTGTGGAAC

TCATGAAAAGAGGAGATCTTCCTGTTTGGCTGGCCTATCAGGTTGCATCTGCCGGAATAACCTACACAGATAGAAGATGG

TGCTTTGATGGCACGACCAACAACACCATAATGGAAGACAGTGTGCCGGCAGAGGTGTGGACCAGACACGGAGAGAAA
```

-continued

```
AGAGTGCTCAAACCGAGGTGGATGGACGCCAGAGTTTGTTCAGATCATGCGGCCCTGAAGTCATTCAAGGAGTTTGCCGC
TGGGAAAAGAGGAGCGGCTTTTGGAGTGATGGAAGCCCTGGGAACACTGCCAGGACACATGACAGAGAGATTCCAGGA
AGCCATTGACAACCTCGCTGTGCTCATGCGGGCAGAGACTGGAAGCAGGCCTTACAAAGCCGCGGCGGCCCAATTGCCG
GAGACCCTAGAGACCATTATGCTTTTGGGGTTGCTGGGAACAGTCTCGCTGGGAATCTTTTTCGTCTTGATGAGGAACAA
GGGCATAGGGAAGATGGGCTTTGGAATGGTGACTCTTGGGGCCAGCGCATGGCTCATGTGGCTCTCGGAAATTGAGCCA
GCCAGAATTGCATGTGTCCTCATTGTTGTGTTCCTATTGCTGGTGGTGCTCATACCTGAGCCAGAAAAGCAAAGATCTCCC
CAGGACAACCAAATGGCAATCATCATCATGGTAGCAGTAGGTCTTCTGGGCTTGATTACCGCCAATGAACTCGGATGGTT
GGAGAGAACAAAGAGTGACCTAAGCCATCTAATGGGAAGGAGAGAGGAGGGGGCAACCATAGGATTCTCAATGGACAT
TGACCTGCGGCCAGCCTCAGCTTGGGCCATCTATGCTGCCTTGACAACTTTCATTACCCCAGCCGTCCAACATGCAGTGAC
CACTTCATACAACAACTACTCCTTAATGGCGATGGCCACGCAAGCTGGAGTGTTGTTTGGTATGGGCAAAGGGATGCCAT
TCTACGCATGGGACTTTGGAGTCCCGCTGCTAATGATAGGTTGCTACTCACAATTAACACCCCTGACCCTAATAGTGGCCA
TCATTTTGCTCGTGGCGCACTACATGTACTTGATCCCAGGGCTGCAGGCAGCAGCTGCGCGTGCTGCCCAGAAGAGAACG
GCAGCTGGCATCATGAAGAACCCTGTTGTGGATGGAATAGTGGTGACTGACATTGACACAATGACAATTGACCCCCAAGT
GGAGAAAAAGATGGGACAGGTGCTACTCATAGCAGTAGCCGTCTCCAGCGCCATACTGTCGCGGACCGCCTGGGGGTGG
GGGGAGGCTGGGGCCCTGATCACAGCCGCAACTTCCACTTTGTGGGAAGGCTCTCCGAACAAGTACTGGAACTCCTCTAC
AGCCACTTCACTGTGTAACATTTTTAGGGGAAGTTACTTGGCTGGAGCTTCTCTAATCTACACAGTAACAAGAAACGCTGG
CTTGGTCAAGAGACGTGGGGGTGGAACAGGAGAGACCCTGGGAGAGAAATGGAAGGCCCGCTTGAACCAGATGTCGGC
CCTGGAGTTCTACTCCTACAAAAAGTCAGGCATCACCGAGGTGTGCAGAGAAGAGGCCCGCCGCGCCCTCAAGGACGGT
GTGGCAACGGGAGGCCATGCTGTGTCCCGAGGAAGTGCAAAGCTGAGATGGTTGGTGGAGCGGGGATACCTGCAGCCC
TATGGAAAGGTCATTGATCTTGGATGTGGCAGAGGGGGCTGGAGTTACTACGCCGCCACCATCCGCAAAGTTCAAGAAG
TGAAAGGATACACAAAAGGAGGCCCTGGTCATGAAGAACCCGTGTTGGTGCAAAGCTATGGGTGGAACATAGTCCGTCT
TAAGAGTGGGGTGGACGTCTTTCATATGGCGGCTGAGCCGTGTGACACGTTGCTGTGTGACATAGGTGAGTCATCATCTA
GTCCTGAAGTGGAAGAAGCACGGACGCTCAGAGTCCTCTCCATGGTGGGGATTGGCTTGAAAAAAGACCAGGAGCCTT
TTGCATAAAAGTGTTGTGCCCATACACCAGCACTATGATGGAAACCCTGGAGCGACTGCAGCGTAGGTATGGGGGAGGA
CTGGTCAGAGTGCCACTCTCCCGCAACTCTACACATGAGATGTACTGGGTCTCTGGAGCGAAAAGCAACACCATAAAAAG
TGTGTCCACCACGAGCCAGCTCCTCTTGGGGCGCATGGACGGGCCTAGGAGGCCAGTGAAATATGAGGAGGATGTGAAT
CTCGGCTCTGGCACGCGGGCTGTGGTAAGCTGCGCTGAAGCTCCCAACATGAAGATCATTGGTAACCGCATTGAAAGGAT
CCGCAGTGAGCACGCGGAAACGTGGTTCTTTGACGAAAACCACCCATATAGGACATGGGCTTACCATGGAAGCTATGTG
GCCCCCACACAAGGGTCAGCGTCCTCTCTAATAAACGGGGTTGTCAGGCTCCTGTCAAACCCTGGGATGTGGTGACTGG
AGTCACAGGAATAGCCATGACCGACACCACACCGTATGGTCAGCAAAGAGTTTTCAAGGAAAAGTGGACACTAGGGTG
CCAGACCCCAAGAAGGCACTCGTCAGGTTATGAGCATGGTCTCTTCCTGGTTGTGGAAAGAGCTAGGCAAACACAAACG
ACCACGAGTCTGTACCAAAGAAGAGTTCATCAACAAGGTTCGTAGCAATGCAGCATTAGGGGCAATATTTGAAGAGGAA
AAAGAGTGGAAGACTGCAGTGGAAGCTGTGAACGATCCAAGGTTCTGGGCTCTAGTGGACAAGGAAAGAGAGCACCAC
CTGAGAGGAGAGTGCCAGAGTTGTGTGTACAACATGATGGGAAAAAGAGAAAAGAAACAAGGGGAATTTGGAAAGGCC
AAGGGCAGCCGCGCCATCTGGTATATGTGGCTAGGGGCTAGATTTCTAGAGTTCGAAGCCCTTGGATTCTTGAACGAGGA
TCACTGGATGGGGAGAGAGAACTCAGGAGGTGGTGTTGAAGGGCTGGATTACAAAGACTCGGATATGTCCTAGAAGA
GATGAGTCGCATACCAGGAGGAAGGATGTATGCAGATGACACTGCTGGCTGGGACACCCGCATCAGCAGGTTTGATCTG
GAGAATGAAGCTCTAATCACCAACCAAATGGAGAAAGGGCACAGGGCCTTGGCATTGGCCATAATCAAGTACACATACC
AAAACAAAGTGGTAAAGGTCCTTAGACCAGCTGAAAAAGGGAAAACAGTTATGGACATTATTTCGAGACAAGACCAAAG
GGGGAGCGGACAAGTTGTCACTTACGCTCTTAACACATTTACCAACCTAGTGGTGCAACTCATTCGGAATATGGAGGCTG
AGGAAGTTCTAGAGATGCAAGACTTGTGGCTGCTGCGGAGGTCAGAGAAAGTGACCAACTGGTTGCAGAGCAACGGAT
```

-continued

GGGATAGGCTCAAACGAATGGCAGTCAGTGGAGATGATTGCGTTGTGAAGCCAATTGATGATAGGTTTGCACATGCCCTC

AGGTTCTTGAATGATATGGGAAAAGTTAGGAAGGACACACAAGAGTGGAAACCCTCAACTGGATGGGACAACTGGGAA

GAAGTTCCGTTTTGCTCCCACCACTTCAACAAGCTCCATCTCAAGGACGGGAGGTCCATTGTGGTTCCCTGCCGCCACCAA

GATGAACTGATTGGCCGGGCCCGCGTCTCTCCAGGGGGGGATGGAGCATCCGGGAGACTGCTTGCCTAGCAAAATCAT

ATGCGCAAATGTGGCAGCTCCTTTATTTCCACAGAAGGGACCTCCGACTGATGGCCAATGCCATTTGTTCATCTGTGCCAG

TTGACTGGGTTCCAACTGGGAGAACTACCTGGTCAATCCATGGAAAGGGAGAATGGATGACCACTGAAGACATGCTTGT

GGTGTGGAACAGAGTGTGGATTGAGGAGAACGACCACATGGAAGACAAGACCCCAGTTACGAAATGGACAGACATTCCC

TATTTGGGAAAAAGGGAAGACTTGTGGTGTGGATCTCTCATAGGGCACAGACCGCGCACCACCTGGGCTGAGAACATTA

AAAATACAGTCAACATGGTGCGCAGGATCATAGGTGATGAAGAAAAGTACATGGACTACCTATCCACCCAAGTTCGCTAC

TTGGGTGAAGAAGGGTCTACACCTGGAGTGCTGTGAGCACCAATCTTAATGTTGTCAGGCCTGCTAGTCAGCCACAGCTT

GGGGAAAGCTGTGCAGCCTGTGACCCCTCCAGGAGAAGCTGGGTAACCAAGCCTATAGTCAGGCCGAGAACGCCATGGC

ACGGAAGAAGCCATGCTGCCTGTGAGCCCCTCAGAGGACACTGAGTCAAAAAACCCCACGCGCTTGGAGGCGCAGGATG

GGAAAAGAAGGTGGCGACCTTCCCCACCCTTCAATCTGGGGCCTGAACTGGAGATCAGCTGTGGATCTCCAGAAGAGGG

ACTAGTGGTTAGAGGAGACCCCCCGGAAAACGCAAAACAGCATATTGACGCTGGGAAAGACCAGAGACTCCATGAGTTT

CCACCACGCTGGCCGCCAGGCACAGATCGCCGAATAGCGGCGGCCGGTGTGGGGAAATCCA

KU501215.1 Zika virus strain PRVABC59, Puerto Rico, complete genome
                                                                 SEQ ID NO: 4
GTTGTTGATCTGTGTGAATCAGACTGCGACAGTTCGAGTTTGAAGCGAAAGCTAGCAACAGTATCAACAGGTTTTATTTTG GATTTGGAAACGAGAGTTTCTGGTCATGAAAAACCCCAAAAAAGAAATCCGGAGGATTCCGGATTGTCAATATGCTAAAAC

GCGGAGTAGCCCGTGTGAGCCCCTTTGGGGGCTTGAAGAGGCTGCCAGCCGGACTTCTGCTGGGTCATGGGCCCATCAG

GATGGTCTTGGCGATTCTAGCCTTTTTGAGATTCACGGCAATCAAGCCATCACTGGGTCTCATCAATAGATGGGGTTCAGT

GGGGAAAAAAGAGGCTATGGAAACAATAAAGAAGTTCAAGAAAGATCTGGCTGCCATGCTGAGAATAATCAATGCTAGG

AAGGAGAAGAAGAGACGAGGCGCAGATACTAGTGTCGGAATTGTTGGCCTCCTGCTGACCACAGCTATGGCAGCGGAG

GTCACTAGACGTGGGAGTGCATACTATATGTACTTGGACAGAAACGATGCTGGGGAGGCCATATCTTTTCCAACCACATT

GGGGATGAATAAGTGTTATATACAGATCATGGATCTTGGACACATGTGTGATGCCACCATGAGCTATGAATGCCCTATGC

TGGATGAGGGGGTGGAACCAGATGACGTCGATTGTTGGTGCAACACGACGTCAACTTGGGTTGTGTACGGAACCTGCCA

TCACAAAAAAGGTGAAGCACGGAGATCTAGAAGAGCTGTGACGCTCCCCTCCCATTCCACCAGGAAGCTGCAAACGCGG

TCGCAAACCTGGTTGGAATCAAGAGAATACACAAAGCACTTGATTAGAGTCGAAAATTGGATATTCAGGAACCCTGGCTT

CGCGTTAGCAGCAGCTGCCATCGCTTGGCTTTTGGGAAGCTCAACGAGCCAAAAAGTCATATACTTGGTCATGATACTGCT

GATTGCCCCGGCATACAGCATCAGGTGCATAGGAGTCAGCAATAGGGACTTTGTGGAAGGTATGTCAGGTGGGACTTGG

GTTGATGTTGTCTTGGAACATGGAGGTTGTGTCACCGTAATGGCACAGGACAAACCGACTGTCGACATAGAGCTGGTTAC

AACAACAGTCAGCAACATGGCGGAGGTAAGATCCTACTGCTATGAGGCATCAATATCAGACATGGCTTCTGACAGCCGCT

GCCCAACACAAGGTGAAGCCTACCTTGACAAGCAATCAGACACTCAATATGTCTGCAAAAGAACGTTAGTGGACAGAGGC

TGGGGAAATGGATGTGGACTTTTTGGCAAAGGGAGCCTGGTGACATGCGCTAAGTTTGCATGCTCCAAGAAAATGACCG

GGAAGAGCATCCAGCCAGAGAATCTGGAGTACCGGATAATGCTGTCAGTTCATGGCTCCCAGCACAGTGGGATGATCGT

TAATGACACAGGACATGAAACTGATGAGAATAGAGCGAAAGTTGAGATAACGCCCAATTCACCGAGAGCCGAAGCCACC

CTGGGGGGTTTTGGAAGCCTAGGACTTGATTGTGAACCGAGGACAGGCCTTGACTTTTCAGATTTGTATTACTTGACTATG

AATAACAAGCACTGGTTGGTTCACAAGGAGTGGTTCCACGACATTCCATTACCTTGGCACGCTGGGGCAGACACCGGAAC

TCCACACTGGAACAACAAAGAAGCACTGGTAGAGTTCAAGGACGCACATGCCAAAAGGCAAACTGTCGTGGTTCTAGGG

AGTCAAGAAGGAGCAGTTCACACGGCCCTTGCTGGAGCTCTGGAGGCTGAGATGGATGGTGCAAAGGGAAGGCTGTCCT

-continued

```
CTGGCCACTTGAAATGTCGCCTGAAAATGGATAAACTTAGATTGAAGGGCGTGTCATACTCCTTGTGTACTGCAGCGTTCA
CATTCACCAAGATCCCGGCTGAAACACTGCACGGGACAGTCACAGTGGAGGTACAGTACGCAGGGACAGATGGACCTTG
CAAGGTTCCAGCTCAGATGGCGGTGGACATGCAAACTCTGACCCCAGTTGGGAGGTTGATAACCGCTAACCCCGTAATCA
CTGAAAGCACTGAGAACTCTAAGATGATGCTGGAACTTGATCCACCATTTGGGGACTCTTACATTGTCATAGGAGTCGGG
GAGAAGAAGATCACCCACCACTGGCACAGGAGTGGCAGCACCATTGGAAAAGCATTTGAAGCCACTGTGAGAGGTGCCA
AGAGAATGGCAGTCTTGGGAGACACAGCCTGGGACTTTGGATCAGTTGGAGGCGCTCTCAACTCATTGGGCAAGGGCAT
CCATCAAATTTTTGGAGCAGCTTTCAAATCATTGTTTGGAGGAATGTCCTGGTTCTCACAAATTCTCATTGGAACGTTGCTG
ATGTGGTTGGGTCTGAACACAAAGAATGGATCTATTTCCCTTATGTGCTTGGCCTTAGGGGAGTGTTGATCTTCTTATCC
ACAGCCGTCTCTGCTGATGTGGGGTGCTCGGTGGACTTCTCAAAGAAGGAGACGAGATGCGGTACAGGGGTGTTCGTCT
ATAACGACGTTGAAGCCTGGAGGGACAGGTACAAGTACCATCCTGACTCCCCCCGTAGATTGGCAGCAGCAGTCAAGCA
AGCCTGGGAAGATGGTATCTGCGGGATCTCCTCTGTTTCAAGAATGGAAAACATCATGTGGAGATCAGTAGAAGGGGAG
CTCAACGCAATCCTGGAAGAGAATGGAGTTCAACTGACGGTCGTTGTGGGATCTGTAAAAAACCCCATGTGGAGAGGTC
CACAGAGATTGCCCGTGCCTGTGAACGAGCTGCCCCACGGCTGGAAGGCTTGGGGGAAATCGTATTTCGTCAGAGCAGC
AAAGACAAATAACAGCTTTGTCGTGGATGGTGACACACTGAAGGAATGCCCACTCAAACATAGAGCATGGAACAGCTTTC
TTGTGGAGGATCATGGGTTCGGGGTATTTCACACTAGTGTCTGGCTCAAGGTTAGAGAAGATTATTCATTAGAGTGTGAT
CCAGCCGTTATTGGAACAGCTGTTAAGGGAAAGGAGGCTGTACACAGTGATCTAGGCTACTGGATTGAGAGTGAGAAGA
ATGACACATGGAGGCTGAAGAGGGCCCATCTGATCGAGATGAAAACATGTGAATGGCCAAAGTCCCACACATTGTGGAC
AGATGGAATAGAAGAGAGTGATCTGATCATACCCAAGTCTTTAGCTGGGCCACTCAGCCATCACAATACCAGAGAGGGCT
ACAGGACCCAAATGAAAGGGCCATGGCACAGTGAAGAGCTTGAAATTCGGTTTGAGGAATGCCCAGGCACTAAGGTCCA
CGTGGAGGAAACATGTGGAACAAGAGGACCATCTCTGAGATCAACCACTGCAAGCGGAAGGGTGATCGAGGAATGGTG
CTGCAGGGAGTGCACAATGCCCCCACTGTCGTTCCGGGCTAAAGATGGCTGTTGGTATGGAATGGAGATAAGGCCCAGG
AAAGAACCAGAAAGCAACTTAGTAAGGTCAATGGTGACTGCAGGATCAACTGATCACATGGACCACTTCTCCCTTGGAGT
GCTTGTGATCCTGCTCATGGTGCAGGAAGGGCTGAAGAAGAGAATGACCACAAAGATCATCATAAGCACATCAATGGCA
GTGCTGGTAGCTATGATCCTGGGAGGATTTTCAATGAGTGACCTGGCTAAGCTTGCAATTTTGATGGGTGCCACCTTCGC
GGAAATGAACACTGGAGGAGATGTAGCTCATCTGGCGCTGATAGCGGCATTCAAAGTCAGACCAGCGTTGCTGGTATCTT
TCATCTTCAGAGCTAATTGGACACCCCGTGAAAGCATGCTGCTGGCCTTGGCCTCGTGTCTTTTGCAAACTGCGATCTCCG
CCTTGGAAGGCGACCTGATGGTTCTCATCAATGGTTTTGCTTTGGCCTGGTTGGCAATACGAGCGATGGTTGTTCCACGCA
CTGATAACATCACCTTGGCAATCCTGGCTGCTCTGACACCACTGGCCCGGGGCACACTGCTTGTGGCGTGGAGAGCAGGC
CTTGCTACTTGCGGGGGGTTTATGCTCCTCTCTCTGAAGGGAAAAGGCAGTGTGAAGAAGAACTTACCATTTGTCATGGC
CCTGGGACTAACCGCTGTGAGGCTGGTCGACCCCATCAACGTGGTGGGACTGCTGTTGCTCACAAGGAGTGGGAAGCGG
AGCTGGCCCCCTAGCGAAGTACTCACAGCTGTTGGCCTGATATGCGCATTGGCTGGAGGGTTCGCCAAGGCAGATATAGA
GATGGCTGGGCCCATGGCCGCGGTCGGTCTGCTAATTGTCAGTTACGTGGTCTCAGGAAAGAGTGTGGACATGTACATTG
AAAGAGCAGGTGACATCACATGGGAAAAAGATGCGGAAGTCACTGGAAACAGTCCCCGGCTCGATGTGGCGCTAGATG
AGAGTGGTGATTTCTCCCTGGTGGAGGATGACGGTCCCCCCATGAGAGAGATCATACTCAAGGTGGTCCTGATGACCATC
TGTGGCATGAACCCAATAGCCATACCCTTTGCAGCTGGAGCGTGGTACGTATACGTGAAGACTGGAAAAAGGAGTGGTG
CTCTATGGGATGTGCCTGCTCCCAAGGAAGTAAAAAAGGGGGAGACCACAGATGGAGTGTACAGAGTAATGACTCGTAG
ACTGCTAGGTTCAACACAAGTTGGAGTGGGAGTTATGCAAGAGGGGGTCTTTCACACTATGTGGCACGTCACAAAAGGA
TCCGCGCTGAGAAGCGGTGAAGGGAGACTTGATCCATACTGGGGAGATGTCAAGCAGGATCTGGTGTCATACTGTGGTC
CATGGAAGCTAGATGCCGCCTGGGATGGGCACAGCGAGGTGCAGCTCTTGGCCGTGCCCCCCGGAGAGAGAGCGAGGA
ACATCCAGACTCTGCCCGGAATATTTAAGACAAAGGATGGGGACATTGGAGCGGTTGCGCTGGATTACCCAGCAGGAAC
```

-continued

```
TTCAGGATCTCCAATCCTAGACAAGTGTGGGAGAGTGATAGGACTTTATGGCAATGGGGTCGTGATCAAAAACGGGAGT

TATGTTAGTGCCATCACCCAAGGGAGGAGGGAGGAAGAGACTCCTGTTGAGTGCTTCGAGCCCTCGATGCTGAAGAAGA

AGCAGCTAACTGTCTTAGACTTGCATCCTGGAGCTGGGAAAACCAGGAGAGTTCTTCCTGAAATAGTCCGTGAAGCCATA

AAAACAAGACTCCGTACTGTGATCTTAGCTCCAACCAGGGTTGTCGCTGCTGAAATGGAGGAGGCCCTTAGAGGGCTTCC

AGTGCGTTATATGACAACAGCAGTCAATGTCACCCACTCTGGAACAGAAATCGTCGACTTAATGTGCCATGCCACCTTCAC

TTCACGTCTACTACAGCCAATCAGAGTCCCCAACTATAATCTGTATATTATGGATGAGGCCCACTTCACAGATCCCTCAAGT

ATAGCAGCAAGAGGATACATTTCAACAAGGGTTGAGATGGGCGAGGCGGCTGCCATCTTCATGACCGCCACGCCACCAG

GAACCCGTGACGCATTTCCGGACTCCAACTCACCAATTATGGACACCGAAGTGGAAGTCCCAGAGAGAGCCTGGAGCTCA

GGCTTTGATTGGGTGACGGATCATTCTGGAAAAACAGTTTGGTTTGTTCCAAGCGTGAGGAACGGCAATGAGATCGCAGC

TTGTCTGACAAAGGCTGGAAAACGGGTCATACAGCTCAGCAGAAAGACTTTTGAGACAGAGTTCCAGAAAACAAAACATC

AAGAGTGGGACTTTGTCGTGACAACTGACATTTCAGAGATGGGCGCCAACTTTAAAGCTGACCGTGTCATAGATTCCAGG

AGATGCCTAAAGCCGGTCATACTTGATGGCGAGAGAGTCATTCTGGCTGGACCCATGCCTGTCACACATGCCAGCGCTGC

CCAGAGGAGGGGCGCATAGGCAGGAATCCCAACAAACCTGGAGATGAGTATCTGTATGGAGGTGGGTGCGCAGAGAC

TGACGAAGACCATGCACACTGGCTTGAAGCAAGAATGCTCCTTGACAATATTTACCTCCAAGATGGCCTCATAGCCTCGCT

CTATCGACCTGAGGCCGACAAAGTAGCAGCCATTGAGGGAGAGTTCAAGCTTAGGACGGAGCAAAGGAAGACCTTTGTG

GAACTCATGAAAAGAGGAGATCTTCCTGTTTGGCTGGCCTATCAGGTTGCATCTGCCGGAATAACCTACACAGATAGAAG

ATGGTGCTTTGATGGCACGACCAACAACACCATAATGGAAGACAGTGTGCCGGCAGAGGTGTGGACCAGACACGGAGA

GAAAAGAGTGCTCAAACCGAGGTGGATGGACGCCAGAGTTTGTTCAGATCATGCGGCCCTGAAGTCATTCAAGGAGTTT

GCCGCTGGGAAAAGAGGAGCGGCTTTTGGAGTGATGGAAGCCCTGGGAACACTGCCAGGACACATGACAGAGAGATTC

CAGGAAGCCATTGACAACCTCGCTGTGCTCATGCGGGCAGAGACTGGAAGCAGGCCTTACAAAGCCGCGGCGGCCCAAT

TGCCGGAGACCCTAGAGACCATAATGCTTTTGGGGTTGCTGGGAACAGTCTCGCTGGGAATCTTCTTCGTCTTGATGAGG

AACAAGGGCATAGGGAAGATGGGCTTTGGAATGGTGACTCTTGGGGCCAGCGCATGGCTCATGTGGCTCTCGGAAATTG

AGCCAGCCAGAATTGCATGTGTCCTCATTGTTGTGTTCCTATTGCTGGTGGTGCTCATACCTGAGCCAGAAAAGCAAAGAT

CTCCCCAGGACAACCAAATGGCAATCATCATCATGGTAGCAGTAGGTCTTCTGGGCTTGATTACCGCCAATGAACTCGGAT

GGTTGGAGAGAACAAAGAGTGACCTAAGCCATCTAATGGGAAGGAGAGAGGAGGGGGCAACCATAGGATTCTCAATGG

ACATTGACCTGCGGCCAGCCTCAGCTTGGGCCATCTATGCTGCCTTGACAACTTTCATTACCCCAGCCGTCCAACATGCAGT

GACCACCTCATACAACAACTACTCCTTAATGGCGATGGCCACGCAAGCTGGAGTGTTGTTTGGCATGGGCAAAGGGATGC

CATTCTACGCATGGGACTTTGGAGTCCCGCTGCTAATGATAGGTTGCTACTCACAATTAACACCCCTGACCCTAATAGTGG

CCATCATTTTGCTCGTGGCGCACTACATGTACTTGATCCCAGGGCTGCAGGCAGCAGCTGCGCGTGCTGCCCAGAAGAGA

ACGGCAGCTGGCATCATGAAGAACCCTGTTGTGGATGGAATAGTGGTGACTGACATTGACACAATGACAATTGACCCCCA

AGTGGAGAAAAAGATGGGACAGGTGCTACTCATAGCAGTAGCCGTCTCCAGCGCCATACTGTCGCGGACCGCCTGGGGG

TGGGGGGAGGCTGGGGCTCTGATCACAGCCGCAACTTCCACTTTGTGGGAAGGCTCTCCGAACAAGTACTGGAACTCCTC

TACAGCCACTTCACTGTGTAACATTTTTAGGGGAAGTTACTTGGCTGGAGCTTCTCTAATCTACACAGTAACAAGAAACGC

TGGCTTGGTCAAGAGACGTGGGGGTGGAACAGGAGAGACCCTGGGAGAGAAATGGAAGGCCCGCTTGAACCAGATGTC

GGCCCTGGAGTTCTACTCCTACAAAAAGTCAGGCATCACCGAGGTGTGCAGAGAAGAGGCCCGCCGCGCCCTCAAGGAC

GGTGTGGCAACGGGAGGCCATGCTGTGTCCCGAGGAAGTGCAAAGCTGAGATGGTTGGTGGAGCGGGATACCTGCAG

CCCTATGGAAAGGTCATTGATCTTGGATGTGGCAGAGGGGCTGGAGTTACTACGTCGCCACCATCCGCAAAGTTCAAGA

AGTGAAAGGATACACAAAAGGAGGCCCTGGTCATGAAGAACCCGTGTTGGTGCAAAGCTATGGGTGGAACATAGTCCGT

CTTAAGAGTGGGGTGGACGTCTTTCATATGGCGGCTGAGCCGTGTGACACGTTGCTGTGTGACATAGGTGAGTCATCATC

TAGTCCTGAAGTGGAAGAAGCACGGACGCTCAGAGTCCTCTCCATGGTGGGGGATTGGCTTGAAAAAAGACCAGGAGCC

TTTTGTATAAAAGTGTTGTGCCCATACACCAGCACTATGATGGAAACCCTGGAGCGACTGCAGCGTAGGTATGGGGGAG
```

-continued

GACTGGTCAGAGTGCCACTCTCCCGCAACTCTACACATGAGATGTACTGGGTCTCTGGAGCGAAAAGCAACACCATAAAA

AGTGTGTCCACCACGAGCCAGCTCCTCTTGGGGCGCATGGACGGGCCTAGGAGGCCAGTGAAATATGAGGAGGATGTGA

ATCTCGGCTCTGGCACGCGGGCTGTGGTAAGCTGCGCTGAAGCTCCCAACATGAAGATCATTGGTAACCGCATTGAAAGG

ATCCGCAGTGAGCACGCGGAAACGTGGTTCTTTGACGAGAACCACCCATATAGGACATGGGCTTACCATGGAAGCTATGA

GGCCCCCACACAAGGGTCAGCGTCCTCTCTAATAAACGGGGTTGTCAGGCTCCTGTCAAAACCCTGGGATGTGGTGACTG

GAGTCACAGGAATAGCCATGACCGACACCACACCGTATGGTCAGCAAAGAGTTTTCAAGGAAAAAGTGGACACTAGGGT

GCCAGACCCCCAAGAAGGCACTCGTCAGGTTATGAGCATGGTCTCTTCCTGGTTGTGGAAAGAGCTAGGCAAACACAAAC

GGCCACGAGTCTGCACCAAAGAAGAGTTCATCAACAAGGTTCGTAGCAATGCAGCATTAGGGGCAATATTTGAAGAGGA

AAAAGAGTGGAAGACTGCAGTGGAAGCTGTGAACGATCCAAGGTTCTGGGCTCTAGTGGACAAGGAAAGAGAGCACCA

CCTGAGAGGAGAGTGCCAGAGCTGTGTGTACAACATGATGGGAAAAAGAGAAAAGAAACAAGGGGAATTTGGAAAGGC

CAAGGGCAGCCGCGCCATCTGGTATATGTGGCTAGGGGCTAGATTTCTAGAGTTCGAAGCCCTTGGATTCTTGAACGAGG

ATCACTGGATGGGGAGAGAGAACTCAGGAGGTGGTGTTGAAGGGCTGGGATTACAAAGACTCGGATATGTCCTAGAAG

AGATGAGTCGTATACCAGGAGGAAGGATGTATGCAGATGACACTGCTGGCTGGGACACCCGCATTAGCAGGTTTGATCT

GGAGAATGAAGCTCTAATCACCAACCAAATGGAGAAAGGGCACAGGGCCTTGGCATTGGCCATAATCAAGTACACATAC

CAAAACAAAGTGGTAAAGGTCCTTAGACCAGCTGAAAAAGGGAAAACAGTTATGGACATTATTTCGAGACAAGACCAAA

GGGGGAGCGGACAAGTTGTCACTTACGCTCTTAACACATTTACCAACCTAGTGGTGCAACTCATTCGGAATATGGAGGCT

GAGGAAGTTCTAGAGATGCAAGACTTGTGGCTGCTGCGGAGGTCAGAGAAAGTGACCAACTGGTTGCAGAGCAACGGA

TGGGATAGGCTCAAACGAATGGCAGTCAGTGGAGATGATTGCGTTGTGAAGCCAATTGATGATAGGTTTGCACATGCCCT

CAGGTTCTTGAATGATATGGGAAAAGTTAGGAAGGACACACAAGAGTGGAAACCCTCAACTGGATGGGACAACTGGGAA

GAAGTTCCGTTTTGCTCCCACCACTTCAACAAGCTCCATCTCAAGGACGGGAGGTCCATTGTGGTTCCCTGCCGCCACCAA

GATGAACTGATTGGCCGGGCCCGCGTCTCTCCAGGGGGGGATGGAGCATCCGGGAGACTGCTTGCCTAGCAAAATCAT

ATGCGCAAATGTGGCAGCTCCTTTATTTCCACAGAAGGGACCTCCGACTGATGGCCAATGCCATTTGTTCATCTGTGCCAG

TTGACTGGGTTCCAACTGGGAGAACTACCTGGTCAATCCATGGAAAGGGAGAATGGATGACCACTGAAGACATGCTTGT

GGTGTGGAACAGAGTGTGGATTGAGGAGAACGACCACATGGAAGACAAGACCCCAGTTACGAAATGGACAGACATTCCC

TATTTGGGAAAAAGGGAAGACTTGTGGTGTGGATCTCTCATAGGGCACAGACCGCGCACCACCTGGGCTGAGAACATTA

AAAACACAGTCAACATGGTGCGCAGGATCATAGGTGATGAAGAAAAGTACATGGACTACCTATCCACCCAAGTTCGCTAC

TTGGGTGAAGAAGGGTCTACACCTGGAGTGCTGTAAGCACCAATCTTAATGTTGTCAGGCCTGCTAGTCAGCCACAGCTT

GGGGAAAGCTGTGCAGCCTGTGACCCCCCCAGGAGAAGCTGGGAAACCAAGCCTATAGTCAGGCCGAGAACGCCATGG

CACGGAAGAAGCCATGCTGCCTGTGAGCCCCTCAGAGGACACTGAGTCAAAAAACCCCACGCGCTTGGAGGCGCAGGAT

GGGAAAAGAAGGTGGCGACCTTCCCCACCCTTCAATCTGGGGCCTGAACTGGAGATCAGCTGTGGATCTCCAGAAGAGG

GACTAGTGGTTAGAGGA

KU509998.1 Zika virus strain Haiti/1225/2014, Haiti, complete genome
SEQ ID NO: 5
GTTGTTACTGTTGCTGACTCAGACTGCGACAGTTCGAGTTTGAAGCGAAAGCTAGCAACAGTATCAACAGGTTTTATTTGG

ATTTGGAAACGAGAGTTTCTGGTCATGAAAAACCCAAAAAGAAATCCGGAGGATTCCGGATTGTCAATATGCTAAAACG

CGGAGTAGCCCGTGTGAGCCCCTTTGGGGCTTGAAGAGGCTGCCAGCCGGACTTCTGCTGGGTCATGGGCCCATCAGG

ATGGTCTTGGCAATTCTAGCCTTTTTGAGATTCACGGCAATCAAGCCATCACTGGGTCTCATCAATAGATGGGGTTCAGTG

GGGAAAAAGAGGCTATGGAAATAATAAGAAGTTCAAGAAAGATCTGGCTGCCATGCTGAGAATAATCAATGCTAGGA

AGGAGAAGAAGAGACGAGGCGCAGATACTAGTGTCGGAATTGTTGGCCTCCTGCTGACCACAGCTATGGCAGCGAGG

TCACTAGACGTGGGAGTGCATACTATATGTACTTGGACAGAAACGATGCTGGGGAGGCCATATCTTTTCCAACCACATTG

-continued

```
GGGATGAATAAGTGTTATATACAGATCATGGATCTTGGACACATGTGTGATGCCACCATGAGCTATGAATGCCCTATGCT
GGATGAGGGGGTGGAACCAGATGACGTCGATTGTTGGTGCAACACGACGTCAACTTGGGTTGTGTACGGAACCTGCCAT
CACAAAAAAGGTGAAGCACGGAGATCTAGAAGAGCTGTGACGCTCCCCTCCCATTCCACTAGGAAGCTGCAAACGCGGT
CGCAAACCTGGTTGGAATCAAGAGAATACACAAAGCACTTGATTAGAGTCGAAAATTGGATATTCAGGAACCCTGGCTTC
GCGTTAGCAGCAGCTGCCATCGCTTGGCTTTTGGGAAGCTCAACGAGCCAAAAAGTCATATACTTGGTCATGATACTGCT
GATTGCCCCGGCATACAGCATCAGGTGCATAGGAGTCAGCAATAGGGACTTTGTGGAAGGTATGTCAGGTGGGACTTGG
GTTGATGTTGTCTTGGAACATGGAGGTTGTGTCACCGTAATGGCACAGGACAAACCGACTGTCGACATAGAGCTGGTTAC
AACAACAGTCAGCAACATGGCGGAGGTAAGATCCTACTGCTATGAGGCATCAATATCAGACATGGCTTCGGACAGCCGCT
GCCCAACACAAGGTGAAGCCTACCTTGACAAGCAATCAGACACTCAATATGTCTGCAAAAGAACGTTAGTGGACAGAGGC
TGGGGAAATGGATGTGGACTTTTTGGCAAAGGGAGTCTGGTGACATGCGCTAAGTTTGCATGCTCCAAGAAAATGACCG
GGAAGAGCATCCAGCCAGAGAATCTGGAGTACCGGATAATGCTGTCAGTTCATGGCTCCCAGCACAGTGGGATGATCGT
TAATGACACAGGACATGAAACTGATGAGAATAGAGCGAAGGTTGAGATAACGCCCAATTCACCAAGAGCCGAAGCCACC
CTGGGGGGTTTTGGAAGCCTAGGACTTGATTGTGAACCGAGGACAGGCCTTGACTTTTCAGATTTGTATTACTTGACTATG
AATAACAAGCACTGGTTGGTTCACAAGGAGTGGTTCCACGACATTCCATTACCTTGGCACGCTGGGGCAGACACCGGAAC
TCCACACTGGAACAACAAAGAAGCACTGGTAGAGTTCAAGGACGCACATGCCAAAAGGCAAACTGTCGTGGTTCTAGGG
AGTCAAGAAGGAGCAGTTCACACGGCCCTTGCTGGAGCTCTGGAGGCTGAGATGGATGGTGCAAAGGGAAGGCTGTCCT
CTGGCCACTTGAAATGTCGCCTGAAAATGGATAAACTTAGATTGAAGGGCGTGTCATACTCCTTGTGTACCGCAGCGTTCA
CATTCACCAAGATCCCGGCTGAAACACTGCACGGACAGTCACAGTGGAGGTACAGTACGCAGGGACAGATGGACCTTG
CAAGGTTCCAGCTCAGATGGCGGTGGACATGCAAACTCTGACCCCAGTTGGGAGGTTGATAACCGCTAACCCCGTAATCA
CTGAAAGCACTGAGAACTCTAAGATGATGCTGGAACTTGATCCACCATTTGGGGACTCTTACATTGTCATAGGAGTCGGG
GAGAAGAAGATCACCCACCACTGGCACAGGAGTGGCAGCACCATTGGAAAAGCATTTGAAGCCACTGTGAGAGGTGCCA
AGAGAATGGCAGTCTTGGGAGACACAGCCTGGGACTTTGGATCAGTTGGAGGCGCTCTCAACTCATTGGGCAAGGGCAT
CCATCAAATTTTTGGAGCAGCTTTCAAATCATTGTTTGGAGGAATGTCCTGGTTCTCACAAATTCTCATTGGAACGTTGCTG
ATGTGGTTGGGTCTGAACACAAAGAATGGATCTATTTCCCTTATGTGCTTGGCCTTAGGGGAGTGTTGATCTTCTTATCC
ACAGCCGTCTCTGCTGATGTGGGGTGCTCGGTGGACTTCTCAAAGAAGGAGACGAGATGCGGTACAGGGGTGTTCGTCT
ATAACGACGTTGAAGCCTGGAGGGACAGGTACAAGTACCATCCTGACTCCCCCCGTAGATTGGCAGCAGCAGTCAAGCA
AGCCTGGGAAGATGGTATCTGCGGGATCTCCTCTGTTTCAAGAATGGAAAACATCATGTGGAGATCAGTAGAAGGGGAG
CTCAACGCAATCCTGGAAGAGAATGGAGTTCAACTGACGGTCGTTGTGGGATCTGTAAAAAACCCCATGTGGAGAGGTC
CACAGAGATTGCCCGTGCCTGTGAACGAGCTGCCCCACGGCTGGAAGGCTTGGGGGAAATCGCACTTCGTCAGAGCAGC
AAAGACAAATAACAGCTTTGTCGTGGATGGTGACACACTGAAGGAATGCCCACTCAAACATAGAGCATGGAACAGCTTTC
TTGTGGAGGATCATGGGTTCGGGGTATTTCACACTAGTGTCTGGCTCAAGGTTAGAGAAGATTATTCATTAGAGTGTGAT
CCAGCCGTTATTGGAACAGCTGTTAAGGGAAAGGAGGCTGTACACAGTGATCTAGGCTACTGGATTGAGAGTGAGAAGA
ATGACACATGGAGGCTGAAGAGGGCCCATCTGATCGAGATGAAAACATGTGAATGGCCAAAGTCCCACACATTGTGGAC
AGATGGAATAGAAGAGAGTGATCTGATCATACCCAAGTCTTTAGCTGGGCCACTCAGCCATCACAATACCAGAGAGGGCT
ACAGGACCCAAATGAAAGGCCATGGCACAGTGAAGAGCTTGAAATTCGGTTTGAGGAATGCCCAGGCACTAAGGTCCA
CGTGGAGGAAACATGTGGAACAAGAGGACCATCTCTGAGATCAACCACTGCAAGCGGAAGGGTGATCGAGGAATGGTG
CTGCAGGGAGTGCACAATGCCCCCACTGTCGTTCCGGGCTAAAGATGGCTGTTGGTATGGAATGGAGATAAGGCCCAGG
AAAGAACCAGAAAGCAACTTAGTAAGGTCAATGGTGACTGCAGGATCAACTGATCACATGGATCACTTCTCCCTTGGAGT
GCTTGTGATTCTGCTCATGGTGCAGGAAGGGCTGAAGAAGAGAATGACCACAAAGATCATCATAAGCACATCAATGGCA
GTGCTGGTAGCTATGATCCTGGGAGGATTTTCAATGAGTGACCTGGCTAAGCTTGCAATTTTGATGGGTGCCACCTTCGC
```

-continued

```
GGAAATGAACACTGGAGGAGATGTAGCTCATCTGGCGCTGATAGCGGCATTCAAAGTCAGACCAGCGTTGCTGGTATCTT

TCATCTTCAGAGCTAATTGGACACCCCGTGAAAGCATGCTGCTGGCCTTGGCCTCGTGTCTTTTGCAAACTGCGATCTCCG

CCTTGGAAGGCGACCTGATGGTTCTCATCAATGGTTTTGCTTTGGCCTGGTTGGCAATACGAGCGATGGTTGTTCCACGCA

CTGATAACATCACCTTGGCAATCCTGGCTGCTCTGACACCACTGGCCCGGGGCACACTGCTTGTGGCGTGGAGAGCAGGC

CTTGCTACTTGCGGGGGGTTTATGCTCCTCTCTCTGAAGGGAAAAGGCAGTGTGAAGAAGAACTTACCATTTGTCATGGC

CCTGGGACTAACCGCTGTGAGGCTGGTCGACCCCATCAACGTGGTGGGGCTGCTGTTGCTCACAAGGAGTGGGAAGCGG

AGCTGGCCCCCTAGCGAAGTACTCACAGCTGTTGGCCTGATATGCGCATTGGCTGGAGGGTTCGCCAAGGCAGATATAGA

GATGGCTGGGCCCATGGCCGCGGTCGGTCTGCTAATTGTCAGTTACGTGGTCTCAGGAAAGAGTGTGGACATGTACATTG

AAAGAGCAGGTGACATCACATGGGAAAAGATGCGGAAGTCACTGGAAACAGTCCCCGGCTCGATGTGGCGCTAGATG

AGAGTGGTGATTTCTCCCTGGTGGAGGATGACGGTCCCCCCATGAGAGAGATCATACTCAAGGTGGTCCTGATGACCATC

TGTGGCATGAACCCAATAGCCATACCCTTTGCAGCTGGAGCGTGGTACGTATACGTGAAGACTGGAAAAAGGAGTGGTG

CTCTATGGGATGTGCCTGCTCCCAAGGAAGTAAAAAGGGGGAGACCACAGATGGAGTGTACAGAGTAATGACTCGTAG

ACTGCTAGGTTCAACACAAGTTGGAGTGGGAGTTATGCAAGAGGGGGTCTTTCACACTATGTGGCACGTCACAAAAGGA

TCCGCGCTGAGAAGCGGTGAAGGGAGACTTGATCCATACTGGGGAGATGTCAAGCAGGATCTGGTGTCATACTGTGGTC

CATGGAAGCTAGATGCCGCCTGGGACGGGCACAGCGAGGTGCAGCTCTTGGCCGTGCCCCCCGGAGAGAGAGCGAGGA

ACATCCAGACTCTGCCCGGAATATTTAAGACAAAGGATGGGACATTGGAGCGGTTGCGCTGGATTACCCAGCAGGAAC

TTCAGGATCTCCAATCCTAGACAAGTGTGGGAGAGTGATAGGACTTTATGGCAATGGGGTCGTGATCAAAAATGGGAGT

TATGTTAGTGCCATCACCCAAGGGAGGAGGGAGGAAGAGACTCCTGTTGAGTGCTTCGAGCCTTCGATGCTGAAGAAGA

AGCAGCTAACTGTCTTAGACTTGCATCCTGGAGCTGGGAAAACCAGGAGAGTTCTTCCTGAAATAGTCCGTGAAGCCATA

AAAACAAGACTCCGTACTGTGATCTTAGCTCCAACCAGGGTTGTCGCTGCTGAAATGGAGGAAGCCCTTAGAGGGCTTCC

AGTGCGTTATATGACAACAGCAGTCAATGTCACCCACTCTGGAACAGAAATCGTCGACTTAATGTGCCATGCCACCTTCAC

TTCACGTCTACTACAGCCAATCAGAGTCCCCAACTATAATCTGTATATTATGGATGAGGCCCACTTCACAGATCCCTCAAGT

ATAGCAGCAAGAGGATACATTTCAACAAGGGTTGAGATGGGCGAGGCGGCTGCCATCTTCATGACCGCCACGCCACCAG

GAACCCGTGACGCATTTCCGGACTCCAACTCACCAATTATGGACACCGAAGTGGAAGTCCCAGAGAGAGCCTGGAGCTCA

GGCTTTGATTGGGTGACGGATTATTCTGGAAAAACAGTTTGGTTTGTTCCAAGCGTGAGGAACGGCAATGAGATCGCAGC

TTGTCTGACAAAGGCTGGAAAACGGGTCATACAGCTCAGCAGAAAGACTTTTGAGACAGAGTTCCAGAAAACAAAACATC

AAGAGTGGGACTTTGTCGTGACAACTGACATTTCAGAGATGGGCGCCAACTTTAAAGCTGACCGTGTCATAGATTCCAGG

AGATGCCTAAAGCCGGTCATACTTGATGGCGAGAGAGTCATTCTGGCTGGACCCATGCCTGTCACACATGCCAGCGCTGC

CCAGAGGAGGGGCGCATAGGCAGGAATCCCAACAAACCTGGAGATGAGTATCTGTATGGAGGTGGGTGCGCAGAGAC

TGACGAAGACCATGCACACTGGCTTGAAGCAAGAATGCTCCTTGACAATATTTACCTCCAAGATGGCCTCATAGCCTCGCT

CTATCGACCTGAGGCCGACAAAGTAGCAGCCATTGAGGGAGAGTTCAAGCTTAGGACGGAGCAAAGGAAGACCTTTGTG

GAACTCATGAAAAGAGGAGATCTTCCTGTTTGGCTGGCCTATCAGGTTGCATCTGCCGGAATAACCTACACAGATAGAAG

ATGGTGCTTTGATGGCACGACCAACAACACCATAATGGAAGACAGTGTGCCGGCAGAGGTGTGGACCAGACACGGAGA

GAAAAGAGTGCTCAAACCGAGGTGGATGGACGCCAGAGTTTGTTCAGATCATGCGGCCCTGAAGTCATTCAAGGAGTTT

GCCGCTGGGAAAAGAGGAGCGGCTTTTGGAGTGATGAAGCCCTGGGAACACTGCCAGGACACATGACAGAGAGATTC

CAGGAAGCCATTGACAACCTCGCTGTGCTCATGCGGGCAGAGACTGGAAGCAGGCCTTACAAAGCCGCGGCGGCCCAAT

TGCCGGAGACCCTAGAGACCATTATGCTTTTGGGGTTGCTGGGAACAGTCTCGCTGGGAATCTTTTTCGTCTTGATGAGG

AACAAGGGCATAGGGAAGATGGGCTTTGGAATGGTGACTCTTGGGGCCAGCGCATGGCTCATGTGGCTCTCGGAAATTG

AGCCAGCCAGAATTGCATGTGTCCTCATTGTTGTGTTCCTATTGCTGGTGGTGCTCATACCTGAGCCAGAAAAGCAAAGAT

CTCCCCAGGACAACCAAATGGCAATCATCATCATGGTAGCAGTAGGTCTTCTGGGCTTGATTACCGCCAATGAACTCGGAT

GGTTGGAGAGAACAAAGAGTGACCTAAGCCATCTAATGGGAAGGAGAGAGGAGGGGGCAACCATGGGATTCTCAATGG
```

-continued

```
ACATTGACCTGCGGCCAGCCTCAGCTTGGGCCATCTATGCTGCCTTGACAACTTTCATTACCCCAGCCGTCCAACATGCAGT
GACCACTTCATACAACAACTACTCCTTAATGGCGATGGCCACGCAAGCTGGAGTGTTGTTTGGTATGGGCAAAGGGATGC
CATTCTACGCATGGGACTTTGGAGTCCCGCTGCTAATGATAGGTTGCTACTCACAATTAACGCCCCTGACCCTAATAGTGG
CCATCATTTTGCTCGTGGCGCACTACATGTACTTGATCCCAGGGCTGCAGGCAGCAGCTGCGCGTGCTGCCCAGAAGAGA
ACGGCAGCTGGCATCATGAAGAACCCTGTTGTGGATGGAATAGTGGTGACTGACATTGACACAATGACAATTGACCCCCA
AGTGGAGAAAAAGATGGGACAGGTGCTACTCATGGCAGTAGCCGTCTCCAGCGCCATACTGTCGCGGACCGCCTGGGGG
TGGGGGGAGGCTGGGGCCCTGATCACAGCCGCAACTTCCACTTTGTGGGAAGGCTCTCCGAACAAGTACTGGAACTCCTC
TACAGCCACTTCACTGTGTAACATTTTTAGGGGAAGTTACTTGGCTGGAGCTTCTCTAATCTACACAGTAACAAGAAACGC
TGGCTTGGTCAAGAGACGTGGGGGTGGAACAGGAGAGACCCTGGGAGAGAAATGGAAGGCCCGCTTGAACCAGATGTC
GGCCCTGGAGTTCTACTCCTACAAAAAGTCAGGCATCACCGAGGTGTGCAGAGAAGAGGCCCGCCGCGCCCTCAAGGAC
GGTGTGGCAACGGGAGGCCATGCTGTGTCCCGAGGAAGTGCAAAGCTGAGATGGTTGGTGGAGCGGGGATACCTGCAG
CCCTATGGAAAGGTCATTGATCTTGGATGTGGCAGAGGGGGCTGGAGTTACTACGCCGCCACCATCCGCAAAGTTCAAGA
AGTGAAAGGATACACAAAAGGAGGCCCTGGTCATGAAGAACCCGTGTTGGTGCAAAGCTATGGGTGGAACATAGTCCGT
CTTAAGAGTGGGGTGGACGTCTTTCATATGGCGGCTGAGCCGTGTGACACGTTGCTGTGTGACATAGGTGAGTCATCATC
TAGTCCTGAAGTGGAAGAAGCACGGACGCTCAGAGTCCTCTCCATGGTGGGGGATTGGCTTGAAAAAAGACCAGGAGCC
TTTTGTATAAAAGTGTTGTGCCCATACACCAGCACTATGATGGAAACCCTGGAGCGACTGCAGCGTAGGTATGGGGGAG
GACTGGTCAGAGTGCCACTCTCCCGCAACTCTACACATGAGATGTACTGGGTCTCTGGAGCGAAAAGCAACACCATAAAA
AGTGTGTCCACCACGAGCCAGCTCCTCTTGGGGCGCATGGACGGGCCTAGGAGGCCAGTGAAATATGAGGAGGATGTGA
ATCTCGGCTCTGGCACGCGGGCTGTGGTAAGCTGCGCTGAAGCTCCCAACATGAAGATCATTGGTAACCGCATTGAAAGG
ATCCGCAGTGAGCACGCGGAAACGTGGTTCTTTGACGAGAACCACCCATATAGGACATGGGCTTACCATGGAAGCTATGA
GGCCCCCACACAAGGGTCAGCGTCCTCTCTAATAAACGGGGTTGTCAGGCTCCTGTCAAAACCCTGGGATGTGGTGACTG
GAGTCACAGGAATAGCCATGACCGACACCACACCGTATGGTCAGCAAAGAGTTTTCAAGGAAAAAGTGGACACTAGGGT
GCCAGACCCCCAAGAAGGCACTCGTCAGGTTATGAGCATGGTCTCTTCCTGGTTGTGGAAAGAGCTAGGCAAACACAAAC
GGCCACGAGTCTGTACCAAAGAAGAGTTCATCAACAAGGTTCGTAGCAATGCAGCATTAGGGGCAATATTTGAAGAGGA
AAAAGAGTGGAAGACTGCAGTGGAAGCTGTGAACGATCCAAGGTTCTGGGCTCTAGTGGACAAGGAAAGAGAGCACCA
CCTGAGAGGAGAGTGCCAGAGTTGTGTGTACAACATGATGGGAAAAAGAGAAAAGAAACAAGGGGAATTTGGAAAGGC
CAAGGGCAGCCGCGCCATCTGGTATATGTGGCTAGGGGCTAGATTTCTAGAGTTCGAAGCCCTTGGATTCTTGAACGAGG
ATCACTGGATGGGGAGAGAGAACTCAGGAGGTGGTGTTGAAGGGCTGGGATTACAAAGACTCGGATATGTCCTAGAAG
AGATGAGTCGCATACCAGGAGGAAGGATGTATGCAGATGACACTGCTGGCTGGGACACCCGCATCAGCAGGTTTGATCT
GGAGAATGAAGCTCTAATCACCAACCAAATGGAGAAAGGGCACAGGGCCTTGGCATTGGCCATAATCAAGTACACATAC
CAAAACAAAGTGGTAAAGGTCCTTAGACCAGCTGAAAAAGGGAAGACAGTTATGGACATTATTTCGAGACAAGACCAAA
GGGGGAGCGGACAAGTTGTCACTTACGCTCTTAACACATTTACCAACCTAGTGGTGCAACTCATTCGGAATATGGAGGCT
GAGGAAGTTCTAGAGATGCAAGACTTGTGGCTGCTGCGGAGGTCAGAGAAAGTGACCAACTGGTTGCAGAGCAACGGA
TGGGATAGGCTCAAACGAATGGCAGTCAGTGGAGATGATTGCGTTGTGAAGCCAATTGATGATAGGTTTGCACATGCCCT
CAGGTTCTTGAATGATATGGGAAAAGTTAGGAAGGACACACAAGAGTGGAAACCCTCAACTGGATGGGACAACTGGGAA
GAAGTTCCGTTTTGCTCCCACCACTTCAACAAGCTCCATCTCAAGGACGGGAGGTCCATTGTGGTTCCCTGCCGCCACCAA
GATGAACTGATTGGCCGGGCCCGCGTCTCTCCAGGGGGGGATGGAGCATCCGGGAGACTGCTTGCCTAGCAAAATCAT
ATGCGCAAATGTGGCAGCTCCTTTATTTCCACAGAAGGGACCTCCGACTGATGGCCAATGCCATTTGTTCATCTGTGCCAG
TTGACTGGGTTCCAACTGGGAGAACTACCTGGTCAATCCATGGAAAGGGAGAATGGATGACCACTGAAGACATGCTTGT
GGTGTGGAACAGAGTGTGGATTGAGGAGAACGACCACATGGAAGACAAGACCCCAGTTACGAAATGGACAGACATTCCC
```

-continued

TATTTGGGAAAAAGGGAAGACTTGTGGTGTGGATCTCTCATAGGGCACAGACCGCGCACCACCTGGGCTGAGAACATTA

AAAACACAGTCAACATGGTGCGCAGGATCATAGGTGATGAAGAAAAGTACATGGACTACCTATCCACCCAAGTTCGCTAC

TTGGGTGAAGAAGGGTCTACACCTGGAGTGCTGTAAGCACCAATCTTAATGTTGTCAGGCCTGCTAGTCAGCCACAGCTT

GGGGAAAGCTGTGCAGCCTGTGACCCCCCCAGGAGAAGCTGGGAAACCAAGCCTATAGTCAGGCCGAGAACGCCATGG

CACGGAAGAAGCCATGCTGCCTGTGAGCCCCTCAGAGGACACTGAGTCAAAAAACCCCACGCGCTTGGAGGCGCAGGAT

GGGAAAAGAAGGTGGCGACCTTCCCCACCCTTCAATCTGGGGCCTGAACTGGAGATCAGCTGTGGATCTCCAGAAGAGG

GACTAGTGGTTAGAGGAGA

KU527068.1 Zika virus strain Natal RGN, Brazil: Rio Grande do Norte, Natal, complete genome

SEQ ID NO: 6

AGTTGTTGATCTGTGTGAATCAGACTGCGACAGTTCGAGTTTGAAGCGAAAGCTAGCAACAGTATCAACAGGTTTTATTTT

GGATTTGGAAACGAGAGTTTCTGGTCATGAAAAACCCAAAAAAGAAATCCGGAGGATTCCGGATTGTCAATATGCTAAAA

CGCGGAGTAGCCCGTGTGAGCCCCTTTGGGGGCTTGAAGAGGCTGCCAGCCGGACTTCTGCTGGGTCATGGGCCCATCA

GGATGGTCTTGGCAATTCTAGCCTTTTTGAGATTCACGGCAATCAAGCCATCACTGGGTCTCATCAATAGATGGGGTTCAG

TGGGGAAAAAAGAGGCTATGGAAATAATAAAGAAGTTCAAGAAAGATCTGGCTGCCATGCTGAGAATAATCAATGCTAG

GAAGGAGAAGAAGAGACGAGGCGCAGATACTAGTGTCGGAATTGTTGGCCTCCTGCTGACCACAGCTATGGCAGCGGA

GGTCACTAGACGTGGGAGTGCATACTATATGTACTTGGACAGAAACGATGCTGGGGAGGCCATATCTTTTCCAACCACAT

TGGGGATGAATAAGTGTTATATACAGATCATGGATCTTGGACACATGTGTGATGCCACCATGAGCTATGAATGCCCTATG

CTGGATGAGGGGGTGGAACCAGATGACGTCGATTGTTGGTGCAACACGACGTCAACTTGGGTTGTGTACGGAACCTGCC

ATCACAAAAAAGGTGAAGCACGGAGATCTAGAAGAGCTGTGACGCTCCCCTCCCATTCCACTAGGAAGCTGCAAACGCG

GTCGCAAACCTGGTTGGAATCAAGAGAATACACAAAGCACTTGATTAGAGTCGAAAATTGGATATTCAGGAACCCTGGCT

TCGCGTTAGCAGCAGCTGCCATCGCTTGGCTTTTGGGAAGCTCAACGAGCCAAAAAGTCATATACTTGGTCATGATACTGC

TGATTGCCCCGGCATACAGCATCAGGTGCATAGGAGTCAGCAATAGGGACTTTGTGGAAGGTATGTCAGGTGGGACTTG

GGTTGATGTTGTCTTGGAACATGGAGGTTGTGTCACCGTAATGGCACAGGACAAACCGACTGTCGACATAGAGCTGGTTA

CAACAACAGTCAGCAACATGGCGGAGGTAAGATCCTACTGCTATGAGGCATCAATATCAGACATGGCTTCGGACAGCCGC

TGCCCAACACAAGGTGAAGCCTACCTTGACAAGCAATCAGACACTCAATATGTCTGCAAAAGAACGTTAGTGGACAGAGG

CTGGGGAAATGGATGTGGACTTTTTGGCAAAGGGAGCCTGGTGACATGCGCTAAGTTTGCATGCTCCAAGAAAATGACC

GGGAAGAGCATCCAGCCAGAGAATCTGGAGTACCGGATAATGCTGTCAGTTCATGGCTCCCAGCACAGTGGGATGATCG

TTAATGACACAGGACATGAAACTGATGAGAATAGAGCGAAGGTTGAGATAACGCCCAATTCACCAAGAGCCGAAGCCAC

CCTGGGGGGTTTTGGAAGCCTAGGACTTGATTGTGAACCGAGGACAGGCCTTGACTTTTCAGATTTGTATTACTTGACTAT

GAATAACAAGCACTGGTTGGTCCACAAGGAGTGGTTCCACGACATTCCATTACCTTGGCACGCTGGGGCAGACACCGGAA

CTCCACACTGGAACAACAAAGAAGCACTGGTAGAGTTCAAGGACGCACATGCCAAAAGGCAAACTGTCGTGGTTCTAGG

GAGTCAAGAAGGAGCAGTTCACACGGCCCTTGCTGGAGCTCTGGAGGCTGAGATGGATGGTGCAAAGGGAAGGCTGTC

CTCTGGCCACTTGAAATGTCGCCTGAAAATGGATAAACTTAGATTGAAGGGCGTGTCATACTCCTTGTGTACCGCAGCGTT

CACATTCACCAAGATCCCGGCTGAAACACTGCACGGGACAGTCACAGTGGAGGTACAGTACGCAGGGACAGATGGACCT

TGCAAGGTTCCAGCTCAGATGGCGGTGGACATGCAAACTCTGACCCCAGTTGGGAGGTTGATAACCGCTAACCCCGTAAT

CACTGAAAGCACTGAGAACTCTAAGATGATGCTGGAACTTGATCCACCATTTGGGGACTCTTACATTGTCATAGGAGTCG

GGGAGAAGAAGATCACCCACCACTGGCACAGGAGTGGCAGCACCATTGGAAAAGCATTTGAAGCCACTGTGAGAGGTG

CCAAGAGAATGGCAGTCTTGGGAGACACAGCCTGGGACTTTGGATCAGTTGGAGGCGCTCTCAACTCATTGGGCAAGGG

CATCCATCAAATTTTTGGAGCAGCTTTCAAATCATTGTTTGGAGGAATGTCCTGGTTCTCACAAATCCTCATTGGAACGTTG

CTGATGTGGTTGGGTCTGAACACAAAGAATGGATCTATTTCCCTTATGTGCTTGGCCTTAGGGGGAGTGTTGATCTTCTTA

-continued

```
TCCACAGCCGTCTCTGCTGATGTGGGGTGCTCGGTGGACTTCTCAAAGAAGGAGACGAGATGCGGTACAGGGGTGTTCG

TCTATAACGACGTTGAAGCCTGGAGGGACAGGTACAAGTACCATCCTGACTCCCCCCGTAGATTGGCAGCAGCAGTCAAG

CAAGCCTGGGAAGATGGTATCTGCGGGATCTCCTCTGTTTCAAGAATGGAGAACATCATGTGGAGATCAGTAGAAGGGG

AGCTCAACGCAATCTTGGAAGAGAATGGAGTTCAACTGACGGTCGTTGTGGGATCTGTAAAAAACCCCATGTGGAGAGG

TCCACAGAGATTGCCCGTGCCTGTGAACGAGCTGCCCCACGGCTGGAAGGCTTGGGGGAAATCGTACTTCGTCAGAGCA

GCAAAGACAAATAACAGCTTTGTCGTGGATGGTGACACACTGAAGGAATGCCCACTCGAACATAGAGCATGGAACAGCT

TTCTTGTGGAGGATCATGGGTTCGGGGTATTTCACACTAGTGTCTGGCTCAAGGTTAGAGAAGATTATTCATTAGAGTGT

GATCCAGCCGTTATTGGAACAGCTGTTAAGGGGAAGGAGGCTGTACACAGTGATCTAGGCTACTGGATTGAGAGTGAGA

AGAATGACACATGGAGGCTGAAGAGGGCCCATCTAATCGAGATGAAAACATGTGAATGGCCAAAGTCCCACACATTGTG

GGCAGATGGAATAGAAGAGAGTGATCTGATCATTCCCAAGTCTTTAGCTGGGCCACTCAGCCATCACAATACCAGAGAGG

GCTACAGGACCCAAATGAAAGGGCCATGGCACAGTGAAGAGCTTGAAATTCGGTTTGAGGAATGCCCGGGCACTAAGGT

CCACGTGGAGGAAACATGTGGAACAAGAGGACCATCTCTGAGATCAACCACTGCAAGCGAAGGGTGATCGAGGAATG

GTGCTGCAGGGAGTGCACAATGCCCCCACTGTCGTTCCGGGCTAAAGATGGCTGTTGGTATGGAATGGAGATAAGGCCC

AGGAAAGAACCAGAAAGCAACTTAGTAAGGTCAGTGGTGACTGCAGGATCAACTGATCACATGGATCACTTCTCCCTTGG

AGTGCTTGTGATTCTGCTCATGGTGCAGGAAGGGCTGAAGAAGAGAATGACCACAAAGATCATCATAAGCACATCAATG

GCAGTGCTGGTAGCTATGATCCTGGGAGGATTTTCAATGAGTGACCTGGCTAAGCTTGCAATTTTGATGGGCGCCACCTT

CGCGGAAATGAACACTGGAGGAGATGTAGCTCATCTGGCGCTGATAGCGGCATTCAAAGTCAGACCAGCGTTGCTGGTA

TCTTTCATCTTCAGAGCTAATTGGACACCCCGTGAAAGCATGCTGCTGGCCTTGGCCTCGTGTCTTTTGCAAACTGCGATCT

CCGCCTTGGAAGGCGACCTGATGGTTCTCATCAATGGTTTTGCTTTGGCCTGGTTGGCAATACGAGCGATGGTTGTTCCAC

GCACTGATAACATCACCTTGGCAATCCTGGCTGCTCTGACACCACTGGCCCGGGGCACACTGCTTGTGGCGTGGAGAGCA

GGCCTTGCTACTTGCGGGGGGTTTATGCTCCTCTCTCTGAAGGGAAAAGGCAGTGTGAAGAAGAACTTACCATTTGTCAT

GGCCCTGGGACTAACCGCTGTGAGGCTGGTCGACCCCATCAACGTGGTGGGACTGCTGTTGCTCACAAGGAGTGGGAAG

CGGAGCTGGCCCCCTAGCGAAGTACTCACAGCTGTTGGCCTGATATGCGCATTGGCTGGAGGGTTCGCCAAGGCAGATAT

AGAGATGGCTGGGCCCATGGCCGCGGTCGGTCTGCTAATTGTCAGTTACGTGGTCTCAGGAAAGAGTGTGGACATGTAC

ATTGAAAGAGCAGGTGACATCACATGGGAAAAAGATGCGGAAGTCACTGGAAACAGTCCCCGGCTCGATGTGGCGCTAG

ATGAGAGTGGTGATTTCTCCCTGGTGGAGGATGACGGTCCCCCCATGAGAGAGATCATACTCAAGGTGGTCCTGATGACC

ATCTGTGGCATGAACCCAATAGCCATACCCTTTGCAGCTGGAGCGTGGTACGTATACGTGAAGACTGGAAAAAGGAGTG

GTGCTCTATGGGATGTGCCTGCTCCCAAGGAAGTAAAAAAGGGGGAGACCACAGATGGAGTGTACAGAGTAATGACTCG

TAGACTGCTAGGTTCAACACAAGTTGGAGTGGGAGTTATGCAAGAGGGGGTCTTTCACACTATGTGGCACGTCACAAAA

GGATCCGCGCTGAGAAGCGGTGAAGGGAGACTTGATCCATACTGGGGAGATGTCAAGCAGGATCTGGTGTCATACTGTG

GTCCATGGAAGCTAGATGCCGCCTGGGACGGGCACAGCGAGGTGCAGCTCTTGGCCGTGCCCCCCGGAGAGAGAGCGA

GGAACATCCAGACTCTGCCCGGAATATTTAAGACAAAGGATGGGGACATTGGAGCGGTTGCGCTGGATTACCCAGCAGG

AACTTCAGGATCTCCAATCCTAGACAAGTGTGGGAGAGTGATAGGACTTTATGGCAATGGGGTCGTGATCAAAAATGGG

AGTTATGTTAGTGCCATCACCCAAGGGAGGAGGGAGGAAGAGACTCCTGTTGAGTGCTTCGAGCCTTCGATGCTGAAGA

AGAAGCAGCTAACTGTCTTAGACTTGCATCCTGGAGCTGGGAAAACCAGGAGAGTTCTTCCTGAAATAGTCCGTGAAGCC

ATAAAAACAAGACTCCGTACTGTGATCTTAGCTCCAACCAGGGTTGTCGCTGCTGAAATGGAGGAAGCCCTTAGAGGGCT

TCCAGTGCGTTATATGACAACAGCAGTCAATGTCACCCACTCTGGAACAGAAATCGTCGACTTAATGTGCCATGCCACCTT

CACTTCACGTCTACTACAGCCAATCAGAGTCCCCAACTATAATCTGTATATTATGGATGAGGCCCACTTCACAGATCCCTCA

AGTATAGCAGCAAGAGGATACATTTCAACAAGGGTTGAGATGGGCGAGGCGGCTGCCATCTTCATGACCGCCACGCCAC

CAGGAACCCGTGACGCATTTCCGGACTCCAACTCACCAATTATGGACACCGAAGTGGAAGTCCCAGAGAGAGCCTGGAG

CTCAGGCTTTGATTGGGTGACGGATCATTCTGGAAAAACAGTTTGGTTTGTTCCAAGCGTGAGGAACGGCAATGAGATCG
```

-continued

```
CAGCTTGTCTGACAAAGGCTGGAAAACGGGTCATACAGCTCAGCAGAAAGACTTTTGAGACAGAGTTCCAGAAAACAAA
ACATCAAGAGTGGGACTTTGTCGTGACAACTGACATTTCAGAGATGGGCGCCAACTTTAAAGCTGACCGTGTCATAGATT
CCAGGAGATGCCTAAAGCCGGTCATACTTGATGGCGAGAGAGTCATTTTGGCTGGACCCATGCCTGTCACACATGCCAGC
GCTGCCCAGAGGAGGGGCGCATAGGCAGGAATCCCAACAAACCTGGAGATGAGTATCTGTATGGAGGTGGGTGCGCA
GAGACTGACGAAGACCATGCACACTGGCTTGAAGCAAGAATGCTCCTTGACAATATTTACCTCCAAGATGGCCTCATAGC
CTCGCTCTATCGACCTGAGGCCGACAAAGTAGCAGCCATTGAGGGAGAGTTCAAGCTTAGGACGGAGCAAAGGAAGACC
TTTGTGGAACTCATGAAAAGAGGAGATCTTCCTGTTTGGCTGGCCTATCAGGTTGCATCTGCCGGAATAACCTACACAGAT
AGAAGATGGTGCTTTGATGGCACGACCAACAACACCATAATGGAAGACAGTGTGCCGGCAGAGGTGTGGACCAGACAC
GGAGAGAAAAGAGTGCTCAAACCGAGGTGGATGGACGCCAGAGTTTGTTCAGATCATGCGGCCCTGAAGTCATTCAAGG
AGTTTGCCGCTGGGAAAAGAGGAGCGGCTTTTGGAGTGATGGAAGCCCTGGGAACACTGCCAGGACACATGACAGAGA
GATTCCAGGAAGCCATTGACAACCTCGCTGTGCTCATGCGGGCAGAGACTGGAAGCAGGCCTTACAAAGCCGCGGCGGC
CCAATTGCCGGAGACCCTAGAGACCATTATGCTTTTGGGGTTGCTGGGAACAGTCTCGCTGGGAATCTTTTTCGTCTTGAT
GAGGAACAAGGGCATAGGGAAGATGGGCTTTGGAATGGTGACTCTTGGGGCCAGCGCATGGCTCATGTGGCTCTCGGA
AATTGAGCCAGCCAGAATTGCATGTGTCCTCATTGTTGTGTTCCTATTGCTGGTGGTGCTCATACCTGAGCCAGAAAAGCA
AAGATCTCCCCAGGACAACCAAATGGCAATCATCATCATGGTAGCAGTAGGTCTTCTGGGCTTGATTACCGCCAATGAACT
CGGATGGTTGGAGAGAACAAAGAGTGACCTAAGCCATCTAATGGGAAGGAGAGAGGAGGGAGCAACCATAGGATTCTC
AATGGACATTGACCTGCGGCCAGCCTCAGCTTGGGCCATCTATGCTGCCTTGACAACTTTCATTACCCCAGCCGTCCAACA
TGCAGTGACCACTTCATACAACAACTACTCCTTAATGGCGATGGCCACGCAAGCTGGAGTGTTGTTTGGTATGGGCAAAG
GGATGCCATTCTACGCATGGGACTTTGGAGTCCCGCTGCTAATGATAGGTTGCTACTCACAATTAACACCCCTGACCCTAA
TAGTGGCCATCATTTTGCTCGTGGCGCACTACATGTACTTGATCCCAGGGCTGCAGGCAGCAGCTGCGCGTGCTGCCCAG
AAGAGAACGGCAGCTGGCATCATGAAGAACCCTGTTGTGGATGGAATAGTGGTGACTGACATTGACACAATGACAATTG
ACCCCCAAGTGGAGAAAAAGATGGGACAGGTGCTACTCATAGCAGTAGCAGTCTCCAGCGCCATACTGTCGCGGACCGC
CTGGGGGTGGGGGAGGCTGGGGCCCTGATCACAGCCGCAACTTCCACTTTGTGGGAAGGCTCTCCGAACAAGTACTGG
AACTCCTCTACAGCCACTTCACTGTGTAACATTTTTAGGGGAAGTTACTTGGCTGGAGCTTCTCTAATCTACATAGTAACAA
GAAACGCTGGCTTGGTCAAGAGACGTGGGGGTGGAACAGGAGAGACCCTGGGAGAGAAATGGAAGGCCCGCTTGAAC
CAGATGTCGGCCCTGGAGTTCTACTCCTACAAAAAGTCAGGCATCACCGAGGTGTGCAGAGAAGAGGCCCGCCGCGCCC
TCAAGGATGGTGTGGCAACGGGAGGCCATGCTGTGTCCCGAGGAAGTGCAAAGCTGAGATGGTTGGTGGAGCGGGGAT
ACCTGCAGCCCTATGGAAAGGTCATTGATCTTGGATGTGGCAGAGGGGCTGGAGTTACTACGCCGCCACCATCCGCAAA
GTTCAAGAAGTGAAAGGATACACAAAAGGAGGCCCTGGTCATGAAGAACCCGTGTTGGTGCAAAGCTATGGGTGGAAC
ATAGTCCGTCTTAAGAGTGGGGTGGACGTCTTTCATATGGCGGCTGAGCCGTGTGACACGTTGCTGTGTGACATAGGTGA
GTCATCATCTAGTCCTGAAGTGGAAGAAGCACGGACGCTCAGAGTCCTCTCCATGGTGGGGATTGGCTTGAAAAAAGA
CCAGGAGCCTTTTGTATAAAAGTGTTGTGCCCATACACCAGCACTATGATGGAAACCCTGGAGCGACTGCAGCGTAGGTA
TGGGGGAGGACTGGTCAGAGTGCCACTCTCCCGCAACTCTACACATGAGATGTACTGGGTCTCTGGAGCGAAAAGCAAC
ACCATAAAAAGTGTGTCCACCACGAGCCAGCTCCTCTTGGGGCGCATGGACGGGCCTAGGAGGCCAGTGAAATATGAGG
AGGATGTGAATCTCGGCTCTGGCACGCGGGCTGTGGTAAGCTGCGCTGAAGCTCCCAACATGAAGATCATTGGTAACCGC
ATTGAAAGGATCCGCAGTGAGCACGCGGAAACGTGGTTCTTTGACGAGAACCACCCATATAGGACATGGCTTACCATG
GAAGCTATGAGGCCCCCACACAAGGGTCAGCGTCCTCTCTAATAAACGGGGTTGTCAGGCTCCTGTCAAAACCCTGGGAT
GTGGTGACTGGAGTCACAGGAATAGCCATGACCGACACCACACCGTATGGTCAGCAAAGAGTTTTCAAGGAAAAAGTGG
ACACTAGGGTGCCAGACCCCCAAGAAGGCACTCGTCAGGTTATGAGCATGGTCTCTTCCTGGTTGTGGAAAGAGCTAGGC
AAACACAAACGGCCACGAGTCTGTACCAAAGAAGAGTTCATCAACAAGGTTCGTAGCAATGCAGCATTAGGGGCAATATT
```

-continued

```
TGAAGAGGAAAAAGAGTGGAAGACTGCAGTGGAAGCTGTGAACGATCCAAGGTTCTGGGCTCTAGTGGACAAGGAAAG

AGAGCACCACCTGAGAGGAGAGTGCCAGAGTTGTGTGTACAACATGATGGGAAAAGAGAAAAGAAACAAGGGGAATT

TGGAAAGGCCAAGGGCAGCCGCGCCATCTGGTATATGTGGCTAGGGGCTAGATTTCTAGAGTTCGAAGCCCTTGGATTCT

TGAACGAGGATCACTGGATGGGGAGAGAGAACTCAGGAGGTGGTGTTGAAGGGCTGGGATTACAAAGACTCGGATATG

TCCTAGAAGAGATGAGTCGCATACCAGGAGGAAGGATGTATGCAGATGACACTGCTGGCTGGGACACCCGCATCAGCAG

GTTCGATCTGGAGAATGAAGCTCTAATCACCAACCAAATGGAGAAAGGGCATAGGGCCTTGGCATTGGCCATAATCAAGT

ACACATACCAAAACAAAGTGGTAAAGGTCCTTAGACCAGCTGAAAAAGGGAAAACAGTTATGGACATTATTTCGAGACAA

GACCAAAGGGGGAGCGGACAAGTTGTCACTTACGCTCTTAACACATTTACCAACCTAGTGGTGCAACTCATTCGGAATAT

GGAGGCTGAGGAAGTTCTAGAGATGCAAGACTTGTGGCTGCTGCGGAGGTCAGAGAAAGTGACCAACTGGTTGCAGAG

CAACGGATGGGATAGGCTCAAACGAATGGCAGTCAGTGGAGATGATTGCGTTGTGAAGCCAATTGATGATAGGTTTGCA

CATGCCCTCAGGTTCTTGAATGATATGGGAAAAGTTAGGAAGGACACACAAGAGTGGAAACCCTCAACTGGATGGGACA

ACTGGGAAGAAGTTCCGTTTTGCTCCCACCACTTCAACAAGCTCCATCTCAAGGACGGGAGGTCCATTGTGGTTCCCTGCC

GCCACCAAGATGAACTGATTGGCCGGGCCCGCGTCTCTCCAGGGGGGGGATGGAGCATCCGGAGACTGCTTGCCTAGC

AAAATCATATGCGCAAATGTGGCAGCTCCTTTATTTCCACAGAAGGGACCTCCGACTGATGGCCAATGCCATTTGTTCATC

TGTGCCAGTTGACTGGGTTCCAACTGGGAGAACTACCTGGTCAATCCATGGAAAGGGAGAATGGATGACCACTGAAGAC

ATGCTTGTGGTGTGGAACAGAGTGTGGATTGAGGAGAACGACCACATGGAAGACAAGACCCCAGTTACGAAATGGACA

GACATTCCCTATTTGGGAAAAAGGGAAGCTTGTGGTGTGGATCTCTCATAGGGCACAGACCGCGCACCACCTGGGCTGA

GAACATTAAAAACACAGTCAACATGGTGCGCAGGATCATAGGTGATGAAGAAAGTACATGGACTACCTATCCACCCAAG

TTCGCTACTTGGGTGAAGAAGGGTCTACACCTGGAGTGCTGTAAGCACCAATCTTAATGTTGTCAGGCCTGCTAGTCAGC

CACAGCTTGGGGAAAGCTGTGCAGCCTGTGACCCCCCCAGGAGAAGCTGGGAAACCAAGCCTATAGTCAGGCCGAGAAC

GCCATGGCACGGAAGAAGCCATGCTGCCTGTGAGCCCCTCAGAGGACACTGAGTCAAAAAACCCCATGCGCTTGGAGGC

GCAGGATGGGAAAAGAAGGTGGCGACCTTCCCCACCCTTCAATCTGGGGCCTGAACTGGAGATCAGCTGTGGATCTCCA

GAAGAGGGACTAGTGGTTAGAGGAGACCCCCCGGAAAACGCAAAACAGCATATTGACGCTGGGAAAGACCAGAGACTC

CATGAGTTTCCACCACGCTGGCCGCCAGGCACAGATCGCCGAATAGCGGCGGCCGGTGTGGGGAAATCCATGGGTCTT
```

KU681081.3 Zika virus isolate Zika virus/*H. sapiens*-tc/THA/2014/SV0127- 14, Thailand, complete genome

SEQ ID NO: 7

```
AGTTGTTGATCTGTGTGAATCAGACTGCGACAGTTCGAGTTTGAAGCGAAAGCTAGCAACAGTATCAACAGGTTTTATTTT

GGATTTGGAAACGAGAGTTTCTGGTCATGAAAAACCCAAAAAAGAAATCCGGAGGATTCCGGATTGTCAATATGCTAAAA

CGCGGAGTAGCCCGTGTGAGCCCCTTTGGGGGCTTGAAGAGGCTGCCAGCCGGACTTCTGCTGGGTCATGGGCCCATCA

GGATGGTCTTGGCGATTCTAGCCTTTTTGAGATTCACGGCAATCAAGCCATCACTGGGTCTCATCAATAGATGGGGTTCAG

TGGGAAAAAAGAGGCTATGGAAATAATAAAGAAGTTCAAGAAAGATCTGGCTGCCATGCTGAGAATAATCAATGCTAG

GAAGGAGAAGAAGAGACGAGGCACAGATACTAGTGTCGGAATTGTTGGCCTCCTGCTGACCACAGCTATGGCAGCGGA

GGTCACTAGACGTGGGAGTGCATACTATATGTACTTGGACAGAAGCGATGCTGGGGAGGCCATATCTTTTCCAACCACAC

TGGGGATGAATAAGTGTTATATACAGATCATGGATCTTGGACACATGTGTGATGCCACCATGAGCTATGAATGCCCTATG

CTGGATGAGGGGTAGAACCAGATGACGTCGATTGTTGGTGCAACACGACGTCAACTTGGGTTGTGTACGGAACCTGCC

ATCACAAAAAAGGTGAAGCACGGAGATCCAGAAGAGCTGTGACGCTCCCCTCCCATTCCACTAGGAAGCTGCAAACGCG

GTCGCAGACCTGGTTGGAATCAAGAGAATACACAAAGCACTTGATTAGAGTCGAAATTGGATATTCAGGAACCCTGGCT

TCGCGTTAGCAGCAGCTGCCATCGCTTGGCTTTTGGGAAGCTCAACGAGCCAAAAGTCATATACTTGGTCATGATACTGC

TGATTGCCCCGGCATACAGCATCAGGTGCATAGGAGTCAGTAATAGGGACTTTGTGGAAGGTATGTCAGGTGGGACTTG

GGTTGATGTTGTCTTGGAACATGGAGGTTGTGTCACCGTAATGGCACAGGACAAACCGACTGTCGACATAGAGCTGGTTA
```

-continued

```
CAACAACAGTCAGCAACATGGCGGAGGTAAGATCCTACTGCTATGAGGCATCAATATCGGACATGGCTTCGGACAGCCG
CTGCCCAACACAAGGTGAAGCCTACCTTGACAAGCAATCAGACACTCAATATGTCTGCAAAAGAACGTTAGTGGACAGAG
GCTGGGGAAATGGATGTGGACTTTTTGGCAAAGGGAGCCTGGTGACATGCGCTAAGTTTGCATGCTCCAAGAAAATGAC
CGGGAAGAGCATCCAGCCAGAGAATCTGGAGTACCGGATAATGCTGTCAGTTCATGGCTCCCAGCACAGTGGGATGATC
GTTAATGACACAGGACATGAAACTGATGAGAATAGAGCGAAGGTTGAGATAACGCCCAATTCACCAAGAGCCGAAGCCA
CCCTGGGGGTTTTGGAAGCCTAGGACTTGATTGTGAACCGAGGACAGGCCTTGACTTTTCAGATTTGTATTACTTGACTA
TGAACAACAAGCACTGGTTGGTTCACAAGGAGTGGTTCCACGACATTCCATTACCTTGGCACACTGGGGCAGACACCGGA
ACTCCACACTGGAACAACAAAGAAGCACTGGTAGAGTTCAAGGACGCACATGCCAAAAGGCAAACTGTCGTGGTTCTAG
GGAGTCAAGAAGGAGCAGTTCACACGGCCCTTGCTGGAGCTCTGGAGGCTGAGATGGATGGTGCAAAGGGAAGGCTGT
CCTCTGGCCACTTGAAATGTCGCCTGAAAATGGATAAACTTAGATTGAAGGGCGTGTCATACTCCTTGTGTACCGCAGCGT
TCACATTCACCAAGATCCCGGCTGAAACACTGCACGGGACAGTCACAGTGGAGGTACAGTACGCAGGGACAGATGGACC
TTGCAAGGTTCCAGCTCAGATGGCGGTGGACATGCAAACTCTGACCCCAGTTGGGAGGTTGATAACCGCTAACCCCGTAA
TCACTGAAGGCACTGAGAACTCTAAGATGATGCTGGAACTTGATCCACCATTTGGGGACTCTTACATTGTCATAGGAGTCG
GGGAGAAGAAGATCACCCACCACTGGCACAGGAGTGGCAGCACCATTGGAAAAGCATTTGAAGCCACTGTGAGAGGTG
CCAAGAGAATGGCAGTCTTGGGAGACACAGCCTGGGACTTTGGATCAGTTGGAGGCGTTCTTAACTCATTGGGCAAGGG
CATCCATCAAATTTTTGGAGCAGCTTTCAAATCATTGTTTGGAGGAATGTCCTGGTTCTCACAAATTCTCATTGGAACGTTG
CTGATGTGGTTGGGTCTGAATACAAAGAATGGATCTATTTCCCTTATGTGCTTGGCCTTAGGGGAGTGTTGATCTTCTTA
TCCACAGCCGTCTCCGCTGATGTGGGGTGCTCGGTGGACTTCTCAAAGAAGGAAACGAGATGCGGTACAGGGGTGTTCG
TCTATAACGACGTTGAAGCCTGGAGGGACAGGTACAAGTACCATCCTGACTCCCCTCGTAGATTGGCAGCAGTAGTCAAG
CAAGCCTGGGAAGATGGTATCTGTGGGATCTCCTCTGTTTCAAGAATGGAAAACATCATGTGGAGATCAGTAGAAGGGG
AGCTCAACGCAATCCTGGAAGAGAATGGAGTTCAACTGACGGTCGTTGTGGGATCTGTAAAAAACCCCATGTGGAGAGG
TCCACAGAGATTGCCCGTGCCTGTGAACGAGCTGCCCCACGGCTGGAAGGCTTGGGGGAAATCGTACTTCGTCAGAGCA
GCAAAGACAAATAACAGCTTTGTCGTGGATGGTGACACACTGAAGGAATGCCCACTCAAACATAGAGCATGGAACAGCTT
TCTTGTGGAGGATCATGGGTTCGGGGTATTTCACACTAGTGTCTGGCTCAAGGTTAGAGAAGATTATTCACTAGAGTGTG
ATCCAGCCGTCATTGGAACAGCTGTTAAGGGAAAGGAGGCTGTACACAGTGATCTAGGCTACTGGATTGAGAGTGAGAA
GAACGACACATGGAGGCTGAGGAGGGCCCACCTGATCGAGATGAAAACATGTGAATGGCCAAAGTCCCACACATTGTGG
ACAGATGGAATAGAAGAGAGTGATCTGATCATACCCAAGTCTTTAGCTGGGCCACTCAGCCATCACAACACCAGAGAGG
GCTACAGGACCCAAATGAAAGGGCCATGGCACAGTGAAGAGCTTGAAATTCGGTTTGAGGAATGCCCAGGCACTAAGGT
CCACGTGGAGGAAACATGTGGAACAAGAGGACCATCTCTGAGATCAACCACTGCAAGCGGAAGGGTGATCGAGGAATG
GTGCTGCAGGGAGTGCACAATGCCCCCACTGTCGTTCCGGGCTAAAGATGGCTGTTGGTATGGAATGGAGATAAGGCCC
AGGAAAGAACCAGAAAGTAACTTAGTAAGGTCAATGGTGACTGCAGGATCAACTGATCACATGGATCACTTTTCCCTTGG
AGTGCTTGTGATTCTGCTCATGGTGCAGGAAGGGCTGAAGAAGAGAATGACCACAAAGATCATCATAAGCACATCAATG
GCAGTGCTGGTAGCTATGATCCTGGGAGGATTTTCAATGAGTGATCTGGCTAAGCTTGCAATTTTGATGGGTGCCACCTTT
GCGGAAATGAACACTGGAGGAGATGTAGCTCATCTGGCGCTGGTAGCGGCATTCAAAGTCAGACCAGCGTTGCTGGTAT
CTTTCATCTTCAGAGCTAATTGGACACCCCGTGAAAGCATGCTGCTGGCCTTGGCCTCGTGTCTTTTGCAAACTGCGATCTC
CGCCTTGGAAGGCGACCTGATGGTTCTCATCAATGGTTTTGCTTTGGCCTGGTTGGCAATACGAGCGATGGTTGTTCCACG
CACTGACAATATCACCTTGGCAATCCTGGCTGCTCTGACACCACTGGCCCGGGGCACACTGCTTGTGGCGTGGAGAGCAG
GCCTTGCTACTTGCGGGGGGTTCATGCTCCTCTCTCTGAAGGGGAAAGGCAGTGTGAAGAAGAACTTACCATTTGTCATG
GCCCTGGGACTAACCGCTGTGAGGCTGGTCGACCCCATCAACGTGGTGGGACTGCTGTTGCTCACAAGGAGTGGGAAGC
GGAGCTGGCCCCCTAGCGAAGTACTCACAGCTGTTGGCCTGATATGCGCATTGGCTGGAGGGGTTCGCCAAGGCAGATAT
```

-continued

```
AGAGATGGCTGGGCCCATGGCCGCGGTCGGTCTGCTAATTGTCAGTTACGTGGTCTCAGGAAAGAGTGTGGACATGTAC
ATTGAAAGAGCAGGTGACATCACATGGGAAAAAGATGCGGAAGTTACTGGAAACAGTCCCCGGCTCGATGTGGCACTAG
ATGAGAGTGGTGATTTCTCCCTGGTGGAGGATGACGGTCCCCCCATGAGAGAGATCATACTCAAAGTGGTCCTGATGACC
ATCTGTGGCATGAACCCAATAGCCATACCCTTTGCAGCTGGAGCGTGGTACGTATACGTGAAAACTGGAAAAAGGAGTG
GTGCTCTATGGGATGTGCCTGCTCCCAAGGAAGTAAAAAAGGGGGAGACCACAGATGGAGTGTACAGAGTAATGACTCG
TAGACTGCTAGGTTCAACACAAGTTGGAGTGGGAGTTATGCAAGAGGGGGTCTTTCACACTATGTGGCATGTCACAAAAG
GATCCGCGCTGAGAAGCGGTGAAGGGAGACTTGATCCATACTGGGGAGATGTCAAGCAGGATCTGGTGTCATACTGTGG
TCCATGGAAGCTAGATGCCGCCTGGGACGGGCACAGCGAGGTGCAGCTCTTGGCCGTGCCCCCCGGAGAGAGAGCGAG
GAACATCCAGACTCTGCCCGGAATATTTAAGACAAAGGATGGGGACATTGGAGCGGTTGCGCTGGACTATCCAGCAGGA
ACTTCAGGATCTCCAATCCTAGACAAGTGTGGGAGAGTGATAGGACTCTATGGCAATGGGGTCGTGATCAAGAATGGGA
GTTATGTCAGTGCCATCACCCAAGGGAGGAGGGAGGAAGAGACTCCTGTTGAGTGCTTCGAGCCTTCGATGCTGAAGAA
GAAGCAGCTAACTGTCTTAGACTTGCATCCTGGAGCTGGAAAAACCAGGAGAGTTCTTCCTGAAATAGTCCGTGAAGCCA
TAAAAACGAGACTCCGTACTGTGATCTTAGCTCCAACCAGGGTTGTCGCTGCTGAAATGGAGGAAGCCCTTAGAGGGCTT
CCAGTGCGTTATATGACAACAGCAGTCAATGTCACCCATTCTGGGACAGAAATCGTTGACTTAATGTGCCATGCCACCTTC
ACTTCACGTCTACTACAGCCAATCAGAGTCCCCAACTATAATCTGTATATTATGGATGAGGCCCACTTCACAGATCCCTCAA
GTATAGCAGCAAGAGGATACATTTCAACAAGGGTTGAGATGGGCGAGGCAGCTGCCATCTTCATGACCGCCACGCCACC
AGGAACCCGTGACGCATTCCCGGACTCCAACTCACCAATTATGGACACCGAAGTGGAAGTCCCAGAGAGAGCCTGGAGC
TCAGGCTTTGATTGGGTGACGGATCATTCTGGAAAAACAGTTTGGTTTGTCCCAAGCGTGAGGAACGGCAATGAGATCGC
AGCTTGTCTGACAAAGGCTGGAAAACGGGTCATACAGCTCAGCAGAAAGACTTTTGAGACAGAGTTCCAGAAAACAAAA
CATCAAGAGTGGGACTTCGTCGTGACAACTGACATTTCAGAGATGGGCGCCAACTTTAAAGCTGACCGTGTCATAGATTC
CAGGAGATGCCTAAAGCCGGTCATACTTGATGGCGAGAGAGTCATTCTGGCTGGACCCATGCCTGTCACACATGCCAGCG
CTGCCCAGAGGAGGGGGCGCATAGGCAGGAATCCCAACAAACCTGGAGATGAGTATCTGTATGGAGGTGGGTGCGCAG
AGACTGATGAAGACCATGCACACTGGCTTGAAGCAAGAATGCTCCTTGACAATATTTACCTCCAAGATGGCCTCATAGCCT
CGCTCTATCGACCTGAGGCCGACAAAGTAGCAGCCATTGAGGGAGAGTTCAAGCTTAGGACGGAGCAAAGGAAGACCTT
TGTGGAACTCATGAAAAGAGGAGATCTTCCTGTTTGGCTGGCCTATCAGGTTGCATCTGCCGGAATAACCTACACAGATA
GAAGATGGTGCTTTGATGGCATGACCAACAACACCATAATGGAAGACAGTGTGCCGGCAGAGGTGTGGACCAGACACG
GAGAGAAAAGAGTGCTCAAACCGAGGTGGATGGACGCCAGAGTTTGTTCAGATCATGCGGCCCTGAAGTCATTCAAGGA
GTTTGCCGCTGGGAAAAGAGGAGCGGCTTTTGGAGTGATGGAAGCCCTGGGAACACTGCCAGGACACATGACGGAGAG
ATTCCAGGAAGCCATTGACAACCTCGCTGTGCTCATGCGGGCAGAGACTGGAAGCAGGCCTTACAAAGCCGCGGCGGCC
CAATTGCCGGAGACCCTAGAGACCATTATGCTTTTGGGGTTGCTGGGAACAGTCTCGCTGGGAATCTTTTTCGTCTTGATG
CGGAACAAGGGCATAGGGAAGATGGGCTTTGGAATGGTGACTCTTGGGGCCAGCGCATGGCTCATGTGGCTCTCGGAAA
TTGAGCCAGCCAGAATTGCATGCGTCCTCATTGTTGTGTTCCTATTGCTGGTGGTGCTCATACCTGAGCCAGAAAAGCAAA
GATCCCCCCAGGACAACCAAATGGCAATCATCATCATGGTAGCAGTAGGTCTTCTGGGCTTGATTACCGCCAATGAACTCG
GATGGTTGGAGAGAACAAAGAGTGACCTAAGCCATCTAATGGGAAGGAGAGAGGAGGGGGCAACCATAGGATTCTCAA
TGGACATTGACCTGCGGCCAGCCTCGGCCTGGGCCATCTATGCTGCCCTGACAACTTTCATTACCCCAGCCGTCCAACATG
CAGTGACCACTTCATACAACAACTACTCCTTAATGGCGATGGCCACGCAAGCTGGAGTGTTGTTTGGTATGGGCAAAGGG
ATGCCATTCTACGCATGGGACTTTGGAGTCCCGCTGCTAATGATAGGTTGCTACTCACAATTAACACCCCTGACCCTAATA
GTGGCTATCATTTTGCTCGTGGCGCACTACATGTACTTGATCCCAGGGCTGCAGGCAGCAGCTGCGCGTGCTGCCCAGAA
GAGAACGGCAGCTGGCATCATGAAGAACCCTGTTGTGGATGGAATAGTGGTGACTGACATTGACACAATGACTATTGAC
CCCCAAGTGGAGAAAAAGATGGGACAGGTGCTACTCATAGCAGTAGCCGTCTCCAGCGCCATACTGTCGCGGACCGCCT
GGGGGTGGGGGGAAGCTGGGGCCCTGATCACAGCTGCAACTTCCACTTTGTGGGAAGGCTCTCCGAACAAGTACTGGAA
```

-continued

```
CTCCTCTACAGCCACTTCACTGTGCAACATTTTTAGGGGAAGTTACTTGGCTGGAGCTTCTCTAATCTACACAGTAACAAGA
AACGCTGGCTTGGTCAAGAGACGTGGGGGTGGAACAGGAGAGACCCTGGGAGAGAAATGGAAGGCCCGCTTGAACCA
GATGTCGGCCCTGGAGTTCTACTCCTACAAAAAGTCAGGCATCACCGAGGTGTGCAGAGAAGAGGCCCGCCGCGCCCTC
AAGGACGGTGTGGCAACGGGAGGCCATGCTGTGTCCCGAGGAAGTGCAAAGCTGAGATGGTTGGTGGAGCGGGGATAC
CTGCAGCCCTATGGAAAGGTCATTGATCTTGGATGTGGCAGAGGGGCTGGAGTTACTACGCCGCCACCATCCGCAAAGT
TCAAGAAGTGAAAGGATACACAAAAGGAGGCCCTGGTCATGAAGAACCCATGTTGGTGCAAAGCTATGGGTGGAACATA
GTCCGTCTTAAGAGTGGGGTGGACGTCTTTCATATGGCGGCTGAGCCGTGTGACACGTTGCTGTGTGACATAGGTGAGTC
ATCATCTAGTCCTGAAGTGGAAGAAGCACGGACGCTCAGAGTCCTCTCCATGGTGGGGGATTGGCTTGAAAAAAGACCA
GGAGCCTTTTGTGTAAAAGTGTTGTGCCCATACACCAGCACTATGATGGAAACCCTGGAGCGACTGCAGCGTAGGTATGG
GGGAGGACTGGTCAGAGTGCCACTCTCCCGCAACTCTACACATGAGATGTACTGGGTCTCTGGAGCGAAAAGCAACACC
ATAAAAGTGTGTCCACCACGAGCCAGCTCCTCTTGGGGCGCATGGACGGGCCCAGGAGGCCAGTGAAATATGAGGAG
GATGTGAATCTCGGCTCTGGCACGCGGGCTGTGGTAAGCTGCGCTGAAGCTCCCAACATGAAGATCATTGGTAACCGCAT
TGAAAGGATCCGCAGTGAGCACGCGGGAAACGTGGTTCTTTGACGAGAACCACCCATATAGGACATGGGCTTACCATGGA
AGCTATGAGGCCCCTACACAAGGGTCAGCGTCCTCTCTAATAAACGGGGTTGTCAGGCTCCTGTCAAAACCCTGGGATGT
GGTGACTGGAGTCACAGGAATAGCCATGACCGACACCACACCGTATGGTCAGCAAAGAGTTTTCAAGGAAAAGTGGAC
ACCAGGGTGCCAGACCCCCAAGAAGGCACTCGTCAGGTTATGAGCATGGTCTCTTCCTGGTTGTGGAAAGAGCTAGGCA
AACACAAACGGCCACGAGTCTGTACCAAAGAAGAGTTCATCAACAAGGTTCGTAGCAATGCAGCATTAGGGGCAATATTT
GAAGAGGAAAAAGAGTGGAAGACCGCAGTGGAAGCTGTGAACGATCCAAGGTTCTGGGCTCTAGTGGACAAGGAAAGA
GAGCACCACCTGAGAGGAGAGTGCCAGAGCTGTGTGTACAACATGATGGGAAAAAGAGAAAAGAAACAAGGGGAATTT
GGAAAGGCCAAGGGCAGCCGCGCCATCTGGTATATGTGGCTAGGGGCTAGATTTCTAGAGTTCGAAGCCCTTGGATTCTT
AAATGAGGATCACTGGATGGGGAGAGAGAACTCAGGAGGTGGTGTTGAAGGGCTGGGATTACAAAGACTCGGATATGT
CCTAGAAGAGATGAGTCGCATACCAGGAGGAAGGATGTATGCAGATGACACTGCTGGCTGGGACACCCGCATCAGCAG
GTTTGATCTGGAGAATGAAGCTTTAATCACCAACCAAATGGAGAAAGGGCACAGGGCCTTAGCATTGGCCATAATCAAGT
ACACATACCAAAACAAAGTGGTAAAGGTCCTTAGACCAGCTGAAAAAGGGAAGACAGTTATGGACATTATTTCAAGACAA
GACCAAAGGGGGAGCGGACAAGTIGTCACTTACGCTCTTAACACATTTACCAACCTAGTGGTGCAACTCATTCGGAATAT
GGAGGCTGAGGAAGTTCTAGAGATGCAAGACTTGTGGCTGCTGCGGAGGTCAGAGAAAGTGACCAACTGGTTGCAGAG
CAACGGATGGGATAGGCTCAAACGAATGGCAGTCAGTGGAGATGATTGCGTTGTGAAGCCAATTGATGATAGGTTTGCA
CATGCCCTCAGGTTCTTGAATGATATGGGAAAAGTTAGGAAGGACACACAAGAGTGGAAACCCTCAACTGGATGGGACA
ACTGGGAAGAAGTTCCGTTTTGTTCCCACCACTTCAACAAGCTCCATCTCAAGGACGGGAGGTCATTGTGGTTCCCTGCC
GCCACCAAGATGAACTGATTGGCCGGGCCCGTGTCTCTCCAGGGGGGGATGGAGCATCCGGGAGACTGCTTGCCTAGC
AAAGTCATATGCGCAAATGTGGCAGCTCCTTTATTTCCACAGAAGGGACCTCCGACTGATGGCCAATGCCATCTGTTCATC
TGTGCCAGTTGACTGGGTTCCAACTGGGAGAACTACCTGGTCAATCCATGGAAAGGGAGAATGGATGACCACTGAAGAC
ATGCTTGTGGTGTGGAACAGAGTGTGGATTGAGGAGAACGACCACATGGAAGACAAGACCCCAGTTACGAAATGGACA
GACATTCCCTATCTGGGAAAAAGGGAAGACTTGTGGTGTGGATCTCTCATAGGGCACAGACCGCGCACCACCTGGGCTG
AGAACATTAAAAACACAGTCAACATGGTGCGCAGGATCATAGGTGATGAAGAAAGTACATGGACTACCTATCCACCCAA
GTTCGCTACTTGGGTGAAGAAGGGTCTACACCTGGAGTGCTATAAGCACCAATCTTAGTGTTGTCAGGCCTGCTAGTCAG
CCACAGCTTGGGGAAAGCTGTGCAGCCTGTGACCCCCCAGGAGAGGCTGGGAAACCAAGCCCATAGTCAGGCCGAGAA
CGCCATGGCACGGAAGAAGCCATGCTGCCTGTGAGCCCCTCAGAGGACACTGAGTCAAAAAACCCCACGCGCTTGGAGG
```

-continued

CGCAGGATGGGAAAAGAAGGTGGCGACCTTCCCCACCCTTCAATCTGGGGCCTGAACTGGAGATCAGCTGTGGATCTCC

AGAAGAGGGACTAGTGGTTAGAGGAGACCCCCCGGAAAACGCAAAACAGCATATTGACGCTGGGAAAGACCAGAGACT

CCATGAGTTTCCACCACGCTGGCCGCCAGGCACAGATCGCCGAATAGCGGCGGCCGGTGTGGGGAAATCCATGGGTCT

KU681082.3 Zika virus isolate Zika virus/H.sapiens-tc/PHL/2012/CPC-0740,
Philippines, complete genome

SEQ ID NO: 8

AGTTGTTGATCTGTGTGAATCAGACTGCGACAGTTCGAGTTTGAAGCGAAAGCTAGCAACAGTATCAACAGGTTTTATTTT

GGATTTGGAAACGAGAGTTTCTGGTCATGAAAAACCCAAAAAAGAAATCCGGAGGATTCCGGATTGTCAATATGCTAAAA

CGCGGAGTAGCCCGTGTGAGCCCCTTTGGGGGCTTGAAGAGGCTGCCAGCCGGACTTCTGCTGGGCCATGGGCCCATCA

GGATGGTCTTGGCGATACTAGCCTTTTTGAGATTCACGGCAATCAAGCCATCACTGGGTCTCATCAATAGATGGGGTTCA

GTGGGGAAAAAAGAGGCTATGGAAATAATAAAGAAGTTCAAGAAAGATCTGGCTGCCATGCTGAGAATAATCAATGCTA

GGAAGGAGAAGAAGAGACGAGGCGCAGATACTAGCGTCGGAATTGTTGGCCTCCTCCTGACCACAGCCATGGCAGTAG

AGGTCACTAGACGTGGGAGTGCATACTATATGTACTTGGACAGAAGCGATGCTGGGGAGGCCATATCTTTTCCAACCACA

CTGGGGATGAATAAGTGTTACATACAAATCATGGATCTTGGACACATGTGTGATGCCACCATGAGCTATGAATGCCCTAT

GTTGGATGAGGGGGTAGAACCAGATGACGTCGATTGCTGGTGCAACACGACATCAACTTGGGTTGTGTATGGAACCTGC

CACCACAAAAAAGGTGAAGCACGGAGATCTAGAAGAGCTGTGACGCTCCCCTCCCATTCCACTAGGAAGCTGCAAACGC

GGTCGCAGACCTGGTTGGAATCAAGAGAATACACAAAGCACCTGATTAGAGTTGAAAATTGGATATTCAGGAACCCTGG

CTTCGCGTTAGCAGCAGCTGTCATCGCTTGGCTTTTGGGAAGTTCAACGAGCCAAAAAGTCATATATCTGGTCATGATACT

GCTGATTGCCCCGGCATACAGCATCAGGTGCATAGGAGTCAGCAATAGGGACTTTGTGGAAGGTATGTCAGGTGGGACT

TGGGTTGATGTTGTCTTGGAACATGGAGGTTGTGTTACCGTAATGGCACAGGACAAACCGACTGTCGACATAGAGCTGGT

TACAACAACAGTCAGCAACATGGCGGAGGTAAGATCCTACTGCTATGAGGCATCAATATCGGATATGGCTTCGGACAGCC

GCTGCCCAACACAAGGTGAGGCCTACCTTGACAAGCAGTCAGACACTCAATATGTCTGCAAAAGAACGTTAGTGGACAGA

GGCTGGGGAAATGGATGTGGACTTTTTGGCAAAGGGAGCCTGGTGACATGCGCTAAGTTTGCATGCTCCAAGAAAATGA

CCGGGAAGAGCATCCAGCCAGAGAATCTGGAGTACCGGATAATGCTGTCAGTTCATGGCTCCCAGCACAGTGGGATGAT

CGTTAATGACACAGGACATGAAACTGATGAGAATAGAGCGAAGGTTGAGATAACGCCCAATTCACCAAGAGCCGAAGCC

ACCCTGGGGGTTTTGGGAGCCTAGGACTTGATTGTGAACCGAGGACAGGCCTTGACTTTTCAGATTTGTATTACCTGACT

ATGAATAACAAGCACTGGTTGGTTCACAAGGAGTGGTTCCACGACATTCCATTACCTTGGCATGCTGGGGCAGACACTGG

AACTCCACATTGGAACAACAAAGAAGCACTGGTAGAGTTCAAGGACGCACATGCAAAAAGGCAAACTGTCGTGGTTCTA

GGGAGTCAAGAAGGAGCAGTTCACACGGCCCTTGCTGGAGCTCTGGAGGCTGAGATGGATGGAGCCAAGGGAAGGCTG

TCCTCTGGCCACTTGAAATGTCGCCTGAAAATGGATAAACTTAGATTGAAGGGCGTGTCATACTCCTTGTGCACTGCAGCG

TTCACATTCACCAAGATCCCGGCTGAAACACTGCACGGGACAGTCACAGTGGAGGTACAGTACGCAGGGACAGATGGAC

CTTGCAAGGTTCCAGCTCAGATGGCGGTGGATATGCAAACTCTGACCCCAGTTGGGAGGTTGATAACCGCTAACCCTGTA

ATCACTGAAAGCACCGAGAACTCTAAGATGATGCTGGAACTTGATCCACCATTTGGGGACTCTTACATTGTCATAGGAGTC

GGGGAGAAGAAGATCACCCATCACTGGCACAGGAGTGGCAGCACCATTGGAAAAGCATTTGAAGCCACTGTGAGAGGT

GCCAAGAGAATGGCAGTCTTGGGAGACACAGCCTGGGACTTTGGATCAGTTGGGGGTGCTCTCAACTCATTGGGCAAGG

GCATCCATCAAATTTTTGGAGCAGCTTTCAAATCATTGTTCGGAGGAATGTCCTGGTTCTCACAAATTCTCATTGGAACGTT

GCTGGTGTGGTTGGGTCTGAATACAAAGAATGGATCTATTTCCCTTACGTGCTTGGCCTTAGGGGGAGTGTTGATCTTCTT

ATCCACAGCCGTTTCTGCTGATGTGGGGTGCTCGGTGGACTTCTCAAAGAAGGAAACGAGATGCGGTACAGGGGTGTTC

GTCTATAACGACGTTGAAGCCTGGAGGGACAGGTACAAGTACCATCCTGACTCCCCTCGTAGATTGGCAGCAGCAGTCAA

GCAAGCCTGGGAAGATGGGATCTGTGGGATCTCCTCTGTCTCAAGAATGGAAAACATCATGTGGAGATCAGTAGAAGGG

GAGCTCAACGCAATCCTGGAAGAGAATGGAGTTCAACTGACGGTCGTTGTGGGATCTGTAAAAAACCCCATGTGGAGAG

-continued

```
GTCCACAGAGATTGCCCGTGCCTGTGAACGAGCTGCCCCACGGCTGGAAGGCTTGGGGGAAATCGTACTTCGTCAGAGC

AGCAAAGACAAATAACAGCTTTGTCGTGGATGGTGACACACTGAAGGAATGCCCACTCAAACATAGAGCATGGAACAGC

TTTCTTGTGGAGGATCATGGGTTTGGGGTATTTCACACTAGTGTCTGGCTCAAGGTTAGAGAAGATTATTCATTAGAGTGT

GATCCAGCCGTCATTGGAACAGCTGCTAAGGGAAAGGAGGCTGTGCACAGCGATCTAGGCTACTGGATTGAGAGTGAGA

AGAACGACACATGGAGGCTGAAGAGGGCCCACCTGATCGAGATGAAAACATGTGAATGGCCAAAGTCCCACACATTGTG

GACAGATGGAGTAGAAGAAAGTGATCTGATCATACCCAAGTCTTTAGCTGGGCCACTCAGCCATCACAACACCAGAGAG

GGCTACAGGACTCAAATGAAAGGGCCATGGCACAGTGAAGAGCTTGAAATTCGGTTTGAGGAATGCCCAGGCACTAAGG

TCCACGTGGAGGAAACATGTGGGACAAGAGGACCATCCCTGAGATCAACCACTGCAAGCGGAAGGGTGATCGAGGAAT

GGTGCTGCAGGGAATGCACAATGCCCCCACTGTCGTTCCGAGCTAAAGATGGCTGTTGGTATGGAATGGAGATAAGGCC

CAGGAAAGAACCAGAAAGTAACTTAGTAAGGTCAATGGTGACTGCAGGATCAACTGATCACATGGATCACTTCTCTCTTG

GAGTGCTTGTGATTTTGCTCATGGTGCAGGAAGGGCTGAAGAAGAGAATGACCACAAAGATCATCATAAGCACATCAAT

GGCAGTGCTGGTAGCCATGATCCTGGGAGGATTTTCAATGAGTGACCTGGCTAAGCTTGCAATTTTGATGGGTGCCACCT

TCGCGGAAATGAACACTGGAGGAGATGTAGCTCATTTGGCGCTGATAGCGGCATTCAAAGTCAGACCTGCGTTGCTGGTA

TCTTTCATCTTCAGAGCTAATTGGACACCCCGTGAGAGCATGCTGCTGGCCTTGGCCTCGTGTCTTCTGCAAACTGCGATCT

CCGCCTTGGAAGGCGACCTGATGGTTCTCATCAATGGTTTTGCTTTGGCCTGGTTGGCAATACGAGCGATGGTTGTTCCAC

GCACTGACAACATCACCTTGGCAATCCTGGCTGCTCTGACACCACTGGCCCGGGGCACACTGCTTGTGGCGTGGAGAGCA

GGCCTTGCTACTTGCGGGGGGTTCATGCTCCTCTCTCTGAAGGGGAAAGGCAGTGTGAAGAAGAACCTACCATTTGTCAT

GGCCTTGGGACTAACTGCTGTGAGGCTGGTCGACCCCATCAACGTGGTGGGACTGCTGTTGCTCACAAGGAGTGGGAAG

CGGAGCTGGCCCCCTAGTGAAGTACTCACAGCTGTTGGCCTGATATGCGCATTGGCTGGAGGGTTCGCCAAGGCGGATA

TAGAGATGGCTGGGCCCATGGCCGCGGTCGGTCTGCTAATTGTCAGTTACGTGGTCTCAGGAAAGAGTGTGGACATGTA

CATTGAAAGAGCAGGTGACATCACATGGGAAAAAGATGCGGAAATCACTGGAAACAGTCCCCGGCTCGATGTGGCACTA

GATGAGAGTGGTGATTTCTCCCTAGTGGAGGATGATGGTCCACCCATGAGAGAGATCATACTCAAAGTGGTCCTGATGAC

CATCTGCGGCATGAACCCAATAGCCATACCCTTTGCAGCTGGAGCGTGGTACGTGTATGTGAAGACTGGAAAAAGGAGT

GGTGCTCTATGGGATGTGCCTGCTCCCAAGGAAGTAAAAAAGGGGGAGACCACAGATGGAGTGTACAGAGTAATGACTC

GTAGACTGCTTGGTTCAACACAAGTTGGAGTGGGAGTCATGCAAGAGGGGGTCTTCCACACTATGTGGCACGTCACAAA

AGGATCCGCGCTGAGAAGCGGTGAAGGGAGACTTGATCCATACTGGGGAGATGTCAAGCAGGATCTGGTGTCATACTGT

GGTCCGTGGAAGCTAGACGCCGCCTGGGACGGGCACAGCGAGGTGCAGCTCTTGGCCGTGCCCCCCGGAGAGAGAGCG

AGGAACATCCAGACTCTGCCCCGGAACATTTAAGACAAAGGATGGGACATTGGAGCAGTTGCGCTGGACTACCCAGCAG

GAACTTCAGGATCTCCAATCCTAGACAAGTGTGGGAGAGTGATAGGACTCTATGGTAATGGGGTCGTGATAAAAAATGG

GAGTTATGTTAGTGCCATCACCCAAGGGAGGAGGGAGGAAGAGACTCCTGTTGAGTGCTTCGAGCCTTCGATGCTGAAG

AAGAAGCAGCTAACTGTCTTAGACCTGCATCCTGGAGCCGGGAAAACCAGGAGAGTTCTTCCTGAAATAGTCCGTGAAGC

CATAAAAACAAGACTCCGTACTGTGATCTTAGCTCCAACCAGGGTCGTCGCTGCTGAAATGGAGGAAGCCCTTAGAGGGC

TTCCAGTTCGTTATATGACAACAGCAGTCAATGTCACCCATTCTGGGACAGAAATCGTTGACTTAATGTGCCATGCTACCTT

CACTTCACGCCTACTACAACCAATCAGAGTCCCCAACTATAATTTGTATATTATGGATGAGGCCCACTTCACAGATCCCTCA

AGTATAGCAGCAAGAGGATACATTTCAACAAGGGTTGAGATGGGCGAGGCGGCTGCCATCTTCATGACCGCCACGCCAC

CAGGAACCCGTGACGCATTCCCGGACTCCAACTCACCAATTATGGACACCGAGGTGGAAGTCCCAGAGAGAGCCTGGAG

CACAGGCTTTGATTGGGTGACGGATCATTCTGGGAAAACAGTCTGGTTTGTTCCAAGCGTGAGGAACGGCAATGAGATC

GCAGCTTGTCTGACAAAGGCTGGAAAACGGGTCATACAGCTCAGCAGAAAGACTTTTGAGACAGAGTTCCAGAAAACGA

AAAATCAAGAGTGGGACTTCGTCGTGACAACCGACATTTCAGAGATGGGCGCCAACTTTAAAGCTGACCGTGTCATAGAT

TCCAGGAGATGCTTAAAGCCGGTCATACTTGATGGCGAGAGAGTCATTTTGGCTGGACCCATGCCTGTCACACATGCCAG
```

-continued

```
CGCTGCTCAGAGGAGGGGCGCATAGGCAGGAATCCCAACAAACCTGGAGATGAGTATCTGTATGGAGGTGGGTGCGC
AGAGACTGATGAAGATCACGCACACTGGCTTGAAGCAAGAATGCTTCTTGACAACATTTACCTCCAAGATGGCCTCATAG
CTTCGCTCTATCGACCTGAGGCCGACAAAGTAGCAGCTATTGAGGGAGAGTTCAAGCTTAGGACGGAGCAAAGGAAGAC
CTTTGTGGAACTCATGAAAAGAGGAGATCTTCCGGTTTGGTTGGCCTATCAGGTTGCATCTGCCGGAATAACCTACACAG
ATAGAAGATGGTGCTTTGATGGCATGACCAACAACACCATAATGGAAGACAGTGTGCCGGCAGAGGTGTGGACCAGATA
CGGAGAGAAAAGAGTGCTCAAACCGAGGTGGATGGACGCCAGAGTTTGTTCAGATCATGCGGCCCTGAAGTCATTCAAA
GAGTTTGCCGCTGGGAAAAGAGGAGCGGCCTTTGGAGTGATAGAAGCCCTGGGAACACTGCCAGGACACATGACAGAG
AGATTCCAGGAAGCCATTGACAACCTCGCTGTGCTCATGCGGGCAGAGACTGGAAGCAGGCCTTACAAAGCCGCGGCGG
CCCAATTGCCGGAGACCCTAGAGACCATTATGCTTTTGGGGTTGCTGGGAACAGTCTCGCTGGGAATCTTTTTCGTCTTGA
TGCGGAACAAGGGCATGGGGAAGATGGGCTTTGGAATGGTGACTCTTGGGGCCAGCGCATGGCTTATGTGGCTCTCGGA
AATTGAGCCAGCCAGAATTGCATGTGTCCTCATTGTCGTGTTCCTATTGCTGGTGGTGCTCATACCTGAGCCAGAAAAGCA
AAGATCTCCTCAGGACAACCAAATGGCAATCATCATCATGGTAGCAGTGGGTCTTCGGGCTTGATTACCGCCAATGAACT
CGGATGGTTGGAGAGAACAAAAAGTGACCTAAGCCATCTAATGGGAAGGAGAGAGGAGGGGGCAACCACAGGATTCTC
AATGGACATTGACCTGCGGCCAGCCTCAGCTTGGGCTATCTATGCTGCTCTGACAACTTTCATCACCCCAGCCGTCCAACA
TGCGGTGACCACTTCATACAACAACTACTCCTTAATGGCGATGGCCACGCAAGCTGGGGTGTTGTTTGGTATGGGCAAAG
GGATGCCATTCTACGCATGGGACTTTGGAGTCCCGCTGCTAATGATGGGTTGCTACTCACAATTAACACCTCTGACCCTAA
TAGTGGCCATCATTTTGCTCGTGGCGCACTACATGTACTTGATCCCAGGGCTGCAGGCAGCAGCTGCGCGGGCTGCCCAG
AAGAGAACGGCAGCTGGCATCATGAAGAACCCTGTTGTGGATGGAATAGTGGTGACTGACATTGACACAATGACAATTG
ACCCCCAAGTGGAAAAAAAGATGGGGCAGGTGCTACTCATAGCAGTAGCCGTCTCCAGCGCCATACTGTCGCGGACCGC
CTGGGGGTGGGGGAGGCTGGGGCCCTGATCACAGCTGCAACTTCCACCTTGTGGGAAGGCTCTCCGAACAAGTACTGG
AACTCCTCCACAGCCACTTCACTGTGTAACATTTTTAGGGGAAGTTACTTGGCTGGAGCTTCTCTAATCTACACAGTAACAA
GAAACGCTGGCTTGGTCAAGAGACGTGGGGGTGGAACGGGAGAGACCCTGGGAGAGAAATGGAAGGCCCGCCTGAAC
CAGATGTCGGCCCTGGAGTTCTACTCCTACAAAAAGTCAGGCATCACCGAGGTGTGCAGAGAAGAGGCCCGCCGTGCCCT
CAAGGACGGTGTGGCAACAGGAGGCCATGCTGTGTCCCGAGGAAGTGCAAAGCTTAGATGGCTGGTGGAGAGAGGATA
CCTGCAGCCCTATGGAAAGGTCATTGATCTTGGATGTGGCAGAGGGGGCTGGAGTTACTATGCCGCCACCATCCGCAAAG
TTCAGGAAGTGAAAGGATACACAAAAGGAGGCCCTGGTCATGAAGAACCCATGTTGGTGCAAAGCTATGGGTGGAACAT
AGTCCGTCTTAAGAGTGGGGTGGACGTCTTTCACATGGCGGCTGAGCCGTGTGACACTTTGCTGTGTGATATAGGTGAGT
CATCATCTAGTCCTGAAGTGGAAGAAGCACGGACGCTCAGAGTCCTCTCCATGGTGGGGATTGGCTTGAAAAAAGACC
AGGAGCCTTTTGTATAAAAGTGTTGTGCCCATACACCAGCACTATGATGGAAACCCTGGAGCGACTGCAGCGTAGGTATG
GGGGAGGACTGGTCAGGGTGCCACTCTCCCGCAACTCTACACATGAGATGTACTGGGTCTCTGGAGCGAAAAGCAACAC
CATAAAAAGTGTGTCCACCACGAGCCAGCTCCTCTTGGGGCGCATGGACGGGCCCAGGAGGCCAGTGAAATATGAGGAG
GATGTGAATCTCGGCTCTGGCACGCGGGCTGTGGTAAGCTGCGCTGAAGCTCCCAACATGAAGATCATTGGTAACCGCAT
TGAGAGGATCCGCAGTGAGCACGCGGAAACGTGGTTCTTTGACGAGAACCACCCATATAGGACATGGGCTTACCATGGA
AGCTATGAGGCCCCTACACAAGGGTCAGCGTCCTCTCTAATAAACGGGGTTGTCAGGCTCCTGTCAAAACCCTGGGATGT
GGTGACTGGAGTCACAGGAATAGCCATGACTGACACCACACCGTATGGTCAGCAAAGAGTTTTCAAGGAAAAAGTGGAC
ACTAGGGTGCCAGACCCCCAAGAAGGCACTCGTCAGGTTATGAGCATGGTCTCTTCCTGGTTATGGAAGGAGCTAGGCAA
ACACAAACGGCCACGAGTCTGTACCAAAGAAGAGTTCATCAACAAGGTTCGTAGCAATGCAGCATTAGGGGCAATATTTG
AAGAGGAAAAGAGTGGAAGACTGCAGTGGAAGCTGTGAATGATCCAAGGTTCTGGGCTCTAGTGGACAAGGAAAGAG
AGCATCACCTGAGAGGAGAGTGTCAGAGCTGTGTGTACAACATGATGGGAAAAAGAGAAAAGAAACAAGGGGAATTTG
GAAAGGCCAAGGGCAGCCGCGCCCATCTGGTATATGTGGCTAGGGGCTAGATTCCTAGAGTTCGAAGCCCTTGGATTCTTG
AATGAGGATCATTGGATGGGGAGAGAGAATTCAGGAGGTGGTGTTGAAGGACTGGGATTACAAAGACTCGGATATGTC
```

-continued

CTAGAAGAGATGAGTCGCATACCAGGAGGAAGGATGTATGCAGATGATACTGCTGGCTGGGACACCCGCATCAGCAGGT
TTGATCTGGAGAATGAAGCTCTAATCACCAACCAAATGGAGAAAGGGCACAGGGCCTTGGCATTGGCCATAATCAAGTAC
ACATACCAAAACAAAGTGGTAAAGGTCCTTAGACCAGCTGAAAAAGGGAAGACAGTTATGGACATTATTTCAAGACAAG
ACCAAAGGGGGAGCGGACAAGTTGTCACTTACGCTCTTAATACATTCACCAACCTGGTGGTGCAGCTCATTCGGAATATG
GAGGCTGAGGAAGTTCTAGAGATGCAAGACTTGTGGCTGCTGCGGAGGCCAGAGAAAGTGACCAACTGGTTGCAAAGC
AACGGATGGATAGGCTCAAAAGAATGGCAGTCAGTGGAGATGATTGCGTTGTGAAACCAATTGATGATAGGTTTGCAC
ATGCCCTCAGGTTCTTGAATGATATGGGAAAAGTTAGGAAGGACACACAAGAGTGGAAACCCTCAACTGGATGGGACAA
CTGGGAAGAAGTTCCGTTTTGCTCCCACCCACTTCAACAAACTCCATCTTAAGGACGGGAGGTCCATTGTGGTTCCCTGCCG
CCACCAAGATGAACTGATTGGCCGAGCCCGCGTATCACCAGGGGGGGATGGAGCATCCGGGAGACTGCTTGCCTAGCA
AAATCATATGCGCAAATGTGGCAGCTCCTTTATTTCCACAGAAGGGACCTCCGACTGATGGCCAATGCCATTTGTTCATCT
GTGCCAGTTGATTGGGTTCCAACTGGGAGAACTACCTGGTCAATCCATGGAAAGGGAGAATGGATGACCACTGAAGACA
TGCTTGTGGTATGGAACAGAGTGTGGATTGAGGAAAACGACCACATGGAAGACAAGACCCCAGTTACAAAATGGACAGA
CATTCCCTATTTGGGAAAAAGAGAAGACTTGTGGTGTGGATCTCTCATAGGGCACAGACCGCGTACTACCTGGGCTGAGA
ACATCAAAAATACAGTCAACATGATGCGCAGGATCATAGGTGATGAAGAAAGTACATGGACTACCTATCCACCCAGGTT
CGCTACTTGGGTGAAGAAGGGTCCACACCTGGAGTGCTGTAAGCACCAATCTTAGTGTTGTCAGGCCTGCTAGTCAGCCA
CAGCTTGGGGAAAGCTGTGCAGCCTGTGACCCCCCCAGGAGAAGCTGGGAAACCAAGCCTATAGTCAGGCCGAGAACGC
CATGGCACGGAAGAAGCCATGCTGCCTGTGAGCCCCTCAGAGGACACTGAGTCAAAAACCCCACGCGCTTGGAGGCGC
AGGATGGGAAAAGAAGGTGGCGACCTTCCCCACCCTTCAATCTGGGGCCTGAACTGGAGATCAGCTGTGGATCTCCAGA
AGAGGGACTAGTGGTTAGAGGAGACCCCCCGGAAAACGCAAAACAGCATATTGACGCTGGGAAAGACCAGAGACTCCA
TGAGTTTCCACCACGCTGGCCGCCAGGCACAGATCGCCGAATAGCGGCGGCCGGTGTGGGGAAATCCATGGGTCT

KU707826.1 Zika virus isolate SSABR1, Brazil, complete genome

SEQ ID NO: 9
GACAGTTCGAGTTTGAAGCGAAAGCTAGCAACAGTATCAACAGGTTTTATTTGGATTTGGAAACGAGAGTTTCTGGTCAT
GAAAAACCCAAAAAAGAAATCCGGAGGATTCCGGATTGTCAATATGCTAAAACGCGGAGTAGCCCGTGTGAGCCCCTTT
GGGGGCTTGAAGAGGCTGCCAGCCGGACTTCTGCTGGGTCATGGGCCCATCAGGATGGTCTTGGCGATTCTAGCCTTTTT
GAGATTCACGGCAATCAAGCCATCACTGGGTCTCATCAATAGATGGGGTTCAGTGGGGAAAAAAGAGGCTATGGAAATA
ATAAAGAAGTTCAAGAAAGATCTGGCTGCCATGCTGAGAATAATCAATGCTAGGAAGGAGAAGAAGAGACGAGGCGCA
GATACTAGTGTCGGAATTGTTGGCCTCCTGCTGACCACAGCTATGGCAGCGGAGGTCACTAGACGTGGGAGTGCATACTA
TATGTACTTGGACAGAAACGATGCTGGGGAGGCCATATCTTTTCCAACCACATTGGGATGAATAAGTGTTATATACAGA
TCATGGATCTTGGACACATGTGTGATGCCACCATGAGCTATGAATGCCCTATGCTGGATGAGGGGGTGGAACCAGATGAC
GTCGATTGTTGGTGCAACACGACGTCAACTTGGGTTGTGTACGGAACCTGCCATCACAAAAAAGGTGAAGCACGGAGAT
CTAGAAGAGCTGTGACGCTCCCCTCCCATTCCACTAGGAAGCTGCAAACGCGGTCGCAAACCTGGTTGGAATCAAGAGAA
TACACAAAGCACTTGATTAGAGTCGAAAATTGGATATTCAGGAACCCTGGCTTCGCGTTAGCAGCAGCTGCCATCGCTTG
GCTTTTGGGAAGCTCAACGAGCCAAAAAGTCATATACTTGGTCATGATACTGCTGATTGCCCCGGCATACAGCATCAGGT
GCATAGGAGTCAGCAATAGGGACTTTGTGGAAGGTATGTCAGGTGGGACCTGGGTTGATGTTGTCTTGGAACATGGAGG
TTGTGTCACCGTAATGGCACAGGACAAACCGACTGTCGACATAGAGCTGGTTACAACAACAGTCAGCAACATGGCGGAG
GTAAGATCCTACTGCTATGAGGCATCAATATCAGACATGGCTTCGGACAGCCGCTGCCCAACACAAGGTGAAGCCTACCT
TGACAAGCAATCAGACACTCAATATGTCTGCAAAAGAACGTTAGTGGACAGAGGCTGGGGAAATGGATGTGGACTTTTT
GGCAAAGGGAGCCTGGTGACATGCGCTAAGTTTGCATGCTCCAAGAAAATGACCGGGAAGAGCATCCAGCCAGAGAATC
TGGAGTACCGGATAATGCTGTCAGTTCATGGCTCCCAGCACAGTGGGATGATTGTTAATGACACAGGACATGAAACTGAT

-continued

```
GAGAATAGAGCGAAAGTTGAGATAACGCCCAATTCACCAAGAGCCGAAGCCACCCTGGGGGGTTTTGGAAGCCTAGGAC

TTGATTGTGAACCGAGGACAGGCCTTGACTTTTCAGATTTGTATTACTTGACTATGAATAACAAGCACTGGTTGGTTCACA

AGGAGTGGTTCCACGACATTCCATTACCTTGGCACGCTGGGGCAGACACCGGAACTCCACACTGGAACAACAAAGAAGC

ACTGGTAGAGTTCAAGGACGCACATGCCAAAAGGCAAACTGTCGTGGTTCTAGGGAGTCAAGAAGGAGCAGTTCACACG

GCCCTTGCTGGAGCTCTGGAGGCTGAGATGGATGGTGCAAAGGGAAGGCTGTCCTCTGGCCACTTGAAATGTCGCCTGA

AAATGGATAAACTTAGATTGAAGGGCGTGTCATACTCCTTGTGTACTGCAGCGTTCACATTCACCAAGATCCCGGCTGAAA

CACTGCACGGGACAGTCACAGTGGAGGTACAGTACGCAGGGACAGATGGACCTTGCAAGGTTCCAGCTCAGATGGCGGT

GGACATGCAAACTCTGACCCCAGTTGGGAGGTTGATAACCGCTAACCCCGTAATCACTGAAAGCACTGAGAACTCTAAGA

TGATGCTGGAACTTGATCCACCATTTGGGGACTCTTACATTGTCATAGGAGTCGGGGAGAAGAAGATCACCCACCACTGG

CACAGGAGTGGCAGCACCATTGGAAAAGCATTTGAAGCCACTGTGAGAGGTGCCAAGAGAATGGCAGTCTTGGGAGAC

ACAGCCTGGGACTTTGGATCAGTTGGAGGCGCTCTCAACTCATTGGGCAAGGGCATCCATCAAATTTTTGGAGCAGCTTT

CAAATCATTGTTTGGAGGAATGTCCTGGTTCTCACAAATTCTCATTGGAACGTTGCTGATGTGGTTGGGTCTGAACACAAA

GAATGGATCTATTTCCCTTATGTGCTTGGCCTTAGGGGGAGTGTTGATCTTCTTATCCACAGCCGTCTCTGCTGATGTGGG

GTGCTCGGTGGACTTCTCAAAGAAGGAGACGAGATGCGGTACAGGGGTGTTCGTCTATAACGACGTTGAAGCCTGGAGG

GACAGGTACAAGTACCATCCTGACTCCCCCCGTAGATTGGCAGCAGCAGTCAAGCAAGCCTGGGAAGATGGTATCTGCG

GGATCTCCTCTGTTTCAAGAATGGAAAACATCATGTGGAGATCAGTAGAAGGGGAGCTCAACGCAATCCTGGAAGAGAA

TGGAGTTCAACTGACGGTCGTTGTGGGATCTGTAAAAAACCCCATGTGGAGAGGTCCACAGAGATTGCCCGTGCCTGTGA

ACGAGCTGCCCCACGGCTGGAAGGCTTGGGGGAAATCGTACTTCGTCAGAGCAGCAAAGACAAATAACAGCTTTGTCGT

GGATGGTGACACACTGAAGGAATGCCCACTCAAACATAGAGCATGGAACAGCTTTCTTGTGGAGGATCATGGGTTCGGG

GTATTTCACACTAGTGTCTGGCTCAAGGTTAGAGAAGATTATTCATTAGAGTGTGATCCAGCCGTTATTGGAACAGCTGTT

AAGGGAAAGGAGGCTGTACACAGTGATCTAGGCTACTGGATTGAGAGTGAGAAGAATGACACATGGAGGCTGAAGAGG

GCCCATCTGATCGAGATGAAAACATGTGAATGGCCAAAGTCCCACACATTGTGGACAGATGGAATAGAAGAGAGTGATC

TGATCATACCCAAGTCTTTAGCTGGGCCACTCAGCCATCACAATACCAGAGAGGGCTACAGGACCCAAATGAAAGGGCCA

TGGCACAGTGAAGAGCTTGAAATTCGGTTTGAGGAATGCCCAGGCACTAAGGTCCACGTGGAGGAAACATGTGGAACAA

GAGGACCATCTCTGAGATCAACCACTGCAAGCGGAAGGGTGATCGAGGAATGGTGCTGCAGGGAGTGCACAATGCCCCC

ACTGTCGTTCCGGGCTAAAGATGGCTGTTGGTATGGAATGGAGATAAGGCCCAGGAAAGAACCAGAAAGCAACTTAGTA

AGGTCAATGGTGACTGCAGGATCAACTGATCACATGGACCACTTCTCCCTTGGAGTGCTTGTGATTCTGCTCATGGTGCAG

GAAGGGCTGAAGAAGAGAATGACCACAAAGATCATCATAAGCACATCAATGGCAGTGCTGGTAGCTATGATCCTGGGAG

GATTTTCAATGAGTGACCTGGCTAAGCTTGCAATTTTGATGGGTGCCACCTTCGCGGAAATGAACACTGGAGGAGATGTA

GCTCATCTGGCGCTGATAGCGGCATTCAAAGTCAGACCAGCGTTGCTGGTATCTTTCATCTTCAGAGCTAATTGGACACCC

CGTGAAAGCATGCTGCTGGCCTTGGCCTCGTGTCTTTTGCAAACTGCGATCTCCGCCTTGGAAGGCGACCTGATGGTTCTC

ATCAATGGTTTTGCTTTGGCCTGGTTGGCAATACGAGCGATGGTTGTTCCACGCACTGATAACATCACCTTGGCAATCCTG

GCTGCTCTGACACCACTGGCCCGGGGCACACTGCTTGTGGCGTGAGAGCAGGCCTTGCTACTTGCGGGGGGTTTATGCT

CCTCTCTCTGAAGGGAAAAGGCAGTGTGAAGAAGAACTTACCATTTGTCATGGCCCTGGGACTAACCGCTGTGAGGCTGG

TCGACCCCATCAACGTGGTGGGACTGCTGTTGCTCACAAGGAGTGGGAAGCGGAGCTGGCCCCCTAGCGAAGTACTCAC

AGCTGTTGGCCTGATATGCGCATTGGCTGGAGGGTTCGCCAAGGCAGATATAGAGATGGCTGGGCCCATGGCCGCGGTC

GGTCTGCTAATTGTCAGTTACGTGGTCTCAGGAAAGAGTGTGGACATGTACATTGAAAGAGCAGGTGACATCACATGGG

AAAAAGATGCGGAAGTCACTGGAAACAGTCCCCGGCTCGATGTGGCGCTAGATGAGAGTGGTGATTTCTCCCTGGTGGA

GGATGACGGTCCCCCCATGAGAGAGATCATACTCAAGGTGGTCCTGATGACCATCTGTGGCATGAACCCAATAGCCATAC

CCTTTGCAGCTGGAGCGTGGTACGTATACGTGAAGACTGGAAAAAGGAGTGGTGCTCTATGGGATGTGCCTGCTCCCAA
```

-continued

```
GGAAGTAAAAAAGGGGGAGACCACAGATGGAGTGTACAGAGTAATGACTCGTAGACTGCTAGGTTCAACACAAGTTGG
AGTGGGAGTTATGCAAGAGGGGGTCTTTCACACTATGTGGCACGTCACAAAAGGATCCGCGCTGAGAAGCGGTGAAGG
GAGACTTGATCCATACTGGGGAGATGTCAAGCAGGATCTGGTGTCATACTGTGGTCCATGGAAGCTAGATGCCGCTGG
GACGGGCACAGCGAGGTGCAGCTCTTGGCCGTGCCCCCCGGAGAGAGAGCGAGGAACATCCAGACTCTGCCCGGAATAT
TTAAGACAAAGGATGGGACATTGGAGCGGTTGCGCTGGATTACCCAGCAGGAACTTCAGGATCTCCAATCCTAGACAA
GTGTGGGAGAGTGATAGGACTTTATGGCAATGGGGTCGTGATCAAAAATGGGAGTTATGTTAGTGCCATCACCCAAGGG
AGGAGGGAGGAAGAGACTCCTGTTGAGTGCTTCGAGCCTTCGATGCTGAAGAAGAAGCAGCTAACTGTCTTAGACTTGC
ATCCTGGAGCTGGGAAAACCAGGAGAGTTCTTCCTGAAATAGTCCGTGAAGCCATAAAAACAAGACTCCGTACTGTGATC
TTAGCTCCAACCAGGGTTGTCGCTGCTGAAATGGAGGAGGCCCTTAGAGGGCTTCCAGTGCGTTATATGACAACAGCAGT
CAATGTCACCCACTCTGGAACAGAAATCGTCGACTTAATGTGCCATGCCACCTTCACTTCACGTCTACTACAGCCAATCAGA
GTCCCCAACTATAATCTGTATATTATGGATGAGGCCCACTTCACAGATCCCTCAAGTATAGCAGCAAGAGGATACATTTCA
ACAAGGGTTGAGATGGGCGAGGCGGCTGCCATCTTCATGACCGCCACGCCACCAGGAACCCGTGACGCATTTCCGGACT
CCAACTCACCAATTATGGACACCGAAGTGGAAGTCCCAGAGAGAGCCTGGAGCTCAGGCTTTGATTGGGTGACGGATCA
TTCTGGAAAAACAGTTTGGTTTGTTCCAAGCGTGAGGAACGGCAATGAGATCGCAGCTTGTCTGACAAAGGCTGGAAAAC
GGGTCATACAGCTCAGCAGAAAGACTTTTGAGACAGAGTTCCAGAAAACAAAACATCAAGAGTGGGACTTTGTCGTGAC
AACTGACATTTCAGAGATGGGCGCCAACTTTAAAGCTGACCGTGTCATAGATTCCAGGAGATGCCTAAAGCCGGTCATAC
TTGATGGCGAGAGAGTCATTCTGGCTGGACCCATGCCTGTCACACATGCCAGCGCTGCCCAGAGGAGGGGGCGCATAGG
CAGGAATCCCAACAAACCTGGAGATGAGTATCTGTATGGAGGTGGGTGCGCAGAGACTGACGAAGACCATGCACACTGG
CTTGAAGCAAGAATGCTCCTTGACAATATTTACCTCCAAGATGGCCTCATAGCCTCGCTCTATCGACCTGAGGCCGACAAA
GTAGCAGCCATTGAGGGAGAGTTCAAGCTTAGGACGGAGCAAAGGAAGACCTTTGTGGAACTCATGAAAAGAGGAGAT
CTTCCTGTTTGGCTGGCCTATCAGGTTGCATCTGCCGGAATAACCTACACAGATAGAAGATGGTGCTTTGATGGCACGACC
AACAACACCATAATGGAAGACAGTGTGCCGGCAGAGGTGTGGACCAGACACGGAGAGAAAAGAGTGCTCAAACCGAGG
TGGATGGACGCCAGAGTTTGTTCAGATCATGCGGCCCTGAAGTCATTCAAGGAGTTTGCCGCTGGGAAAAGAGGAGCGG
CTTTTGGAGTGATGGAAGCCCTGGGAACACTGCCAGGACACATGACAGAGAGATTCCAGGAAGCCATTGACAACCTCGC
TGTGCTCATGCGGGCAGAGACTGGAAGCAGGCCTTACAAAGCCGCGGCGGCCCAATTGCCGGAGACCCTAGAGACCATT
ATGCTTTTGGGGTTGCTGGGAACAGTCTCGCTGGGAATCTTCTTCGTCTTGATGAGGAACAAGGGCATAGGGAAGATGG
GCTTTGGAATGGTGACTCTTGGGGCCAGCGCATGGCTCATGTGGCTCTCGGAAATTGAGCCAGCCAGAATTGCATGTGTC
CTCATTGTTGTGTTTCTATTGCTGGTGGTGCTCATACCTGAGCCAGAAAAGCAAAGATCTCCCCAGGACAACCAAATGGCA
ATCATCATCATGGTAGCAGTAGGTCTTCTGGGCTTGATTACCGCCAATGAACTCGGATGGTTGGAGAGAACAAAGAGTGA
CCTAAGCCATCTAATGGGAAGGAGAGAGGAGGGGGCAACCATAGGATTCTCAATGGACATTGACCTGCGGCCAGCCTCA
GCTTGGGCCATCTATGCTGCCTTGACAACTTTCATTACCCCAGCCGTCCAACATGCAGTGACCACTTCATACAACAACTACT
CCTTAATGGCGATGGCCACGCAAGCTGGAGTGTTGTTTGGTATGGGCAAAGGGATGCCATTCTACGCATGGGACTTTGGA
GTCCCGCTGCTAATGATAGGTTGCTACTCACAATTAACACCCCTGACCCTAATAGTGGCCATCATTTTGCTCGTGGCGCACT
ACATGTACTTGATCCCAGGGCTGCAGGCAGCAGCTGCGCGTGCTGCCCAGAAGAGAACGGCAGCTGGCATCATGAAGAA
CCCTGTTGTGGATGGAATAGTGGTGACTGACATTGACACAATGACAATTGACCCCCAAGTGGAGAAAAAGATGGGACAG
GTGCTACTCATAGCAGTAGCCGTCTCCAGCGCCATACTGTCGCGGACCGCCTGGGGTGGGGGAGGCTGGGCCCTGA
TCACAGCCGCAACTTCCACTTTGTGGGAAGGCTCTCCGAACAAGTACTGGAACTCCTCTACAGCCACTTCACTGTGTAACA
TTTTTAGGGGAAGTTACTTGGCTGAGCTTCTCTAATCTACACAGTAACAAGAAACGCTGGCTTGGTCAAGAGACGTGGG
GGTGGAACAGGAGAGACCCTGGGAGAGAAATGGAAGGCCCGCTTGAACCAGATGTCGGCCCTGGAGTTCTACTCCTACA
AAAGTCAGGCATCACCGAGGTGTGCAGAGAAGAGGCCCGCCGCGCCCTCAAGGACGGTGTGGCAACGGGAGGCCATG
CTGTGTCCCGAGGAAGTGCAAAGCTGAGATGGTTGGTGGAGCGGGGATACCTGCAGCCCTATGGAAAGGTCATTGATCT
```

TGGATGTGGCAGAGGGGGCTGGAGTTACTACGCCGCCACCATCCGCAAAGTTCAAGAAGTGAAAGGATACACAAAAGG

AGGCCCTGGTCATGAAGAACCCGTGTTGGTGCAAAGCTATGGGTGGAACATAGTCCGTCTTAAGAGTGGGGTGGACGTC

TTTCATATGGCGGCTGAGCCGTGTGACACGTTGCTGTGTGACATAGGTGAGTCATCATCTAGTCCTGAAGTGGAAGAAGC

ACGGACGCTCAGAGTCCTCTCCATGGTGGGGGATTGGCTTGAAAAAAGACCAGGAGCCTTTTGTATAAAGGTGTTGTGCC

CATACACCAGCACTATGATGGAAACCCTGGAGCGACTGCAGCGTAGGTATGGGGAGGACTGGTCAGAGTGCCACTCTC

CCGCAACTCTACACATGAGATGTATTGGGTCTCTGGAGCGAAAAGCAACACCATAAAAAGTGTGTCCACCACGAGCCAGC

TCCTCTTGGGGCGCATGGACGGGCCTAGGAGGCCAGTGAAATATGAGGAGGATGTGAATCTCGGCTCTGGCACGCGGGC

TGTGGTAAGCTGCGCTGAAGCTCCCAACATGAAGATCATTGGTAACCGCATTGAAAGGATCCGCAGTGAGCACGCGGAA

ACGTGGTTCTTTGACGAGAACCACCCATATAGGACATGGGCTTACCATGGAAGCTATGAGGCCCCCACACAAGGGTCAGC

GTCCTCTCTAATAAACGGGGTTGTCAGGCTCCTGTCAAAACCCTGGGATGTGGTGACTGGAGTCACAGGAATAGCCATGA

CCGACACCACACCGTATGGTCAGCAAAGAGTTTTCAAGGAAAAAGTGGACACTAGGGTGCCAGACCCCCAAGAAGGCAC

TCGTCAGGTTATGAGCATGGTCTCTTCCTGGTTGTGGAAAGAGCTAGGCAAACACAAACGGCCACGAGTCTGTACCAAAG

AAGAGTTCATCAACAAGGTTCGTAGCAATGCAGCATTAGGGGCAATATTTGAAGAGGAAAAGAGTGGAAGACTGCAGT

GGAAGCTGTGAACGATCCAAGGTTCTGGGCTCTAGTGGATAAGGAAAGAGAGCACCACCTGAGAGGAGAGTGCCAGAG

TTGTGTGTACAACATGATGGGAAAAAGAGAAAAGAAACAAGGGGAATTTGGAAAGGCCAAGGGCAGCCGCGCCATCTG

GTATATGTGGCTAGGGGCTAGATTTCTAGAGTTCGAAGCCCTTGGATTCTTGAACGAGGATCACTGGATGGGGAGAGAG

AACTCAGGAGGTGGTGTTGAAGGGCTGGGATTACAAAGACTCGGATATGTCCTAGAAGAGATGAGTCGTATACCAGGAG

GAAGGATGTATGCAGATGACACTGCTGGCTGGGACACCCGCATCAGCAGGTTTGATCTGGAGAATGAAGCTCTAATCACC

AACCAAATGGAAAAAGGGCACAGGGCCTTGGCATTGGCCATAATCAAGTACACATACCAAAACAAAGTGGTAAAGGTCC

TTAGACCAGCTGAAAAAGGGAAAACAGTTATGGACATTATTTCGAGACAAGACCAAAGGGGGAGCGGACAAGTTGTCAC

TTACGCTCTTAACACATTTACCAACCTAGTGGTGCAACTCATTCGGAATATGGAGGCTGAGGAAGTTCTAGAGATGCAAG

ACTTGTGGCTGCTGCGGAGGTCAGAGAAAGTGACCAACTGGTTGCAGAGCAACGGATGGGATAGGCTCAAACGAATGG

CAGTCAGTGGAGATGATTGCGTTGTGAAGCCAATTGATGATAGGTTTGCACATGCCCTCAGGTTCTTGAATGATATGGGA

AAAGTTAGGAAGGACACACAAGAGTGGAAACCCTCAACTGGATGGGACAACTGGGAAGAAGTTCCGTTTTGCTCCCACC

ACTTCAACAAGCTCCATCTCAAGGACGGGAGGTCCATTGTGGTTCCCTGCCGCCACCAAGATGAACTGATTGGCCGGGCC

CGCGTCTCTCCAGGGGGGGGATGGAGCATCCGGGAGACTGCTTGCCTAGCAAAATCATATGCGCAAATGTGGCAGCTCCT

TTATTTCCACAGAAGGGACCTCCGACTGATGGCCAATGCCATTTGTTCATCTGTGCCAGTTGACTGGGTTCCAACTGGGAG

AACTACCTGGTCAATCCATGGAAAGGGAGAATGGATGACCACTGAAGACATGCTTGTGGTGTGGAACAGAGTGTGGATT

GAGGAGAACGACCACATGGAAGACAAGACCCCAGTTACGAAATGGACAGACATCCCCTATTTGGGAAAAAGGGAAGACT

TGTGGTGTGGATCTCTCATAGGGCACAGACCGCGCACCACCTGGGCTGAGAACATTAAAAACACAGTCAACATGGTGCGC

AGGATCATAGGTGATGAAGAAAAGTACATGGACTACCTATCCACCCAAGTTCGCTACTTGGGTGAAGAAGGGTCTACACC

TGGAGTGCTGTAAGCACCAGTCTTAATGTTGTCAGGCCTGCTAGTCAGCCACAGCTTGGGGAAAGCTGTGCAGCCTGTGA

CCCCCCAGGAGAAGCTGGGAAACCAAGCCTATAGTCAGGCCGAGAACGCCATGGCACGGAAGAAGCCATGCTGCCTGT

GAGCCCCTCAGAGGACACTGAGTCAAAAAACCCCACGCGCTTGGAGGCGCAGGATGGGAAAAGAAGGTGGCGACCTTC

CCCACCCTTCAATCTGGGGCCTGAACTGGAGATCAGCTGTGGATCTCCAGAAGAGGGACTAGTGGTTAGAGGAG

KU744693.1 Zika virus isolate VE_Ganxian, China, complete genome
SEQ ID NO: 10
GTTGTTACTGTTGCTGACTCAGACTGCGACAGTTCGAGTTTGAAGCGAAAGCTAGCAACAGTATCAACAGGTTTTATTTGG

ATTTGGAAACGAGAGTTTCTGGTCATGAAAAACCCAAAAAAGAAATCCGGAGGATTCCGGATTGTCAATATGCTAAAACG

CGGAGTAGCCCGTGTGAGCCCCTTTGGGGGCTTGAAGAGGCTGCCAGCCGGACTTCTGCTGGGTCATGGGCCCATCAGG

-continued

```
ATGGTCTTGGCAATTCTAGCCTTTTTGAGATTCACGGCAATCAAGCCATCACTGGGTCTCATCAATAGATGGGGTTCAGTG
GGGAAAAAAGATGCTATGGAAATAATAAAGAAGTTCAAGAAAGATCTGGCTGCCATGCTGAGAATAATCAATGCTAGGA
AGGAGAAGAAGAGACGAGGCGCAGATACTAGTGTCGGAATTGTTGGCCTCCTGCTGACCACAGCTATGGCAGCGGAGG
TCACTAGACGTGGGAGTGCATACTATATGTACTTGGACAGAAACGATGCTGGGGAGGCCATATCTTTTCCAACCACATTG
GGGATGAATAAGTGTTATATACAGATCATGGATCTTGGACACATGTGTGATGCCACCATGAGCTATGAATGCCCTATGCT
GGATGAGGGGGTGGAACCAGATGACGTCGATTGTTGGTGCAACACGACGTCAACTTGGGTTGTGTACGGAACCTGCCAT
CACAAAAAGGTGAAGCACGGAGATCTAGAAGAGCTGTGACGCTCCCTTCCCATTCCACTAGGAAGCTGCAAACGCGGT
CGCAAACCTGGTTGGAATCAAGAGAATACACAAAGCACTTGATTAGAGTCGAAAATTGGATATTCAGGAACCCTGGCTTC
GCGTTAGCAGCAGCTGCCATCGCTTGGCTTTTGGGAAGCTCAACGAGCCAAAAGTCATATACTTGGTCATGATACTGCT
GATTGCCCCGGCATACAGCATCAGGTGCATAGGAGTCAGCAATAGGGACTTTGTGGAAGGTATGTCAGGTGGGACTTGG
GTTGATGTTGTCTTGGAACATGGAGGTTGTGTCACCGCAATGGCACAGGACAAACCGACTGTCGACATAGAGCTGGTTAC
AACAACAGTCAGCAACATGGCGGAGGTAAGATCCTACTGCTATGAGGCATCAATATCAGACATGGCTTCGGACAGCCGCT
GCCCAACACAAGGTGAAGCCTACCTTGACAAGCAATCAGACACTCAATATGTTTGCAAAAGAACGTTAGTGGACAGAGGC
TGGGGAAATGGATGTGGACTTTTTGGCAAAGGGAGTCTGGTGACATGCGCTAAGTTTGCATGCTCCAAGAAAATGACCG
GGAAGAGCATCCAGCCAGAGAATCTGGAGTACCGGATAATGCTGTCAGTTCATGGCTCCCAGCACAGTGGGATGCTCGTT
AATGACACAGGACATGAAACTGATGAGAATAGAGCGAAGGTTGAGATAACGCCCAATTCACCAAGAGCCGAAGCCACCC
TGGGGGGTTTTGGAAGCCTAGGACTTGATTGTGAACCGAGGACAGGCCTTGACTTTTCAGATTTGTATTACTTGACTATGA
ATAACAAGCACTGGTTGGCTCACAAGGAGTGGTTCCACGACATTCCATTACCTTGGCACGCTGGGGCAGCCACCGGAACT
CCACACTGGAACAACAAAGAAGCACTGGTAGAGTTCAAGGACGCACATGCCAAAAGGCAAACTGTCGTGGTTCTAGGGA
GTCAAGAAGGAGCAGTTCACACGGCCCTTGCTGGAGCTCTGGAGGCTGAGATGGATGGTGCAAAGGGAAGGCTGTCCTC
TGGCCACTTGAAATGTCGCCTGAAAATGGATAAACTTAGATTGAAGGGCGTGTCATACTCCTTGTGTACCGCAGCGTTCAC
ATTCACCAAGATCCCGGCTGAAACAGTGGACGGGACAGTCACAGTGGAGGGACAGTACGGAGGGACAGATGGACCTTG
CAAGGTTCCAGCTCAGATGGCGGTGGACATGCAGACTCTGACCCCAGTTGGGAGGTTGATAACCGCTAACCCCGTAATCA
CTGAAAGCACTGAGAACTCTAAGATGATGCTGGAACTTGATCCACCATTTGGGGACTCTTACATTGTCATAGGAGTCGGG
GAGAAGAAGATCACCCACCACTGGCACAGGAGTGGCAGCACCATTGGAAAAGCATTTGAAGCCACTGTGAGAGGTGCCA
AGAGAATGGCAGTCTTGGGAGACACAGCCTGGGACTTTGGATCAGTTGGAGGCGCTCTCAACTCATTGGGCAAGGGCAT
CCATCAAATTATTGGAGCAGCTTTCAAATCATTGTTTGGAGGAATGTCCTGGTTCTCACAAATTCTCATTGGGACGTTGCTG
ATGTGGTTGGGTCTGAACACAAAGAATGGATCTATTTCCCTTATGTGCTTGGCCTTAGGGGAGTGTTGATCTTCTTATCC
ACAGCCGTCTCAGGTGGTGTGGGGTGCTCGGTGGACTTCTCAAAGAAGGAGACGAGATGCGGTACAGGGGTGTTCGTCT
ATAACGATGTTGAAGCCTGGAGGGACAGGTACAAGTACCATCCTGACTCCCCCCGTAGATTGGCAGCAGCAGTCAAGCA
AGCCTGGGAAGATGGTATCTGCGGGATCTCCTCTGTTTCAAGAATGGAAAACATCATGTGGAGATCAGTAGAAGGGGAG
CTCAACGCAATCCTGGAAGAGAATGGAGTTCAACTGACGGTCGTTGTGGGATCTGTAAAAAACCCCATGTGGAGAGGTC
CACAGAGATTGCCCGTGCCTGTGAACGAGCTGCCCCACGGCTGGAAGGCTTGGGGGAAATCGTACTTCGTCAGAGCAGC
AAAGACAAATAACAGCTTTGTCGTGGATGGTGACACACTGAAGGAATGCCCACTCAAACATAGAGCATGGAACAGCTTTC
TTGTGGAGGATCATGGGTTCGGGGTATTTCACACTAGTGTCTGGCTCAAGGTTAGAGAAGACTATTGGTTAGAGTGTGAT
CCAGCCGTTATTGGAACAGCTGTTAAGGGAAAGGAGGCTGTACACAGTGATCTAGGCTACTGGATTGAGAGTGAGAAGA
ATGACACATGGTGGCTGAAGAGGGCCCATCTGATCGAGATGAAAACATGTGAATGGCCAAAGTCCCACACATTGTGGAC
AGATGGAATAGAAGAGAGTGATCTGATCATACCCAAGTCTTTAGCTGGGCCACTCAGCCATCACAATGCCAGAGAGGGCT
ACAGGACCCAAATGAAAGGCCATGGCACAGTGAAGAGCTTGAAATTCGGTTTGAGGAATGCCCAGGCACTAAGGTCCA
CGTGGAGGAAACATGTGGAACAAGAGGACCATCTCTGAGATCAACCACTGCAAGCGGAAGGGTGATCGAGGAATGGTG
```

-continued

```
CTCCAGGGAGTGCACAATGCCCCCACTGTCCTTCCAGGCTAAAGATGGCTGTTGGTATGGAATGGAGATAAGGCCCAGG
AAAGAACCAGAAAGCAACTTAGTAAGGTCAATGGTGACTGCAGGATCAACTGATCACATGGATCACTTCTCCCTTGGAGT
GCTTGTGATTCTGCTCATGGTGCAGGAAGGGCTGAAGAAGAGAATGACCACAAAGATCATCATAAGCACATCAATGGCA
GTGCTGGTAGCTATGATCCTGGGAGGATTTTCAATGAGTGACCTGGCTAAGCTTGCAATTTTGATGGGTGCCACCTTCGC
GGAAATGAACACTGGAGGAGATGTAGCTCATCTGGCGCTGATAGCGGCATTCAAAGTCAGACCAGCGTTGCTGGTATCTT
TCATCTTCAGAGCTAATTGGACACCCCGTGAAAGCATGCTGCTGGCCTTGGCCTCGTGTCTTTTGCAAACTGCGATCTCCG
CCTTGGAAGGCGACCTGATGGTTCTCATCAATGGTTTTGCTTTGGCCTGGTTGGCAATACGAGCGATGGTTGTTCCACGCA
CTGATAACATCACCTTAGCAATCCTGGCTGCTCTGACACCACTGGCCCGGGGCACACTGCTTGTGGCGTGGAGAGCAGGC
CTTGCTACTTGCGGGGGGTTTATGCTCCTCTCTCTGAAGGGAAAAGGCAGTGTGAAGAAGAACTTACCATTTGTCATGGC
CCTGGGACTAACCGCTGTGAGGCTGGTCGACCCCATCAACGTGGTGGGACTGCTGTTGCTCACAAGGAGTGGGAAGCGG
AGCTGGCCCCCTAGCGAAGTACTCACAGCTGTTGGCCTGATATGCGCATTGGCTGGAGGGTTCGCCAAGGCAGATATAGA
GATGGCTGGGCCCATGGCCGCGGTCGGTCTGCTAATTGTCAGTTACGTGGTCTCAGGAAAGAGTGTGGACATGTACATTG
AAAGAGCAGGTGACATCACATGGGAAAAAGATGCGGAAGTCACTGGAAACAGTCCCCGGCTCGATGTGGCGCTAGATG
AGAGTGGTGATTTCTCCCTGGTGGAGGATGACGGTCCCCCCATGAGAGAGATCATACTCAAGGTGGTCCTGATGACCATC
TGTGGCATGAACCCAATAGCCATACCCTTTGCAGCTGGAGCGTGGTACGTATACGTGAAGACTGGAAAAAGGAGTGGTG
CTCTATGGGATGTGCCTGCTCCCAAGGAAGTAAAAAAGGGGGAGACCACAGATGGAGTGTACAGAGTAATGACTCGCAG
ACTGCTAGGTTCAACACAAGTTGGAGTGGGAGTTATGCAAGAGGGGGTCTTTCACACTATGTGGCACGTCACAAAAGGA
TCCGCGCTGAGAAGCGGTGAAGGGAGACTTGATCCATACTGGGGAGATGTCAAGCAGGATCTGGTGTCATACTGTGGTC
CATGGAAGCTAGATGCCGCCTGGGACGGGCACAGCGAGGTGCAGCTCTTGGCCGTGCCCCCCGGAGAGAGAGCGAGGA
ACATCCAGACTCTGCCCGGAATATTTAAGACAAAGGATGGGGACATTGGAGCGGTTGCACTGGATTACCCAGCAGGAAC
TTCAGGATCTCCAATCCTAGACAAGTGTGGGAGAGTGATAGGACTTTATGGCAATGGGGTCGTGATCAAAAATGGGAGT
TATGTTAGTGCCATCACCCAAGGGAGGAGGGAGGAAGAGACTCCTGTTGAGTGCTTCGAGCCTTCGATGCTGAAGAAGA
AGCAGCTAACTGTCTTAGACTTGCATCCTGGAGCTGGGAAAACCAGGAGAGTTCTTCCTGAAATAGTCCGTGAAGCCATA
AAAACAAGACTCCGTACTGTGATCTTGGCTCCAACCAGGGTTGTCGCTGCTGAAATGGAGGAGGCCCTTAGAGGGCTTCC
AGTGCGTTATATGACAACAGCAGTCAATGTCACCCACTCTGGAACAGAAATCGTCGACTTAATGTGCCATGCCACCTTCAC
TTCACGTCTACTACAGCCAATTAGAGTCCCCAACTATAATCTGTATATTATGGATGAGGCCCACTTCACAGATCCCTCAAGT
ATAGCAGCAAGAGGATACATTTCAACAAGGGTTGAGATGGGCGAGGCGGCTGCCATCTTCATGACCGCCACGCCACCAG
GAACCCGTGACGCATTTCCGGACTCCAACTCACCAATTATGGACACCGAAGTGGAAGTCCCAGAGAGAGCCTGGAGCTCA
GGCTTTGATTGGGTGACGGAGTATTCTGGAAAAACAGTTTGGTTTGTTCCACGCGTGAGGAACGGCAATGAGATCGCAG
CTTGTCTGACAAAGGCTGGAAAACGGGTCATACAGCTCAGCAGAAAGACTTTTGAGACAGAGTTCCAGAAAACAAAACAT
CAAGAGTGGGACTTTGTCGTGACAACTGACATTTCAGAGATGGGCGCCAACTTTAAAGCTGACCGTGTCATAGATTCCAG
GAGATGCCTAAAGCCGGTCATACTTGGTGGCGAGAGAGTCATTCTGGCTGGACCCATGCCTGTCACACATGCCAGCGCTG
CCCAGAGGAGGGGGCGCATAGGCAGGAATCCCAACAAACCTGGAGATGAGTATCTGTATGGAGGTGGGTGCGCAGAGA
CTGACGAAGACCATGCACACTGGCTTGAAGCAAGAATGCTCCTTGACAATATTTACCTCCAAGATGGCCTCATAGCCTCGC
TCTATCGACCTGAGGCCGACAAAGTAGCAGCCATTGAGGGAGAGTTCAAGCTTAGGACGGAGCAAAGGAAGACCTTTGT
GGAACTCATGAAAAGAGGAGATCTTCCTGTTTGGCTGGCCTATCAGGTTGCATCTGCCGGAATAACCTACACAGATAGAA
GATGGTGCTTTGATGGCACGACCAACAACACCATAATGGAAGACAGTGTGCCGGCAGAGGTGTGGACCAGACACGGAG
AGAAAAGAGTGCTCAAACCGAGGTGGATGGACGCCAGAGTTTGTTCAGATCATGCGGCCCTGAAGTCATTCAAGGAGTT
TGCCGCTGGGAAAAGAGGAGCGGCTTTTGGAGTGATGGAAGCCCTGGGAACACTGCCAGGACACATGACAGAGAGATT
CCAGGAAGCCATTGACAACCTCGCTGTGCTCATGCGGGCAGAGACTGGAAGCAGGCCTTACAAAGCCGCGGCGGCCCAA
TTGCCGGAGACCCTAGAGACCATTATGCTTTTGGGGTTGCTGGGAACAGTCTCGCTGGGAATCTTTTTCGTCTTGATGAGG
```

-continued

```
AACAAGGGCATAGGGAAGATGGGCTTTGGAATGGTGACTCTTGGGGCCAGCGCATGGCTCATGTGGCTCTCGGAAATTG
AGCCAGCCAGAATTGCATGTGTCCTCATTGTTGTGTTCCTATTGCTGGTGGTGCTCATACCTGAGCCAGAAAAGCAAAGAT
CTCCCCAGGACAACCAAATGGCCATCATCATCATGGTAGCAGTAGGTCTTCTGGGCTTGATTACCGCCAATGAACTCGGAT
GGTTGGAGAGAACAAAGAGTGACCTAAGCCATCTAATGGGAAGGAGAGAGGAGGGGGCAACCATGGGATTCTCAATGG
ACATTGACCTGCGGCCAGCCTCAGCTTGGGCCATCTATCCTGCCTTGACATCTTTCATTACCCCAGCCGTCCAACATGCAGT
GACCACTTCATACAACAACTACTCCTTAATGGCGATGGCCACGCAAGCTGGAGTGTTGTTTGGTATGGGCAAAGGGATGC
CATTCTACGCATGGGACTTTGGAGTCCCGCTGCTAATGATAGGTTGCTACTCACAATTAACGCCCCTGACCCTAATAGTGG
CCATCATTTTGCTCGTGGCGCACTACATGTACTTGATCCCAGGGCTGCAGGCAGCAGCTGCGCGTGCTGCCCAGAAGAGA
ACGGCAGCTGGCATCATGAAGAACCCTGTTGTGGAGGGAATAGTGGTGACTGACATTGACACAATGACAATTGACCCCC
AAGTGGAGAAAAAGATGGGACAGGTGCTACTCATGGCAGTAGCCGTCTCCAGCGCCATACTGTCGAGGACCGCCTGGGG
GTGGGGGAGGCTGGGGCCCTGATCACAGCCGCAACTTCCACTTTGTGGGAAGGCTCTCCGAACAAGTACTGGAACTCC
TCTACAGCCACCTCACTGTGTAACATTTTTAGGGGAAGTTACTTGGCTGGAGCTTCTCTAATCTACACAGTAACAAGAAAC
GCTGGCTTGGTCAAGAGACGTGGGGGTGGAACAGGAGAGACCCTGGGAGAGAAATGGAAGGCCCGCTTGAACCAGAT
GTCGGCCCTGGAGTTCTACTCCTACAAAAAGTCAGGCATCACCGAGGTGTGCAGAGAAGAGGCCCGCCGCGCCCTCAAG
GACGGTGTGGCAACGGGAGGCCATGCTGTGTCCCGAGGAAGTGCAAAGCTGAGATGGTTGGTGGAGCGGGGATACCTG
CAGCCCTATGGAAAGGTCATTGATCTTGGATGTGGCAGAGGGGCTGGAGTTACTACGCCGCCACCATCCGCAAAGTTCA
AGAAGTGAAAGGATACACAAAAGGAGGCCCTGGTCATGAAGAACCCGTGTTGGTGCAAAGCTATGGGTGGAACATAGT
CCGTCTTAAGAGTGGGGTGGACGTCTTTCATATGGCGGCTGAGCCGTGTGACACGTTGCTGTGTGACATAGGTGAGTCAT
CATCTAGTCCTGAAGTGGAAGAAGCACGGACGCTCAGAGTCCTCTCCATGGTGGGGATTGGCTTGAAAAAAGACCAGG
AGCCTTTTGTATAAAAGTGTTGTGCCCATACACCAGCACTATGATGGAAACCCTGGAGCGACTGCAGCGTAGGTATGGGG
GAGGACTGGTCAGAGTGCCACTCTCCCGCAACTCTACACATGAGATGTACTGGGTCTCTGGAGCGAAAAGCAACACCATA
AAAAGTGTGTCCACCACGAGCCAGCTCCTCTTGGGGCGCATGGACGGGCCTAGGAGGCCAGTGAAATATGAGGAGGAT
GTGAATCTCGGCTCTGGCACGCGGGCTGTGGTAAGCTGCGCTGAAGCTCCCAACATGAAGATCATTGGTAACCGCATTGA
AAGGATCCGCGCTGAGAAAGCGGAAACGTGGTTCTTTGACGAGAACCACCCATATAGGACATGGGCTTACCATGGAAGC
TATGATGCCGCCACACAAGGGTCAGCGTCCTCTCTAATAAACGGGGTTGTCAGGCTCCTGTCAAAACCCTGGGATGTGGT
GACTGGAGTCACAGGAATAGCCATGACCGACACCACACCGTATGGTCAGCAAAGAGTTTTCAAGGAAAAAGTGGACACT
AGGGTGCCAGACCCCCAAGAAGGCACTCGTCAGGTTATGAGCATGGTCTCTTCCTGGTTGTGGAAAGAGCTAGGCAAAC
ACAAACGGCCACGAGTCTGTACCAAAGAAGAGTTCATCAACAAGGTTCGTAGCAATGCAGCATTAGGGGCAATATTTGAA
GAGGAAAAAGAGTGGAAGACTGCAGTGGAAGCTGTGAACGATCCAAGGTTCTGGGCTCTAGTGGACAAGGAAAGAGAG
CACCACCTGAGAGGAGAGTGCCAGAGTTGTGTGTACATCACAATGGGAAAAAGAGAAAAGAAACAAGGGGAATTTGGA
AAGGCCAAGGGCAGCCGCGCCATCTGGTATATGTGGCTAGGGGCTAGATTTCTAGAGTTCGAAGCCCTTGGATTCTTGAA
CGAGGATCACTGGATGGGGAGAGAGAACTCAGGAGGTGGTGTTGAAGGGCTGGGATTACAAAGACTCGGATATGTCCT
AGAAGAGATGAGTCGCATACCAGGAGGAAGGATGTATGCAGATGACACTGCTGGCTGGGACACCCGCATCAGCAGGTTT
GATCTGGAGAATGAAGCTCTAATCACCAACCAAATGGAGAAAGGGCACAGGGCCTTGGCATTGGCCATAATCAAGTACA
CATACCAAAACAAAGTGGTAAAGGTCCTTAGACCAGCTGAAAAAGGGAAGACAGTTATGGACATTATTTCGAGACAAGA
CCAAAGGGGAGCGGACAAGTTGTCACTTACGCTCTCAACACATTTACCAACCTAGTGGTGCAACTCATTCGGAATATGG
AGGCTGAGGAAGTTCTAGAGATGCAAGACTTGTGGCTGCTGCGGAGGTCAGAGAAAGTGACCAACTGGTTGCAGAGCA
ACGGATGGGATAGGCTCAAACGAATGGCGGTCAGTGGAGATGATTGCGTTGTGAAACCAATTGATGATAGGTTTGCACA
TGCCCTCAGGTTCTTGAATGATATGGGAAAAGTTAGGAAGGACACACAAGAGTGGAAACCCTCAACTGGATGGGACAAC
TGGGAAGAAGTTCCCTTCTGCTCCCACCACTTCAACAAGCTCCATCTCAAGGACGGGAGGTCCATTGTGGTTCCCTGCCGC
```

-continued

CACCAAGATGAACTGATTGGCCGGGCCCGCGTCTCTCCAGGGGGGGATGGAGCATCCGGGAGACTGCTTGCCTAGCAA

AATCATATGCGCAAATGTGGCAGCTCCTTTATTTCCACAGAAGGGACCTCCGACTGATGGCCAATGCCATTTGTTCATCTG

TGCCAGTTGACTGGGTTCCAACTGGGAGAACTACCTGGTCAATCCATGGAAAGGGAGAATGGATGACCACTGAAGACAT

GCTTGTGGCGTGGAACAGAGTGTGGATTGAGGAGAACGACCACATGGAAGACAAGACCCCAGTCACGAAATGGACAGA

CATTCCCTATTTGGGAAAAAGGGAAGACTTGTGGTGTGGATCTCTCATAGGGCACAGACCGCGCACCACCTGGGCTGAGA

ACATTAAAAACACAGTCAACATGGTGCGCAGGATCATAGGTGATGAAGAAAAGTACATGGACTACCTATCCACCCAAGTT

CGCTACTTGGGTGAAGAAGGGTCTACACCTGGAGTGCTGTAAGCACCAATCTTAATGTTGTCAGGCCTGCTAGTCAGCCA

CAGCTTGGGGAAAGCTGTGCAGCCTGTGACCCCCCCAGGAGAAGCTGGGAAACCAAGCCTATAGTCAGGCCGAGAACGC

CATGGCACGGAAGAAGCCATGCTGCCTGTGAGCCCCTCAGAGGACACTGAGTCAAAAAACCCCACGCGCTTGGAGGCGC

AGGATGGGAAAAGAAGGTGGCGACCTTCCCCACCCTTCAATCTGGGGCCTGAACTGGAGATCAGCTGTGGATCTCCAGA

AGAGGGACTAGTGGTTAGAGGAGA

LC002520.1 Zika virus genomic RNA, strain: MR766-NIID, Uganda, complete genome
SEQ ID NO: 11
AGTTGTTGATCTGTGTGAGTCAGACTGCGACAGTTCGAGTCTGAAGCGAGAGCTAACAACAGTATCAACAGGTTTAATTT

GGATTTGGAAACGAGAGTTTCTGGTCATGAAAAACCCAAAGAAGAAATCCGGAGGATTCCGGATTGTCAATATGCTAAA

ACGCGGAGTAGCCCGTGTAAACCCCTTGGGAGGTTTGAAGAGGTTGCCAGCCGGACTTCTGCTGGGTCATGGACCCATCA

GAATGGTTTTGGCGATACTAGCCTTTTTGAGATTTACAGCAATCAAGCCATCACTGGGCCTTATCAACAGATGGGGTTCCG

TGGGGAAAAAAGAGGCTATGGAAATAATAAAGAAGTTCAAGAAAGATCTTGCTGCCATGTTGAGAATAATCAATGCTAG

GAAAGAGAGGAAGAGACGTGGCGCAGACACCAGCATCGGAATCATTGGCCTCCTGCTGACTACAGCCATGGCAGCAGA

GATCACTAGACGCGGGAGTGCATACTACATGTACTTGGATAGGAGCGATGCCGGGAAGGCCATTTCGTTTGCTACCACAT

TGGGAGTGAACAAGTGCCACGTACAGATCATGGACCTCGGGCACATGTGTGACGCCACCATGAGTTATGAGTGCCCTATG

CTGGATGAGGGAGTGGAACCAGATGATGTCGATTGCTGGTGCAACACGACATCAACTTGGGTTGTGTACGGAACCTGTC

ATCACAAAAAAGGTGAGGCACGGCGATCTAGAAGAGCCGTGACGCTCCCTTCTCACTCTACAAGGAAGTTGCAAACGCG

GTCGCAGACCTGGTTAGAATCAAGAGAATACACGAAGCACTTGATCAAGGTTGAAAACTGGATATTCAGGAACCCCGGG

TTTGCGCTAGTGGCCGTTGCCATTGCCTGGCTTTTGGGAAGCTCGACGAGCCAAAAAGTCATATACTTGGTCATGATACTG

CTGATTGCCCCGGCATACAGTATCAGGTGCATTGGAGTCAGCAATAGAGACTTCGTGGAGGGCATGTCAGGTGGGACCT

GGGTTGATGTTGTCTTGGAACATGGAGGCTGCGTTACCGTGATGGCACAGGACAAGCCAACAGTTGACATAGAGTTGGT

CACGACGACGGTTAGTAACATGGCCGAGGTAAGATCCTATTGCTACGAGGCATCGATATCGGACATGGCTTCGGACAGTC

GTTGCCCAACACAAGGTGAAGCCTACCTTGACAAGCAATCAGACACTCAATATGTCTGCAAAAGAACATTAGTGGACAGA

GGTTGGGGAAACGGTTGTGGACTTTTTGGCAAAGGGAGCTTGGTGACATGTGCCAAGTTTACGTGTTCTAAGAAGATGA

CCCGGAAGAGCATTCAACCGGAAAATCTGGAGTATCGGATAATGCTATCAGTGCATGGCTCCCAGCATAGCGGGATGAC

TGTCAATGATATAGGATATGAAACTGACGAAAATAGAGCGAAAGTCGAGGTTACGCCTAATTCACCAAGAGCGGAAGCA

ACCTTGGGAGGCTTTGGAAGCTTAGGACTTGACTGTGAACCAAGGACAGGCCTTGACTTTTCAGATCTGTATTACCTGACC

ATGAACAATAAGCATTGGTTGGTGCACAAAGAGTGGTTTCATGACATCCCATTGCCTTGGCATGCTGGGGCAGACACTGG

AACTCCACACTGGAACAACAAAGAGGCATTGGTAGAATTCAAGGATGCCCACGCCAAGAGGCAAACCGTCGTCGTTCTG

GGGAGCCAGGAAGGAGCCGTTCACACGGCTCTCGCTGGAGCTCTAGAGGCTGAGATGGATGGTGCAAAGGGAAAGCTG

TTCTCTGGCCATTTGAAATGCCGCCTAAAAATGGACAAGCTTAGATTGAAGGGCGTGTCATATTCCTTGTGCACTGCGGCA

TTCACATTCACCAAGGTCCCAGCTGAAACACTGCATGGAACAGTCACAGTGGAGGTGCAGTATGCAGGGACAGATGGAC

CCTGCAAGATCCCAGTCCAGATGGCGGTGGACATGCAGACCCTGACCCCAGTTGAAGGCTGATAACCGCCAACCCCGTG

ATTACTGAAAGCACTGAGAACTCAAAGATGATGTTGGAGCTTGACCCACCATTTGGGGATTCTTACATTGTCATAGGAGTT

-continued

```
GGGGACAAGAAAATCACCCACCACTGGCATAGGAGTGGTAGCACCATCGGAAAGGCATTTGAGGCCACTGTGAGAGGC
GCCAAGAGAATGGCAGTCCTGGGGGATACAGCCTGGGACTTCGGATCAGTCGGGGGTGTGTTCAACTCACTGGGTAAGG
GCATTCACCAGATTTTTGGAGCAGCCTTCAAATCACTGTTTGGAGGAATGTCCTGGTTCTCACAGATCCTCATAGGCACGC
TGCTAGTGTGGTTAGGTTTGAACACAAAGAATGGATCTATCTCCCTCACATGCTTGGCCCTGGGGGGAGTGATGATCTTCC
TCTCCACGGCTGTTTCTGCTGACGTGGGGTGCTCAGTGGACTTCTCAAAAAAGGAAACGAGATGTGGCACGGGGGTATTC
ATCTATAATGATGTTGAAGCCTGGAGGGACCGGTACAAGTACCATCCTGACTCCCCCCGCAGATTGGCAGCAGCAGTCAA
GCAGGCCTGGGAAGAGGGGATCTGTGGGATCTCATCCGTTTCAAGAATGGAAAACATCATGTGGAAATCAGTAGAAGGG
GAGCTCAATGCTATCCTAGAGGAGAATGGAGTTCAACTGACAGTTGTTGTGGGATCTGTAAAAAACCCCATGTGGAGAG
GTCCACAAAGATTGCCAGTGCCTGTGAATGAGCTGCCCCATGGCTGGAAAGCCTGGGGGAAATCGTATTTTGTTAGGGCG
GCAAAGACCAACAACAGTTTTGTTGTCGACGGTGACACACTGAAGGAATGTCCGCTTGAGCACAGAGCATGGAATAGTTT
TCTTGTGGAGGATCACGGGTTTGGAGTCTTCCACACCAGTGTCTGGCTTAAGGTCAGAGAAGATTACTCATTAGAATGTG
ACCCAGCCGTCATAGGAACAGCTGTTAAGGGAAGGGAGGCCGCGCACAGTGATCTGGGCTATTGGATTGAAAGTGAAAA
GAATGACACATGGAGGCTGAAGAGGGCCCACCTGATTGAGATGAAAACATGTGAATGGCCAAAGTCTCACACATTGTGG
ACAGATGGAGTAGAAGAAAGTGATCTTATCATACCCAAGTCTTTAGCTGGTCCACTCAGCCACCACAACACCAGAGAGGG
TTACAGAACCCAAGTGAAAGGGCCATGGCACAGTGAAGAGCTTGAAATCCGGTTTGAGGAATGTCCAGGCACCAAGGTT
TACGTGGAGGAGACATGCGGAACTAGAGGACCATCTCTGAGATCAACTACTGCAAGTGGAAGGGTCATTGAGGAATGGT
GCTGTAGGGAATGCACAATGCCCCCACTATCGTTTCGAGCAAAAGACGGCTGCTGGTATGGAATGGAGATAAGGCCCAG
GAAAGAACCAGAGAGCAACTTAGTGAGGTCAATGGTGACAGCGGGGTCAACCGATCATATGGACCACTTCTCTCTTGGA
GTGCTTGTGATTCTACTCATGGTGCAGGAGGGGTTGAAGAAGAGAATGACCACAAAGATCATCATGAGCACATCAATGG
CAGTGCTGGTAGTCATGATCTTGGGAGGATTTTCAATGAGTGACCTGGCCAAGCTTGTGATCCTGATGGGTGCTACTTTCG
CAGAAATGAACACTGGAGGAGATGTAGCTCACTTGGCATTGGTAGCGGCATTTAAAGTCAGACCAGCCTTGCTGGTCTCC
TTCATTTTCAGAGCCAATTGGACACCCCGTGAGAGCATGCTGCTAGCCCTGGCTTCGTGTCTTCTGCAAACTGCGATCTCT
GCTCTTGAAGGTGACTTGATGGTCCTCATTAATGGATTTGCTTTGGCCTGGTTGGCAATTCGAGCAATGGCCGTGCCACGC
ACTGACAACATCGCTCTACCAATCTTGGCTGCTCTAACACCACTAGCTCGAGGCACACTGCTCGTGGCATGGAGAGCGGG
CCTGGCTACTTGTGGAGGGATCATGCTCCTCTCCCTGAAAGGGAAAGGTAGTGTGAAGAAGAACCTGCCATTTGTCATGG
CCCTGGGATTGACAGCTGTGAGGGTAGTAGACCCTATTAATGTGGTAGGACTACTGTTACTCACAAGGAGTGGGAAGCG
GAGCTGGCCCCCTAGTGAAGTTCTCACAGCCGTTGGCCTGATATGTGCACTGGCCGGAGGGTTTGCCAAGGCAGACATTG
AGATGGCTGGACCCATGGCTGCAGTAGGCTTGCTAATTGTCAGCTATGTGGTCTCGGGAAAGAGTGTGGACATGTACATT
GAAAGAGCAGGTGACATCACATGGGAAAAGGACGCGGAAGTCACTGGAAACAGTCCTCGGCTTGACGTGGCACTGGAT
GAGAGTGGTGATTTCTCCTTGGTAGAGGAAGATGGTCCACCCATGAGAGAGATCATACTTAAGGTGGTCCTGATGGCCAT
CTGTGGCATGAACCCAATAGCTATACCTTTTGCTGCAGGAGCGTGGTATGTGTATGTGAAGACTGGGAAAAGGAGTGGC
GCCCTCTGGGACGTGCCTGCTCCCAAAGAAGTGAAGAAAGGAGAGACCACAGATGGAGTGTACAGAGTGATGACTCGCA
GACTGCTAGGTTCAACACAGGTTGGAGTGGGAGTCATGCAAGAGGGAGTCTTCCACACCATGTGGCACGTTACAAAAGG
AGCCGCACTGAGGAGCGGTGAGGGAAGACTTGATCCATACTGGGGGGATGTCAAGCAGGACTTGGTGTCATACTGTGG
GCCTTGGAAGTTGGATGCAGCTTGGGATGGACTCAGCGAGGTACAGCTTTTGGCCGTACCTCCCGGAGAGAGGGCCAGA
AACATTCAGACCCTGCCTGGAATATTCAAGACAAAGGACGGGGACATCGGAGCAGTTGCTCTGGACTACCCTGCAGGGA
CCTCAGGATCTCCGATCCTAGACAAATGTGGAAGAGTGATAGGACTCTATGGCAATGGGGTTGTGATCAAGAATGGAAG
CTATGTTAGTGCTATAACCCAGGGAAAGAGGGAGGAGGAGACTCCGGTTGAATGTTTCGAACCCTCGATGCTGAAGAAG
AAGCAGCTAACTGTCTTGGATCTGCATCCAGGAGCCGGAAAAACCAGGAGAGTTCTTCCTGAAATAGTCCGTGAAGCCAT
AAAAAAGAGACTCCGGACAGTGATCTTGGCACCAACTAGGGTTGTCGCTGCTGAGATGGAGGAGGCCTTGAGAGGACTT
CCGGTGCGTTACATGACAACAGCAGTCAACGTCACCCATTCTGGGACAGAAATCGTTGATTTGATGTGCCATGCCACTTTC
```

-continued

```
ACTTCACGCTTACTACAACCCATCAGAGTCCCTAATTACAATCTCTACATCATGGATGAAGCCCACTTCACAGACCCCTCAA
GTATAGCTGCAAGAGGATATATATCAACAAGGGTTGAAATGGGCGAGGCGGCTGCCATTTTTATGACTGCCACACCACCA
GGAACCCGTGATGCGTTTCCTGACTCTAACTCACCAATCATGGACACAGAAGTGGAAGTCCCAGAGAGAGCCTGGAGCTC
AGGCTTTGATTGGGTGACAGACCATTCTGGGAAAACAGTTTGGTTCGTTCCAAGCGTGAGAAACGGAAATGAAATCGCA
GCCTGTCTGACAAAGGCTGGAAAGCGGGTCATACAGCTCAGCAGGAAGACTTTTGAGACAGAATTTCAGAAAACAAAAA
ATCAAGAGTGGGACTTTGTCATAACAACTGACATCTCAGAGATGGGCGCCAACTTCAAGGCTGACCGGGTCATAGACTCT
AGGAGATGCCTAAAACCAGTCATACTTGATGGTGAGAGAGTCATCTTGGCTGGGCCCATGCCTGTCACGCATGCTAGTGC
TGCTCAGAGGAGAGGACGTATAGGCAGGAACCCTAACAAACCTGGAGATGAGTACATGTATGGAGGTGGGTGTGCAGA
GACTGATGAAGGCCATGCACACTGGCTTGAAGCAAGAATGCTTCTTGACAACATCTACCTCCAGGATGGCCTCATAGCCTC
GCTCTATCGGCCTGAGGCCGATAAGGTAGCCGCCATTGAGGGAGAGTTTAAGCTGAGGACAGAGCAAAGGAAGACCTTC
GTGGAACTCATGAAGAGAGGAGACCTTCCCGTCTGGCTAGCCTATCAGGTTGCATCTGCCGGAATAACTTACACAGACAG
AAGATGGTGCTTTGATGGCACAACCAACAACACCATAATGGAAGACAGCGTACCAGCAGAGGTGTGGACAAAGTATGGA
GAGAAGAGAGTGCTCAAACCGAGATGGATGGATGCTAGGGTCTGTTCAGACCATGCGGCCCTGAAGTCGTTCAAAGAAT
TCGCCGCTGGAAAAAGAGGAGCGGCTTTGGGAGTAATGGAGGCCCTGGGAACACTGCCAGGACACATGACAGAGAGGT
TTCAGGAAGCCATTGACAACCTCGCCGTGCTCATGCGAGCAGAGACTGGAAGCAGGCCTTATAAGGCAGCGGCAGCCCA
ACTGCCGGAGACCCTAGAGACCATTATGCTCTTAGGTTTGCTGGGAACAGTTTCACTGGGGATCTTCTTCGTCTTGATGCG
GAATAAGGGCATCGGGAAGATGGGCTTTGGAATGGTAACCCTTGGGGCCAGTGCATGGCTCATGTGGCTTTCGGAAATT
GAACCAGCCAGAATTGCATGTGTCCTCATTGTTGTGTTTTTATTACTGGTGGTGCTCATACCCGAGCCAGAGAAGCAAAGA
TCTCCCCAAGATAACCAGATGGCAATTATCATCATGGTGGCAGTGGGCCTTCTAGGTTTGATAACTGCAAACGAACTTGGA
TGGCTGGAAAGAACAAAAAATGACATAGCTCATCTAATGGGAAGGAGAGAAGAAGGAGCAACCATGGGATTCTCAATG
GACATTGATCTGCGGCCAGCCTCCGCCTGGGCTATCTATGCCGCATTGACAACTCTCATCACCCCAGCTGTCCAACATGCG
GTAACCACTTCATACAACAACTACTCCTTAATGGCGATGGCCACACAAGCTGGAGTGCTGTTTGGCATGGGCAAAGGGAT
GCCATTTTATGCATGGGACCTTGGAGTCCCGCTGCTAATGATGGGTTGCTATTCACAATTAACACCCCTGACTCTGATAGT
AGCTATCATTCTGCTTGTGGCGCACTACATGTACTTGATCCCAGGCCTACAAGCGGCAGCAGCGCGTGCTGCCCAGAAAA
GGACAGCAGCTGGCATCATGAAGAATCCCGTTGTGGATGGAATAGTGGTAACTGACATTGACACAATGACAATAGACCC
CCAGGTGGAGAAGAAGATGGGACAAGTGTTACTCATAGCAGTAGCCATCTCCAGTGCTGTGCTGCTGCGGACCGCCTGG
GGATGGGGGGAGGCTGGAGCTCTGATCACAGCAGCGACCTCCACCTTGTGGGAAGGCTCTCCAAACAAATACTGGAACT
CCTCTACAGCCACCTCACTGTGCAACATCTTCAGAGGAAGCTATCTGGCAGGAGCTTCCCTTATCTATACAGTGACGAGAA
ACGCTGGCCTGGTTAAGAGACGTGGAGGTGGGACGGGAGAGACTCTGGGAGAGAAGTGGAAAGCTCGTCTGAATCAGA
TGTCGGCCCTGGAGTTCTACTCTTATAAAAAGTCAGGTATCACTGAAGTGTGTAGAGAGGAGGCTCGCCGTGCCCTCAAG
GATGGAGTGGCCACAGGAGGACATGCCGTATCCCGGGGAAGTGCAAAGCTCAGATGGTTGGTGGAGAGAGGATATCTG
CAGCCCTATGGGAAGGTTGTTGACCTCGGATGTGGCAGAGGGGGCTGGAGCTATTATGCCGCCACCATCCGCAAAGTGC
AGGAGGTGAGAGGATACACAAAGGGAGGTCCCGGTCATGAAGAACCCATGCTGGTGCAAAGCTATGGGTGGAACATAG
TTCGTCTCAAGAGTGGAGTGGACGTCTTCCACATGGCGGCTGAGCCGTGTGACACTCTGCTGTGTGACATAGGTGAGTCA
TCATCTAGTCCTGAAGTGGAAGAGACACGAACACTCAGAGTGCTCTCTATGGTGGGGACTGGCTTGAAAAAAGACCAG
GGGCCTTCTGTATAAAGGTGCTGTGCCCATACACCAGCACTATGATGGAAACCATGGAGCGACTGCAACGTAGGCATGG
GGGAGGATTAGTCAGAGTGCCATTGTCTCGCAACTCCACACATGAGATGTACTGGGTCTCTGGGCAAAGAGCAACATCA
TAAAAAGTGTGTCCACCACAAGTCAGCTCCTCCTGGGACGCATGGATGGCCCCAGGAGGCCAGTGAAATATGAGGAGGA
TGTGAACCTCGGCTCGGGTACACGAGCTGTGGCAAGCTGTGCTGAGGCTCCTAACATGAAAATCATCGGCAGGCGCATTG
AGAGAATCCGCAATGAACATGCAGAAACATGGTTTCTTGATGAAAACCACCCATACAGGACATGGGCCTACCATGGGAGC
```

-continued

TACGAAGCCCCCACGCAAGGATCAGCGTCTTCCCTCGTGAACGGGGTTGTTAGACTCCTGTCAAAGCCTTGGGACGTGGT
GACTGGAGTTACAGGAATAGCCATGACTGACACCACACCATACGGCCAACAAAGAGTCTTCAAAGAAAAAGTGGACACC
AGGGTGCCAGATCCCCAAGAAGGCACTCGCCAGGTAATGAACATAGTCTCTTCCTGGCTGTGGAAGGAGCTGGGGAAAC
GCAAGCGGCCACGCGTCTGCACCAAAGAAGAGTTTATCAACAAGGTGCGCAGCAATGCAGCACTGGGAGCAATATTTGA
AGAGGAAAAAGAATGGAAGACGGCTGTGGAAGCTGTGAATGATCCAAGGTTTTGGGCCCTAGTGGATAGGGAGAGAGA
ACACCACCTGAGAGGAGAGTGTCACAGCTGTGTGTACAACATGATGGGAAAAAGAGAAAAGAAGCAAGGAGAGTTCGG
GAAAGCAAAAGGTAGCCGCGCCATCTGGTACATGTGGTTGGGAGCCAGATTCTTGGAGTTTGAAGCCCTTGGATTCTTGA
ACGAGGACCATTGGATGGGAAGAGAAAACTCAGGAGGTGGAGTCGAAGGGTTAGGATTGCAAAGACTTGGATACATTC
TAGAAGAAATGAATCGGGCACCAGGAGGAAAGATGTACGCAGATGACACTGCTGGCTGGGACACCCGCATTAGTAAGTT
TGATCTGGAGAATGAAGCTCTGATTACCAACCAAATGGAGGAAGGGCACAGAACTCTGGCGTTGGCCGTGATTAAATAC

ACATACCAAAACAAAGTGGTGAAGGTTCTCAGACCAGCTGAAGGAGGAAAAACAGTTATGGACATCATTTCAAGACAAG

ACCAGAGAGGGAGTGGACAAGTTGTCACTTATGCTCTCAACACATTCACCAACTTGGTGGTGCAGCTTATCCGGAACATG
GAAGCTGAGGAAGTGTTAGAGATGCAAGACTTATGGTTGTTGAGGAAGCCAGAGAAAGTGACCAGATGGTTGCAGAGC
AATGGATGGGATAGACTCAAACGAATGGCGGTCAGTGGAGATGACTGCGTTGTGAAGCCAATCGATGATAGGTTTGCAC
ATGCCCTCAGGTTCTTGAATGACATGGGAAAAGTTAGGAAAGACACACAGGAGTGGAAACCCTCGACTGGATGGAGCAA
TTGGGAAGAAGTCCCGTTCTGCTCCCACCACTTCAACAAGCTGTACCTCAAGGATGGGAGATCCATTGTGGTCCCTTGCCG
CCACCAAGATGAACTGATTGGCCGAGCTCGCGTCTCACCAGGGGCAGGATGGAGCATCCGGGAGACTGCCTGTCTTGCA
AAATCATATGCGCAGATGTGGCAGCTCCTTTATTTCCACAGAAGAGACCTTCGACTGATGGCTAATGCCATTTGCTCGGCT
GTGCCAGTTGACTGGGTACCAACTGGGAGAACCACCTGGTCAATCCATGGAAAGGGAGAATGGATGACCACTGAGGACA
TGCTCATGGTGTGGAATAGAGTGTGGATTGAGGAGAACGACCATATGGAGGACAAGACTCCTGTAACAAAATGGACAGA
CATTCCCTATCTAGGAAAAAGGGAGGACTTATGGTGTGGATCCCTTATAGGGCACAGACCCCGCACCACTTGGGCTGAAA
ACATCAAAGACACAGTCAACATGGTGCGCAGGATCATAGGTGATGAAGAAAAGTACATGGACTATCTATCCACCCAAGTC
CGCTACTTGGGTGAGGAAGGGTCCACACCCGGAGTGTTGTAAGCACCAATTTTAGTGTTGTCAGGCCTGCTAGTCAGCCA
CAGTTTGGGGAAAGCTGTGCAGCCTGTAACCCCCCCAGGAGAAGCTGGGAAACCAAGCTCATAGTCAGGCCGAGAACGC

CATGGCACGGAAGAAGCCATGCTGCCTGTGAGCCCCTCAGAGGACACTGAGTCAAAAAACCCCACGCGCTTGGAAGCGC

AGGATGGGAAAAGAAGGTGGCGACCTTCCCCACCCTTCAATCTGGGGCCTGAACTGGAGACTAGCTGTGAATCTCCAGC
AGAGGGACTAGTGGTTAGAGGAGACCCCCCGGAAAACGCAAAACAGCATATTGACGCTGGGAAAGACCAGAGACTCCA
TGAGTTTCCACCACGCTGGCCGCCAGGCACAGATCGCCGAACAGCGGCGGCCGGTGTGGGGAAATCCATGGTTTCT

AY632535.2 NC_012532.1 Zika virus strain MR 766, Uganda, complete genome
SEQ ID NO: 12

AGTTGTTGATCTGTGTGAGTCAGACTGCGACAGTTCGAGTCTGAAGCGAGAGCTAACAACAGTATCAACAGGTTTAATTT

GGATTTGGAAACGAGAGTTTCTGGTCATGAAAAACCCCAAAGAAGAAATCCGGAGGATCCGGATTGTCAATATGCTAAA

ACGCGGAGTAGCCCGTGTAAACCCCTTGGGAGGTTTGAAGAGGTTGCCAGCCGGACTTCTGCTGGGTCATGGACCCATCA

GAATGGTTTTGGCGATACTAGCCTTTTTGAGATTTACAGCAATCAAGCCATCACTGGGCCTTATCAACAGATGGGGTTCCG

TGGGGAAAAAAGAGGCTATGGAAATAATAAAGAAGTTCAAGAAAGATCTTGCTGCCATGTTGAGAATAATCAATGCTAG

GAAAGAGAGGAAGAGACGTGGCGCAGACACCAGCATCGGAATCATTGGCCTCCTGCTGACTACAGCCATGGCAGCAGA

GATCACTAGACGCGGGAGTGCATACTACATGTACTTGGATAGGAGCGATGCCGGGAAGGCCATTTCGTTTGCTACCACAT

TGGGAGTGAACAAGTGCCACGTACAGATCATGGACCTCGGGCACATGTGTGACGCCACCATGAGTTATGAGTGCCCTATG

CTGGATGAGGGAGTGGAACCAGATGATGTCGATTGCTGGTGCAACACGACATCAACTTGGGTTGTGTACGGAACCTGTC

ATCACAAAAAAGGTGAGGCACGGCGATCTAGAAGAGCCGTGACGCTCCCTTCTCACTCTACAAGGAAGTTGCAAACGCG

-continued

```
GTCGCAGACCTGGTTAGAATCAAGAGAATACACGAAGCACTTGATCAAGGTTGAAAACTGGATATTCAGGAACCCCGGG

TTTGCGCTAGTGGCCGTTGCCATTGCCTGGCTTTTGGGAAGCTCGACGAGCCAAAAAGTCATATACTTGGTCATGATACTG

CTGATTGCCCCGGCATACAGTATCAGGTGCATTGGAGTCAGCAATAGAGACTTCGTGGAGGGCATGTCAGGTGGGACCT

GGGTTGATGTTGTCTTGGAACATGGAGGCTGCGTTACCGTGATGGCACAGGACAAGCCAACAGTCGACATAGAGTTGGT

CACGACGACGGTTAGTAACATGGCCGAGGTAAGATCCTATTGCTACGAGGCATCGATATCGGACATGGCTTCGGACAGTC

GTTGCCCAACACAAGGTGAAGCCTACCTTGACAAGCAATCAGACACTCAATATGTCTGCAAAAGAACATTAGTGGACAGA

GGTTGGGGAAACGGTTGTGGACTTTTTGGCAAAGGGAGCTTGGTGACATGTGCCAAGTTTACGTGTTCTAAGAAGATGA

CCGGGAAGAGCATTCAACCGGAAAATCTGGAGTATCGGATAATGCTATCAGTGCATGGCTCCCAGCATAGCGGGATGAT

TGGATATGAAACTGACGAAGATAGAGCGAAAGTCGAGGTTACGCCTAATTCACCAAGAGCGGAAGCAACCTTGGGAGGC

TTTGGAAGCTTAGGACTTGACTGTGAACCAAGGACAGGCCTTGACTTTTCAGATCTGTATTACCTGACCATGAACAATAAG

CATTGGTTGGTGCACAAAGAGTGGTTTCATGACATCCCATTGCCTTGGCATGCTGGGGCAGACACCGGAACTCCACACTG

GAACAACAAAGAGGCATTGGTAGAATTCAAGGATGCCCACGCCAAGAGGCAAACCGTCGTCGTTCTGGGGAGCCAGGAA

GGAGCCGTTCACACGGCTCTCGCTGGAGCTCTAGAGGCTGAGATGGATGGTGCAAAGGGAAGGCTGTTCTCTGGCCATT

TGAAATGCCGCCTAAAAATGGACAAGCTTAGATTGAAGGGCGTGTCATATTCCTTGTGCACTGCGGCATTCACATTCACCA

AGGTCCCAGCTGAAACACTGCATGAACAGTCACAGTGGAGGTGCAGTATGCAGGGACAGATGGACCCTGCAAGATCCC

AGTCCAGATGGCGGTGGACATGCAGACCCTGACCCCAGTTGGAAGGCTGATAACCGCCAACCCCGTGATTACTGAAAGC

ACTGAGAACTCAAAGATGATGTTGGAGCTTGACCCACCATTTGGGGATTCTTACATTGTCATAGGAGTTGGGGACAAGAA

AATCACCCACCACTGGCATAGGAGTGGTAGCACCATCGGAAAGGCATTTGAGGCCACTGTGAGAGGCGCCAAGAGAATG

GCAGTCCTGGGGGATACAGCCTGGGACTTCGGATCAGTCGGGGGTGTGTTCAACTCACTGGGTAAGGGCATTCACCAGA

TTTTTGGAGCAGCCTTCAAATCACTGTTTGGAGGAATGTCCTGGTTCTCACAGATCCTCATAGGCACGCTGCTAGTGTGGT

TAGGTTTGAACACAAAGAATGGATCTATCTCCCTCACATGCTTGGCCCTGGGGGAGTGATGATCTTCCTCTCCACGGCTG

TTTCTGCTGACGTGGGGTGCTCAGTGGACTTCTCAAAAAAGGAAACGAGATGTGGCACGGGGTATTCATCTATAATGAT

GTTGAAGCCTGGAGGGACCGGTACAAGTACCATCCTGACTCCCCCCGCAGATTGGCAGCAGCAGTCAAGCAGGCCTGGG

AAGAGGGGATCTGTGGGATCTCATCCGTTTCAAGAATGGAAAACATCATGTGGAAATCAGTAGAAGGGGAGCTCAATGC

TATCCTAGAGGAGAATGGAGTTCAACTGACAGTTGTTGTGGGATCTGTAAAAAACCCCATGTGGAGAGGTCCACAAAGAT

TGCCAGTGCCTGTGAATGAGCTGCCCCATGGCTGGAAAGCCTGGGGGAAATCGTATTTTGTTAGGGCGGCAAAGACCAA

CAACAGTTTTGTTGTCGACGGTGACACACTGAAGGAATGTCCGCTTGAGCACAGAGCATGGAATAGTTTTCTTGTGGAGG

ATCACGGGTTTGGAGTCTTCCACACCAGTGTCTGGCTTAAGGTCAGAGAAGATTACTCATTAGAATGTGACCCAGCCGTCA

TAGGAACAGCTGTTAAGGGAAGGGAGGCCGCGCACAGTGATCTGGGCTATTGGATTGAAAGTGAAAAGAATGACACAT

GGAGGCTGAAGAGGGCCCACCTGATTGAGATGAAAACATGTGAATGGCCAAAGTCTCACACATTGTGGACAGATGGAGT

AGAAGAAAGTGATCTTATCATACCCAAGTCTTTAGCTGGTCCACTCAGCCACCACAACACCAGAGAGGGTTACAGAACCC

AAGTGAAAGGGCCATGGCACAGTGAAGAGCTTGAAATCCGGTTTGAGGAATGTCCAGGCACCAAGGTTTACGTGGAGG

AGACATGCGGAACTAGAGGACCATCTCTGAGATCAACTACTGCAAGTGGAAGGGTCATTGAGGAATGGTGCTGTAGGGA

ATGCACAATGCCCCCACTATCGTTTCGAGCAAAAGACGGCTGCTGGTATGGAATGGAGATAAGGCCCAGGAAAGAACCA

GAGAGCAACTTAGTGAGGTCAATGGTGACAGCGGGGTCAACCGATCATATGGACCACTTCTCTCTTGGAGTGCTTGTGAT

TCTACTCATGGTGCAGGAGGGGTTGAAGAAGAGAATGACCACAAAGATCATCATGAGCACATCAATGGCAGTGCTGGTA

GTCATGATCTTGGGAGGATTTTCAATGAGTGACCTGGCCAAGCTTGTGATCCTGATGGGTGCTACTTTCGCAGAAATGAA

CACTGGAGGAGATGTAGCTCACTTGGCATTGGTAGCGGCATTTAAAGTCAGACCAGCCTTGCTGGTCTCCTTCATTTTCAG

AGCCAATTGGACACCCCGTGAGAGCATGCTGCTAGCCCTGGCTTCGTGTCTTCTGCAAACTGCGATCTCTGCTCTTGAAGG

TGACTTGATGGTCCTCATTAATGGATTTGCTTTGGCCTGGTTGGCAATTCGAGCAATGGCCGTGCCACGCACTGACAACAT

CGCTCTACCAATCTTGGCTGCTCTAACACCACTAGCTCGAGGCACACTGCTCGTGGCATGGAGAGCGGGCCTGGCTACTT
```

-continued

```
GTGGAGGGATCATGCTCCTCTCCCTGAAAGGGAAAGGTAGTGTGAAGAAGAACCTGCCATTTGTCATGGCCCTGGGATT
GACAGCTGTGAGGGTAGTAGACCCTATTAATGTGGTAGGACTACTGTTACTCACAAGGAGTGGGAAGCGGAGCTGGCCC
CCTAGTGAAGTTCTCACAGCCGTTGGCCTGATATGTGCACTGGCCGGAGGGTTTGCCAAGGCAGACATTGAGATGGCTG
GACCCATGGCTGCAGTAGGCTTGCTAATTGTCAGCTATGTGGTCTCGGGAAAGAGTGTGGACATGTACATTGAAAGAGCA
GGTGACATCACATGGGAAAAGGACGCGGAAGTCACTGGAAACAGTCCTCGGCTTGACGTGGCACTGGATGAGAGTGGT
GACTTCTCCTTGGTAGAGGAAGATGGTCCACCCATGAGAGAGATCATACTCAAGGTGGTCCTGATGGCCATCTGTGGCAT
GAACCCAATAGCTATACCTTTTGCTGCAGGAGCGTGGTATGTGTATGTGAAGACTGGGAAAAGGAGTGGCGCCCTCTGG
GACGTGCCTGCTCCCAAAGAAGTGAAGAAAGGAGAGACCACAGATGGAGTGTACAGAGTGATGACTCGCAGACTGCTA
GGTTCAACACAGGTTGGAGTGGGAGTCATGCAAGAGGGAGTCTTCCACACCATGTGGCACGTTACAAAAGGAGCCGCAC
TGAGGAGCGGTGAGGGAAGACTTGATCCATACTGGGGGGATGTCAAGCAGGACTTGGTGTCATACTGTGGGCCTTGGAA
GTTGGATGCAGCTTGGGATGGACTCAGCGAGGTACAGCTTTTGGCCGTACCTCCCGGAGAGAGGGCCAGAAACATTCAG
ACCCTGCCTGGAATATTCAAGACAAAGGACGGGGACATCGGAGCAGTTGCTCTGGACTACCCTGCAGGGACCTCAGGAT
CTCCGATCCTAGACAAATGTGGAAGAGTGATAGGACTCTATGGCAATGGGGTTGTGATCAAGAATGGAAGCTATGTTAGT
GCTATAACCCAGGGAAAGAGGGAGGAGGAGACTCCGGTTGAATGTTTCGAACCCTCGATGCTGAAGAAGAAGCAGCTA
ACTGTCTTGGATCTGCATCCAGGAGCCGGAAAAACCAGGAGAGTTCTTCCTGAAATAGTCCGTGAAGCCATAAAAAAGAG
ACTCCGGACAGTGATCTTGGCACCAACTAGGGTTGTCGCTGCTGAGATGGAGGAGGCCTTGAGAGGACTTCCGGTGCGT
TACATGACAACAGCAGTCAACGTCACCCATTCTGGGACAGAAATCGTTGATTTGATGTGCCATGCCACTTTCACTTCACGC
TTACTACAACCCATCAGAGTCCCTAATTACAATCTCAACATCATGGATGAAGCCCACTTCACAGACCCCTCAAGTATAGCTG
CAAGAGGATACATATCAACAAGGGTTGAAATGGGCGAGGCGGCTGCCATTTTTATGACTGCCACACCACCAGGAACCCGT
GATGCGTTTCCTGACTCTAACTCACCAATCATGGACACAGAAGTGGAAGTCCCAGAGAGAGCCTGGAGCTCAGGCTTTGA
TTGGGTGACAGACCATTCTGGGAAAACAGTTTGGTTCGTTCCAAGCGTGAGAAACGGAAATGAAATCGCAGCCTGTCTGA
CAAAGGCTGGAAAGCGGGTCATACAGCTCAGCAGGAAGACTTTTGAGACAGAATTTCAGAAAACAAAAAATCAAGAGTG
GGACTTTGTCATAACAACTGACATCTCAGAGATGGGCGCCAACTTCAAGGCTGACCGGGTCATAGACTCTAGGAGATGCC
TAAAACCAGTCATACTTGATGGTGAGAGAGTCATCTTGGCTGGGCCCATGCCTGTCACGCATGCTAGTGCTGCTCAGAGG
AGAGGACGTATAGGCAGGAACCCTAACAAACCTGGAGATGAGTACATGTATGGAGGTGGGTGTGCAGAGACTGATGAA
GGCCATGCACACTGGCTTGAAGCAAGAATGCTTCTTGACAACATCTACCTCCAGGATGGCCTCATAGCCTCGCTCTATCGG
CCTGAGGCCGATAAGGTAGCCGCCATTGAGGGAGAGTTTAAGCTGAGGACAGAGCAAAGGAAGACCTTCGTGGAACTC
ATGAAGAGAGGAGACCTTCCCGTCTGGCTAGCCTATCAGGTTGCATCTGCCGGAATAACTTACACAGACAGAAGATGGTG
CTTTGATGGCACAACCAACAACACCATAATGGAAGACAGTGTACCAGCAGAGGTTTGGACAAAGTATGGAGAGAAGAGA
GTGCTCAAACCGAGATGGATGGATGCTAGGGTCTGTTCAGACCATGCGGCCCTGAAGTCGTTCAAAGAATTCGCCGCTGG
AAAAAGAGGAGCGGCTTTGGGAGTAATGGAGGCCCTGGGAACACTGCCAGGACACATGACAGAGAGGTTTCAGGAAGC
CATTGACAACCTCGCCGTGCTCATGCGAGCAGAGACTGGAAGCAGGCCTTATAAGGCAGCGGCAGCCCAACTGCCGGAG
ACCCTAGAGACCATTATGCTCTTAGGTTTGCTGGGAACAGTTTCACTGGGGATCTTCTTCGTCTTGATGCGGAATAAGGGC
ATCGGGAAGATGGGCTTTGGAATGGTAACCCTTGGGGCCAGTGCATGGCTCATGTGGCTTTCGGAAATTGAACCAGCCA
GAATTGCATGTGTCCTCATTGTTGTGTTTTTATTACTGGTGGTGCTCATACCCGAGCCAGAGAAGCAAAGATCTCCCCAAG
ATAACCAGATGGCAATTATCATCATGGTGGCAGTGGGCCTTCTAGGTTTGATAACTGCAAACGAACTTGGATGCTGGAA
AGAACAAAAAATGACATAGCTCATCTAATGGGAAGGAGAAGAAGGAGCAACCATGGGATTCTCAATGGACATTGATC
TGCGGCCAGCCTCCGCCTGGGCTATCTATGCCGCATTGACAACTCTCATCACCCCAGCTGTCCAACATGCGGTAACCACTT
CATACAACAACTACTCCTTAATGGCGATGGCCACACAAGCTGGAGTGCTGTTTGGCATGGGCAAAGGGATGCCATTTATG
CATGGGACCTTGGAGTCCCGCTGCTAATGATGGGTTGCTATTCACAATTAACACCCCTGACTCTGATAGTAGCTATCATT
```

```
CTGCTTGTGGCGCACTACATGTACTTGATCCCAGGCCTACAAGCGGCAGCAGCGCGTGCTGCCCAGAAAAGGACAGCAG

CTGGCATCATGAAGAATCCCGTTGTGGATGGAATAGTGGTAACTGACATTGACACAATGACAATAGACCCCCAGGTGGA

GAAGAAGATGGGACAAGTGTTACTCATAGCAGTAGCCATCTCCAGTGCTGTGCTGCTGCGGACCGCCTGGGGATGGGGG

GAGGCTGGAGCTCTGATCACAGCAGCGACCTCCACCTTGTGGGAAGGCTCTCCAAACAAATACTGGAACTCCTCTACAGC

CACCTCACTGTGCAACATCTTCAGAGGAAGCTATCTGGCAGGAGCTTCCCTTATCTATACAGTGACGAGAAACGCTGGCCT

GGTTAAGAGACGTGGAGGTGGGACGGGAGAGACTCTGGGAGAGAAGTGGAAAGCTCGTCTGAATCAGATGTCGGCCCT

GGAGTTCTACTCTTATAAAAAGTCAGGTATCACTGAAGTGTGTAGAGAGGAGGCTCGCCGTGCCCTCAAGGATGGAGTG

GCCACAGGAGGACATGCCGTATCCCGGGGAAGTGCAAAGATCAGATGGTTGGAGGAGAGAGGATATCTGCAGCCCTAT

GGGAAGGTTGTTGACCTCGGATGTGGCAGAGGGGCTGGAGCTATTATGCCGCCACCATCCGCAAAGTGCAGGAGGTG

AGAGGATACACAAAGGGAGGTCCCGGTCATGAAGAACCCATGCTGGTGCAAAGCTATGGGTGGAACATAGTTCGTCTCA

AGAGTGGAGTGGACGTCTTCCACATGGCGGCTGAGCCGTGTGACACTCTGCTGTGTGACATAGGTGAGTCATCATCTAGT

CCTGAAGTGGAAGAGACACGAACACTCAGAGTGCTCTCTATGGTGGGGACTGGCTTGAAAAAAGACCAGGGGCCTTCT

GTATAAAGGTGCTGTGCCCATACACCAGCACTATGATGGAAACCATGGAGCGACTGCAACGTAGGCATGGGGAGGATT

AGTCAGAGTGCCATTGTGTCGCAACTCCACACATGAGATGTACTGGGTCTCTGGGGCAAAGAGCAACATCATAAAAAGTG

TGTCCACCACAAGTCAGCTCCTCCTGGGACGCATGGATGGCCCCAGGAGGCCAGTGAAATATGAGGAGGATGTGAACCT

CGGCTCGGGTACACGAGCTGTGGCAAGCTGTGCTGAGGCTCCTAACATGAAAATCATCGGCAGGCGCATTGAGAGAATC

CGCAATGAACATGCAGAAACATGGTTTCTTGATGAAAACCACCCATACAGGACATGGGCCTACCATGGGAGCTACGAAGC

CCCCACGCAAGGATCAGCGTCTTCCCTCGTGAACGGGGTTGTTAGACTCCTGTCAAAGCCTTGGGACGTGGTGACTGGAG

TTACAGGAATAGCCATGACTGACACCACACCATACGGCCAACAAAGAGTCTTCAAAGAAAAAGTGGACACCAGGGTGCC

AGATCCCCAAGAAGGCACTCGCCAGGTAATGAACATAGTCTCTTCCTGGCTGTGGAAGGAGCTGGGGAAACGCAAGCGG

CCACGCGTCTGCACCAAAGAAGAGTTTATCAACAAGGTGCGCAGCAATGCAGCACTGGGAGCAATATTTGAAGAGGAAA

AAGAATGGAAGACGGCTGTGGAAGCTGTGAATGATCCAAGGTTTTGGGCCCTAGTGGATAGGGAGAGAGAACACCACC

TGAGAGGAGAGTGTCACAGCTGTGTGTACAACATGATGGGAAAAAGAGAAAAGAAGCAAGGAGAGTTCGGGAAAGCA

AAAGGTAGCCGCGCCATCTGGTACATGTGGTTGGGAGCCAGATTCTTGGAGTTTGAAGCCCTTGGATTCTTGAACGAGGA

CCATTGGATGGGAAGAGAAAACTCAGGAGGTGGAGTCGAAGGGTTAGGATTGCAAAGACTTGGATACATTCTAGAAGA

AATGAATCGGGCACCAGGAGGAAAGATGTACGCAGATGACACTGCTGGCTGGGACACCCGCATTAGTAAGTTTGATCTG

GAGAATGAAGCTCTGATTACCAACCAAATGGAGGAAGGGCACAGAACTCTGGCGTTGGCCGTGATTAAATACACATACC

AAAACAAAGTGGTGAAGGTTCTCAGACCAGCTGAAGGAGGAAAAACAGTTATGGACATCATTTCAAGACAAGACCAGAG

AGGGAGTGGACAAGTTGTCACTTATGCTCTCAACACATTCACCAACTTGGTGGTGCAGCTTATCCGGAACATGGAAGCTG

AGGAAGTGTTAGAGATGCAAGACTTATGGTTGTTGAGGAAGCCAGAGAAAGTGACCAGATGGTTGCAGAGCAATGGAT

GGGATAGACTCAAACGAATGGCGGTCAGTGGAGATGACTGCGTTGTGAAGCCAATCGATGATAGGTTTGCACATGCCCT

CAGGTTCTTGAATGACATGGGAAAAGTTAGGAAAGACACACAGGAGTGGAAACCCTCGACTGGATGGAGCAATTGGGA

AGAAGTCCCGTTCTGCTCCCACCACTTCAACAAGCTGTACCTCAAGGATGGGAGATCCATTGTGGTCCCTTGCCGCCACCA

AGATGAACTGATTGGCCGAGCTCGCGTCTCACCAGGGGCAGGATGGAGCATCCGGGAGACTGCCTGTCTTGCAAAATCA

TATGCGCAGATGTGGCAGCTCCTTTATTTCCACAGAAGAGACCTTCGACTGATGGCTAATGCCATTTGCTCGGCTGTGCCA

GTTGACTGGGTACCAACTGGGAGAACCACCTGGTCAATCCATGGAAAGGGAGAATGGATGACCACTGAGGACATGCTCA

TGGTGTGGAATAGAGTGTGGATTGAGGAGAACGACCATATGGAGGACAAGACTCCTGTAACAAAATGGACAGACATTCC

CTATCTAGGAAAAAGGGAGGACTTATGGTGTGGATCCCTTATAGGGCACAGACCCCGCACCACTTGGGCTGAAAACATCA

AAGACACAGTCAACATGGTGCGCAGGATCATAGGTGATGAAGAAAAGTACATGGACTATCTATCCACCCAAGTCCGCTAC

TTGGGTGAGGAAGGGTCCACACCCGGAGTGTTGTAAGCACCAATTTTAGTGTTGTCAGGCCTGCTAGTCAGCCACAGTTT

GGGGAAAGCTGTGCAGCCTGTAACCCCCCCAGGAGAAGCTGGGAAACCAAGCTCATAGTCAGGCCGAGAACGCCATGG
```

-continued

CACGGAAGAAGCCATGCTGCCTGTGAGCCCCTCAGAGGACACTGAGTCAAAAACCCCACGCGCTTGGAAGCGCAGGAT

GGGAAAAGAAGGTGGCGACCTTCCCCACCCTTCAATCTGGGGCCTGAACTGGAGACTAGCTGTGAATCTCCAGCAGAGG

GACTAGTGGTTAGAGGAGACCCCCCGGAAAACGCAAAACAGCATATTGACGTGGGAAAGACCAGAGACTCCATGAGTTT

CCACCACGCTGGCCGCCAGGCACAGATCGCCGAACTTCGGCGGCCGGTGTGGGGAAATCCATGGTTTCT

KJ776791.1, Zika virus strain H/PF/2013 polyprotein gene, complete cds

SEQ ID NO: 13

AGTATCAACAGGTTTTATTTTGGATTTGGAAACGAGAGTTTCTGGTCATGAAAAACCCAAAAAAGAAATCCGGAGGATTC

CGGATTGTCAATATGCTAAAACGCGGAGTAGCCCGTGTGAGCCCCTTTGGGGGCTTGAAGAGGCTGCCAGCCGGACTTCT

GCTGGGTCATGGGCCCATCAGGATGGTCTTGGCGATTCTAGCCTTTTTGAGATTCACGGCAATCAAGCCATCACTGGGTCT

CATCAATAGATGGGGTTCAGTGGGAAAAAAGAGGCTATGGAAATAATAAAGAAGTTCAAGAAAGATCTGGCTGCCATG

CTGAGAATAATCAATGCTAGGAAGGAGAAGAAGAGACGAGGCGCAGATACTAGTGTCGGAATTGTTGGCCTCCTGCTGA

CCACAGCTATGGCAGCGGAGGTCACTAGACGTGGGAGTGCATACTATATGTACTTGGACAGAAACGACGCTGGGGAGGC

CATATCTTTTCCAACCACATTGGGGATGAATAAGTGTTATATACAGATCATGGATCTTGGACACATGTGTGATGCCACCAT

GAGCTATGAATGCCCTATGCTGGATGAGGGGGTGGAACCAGATGACGTCGATTGTTGGTGCAACACGACGTCAACTTGG

GTTGTGTACGGAACCTGCCATCACAAAAAAGGTGAAGCACGGAGATCTAGAAGAGCTGTGACGCTCCCCTCCCATTCCAC

TAGGAAGCTGCAAACGCGGTCGCAAACCTGGTTGGAATCAAGAGAATACACAAAGCACTTGATTAGAGTCGAAAATTGG

ATATTCAGGAACCCTGGCTTCGCGTTAGCAGCAGCTGCCATCGCTTGGCTTTTGGGAAGCTCAACGAGCCAAAAAGTCAT

ATACTTGGTCATGATACTGCTGATTGCCCCGGCATACAGCATCAGGTGCATAGGAGTCAGCAATAGGGACTTTGTGGAAG

GTATGTCAGGTGGGACTTGGGTTGATGTTGTCTTGGAACATGGAGGTTGTGTCACCGTAATGGCACAGGACAAACCGACT

GTCGACATAGAGCTGGTTACAACAACAGTCAGCAACATGGCGGAGGTAAGATCCTACTGCTATGAGGCATCAATATCGG

ACATGGCTTCGGACAGCCGCTGCCCAACACAAGGTGAAGCCTACCTTGACAAGCAATCAGACACTCAATATGTCTGCAAA

AGAACGTTAGTGGACAGAGGCTGGGGAAATGGATGTGGACTTTTTGGCAAAGGGAGCCTGGTGACATGCGCTAAGTTTG

CATGCTCCAAGAAAATGACCGGGAAGAGCATCCAGCCAGAGAATCTGGAGTACCGGATAATGCTGTCAGTTCATGGCTCC

CAGCACAGTGGGATGATCGTTAATGACACAGGACATGAAACTGATGAGAATAGAGCGAAGGTTGAGATAACGCCCAATT

CACCAAGAGCCGAAGCCACCCTGGGGGGTTTTGGAAGCCTAGGACTTGATTGTGAACCGAGGACAGGCCTTGACTTTTCA

GATTTGTATTACTTGACTATGAATAACAAGCACTGGTTGGTTCACAAGGAGTGGTTCCACGACATTCCATTACCTTGGCAC

GCTGGGGCAGACACCGGAACTCCACACTGGAACAACAAAGAAGCACTGGTAGAGTTCAAGGACGCACATGCCAAAAGG

CAAACTGTCGTGGTTCTAGGGAGTCAAGAAGGAGCAGTTCACACGGCCCTTGCTGGAGCTCTGGAGGCTGAGATGGATG

GTGCAAAGGGAAGGCTGTCCTCTGGCCACTTGAAATGTCGCCTGAAAATGGATAAACTTAGATTGAAGGGCGTGTCATAC

TCCTTGTGTACCGCAGCGTTCACATTCACCAAGATCCCGGCTGAAACACTGCACGGGACAGTCACAGTGGAGGTACAGTA

CGCAGGGACAGATGGACCTTGCAAGGTTCCAGCTCAGATGGCGGTGGACATGCAAACTCTGACCCCAGTTGGGAGGTTG

ATAACCGCTAACCCCGTAATCACTGAAAGCACTGAGAACTCTAAGATGATGCTGGAACTTGATCCACCATTTGGGGACTCT

TACATTGTCATAGGAGTCGGGGAGAAGAAGATCACCCACCACTGGCACAGGAGTGGCAGCACCATTGGAAAAGCATTTG

AAGCCACTGTGAGAGGTGCCAAGAGAATGGCAGTCTTGGGAGACACAGCCTGGGACTTTGGATCAGTTGGAGGCGCTCT

CAACTCATTGGGCAAGGGCATCCATCAAATTTTTGGAGCAGCTTTCAAATCATTGTTTGGAGGAATGTCCTGGTTCTCACA

AATTCTCATTGGAACGTTGCTGATGTGGTTGGGTCTGAACACAAAGAATGGATCTATTTCCCTTATGTGCTTGGCCTTAGG

GGGAGTGTTGATCTTCTTATCCACAGCTGTCTCTGCTGATGTGGGGTGCTCGGTGGACTTCTCAAAGAAGGAGACGAGAT

GCGGTACAGGGGTGTTCGTCTATAACGACGTTGAAGCCTGGAGGGACAGGTACAAGTACCATCCTGACTCCCCCCGTAGA

TTGGCAGCAGCAGTCAAGCAAGCCTGGGAAGATGGTATCTGTGGGATCTCCTCTGTTTCAAGAATGGAAAACATCATGTG

GAGATCAGTAGAAGGGGAGCTCAACGCAATCCTGGAAGAGAATGGAGTTCAACTGACGGTCGTTGTGGGATCTGTAAAA

```
AACCCCATGTGGAGAGGTCCACAGAGATTGCCCGTGCCTGTGAACGAGCTGCCCCACGGCTGGAAGGCTTGGGGGAAAT
CGTACTTCGTCAGAGCAGCAAAGACAAATAACAGCTTTGTCGTGGATGGTGACACACTGAAGGAATGCCCACTCAAACAT
AGAGCATGGAACAGCTTTCTTGTGGAGGATCATGGGTTCGGGGTATTTCACACTAGTGTCTGGCTCAAGGTTAGAGAAGA
TTATTCATTAGAGTGTGATCCAGCCGTTATTGGAACAGCTGTTAAGGGAAAGGAGGCTGTACACAGTGATCTAGGCTACT
GGATTGAGAGTGAGAAGAATGACACATGGAGGCTGAAGAGGGCCCATCTGATCGAGATGAAAACATGTGAATGGCCAA
AGTCCCACACATTGTGGACAGATGGAATAGAAGAGAGTGATCTGATCATACCCAAGTCTTTAGCTGGGCCACTCAGCCAT
CACAATACCAGAGAGGGCTACAGGACCCAAATGAAAGGGCCATGGCACAGTGAAGAGCTTGAAATTCGGTTTGAGGAAT
GCCCAGGCACTAAGGTCCACGTGGAGGAAACATGTGGAACAAGAGGACCATCTCTGAGATCAACCACTGCAAGCGGAAG
GGTGATCGAGGAATGGTGCTGCAGGGAGTGCACAATGCCCCCACTGTCGTTCCGGGCTAAAGATGGCTGTTGGTATGGA
ATGGAGATAAGGCCCAGGAAAGAACCAGAAAGTAACTTAGTAAGGTCAATGGTGACTGCAGGATCAACTGATCACATGG
ATCACTTCTCCCTTGGAGTGCTTGTGATTCTGCTCATGGTGCAGGAAGGGCTGAAGAAGAGAATGACCACAAAGATCATC
ATAAGCACATCGATGGCAGTGCTGGTAGCTATGATCCTGGGAGGATTTTCAATGAGTGACCTGGCTAAGCTTGCAATTTT
GATGGGTGCCACCTTCGCGGAAATGAACACTGGAGGAGATGTAGCTCATCTGGCGCTGATAGCGGCATTCAAAGTCAGA
CCAGCGTTGCTGGTATCTTTCATCTTCAGAGCTAATTGGACACCCCGTGAAAGCATGCTGCTGGCCTTGGCCTCGTGTCTTT
TGCAAACTGCGATCTCCGCCTTGGAAGGCGACCTGATGGTTCTCATCAATGGTTTTGCTTTGGCCTGGTTGGCAATACGAG
CGATGGTTGTTCCACGCACTGATAACATCACCTTGGCAATCCTGGCTGCTCTGACACCACTGGCCCGGGGCACACTGCTTG
TGGCGTGGAGAGCAGGCCTTGCTACTTGCGGGGGGTTTATGCTCCTCTCTCTGAAGGGAAAAGGCAGTGTGAAGAAGAA
CTTACCATTTGTCATGGCCCTGGGACTAACCGCTGTGAGGCTGGTCGACCCCATCAACGTGGTGGGACTGCTGTTGCTCAC
AAGGAGTGGGAAGCGGAGCTGGCCCCCTAGCGAAGTACTCACAGCTGTTGGCCTGATATGCGCATTGGCTGGAGGGTTC
GCCAAGGCAGATATAGAGATGGCTGGGCCCATGGCCGCGGTCGGTCTGCTAATTGTCAGTTACGTGGTCTCAGGAAAGA
GTGTGGACATGTACATTGAAAGAGCAGGTGACATCACATGGGAAAAAGATGCGGAAGTCACTGGAAACAGTCCCCGGCT
CGATGTGGCGCTAGATGAGAGTGGTGATTTCTCCCTGGTGGAGGATGACGGTCCCCCCATGAGAGAGATCATACTCAAG
GTGGTCCTGATGACCATCTGTGGCATGAACCCAATAGCCATACCCTTTGCAGCTGGAGCGTGGTACGTATACGTGAAGAC
TGGAAAAAGGAGTGGTGCTCTATGGGATGTGCCTGCTCCCAAGGAAGTAAAAAAGGGGGAGACCACAGATGGAGTGTA
CAGAGTAATGACTCGTAGACTGCTAGGTTCAACACAAGTTGGAGTGGGAGTTATGCAAGAGGGGGTCTTTCACACTATGT
GGCACGTCACAAAAGGATCCGCGCTGAGAAGCGGTGAAGGGAGACTTGATCCATACTGGGGAGATGTCAAGCAGGATC
TGGTGTCATACTGTGGTCCATGGAAGCTAGATGCCGCCTGGGACGGGCACAGCGAGGTGCAGCTCTTGGCCGTGCCCCC
CGGAGAGAGAGCGAGGAACATCCAGACTCTGCCCGGAATATTTAAGACAAAGGATGGGGACATTGGAGCGGTTGCGCT
GGATTACCCAGCAGGAACTTCAGGATCTCCAATCCTAGACAAGTGTGGGAGAGTGATAGGACTTTATGGCAATGGGGTC
GTGATCAAAAATGGGAGTTATGTTAGTGCCATCACCCAAGGGAGGAGGGAGGAAGAGACTCCTGTTGAGTGCTTCGAGC
CTTCGATGCTGAAGAAGAAGCAGCTAACTGTCTTAGACTTGCATCCTGGAGCTGGGAAAACCAGGAGAGTTCTTCCTGAA
ATAGTCCGTGAAGCCATAAAAACAAGACTCCGTACTGTGATCTTAGCTCCAACCAGGGTTGTCGCTGCTGAAATGGAGGA
AGCCCTTAGAGGGCTTCCAGTGCGTTATATGACAACAGCAGTCAATGTCACCCACTCTGGAACAGAAATCGTCGACTTAAT
GTGCCATGCCACCTTCACTTCACGTCTACTACAGCCAATCAGAGTCCCCAACTATAATCTGTATATTATGGATGAGGCCCAC
TTCACAGATCCCTCAAGTATAGCAGCAAGAGGATACATTTCAACAAGGGTTGAGATGGGCGAGGCGGCTGCCATCTTCAT
GACCGCCACGCCACCAGGAACCCGTGACGCATTTCCGGACTCCAACTCACCAATTATGGACACCGAAGTGGAAGTCCCAG
AGAGAGCCTGGAGCTCAGGCTTTGATTGGGTGACGGATCATTCTGGAAAAACAGTTTGGTTTGTTCCAAGCGTGAGGAAC
GGCAATGAGATCGCAGCTTGTCTGACAAAGGCTGGAAAACGGGTCATACAGCTCAGCAGAAAGACTTTTGAGACAGAGT
TCCAGAAAACAAAACATCAAGAGTGGGACTTTGTCGTGACAACTGACATTTCAGAGATGGGCGCCAACTTTAAAGCTGAC
CGTGTCATAGATTCCAGGAGATGCCTAAAGCCGGTCATACTTGATGGCGAGAGAGTCATTCTGGCTGGACCCATGCCTGT
```

-continued

```
CACACATGCCAGCGCTGCCCAGAGGAGGGGCGCATAGGCAGGAATCCCAACAAACCTGGAGATGAGTATCTGTATGGA
GGTGGGTGCGCAGAGACTGACGAAGACCATGCACACTGGCTTGAAGCAAGAATGCTCCTTGACAATATTTACCTCCAAGA
TGGCCTCATAGCCTCGCTCTATCGACCTGAGGCCGACAAAGTAGCAGCCATTGAGGGAGAGTTCAAGCTTAGGACGGAG
CAAAGGAAGACCTTTGTGGAACTCATGAAAAGAGGAGATCTTCCTGTTTGGCTGGCCTATCAGGTTGCATCTGCCGGAAT
AACCTACACAGATAGAAGATGGTGCTTTGATGGCACGACCAACAACACCATAATGGAAGACAGTGTGCCGGCAGAGGTG
TGGACCAGACACGGAGAGAAAAGAGTGCTCAAACCGAGGTGGATGGACGCCAGAGTTTGTTCAGATCATGCGGCCCTGA
AGTCATTCAAGGAGTTTGCCGCTGGGAAAAGAGGAGCGGCTTTTGGAGTGATGGAAGCCCTGGGAACACTGCCAGGACA
CATGACAGAGATTCCAGGAAGCCATTGACAACCTCGCTGTGCTCATGCGGGCAGAGACTGGAAGCAGGCCTTACAAA
GCCGCGGCGGCCCAATTGCCGGAGACCCTAGAGACCATTATGCTTTTGGGGTTGCTGGGAACAGTCTCGCTGGGAATCTT
TTTCGTCTTGATGAGGAACAAGGGCATAGGGAAGATGGGCTTTGGAATGGTGACTCTTGGGGCCAGCGCATGGCTCATG
TGGCTCTCGGAAATTGAGCCAGCCAGAATTGCATGTGTCCTCATTGTTGTGTTCCTATTGCTGGTGGTGCTCATACCTGAG
CCAGAAAAGCAAAGATCTCCCCAGGACAACCAAATGGCAATCATCATCATGGTAGCAGTAGGTCTTCTGGGCTTGATTAC
CGCCAATGAACTCGGATGGTTGGAGAGAACAAAGAGTGACCTAAGCCATCTAATGGGAAGGAGAGAGGAGGGGGCAAC
CATAGGATTCTCAATGGACATTGACCTGCGGCCAGCCTCAGCTTGGGCCATCTATGCTGCCTTGACAACTTTCATTACCCCA
GCCGTCCAACATGCAGTGACCACTTCATACAACAACTACTCCTTAATGGCGATGGCCACGCAAGCTGGAGTGTTGTTTGGT
ATGGGCAAAGGGATGCCATTCTACGCATGGGACTTTGGAGTCCCGCTGCTAATGATAGGTTGCTACTCACAATTAACACC
CCTGACCCTAATAGTGGCCATCATTTTGCTCGTGGCGCACTACATGTACTTGATCCCAGGGCTGCAGGCAGCAGCTGCGC
GTGCTGCCCAGAAGAGAACGGCAGCTGGCATCATGAAGAACCCTGTTGTGGATGGAATAGTGGTGACTGACATTGACAC
AATGACAATTGACCCCCAAGTGGAGAAAAAGATGGGACAGGTGCTACTCATAGCAGTAGCCGTCTCCAGCGCCATACTGT
CGCGGACCGCCTGGGGGTGGGGGGAGGCTGGGGCCCTGATCACAGCGGCAACTTCCACTTTGTGGGAAGGCTCTCCGA
ACAAGTACTGGAACTCCTCTACAGCCACTTCACTGTGTAACATTTTTAGGGGAAGTTACTTGGCTGGAGCTTCTCTAATCTA
CACAGTAACAAGAAACGCTGGCTTGGTCAAGAGACGTGGGGGTGGAACAGGAGAGACCCTGGGAGAGAAATGGAAGG
CCCGCTTGAACCAGATGTCGGCCCTGGAGTTCTACTCCTACAAAAAGTCAGGCATCACCGAGGTGTGCAGAGAAGAGGCC
CGCCGCGCCCTCAAGGACGGTGTGGCAACGGGAGGCCATGCTGTGTCCCGAGGAAGTGCAAAGCTGAGATGGTTGGTG
GAGCGGGGATACCTGCAGCCCTATGGAAAGGTCATTGATCTTGGATGTGGCAGAGGGGCTGGAGTTACTACGCCGCCA
CCATCCGCAAAGTTCAAGAAGTGAAAGGATACACAAAAGGAGGCCCTGGTCATGAAGAACCCATGTTGGTGCAAAGCTA
TGGGTGGAACATAGTCCGTCTTAAGAGTGGGGTGGACGTCTTTCATATGGCGGCTGAGCCGTGTGACACGTTGCTGTGTG
ACATAGGTGAGTCATCATCTAGTCCTGAAGTGGAAGAAGCACGGACGCTCAGAGTCCTCTCCATGGTGGGGATTGGCTT
GAAAAAAGACCAGGAGCCTTTTGTATAAAAGTGTTGTGCCCATACACCAGCACTATGATGGAAACCCTGGAGCGACTGCA
GCGTAGGTATGGGGAGGACTGGTCAGAGTGCCACTCTCCCGCAACTCTACACATGAGATGTACTGGGTCTCTGGAGCG
AAAAGCAACACCATAAAAAGTGTGTCCACCACGAGCCAGCTCCTCTTGGGGCGCATGGACGGGCCCAGGAGGCCAGTGA
AATATGAGGAGGATGTGAATCTCGGCTCTGGCACGCGGGCTGTGGTAAGCTGCGCTGAAGCTCCCAACATGAAGATCAT
TGGTAACCGCATTGAAAGGATCCGCAGTGAGCACGCGGAAACGTGGTTCTTTGACGAGAACCACCCATATAGGACATGG
GCTTACCATGGAAGCTATGAGGCCCCCACACAAGGGTCAGCGTCCTCTCTAATAAACGGGGTTGTCAGGCTCCTGTCAAA
ACCCTGGGATGTGGTGACTGGAGTCACAGGAATAGCCATGACCGACACCACACCGTATGGTCAGCAAAGAGTTTTCAAG
GAAAAAGTGGACACTAGGGTGCCAGACCCCCAAGAAGGCACTCGTCAGGTTATGAGCATGGTCTCTTCCTGGTTGTGGA
AAGAGCTAGGCAAACACAAACGGCCACGAGTCTGTACCAAAGAAGAGTTCATCAACAAGGTTCGTAGCAATGCAGCATT
AGGGGCAATATTTGAAGAGGAAAAAGAGTGGAAGACTGCAGTGGAAGCTGTGAACGATCCAAGGTTCTGGGCTCTAGT
GGACAAGGAAAGAGAGCACCACCTGAGAGGAGAGTGCCAGAGTTGTGTGTACAACATGATGGGAAAAAGAGAAAAGA
AACAAGGGGAATTTGGAAAGGCCAAGGGCAGCCGCGCCATCTGGTATATGTGGCTAGGGGCTAGATTTCTAGAGTTCGA
AGCCCTTGGATTCTTGAACGAGGATCACTGGATGGGGAGAGAGAACTCAGGAGGTGGTGTTGAAGGGCTGGGATTACA
```

```
AAGACTCGGATATGTCCTAGAAGAGATGAGTCGCATACCAGGAGGAAGGATGTATGCAGATGACACTGCTGGCTGGGAC

ACCCGCATCAGCAGGTTTGATCTGGAGAATGAAGCTCTAATCACCAACCAAATGGAGAAAGGGCACAGGGCCTTGGCAT

TGGCCATAATCAAGTACACATACCAAAACAAAGTGGTAAAGGTCCTTAGACCAGCTGAAAAAGGGAAGACAGTTATGGA

CATTATTTCGAGACAAGACCAAAGGGGGAGCGGACAAGTTGTCACTTACGCTCTTAACACATTTACCAACCTAGTGGTGC

AACTCATTCGGAATATGGAGGCTGAGGAAGTTCTAGAGATGCAAGACTTGTGGCTGCTGCGGAGGTCAGAGAAAGTGAC

CAACTGGTTGCAGAGCAACGGATGGGATAGGCTCAAACGAATGGCAGTCAGTGGAGATGATTGCGTTGTGAAGCCAATT

GATGATAGGTTTGCACATGCCCTCAGGTTCTTGAATGATATGGGAAAAGTTAGGAAGGACACACAAGAGTGGAAACCCT

CAACTGGATGGGACAACTGGGAAGAAGTTCCGTTTTGCTCCCACCACTTCAACAAGCTCCATCTCAAGGACGGGAGGTCC

ATTGTGGTTCCCTGCCGCCACCAAGATGAACTGATTGGCCGGGCCCGCGTCTCTCCAGGGGGGGATGGAGCATCCGGG

AGACTGCTTGCCTAGCAAAATCATATGCGCAAATGTGGCAGCTCCTTTATTTCCACAGAAGGGACCTCCGACTGATGGCCA

ATGCCATTTGTTCATCTGTGCCAGTTGACTGGGTTCCAACTGGGAGAACTACCTGGTCAATCCATGGAAAGGGAGAATGG

ATGACCACTGAAGACATGCTTGTGGTGTGAACAGAGTGTGGATTGAGGAGAACGACCACATGGAAGACAAGACCCCA

GTTACGAAATGGACAGACATTCCCTATTTGGGAAAAAGGGAAGACTTGTGGTGTGGATCTCTCATAGGGCACAGACCGC

GCACCACCTGGGCTGAGAACATTAAAAACACAGTCAACATGGTGCGCAGGATCATAGGTGATGAAGAAAAGTACATGGA

CTACCTATCCACCCAAGTTCGCTACTTGGGTGAAGAAGGGTCTACACCTGGAGTGCTGTAAGCACCAATCTTAGTGTTGTC

AGGCCTGCTAGTCAGCCACAGCTTGGGGAAAGCTGTGCAGCCTGTGACCCCCCAGGAGAAGCTGGGAAACCAAGCCTA

TAGTCAGGCCGAGAACGCCATGGCACGGAAGAAGCCATGCTGCCTGTGAGCCCCTCAGAGGACACTGAGTCAAAAAACC

CCACGCGCTTGGAGGCGCAGGATGGGAAAAGAAGGTGGCGACCTTCCCCACCCTTCAATCTGGGGCCTGAACTGGAGAT

CAGCTGTGGATCTCCAGAAGAGGGACTAGTGGTTAGAGGAG
```

In some embodiments, the Zika virus has a RNA genome corresponding to the DNA sequence provided by the nucleic acid sequence of any one of SEQ ID NOs: 2-13 or 72. In some embodiments, the Zika virus has a variant genome that is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-13 or 72.

Provided below are amino acid sequences of the E-proteins of Zika strains that may be used in the methods, compositions, and/or vaccines described herein.

isol-ARB15076.AHF49784.1.Central_African_Republic/
291-788 Flavivirus envelope glycoprotein E.
SEQ ID NO: 14
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIVNDENRAKVEVTPNSPRAEATLGGFGSLGLDCEPRTGLDFSDLYYLTM

NNKHWLVHKEWFHDIPLPWHAGADTGTPHWNNKEALVEFKDAHAKRQTVV

VLGSQEGAVHTALAGALEAEMDGAKGRLFSGHLKCRLKMDKLRLKGVSYS

LCTAAFTFTKVPAETLHGTVTVEVQYAGTDGPCKVPAQMAVDMQTLTPVG

RLITANPVITESTENSKMMLELDPPFGDSYIVIGVGDKKITHHWHRSGST

IGKAFEATVRGAKRMAVLGDTAWDFGSVGGVFNSLGKGIHQIFGAAFKSL

FGGMSWFSQILIGTLLVWLGLNTKNGSISLTCLALGGVMIFLSTAVSA isol-lbH_30656.AEN75265.1.Nigeria/291-788
Flavivirus envelope glycoprotein E.
SEQ ID NO: 15
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIVNDENRAKVEVTPNSPRAEATLGGFGSLGLDCEPRTGLDFSDLYYLTM

NNKHWLVHKEWFHDIPLPWHSGADTETPHWNNKEALVEFKDAHAKRQTVV

VLGSQEGAVHTALAGALEAEMDGAKGRLSSGHLKCRLKMDKLRLKGVSYS

LCTAAFTFTKVPAETLHGTVTVEVQYAGRDGPCKVPAQMAVDMQTLTPVG

RLITANPVITESTENSKMMLELDPPFGDSYIVIGVGDKKITHHWHRSGSI

IGKAFEATVRGAKRMAVLGDTAWDFGSVGGVFNSLGKGIHQIFGAAFKSL

FGGMSWFSQILIGTLLVWLGLNTKNGSISLTCLALGGVMIFLSTAVSA

ArB1362.AHL43500.1.-/291-794 Flavivirus
envelope glycoprotein E.
SEQ ID NO: 16
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIVNDXXXXXXXNRAEVEVTPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLFSGHLKCRLKMDKLRL

ArD128000.AHL43502.1.1.-/291-794 Flavivirus
envelope glycoprotein E.
SEQ ID NO: 17
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MXXXXXGHETDENRAKVEVTPNSPRAEATLGGFGSLGLDCEPRTGLDFSD

LYYLTMNNKHRLVRKEWFHDIPLPWHAGADTGTPHWNNKEALVEFKDAHA

KRQTVVVLGSQEGAVHTALAGALEAEMDGAKGRLFSGHLKCRLKMDKLRL

KGVSYSLCTAAFTFTKVPAETLHGTVTVEVQYAGTDGPCKVPAQMAVDMQ

TLTPVGRLITANPVITESTENSKMMLELDPPFGDSYIVIGVGDKKITHHW

LKKGSSIGKAFEATVRGAKRMAVLGDTAWDFGSVGGVFNSLGKGVHQIFG

AAFKSLFGGMSWFSQILIGTLLVWLGLNTKNGSISLTCLALGGVMIFLST

AVSA

ArD158095.AHL43505.1.1.-/291-794 Flavivirus
envelope glycoprotein E.
SEQ ID NO: 18
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIVNDIGHETDENRAKVEVTPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLFSGHLKCRLKMDKLRL

KGVSYSLCTAAFTFTKVPAETLHGTVTVEVQYAGTDGPCKVPAQMAVDMQ

TLTPVGRLITANPVITESTENSKMMLELDPPFGDSYIVIGVGDKKITHHW

HRSGSTIGKAFEATVRGAKRMAVLGDTAWDFGSVGGVFNSLGKGIHQIFG

AAFKSLFGGMSWFSQILIGTLLVWLGLNTKNGSISLTCLALGGVMIFLST

AVSA

ArD158084.AHL43504.1.1.-/291-794 Flavivirus
envelope glycoprotein E.
SEQ ID NO: 19
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIVNDIGHETDENRAKVEVTPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLFSGHLKCRLKMDKLRL

KGVSYSLCTAAFTFTKVPAETLHGTVTVEVQYAGTDGPCKVPAQMAVDMQ

TLTPVGRLITANPVITESTENSKMMLELDPPFGDSYIVIGVGDKKITHHW

HRSGSTIGKAFEATVRGAKRMAVLGDTAWDFGSVGGVFNSLGKGIHQIFG

AAFKSLFGGMSWFSQILIGTLLVWLGLNTKNGSISLTCLALGGVMIFLST

AVSA isol-ARB13565.AHF49783.1.Central_African_Republic/
291-794 Flavivirus envelope glycoprotein E.
SEQ ID NO: 20
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIVNDIGHETDENRAKVEVTPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLFSGHLKCRLKMDKLRL

KGVSYSLCTAAFTFTKVPAETLHGTVTVEVQYAGTDGPCKVPAQMAVDMQ

TLTPVGRLITANPVITESTENSKMMLELDPPFGDSYIVIGVGDKKITHHW

HRSGSTIGKAFEATVRGAKRMAVLGDTAWDFGSVGGVFNSLGKGVHQIFG

AAFKSLFGGMSWFSQILIGTLLVWLGLNTKNGSISLTCLALGGVMIFLST

AVSA isol-ARB7701.AHF49785.1.Central_African_Republic/
291-794 Flavivirus envelope glycoprotein E.
SEQ ID NO: 21
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIVNDIGHETDENRAKVEVTPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLFSGHLKCRLKMDKLRL

KGVSYSLCTAAFTFTKVPAETLHGTVTVEVQYAGTDGPCKVPAQMAVDMQ

TLTPVGRLITANPVITESTENSKMMLELDPPFGDSYIVIGVGDKKITHHW

HRSGSTIGKAFEATVRGAKRMAVLGDTAWDFGSVGGVFNSLGKGVHQIFG

AAFKSLFGGMSWFSQILIGTLLVWLGLNTKNGSISLTCLALGGVMIFLST

AVSA isol-ArD_41519.AEN75266.1.Senegal/291-794
Flavivirus envelope glycoprotein E.
SEQ ID NO: 22
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIVNDTGHETDENRAKVEVTPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLFSGHLKCRLKMDKLRL

KGVSYSLCTAAFTFTKVPAETLHGTVTVEVQYAGTDGPCKVPAQMAVDMQ

TLTPVGRLITANPVITESTENSKMMLELDPPFGDSYIVIGVGDKKITHHW

HRSGSTIGKAFEATVRGAKRMAVLGDTAWDFGSVGGVFNSLGKGIHQIFG

AAFKSLFGGMSWFSQILIGTLLVWLGLNTKNGSISLTCLALGGVMIFLST

AVSA

MR766-NIID.BAP47441.1.Uganda/291-794
Flavivirus envelope glycoprotein E.
SEQ ID NO: 23
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MTVNDIGYETDENRAKVEVTPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGKLFSGHLKCRLKMDKLRL

KGVSYSLCTAAFTFTKVPAETLHGTVTVEVQYAGTDGPCKIPVQMAVDMQ

TLTPVGRLITANPVITESTENSKMMLELDPPFGDSYIVIGVGDKKITHHW

HRSGSTIGKAFEATVRGAKRMAVLGDTAWDFGSVGGVFNSLGKGIHQIFG

AAFKSLFGGMSWFSQILIGTLLVWLGLNTKNGSISLTCLALGGVMIFLST

AVSA

LC002520.1/326-829 Zika virus genomic RNA,
strain: MR766-NIID, Uganda, Flavivirus envelope
glycoprotein E.
SEQ ID NO: 24
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MTVNDIGYETDENRAKVEVTPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGKLFSGHLKCRLKMDKLRL

KGVSYSLCTAAFTFTKVPAETLHGTVTVEVQYAGTDGPCKIPVQMAVDMQ

TLTPVGRLITANPVITESTENSKMMLELDPPFGDSYIVIGVGDKKITHHW

HRSGSTIGKAFEATVRGAKRMAVLGDTAWDFGSVGGVFNSLGKGIHQIFG

AAFKSLFGGMSWFSQILIGTLLVWLGLNTKNGSISLTCLALGGVMIFLST

AVSA isol-MR_766.AEN75263.1.Uganda/291-794 Flavivirus
envelope glycoprotein E.
SEQ ID NO: 25
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIVNDTGYETDENRAKVEVTPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGKLFSGHLKCRLKMDKLRL

KGVSYSLCTAAFTFTKVPAETLHGTVTVEVQYAGTDGPCKIPVQMAVDMQ

TLTPVGRLITANPVITESTENSKMMLELDPPFGDSYIVIGVGDKKITHHW

HRSGSTIGKAFEATVRGAKRMAVLGDTAWDFGSVGGVFNSLGKGIHQIFG

AAFKSLFGGMSWFSQILIGTLLVWLGLNTKNGSISLTCLALGGVMIFLST

AVSA

ArD7117.AHL43501.1.1.—/291-794 Flavivirus
envelope glycoprotein E.
SEQ ID NO: 26
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIVNDIGHETDENRAKVEVTPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLFSGHLKCRLKMDKLRL

KGVSYSLCTAVCTAAKVPAETLHGTVTVEVQYAGTDGPCKVPAQMAVDMQ

TLTPVGRLITANPVITESTENSKMMLELDPPFGDSYIVIGVGDKKITHHW

HRSGSTIGKAFEATVRGAKRMAVLGDTAWDFGSVGGVFNSLGKGIHQIFG

AAFKSLFGGMSWFSQILIGTLLVWLGLNTKNGSISLTCLALGGVMIFLST

AVSA

AY632535.2/326-825 NC_012532.1 Zika virus
strain MR 766, Uganda, Flavivirus envelope
glycoprotein E.
SEQ ID NO: 27
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIGYETDEDRAKVEVTPNSPRAEATLGGFGSLGLDCEPRTGLDFSDLYYL

TMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVS

YSLCTAAFTFTKVPAETLHGTVTVEVQYAGTDGPCKIPVQMAVDMQTLTP

VGRLITANPVITESTENSKMMLELDPPFGDSYIVIGVGDKKITHHWHRSG

STIGKAFEATVRGAKRMAVLGDTAWDFGSVGGVFNSLGKGIHQIFGAAFK

SLFGGMSWFSQILIGTLLVWLGLNTKNGSISLTCLALGGVMIFLSTAVSA

MR_766.AAV34151.1.Uganda/291-790 Flavivirus
envelope glycoprotein E. |Q32ZE1|Q32ZE1_9FL
SEQ ID NO: 28
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIGYETDEDRAKVEVTPNSPRAEATLGGFGSLGLDCEPRTGLDFSDLYYL

-continued

TMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVS

YSLCTAAFTFTKVPAETLHGTVTVEVQYAGTDGPCKIPVQMAVDMQTLTP

VGRLITANPVITESTENSKMMLELDPPFGDSYIVIGVGDKKITHHWHRSG

STIGKAFEATVRGAKRMAVLGDTAWDFGSVGGVFNSLGKGIHQIFGAAFK

SLFGGMSWFSQILIGTLLVWLGLNTKNGSISLTCLALGGVMIFLSTAVSA

MR_766.YP_009227198.1.Uganda/1-500 envelope
protein E [Zika virus]
SEQ ID NO: 29
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIGYETDEDRAKVEVTPNSPRAEATLGGFGSLGLDCEPRTGLDFSDLYYL

TMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVS

YSLCTAAFTFTKVPAETLHGTVTVEVQYAGTDGPCKIPVQMAVDMQTLTP

VGRLITANPVITESTENSKMMLELDPPFGDSYIVIGVGDKKITHHWHRSG

STIGKAFEATVRGAKRMAVLGDTAWDFGSVGGVFNSLGKGIHQIFGAAFK

SLFGGMSWFSQILIGTLLVWLGLNTKNGSISLTCLALGGVMIFLSTAVSA

KU681081.3/308-811 Zika virus isolate Zika virus/ *H.sapiens*-tc/THA/2014/SV0127- 14, Thailand, Flavivirus envelope glycoprotein E.

SEQ ID NO: 30

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHTGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITEGTENSKMMLELDPPFGDSYIVIGVGEKKITHHW

HRSGSTIGKAFEATVRGAKRMAVLGDTAWDFGSVGGVLNSLGKGIHQIFG

AAFKSLFGGMSWFSQILIGTLLMWLGLNTKNGSISLMCLALGGVLIFLST

AVSA isol-Zika_virus%*H.sapiens*-tc%THA%2014%SV0127-_14.AMD61710.1.Thailand/291-794 Flavivirus envelope glycoprotein E.

SEQ ID NO: 31

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

-continued

LYYLTMNNKHWLVHKEWFHDIPLPWHTGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITEGTENSKMMLELDPPFGDSYIVIGVGEKKITHHW

HRSGSTIGKAFEATVRGAKRMAVLGDTAWDFGSVGGVLNSLGKGIHQIFG

AAFKSLFGGMSWFSQILIGTLLMWLGLNTKNGSISLMCLALGGVLIFLST

AVSA

CK-ISL_2014.AIC06934.1.Cook_Islands/1-504 Flavivirus envelope glycoprotein E. (Fragment) OS = Zika virus GN = E PE = 4 SV = 1

SEQ ID NO: 32

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA

Natal_RGN.AMB18850.1.Brazil:_Rio_Grande_do_Norte, _Natal/291-794 Flavivirus envelope glycoprotein E.]

SEQ ID NO: 33

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA isol-Si323.AMC37200.1.Colombia/1-504 Flavivirus envelope glycoprotein E.

SEQ ID NO: 34

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA

KU707826.1/317-820 Zika virus isolate SSABR1,
Brazil, Flavivirus envelope glycoprotein E.
SEQ ID NO: 35
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA

KU509998.1/326-829 Zika virus strain Haiti/1225/
2014, Haiti, Flavivirus envelope glycoprotein E.
SEQ ID NO: 36
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA isol-GDZ16001.AML82110.1.China/291-794 Flavivirus
envelope glycoprotein E.
SEQ ID NO: 37
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA

BeH819015.AMA12085.1.Brazil/291-794 Flavivirus
envelope glycoprotein E.]
SEQ ID NO: 38
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA

MRS_OPY_Martinique_PaRi_2015.AMC33116.1.Martinique/291-794 Flavivirus envelope glycoprotein
E.
SEQ ID NO: 39
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA

KU501215.1/308-811 Zika virus strain PRVABC59,
Puerto Rico, Flavivirus envelope glycoprotein E.

SEQ ID NO: 40

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA

Haiti%1225%2014.AMB37295.1.Haiti/291-794 Flavivirus envelope glycoprotein E.

SEQ ID NO: 41

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA

KU527068.1/308-811 Zika virus strain Natal RGN, Brazil: Rio Grande do Norte, Natal, Flavivirus envelope glycoprotein E.

SEQ ID NO: 42

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA isol-Z1106027.ALX35662.1.Suriname/5-508 Flavivirus envelope glycoprotein E.

SEQ ID NO: 43

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA isol-FLR.AMM39804.1.Colombia:_Barranquilla/291-794 Flavivirus envelope glycoprotein E.

SEQ ID NO: 44

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA

PLCal_ZV_isol-From_Vero_E6_cells.AHL37808.1.Canada/254-757 Flavivirus envelope glycoprotein E.

SEQ ID NO: 45

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA

BeH818995.AMA12084.1.Brazil/291-794 Flavivirus
envelope glycoprotein E. [Zika virus].
SEQ ID NO: 46
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNTKNGSISLMCLALGGVLIFLST
AVSA H/PF/2013.AHZ13508.1.French_Polynesia/291-794
Flavivirus envelope glycoprotein E.
SEQ ID NO: 47
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNTKNGSISLMCLALGGVLIFLST
AVSA PRVABC59.AMC13911.1.Puerto_Rico/291-794
Flavivirus envelope glycoprotein E.
SEQ ID NO: 48
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNTKNGSISLMCLALGGVLIFLST
AVSA KU321639.1/326-829 Zika virus strain ZikaSPH2015,
Brazil, Flavivirus envelope glycoprotein E.
SEQ ID NO: 49
IRCIGVSNRDFVEGMSGGTWVDIVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNTKNGSISLMCLALGGVLIFLST
AVSA ZikaSPH2015.ALU33341.1.Brazil/291-794
Flavivirus envelope glycoprotein E.
SEQ ID NO: 50
IRCIGVSNRDFVEGMSGGTWVDIVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNTKNGSISLMCLALGGVLIFLST
AVSA 103344.AMC13912.1.Guatemala/291-794 polyprotein
[Zika virus]. 103344.AMC13912.1.Guatemala
Flavivirus envelope glycoprotein E.
SEQ ID NO: 51
IRCIGVSNRDFVEGMSGGTWVDVVLEHGGCVTVMAQDKPTVDIELVTTTV
SNMAEIRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNTKNGSISLMCLALGGVLIFLST
AVSA isol-Brazil-ZKV2015.AMD16557.1.Brazil/291-794
Flavivirus envelope glycoprotein E.
SEQ ID NO: 52
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGTQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNTKNGSISLMCLALGGVLIFLST
AVSA KU497555.1/308-811 Zika virus isolate
Brazil-ZKV2015, Flavivirus envelope glycoprotein E.
SEQ ID NO: 53
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGTQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNTKNGSISLMCLALGGVLIFLST
AVSA isol-ZJ03.AMM39806.1.China/291-794 Flavivirus
envelope glycoprotein E.
SEQ ID NO: 54
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGARRMAVLGDTAWDFGSVGGALNSLGKGIHQIFG
AAFKSLFGGMSWFSQILIGTLLMWLGLNTKNGSISLMCLALGGVLIFLST
AVSA isol-FSS13025.AFD30972.1.Cambodia/291-794
Flavivirus envelope glycoprotein E.
SEQ ID NO: 55
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLVWLGLNTKNGSISLMCLALGGVLIFLST
AVSA isol-Z1106032.ALX35660.1.Suriname/291-794
Flavivirus envelope glycoprotein E. [Zika virus]
SEQ ID NO: 56
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNAKNGSISLMCLALGGVLIFLST
AVSA isol-Z1106033.ALX35659.1.Suriname/291-794
Flavivirus envelope glycoprotein E. [Zika virus]
SEQ ID NO: 57
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNAKNGSISLMCLALGGVLIFLST
AVSA isol-BeH828305.AMK49165.1.Brazil/291-794
Flavivirus envelope glycoprotein E.
SEQ ID NO: 58
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDTQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNTKNGSISLMCLALGGVLIFLST
AVSA isol-GD01.AMK79468.1.China/291-794 Flavivirus
envelope glycoprotein E.
SEQ ID NO: 59
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNGTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNTKNGSISLMCLALGGVLIFLST
AVSA isol-Z1106031.ALX35661.1.Suriname/291-794
Flavivirus envelope glycoprotein E.
SEQ ID NO: 60
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVLAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNTKNGSISLMCLALGGVLIFLST
AVSA ACD75819.1.Micronesia/291-794 Flavivirus
envelope glycoprotein E.
SEQ ID NO: 61
IRCIGVSNRDFVEGMSGGTWVDVVLEHGGCVTVMAQDKPAVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLVWLGLNTKNGSISLTCLALGGVLIFLST
AVSA KU681082.3/308-811 Zika virus isolate Zika virus/
H.sapiens-tc/PHL/2012/CPC-0740, Philippines,
Flavivirus envelope glycoprotein E.
SEQ ID NO: 62
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLVWLGLNTKNGSISLTCLALGGVLIFLST
AVSA isol-Zika_virus%H.sapiens-tc%PHL%2012%CPC-
0740.AMD61711.1.Philippines/291-794
Flavivirus envelope glycoprotein E.
SEQ ID NO: 63
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLVWLGLNTKNGSISLTCLALGGVLIFLST
AVSA isol-BeH823339.AMK49164.2.Brazil/291-794
Flavivirus envelope glycoprotein E.
SEQ ID NO: 64
IRCIGVSNRDFVEGMSGGTWVDVVLEHGGCVTVMAQDKPTVDIELVSTTV
SNMAEVRSYCYEATISDIASDSRCPTQGEAYLDKQSDTQYVCKRTLVDRG
WGNGCGLFGKGSLVTCAKFACSKKMTGKSIQPENLEYRIMLSVHGSQHSG
MIVNDTGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTAVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIFG
AAFKSLFGGMSWFSQILIGTLLMWLGLNTKNGSISLMCLALGGVLIFLST
AVSA isol-P6-740.AEN75264.1.Malaysia/291-794
Flavivirus envelope glycoprotein E.
SEQ ID NO: 65
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MIVNDXGHETDENRAKVEITPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRL
KGVSYSLCTAAFTFTKIPAETLHGTVTVEVQYAGTDGPCKVPAQMAVDMQ
TLTPVGRLITANPVITESTENSKMMLELDPPFGDSYIVIGVGDKKITHHW
XRSGSTIGKAFEATVRGAKRMAVLGDTAWDFGSVGGALNSLGKGIHQIFG
AAFKSLFGGMSWFSQILIGTLLVWLGLNTKNGSISLTCLALGGVLIFLST
AVSA KU744693.1/326-829 Zika virus isolate VE_Ganxian,
China, Flavivirus envelope glycoprotein E.
SEQ ID NO: 66
IRCIGVSNRDFVEGMSGGTWVDVVLEHGGCVTAMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MLVNDTGHETDENRAKVEITPNSPRAEATLGGFGSLGLDCEPRTGLDFSD
LYYLTMNNKHWLAHKEWFHDIPLPWHAGAATGTPHWNNKEALVEFKDAHA
KRQTVVVLGSQEGAVHTALAGALEAEMDGAKGRLSSGHLKCRLKMDKLRL
KGVSYSLCTAAFTFTKIPAETVDGTVTVEGQYGGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIIG
AAFKSLFGGMSWFSQILIGTLLMWLGLNTKNGSISLMCLALGGVLIFLST
AVSG isol-VE_Ganxian.AMK79469.1.China/291-794
Flavivirus envelope glycoprotein E.
SEQ ID NO: 67
IRCIGVSNRDFVEGMSGGTWVDVVLEHGGCVTAMAQDKPTVDIELVTTTV
SNMAEVRSYCYEASISDMASDSRCPTQGEAYLDKQSDTQYVCKRTLVDRG
WGNGCGLFGKGSLVTCAKFACSKKMTGKSIQPENLEYRIMLSVHGSQHSG
MLVNDTGHETDENRAKVEITPNSPRAEATLGGFGSLGLDCEPRTGLDFSD
LYYLTMNNKHWLAHKEWFHDIPLPWHAGAATGTPHWNNKEALVEFKDAHA
KRQTVVVLGSQEGAVHTALAGALEAEMDGAKGRLSSGHLKCRLKMDKLRL
KGVSYSLCTAAFTFTKIPAETVDGTVTVEGQYGGTDGPCKVPAQMAVDMQ
TLTPVGRLITANPVITESTENSKMMLELDPPFGDSYIVIGVGEKKITHHW
HRSGSTIGKAFEATVRGAKRMAVLGDTAWDFGSVGGALNSLGKGIHQIIG
AAFKSLFGGMSWFSQILIGTLLMWLGLNTKNGSISLMCLALGGVLIFLST
AVSG ArD157995.AHL43503.1.—/291-794 Flavivirus
envelope glycoprotein E.
SEQ ID NO: 68
ISCIGVSNRDLVEGMSGGTWVDVVLEHGGCVTEMAQDKPTVDIELVTMTV
SNMAEVRSYCYEASLSDMASASRCPTQGEPSLDKQSDTQSVCKRTLGDRG
WGNGCGIFGKGSLVTCSKFTCCKKMPGKSIQPENLEYRIMLPVHGSQHSG
MIVNDIGHETDENRAKVEVTPNSPRAEATLGGFGSLGLDCEPRTGLDFSD
LYYLTMNNKHWLVHKEWFHDIPLPWHAGADTGTPHWNNKEALVEFKDAHA
KRQTVVVLGSQEGAVHTALAGALEAEMDGAKGRLFSGHLKCRLKMDKLRL
KGVSYSLCTAAFTFTKVPAETLHGTVTVEVQSAGTDGPCKVPAQMAVDMQ
TLTPVGRLITANPVITESTENSKMMLELDPPFGDSYIVIGVGDKKITHHW
HRSGSTIGKAFEATVRGAKRMAVLGDTAWDFGSVGGVFNSLGKGIHQIFG
AAFKSLFGGMSWFSQILIGTLLVWLGLNTKNGSISLTCLALGGVMIFLST
AVSA MR_766.ABI54475.1.Uganda/291-788 Flavivirus
envelope glycoprotein E.
SEQ ID NO: 69
IRCIGVSNRDFVEGMSGGTWVDVVLEHGGCVTVMAQDKPTVDIELVTTTV
SNMAEVRSYCYEASISDMASDSRCPTQGEAYLDKQSDTQYVCKRTLVDRG
WGNGCGLFGKGSLVTCAKFTCSKKMTGKSIQPENLEYRIMLSVHGSQHSG
MIVNDENRAKVEVTPNSPRAEATLGGFGSLGLDCEPRTGLDFSDLYYLTM
NNKHWLVHKEWFHDIPLPWHAGADTGTPHWNNKEALVEFKDAHAKRQTVV
VLGSQEGAVHTALAGALEAEMDGAKGRLFSGHLKCRLKMDKLRLKGVSYS
LCTAAFTFTKVPAETLHGTVTVEVQYAGTDGPCKVPAQMAVDMQTLTPVG -continued
RLITANPVITESTENSKMMLELDPPFGDSYIVIGVGDKKITHHWHRSGST

IGKAFEATVRGAKRMAVLGDTAWDFGSVGGVFNSLGKGIHQIFGAAFKSL

FGGMSWFSQILIGTLLVWLGLNTKNGSISLTCLALGGVMIFLSTAVSA

5'-(dldC)₁₃-3'
SEQ ID NO: 70 dldC dldC dldC dldC dldC dldC dldC dldC dldC dldC dldC dldC dldC

KLK peptide
SEQ ID NO: 71
KLKLLLLLKLK

ZIKV Sequence H/PF/2013 as sequenced
SEQ ID NO: 72

CAGACTGCGACAGTTCGAGTTTGAAGCGAAAGCTAGCAACAGTATCAACAGGTTTTATTTTGGATTTGGAAACGAGAGTT

TCTGGTCATGAAAAACCCAAAAAAGAAATCCGGAGGATTCCGGATTGTCAATATGCTAAAACGCGGAGTAGCCCGTGTG

AGCCCCTTTGGGGGCTTGAAGAGGCTGCCAGCCGGACTTCTGCTGGGTCATGGGCCCATCAGGATGGTCTTGGCGATTCT

AGCCTTTTTGAGATTCACGGCAATCAAGCCATCACTGGGTCTCATCAATAGATGGGGTTCAGTGGGGAAAAAGAGGCTA

TGGAAATAATAAAGAAGTTCAAGAAAGATCTGGCTGCCATGCTGAGAATAATCAATGCTAGGAAGGAGAAGAAGAGAC

GAGGCGCAGATACTAGTGTCGGAATTGTTGGCCTCCTGCTGACCACAGCTATGGCAGCGGAGGTCACTAGACGTGGGAG

TGCATACTATATGTACTTGGACAGAAACGACGCTGGGGAGGCCATATCTTTTCCAACCACATTGGGGATGAATAAGTGTT

ATATACAGATCATGGATCTTGGACACATGTGTGATGCCACCATGAGCTATGAATGCCCTATGCTGGATGAGGGGGTGGAA

CCAGATGACGTCGATTGTTGGTGCAACACGACGTCAACTTGGGTTGTGTACGGAACCTGCCATCACAAAAAAGGTGAAGC

ACGGAGATCTAGAAGAGCTGTGACGCTCCCCTCCCATTCCACTAGGAAGCTGCAAACGCGGTCGCAAACCTGGTTGGAAT

CAAGAGAATACACAAAGCACTTGATTAGAGTCGAAAATTGGATATTCAGGAACCCTGGCTTCGCGTTAGCAGCAGCTGCC

ATCGCTTGGCTTTTGGGAAGCTCAACGAGCCAAAAAGTCATATACTTGGTCATGATACTGCTGATTGCCCCGGCATACAGC

ATCAGGTGCATAGGAGTCAGCAATAGGGACTTTGTGGAAGGTATGTCAGGTGGGACTTGGGTTGATGTTGTCTTGGAAC

ATGGAGGTTGTGTCACCGTAATGGCACAGGACAAACCGACTGTCGACATAGAGCTGGTTACAACAACAGTCAGCAACAT

GGCGGAGGTAAGATCCTACTGCTATGAGGCATCAATATCGGACATGGCTTCGGACAGCCGCTGCCCAACACAAGGTGAA

GCCTACCTTGACAAGCAATCAGACACTCAATATGTCTGCAAAAGAACGTTAGTGGACAGAGGCTGGGGAAATGGATGTG

GACTTTTTGGCAAAGGGAGCCTGGTGACATGCGCTAAGTTTGCATGCTCCAAGAAAATGACCGGGAAGAGCATCCAGCC

AGAGAATCTGGAGTACCGGATAATGCTGTCAGTTCATGGCTCCCAGCACAGTGGGATGATCGTTAATGACACAGGACATG

AAACTGATGAGAATAGAGCGAAGGTTGAGATAACGCCCAATTCACCAAGAGCCGAAGCCACCCTGGGGGGTTTTGGAAG

CCTAGGACTTGATTGTGAACCGAGGACAGGCCTTGACTTTTCAGATTTGTATTACTTGACTATGAATAACAAGCACTGGTT

GGTTCACAAGGAGTGGTTCCACGACATTCCATTACCTTGGCACGCTGGGGCAGACACCGGAACTCCACACTGGAACAACA

AAGAAGCACTGGTAGAGTTCAAGGACGCACATGCCAAAAGGCAAACTGTCGTGGTTCTAGGGAGTCAAGAAGGAGCAG

TTCACACGGCCCTTGCTGGAGCTCTGGAGGCTGAGATGGATGGTGCAAAGGGAAGGCTGTCCTCTGGCCACTTGAAATG

TCGCCTGAAAATGGATAAACTTAGATTGAAGGGCGTGTCATACTCCTTGTGTACCGCAGCGTTCACATTCACCAAGATCCC

GGCTGAAACACTGCACGGGACAGTCACAGTGGAGGTACAGTACGCAGGGACAGATGGACCTTGCAAGGTTCCAGCTCAG

ATGGCGGTGGACATGCAAACTCTGACCCCAGTTGGGAGGTTGATAACGCTAACCCCGTAATCACTGAAAGCACTGAGAA

CTCTAAGATGATGCTGGAACTTGATCCACCATTTGGGGACTCTTACATTGTCATAGGAGTCGGGGAGAAGAAGATCACCC

ACCACTGGCACAGGAGTGGCAGCACCATTGGAAAAGCATTTGAAGCCACTGTGAGAGGTGCCAAGAGAATGGCAGTCTT

GGGAGACACAGCCTGGGACTTTGGATCAGTTGGAGGCGCTCTCAACTCATTGGGCAAGGGCATCCATCAAATTTTTGGAG

CAGCTTTCAAATCATTGTTTGGAGGAATGTCCTGGTTCTCACAAATTCTCATTGGAACGTTGCTGATGTGGTTGGGTCTGA

ACACAAAGAATGGATCTATTTCCCTTATGTGCTTGGCCTTAGGGGAGTGTTGATCTTCTTATCCACAGCTGTCTCTGCTGA

TGTGGGGTGCTCGGTGGACTTCTCAAAGAAGGAGACGAGATGCGGTACAGGGGTGTTCGTCTATAACGACGTTGAAGCC

-continued

```
TGGAGGGACAGGTACAAGTACCATCCTGACTCCCCCCGTAGATTGGCAGCAGCAGTCAAGCAAGCCTGGGAAGATGGTA
TCTGTGGGATCTCCTCTGTTTCAAGAATGGAAAACATCATGTGGAGATCAGTAGAAGGGGAGCTCAACGCAATCCTGGAA
GAGAATGGAGTTCAACTGACGGTCGTTGTGGGATCTGTAAAAAACCCCATGTGGAGAGGTCCACAGAGATTGCCCGTGC
CTGTGAACGAGCTGCCCCACGGCTGGAAGGCTTGGGGGAAATCGTACTTCGTCAGAGCAGCAAAGACAAATAACAGCTT
TGTCGTGGATGGTGACACACTGAAGGAATGCCCACTCAAACATAGAGCATGGAACAGCTTTCTTGTGGAGGATCATGGGT
TCGGGGTATTTCACACTAGTGTCTGGCTCAAGGTTAGAGAAGATTATTCATTAGAGTGTGATCCAGCCGTTATTGGAACAG
CTGTTAAGGGAAAGGAGGCTGTACACAGTGATCTAGGCTACTGGATTGAGAGTGAGAAGAATGACACATGGAGGCTGA
AGAGGGCCCATCTGATCGAGATGAAAACATGTGAATGGCCAAAGTCCCACACATTGTGGACAGATGGAATAGAAGAGAG
TGATCTGATCATACCCAAGTCTTTAGCTGGGCCACTCAGCCATCACAATACCAGAGAGGGCTACAGGACCCAAATGAAAG
GGCCATGGCACAGTGAAGAGCTTGAAATTCGGTTTGAGGAATGCCCAGGCACTAAGGTCCACGTGGAGGAAACATGTGG
AACAAGAGGACCATCTCTGAGATCAACCACTGCAAGCGGAAGGGTGATCGAGGAATGGTGCTGCAGGGAGTGCACAAT
GCCCCCACTGTCGTTCCGGCTAAAGATGGCTGTTGGTATGGAATGGAGATAAGGCCCAGGAAAGAACCAGAAAGTAAC
TTAGTAAGGTCAATGGTGACTGCAGGATCAACTGATCACATGGATCACTTCTCCCTTGGAGTGCTTGTGATTCTGCTCATG
GTGCAGGAAGGGCTGAAGAAGAGAATGACCACAAAGATCATCATAAGCACATCGATGGCAGTGCTGGTAGCTATGATCC
TGGGAGGATTTTCAATGAGTGACCTGGCTAAGCTTGCAATTTTGATGGGTGCCACCTTCGCGGAAATGAACACTGGAGGA
GATGTAGCTCATCTGGCGCTGATAGCGGCATTCAAAGTCAGACCAGCGTTGCTGGTATCTTTCATCTTCAGAGCTAATTGG
ACACCCCGTGAAAGCATGCTGCTGGCCTTGGCCTCGTGTCTTTTGCAAACTGCGATCTCCGCCTTGGAAGGCGACCTGATG
GTTCTCATCAATGGTTTTGCTTTGGCCTGGTTGGCAATACGAGCGATGGTTGTTCCACGCACTGATAACATCACCTTGGCA
ATCCTGGCTGCTCTGACACCACTGGCCCGGGGCACACTGCTTGTGGCGTGGAGAGCAGGCCTTGCTACTTGCGGGGGTT
TATGCTCCTCTCTCTGAAGGGAAAAGGCAGTGTGAAGAAGAACTTACCATTTGTCATGGCCCTGGGACTAACCGCTGTGA
GGCTGGTCGACCCCATCAACGTGGTGGGACTGCTGTTGCTCACAAGGAGTGGGAAGCGGAGCTGGCCCCCTAGCGAAGT
ACTCACAGCTGTTGGCCTGATATGCGCATTGGCTGGAGGGTTCGCCAAGGCAGATATAGAGATGGCTGGGCCCATGGCC
GCGGTCGGTCTGCTAATTGTCAGTTACGTGGTCTCAGGAAAGAGTGTGGACATGTACATTGAAAGAGCAGGTGACATCAC
ATGGGAAAAAGATGCGGAAGTCACTGGAAACAGTCCCCGGCTCGATGTGGCGCTAGATGAGAGTGGTGATTTCTCCCTG
GTGGAGGATGACGGTCCCCCCATGAGAGAGATCATACTCAAGGTGGTCCTGATGACCATCTGTGGCATGAACCCAATAGC
CATACCCTTTGCAGCTGGAGCGTGGTACGTATACGTGAAGACTGGAAAAAGGAGTGGTGCTCTATGGGATGTGCCTGCTC
CCAAGGAAGTAAAAAAGGGGGAGACCACAGATGGAGTGTACAGAGTAATGACTCGTAGACTGCTAGGTTCAACACAAGT
TGGAGTGGGAGTTATGCAAGAGGGGGTCTTTCACACTATGTGGCACGTCACAAAAGGATCCGCGCTGAGAAGCGGTGAA
GGGAGACTTGATCCATACTGGGGAGATGTCAAGCAGGATCTGGTGTCATACTGTGGTCCATGGAAGCTAGATGCCGCCT
GGGACGGGCACAGCGAGGTGCAGCTCTTGGCCGTGCCCCCCGGAGAGAGAGCGAGGAACATCCAGACTCTGCCCGGAA
TATTTAAGACAAAGGATGGGGACATTGGAGCGGTTGCGCTGGATTACCCAGCAGGAACTTCAGGATCTCCAATCCTAGAC
AAGTGTGGGAGAGTGATAGGACTTTATGGCAATGGGTCGTGATCAAAAATGGGAGTTATGTTAGTGCCATCACCCAAG
GGAGGAGGGAGGAAGAGACTCCTGTTGAGTGCTTCGAGCCTTCGATGCTGAAGAAGAAGCAGCTAACTGTCTTAGACTT
GCATCCTGGAGCTGGGAAAACCAGGAGAGTTCTTCCTGAAATAGTCCGTGAAGCCATAAAAACAAGACTCCGTACTGTGA
TCTTAGCTCCAACCAGGGTTGTCGCTGCTGAAATGGAGGAAGCCCTTAGGGGCTTCCAGTGCGTTATATGACAACAGCA
GTCAATGTCACCCACTCTGGAACAGAAATCGTCGACTTAATGTGCCATGCCACCTTCACTTCACGTCTACTACAGCCAATCA
GAGTCCCCAACTATAATCTGTATATTATGGATGAGGCCCACTTCACAGATCCCTCAAGTATAGCAGCAAGAGGATACATTT
CAACAAGGGTTGAGATGGGCGAGGCGGCTGCCATCTTCATGACCGCCACGCCACCAGGAACCCGTGACGCATTTCCGGA
CTCCAACTCACCAATTATGGACACCGAAGTGGAAGTCCCAGAGAGAGCCTGGAGCTCAGGCTTTGATTGGGTGACGGATC
ATTCTGGAAAAACAGTTTGGTTTGTTCCAAGCGTGAGGAACGGCAATGAGATCGCAGCTTGTCTGACAAAGGCTGGAAA
```

-continued

```
ACGGGTCATACAGCTCAGCAGAAAGACTTTTGAGACAGAGTTCCAGAAAACAAAACATCAAGAGTGGGACTTTGTCGTG
ACAACTGACATTTCAGAGATGGGCGCCAACTTTAAAGCTGACCGTGTCATAGATTCCAGGAGATGCCTAAAGCCGGTCAT
ACTTGATGGCGAGAGAGTCATTCTGGCTGGACCCATGCCTGTCACACATGCCAGCGCTGCCCAGAGGAGGGGCGCATA
GGCAGGAATCCCAACAAACCTGGAGATGAGTATCTGTATGGAGGTGGGTGCGCAGAGACTGACGAAGACCATGCACACT
GGCTTGAAGCAAGAATGCTCCTTGACAATATTTACCTCCAAGATGGCCTCATAGCCTCGCTCTATCGACCTGAGGCCGACA
AAGTAGCAGCCATTGAGGGAGAGTTCAAGCTTAGGACGGAGCAAAGGAAGACCTTTGTGGAACTCATGAAAAGAGGAG
ATCTTCCTGTTTGGCTGGCCTATCAGGTTGCATCTGCCGGAATAACCTACACAGATAGAAGATGGTGCTTTGATGGCACGA
CCAACAACACCATAATGGAAGACAGTGTGCCGGCAGAGGTGTGGACCAGACACGGAGAGAAAAGAGTGCTCAAACCGA
GGTGGATGGACGCCAGAGTTTGTTCAGATCATGCGGCCCTGAAGTCATTCAAGGAGTTTGCCGCTGGGAAAAGAGGAGC
GGCTTTTGGAGTGATGGAAGCCCTGGGAACACTGCCAGGACACATGACAGAGAGATTCCAGGAAGCCATTGACAACCTC
GCTGTGCTCATGCGGGCAGAGACTGGAAGCAGGCCTTACAAAGCCGCGGCGGCCCAATTGCCGGAGACCCTAGAGACCA
TTATGCTTTTGGGGTTGCTGGGAACAGTCTCGCTGGGAATCTTTTTCGTCTTGATGAGGAACAAGGGCATAGGGAAGATG
GGCTTTGGAATGGTGACTCTTGGGGCCAGCGCATGGCTCATGTGGCTCTCGGAAATTGAGCCAGCCAGAATTGCATGTGT
CCTCATTGTTGTGTTCCTATTGCTGGTGGTGCTCATACCTGAGCCAGAAAAGCAAAGATCTCCCCAGGACAACCAAATGGC
AATCATCATCATGGTAGCAGTAGGTCTTCTGGGCTTGATTACCGCCAATGAACTCGGATGGTTGGAGAGAACAAAGAGTG
ACCTAAGCCATCTAATGGGAAGGAGAGAGGAGGGGGCAACCATAGGATTCTCAATGGACATTGACCTGCGGCCAGCCTC
AGCTTGGGCCATCTATGCTGCCTTGACAACTTTCATTACCCCAGCCGTCCAACATGCAGTGACCACTTCATACAACAACTAC
TCCTTAATGGCGATGGCCACGCAAGCTGGAGTGTTGTTTGGTATGGGCAAAGGGATGCCATTCTACGCATGGGACTTTGG
AGTCCCGCTGCTAATGATAGGTTGCTACTCACAATTAACACCCCTGACCCTAATAGTGGCCATCATTTTGCTCGTGGCGCAC
TACATGTACTTGATCCCAGGGCTGCAGGCAGCAGCTGCGCGTGCTGCCCAGAAGAGAACGGCAGCTGGCATCATGAAGA
ACCCTGTTGTGGATGGAATAGTGGTGACTGACATTGACACAATGACAATTGACCCCCAAGTGGAGAAAAAGATGGGACA
GGTGCTACTCATAGCAGTAGCCGTCTCCAGCGCCATACTGTCGCGGACCGCCTGGGGGTGGGGGAGGCTGGGGCCCTG
ATCACAGCGGCAACTTCCACTTTGTGGGAAGGCTCTCCGAACAAGTACTGGAACTCCTCTACAGCCACTTCACTGTGTAAC
ATTTTTAGGGGAAGTTACTTGGCTGGAGCTTCTCTAATCTACACAGTAACAAGAAACGCTGGCTTGGTCAAGAGACGTGG
GGGTGGAACAGGAGAGACCCTGGGAGAGAAATGGAAGGCCCGCTTGAACCAGATGTCGGCCCTGGAGTTCTACTCCTAC
AAAAAGTCAGGCATCACCGAGGTGTGCAGAGAAGAGGCCCGCCGCGCCCTCAAGGACGGTGTGGCAACGGGAGGCCAT
GCTGTGTCCCGAGGAAGTGCAAAGCTGAGATGGTTGGTGGAGCGGGGATACCTGCAGCCCTATGGAAAGGTCATTGATC
TTGGATGTGGCAGAGGGGGCTGGAGTTACTACGCCGCCACCATCCGCAAAGTTCAAGAAGTGAAAGGATACACAAAAGG
AGGCCCTGGTCATGAAGAACCCATGTTGGTGCAAAGCTATGGGTGGAACATAGTCCGTCTTAAGAGTGGGGTGGACGTC
TTTCATATGGCGGCTGAGCCGTGTGACACGTTGCTGTGTGACATAGGTGAGTCATCATCTAGTCCTGAAGTGGAAGAAGC
ACGGACGCTCAGAGTCCTCTCCATGGTGGGGATTGGCTTGAAAAAAGACCAGGAGCCTTTTGTATAAAAGTGTTGTGCC
CATACACCAGCACTATGATGGAAACCCTGGAGCGACTGCAGCGTAGGTATGGGGAGGACTGGTCAGAGTGCCACTCTC
CCGCAACTCTACACATGAGATGTACTGGGTCTCTGGAGCGAAAAGCAACACCATAAAAAGTGTGTCCACCACGAGCCAGC
TCCTCTTGGGCGCATGGACGGGCCCAGGAGGCCAGTGAAATATGAGGAGGATGTGAATCTCGGCTCTGGCACGCGGG
CTGTGGTAAGCTGCGCTGAAGCTCCCAACATGAAGATCATTGGTAACCGCATTGAAAGGATCCGCAGTGAGCACGCGGA
AACGTGGTTCTTTGACGAGAACCACCCATATAGGACATGGGCTTACCATGGAAGCTATGAGGCCCCCACACAAGGGTCAG
CGTCCTCTCTAATAAACGGGGTTGTCAGGCTCCTGTCAAAACCCTGGGATGTGGTGACTGGAGTCACAGGAATAGCCATG
ACCGACACCACACCGTATGGTCAGCAAAGAGTTTTCAAGGAAAAAGTGGACACTAGGGTGCCAGACCCCCAAGAAGGCA
CTCGTCAGGTTATGAGCATGGTCTCTTCCTGGTTGTGGAAAGAGCTAGGCAAACACAAACGGCCACGAGTCTGTACCAAA
GAAGAGTTCATCAACAAGGTTCGTAGCAATGCAGCATTAGGGGCAATATTTGAAGAGGAAAAAGAGTGGAAGACTGCAG
TGGAAGCTGTGAACGATCCAAGGTTCTGGGCTCTAGTGGACAAGGAAAGAGAGCACCACCTGAGAGGAGAGTGCCAGA
```

-continued

GTTGTGTGTACAACATGATGGGAAAAAGAGAAAAGAAACAAGGGGAATTTGGAAAGGCCAAGGGCAGCCGCGCCATCT

GGTATATGTGGCTAGGGGCTAGATTTCTAGAGTTCGAAGCCCTTGGATTCTTGAACGAGGATCACTGGATGGGGAGAGA

GAACTCAGGAGGTGGTGTTGAAGGGCTGGGATTACAAAGACTCGGATATGTCCTAGAAGAGATGAGTCGCATACCAGGA

GGAAGGATGTATGCAGATGACACTGCTGGCTGGGACACCCGCATCAGCAGGTTTGATCTGGAGAATGAAGCTCTAATCA

CCAACCAAATGGAGAAAGGGCACAGGGCCTTGGCATTGGCCATAATCAAGTACACATACCAAAACAAAGTGGTAAAGGT

CCTTAGACCAGCTGAAAAAGGGAAGACAGTTATGGACATTATTTCGAGACAAGACCAAAGGGGGAGCGGACAAGTTGTC

ACTTACGCTCTTAACACATTTACCAACCTAGTGGTGCAACTCATTCGGAATATGGAGGCTGAGGAAGTTCTAGAGATGCAA

GACTTGTGGCTGCTGCGGAGGTCAGAGAAAGTGACCAACTGGTTGCAGAGCAACGGATGGGATAGGCTCAAACGAATG

GCAGTCAGTGGAGATGATTGCGTTGTGAAGCCAATTGATGATAGGTTTGCACATGCCCTCAGGTTCTTGAATGATATGGG

AAAAGTTAGGAAGGACACACAAGAGTGGAAACCCTCAACTGGATGGGACAACTGGGAAGAAGTTCCGTTTTGCTCCCAC

CACTTCAACAAGCTCCATCTCAAGGACGGGAGGTCCATTGTGGTTCCCTGCCGCCACCAAGATGAACTGATTGGCCGGGC

CCGCGTCTCTCCAGGGGGGGGATGGAGCATCCGGGAGACTGCTTGCCTAGCAAAATCATATGCGCAAATGTGGCAGCTC

CTTTATTTCCACAGAAGGGACCTCCGACTGATGGCCAATGCCATTTGTTCATCTGTGCCAGTTGACTGGGTTCCAACTGGG

AGAACTACCTGGTCAATCCATGGAAAGGGAGAATGGATGACCACTGAAGACATGCTTGTGGTGTGGAACAGAGTGTGGA

TTGAGGAGAACGACCACATGGAAGACAAGACCCCAGTTACGAAATGGACAGACATTCCCTATTTGGGAAAAAGGGAAGA

CTTGTGGTGTGGATCTCTCATAGGGCACAGACCGCGCACCACCTGGGCTGAGAACATTAAAAACACAGTCAACATGGTGC

GCAGGATCATAGGTGATGAAGAAAAGTACATGGACTACCTATCCACCCAAGTTCGCTACTTGGGTGAAGAAGGGTCTACA

CCTGGAGTGCTGTAAGCACCAATCTTAGTGTTGTCAGGCCTGCTAGTCAGCCACAGCTTGGGGAAAGCTGTGCAGCCTGT

GACCCCCCCAGGAGAAGCTGGGAAACCAAGCCTATAGTCAGGCCGAGAACGCCATGGCACGGAAGAAGCCATGCTGCCT

GTGAGCCCCTCAGAGGACACTGAGTCAAAAAACCCCACGCGCTTGGAGGCGCAGGATGGGAAAAGAAGGTGGCGACCT

TCCCCACCCTTCAATCTGGGGCCTGAACTGGAGATCAGCTGTGGATCTCCAGAAGAGGGACTAGTGGTTAGAGGAGACCC

CCCGGAAAACGCAAAACAGCATATTGACGCTGGGAAAGACCAGAGACTCCATGAGTTTCCACCACGCTGGCCGCCAGGC

ACAGATCGCCGAATAGCGGCGGCCGGTGTGGGG

AHZ13508.1, Zika virus polyprotein from Polynesian outbreak (H/PF/2013)

SEQ ID NO: 73

MKNPKKKSGGFRIVNMLKRGVARVSPFGGLKRLPAGLLLGHGPIRMVLAI

LAFLRFTAIKPSLGLINRWGSVGKKEAMEIIKKFKKDLAAMLRIINARKE

KKRRGADTSVGIVGLLLTTAMAAEVTRRGSAYYMYLDRNDAGEAISFPTT

LGMNKCYIQIMDLGHMCDATMSYECPMLDEGVEPDDVDCWCNTTSTWVVY

GTCHHKKGEARRSRRAVTLPSHSTRKLQTRSQTWLESREYTKHLIRVENW

IFRNPGFALAAAAIAWLLGSSTSQKVIYLVMILLIAPAYSIRCIGVSNRD

FVEGMSGGTWVDVVLEHGGCVTVMAQDKPTVDIELVTTTVSNMAEVRSYC

YEASISDMASDSRCPTQGEAYLDKQSDTQYVCKRTLVDRGWGNGCGLFGK

GSLVTCAKFACSKKMTGKSIQPENLEYRIMLSVHGSQHSGMIVNDTGHET

DENRAKVEITPNSPRAEATLGGFGSLGLDCEPRTGLDFSDLYYLTMNNKH

WLVHKEWFHDIPLPWHAGADTGTPHWNNKEALVEFKDAHAKRQTVVVLGS

QEGAVHTALAGALEAEMDGAKGRLSSGHLKCRLKMDKLRLKGVSYSLCTA

AFTFTKIPAETLHGTVTVEVQYAGTDGPCKVPAQMAVDMQTLTPVGRLIT

ANPVITESTENSKMMLELDPPFGDSYIVIGVGEKKITHHWHRSGSTIGKA

-continued

FEATVRGAKRMAVLGDTAWDFGSVGGALNSLGKGIHQIFGAAFKSLFGGM

SWFSQILIGTLLMWLGLNTKNGSISLMCLALGGVLIFLSTAVSADVGCSV

DFSKKETRCGTGVFVYNDVEAWRDRYKYHPDSPRRLAAAVKQAWEDGICG

ISSVSRMENIMWRSVEGELNAILEENGVQLTVVVGSVKNPMWRGPQRLPV

PVNELPHGWKAWGKSYFVRAAKTNNSFVVDGDTLKECPLKHRAWNSFLVE

DHGFGVFHTSVWLKVREDYSLECDPAVIGTAVKGKEAVHSDLGYWIESEK

NDTWRLKRAHLIEMKTCEWPKSHTLWTDGIEESDLIIPKSLAGPLSHHNT

REGYRTQMKGPWHSEELEIRFEECPGTKVHVEETCGTRGPSLRSTTASGR

VIEEWCCRECTMPPLSFRAKDGCWYGMEIRPRKEPESNLVRSMVTAGSTD

HMDHFSLGVLVILLMVQEGLKKRMTTKIIISTSMAVLVAMILGGFSMSDL

AKLAILMGATFAEMNTGGDVAHLALIAAFKVRPALLVSFIFRANWTPRES

MLLALASCLLQTAISALEGDLMVLINGFALAWLAIRAMVVPRTDNITLAI

LAALTPLARGTLLVAWRAGLATCGGFMLLSLKGKGSVKKNLPFVMALGLT

AVRLVDPINVVGLLLLTRSGKRSWPPSEVLTAVGLICALAGGFAKADIEM

AGPMAAVGLLIVSYVVSGKSVDMYIERAGDITWEKDAEVTGNSPRLDVAL

DESGDFSLVEDDGPPMREIILKVVLMTICGMNPIAIPFAAGAWYVYVKTG

-continued

KRSGALWDVPAPKEVKKGETTDGVYRVMTRRLLGSTQVGVGVMQEGVFHT
MWHVTKGSALRSGEGRLDPYWGDVKQDLVSYCGPWKLDAAWDGHSEVQLL
AVPPGERARNIQTLPGIFKTKDGDIGAVALDYPAGTSGSPILDKCGRVIG
LYGNGVVIKNGSYVSAITQGRREEETPVECFEPSMLKKKQLTVLDLHPGA
GKTRRVLPEIVREAIKTRLRTVILAPTRVVAAEMEEALRGLPVRYMTTAV
NVTHSGTEIVDLMCHATFTSRLLQPIRVPNYNLYIMDEAHFTDPSSIAAR
GYISTRVEMGEAAAIFMTATPPGTRDAFPDSNSPIMDTEVEVPERAWSSG
FDWVTDHSGKTVWFVPSVRNGNEIAACLTKAGKRVIQLSRKTFETEFQKT
KHQEWDFVVTTDISEMGANFKADRVIDSRRCLKPVILDGERVILAGPMPV
THASAAQRRGRIGRNPNKPGDEYLYGGGCAETDEDHAHWLEARMLLDNIY
LQDGLIASLYRPEADKVAAIEGEFKLRTEQRKTFVELMKRGDLPVWLAYQ
VASAGITYTDRRWCFDGTTNNTIMEDSVPAEVWTRHGEKRVLKPRWMDAR
VCSDHAALKSFKEFAAGKRGAAFGVMEALGTLPGHMTERFQEAIDNLAVL
MRAETGSRPYKAAAAQLPETLETIMLLGLLGTVSLGIFFVLMRNKGIGKM
GFGMVTLGASAWLMWLSEIEPARIACVLIVVFLLLVVLIPEPEKQRSPQD
NQMAIIIMVAVGLLGLITANELGWLERTKSDLSHLMGRREEGATIGFSMD
IDLRPASAWAIYAALTTFITPAVQHAVTTSYNNYSLMAMATQAGVLFGMG
KGMPFYAWDFGVPLLMIGCYSQLTPLTLIVAIILLVAHYMYLIPGLQAAA
ARAAQKRTAAGIMKNPVVDGIVVTDIDTMTIDPQVEKKMGQVLLIAVAVS
SAILSRTAWGWGEAGALITAATSTLWEGSPNKYWNSSTATSLCNIFRGSY
LAGASLIYTVTRNAGLVKRRGGGTGETLGEKWKARLNQMSALEFYSYKKS
GITEVCREEARRALKDGVATGGHAVSRGSAKLRWLVERGYLQPYGKVIDL
GCGRGGWSYYAATIRKVQEVKGYTKGGPGHEEPMLVQSYGWNIVRLKSGV
DVFHMAAEPCDTLLCDIGESSSSPEVEEARTLRVLSMVGDWLEKRPGAFC
IKVLCPYTSTMMETLERLQRRYGGGLVRVPLSRNSTHEMYWVSGAKSNTI
KSVSTTSQLLLGRMDGPRRPVKYEEDVNLGSGTRAVVSCAEAPNMKIIGN
RIERIRSEHAETWFFDENHPYRTWAYHGSYEAPTQGSASSLINGVVRLLS
KPWDVVTGVTGIAMTDTTPYGQQRVFKEKVDTRVPDPQEGTRQVMSMVSS
WLWKELGKHKRPRVCTKEEFINKVRSNAALGAIFEEEKEWKTAVEAVNDP
RFWALVDKEREHHLRGECQSCVYNMMGKREKKQGEFGKAKGSRAIWYMWL
GARFLEFEALGFLNEDHWMGRENSGGGVEGLGLQRLGYVLEEMSRIPGGR
MYADDTAGWDTRISRFDLENEALITNQMEKGHRALALAIIKYTYQNKVVK
VLRPAEKGKTVMDIISRQDQRGSGQVVTYALNTFTNLVVQLIRNMEAEEV
LEMQDLWLLRRSEKVTNWLQSNGWDRLKRMAVSGDDCVVKPIDDRFAHAL
RFLNDMGKVRKDTQEWKPSTGWDNWEEVPFCSHHFNKLHLKDGRSIVVPC
RHQDELIGRARVSPGAGWSIRETACLAKSYAQMWQLLYFHRRDLRLMANA
ICSSVPVDWVPTGRTTWSIHGKGEWMTTEDMLVVWNRVWIEENDHMEDKT
PVTKWTDIPYLGKREDLWCGSLIGHRPRTTWAENIKNTVNMVRRIIGDEE
KYMDYLSTQVRYLGEEGSTPGVL

9320_Zika_PF_1F
SEQ ID NO: 74
ttaggatccGTTGTTGATCTGTGTGAAT

9321_Zika_PF_1R
SEQ ID NO: 75
taactcgagCGTACACAACCCAAGTT

9322_Zika_PF_2F
SEQ ID NO: 76
ttaggatccTCACTAGACGTGGGAGTG

9323_Zika_PF_2R
SEQ ID NO: 77
taactcgagAAGCCATGTCYGATATTGAT

9324_Zika_PF_3F
SEQ ID NO: 78
ttaggatccGCATACAGCATCAGGTG

9325_Zika_PF_3R
SEQ ID NO: 79
taactcgagTGTGGAGTTCCGGTGTCT

9326_Zika_PF_4F
SEQ ID NO: 80
ttaggatccGAATAGAGCGAARGTTGAGATA

9327_Zika_PF_4R
SEQ ID NO: 81
taactcgAGTGGTGGGTGATCTTCTTCT

9328_Zika_PF_5F
SEQ ID NO: 82
ttaggatcCAGTCACAGTGGAGGTACAGTAC

9329_Zika_PF_5R
SEQ ID NO: 83
taactcgagCRCAGATACCATCTTCCC

9330_Zika_PF_6F
SEQ ID NO: 84
ttaggatCCCTTATGTGCTTGGCCTTAG

9331_Zika_PF_6R
SEQ ID NO: 85
taactcgagTCTTCAGCCTCCATGTG

9332_Zika_PF_7F
SEQ ID NO: 86
ttaggatccAATGCCCACTCAAACATAGA

9333_Zika_PF_7R
SEQ ID NO: 87
taactcgagTCATTCTCTTCTTCAGCCCTT

9334_Zika_PF_8F
SEQ ID NO: 88
ttaggatccAAGGGTGATCGAGGAAT

9335_Zika_PF_8R
SEQ ID NO: 89
taactcgagTTCCCTTCAGAGAGAGGAGC

9336_Zika_PF_9F
SEQ ID NO: 90
ttaggatccTCTTTTGCAAACTGCGATC

9337_Zika_PF_9R
SEQ ID NO: 91
taactcgagTCCAGCTGCAAAGGGTAT

9338_Zika_PF_10F
SEQ ID NO: 92
ttaggatccGTGTGGACATGTACATTGA

9339_Zika_PF_10R
SEQ ID NO: 93
taactcgagCCCATTGCCATAAAGTC

9340_Zika_PF_11F
SEQ ID NO: 94
ttaggatccTCATACTGTGGTCCATGGA

9341_Zika_PF_11R
SEQ ID NO: 95
taactcgagGCCCATCTCAACCCTTG

9342_Zika_PF_12F
SEQ ID NO: 96
ttaggatccTAGAGGGCTTCCAGTGC

9343_Zika_PF_12R
SEQ ID NO: 97
taactcgAGATACTCATCTCCAGGTTTGTTG

9344_Zika_PF_13F
SEQ ID NO: 98
ttaggatccGAAAACAAAACATCAAGAGTG

9345_Zika_PF_13R
SEQ ID NO: 99
taactcgagGAATCTCTCTGTCATGTGTCCT

9346_Zika_PF_14F
SEQ ID NO: 100
ttaggatccTTGATGGCACGACCAAC

9347_Zika_PF_14R
SEQ ID NO: 101
ttaggatccGTTGTTGATCTGTGTGAAT

9348_Zika_PF_15F
SEQ ID NO: 102
taactcgagCAGGTCAATGTCCATTG

9349_Zika_PF_15R
SEQ ID NO: 103
ttaggatccTGTTGTGTTCCTATTGCTGGT

9350_Zika_PF_16F
SEQ ID NO: 104
taactcgaGTGATCAGRGCCCCAGC

9351_Zika_PF_16R
SEQ ID NO: 105
ttaggatccTGCTGCCCAGAAGAGAA

9352_Zika_PF_17F
SEQ ID NO: 106
taactcgaGCACCAACAYGGGTTCTT

9353_Zika_PF_17R
SEQ ID NO: 107
ttaggatcCTCAAGGACGGTGTGGC

9354_Zika_PF_18F
SEQ ID NO: 108
taactcgagCAATGATCTTCATGTTGGG

9355_Zika_PF_18R
SEQ ID NO: 109
ttaggatccTATGGGGGAGGACTGGT

9356_Zika_PF_19F
SEQ ID NO: 110
taactcGAGCCCAGAACCTTGGATC

9357_Zika_PF_19R
SEQ ID NO: 111
ttaggatcCAGACCCCCAAGAAGGC

9358_Zika_PF_20F
SEQ ID NO: 112
taactcgagCCCCTTTGGTCTTGTCT

9359_Zika_PF_20R
SEQ ID NO: 113
ttaggatccAGGAAGGATGTATGCAGATG

9360_Zika_PF_21F
SEQ ID NO: 114
taactcgagACATTTGCGCATATGATTTTG

9361_Zika_PF_21R
SEQ ID NO: 115
ttaggatccAGGAAGGACACACAAGAGT

9362_Zika_PF_22F
SEQ ID NO: 116
taactcgagACAGGCTGCACAGCTTT

9363_Zika_PF_22R
SEQ ID NO: 117
ttaggatccTCTCTCATAGGGCACAGAC

In some embodiments, the Zika virus has polyprotein, including an envelope (E) protein, with an amino acid sequence provided by any one of SEQ ID NOs: 14-69 or 72. In some embodiments, the polyprotein or E protein sequence is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-69 or 72.

The terms "identical" or percent "identity" in the context of two or more nucleic acids or amino acid sequences refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, or 99% identity) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. In some embodiments, the identity exists over the length of a protein, such as the E protein.

For sequence comparison, typically one sequence acts as a reference sequence, to which test sequences are compared. Methods of alignment of sequences for comparison are well known in the art. See, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman Proc. Natl. Acad. Sci. USA 85:2444, 1988, by computerized implementations of these algorithms (GAP, BESTFIT, FASTA, Jalview and TFASTA in the Wisconsin Genetics Software Package, Genetics Computer Group. 575 Science Dr., Madison. WI), by multi sequence alignment implementation using e.g. CLUSTALW (Larkin et al., (2007). Bioinformatics, 23, 2947-2948.) or MAFFT (Katoh Toh 2008 *Briefings in Bioinformatics* 9:286-298), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977 and Altschul et al., J. Mol. Biol. 215:403-410, 1990, respectively.

EXAMPLES

Figure 9A:
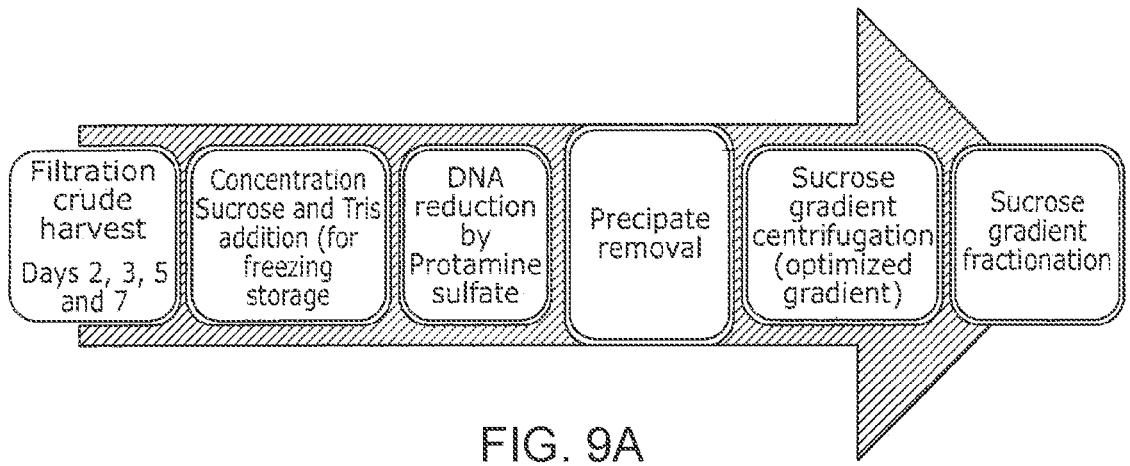
FIGS. 9A-9B: An exemplary downstream virus purification process from the crude harvest to formulation of the drug substance (vaccine), a preferred embodiment of the process of the invention (FIG. 9A). A flow-chart of an exemplary virus inactivation process is shown in (FIG. 9B).
Figure 9B:
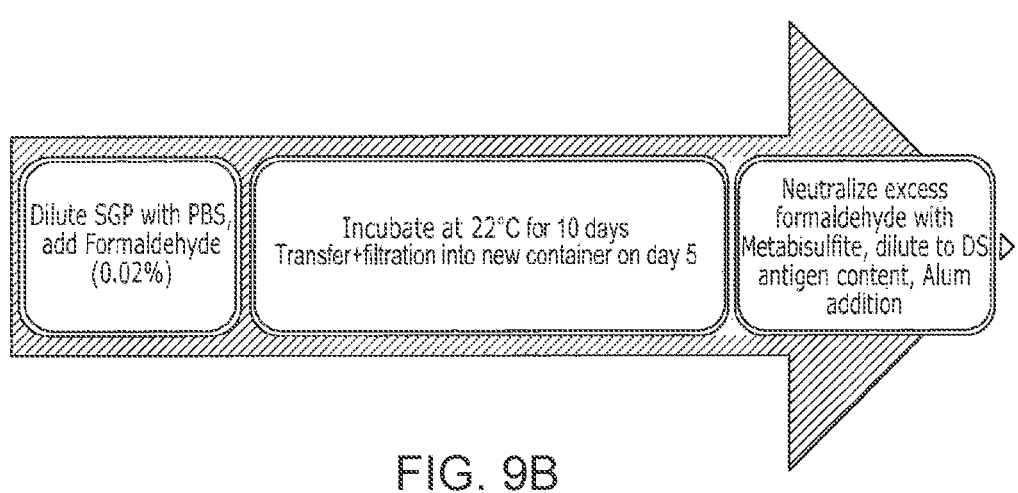
Figure 10:
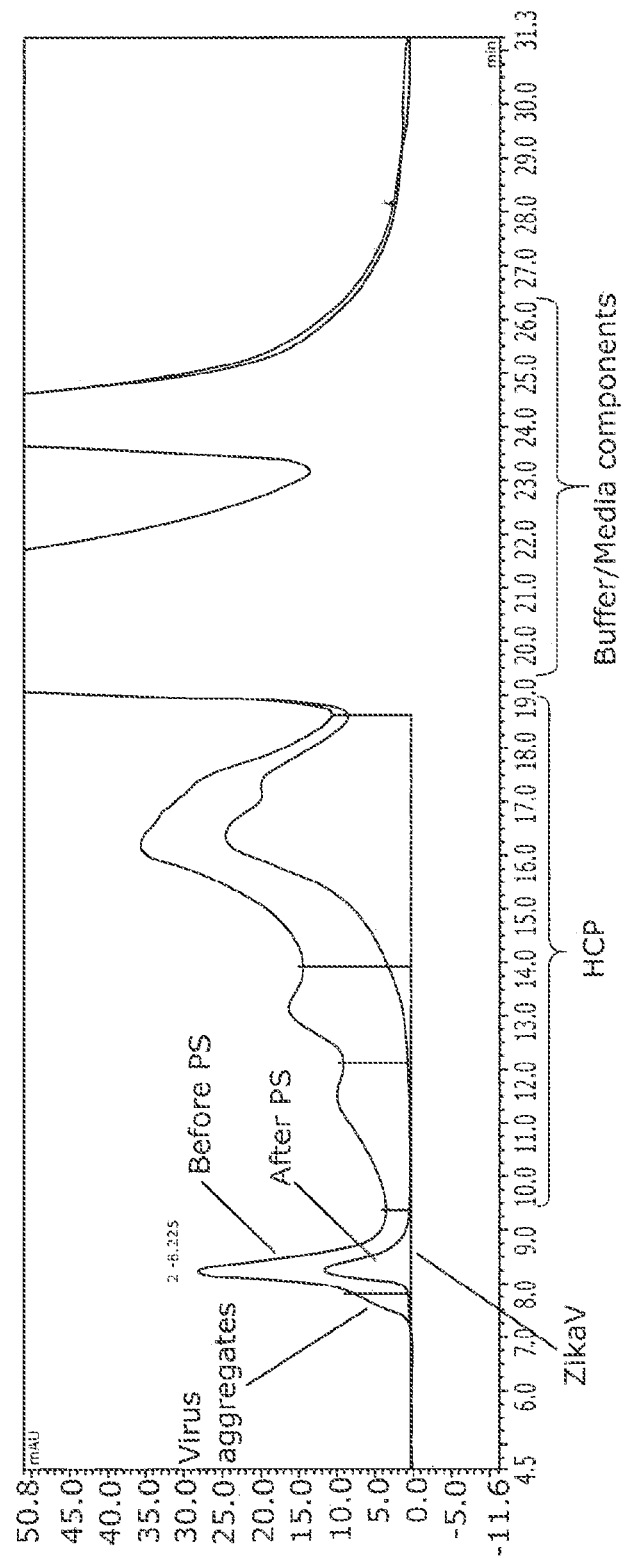
FIG. 10: PS treatment results in selective removal of Zika virus aggregates and Vero HCP and LMW impurities (SEC-HPLC of 30× concentrated Zika Virus harvest day 5).

Example 1: Production of a Zika Drug Substance Suitable for Application as a Vaccine in Humans and Animals Materials and Methods:
For the production of ZikaV the JEV process platform (Srivastava et al., Vaccine 19 (2001) 4557-4565; U.S. Pat. No. 6,309,650B1) was used as a basis Small changes of certain process steps were adapted to ZikaV properties and to improve purity. A short summary of the process steps is outlined below (see also FIGS. 9A and B). Briefly, the unexpected and novel purification properties of protamine sulphate (PS) were evaluated in purification processes for Zika Virus. As shown in FIG. 10, non-infectious virus particle aggregates, HCP and other LMW impurities were removed by PS precipitation as shown by removal of aggregate shoulder in SEC-HPLC and no loss of infectious virus titer by PS treatment. Further optimization of the Zika purification protocol is provided below.

Upstream:
Roller Bottle based Vero cell expansion (25×850 cm2 CellBind):
5% $CO_2$, 35° C., MEM+2 mM L-Glutamine+10% FBS
Infection with ZikaV research Master Seed Bank (rMSB) at MOI 0.01
Virus Production without serum
5% $CO_2$, 35° C., MEM+2 mM L-Glutamine
Multiple harvests (days 2, 3, 5 and 7) with re-feed
Sterile filtration of harvests and storage at 2-8° C. until further processing Downstream:
Pooling of harvests and concentration by ultrafiltration (100 kDa)
Stabilization of concentrated harvest (Tris/10% sucrose) for storage if required (−80° C.)
Removal of hcDNA by Protamine Sulphate (2 mg/mL)
Sucrose Gradient Purification (optimized three layered gradient)
Formaldehyde Inactivation (0.02%, 22° C., 10 days), neutralization with Na-metabisulfite
Dilution to DS antigen target content and formulation with Aluminium hydroxide (0.5 mg Al/mL)

Zika Virus Strain H/PF/2013 was originally isolated from a 51-year-old woman (accession number KJ776791.1, also SEQ ID NO: 13 herein) from French Polynesia. A sample was obtained from the European Virus Archive (EVAg; Ref-SKU: 001v-EVA1545). Based on this material, a research master seed bank (rMSB) was prepared on Vero cells as the cell substrate and the genomic sequence was checked by sequencing. Because the genomic sequence at the 5' and 3' flanking sequences of Zika virus strain H/PF/2013 was unknown, primers for sequencing were designed in those regions based on other Zika virus strains whereas the internal primers were designed from the published sequence (SEQ ID NOs: 74 to 117, see also Table A). The sequence obtained from the rMSB by use of these primers is provided by SEQ ID NO: 72. There was 100% overlap of the sequence with the published sequence of Zika Virus Strain H/PF/2013 (SEQ ID NO: 13). However, we sequenced additional regions 5' (an additional 40 bp) and 3' (an additional 160 bp) represented in SEQ ID NO: 72. In a preferred embodiment, the Zika virus of the invention comprises SEQ ID NO: 72. The genomic RNA is somewhat longer than the sequence according to SEQ ID NO: 72 (perhaps an additional 200 bp). Additionally, a Zika virus adapted to a host cell such as e.g. Vero cells may be expected to contain one or more mutations. For these reasons, the Zika virus of the current invention comprises the sequence of SEQ ID NO: 72 or, preferably, a sequence with at least 95%, 96%, 97%, 98%, or at least 99% sequence identity to the sequence provided by SEQ ID NO: 72. Furthermore, because the viral genome is likely to contain even further flanking regions to SEQ ID NO: 72; in one embodiment, the Zika virus of the invention contains the sequence of SEQ ID NO: 72 and optionally further comprises extensions at the 5' and/or 3' ends of at least 10, at least 20, at least 30, at least 40, at least 50, at least at least 70, at least 80, at least 90, at least 100, at least 110, at least 120 or at least 130 nucleotides. In a preferred embodiment, the Zika virus comprises at least the coding sequence for the entire polyprotein of Zika Virus Strain H/PF/2013 of the invention i.e. the amino acid sequence of SEQ ID NO: 73 or a polyprotein with at least 95%, 96%, 97%, 98%, or at least 99% sequence identity to the sequence provided by SEQ ID NO: 73. Furthermore, the Zika virus comprises at least the coding sequence for the E-protein of Zika Virus Strain H/PF/2013 of the invention SEQ ID NO: 47 or an E-protein thereof with at least 95%, 96%, 97%, 98%, or at least 99% sequence identity to the sequence provided by SEQ ID NO: 47.

Virus Growth on Vero Cells

Vero cells were grown in Eagle's minimal essential medium (EMEM) containing 10% fetal bovine serum (FBS). Roller bottle cultures of Vero cell monolayers were infected with Zika Virus Strain H/PF/2013 at a multiplicity of infection (moi) of 0.01 plaque forming units (pfu) per cell. After 2 hours of virus adsorption, the cultures were washed 3 times with PBS and fed with EMEM without FBS and incubated at +35° C. with 5% $CO_2$. Infected Vero cell cultures were incubated until the virus titer reaches a desired level.

The culture medium was harvested at days 2, 3, 5 and 7 and were pooled from those harvest days and then centrifuged in a standard centrifuge. The supernatants were then filtered. Virus culture supernatants were concentrated by TFF ultrafiltration to remove cell culture media components and to reduce batch volume.

Evaluation of Harvest Procedure

The current JEV harvest process has scheduled harvests on days 3, 5, 7 and 9 post infection. To mimic the JEV process roller bottles were infected with ZIKV bank P4-FBS at an MOI of 0.01 in infection medium (MEM with 2% FBS+2 mM L-glutamine) for 2 hours. After removing the inoculum the cells were washed twice with PBS and 200 mL production medium (MEM+2 mM L-glutamine) was added.

After taking a sample on day 2 the first virus harvest was conducted on day 3 after infection. At this point significantly higher CPE could be observed compared to cells where virus was removed on day 2. Plaque assay analysis showed that the viral titers on day 2 were in the same range as for the standard harvesting schedule. However, starting with the day 3 harvest, the observed titers were significantly lower correlating with the increased CPE observed compared to the standard harvest schedule. On day 5 post infection no more living cells could be observed at all and the experiment was terminated with a final day 5 harvest.

TABLE 3

The calculated titers per plaque assay are summarized in the list below.

| | Log 10 PFU/mL |
|---|---|
| sample day 2 | 7.02 |
| harvest day 3 | 6.66 |
| harvest day 5 | 6.26 |

Figure 15:
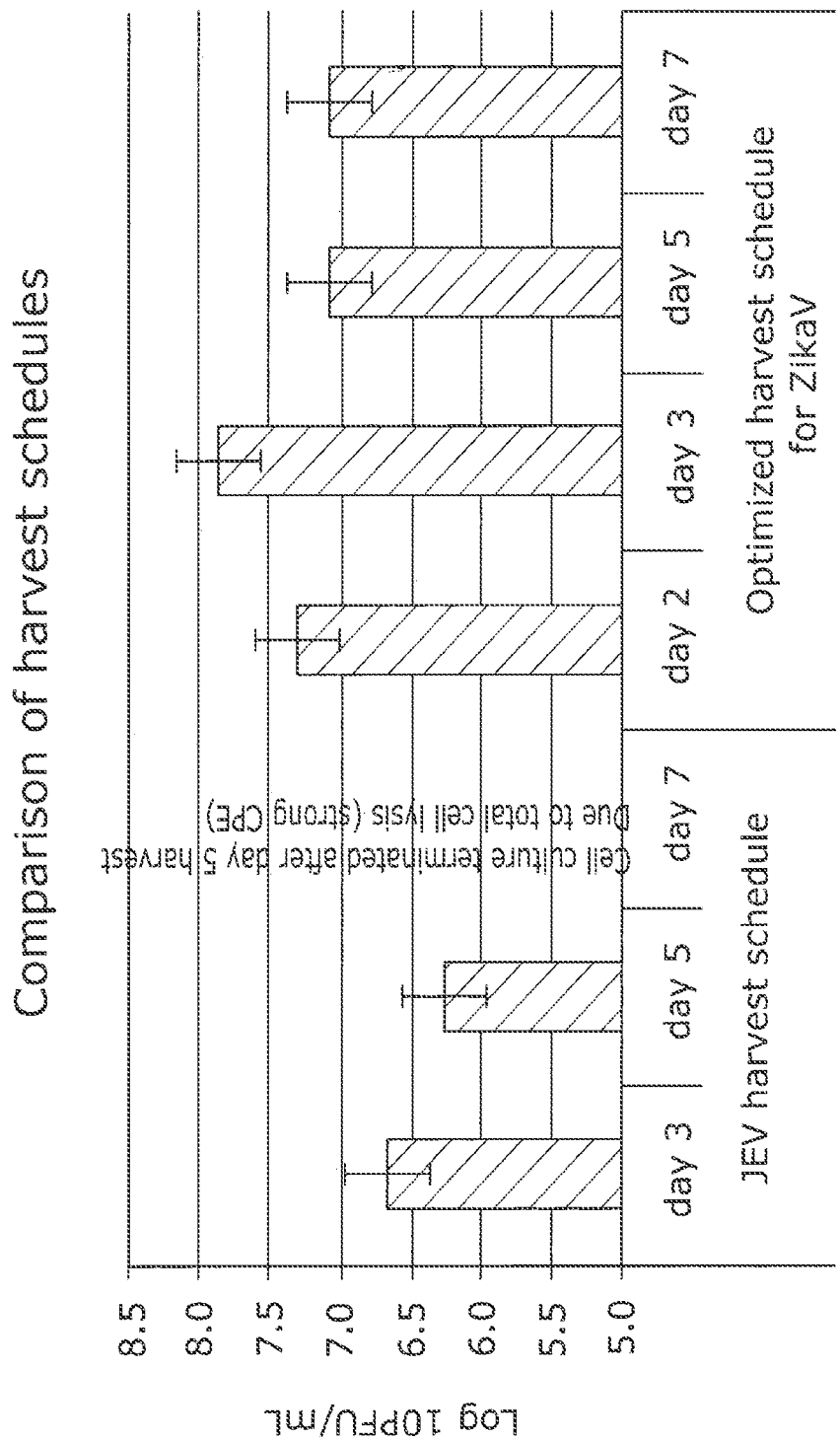
FIG. 15: Comparison of JEV and ZikaV harvest schedules/yields.

This finding led to an optimized harvest schedule to better control of CPE and allow additional harvest day 5 and 7, see FIG. 15. For both harvest days the optimized ZikaV protocol yield significant higher virus titers compared to the modified protocol showing that the time of the first harvest is crucial for production yields. Additionally first harvesting at day 3 results in maximum 2 harvest points whereas first harvesting at day 2 allows for 4 harvest points further increasing the yield gain.

Downstream Purification of Zika Virus

Figure 11:
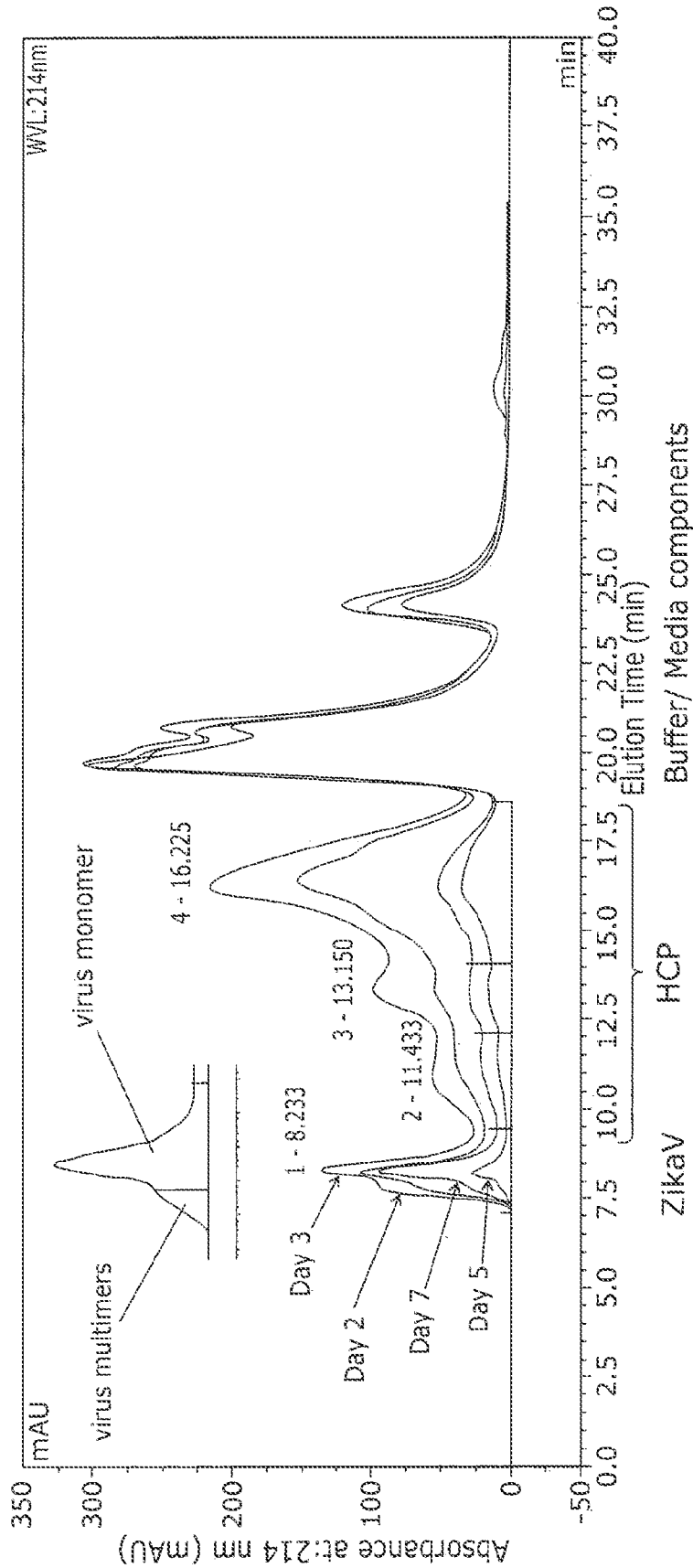
FIG. 11: SEC-HPLC of individual 30× concentrated Zika harvest prior to PS treatment at different time points.

The purification process was carried out at room temperature (18-22° C.) unless stated otherwise. Virus purification started with concentration of filtered combined harvest using 100 kDa cut-off TFF ultrafiltration modules to remove cell culture media components and reduce batch volume. After concentration, the pooled filtered harvest material was adjusted to a final concentration of 25 mM Tris pH 7.5 and 10% sucrose (w/w) using stock solution of both components (see FIG. 11 for SEC-HPLC of different harvests prior to PS treatment). This allowed for freezing the concentrated harvest at <−65° C. if required.

Figure 20:
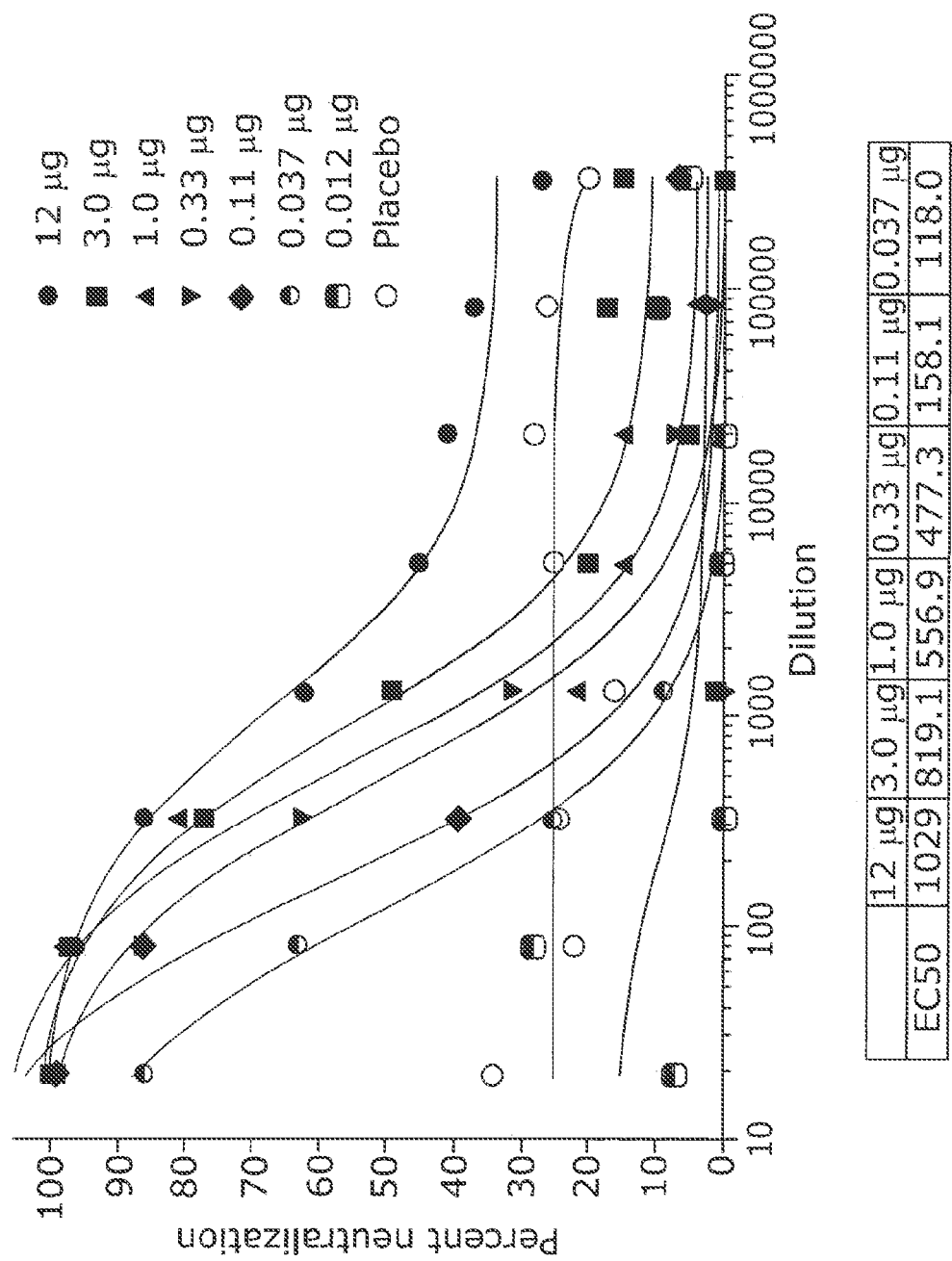
FIG. 20: Graphical representation of the neutralization of the Zika virus MR766 with pooled mouse sera. The number of plaques without serum was set to 100%. The EC50 was calculated using the 3-parameter method.
Figure 21:
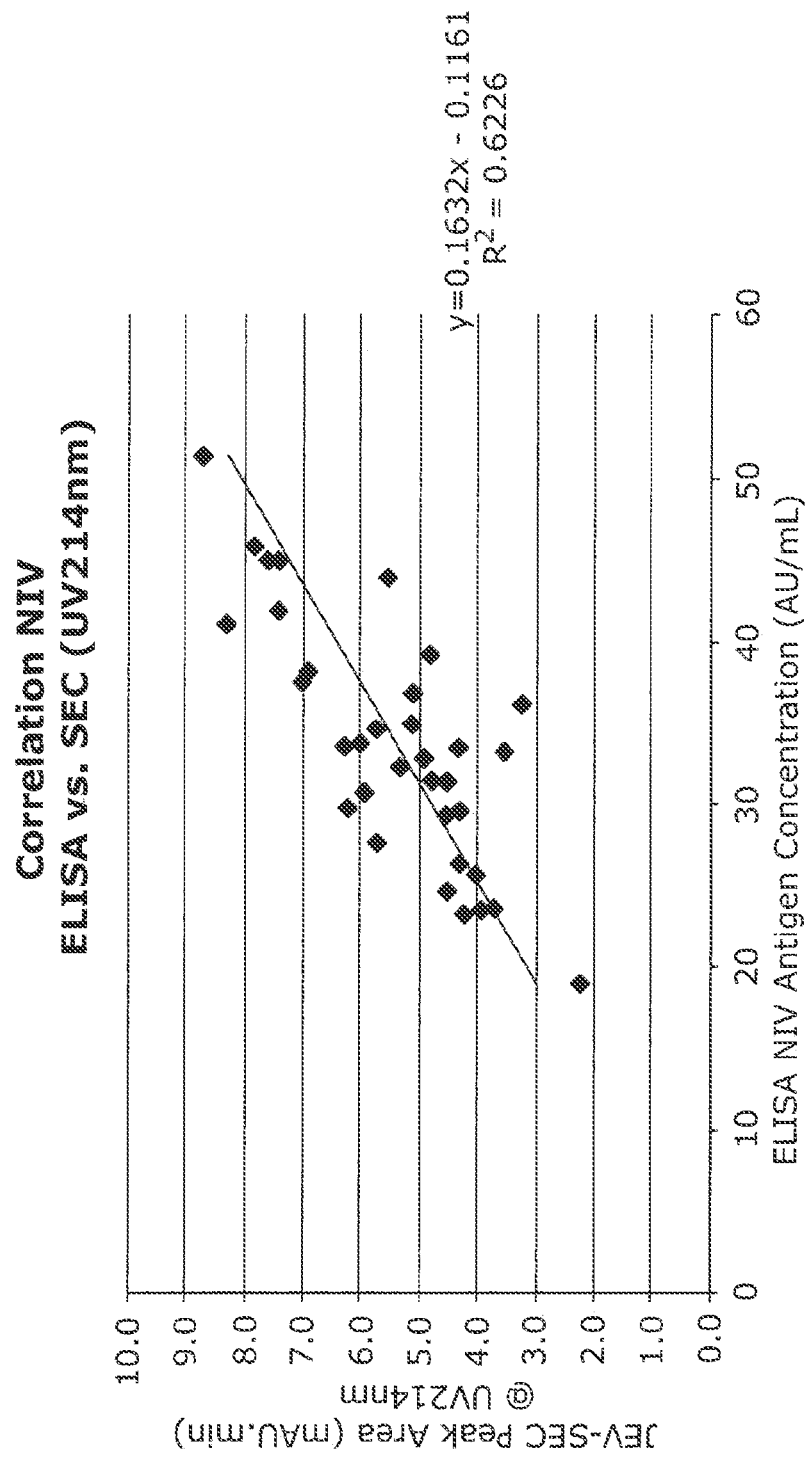
FIG. 21: Correlation between JEV antigen content in neutralized inactivated virus (NIV) analysed by ELISA and SEC-HPLC (Dionex Ultimate 3000, Superose 6 column).

Host cell DNA and protein reduction as well reduction of non-infectious virus aggregates in the concentrated material was achieved by precipitation with protamine sulphate (2 mg/mL) followed by sucrose density centrifugation (2-8° C.) as final polishing step (see FIG. 20 for SEC-HPLC of different harvests post PS treatment). The purification process was designed to be completed within 2 working days with SGC starting on end of day 1 followed by fractionation and SDS-PAGE analysis on day 2. The sucrose gradient fractions were stored at 2-8° C. during the SDS-PAGE analysis (Silver staining) to identify the pure fractions containing ZikaV (see FIG. 21). After pooling the relevant fractions, the pool was diluted and inactivated by Formalin After pooling the relevant fractions of sucrose gradient centrifugation, the pool was diluted 1:3 in PBS and inactivated by Formalin (0.02% v/v, 200 ppm). Fractions were subjected to analysis by SDS-PAGE.

Effect of PS Treatment on Virus Recovery

Figure 12:
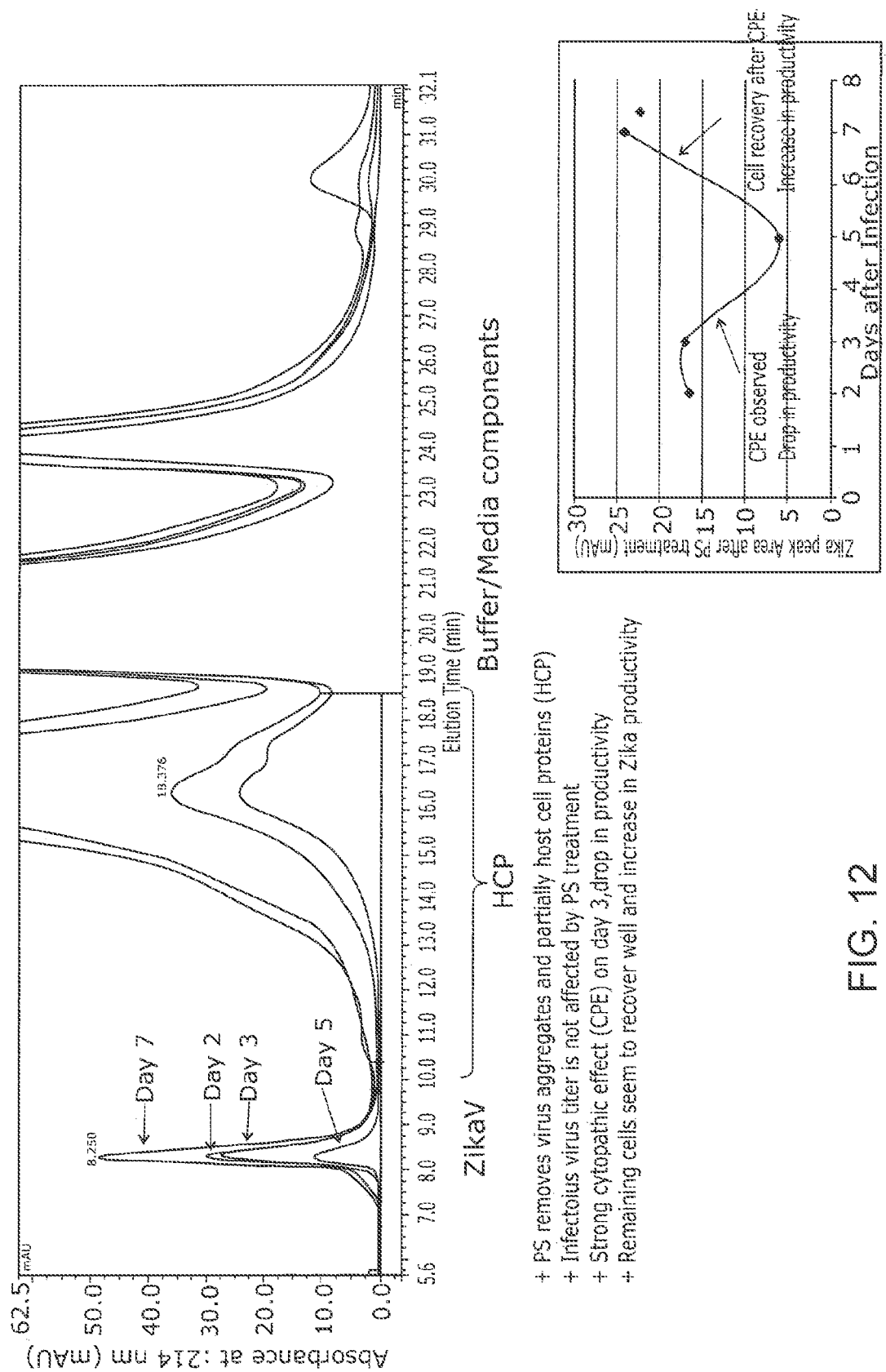
FIG. 12: SEC-HPLC of individual 30× concentrated Zika harvest post PS treatment at different time points. The smaller graph indicates the observed cytopathic effect (CPE) over time.
Figure 13:
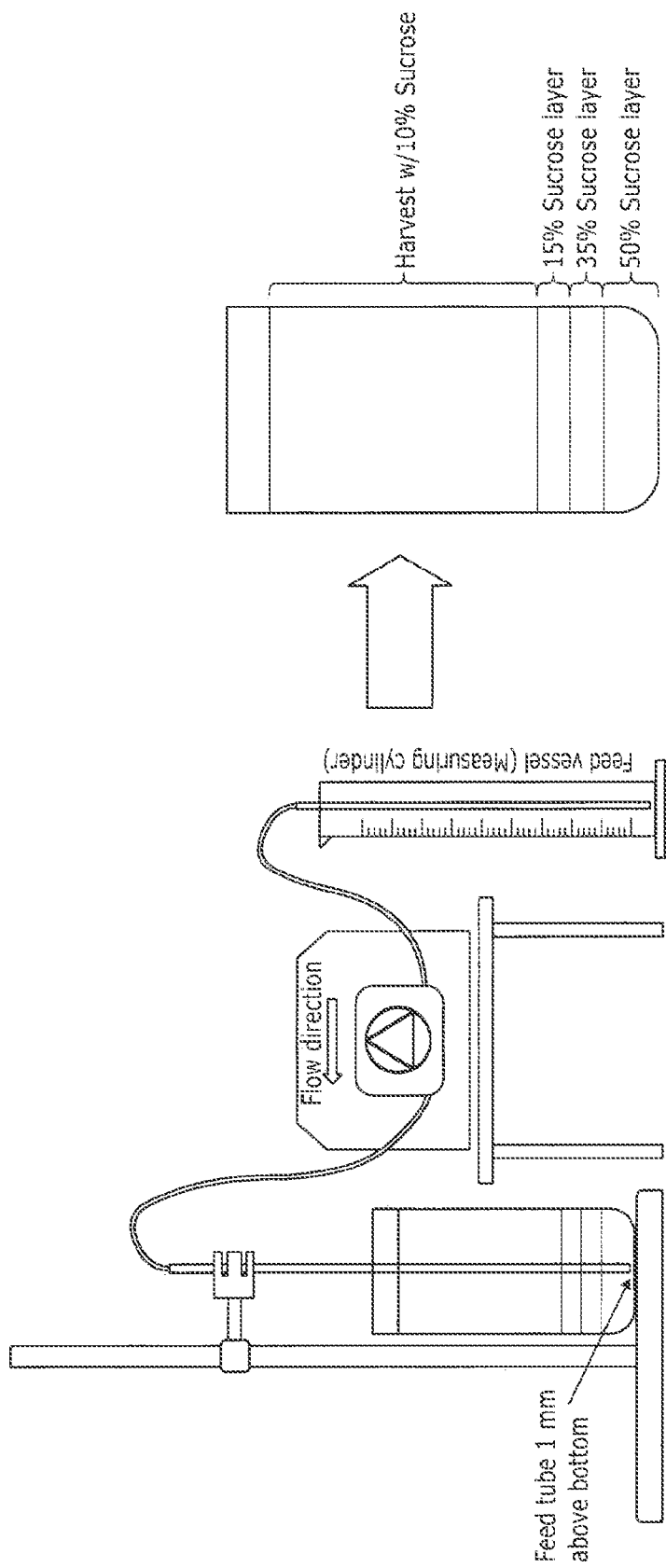
FIG. 13: Preparation of the sucrose gradient.

Samples of individual 30× concentrated harvests days 2, 3, 5 and 7 were analysed before (FIG. 11) and after PS (FIG. 12) treatment by SEC-HPLC and plaque assay. SEC-HPLC was used for determination of relative total ZikaV content (active+inactive) expressed as peak area, whereas the rel. ZikaV peak purity is given as relative content of virus monomer population to total virus peak. Plaque assay states the content of total active virus particles in each sample. Experimental results are summarized in Table 4. The virus peak recovery by SEC-HPLC was only between 12 to 36% with peak purity after PS treatment in the range of >90% (no virus aggregates detected). The recovery of active virus particles by plaque assay was all >100% (130-700%, range within the variability of the assay) showing that no active virus particles were lost during PS treatment. These results show that during PS treatment only non-infective (immature and/or aggregated virus) particles were removed.

TABLE 4

ZikaV recovery by SEC-HPLC and plaque assay before and after PS treatment.

SEC-HPLC

| Harvest day | Peak area mAU * min | | SEC Recovery (%) | rel. virus monomer content after PS (%) |
|---|---|---|---|---|
| | 30× conc | 30× + PS | | |
| Day 2 | 101.36 | 18.63 | 18 | 89% |
| Day 3 | 144.51 | 17.48 | 12 | 90% |
| Day 5 | 19.97 | 5.92 | 30 | 96% |
| Day 7 | 68.80 | 24.43 | 36 | 99% |

Plaque Assay

| Harvest day | PFU/mL | | Plaque Recovery (%) |
|---|---|---|---|
| | 30× conc | 30× + PS | |
| Day 2 | 3E+08 | 5E+08 | 179 |
| Day 3 | 2E+08 | 4E+08 | 193 |
| Day 5 | 1E+08 | 9E+08 | 700 |
| Day 7 | 3E+08 | 4E+08 | 132 |

Sucrose Gradient Centrifugation

The PS treated harvest was split in two parts and loaded on two centrifuge bottles. Sucrose density gradient centrifugation (SGC) was used for final concentration and polishing of the ZikaV material. The ZikaV PS treated concentrated harvest was loaded on top of a solution consisting of three layers of sucrose with different densities. The three sucrose layers were selected based on a preliminary study which showed the formation of a linear sucrose gradient and complete separation of the virus particles from residual contaminants as demonstrated for ChikV (FIG. 15D). The optimal volumes of the sucrose solutions were determined empirically. The volumes of individual layers for a centrifugation in 100 mL bottle scale are shown in Table 5.

TABLE 5

Individual layers/volumes for a centrifugation in bottle.

| Solution | Volume (mL) |
|---|---|
| PS treated harvest in 10% sucrose (L) | 40 |
| 15% sucrose (J) | 15 |
| 35% sucrose (I) | 15 |
| 50% sucrose (H) | 20 |
| Total volume | 90 |

Figure 14:
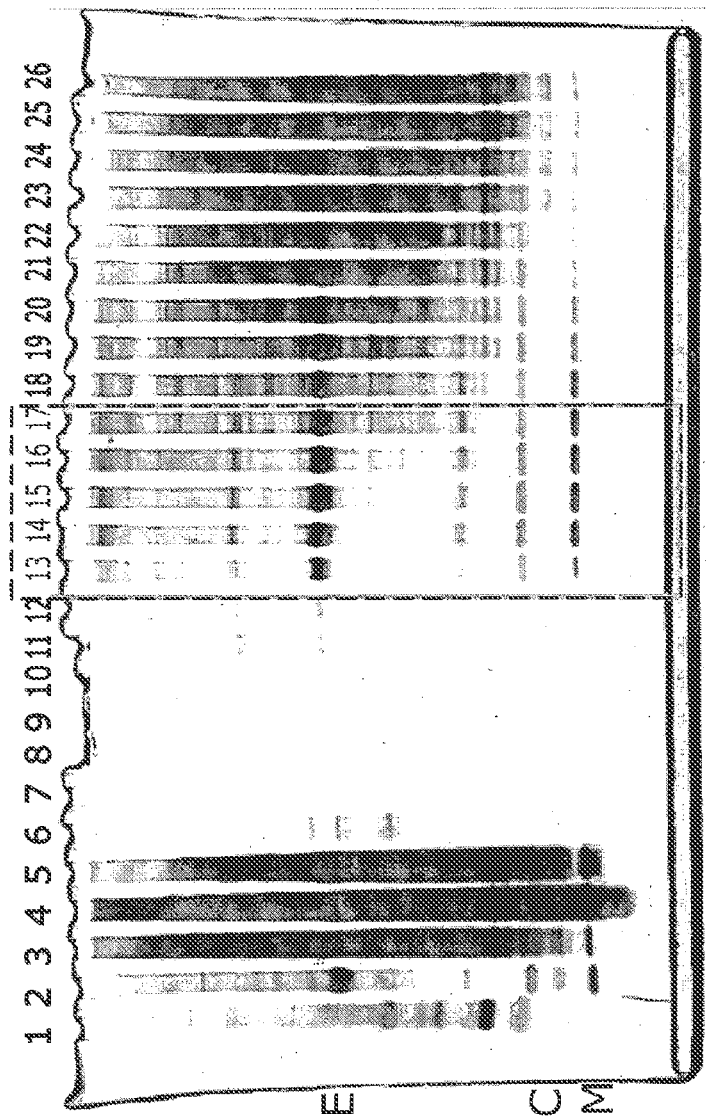
FIG. 14: Representative SDS-PAGE from the sucrose gradient harvest of a Zika purification is shown.

The sucrose gradient bottles were prepared by stratifying the individual sucrose layers. A plastic tube was attached to peristaltic pump tubing. The plastic tube was mounted on a laboratory stand using a clamp and placed into the centrifuge bottle. The nozzle of the plastic tube was touching the bottom of the bottle. Using a peristaltic pump the ZikaV material and the sucrose solutions were pumped into the cylinder. A measuring cylinder was used as feed vessel. The first solution pumped was the ZikaV material as it represented the solution of lowest density (10% sucrose (w/w)). After the ZikaV material the sucrose solutions were pumped in ascending order starting with the 15 (w/w) solution J, followed by 35% sucrose solution I and finishing with the highest density sucrose solution H (50% (w/w)). The described setup is shown in FIG. 14. After all sucrose solutions were transferred the plastic tubing was carefully removed in order not to disturb the layers.

Prior to centrifugation the centrifuge was pre-cooled to 4° C. The prepared SG bottles were carefully transferred into the pre-cooled rotor. (Note: Sudden movement of the bottles during transfer to the rotor must be avoided in order not to disturb the sucrose layers.) The bottles were centrifuged at ~11.000 RCF max at 4° C. for at least 20 hours, no brake/deceleration activated. In case a different centrifuge system with a different rotor is used the necessary speed and centrifugation times need to be calculated based on the k-factor in order to achieve comparable centrifugation efficiency.

Harvesting of the sucrose gradient was done manually using a peristaltic pump. A plastic tube attached to peristaltic pump tubing was used for harvesting the sucrose gradient. The bottle containing the gradient was mounted onto a laboratory stand in a tilted position (~12°) using a clamp. The plastic tubing was then placed into the bottle touching the bottom edge of the bottle and was fastened in position using a clamp. This resulted in a small gap of 1-2 mm between the tubing inlet and the bottom of the bottle (see FIG. 14).

Using a peristaltic pump set to a flow rate of 30 mL per minute the gradient was harvested and manually split into 2 mL fractions. A total number of 32 fractions per bottle were harvested (~64 mL) and the remaining volume was discarded. The fractions were immediately tested by SDS-PAGE/silver stain to identify the virus containing fractions with sufficient high purity. Representative SDS-PAGE is shown in FIG. 14. Fraction 10-14 were pooled and further processed.

The purified viral solution was inactivated by incubation with 0.02% formaldehyde over a period of ten days in a 22° C. controlled-temperature incubator. The formaldehyde is neutralized by addition of sodium metabisulphite on the tenth day.

The sucrose gradient pool (~17 mL after sampling) was further diluted 3-fold with PBS to a final volume of 51 mL in a PETG container. A volume of 1% formaldehyde (10,000 ppm) solution equivalent to 1/50 of the final volume of the pre-formaldehyde pool was added to this pool resulting in an effective concentration of 200 ppm. The formaldehyde-treated solution was mixed on a magnetic stirrer for 10 minutes. After sampling, the formaldehyde-treated viral solution was placed within a cooled incubator at 22° C.±2° C. On Day 5 post addition of formaldehyde, the formaldehyde-treated viral solution was filtered through a 0.2 μm filter and then placed in the incubator at 22° C.±2° C. again. On Day 10, after removing the 10-Day inactivation final sample, a volume of 1% (of the weight of the final formaldehyde-treated viral solution) of 200 mM-sodium metabisulphite solution (2 mM final concentration) was aseptically transferred into the PETG container containing the formaldehyde-treated viral solution. After mixing for 5 minutes on a magnetic stirrer, the neutralized inactivated viral solution is held at room temperature (20 to 25° C.) for a minimum of 30 minutes. After sampling, the neutralized inactivated viral solution is stored at 5° C.±3° C. until further processing.

Inactivation by Formaldehyde

Critical parameters for this step are final formalin concentration, temperature, mixing and transfer into a new container. A preliminary acceptance criterion for maximum pfu/mL (determined by plaque assay) has been set on the diluted pool pre formaldehyde treatment.

The quality of the neutralized inactivated viral solution was monitored by the following parameters: Plaque assay on Day 10, SEC-HPLC, SDS-PAGE/Western Blot.

Interestingly, SEC-HPLC analysis of samples taken during the inactivation period followed by neutralization with bisulfite showed more or less constant peak area throughout the inactivation period. This is in contrast to JEV where losses of viral particles up to 60% are observed using the process disclosed by Srivastava et al. Vaccine 19 (2001) 4557-4565. In a scale-down model the viral losses were even much higher due to surface/area ratio at smaller scale and high losses due to unspecific adsorption. Differences of the ZikaV inactivation experiment and JEV inactivation were noticed as follows:

A) Much higher purity of ZikaV SGP pool with regard to residual PS (<2 µg/mL) compared to JEV. The 3-fold ZikaV inactivated sample contained therefore <<1 µg/mL of residual PS. Commercial JEV SGP pool contains on average ~120 µg/mL (up to 152 µg/mL possible). The average dilution to inactivation solution of ~14-fold results in a residual PS content up to ~11 µg/mL. It may be that higher amount of residual PS could cause virus precipitation due to cross-linking/reaction with formalin B) ZikaV inactivation sample contained ~10% sucrose (3-fold dilution of SGP pool containing ~30-35% sucrose). Sucrose might have stabilizing effect of viral ZikaV particles during treatment with formalin.

Dilution to DS and Formulation with Aluminium Hydroxide (DP)

For preparation of ZikaV drug substance used in mouse potency assay an antigen content (expressed as total viral particles or SEC peak area) of 5 times higher compared to Ixiaro was targeted. The basis for determination of antigen content was SEC-HPLC. Briefly, a Superose 6 10/300 Increase column (GE Healthcare) equilibrated with PBS+ 250 mM NaCl, pH 7.4 at 1 ml/min and 25° C., was used to detect ZikaV at 214 nm detection wavelength in harvest samples and throughout the downstream process. In the current JEV process the antigen content in NIV is determined by a specific ELISA. A good correlation was observed between antigen content determined by ELISA and SEC-HPLC. On average, the antigen content in commercial NIV samples is in the range of 33 AU/mL corresponding to ~5.2 mAU JEV peak area, see FIG. 21.

ZikaV NIV day 10 (Zika peak ~36 mAU, analysed on Waters HPLC/Superose6 Increase column) was diluted with PBS to a target of 6.3 (~5.7× dilution). Aluminium hydroxide was added to a final concentration of 0.5 mg/mL Aluminium (1/20 v/v Alum 2% stock solution added) to prepare ZikaV Drug Product (DP). The DP was gently mixed for 5 min. An aliquot of the DP was removed, Alum sedimented by centrifugation and the clear supernatant analysed by SEC-HPLC. No ZikaV peak was detected in the supernatant indicating complete adsorption (estimated as >95%) of viral particles on the mineral adjuvant. Formulated ZikaV DP was stored at 2-8° C.

The impurity profile of the inactivated Zika virus DS is comparable to the profile of JEV DS with the exception of a lower PS content (Table 6).

TABLE 6

Determination of impurity profile in Zika and JEV DS samples:

| | Specification (JEV DS) | JEV | Zika |
|---|---|---|---|
| HCP (ng/mL) | <100 LOQ 12 ng/mL | <LOQ | <LOQ |
| DNA (pg/mL) | <200 LOQ 40 pg/mL | <40 | <40 |
| Aggregates by SEC-MALLS (%) | Not specified, part of characterization LOQ 5% | <LOQ | <LOQ |
| PS (µg/mL) | Specification only at SGP pool to demonstrate consistent process performance (19-152 µg/mL), *PS content in DS calculated based on PS content in SGP pool (~100 µg/mL) and average dilution factor (~28×) to DS; LOQ 2 µg/mL | ~4* | <<LOQ |

*Typical PS impurity in a JEV sample produced in accordance with protocol disclosed in Srivastava et al. Vaccine 19 (2001) 4557-4565.

SEC-MALLS Results

Figure 16:
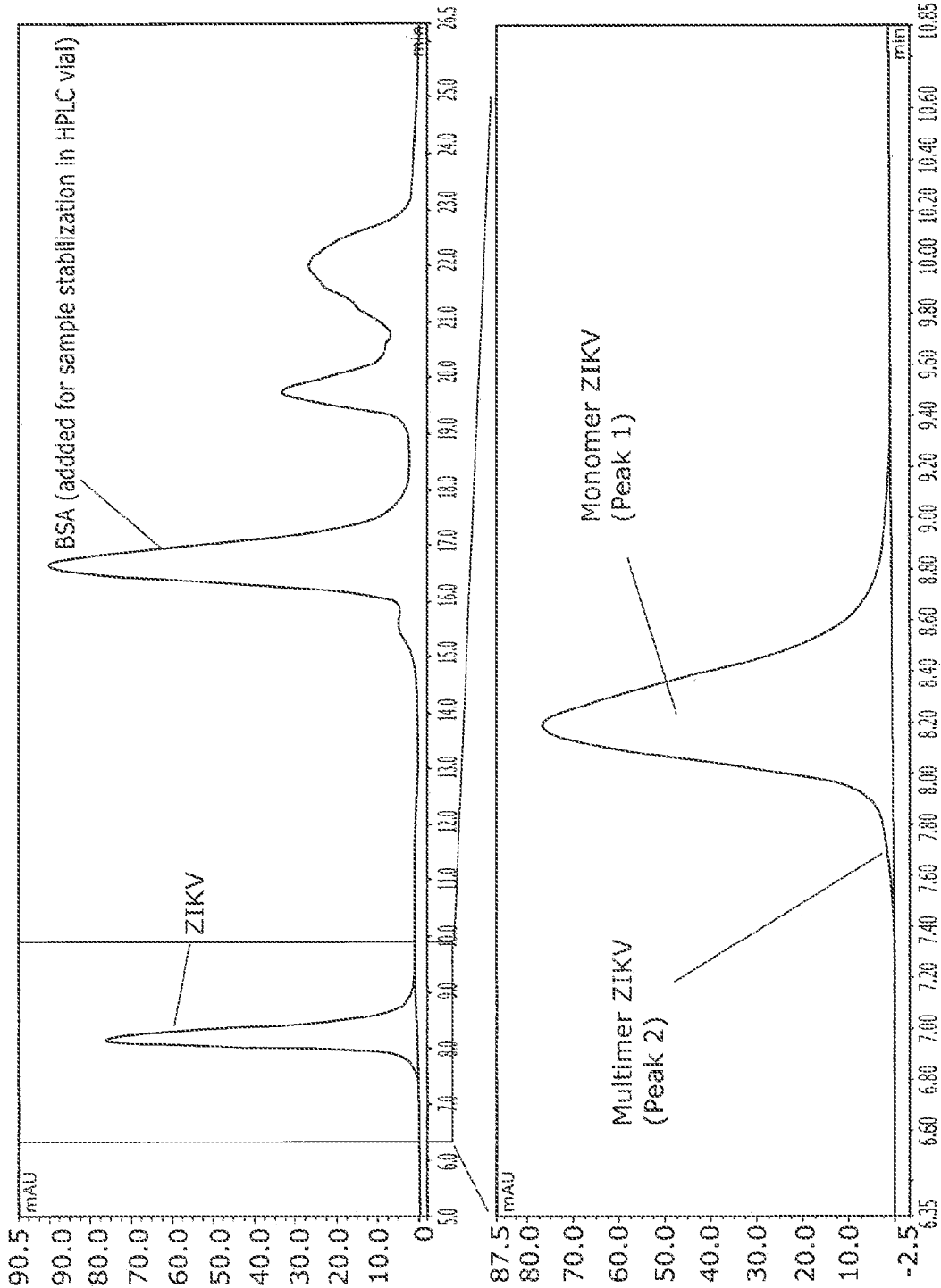
FIG. 16: SEC-HPLC elution profile of ZikaV NIV. Data were processed on Dionex Ultimate 3000/Superose 6 Increase column. Both panels are from the same chromatogram. The upper graph is the complete elution profile; the lower graph is an enlargement of the ZIKAV elution peak.

A representative SEC-HPLC elution profile of ZikaV NIV at 214 nm detection wave length is shown in FIG. 16. Note that BSA (50 µg/mL) was added to the sample to minimize losses in HPLC glass vial due to unspecific surface adsorption. ZikaV monomer content was estimated as ~98% with a multimer content of ~2%.

Figure 17:
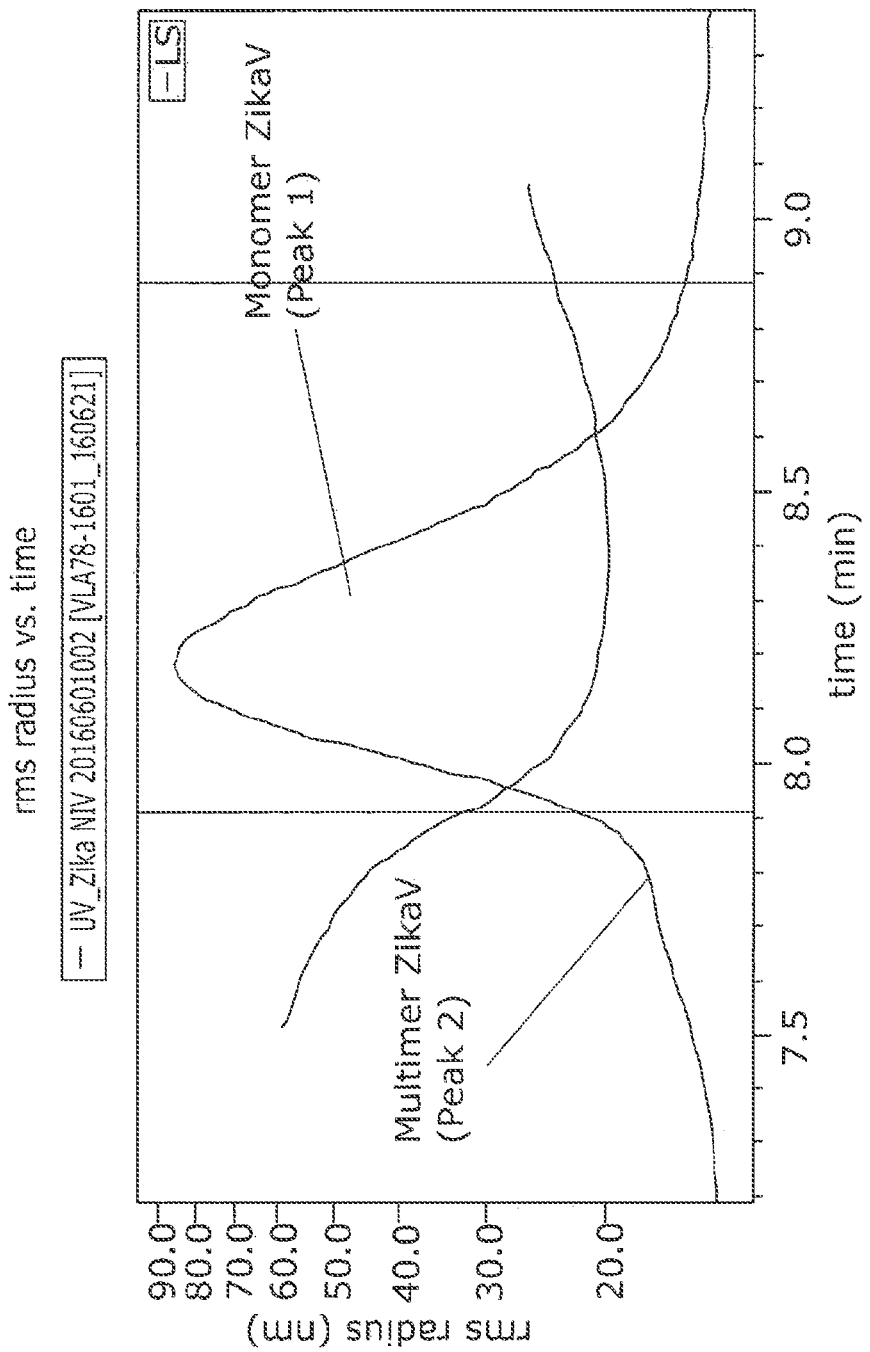
FIG. 17: SEC-MALLS analysis of inactivated ZikaV.
Figure 18:
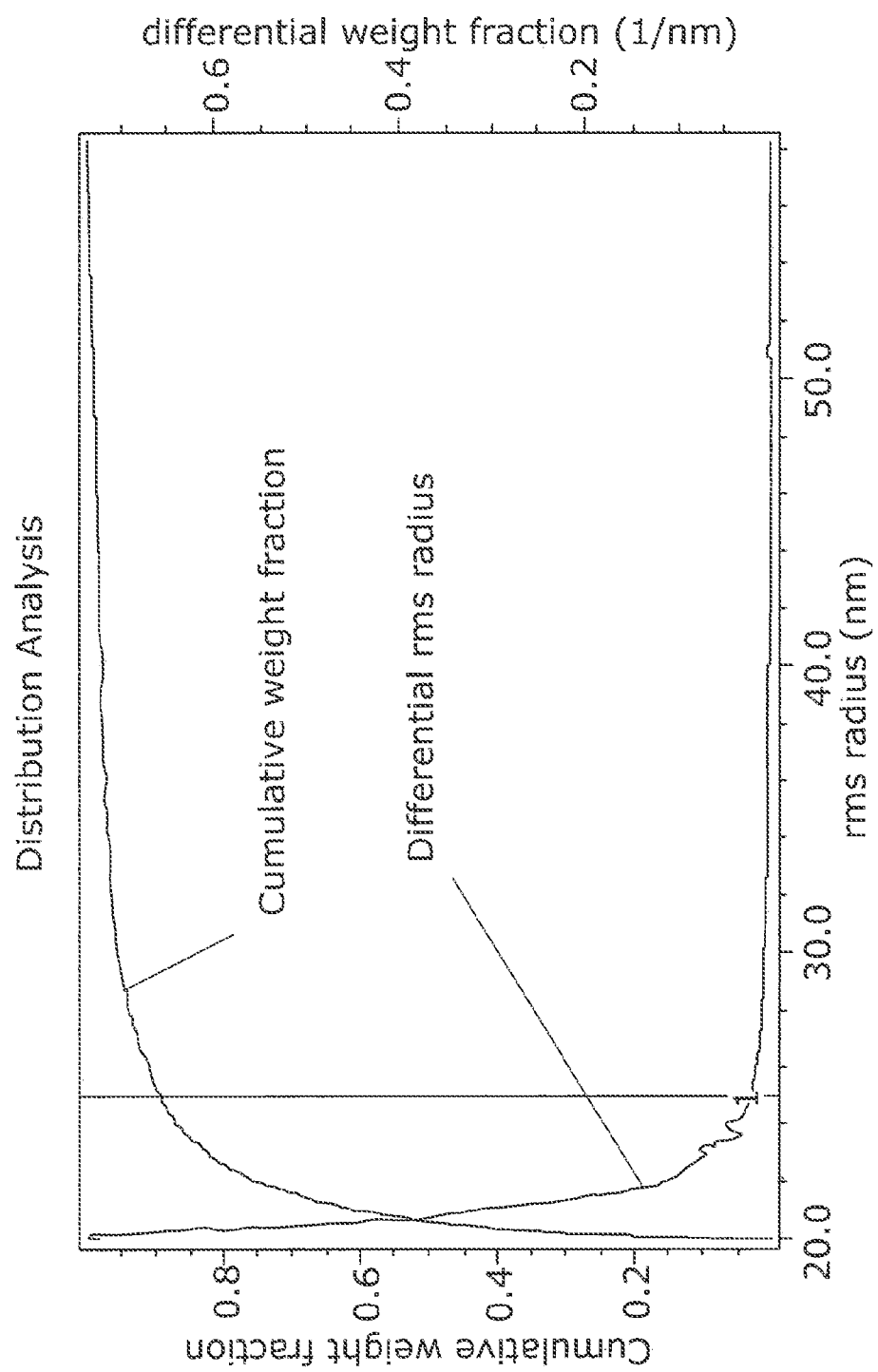
FIG. 18: Cumulative particle size distribution of Zika NIV.

SEC-MALLS analysis (FIG. 17) of the sample confirmed the radius Rz of the monomer ZikaV population peak 1 as 21.6 nm and ~49 nm for the multimer peak 2. Cumulative particle size distribution showed that 89% of all viral particles are within a radius range between 18 to 25 nm (FIG. 18).

Results confirm purity and homogeneity of ZikaV NIV.

Viral Titer by Plaque Assay

TABLE 7

Active ZikaV pfus were quantified by plaque assay throughout the process.

| Sample | Pfu/mL |
|---|---|
| Harvest day 2 (filtered) | $6.4 \times 10^7$ |
| Harvest day 3 (filtered) | $1.0 \times 10^8$ |
| Harvest day 5 (filtered) | $1.5 \times 10^8$ |
| Harvest day 7 (filtered) | $1.1 \times 10^8$ |
| PS treated harvest 300× concentrate (=SGP load) | $9.0 \times 10^8$ |
| SGP pool | $8.9 \times 10^8$ |
| Inactivation start (SGP pool 1:3 diluted) | $3.4 \times 10^8$ |
| Inactivation day 5 | <LOD |
| Inactivation day 10 | <LOD |

Comparison of PS and Benzonase on Process Performance

A direct comparison of DNA removal method of concentrated ZikaV harvest pool was done. One aliquot was treated with PS (2 mg/mL, 15 min at room temperature), the other aliquot was treated with Benzonase (50 U/mL, 2 mM MgCl2, 4 h RT, 48 h 2-8° C.). Both samples were further purified by sucrose gradient as described in this report. Interestingly, the Benzonase treated samples did not yield any pure fractions after sucrose gradient centrifugation of the treated ZikaV harvest. In those fractions where the specific virus bands were detected, a high amount of host cell protein was detected throughout the collected fractions. The PS treated material resulted in pure ZikaV containing fractions as expected. This finding may suggest that PS is not only effective for DNA removal by precipitation; in addition it improves the recovery of virus particles in the gradient by disrupting interaction of DNA (fragments) and virus particles. Benzonase treatment does not remove DNA, it only results in its fragmentation. Residual DNA fragments might still interact with virus particles and residual HCPs resulting in cross-contamination and co-purification in the sucrose gradient. Pooled SGP fractions were also analysed by SEC-HPLC. Although a large peak was detected, SDS-PAGE confirmed that this sample was highly contaminated with HCPs. A large peak might be detected at UV214 and 280 nm after SEC-HPLC analysis due to possible interaction of HCPs with large virus particles, changing the UV absorbance.

Immunogenicity of Vero Grown Zika Virus
Immunization of Mice

Prior to immunization, groups of ten 6-week-old female CD1 mice were bled via vena facialis and pre-immune sera were prepared. One intraperitoneal immunizations of 200 µL were administered. A dose titration (12 µg, 3 µg, 1 µg, 0.33 µg, 0.11 µg, 0.037 µg and 0.012 µg, equivalent to the protein amount in IXIARO) of inactivated Zika virus formulated with aluminium hydroxide (Al(OH)3) at a final concentration of 0.7%. Three weeks after immunization, blood was collected and immune sera were prepared. All animal experiments were conducted in accordance with Austrian law (BGB1 Nr. 501/1989) and approved by "Magistratsabteilung 58".

Plaque Reduction Neutralization Test (PRNT)

Twelve well plates were used for PRNT. Each well was seeded with 1 mL medium containing $4\times10^5$ Vero cells and incubated 35° C. with 5% $CO_2$ overnight. Pools of heat inactivated sera from each dose group were tested in triplicate. The target viruses (H/PF/2013 (SEQ ID NO: 13) or MR766 (SEQ ID NO: 11)) were diluted to 100 pfu/165 µL. Equal volumes of target virus and serum dilution were incubated at 35° C. with 5% $CO_2$ for 1 hour. The cell culture medium was aspirated from the Vero cells and 330 µL of the mixture target virus/serum dilution were added to each well and the plates were rocked back and forth 5 times before incubating for 2 hours at 35° C. with 5% $CO_2$. To each well 1 mL of a 2% methylcellulose solution containing EMEM and nutrients was added, the plates were then incubated for 5 days at 35° C. with 5% $CO_2$ before staining the cells for 1 hour with crystal violet/5% formaldehyde and subsequently washed 3 times with deionized water. The plates were air dried and the numbers of plaques in each well were manually counted.

Results

Figure 19:
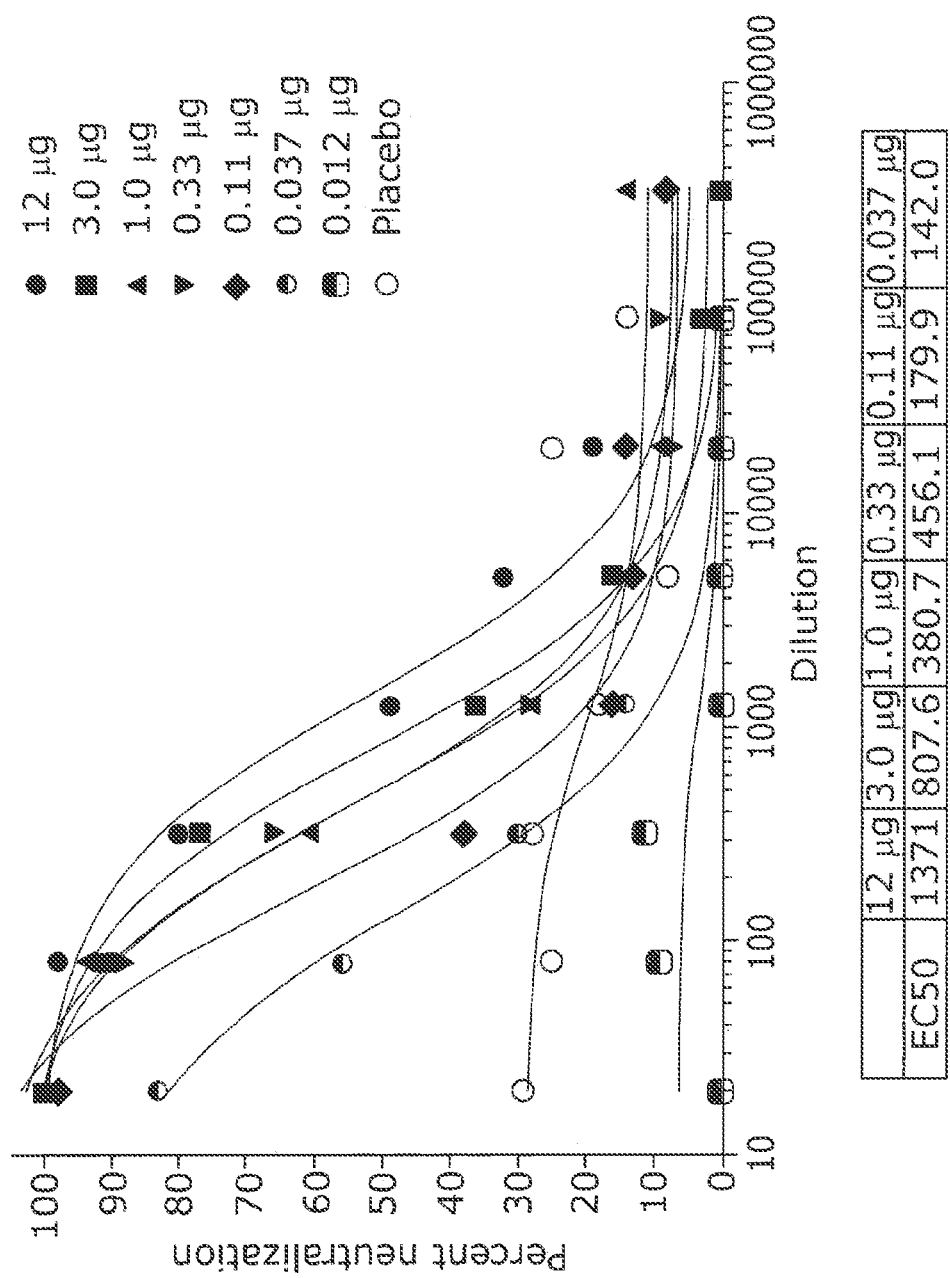
FIG. 19: Graphical representation of the neutralization of the Zika virus H/PF/2013 with pooled mouse sera. The number of plaques without serum was set to 100%. The EC50 was calculated using the 3-parameter method.

Neutralization was observed with serum pools from mice immunized with inactivated Zika virus vaccine (H/PF/2013) down to 37 ng (dosing equivalent to the amount protein in IXIARO®) against Zika viruses of both the Asian (H/PF/2013) and African (MR766) lineages (FIGS. 19 and 20, respectively). Complete inhibition was seen at the 1:20 serum dilution with an immunization dose down to 110 ng (dosing equivalent to the amount protein in IXIARO®). The neutralization of both the Asian (H/PF/2013) and African (MR766) lineages of the Zika virus was equivalent, which indicates high cross-neutralization between different Zika virus strains of the inactivated Zika virus vaccine (H/PF/2013).

Another neutralization assay was performed using the microneutralization assay as described by Larocca, et al. (2016, Nature doi:10.1038/nature18952). It was found that the inactivated Zika virus of the current invention had an MN50 (microneutralization) titer of 90 at 1 µg of inactivated purified virus.

Further methods: The immunogenicity of inactivated Zika virus preparations is assessed using a mouse model of Zika infection. Groups of adult mice are immunized subcutaneously (s.c.) with 500, 50, or 5 ng of inactivated Zika virus with adjuvant (e.g. aluminium hydroxide with or without IC31®), or without adjuvant. An additional group of mice receive PBS as a negative control. Each group is administered the indicated inoculum at t=0 and in some cases also at three to four weeks later (t=3/4). Beginning approximately three weeks after administration of the last immunization, serum samples are obtained from each of the mice at regular intervals. The serum samples are tested for the presence of neutralizing antibodies using PRNT.

The in vivo protective efficacy of the inactivated Zika virus preparations is also assessed using a mouse model of Zika infection, i.e. IFN-alpha/beta receptor knock-out mice (A129) (see e.g. Dowall et al., 4. Mar. 2016, dx.doi.org/10.1101/042358) or blocking of the IFN-alpha/beta receptor by administration of anti-IFN-alpha/beta receptor monoclonal antibodies to C57BL/6 or BALB/c mice (see e.g. Pinto et al., 7. Dec. 2011, DOI: 10.1371/journal.ppat.1002407). For protection assays, groups of 10 three- to eight-weeks-old A129, C57BL/6 of BALB/c mice are inoculated subcutaneously in the hindquarters with inactivated Zika virus with adjuvant (aluminium hydroxide) or without adjuvant at t=0. Age-matched controls are inoculated with PBS or non-specific antigens in alum. Mice are optionally boosted with a second administration of the indicated inoculation three to four weeks later. The mice are then challenged subcutaneously at three to eight weeks post immunization by inoculation with a deadly dose of live Zika virus. One day prior to challenge of C57BL/6 and BALB/c mice, they are passively administered (intraperitoneally) anti-IFN-alpha/beta receptor monoclonal antibodies. Challenged mice are monitored daily for morbidity and mortality for up to twenty-one days. Another alternative is to challenge intracranially adult vaccinated/non-vaccinated adult mice and observe protection.

It is expected that the Zika virus produced by the process of the invention will provide very similar functional readouts in in vitro, in vivo and finally human trials as the currently licensed JEV vaccine in the EU and US and elsewhere, IXIARO®. The dosage may alter but due to the very similar impurity profile and almost identical manufacture, a very similar efficacy and safety result will be expected as was determined for the currently licensed JEV vaccine (licensed in the EU and US and elsewhere).

Discussion & Conclusion

The existing manufacturing platform for production of inactivated JEV vaccine IXIARO® was used as a basis for a manufacturing feasibility study of inactivated ZikaV vaccine candidate (Asian strain H/PF/2013). The virus was produced on Vero cells cultivated in roller bottles. The virus was purified by PS treatment followed by an optimized sucrose gradient. Inactivation was done by formalin treat (0.02%, 10 days at 22° C.). For exploratory immunization studies in mice, a DP formulated with Alum was prepared with an estimated 5-fold higher virus particle content compared to IXIARO®, the commercial JEV Vaccine. The impurity profile of the DS met all criteria as defined in the specification for IXIARO®, the commercial JEV vaccine. The neutralization of both the Asian (H/PF/2013) and African (MR766) lineages of the Zika virus was equivalent, which indicates high cross-neutralization between different Zika virus strains of the inactivated Zika virus vaccine (H/PF/2013).

The in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was higher than the recently reported inactivated Zika virus vaccine candidate (Larocca, et. al, 2016, supra.). Inactivated viruses are among the safest vaccines and especially preferred for deliver to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Further more detailed aspects of the invention:

A1. A Zika virus vaccine comprising an inactivated Zika virus particle, wherein the Zika virus particle is able to seroconvert a subject that is administered the Zika virus vaccine with at least a 70% probability.

A2. The Zika virus vaccine of A1, wherein the Zika virus particle is able to seroconvert the subject that is administered the Zika virus vaccine with at least a 80%, 85%, 90%, or 95% probability.

A3. The vaccine of A1 or A2, wherein the Zika virus particle has a RNA genome corresponding to the DNA sequence provided by any one of the nucleic acid sequences of SEQ ID NOs: 2-13 or 72, or a variant nucleic acid sequence that is at least 88% identical to any one of SEQ ID NOs: 2-13 or 72 and able to pack a virulent Zika virus.

A4. The vaccine of any one of A1-A3, wherein the Zika virus particle has an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

A5. The vaccine of any one of A1-A4, wherein the Zika virus is inactivated by chemical inactivation, thermal inactivation, pH inactivation, or UV inactivation.

A6. The vaccine of A5, wherein the chemical inactivation comprises contacting the Zika virus with a chemical inactivation agent to completely inactivate the Zika virus as measured by plaque assay.

A7. The vaccine of A6, wherein the chemical inactivation comprises contacting the Zika virus with formaldehyde.

A8. The vaccine of A7, wherein the formaldehyde inactivation comprises contacting the Zika virus with formaldehyde for between 2-10 days.

A9. The vaccine of any one of A5-A8, wherein the chemical activation is performed at about +4° C. or about +22° C.

A10. The vaccine of any one of A1-A9, further comprising an adjuvant.

A11. The vaccine of A10, wherein the adjuvant is an aluminum salt adjuvant.

A12. The vaccine of A11, wherein the aluminum salt adjuvant is aluminium hydroxide or aluminium phosphate salt.

A13. The vaccine of any one of A10-A12, wherein the vaccine comprises or further comprises an adjuvant comprising a peptide and a deoxyinosine-containing immunostimulatory oligodeoxynucleic acid molecule (I-ODN).

A14. The vaccine of A13, wherein the peptide comprises the sequence KLKL5KLK (SEQ ID NO: 71) and the I-ODN comprises oligo-d(IC)13 (SEQ ID NO: 70).

A15. The vaccine of any one of A1-A14, further comprising one or more pharmaceutically acceptable excipient.

A16. The vaccine of any one of A1-A15, wherein the vaccine contains protamine sulphate or fragments or break-down products of PS at amounts too low to detect by HPLC, i.e., below 1 µg/mL, especially below 100 ng/mL.

A17. The vaccine of A16, wherein said protamine sulphate or fragments or break-down products of PS can be detected by mass spectroscopy or another sensitive method.

B1. A kit comprising a Zika virus vaccine of any one of A1-A15.

B2. The kit of B1, further comprising a second vaccine.

B3. The kit of B2, wherein the second vaccine is a West Nile virus vaccine, a Japanese Encephalitis virus vaccine, a Yellow Fever virus vaccine, a Dengue virus vaccine or a Chikungunya virus vaccine.

C1. A method, comprising administering a first dose of a therapeutically effective amount of the Zika virus vaccine of any one of A1-A15 to a subject in need thereof.

C2. The method of C1, further comprising administering a second dose of a therapeutically effective amount of the Zika virus vaccine.

C3. The method of C1 or C2, wherein the second dose of the Zika virus vaccine is administered about 7 days after the first dose of the Zika virus vaccine.

C4. The method of C1 or C2, wherein the second dose of the Zika virus vaccine is administered about 14 days after the first dose of the Zika virus vaccine.

C5. The method of C1 or C2, wherein the second dose of the Zika virus vaccine is administered about 28 days after the first dose of the Zika virus vaccine.

C6. The method of any one of C1-05, wherein the administering results in production of Zika virus neutralizing antibodies.

D1. A method of producing a Zika virus vaccine, comprising
   (i) passaging a Zika virus on Vero cells, thereby producing a culture supernatant comprising the Zika virus;
   (ii) harvesting the culture medium of (i);
   (iii) precipitating the harvested culture medium of (ii), thereby producing a Zika virus supernatant; and
   (iv) optimally inactivating the Zika virus in the Zika virus supernatant of (iii) thereby producing an inactivated Zika virus.

D2. The method of D1, further comprising concentrating the culture medium of (ii) prior to step (iii).

D3. The method of D1 or D2, wherein the precipitating of (iii) comprises contacting the culture medium of (ii) with protamine sulfate or benzoate.

D4. The method of any one of D1-D3, further comprising (v) dialyzing the inactivated Zika virus of (iv), thereby producing a dialyzed Zika virus.

D5. The method of D4, further comprising (vi) filtering the dialyzed Zika virus of (v).

D6. The method of any one of D1-D5, wherein the inactivating is by chemical inactivation, thermal inactivation, pH inactivation, or UV inactivation.

D7. The method of D6, wherein the chemical inactivation comprises contacting the Zika virus with a chemical inactivation agent for at least 4 days.

D8. The method of D6 or D7, wherein the chemical inactivation agent comprises formaldehyde.

D9. The method of any one of D6-D8, wherein the chemical activation is performed at about +4° C. or about +22° C.

D10. The method of D8 or D9, further comprising neutralizing the formaldehyde.

D11. The method of D10, wherein the neutralizing is performed with sodium metabisulfite.

E1. The use of the optimally inactivated Zika virus vaccine of any one of A1-A15 for the treatment and/or prevention of a Zika virus infection.

E2. The use of E1, wherein the inactivated Zika virus vaccine is administered in a first dose of a therapeutically effective amount to a subject in need thereof.

E3. The use of E2, wherein the inactivated Zika virus vaccine is administered in a second dose of a therapeutically effective amount to the subject.

E4. The use of E3, wherein the second dose of the inactivated Zika virus vaccine is administered about 7 days after the first dose of the Zika virus vaccine.

E5. The use of E3, wherein the second dose of the Zika virus vaccine is administered about 14 days after the first dose of the Zika virus vaccine.

E6. The use of E3, wherein the second dose of the Zika virus vaccine is administered about 28 days after the first dose of the Zika virus vaccine.

E7. The use of any one of E1-E6, wherein the vaccine administration results in production of Zika virus neutralizing antibodies.

F1. A pharmaceutical composition for use in the treatment or prevention of a Zika virus infection, wherein said pharmaceutical composition comprises the optimally inactivated Zika virus vaccine of any one of A1-A15.

F2. The pharmaceutical composition of F1, wherein the inactivated Zika virus vaccine is administered in a first dose of a therapeutically effective amount to a subject in need thereof.

F3. The use of F2, wherein the inactivated Zika virus vaccine is administered in a second dose of a therapeutically effective amount to the subject.

F4. The use of F3, wherein the second dose of the inactivated Zika virus vaccine is administered about 7 days after the first dose of the Zika virus vaccine.

F5. The use of F3, wherein the second dose of the Zika virus vaccine is administered about 14 days after the first dose of the Zika virus vaccine.

F6. The use of F3, wherein the second dose of the Zika virus vaccine is administered about 28 days after the first dose of the Zika virus vaccine.

F7. The use of any one of F1-F6, wherein the vaccine administration results in production of Zika virus neutralizing antibodies.

G1. Use of an optimized sucrose gradient centrifugation for removal of protamine sulphate from purified infectious Zika virus particles.

G2. The use according to G1, wherein said optimized sucrose gradient centrifugation comprises a virus comprising fraction in a 10%+/−1% (w/w) sucrose solution and three further layers of sucrose solutions with different densities, i.e. a first sucrose solution with 15%+/−1% (w/w) sucrose, a second sucrose solution with 35%+/−1% (w/w) sucrose, and a third sucrose solution with a 50%+/−1% (w/w) sucrose.

G3. A process of purification of infectious Zika virus particles, comprising the steps of:
  a) providing a crude harvest (a) comprising virus particles and impurities, wherein the impurities are generated from growing said virus particles on a cell substrate;
  b) reducing impurities from the crude harvest (a) by precipitation with an agent comprising protamine, preferably a protamine salt, more preferably a protamine sulphate, even preferably a recombinant protamine sulphate, to obtain a virus preparation (b);
  c) further purifying the virus preparation (b) by an optimized sucrose density gradient centrifugation, wherein the optimized sucrose gradient is provided such that the protamine can be completely or almost completely separated from the virus fraction; and wherein the protamine concentration is reduced by this step to the extent that the protamine concentration in the final drug substance is below 1 µg/ml, preferably below µg/mL, more preferably below 0.1 µg/mL, most preferably below 0.05 µg/mL.

G4. The process of G3, wherein said optimized sucrose density gradient centrifugation comprises a virus comprising fraction in a 10%+/−1% (w/w) sucrose solution and three layers of sucrose with different densities, i.e. a first sucrose solution with 15%+/−1% (w/w) sucrose, a second sucrose solution with 35%+/−1% (w/w) sucrose, and a third sucrose solution with a 50%+/−1% (w/w) sucrose.

G5. The process of any one of G3 to G4, additionally comprising a further purification step of:
  (d) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles.

G6. The process of any of G3 to G5, wherein the residual host cell DNA content of the Zika virus preparation (c) is less than 10 ng/mL and the residual host cell protein content of the final virus preparation (c) is less than 100 ng/mL.

G7. The process of any of G3 to G6, wherein said crude harvest (a) comprising Zika virus particles and impurities is subjected to one or more pre-purification step(s) prior to step (b).

G8. The process of G7, wherein the one or more pre-purification step(s) comprises
  a) filtration using a filter having a pore size equal to or less than 0.2 µm; and/or
  b) digestion of host cell genomic DNA by enzymatic treatment; and/or
  c) ultra/diafiltration using a hollow fiber membrane having a pore size equal to or greater than 300 kDa, preferably equal to or greater than 100 kDa.

G9. The process of any one of G3 to G8, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml or 2 mg/ml.

G10. The process of any of G3 to G9, wherein the enrichment of infectious Zika virus particles in the virus preparation (c) or any final virus preparation relative to total virus products in the crude harvest (a) is in the range from at least 50% to 95%, preferably at least 80%.

G11. The process of any one of G7 to G10, wherein the one or more pre-purification step(s) prior to step (b) of any of G8 to G11 is performed using a filter having a pore size equal to or less than 1 µm, preferably 0.2 µm.

G12. The process of any of G3 to G11, wherein the residual impurity of the Zika virus preparation (c) is less than 10%.

G13. The process of any of G3 to G12, wherein the Zika virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

G14. The process of G13, wherein said cell line is a Vero cell line.

G15. The process of any one of G3 to G14, wherein said infectious Zika virus particle is an infectious virus particle that is a live virus, a live attenuated virus, a chimeric virus, a modified live virus, or a recombinant live virus.

G16. The process of any one of G3 to G15, wherein said Zika virus is preferably a strain of the Asian lineage.

G17. The process of any one of G3 to G16, wherein said process resulting in final virus preparation (c) or (d) is followed by an inactivation step, wherein the virus is inactivated preferably by formaldehyde.

G18. Use of the process according to any one of G3 to G17 for manufacturing a composition for immunization against a virus infection.

G19. The use according to G18, wherein said virus infection is an infection caused by a Zika virus.

Q1. A process of purification of infectious Zika virus particles, comprising the steps of:
(a) providing a crude harvest (a) comprising Zika virus particles and impurities, wherein the impurities are generated from growing said virus particles on a cell substrate;
(b) reducing impurities from the crude harvest (a) by precipitation with an agent comprising protamine, preferably a protamine salt, more preferably a protamine sulphate, even more preferably a recombinant protamine sulphate, to obtain a virus preparation (b);
(c) further purifying the virus preparation (b) by an optimized sucrose density gradient centrifugation, wherein the optimized sucrose gradient is provided such that the protamine can be completely or almost completely separated from the virus fraction; and wherein the protamine concentration is reduced by this step to the extent that the protamine concentration in the final drug substance is below 1 μg/ml, preferably below 0.5 μg/mL, more preferably below 0.1 μg/mL, most preferably below 0.05 μg/mL.

Q2. The process of Q2, wherein the virus particles are from Zika virus.

Q3. The process of Q1 or Q2, additionally comprising the step of:
(d) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles.

Q4. The process of any of Q1 to 3, wherein the residual host cell DNA of the virus preparation (c) is less than 10 ng/mL and the residual host cell protein of the final virus preparation (c) is less than 100 ng/mL.

Q5. The process of any of Q1 to 4, wherein the crude harvest (a) comprising virus particles and impurities is subjected to one or more pre-purification step(s) prior to step (b).

Q6. The process of Q5, wherein the one or more pre-purification step(s) comprises
(a) filtration using a filter having a pore size equal to or less than 0.2 μm; and/or
(b) digestion of host cell genomic DNA by enzymatic treatment; and/or
(c) ultra/diafiltration using a hollow fiber membrane having a pore size equal to or greater than 300 kDa, preferably equal to or greater than 100 kDa.

Q7. The process of any one of Q1 to 6, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml or 2 mg/ml.

Q8. The process of any one of Q1 to 7, wherein the enrichment of infectious virus particles in the virus preparation (c) or any final virus preparation relative to total virus products in the crude harvest (a) is in the range from at least 50% to 95%, preferably at least 80%.

Q9. The process of any one of Q5 to 8, wherein the one or more pre-purification step(s) prior to step (b) of any of Q5 to 8 is performed using a filter having a pore size equal to or less than 1 μm, preferably 0.2 μm.

Q10. The process of any one of Q1 to 9, wherein the residual impurity of the virus preparation (c) is less than 10%.

Q11. The process of any one of Q1 to 10, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

Q12. The process of Q11, wherein said cell line is a Vero cell line.

Q13. The process of any one of Q1 to 12, wherein the infectious virus particles is an infectious Zika virus particle that is a live virus, an attenuated live virus, a chimeric virus, a modified live virus, or a recombinant live virus.

Q14. The process of any one of Q1 to 13, wherein the Zika virus is a Zika virus strain of the Asian lineage or an immunogenic variant thereof.

Q15. The process of any one of Q1 to 14, wherein said process resulting in final virus preparation (c) or (d) is followed by an inactivation step, wherein the virus is inactivated preferably by formaldehyde.

Q16. Use of the process according to any one of Q1 to 15 for manufacturing a composition for immunization against a virus infection.

Q17. The use according to Q16, wherein the composition for immunization against a virus infection is an infection caused by Zika virus.

Q18. A composition comprising the virus particles obtainable or obtained by the process of any one of Q1 to 17 for treating and/or preventing an infection, such as e.g. a Zika virus infection.

Q19. A Zika virus vaccine comprising an inactivated Zika virus particle grown on vero cells, wherein the Zika virus particle is able to seroconvert a subject that is administered the Zika virus vaccine with at least a 70% probability and comprises minor amounts of protamine sulphate, preferably below the detection limit.

Q20. The Zika virus vaccine of Q19, wherein the Zika virus particle is able to seroconvert the subject that is administered the Zika virus vaccine with at least a 80%, 85%, 90%, or 95% probability, preferably a 80% probability.

Q21. The vaccine of Q19 or 20, wherein the Zika virus particle has a RNA genome corresponding to the DNA sequence provided by any one of the nucleic acid sequences of SEQ ID NOs: 2-13, or a variant nucleic acid sequence that is at least 88% identical to any one of SEQ ID NOs: 2-13 and able to pack a virulent Zika virus.

Q22. The vaccine of any of Q19, 20 and 21, wherein the Zika virus particle has an E protein selected from the amino acid sequences provided by any one of SEQ ID NOs:

14-69 or 72, or a variant amino acid sequence that is at least 95% identical to any one of SEQ ID NOs: 14-69 or 72 and able to pack a virulent Zika virus.

Q23. The vaccine of any one of Q19, 20 to 22, wherein the Zika virus obtained by culturing on Vero cells is purified by protamine sulfate precipitation and sucrose gradient centrifugation.

Q24. The vaccine of Q23, wherein the sucrose gradient centrifugation is an optimized sucrose gradient centrifugation.

Q25. The vaccine of Q24, wherein the optimized sucrose gradient centrifugation comprises a virus comprising fraction in a 10% (w/w) sucrose solution and three layers of sucrose with different densities, i.e. a first sucrose solution with 15% (w/w) sucrose solution, a second sucrose solution with 35% (w/w) sucrose solution, and a third sucrose solution with a 50% (w/w) sucrose solution.

Q26. The vaccine of any one of Q19, 20 to 25, wherein the Zika virus is inactivated by chemical inactivation, thermal inactivation, pH inactivation, or UV inactivation.

Q27. The vaccine of Q26, wherein the chemical inactivation comprises contacting the Zika virus with a chemical inactivation agent for longer than is required to completely inactivate the Zika virus as measured by plaque assay.

Q28. The vaccine of Q27, wherein the chemical inactivation comprises contacting the Zika virus with formaldehyde.

Q29. The vaccine of Q28, wherein the formaldehyde inactivation comprises contacting the Zika virus with formaldehyde for between 2-10 days.

Q30. The vaccine of any one of Q27-29, wherein the chemical activation is performed at about +4° C. or about +22° C.

Q31. The vaccine of any one of Q19 to 30, further comprising an adjuvant.

Q32. The vaccine of Q31, wherein the adjuvant is an aluminum salt adjuvant.

Q33. The vaccine of Q32, wherein the aluminum salt adjuvant is aluminium hydroxide or aluminium phosphate salt.

Q34. The vaccine of Q32, wherein the aluminum salt adjuvant is aluminium hydroxide with less than 1.25 ppb Cu based on the final pharmaceutical composition comprising the Zika virus, preferably the inactivated Zika virus.

Q35. The vaccine of any one of Q19 to 34, further comprising one or more pharmaceutically acceptable excipient.

R1. Use of protamine, preferably a protamine salt, to separate infectious and non-infectious Zika virus particles, host cell proteins and/or undefined low molecular weight materials.

R2. A process of purification of infectious Zika virus particles, comprising the steps of:
 (a) providing a crude harvest (a) comprising Zika virus particles and impurities, wherein the impurities are generated from growing said virus particles on a cell substrate;
 (b) reducing impurities from the crude harvest (a) by precipitation with an agent comprising protamine, preferably a protamine salt, more preferably a protamine sulphate, even more preferably a recombinant protamine sulphate, to obtain a virus preparation (b), wherein the enrichment of infectious virus particles in the virus preparation (b) relative to total virus products in the crude harvest (a) is in the range from at least 50% to 95%, preferably at least 80%.

R3. The use of R1 or the process of R2, wherein the virus particles are from Zika virus.

R4. A process of purification of infectious Zika virus particles, comprising the steps of:
 (a) providing a crude harvest (a) comprising Zika virus particles and impurities, wherein the impurities are generated from growing said virus particles on a cell substrate;
 (b) reducing impurities from the crude harvest (a) by precipitation with an agent comprising protamine, preferably a protamine salt, more preferably a protamine sulphate, even more preferably a recombinant protamine sulphate, to obtain a virus preparation (b);
 (c) further purifying the virus preparation (b) by one or more size exclusion methods such as (i) a sucrose density gradient centrifugation, (ii) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles, and/or (iii) size exclusion chromatography to obtain a virus preparation (c) comprising the infectious virus particles, wherein the residual host cell DNA of the virus preparation (c) is less than 100 ng/mL and the residual host cell protein and the residual aggregates of infectious virus particles of the final virus preparation (c) is less than 1 µg/mL.

R5. The process of R4, wherein the residual host cell DNA of the virus preparation (c) is less than ng/mL and the residual host cell protein of the final virus preparation (c) is less than 100 ng/mL.

R6. The process of any of R2 to 5, wherein the crude harvest (a) comprising virus particles and impurities is subjected to one or more pre-purification step(s) prior to step (b).

R7. The process of R6, wherein the one or more pre-purification step(s) comprises
 (a) filtration using a filter having a pore size equal to or less than 0.2 µm; and/or
 (b) digestion of host cell genomic DNA by enzymatic treatment; and/or
 (c) ultra/diafiltration using a hollow fiber membrane having a pore size equal to or greater than 300 kDa, preferably equal to or greater than 100 kDa.

R8. The process of any one of R2 to 7, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml.

R9. The process of any one of R2 to 8, wherein the enrichment of infectious virus particles in the virus preparation (c) or any final virus preparation relative to total virus products in the crude harvest (a) is in the range from at least 50% to 95%, preferably at least 80%.

R10. The process of any one of R6 to 9, wherein the one or more pre-purification step(s) prior to step (b) of any of R6 to 9 is performed using a filter having a pore size equal to or less than 1 µm, preferably 0.2 µm.

R11. The process of any one of R2 to 10, wherein the residual impurity of the virus preparation (c) is less than 10%.

R12. The process of any one of R2 to 11, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

R13. The process of R12, wherein said cell line is a Vero cell line.

R14. The process of any one of R2 to 13, wherein the Zika virus is a live virus, an attenuated live virus, a chimeric virus, a modified live virus, or a recombinant live virus.

R15. The process of any one of R2 to 14, wherein the Zika virus is a Zika virus strain of the Asian lineage or an immunogenic variant thereof.

R16. The process of any one of R2 to 15, wherein said process resulting in final virus preparation (c) is followed by an inactivation step, wherein the virus is inactivated preferably by formaldehyde.

R17. Use of the process according to any one of R1 to 16 for manufacturing a composition for immunization against a virus infection.

R18. The use according to R17, wherein the composition for immunization against a virus infection is an infection caused by a Zika virus.

R19. A composition comprising the virus particles obtainable or obtained by the process of any one of R2 to 16 for treating and/or preventing an infection.

What is claimed is:

1. A Zika virus vaccine comprising a Zika virus having an RNA genome corresponding to the DNA sequence provided by SEQ ID NO: 4 or a variant nucleic acid having at least 99% identity to SEQ ID NO: 4, wherein the sequence identity is determined by Needleman-Wunsch homology alignment, wherein said Zika virus vaccine is capable of stimulating a neutralizing antibody titer greater than 15 in at least 70% of vaccinated subjects, wherein the neutralizing antibody titer is determined using a microneutralization assay (MN50) following a single administration of the Zika virus vaccine to a subject;
   wherein the Zika virus comprises an E protein having an amino acid sequence provided by SEQ ID NO: 47; and
   wherein the Zika virus is Vero cell adapted and is able to pack a virulent Zika virus.

2. The Zika virus vaccine of claim 1, wherein the RNA genome corresponds to the DNA sequence provided by SEQ ID NO: 4.

3. The Zika virus vaccine of claim 1, wherein the variant nucleic acid has at least 99.5% identity to SEQ ID NO: 4, wherein the sequence identity is determined by Needleman-Wunsch homology alignment.

4. The Zika virus vaccine of claim 1, wherein said MN50 is greater than 20.

5. The Zika virus vaccine of claim 1, wherein said MN50 is greater than 30.

6. The Zika virus vaccine of claim 1, wherein said MN50 is greater than 40.

7. The Zika virus vaccine of claim 1, wherein said MN50 is greater than 50.

8. The Zika virus vaccine of claim 1, wherein said MN50 is greater than 60.

9. The Zika virus vaccine of claim 1, wherein said MN50 is greater than 70.

10. The Zika virus vaccine of claim 1, wherein said MN50 is greater than 80.

11. The Zika virus vaccine of claim 1, wherein said MN50 is greater or equal to 90.

12. The Zika virus vaccine of claim 1, wherein the Zika virus vaccine is capable of stimulating a MN50 titer greater than 15 in at least 80% of vaccinated subjects.

13. The Zika virus vaccine of claim 1, wherein the Zika virus vaccine is capable of stimulating a MN50 titer greater than 15 in at least 90% of vaccinated subjects.

14. The Zika virus vaccine of claim 1, wherein the Zika virus vaccine is capable of stimulating a MN50 titer greater than 15 in at least 95% of vaccinated subjects.

15. The Zika virus vaccine of claim 1, wherein the Zika virus vaccine is capable of stimulating a MN50 titer greater than 15 in at least 99% of vaccinated subjects.

16. The Zika virus vaccine of claim 1, wherein the Zika virus is inactivated by chemical inactivation, thermal inactivation, pH inactivation, or UV inactivation.

17. The Zika virus vaccine of claim 16, wherein the chemical inactivation comprises contacting the Zika virus with a chemical inactivation agent for longer than is required to completely inactivate the Zika virus as measured by plaque assay.

18. The Zika virus vaccine of claim 16, wherein the chemical inactivation comprises contacting the Zika virus with formaldehyde.

19. The Zika virus vaccine of claim 18, wherein the chemical inactivation comprises contacting the Zika virus with formaldehyde for between 2-10 days.

20. The Zika virus vaccine of claim 18, wherein the chemical activation is performed at about +4° C. or about +22° C.

21. The Zika virus vaccine of claim 1, further comprising an adjuvant.

22. The Zika virus vaccine of claim 21, wherein the adjuvant is an aluminium salt adjuvant.

23. The Zika virus vaccine of claim 22, wherein said aluminium salt adjuvant is aluminium hydroxide with less than 1.25 parts per billion copper based on a final pharmaceutical composition comprising the Zika virus.

24. The Zika virus vaccine of claim 21, wherein the adjuvant comprises a peptide and a deoxyinosine-containing immunostimulatory oligodeoxynucleic acid molecule (I-ODN).

25. The Zika virus vaccine of claim 24, wherein the peptide comprises the sequence KLKL$_5$KLK (SEQ ID NO: 71) and the I-ODN comprises oligo-d(IC)$_{13}$ (SEQ ID NO: 70).

26. The Zika virus vaccine of claim 1, further comprising one or more pharmaceutically acceptable excipients.

27. The Zika virus vaccine of claim 1, wherein the vaccine comprises protamine sulphate (PS) or fragments or break-down products of PS at amounts below the limits of detection by high performance liquid chromatography (HPLC).

28. The Zika virus vaccine of claim 27, wherein said PS or fragments or break-down products of PS are detectable by mass spectroscopy.

29. The Zika virus vaccine of claim 1, wherein the vaccine comprises protamine sulphate (PS) or fragments or break-down products of PS at amounts below 1 μg/mL or below 100 ng/mL.

30. The Zika virus vaccine of claim 1, further comprising a TLR9 agonist.

31. A Zika virus vaccine comprising a Zika virus having an RNA genome corresponding to a DNA sequence having at least 99.9% identity to SEQ ID NO: 4, wherein the sequence identity is determined by Needleman-Wunsch homology alignment, wherein said Zika virus vaccine is capable of stimulating a neutralizing antibody titer greater than 15 in at least 70% of vaccinated subjects, wherein the neutralizing antibody titer is determined using a microneutralization assay (MN50) following a single administration of the Zika virus vaccine to a subject;
wherein the Zika virus comprises an E protein having an amino acid sequence provided by SEQ ID NO: 47; and
wherein the Zika virus is Vero cell adapted and is able to pack a virulent Zika virus.

32. The Zika virus vaccine of claim 31, wherein said MN50 is greater than 20.

33. The Zika virus vaccine of claim 31, wherein said MN50 is greater than 30.

34. The Zika virus vaccine of claim 31, wherein said MN50 is greater than 40.

35. The Zika virus vaccine of claim 31, wherein said MN50 is greater than 50.

36. The Zika virus vaccine of claim 31, wherein said MN50 is greater than 60.

37. The Zika virus vaccine of claim 31, wherein said MN50 is greater than 70.

38. The Zika virus vaccine of claim 31, wherein said MN50 is greater than 80.

39. The Zika virus vaccine of claim 31, wherein said MN50 is greater or equal to 90.

40. The Zika virus vaccine of claim 31, wherein the Zika virus vaccine is capable of stimulating a MN50 titer greater than 15 in at least 80% of vaccinated subjects.

41. The Zika virus vaccine of claim 31, wherein the Zika virus vaccine is capable of stimulating a MN50 titer greater than 15 in at least 90% of vaccinated subjects.

42. The Zika virus vaccine of claim 31, wherein the Zika virus vaccine is capable of stimulating a MN50 titer greater than 15 in at least 95% of vaccinated subjects.

43. The Zika virus vaccine of claim 31, wherein the Zika virus vaccine is capable of stimulating a MN50 titer greater than 15 in at least 99% of vaccinated subjects.

44. The Zika virus vaccine of claim 31, wherein the Zika virus is inactivated by chemical inactivation, thermal inactivation, pH inactivation, or UV inactivation.

45. The Zika virus vaccine of claim 44, wherein the chemical inactivation comprises contacting the Zika virus with a chemical inactivation agent for longer than is required to completely inactivate the Zika virus as measured by plaque assay.

46. The Zika virus vaccine of claim 44, wherein the chemical inactivation comprises contacting the Zika virus with formaldehyde.

47. The Zika virus vaccine of claim 46, wherein the chemical inactivation comprises contacting the Zika virus with formaldehyde for between 2-10 days.

48. The Zika virus vaccine of claim 46, wherein the chemical activation is performed at about +4° C. or about +22° C.

49. The Zika virus vaccine of claim 31, further comprising an adjuvant.

50. The Zika virus vaccine of claim 49, wherein the adjuvant is an aluminium salt adjuvant.

51. The Zika virus vaccine of claim 50, wherein said aluminium salt adjuvant is aluminium hydroxide with less than 1.25 parts per billion copper based on a final pharmaceutical composition comprising the Zika virus.

52. The Zika virus vaccine of claim 49, wherein the adjuvant comprises a peptide and a deoxyinosine-containing immunostimulatory oligodeoxynucleic acid molecule (I-ODN).

53. The Zika virus vaccine of claim 52, wherein the peptide comprises the sequence $KLKL_5KLK$ (SEQ ID NO: 71) and the I-ODN comprises oligo-d(IC)$_{13}$ (SEQ ID NO: 70).

54. The Zika virus vaccine of claim 31, further comprising one or more pharmaceutically acceptable excipients.

55. The Zika virus vaccine of claim 31, wherein the vaccine comprises protamine sulphate (PS) or fragments or break-down products of PS at amounts below the limits of detection by high performance liquid chromatography (HPLC).

56. The Zika virus vaccine of claim 55, wherein said PS or fragments or break-down products of PS are detectable by mass spectroscopy.

57. The Zika virus vaccine of claim 31, wherein the vaccine comprises protamine sulphate (PS) or fragments or break-down products of PS at amounts below 1 μg/mL or below 100 ng/mL.

58. The Zika virus vaccine of claim 31, further comprising a TLR9 agonist.

* * * * *

SEQUENCE LISTING

```
Sequence total quantity: 117
SEQ ID NO: 1            moltype = AA  length = 32
FEATURE                 Location/Qualifiers
REGION                  1..32
                        note = synthetic peptide
source                  1..32
                        mol_type = protein
                        organism = synthetic construct
SEQUENCE: 1
PRRRRSSSRP VRRRRRPRVS RRRRRRGGRR RR                                  32

SEQ ID NO: 2            moltype = DNA  length = 10676
FEATURE                 Location/Qualifiers
source                  1..10676
                        mol_type = genomic DNA
                        organism = Zika virus
SEQUENCE: 2
gttgttactg ttgctgactc agactgcgac agttcgagtt tgaagcgaaa gctagcaaca    60
gtatcaacag gttttatttg gatttggaaa cgagagtttc tggtcatgaa aaacccaaaa   120
aagaaatccg gaggattccg gattgtcaat atgctaaaac gcggagtagc ccgtgtgagc   180
ccctttgggg gcttgaagag gctgccagcc ggacttctgc tgggtcatgg gcccatcagg   240
atggtcttgg caattctagc ctttttgaga ttcacggcaa tcaagccatc actgggtctc   300
atcaatagat ggggttcagt ggggaaaaaa gaggctatgg aaataataaa gaagttcaag   360
aaagatctgg ctgccatgct gagaataatc aatgctagga aggagaagaa gagacggggc   420
gcagatacta gtgtcggaat tgttggcctc ctgctgacca cagctatggc agcggaggtc   480
actagacgtg ggagtgcata ctatatgtac ttggacagaa acgatgctgg ggaggccata   540
tcttttccaa ccacattggg gatgaataag tgttatatac agatcatgga tcttggacac   600
atgtgtgatg ccaccatgag ctatgaatgc cctatgctgg atgaggggt ggaaccagat   660
gacgtcgatt gttggtgcaa cacgacgtca acttgggttg tgtacggaac ctgccatcac   720
aaaaaaggtg aagcacggag atctagaaga gctgtgacgc tcccctccca ttccactagg   780
aagctgcaaa cgcggtcgca aacctggttg gaatcaagag aatacacaaa gcacttgatt   840
agagtcgaaa attggatatt caggaaccct ggcttcgcgt tagcagcagc tgccatcgct   900
tggcttttgg gaagctcaac gagccaaaaa gtcatatact tggtcatgat actgctgatt   960
gccccggcat acagcatcag gtgcatagga gtcagcaata gggactttgt ggaaggtatg  1020
tcaggtggga cttgggttga tattgtcttg gaacatggag gttgtgtcac cgtaatggca  1080
caggacaaac cgactgtcga catagagctg gttacaacaa cagtcagcaa catggcggag  1140
gtaagatcct actgctatga ggcatcaata tcagacatgg cttcggacag ccgctgccca  1200
acacaaggtg aagcctacct tgacaagcaa tcagacactc aatatgtctg caaaagaacg  1260
ttagtggaca gaggctgggg aaatggatgt ggactttttg gcaaagggag tctggtgaca  1320
tgcgctaagt ttgcatgctc caagaaaatg accgggaaga catccagcc agagaatctg  1380
gagtaccgga taatgctgtc agttcatggc tcccagcaca gtgggatgat cgttaatgac  1440
acaggacatg aaactgatga gaatagacg aaggttgaga taacgcccaa ttcaccaaga  1500
gccgaagcca ccctgggggg ttttggaagc ctaggactt attgtgaacc gaggacaggc  1560
cttgactttt cagatttgta ttacttgact atgaataaca agcactggtt ggttcacaag  1620
gagtggttcc acgacattcc attaccttgg cacgctgggg cagacaccgg aactccacac  1680
tggaacaaca agaagcact ggtagagttc aaggacgcac atgccaaaag gcaaactgtc  1740
gtggttctag ggagtcaaga aggagcagtt cacacgccc ttgctggagc tctggaggct  1800
gagatggatg gtgcaaaggg aaggctgtcc tctgccact tgaaatgtcg cctgaaaatg  1860
gataaactta gattgaaggg cgtgtcatac tccttgtgta ccgcagcgtt cacattcacc  1920
aagatcccgg ctgaaacact gcacgggaca gtcacagtgg aggtacagta cgcagggaca  1980
gatggacctt gcaaggttcc agctcagatg gcggtggaca tgcaaactct gacccagtt  2040
gggaggttga taaccgctaa ccccgtaatc actgaaagca ctgagaactc taagatgatg  2100
ctggaacttg atccaccatt tggggactct tacattgtca taggagtcgg ggagaagaag  2160
atcacccacc actggcacag gagtggcagc accattgaa aagcatttga agccactgtg  2220
agaggtgcca agaaatggc agtcttggga gacacagcct gggactttgg atcagttgga  2280
ggcgctctca actcattggg caagggcatc catcaaattt ttggagcagc tttcaaatca  2340
ttgtttggag gaatgtcctg gttctcacaa attctcattg gaacgttgct gatgtggttg  2400
ggtctgaaca caagaatgg atctatttcc cttatgtgct tggccttagg gggagtgttg  2460
atcttcttat ccacagccgt ctctgctgat gtgggtgct cggtggactt ctcaaagaag  2520
gagacgagat gcggtacagg ggtgttcgtc tataacgacg ttgaagcctg agggacagg  2580
tacaagtacc atcctgactc cccccgtaga ttggcagcag cagtcaagca agcctgggaa  2640
```

```
gatggtatct gcgggatctc ctctgtttca agaatggaaa acatcatgtg gagatcagta  2700
gaaggggagc tcaacgcaat cctggaagag aatggagttc aactgacggt cgttgtggga  2760
tctgtaaaaa accccatgtg gagaggtcca cagagattgc ccgtgcctgt gaacgagctg  2820
ccccacggct ggaaggcttg ggggaaatcg cacttcgtca gagcagcaaa gacaaataac  2880
agctttgtcg tggatggtga cacactgaag gaatgcccac tcaaacatag agcatggaac  2940
agctttcttg tggaggatca tgggttcggg gtatttcaca ctagtgtctg gctcaaggtt  3000
agagaagatt attcattaga gtgtgatcca gccgttattg gaacagctgt taagggaaag  3060
gaggctgtac acagtgatct aggctactgg attgagagtg agaagaatga cacatggagg  3120
ctgaagaggg cccatctgat cgagatgaaa acatgtgaat ggccaaagtc ccacacattg  3180
tggacagatg gaatagaaga gagtgatctg atcatacccc agtctttagc tgggccactc  3240
agccatcaca ataccagaga gggctacagg acccaaatga aagggccatg gcacagtgaa  3300
gagcttgaaa ttcggtttga ggaatgccca ggcactaagg tccacgtgga ggaaacatgt  3360
ggaacaagag gaccatctct gagatcaacc actgcaagcg aagggtgat cgaggaatgg  3420
tgctgcaggga agtgcacaat gcccccactg tcgttccggg ctaaagatgg ctgttggtat  3480
ggaatggaga taaggcccag gaaagaacca gaaagcaact tagtaaggtc aatggtgact  3540
gcaggatcaa ctgatcacat ggatcacttc tcccttggag tgcttgtgat tctgctcatg  3600
gtgcaggaag ggctgaagaa gagaatgacc acaaagatca tcataagcac atcaatggca  3660
gtgctggtag ctatgatcct gggaggattt tcaatgagtg acctggctaa gcttgcaatt  3720
ttgatgggtg ccaccttcgc ggaaatgaac actggaggag atgtagctca tctggcgctg  3780
atagcggcat tcaaagtcag accagcgttg ctggtatctt tcatcttcag agctaattgg  3840
acaccccgtg aaagcatgct gctggccttg gcctcgtgtc ttttgcaaac tgcgatctcc  3900
gccttggaag gcgacctgat ggttctcatc aatggttttg ctttggcctg gttggcaata  3960
cgagcgatgg ttgttccacg cactgataac atcaccttgg caatcctggc tgctctgaca  4020
ccactggccc ggggcacact gcttgtggcg tggagagcag gccttgctac ttgcgggggg  4080
tttatgctcc tctctctgaa gggaaaaggc agtgtgaaga agaacttacc atttgtcatg  4140
gccctgggac taaccgctgt gaggctggtc gaccccatca acgtggtggg gctgctgttg  4200
ctcacaagga gtgggaagcg gagctggccc cctagcgaag tactcacagc tgttggcctg  4260
atatgcgcat tggctggagg gttcgccaag gcagatatag agatgctgg gcccatggcc  4320
gcggtcggtc tgctaattgt cagttacgtg gtctcaggaa agagtgtgga catgtacatt  4380
gaaagagcag gtgacatcac atgggaaaaa gatgcggaag tcactcccca gg  4440
ctcgatgtgg cgctagatga gagtggtgat ttctccctgg tggaggatga cggtcccccc  4500
atgagagaga tcatactcaa ggtggtcctg atgaccatct gtggcatgaa cccaatagcc  4560
ataccctttg cagctggagc gtggtacgta tacgtgaaga ctggaaaaag gagtggtgct  4620
ctatgggatg tgcctgctcc caaggaagta aaaaaggggg agaccacaga tggagtgtac  4680
agagtaatga ctcgtagact gctaggttca acacaagttg gagtgggagt tatgcaagag  4740
ggggtctttc acactatgtg gcacgtcaca aaaggatccg cgctgagaag cggtgaaggg  4800
agacttgatc catactgggg agatgtcaag caggatctgg tgtcatactg tggtccatgg  4860
aagctagatg ccgcctggga cgggcacagc gaggtgcagc tcttggccgt gcccccgga  4920
gagagagca ggaacatcca gactctgccc ggaatattta agcaaaggta tgggacatt  4980
ggagcggttg cgctggatta cccagcagga acttcaggat ctccaatcct agacaagtgt  5040
gggagagtga taggactta tggcaatggg gtcgtgatca aaaatgggag ttatgttagt  5100
gccatcaccc aagggaggag ggaggaagag actcctgttg agtgcttcga gccttcgatg  5160
ctgaagaaga agcagctaac tgtcttagac ttgcatcctg gagctgggaa aaccaggaga  5220
gttcttcctg aaatagtccg tgaagccata aaaacaagac tccgtactgt gatcttagct  5280
ccaaccaggg ttgtcgctgc tgaaatggag gaagcctta gagggcttcc agtgcgttat  5340
atgacaacag cagtcaatgt cacccactct ggaacagaaa tcgtcgactt aatgtgccat  5400
gccaccttca cttcacgtct actacagcca atcagagtcc ccaactataa tctgtatatt  5460
atggatgagg cccacttcac agatcccctca agtatagcag caagaggata catttcaaca  5520
agggttgaga tgggcgaggc ggctgccatc ttcatgaccg ccacgccacc aggaacccgt  5580
gacgcatttc cggactccaa ctcaccaatt atggacaccg aagtggaagt cccagagaga  5640
gcctggagct caggcttga ttgggtgacg gattattctg gaaaaacagt ttggtttgtt  5700
ccaagcgtga ggaacggcaa tgagatcgca gcttgtctga caaaggctgg aaaacgggtc  5760
atacagctca gcagaaagac ttttgagaca gagttccaga aaacaaaaca tcaagagtgg  5820
gactttgtcg tgacaactga catttcagag atgggcgcca actttaaagc tgaccgtgtc  5880
atagattcca ggagatgcct aaagccggtc atacttgatg gagagaggt cattctggct  5940
ggacccatgc ctgtcacaca tgccagcgct gcccagagga ggggcgcat aggcaggaat  6000
cccaacaaac ctgagatga gtatctgtat ggaggtgggt gcgcagagac tgacgaagac  6060
catgcacact ggcttgaagc aagaatgctc cttgacaata tttacctcca agatggcctc  6120
atagcctcgc tctatcgacc tgaggccgac aaagtagcag ccattgaggg agagttcaag  6180
cttaggacga gcaaaggaa gaccttttgt gaactcatga aaagaggaga tcttcctgtt  6240
tggctgccct atcaggttgc atctgccgga ataacctaca cagatagaag atggtgcttt  6300
gatggcacga ccaacaacac cataatgaa gacagtgtgc cggcagaggt gtggaccaga  6360
cacggagaga aaagagtgct caaaccgagg tggatggacg ccagagtttg ttcagatcat  6420
gcggccctga gtcattcaa ggagtttgcc gctgggaaa gaggagcgc ttttggagtg  6480
atggaagccc tgggaacact gccaggacac atgacagaga gattccagga agccattgac  6540
aacctcgctg tgctcatgcg ggcagagact ggaagcaggc cttacaaagc cgcggcggcc  6600
caattgccga gaccctaga gaccattatg ctttttgggt tgctgggaac agtctcgctg  6660
ggaatctttt tcgtcttgat gaggaacaag gcataggga agatgggctt tggaatggtg  6720
actcttgggg ccagcgcaat gctcatgtgg ctctcggaaa ttgagccagc cagaattgca  6780
tgtgtcctca ttgttgtgtt cctattgctg gtggtgctca tacctgagcc agaaaagcaa  6840
agatctcccc aggacaacca aatggcaatc atcatcatgg tagcagtagg tcttctgggc  6900
ttgattaccg ccaatgaact cggatggttg gagagaacaa agagtgacct aagccatcta  6960
atgggaagga gagaggaggg ggcaaccatg ggattctcaa tggacattga cctgcggcca  7020
gcctcgccct gggcatcta tgctgcctta acaacttca ttaccccagc cgtccaacat  7080
gcagtgacca cttcatacaa caactactcc ttaatggcga tggccacgca agctggagtg  7140
ttgtttggta tgggcaaagg gatgccattc tacgcatggg actttggagt cccgctgcta  7200
atgataggtt gctactcaca attaacgccc ctgaccctaa tagtggccat cattttgctc  7260
gtggcgcact acatgtactt gatcccaggg ctgcaggcag cagctgcgcg tgctgcccag  7320
aagagaacgg cagctggcat catgaagaac cctgttgtgg atggaatagt ggtgactgac  7380
```

```
attgacacaa tgacaattga cccccaagtg gagaaaaaga tgggacaggt gctactcatg   7440
gcagtagccg tctccagcgc catactgtcg cggaccgcct gggggtgggg ggaggctggg   7500
gccctgatca cagccgcaac ttccactttg tgggaaggct ctccgaacaa gtactggaac   7560
tcctctacag ccacttcact gtgtaacatt tttaggggaa gttacttggc tggagcttct   7620
ctaatctaca cagtaacaag aaacgctggc ttggtcagga gacgtggggg tggaacagga   7680
gagaccctgg gagagaaatg gaaggcccgc ttgaaccaga tgtcggccct ggagttctac   7740
tcctacaaaa agtcaggcat caccgaggtg tgcagagaag aggcccgccg cgccctcaag   7800
gacggtgtgg caacgggagg ccatgctgtg tcccgaggaa gtgcaaagct gagatggttg   7860
gtggagcggg gatacctgca gccctatgga aaggtcattg atcttggatg tggcagaggg   7920
ggctggagtt actacgccgc caccatccgc aaagttcaag aagtgaaagg atacacaaaa   7980
ggaggccctg gtcatgaaga acccgtgttg gtgcaaagct atgggtggaa catagtccgt   8040
cttaagagtg gggtggacgt cttttcatatg gcggctgagc cgtgtgacac gttgctgtgt   8100
gacataggtg agtcatcatc tagtcctgaa gtggaagaag cacggacgct cagagtcctc   8160
tccatggtgg gggattggct tgaaaaaaga ccaggagcct tttgtataaa agtgttgtgc   8220
ccatacacca gcactatgat ggaaaccctg gagcgactgc agcgtaggta tgggggagga   8280
ctggtcagag tgccactctc ccgcaactct acacatgaga tgtactgggt ctctggagcg   8340
aaaagcaaca ccataaaaag tgtgtccacc acgagccagc tcctcttggg gcgcatggac   8400
gggcctagga ggccagtgaa atatgaggag gatgtgaatc tcggctctgg cacgcgggct   8460
gtggtaagct gcgctgaagc tcccaacatg aagatcattg gtaaccgcat tgaaaggatc   8520
cgcagtgagc acgcggaaac gtggttcttt gacgagaacc acccatatag gacatgggct   8580
taccatggaa gctatgaggc ccccacacaa gggtcagcgt cctctctaat aaacggggtt   8640
gtcaggctcc tgtcaaaacc ctgggatgtg gtgactggag tcacaggaat agccatgacc   8700
gacaccacac cgtatggtca gcaaagagtt ttcaaggaaa aagtggacac tagggtgcca   8760
gacccccaag aagtactcgt caggttatg agcatggtct cttcctggtt gtggaaagag   8820
ctaggcaaac acaaacggcc acgagtctgt accaaagaag agttcatcaa caaggttcgt   8880
agcaatgcag cattagggc aatatttgaa gaggaaaaag agtggaagac tgcagtggaa   8940
gctgtgaacg atccaaggtt ctgggctcta gtggacaagg aaagagagca ccacctgaga   9000
ggagagtgcc agagttgtgt gtacaacatg atgggaaaaa gagaaaagaa acaagggaa   9060
tttggaaagg ccaagggcag ccgcgccatc tggtatatgt ggctaggggc tagatttcta   9120
gagttcgaag cccttggatt cttgaacgag gatcactgga tgggaagaga gaactcagga   9180
ggtggtgttg aagggctggg attacaaaga ctcggatatg tcctagaaga gatgagtcgc   9240
ataccaggag gaaggatgta tgcagatgac actgctggct gggacacccg catcagcagg   9300
tttgatctgg agaatgaagc tctaatcacc aaccaaatgg agaaagggca gggccttg   9360
gcattggcca taatcaagta cacataccaa aacaaagtgt taaaggtcct tagaccagct   9420
gaaaaaggga aaacagttat ggacattatt tcgagacaag accaagggg gagcggacaa   9480
gttgtcactt acgctcttaa cacatttacc aacctagtgg tgcaactcat tcggaatatg   9540
gaggctgagg aagtcctaga gatgcaagac ttgtggctgc tgcggaggtc agagaaagtg   9600
accaactggt tgcagagcaa cggatgggat aggctcaaac gaatggcagt cagtggagat   9660
gattgcgttg tgaagccaat tgatgataggt tttgcacatg ccctcaggtt cttgaatgat   9720
atgggaaaag ttaggaagga cacacaagag tggaaaccct caactgatg ggacaactgg   9780
gaagaagttc cgttttgctc ccaccacttc aacaagctcc atctcaagga cgggaggtcc   9840
attgtggttc cctgccgcca ccaagatgaa ctgattggcc gggcccgcgt ctctccaggg   9900
gcgggatgga gcatccggga gactgcttgc tagcaaaat catatgcgca aatgtggcag   9960
ctccttttatt tccacagaag ggacctccga ctgatggcca atgccatttg ttcatctgtg  10020
ccagttgact gggttccaac tgggagaact acctggtcaa tccatggaaa gggagaatgg  10080
atgaccactg aagacatgct tgtggtgtgg aacagagtgt ggattgagga gaacgaccac  10140
atggaagaca agaccccagt tacgaaatgg acagacattc cctatttggg aaaaagggaa  10200
gacttgtggt gtgagaatct catagggcac agaccgcgca ccacctgggc tgagaacatt  10260
aaaaacacag tcaacatggt gcgcaggatc ataggtgatg aagaaaagta catggactac  10320
ctatccaccc aagttcgcta cttgggtgaa gaagggtcta cacctggagt gctgtaagca  10380
ccaatcttaa tgttgtcagg cctgctagtc agccacagct tggggaaagc tgtgcagcct  10440
gtgacccccc caggagaagc tgggaaacca agcctatagt caggccgaga acgccatggc  10500
acggaagaag ccatgctgcc tgtgagcccc tcagaggaca ctgagtcaaa aaccccacg  10560
cgcttggagg cgcaggatgg gaaaagaagg tggcgacctt cccccacctt caatctgggg  10620
cctgaactgg agatcagctg tggatctcca gaagagggac tagtggttag aggaga      10676
```

```
SEQ ID NO: 3            moltype = DNA   length = 10793
FEATURE                 Location/Qualifiers
source                  1..10793
                        mol_type = genomic DNA
                        organism = Zika virus
SEQUENCE: 3
ccaatctgtg aatcagactg cgacagttcg agtttgaagc gaaagctagc aacagtatca   60
acaggtttta ttttggattt ggaaacgaga gtttctgtc atgaaaaacc caaaaaagaa  120
atccggagga ttccggattg tcaatatgct aaaacgcgga gtagccgtg tgagcccctt  180
tgggggcttg aagaggctgc cagccggact tctgctgggt catgggccca tcaggatggt  240
cttggcgatt ctagcctttt tgagattcac ggcaatcaag ccatcactgg gtctcatcaa  300
tagatggggt tcagtgggga aaaagaggc tatggaaata ataaagaagt tcaagaaa  360
tctggctgcc atgctgagaa taatcaatgc caggaaggaa aagaagac gaggcgcaga  420
tactagtgtc ggaatcgttg gcctcctgct gaccacagct atggcagcgg aggtcactag  480
acgtgggagt gcatactata tgtacttgga cagaaacgat gctggggagg ccatatcttt  540
tccaaccaca ttggggatga taagtgttta tacagatc atggatcttg acacatgtg  600
tgatgccacc atgagctatg aatgcccat gctggatgag gggtggaac cagatgacgt  660
tgattgttg tgcaacacga cgtcaacttg gtttgtgtac ggaacctgcc atcacaaaa  720
aggtgaagca cggagatcta aagagctgt gacgctcccc tcccattcca ctaggaagct  780
gcaaacgcgg tcgcaaacct ggttggaatc aagagaatac acaaagcact tgattagagt  840
cgaaaattgg atattcagga accctggctt cgcgttagca gcagctgcca tcgcttggct  900
tttgggaagc tcaacgagcc aaaaagtcat atacttggtc atgatactgc tgattgcccc  960
ggcatacagc atcaggtgca taggagtcag caatagggac tttgtggaag gtatgtcagg 1020
```

```
tgggacttgg gttgatgttg tcttggaaca tgggggttgt gtcaccgtaa tggcacagga   1080
caaaccgact gtcgacatag agctggttac aacaacagtc agcaacatgg cggaggtaag   1140
atcctactgc tatgaggcat caatatcaga catggcttcg gacagccgct gcccaacaca   1200
aggtgaagcc taccttgaca agcaatcaga cactcaatat gtctgcaaaa gaacgttagt   1260
ggacagaggc tggggaaatg gatgtggact ttttgggagc ctgg tgacatgcgc        1320
taagtttgca tgctccaaga aaatgaccgg gaagagcatc cagccagaga atctggagta   1380
ccggataatg ctgtcagttc atggctccca gcacagtggg atgatcgtta atgcacagg    1440
acatgaaact gatgagaata gagcgaaggt tgagataacg cccaattcac caagagccga   1500
agccaccctg gggggttttg gaagcttagg acttgattgt gaaccgagga caggccttga   1560
cttttcagat ttgtattact tgactatgaa taacaagcac tggttggttc acaaggagtg   1620
gttccacgac attccattac cttggcacgc tggggcagac accggaactc cacactggaa   1680
caacaaagaa gcactggtag agttcaagga cgcacatgcc aaaaggcaaa ctgtcgtggt    1740
tctagggact caagaaggag cagttcacac ggcccttgct ggagctctgg aggctgagat   1800
ggatggtgca aagggaaggc tgtcctctgg ccacttgaaa tgtcgcctga aatgataa     1860
acttagattg aagggcgtgt catactcctt gtgtaccgca gcgttcacat tcaccaagat   1920
cccggctgaa acactgcacg ggacagtcac agtggaggta cagtacgcag ggacagatgg   1980
accttgcaag gttccagctc agatggcggt ggacatgcaa actctgaccc cagttgggag   2040
gttgataacc gctaacccgg taatcactga aagcactgga aactctaaga tgatgctgga   2100
acttgatcca ccatttgggg actcttacat tgtcatagga gtcggggaga agaagatcac   2160
ccaccactgg cacaggagtg gcagcaccat tggaaaagca tttgaagcca ctgtgagagg   2220
tgccaagaga atggcagtct tgggagacac agcctggac tttggatcag ttggaggcgc    2280
tctcaactca ttgggcaagg gcatccatca aatttttgga gcagctttca atcattgtt   2340
tggaggaatg tcctggttct cacaaattct cattggaacg ttgctgatgt ggttgggtct   2400
gaacacaaag aatggatcta tttcccttat gtgcttggcc ttaggggagt gttgatctt    2460
cttatccaca gccgtctctg ctgatgtggg gtgctcggtg gacttctcaa agaaggagac   2520
gagatgtggt acagggtgt tcgtctataa cgacgttgaa gcctgaaggg acaggtacaa    2580
gtaccatcct gactctcccc gtagattggc agcagcagtc aagcaagcct gggaagatgg   2640
tatctgcggg atctcctctg tttcaagaat ggaaaacatc atgtgagat cagtagaagg    2700
ggagcttaac gcaatcctgg aagagaatgg agttcaactg acggtcgttg tgggatctgt   2760
aaaaaacccc atgtggagag gtcccacagag attgcccgtg cctgtgaacg agctgcccca   2820
cggctgaaag gcttggggga aatcgtactt cgtcagagca gcaaagacaa ataacagctt   2880
tgtcgtggat ggtgacacac tgaaggaatg cccactcaaa catagagcat ggaacagctt    2940
tcttgtggag gatcatgggt tcggggtatt tcacactagt gtctggctca aggttagaga   3000
agattattca ttagagtgtg atccagccgt tattggaaca gctgttaagg gaaaggaggc   3060
tgtacacagt gatctaggct actgattga gagtgagaag aatgacacat ggaggctgaa   3120
gagggcccat ctgatcgaga tgaaaacatg tgaatggcca aagtcccaca cattgtggac   3180
agatggaata aagagagtg atctgatcat acccaagtct ttagctgggc cactcagcca    3240
tcacaatacc agagagggct acaggaccca aatgaaaggg ccatggcaca gtgaagagct   3300
tgaaattcgg tttgaggaat gcccaggcac taaggtccac gtggaggaaa catgtggaac   3360
aagaggacca tctctgagat caaccactgc aagcggaagg gtgatcgagg aatggtgctg   3420
cagggagtgc acaatgcccc cactgtcgtt ccgggctaaa gatggctgtt ggtatgaat    3480
ggagataagg cccaggaaag aaccagaaag caacttagta aggtcaatgg tgactgcagg   3540
atcaactgat cacatggatc acttctccct tggagtgctt gtgattctgc tcatggtgca   3600
ggaagggctg aagaagagaa tgaccacaaa gatcatcata agcacatcaa tggcagtgct   3660
ggtagctatg atcctgggag gattttcaat gagtgacctg gctaagcttg caattttgat   3720
gggtgccacc ttcgcggaaa tgaacactgg aggagatgta gctcatctgg cgctgatagc   3780
ggcattcaaa gtcagaccag cgttgctggt atctttcatc ttcagagcta attggacacc   3840
ccgtgaaagc atgctgctgg ccttggcctc gtgtttttt gcaaactgcga ctctccgcct   3900
ggaaggcgac ctgatggttc tcatcaatgg ttttgctttg gcctggtgg caatacgagc    3960
gatggttgtt ccacgcactg acaacatcac cttggcaatc ctggctgctc tgacaccact   4020
ggcccggggc acactgcttg tggcgtggag agcaggcctt gctacttgcg gggggtttat   4080
gctcctctct ctgaagggaa aaggcagtgt gaagaagaac ttaccatttg tcatggcct    4140
gggactaacc gctgtgaggc tggtcgaccc catcaacgtg gtgggactgc tgttgctcac   4200
aaggagtggg aagcggagct ggcccctag cgaagtactc acagctgttg gcctgatatg   4260
cgcattggct ggagggttcg ccaaggcaga tatagagatg gctgggccca tggccgacgt   4320
cggtctgcta attgtcagtt acgtggtctc aggaaagagt gtggacatgt acattgaaag   4380
agcaggtgac atcacatggg aaaagatgc ggaagtcact ggaaacagtc cccggctcga   4440
tgtgcgcta gatgagagtg tgacttctc cctggtggag gatgacggtc cccccatgag    4500
agagatcata ctcaaggtgg tcctgatgac catctgtggc atgaacccaa tagccatacc   4560
ctttgcagct ggagcgtggt acgtatacgt gaagactgga aaaaggagtg gtgctctatg   4620
ggatgtgcct gctcccaagg aagtaaaaaa ggggagacc acagatggag tgtacagagt   4680
aatgactcgt agactgctag gttcaacaca agttggagtg ggagttatgc aagagggggt   4740
cttccacact atgtggcacg tcacaaaagg atccgcgctg agaagcggtg aagggagact   4800
tgatccatac tgggggagatg tcaagcagga tctggtgtca tctgtggctc catgaagct    4860
agatgccgcc tgggacgggc acagcgaggt gcagctcttg gccgtgcccc cggagagag    4920
agcgaggaac atccagactc tgcccggaat atttaagaca aaggatgggg acattggagc   4980
ggttgcgctg gattacccag caggaacttc aggatctcca atcctagaca gtgtgggag    5040
agtgatagga ctttatggca atgggtcgt gataaaaat gggagttatg ttagtgccat   5100
cacccaaggg aggaggggagg aagagactcc tgttgagtgc ttcgagccct cgatgctgaa   5160
gaagaagcag ctaactgtct tagacttgca tcctggagct gggaaaacca ggagagttct   5220
tcctgaaata gtccgtgaag ccataaaaac aagactccgt actgtgatct tagctccaac   5280
cagggttgtc gctgctgaaa tggaggaagc cttagagg cttccagtgc gttatatgac    5340
aacagcagtc aatgtcaccc actctggaac agaaatcgtc gacttaatgt gccatgccac   5400
cttcacttca cgtctactac agccaatcag agtcccaac tataatctgt atattatga   5460
tgaggcccac ttcacagatc cctcaagcat agcagcaaga ggatacttt caacaagggt    5520
tgagatgggc gaggcggctg ccatcttcat gaccgccacg ccaccaggaa cccgtgacgc   5580
atttccggac tccaactcac caattatgga caccgaagtg gaagtccag agagagcctg    5640
gagctcaggc tttgattggg tgacggatca ttctggaaaa acagtttggt tgttccaag    5700
cgtgaggaac ggcaatgaga tcgcagcttg tctgacaaag gctggaaaac gggtcataca   5760
```

```
gctcagcaga aagactttg agacagagtt ccagaaaaca aaacatcaag agtgggactt    5820
tgtcgtgaca actgacattt cagagatggg cgccaacttt aaagctgacc gtgtcataga    5880
ttccaggaga tgcctaaagc cggtcatact tgatggcgag agagtcattc tggctggacc    5940
catgcctgtc acacatgcca gcgctgccca gaggaggggg cgcataggca ggaatcccaa    6000
caaacctgga gatgagtacc tgtatggagg tgggtgcgca gagactgacg aagaccatgc    6060
acactggctt gaagcaagaa tgctccttga caatatttac ctccaagatg gcctcatagc    6120
ctcgctctat cgacctgagg ccgacaaagt agcagccatt gagggagagt tcaagcttag    6180
gacggagcaa aggaagacct tgtggaact catgaaaaga ggagatcttc ctgtttggct    6240
ggcctatcag gttgcatctg ccggaataac ctacacagat agaagatggt gctttgatgg    6300
cacgaccaac aacaccataa tggaagacag tgtgccggca gaggtgtgga ccagacacgg    6360
agagaaaaga gtgctcaaac cgaggtggat ggacgccaga gtttgttcag atcatgcggc    6420
cctgaagtca ttcaaggagt tgccgctgg gaaaagagga cggcttttg gagtgatgga    6480
agccctggga acactgccag gacacatgac agagagattc caggaagcca ttgacaacct    6540
cgctgtgctc atgcgggcag agactggaag caggccttac aaagccgcgg cggcccaatt    6600
gccggagacc ctagagacca ttatgctttt ggggttgctg gaacagtct cgctgggaat    6660
cttttttcgtc ttgatgagga acaagggcat agggaagatg gcctttggaa tggtgactct    6720
tggggccagc gcatggctca tgtggctctc ggaaattgag ccagccagaa ttgcatgtgt    6780
cctcattgtt gtgttcctat tgctgcatcct gagccagaaa agcaaagatc    6840
tccccaggac aaccaaatgg caatcatcat catggtagca gtaggtcttc tgggcttgat    6900
taccgccaat gaactcggat ggttggagag aacaaagagt gacctaagcc atctaatggg    6960
aaggagagag gaggggggcaa ccataggatt ctcaatggac attgacctgc ggccagcctc    7020
agcttgggcc atcatctg ccttgacaac tttcattacc ccagccgtcc aacatgcagt    7080
gaccacttca tacaacaact actccttaat ggccatggcc acgcaagctg gagtgttgtt    7140
tggtatgggc aaagggatgc cattctacgc atgggacttt ggagtcccgc tgctaatgat    7200
aggttgctac tcacaattaa cacccctgac cctaatagtg gccatcattt tgctcgtggc    7260
gcactacatg tacttgatcc cagggctgca ggcagagct gcgtgctg cccagaaag    7320
aacggcagct ggcatcatga agaaccctgt tgtggatgga atagtggtga ctgacattga    7380
cacaatgaca attgaccccc aagtggagaa aaagatggga caggtgctac tcatagcagt    7440
agccgtctcc agcgccatac tgtcgcggac cgcctgggg tgggggagg ctggggccct    7500
gatcacagcc gcaacttcca cttttgtggga aggctccg aacaagtact ggaactcctc    7560
tacagccact tcactgtgta acatttttag gggaagttac ttggctggag cttctctaat    7620
ctacacagta acaagaaacg ctggcttggt caagagacgt gggggtggaa caggagagac    7680
cctgggagag aaatgaagg cccgcttgaa ccagatgtcg gccctggagt tctactccta    7740
caaaaagtca ggcatcaccg aggtgtgcag agaagaggcc cgccgcgcc tcaaggacgg    7800
tgtggcaacg gaggccatg ctgtgtcccg aggaagtgca aagctgagat ggttggtgga    7860
gcggggatac ctgcagccct atggaaaggt cattgatctt ggatgtggca ggggggctg    7920
gagttactac gccgccacca tccgcaaagt tcaagaagtg aaaggataca caaaaggagg    7980
ccctggtcat gaagaaccgg tgttggtgca aagctatggg tggaacatag tccgtcttaa    8040
gagtgggtg gacgtctttc atatggcgg tgagccgtgt gacacgttgc tgtgtgacat    8100
aggtgagtca tcatctagtc ctgaagtgga agaagcacgg acgctcagag tcctctccat    8160
ggtggggat tggcttgaaa aaagaccagg agcctttgc ataaagtgt tgtgcccata    8220
caccagcact atgatggaaa ccctggagcg actgcagcgt aggtatgggg aggactggt    8280
cagagtgcca ctctcccgca actctacaca tgagatgtac tgggtctctg gagcgaaaag    8340
caacaccata aaaagtgtgt ccaccacgag ccagctcctc ttggggcgca tggacgggcc    8400
taggaggcca gtgaaatatg aggaggatgt gaatctcggc tctggcacgc gggctgtggt    8460
aagctgcgct gaagctccca acatgaagat cattggtaac cgcattgaaa ggatccgcag    8520
tgagcacgcg gaaacgtggt tcttgacga aaaccaccca tataggacat gggcttacca    8580
tggaagctat gtgccccca cacagggtc agcgtcctct ctaataaacg gggttgtcag    8640
gctcctgtca aaaccctggg atgtggtgac tggagtcaca ggaatagcca tgaccgacac    8700
cacaccgtat ggtcagcaaa gagttttcaa ggaaaaagtg gacactaggg tgccagaccc    8760
ccaagaaggc actcgtcagg ttatgcagat ggtctcttcc tggttgtgga aagagctagg    8820
caaacacaaa cgaccacgag tctgtaccaa agaagagttc atcaacaagg ttcgtagcaa    8880
tgcagcatta gggcaatat ttgaagagga aaaagagtgg aagactcag tggaagctgt    8940
gaacgatcca aggttctggg ctctagtgga caaggaaaga gagcaccacc tgagaggaga    9000
gtgccagagt tgtgtgtaca acatgatggg aaaaagagaa agaaaaacaag gggaattgg    9060
aaaggccaag ggcagccgcg ccatctggta tatgtggcta ggggctagat ttctagagtt    9120
cgaagccctt ggattcttga acgaggatca ctggatgggg agagaaact caggaggtgg    9180
tgttgaaggg ctgggattac aaagactcgg atatgtccta aagagatga gtcgcatacc    9240
aggaggaagg atgtatgcag atgacactgc tggctgggac acccgcatca gcaggtttga    9300
tctggagaat gaagctctaa tcaccaacca aatggagaaa gggcacaggg ccttggcatt    9360
ggccataatc aagtacacat accaaaacaa agtggtaaag gtccttagac cagctgaaaa    9420
agggaaaaca gttatggaca ttatttcgag acaagaccaa aggggagcg acaagttgt    9480
cacttacgct cttaacacat ttaccaacct agtggtgcaa ctcattcgga atatggaggc    9540
tgaggaagtt ctagatgc aagacttgtg gctgctgcgg aagtcagcaa aagtgaccaa    9600
ctggttgcag agcaacggat gggataggct caaacgaatg gcagtcagtg gagatgattg    9660
cgttgtgaag ccaattgatg ataggtttgc acatgccctc aggttcttga atgatatggg    9720
aaaagttagg aaggacacac aagagtggaa accctcaact ggatgggaca ctgggaagaa    9780
agttccgctt tgctcccacc acttcaacaa gctccatctc aaggacggga ggtccattgt    9840
ggttccctgc cgccaccaag atgaactgat tggccgggcc cgcgtctctc caggggcgg    9900
atggagcatc cgggagactg cttgcctagc aaaatcatat gcgcaaatgt ggcagctcct    9960
ttatttccac agaagggacc tccgactgat ggccaatgcc atttgttcat ctgtgccagt    10020
tgactggttt ccaactggga gaactacctg gtcaatccat ggaaaggag aatggatgac    10080
cactgaagac atgcttgtgg tgtggaacag agtgtggatt gaggagaacg accacatgga    10140
agacaagacc ccagttacga aatgacaaga cattccctat ttgggaaaaa gggaagactt    10200
gtggtgtgga tctctcatag ggcacagacc gcgcaccacc tggctgaga acattaaaaa    10260
tacagtcaac atggtgcgca ggatcatagg tgatgaagaa aagtacatgg actacctatc    10320
cacccaagtt cgctacttgg gtgaagaagg gtctacacct ggagtgctgt gagcaccaat    10380
cttaatgttg tcaggcctgc tagtcagcca cagcttgggg aaagctgtgc agcctgtgac    10440
ccctccagga gaagctgggt aaccaagcct atagtcaggc cgagaacgcc atggcacgga    10500
```

```
agaagccatg ctgcctgtga gcccctcaga ggacactgag tcaaaaaacc ccacgcgctt   10560
ggaggcgcag gatgggaaaa gaaggtggcg accttcccca cccttcaatc tggggcctga   10620
actggagatc agctgtggat ctccagaaga gggactagtg gttagaggag acccccggga   10680
aaacgcaaaa cagcatattg acgctgggaa agaccagaga ctccatgagt ttccaccacg   10740
ctggccgcca ggcacagatc gccgaatagc ggcggccggt gtggggaaat cca          10793

SEQ ID NO: 4          moltype = DNA   length = 10675
FEATURE               Location/Qualifiers
source                1..10675
                      mol_type = genomic DNA
                      organism = Zika virus
SEQUENCE: 4
gttgttgatc tgtgtgaatc agactgcgac agttcgagtt tgaagcgaaa gctagcaaca     60
gtatcaacag gttttatttt ggatttggaa acgagagttt ctggtcatga aaaacccaaa    120
aaagaaatcc ggaggattcc ggattgtcaa tatgctaaaa cgcggagtag cccgtgtgag    180
cccctttggg ggcttgaaga ggctgccagc cggacttctg ctgggtcatg ggcccatcag    240
gatggtcttg gcgattctag ccttttttgag attcacggca atcaagccat cactgggtct    300
catcaataga tgggghtcag tggggaaaaa agaggctatg agaacaataa agaagttcaa    360
gaaagatctg gctgccatgc tgagaataat caatgctagg aaggagaaga gagacgagg    420
cgcagatact agtgtcggaa ttgttggcct cctgctgacc acagctatgg cagcggaggt    480
cactagacgt gggagtgcat actatatgta cttggacaga aacgatgctg gggaggccat    540
atcttttcca accacattgg ggatgaataa gtgttatata cagatcatgg atcttggaca    600
catgtgtgat gccaccatga gctatgaatg ccctatgctg gatgagggg tggaaccaga    660
tgacgtcgat tgttggtgca acgacgtc aacttgggtt gtgtacgaa cctgccatca    720
caaaaaggt gaagcacgga gatctagaag agctgtgacg ctcccctccc attccaccag    780
gaagctgcaa acgcggtcgc aaacctggtt ggaatcacaa gaatacacaa agcacttgat    840
tagagtcgaa aattggatat tcaggaaccc tggcttcgcg ttagcagcag ctgccatcgc    900
ttggcttttg ggaagctcaa cgagccaaaa agtcatatac ttggtcatga tactgctgat    960
tgccccggca tacagcatca ggtgcatagg agtcagcaat agggactttg tggaaggtat   1020
gtcaggtggg acttgggttg atgttgtctt ggaacatgga ggttgtgtca ccgtaatggc   1080
acaggacaaa ccgactgtcg acatagagct ggttacaaca acagtcagca catggcggc   1140
ggtaagatcc tactgctatg aggcatcaat atcagacatg gcttctgaca gccgctgccc   1200
aacacaaggt gaagcctacc ttgacaagca atcagacact caatatgtct gcaaaagaac   1260
gttagtggac agaggctggg gaaatggatg tggactttttt ggcaaaggga gcctggtgac   1320
atgcgctaag tttgcatgct ccaagaaaat gaccgggaag agcatccagc cagagaatct   1380
ggagtaccgg ataatgctgt cagttcatgg ctcccagcac agtgggatga tcgttaatga   1440
cacaggacat gaaactgatg agaatagagc gaaagttgag ataacgccca ttcaccgag   1500
agccgaagcc accctggggg gttttggaag cctaggactt gattgtgaac cgaggacagg   1560
ccttgacttt tcagatttgt attacttgac tatgaataac aagcactggt tggttcacaa   1620
ggagtggttc cacgacattc cattaccttg gcacgctggg gcagacaccg gaactccaca   1680
ctggaacaac aaaagagcac tggtagagtt caaggacgca catgccaaaa ggcaaactgt   1740
cgtggttcta gggagtcaag aaggagcagt tcacacggcc cttgctggag ctctggaggc   1800
tgagatggat ggtgcaaagg gaaggctgtc tctggccac ttgaaatgtc gcctgaaaat   1860
ggataaactt agattgaagg gcgtgtcata ctccttgtgt actgcagcgt tcacattcac   1920
caagatcccg gctgaaacac tgcacgggac agtcacagtg gaggtacagt acgcagggac   1980
agatggacct tgcaaggttc cagctcagat ggcggtggac atgcaaactc tgacccagt   2040
tgggaggttg ataaccgcta accccgtaat cactgaaagc actgagaact ctaagatgat   2100
gctggaactt gatccaccat tgggggactc ttacattgtc ataggagtcg gggagaagaa   2160
gatcacccac cactggcaca ggagtggcag caccattgga aaagcatttg aagccactgt   2220
gagaggtgcc aagagaatgg cagtcttggg agacacagcc tgggacttg atcagttgg   2280
aggcgctctc aactcattgg gcaagggcat ccatcaaatt tttggagcag ctttcaaatc   2340
attgtttgga ggaatgtcct ggttctcaca aattctcatt ggaacgttgc tgatgtggtt   2400
gggtctgaac acaaagaatg gatctatttc ccttatgtgc ttggccttag ggggagtgtt   2460
gatcttctta tccacagccg tctctgctga tgtggggtgc tcggtggact ctcaaagaa   2520
ggagacgaca tgcggtacag gggtgttcgt ctataacgac gttgaagcct ggagggacag   2580
gtacaagtac catcctgact ccccccgtag attggcagca gcagtcaagc aagcctggga   2640
agtggtatc tgcgggatct cctctgtttc aagaatggaa aacatcatgt gaagatcagt   2700
agaagggag ctcaacgcaa tcctggaaga gaatggagtt caactgacgg tcgttgtggg   2760
atctgtaaaa aaccccatgt ggagaggtcc acagagattg cccgtgcctg tgaacgagct   2820
gcccacggc tggaaggctt gggggaaatc gtattcgtc agagcagcaa agacaaataa   2880
cagctttgtc gtggatggtg acacactgaa ggaatgccca ctcaaacata gagcatgaa   2940
cagctttctt gtggaggatc atgggttcgg ggtattccac actagtgtct ggctcaaggt   3000
tagagaagat tattcattag agtgtgatcc agccgttatt ggaacagctg ttaagggaaa   3060
ggaggctgta cacagtgatc taggctactg gattgagagt gagaagaatg acacatggaga   3120
gctgaagagg gcccatctga tcgagatgaa aacatgtgaa tggccaaagt cccacacatt   3180
gtggacagat ggaatagaag agagtgatct gatcataccc aagtctttag ctgggccact   3240
cagccatcac aataccagag agggctacag gacccaaatg aaagggccat ggcacagtga   3300
agagcttgaa attcggtttg aggaatgccc aggcactaag gtccacgtgg aggaaacatg   3360
tggaacaaga ggaccatctc tgagatcaac cactgcaagc ggaagggtga tcgaggaatg   3420
gtgctgcagg gagtgcacaa tgccccccac tgtcttccgg gctaaagatg gctgttgta   3480
tggaatggag ataaggccca ggaaagaacc agaaagcaac ttagtaaggt caatggtgac   3540
tgcaggatca actgatcaca tggaccactt ctcccttgga gtgcttgtga tcctgctcat   3600
ggtgcaggaa gggctgaaga gagaatgac cacaaagatc atcataagca catcaatggc   3660
agtgctgtc gctatgatcc tgggaggatt tccaatgagt gacctggcta gcttgcaat   3720
tttgatgggt gccaccttcg cggaaatgaa cactggagga gatgtagctc atctggcgct   3780
gatagcggca ttcaaagtca gaccagcgtt gctggtatct ttcatcttca gagctaattg   3840
gacacccgt gaaagcatgc tgctggcctt gggcatcgt cttttgcaaa ctgcgatctc   3900
cgccttggaa ggcgacctga tggttctcat caatggtttt gctttggcct ggttggcaat   3960
acgagcgatg gttgttccac gcactgataa catcaccttg gcaatcctgg ctgctctgac   4020
```

```
accactggcc cggggcacac tgcttgtggc gtggagagca ggccttgcta cttgcggggg  4080
gtttatgctc ctctctctga agggaaaagg cagtgtgaag aagaacttac catttgtcat  4140
ggccctggga ctaaccgctg tgaggctggt cgacccatc aacgtggtgg gactgctgtt  4200
gctcacaagg agtgggaagc ggagctggcc cctagcgaa gtactcacag ctgttggcct  4260
gatatgcgca ttggctggag ggttcgccaa ggcagatata gagatgcctg ggcccatggc  4320
cgcggtcggt ctgctaattg tcagttacgt ggtctcagga aagagtgtgg acatgtacat  4380
tgaaagagca ggtgacatca catgggaaaa agatgcggaa gtcactggaa acagtccccg  4440
gctcgatgtg gcgctagatg agagtggtga tttctccctg gtggaggatg acggtccccc  4500
catgagagag atcatactca aggtggtcct gatgaccatc tgtggcatga acccaatagc  4560
catacccttt gcagctggag cgtggtacgt atacgtgaag actgaaaaa ggagtggtgc  4620
tctatgggat gtgcctgctc caaggaagt aaaaaggggg gagaccacag atggagtgta  4680
cagagtaatg actcgtagac tgctaggttc aacacaagtt ggagtgggag ttatgcaaga  4740
gggggtcttt cacactatgt ggcacgtcac aaaaggatcc gcgctgagaa gcggtgaagg  4800
gagacttgat ccatactggg gagatgtcaa gcaggatctg gtgtcatact gtggtccata  4860
gaagctagat gccgcctggg atgggcacag cgaggtgcag ctcttggccg tgccccccgg  4920
agagagagcg aggaacatcc agactctgcc cggaatattt aagacaaagg atgggggacat  4980
tggagcggtt gcgctggatt acccagcagg aacttcagga tctccaatcc tagacaagtg  5040
tgggagagtg ataggactt atggcaatgg ggtcgtgatc aaaaacggga gttatgttag  5100
tgccatcacc caaggagga gggaggaaga gactcctgtt gagtgcttcg agccctcgat  5160
gctgaagaag aagcagctaa ctgtcttaga cttgcatcct ggagctggga aaaccaggag  5220
agttcttcct gaaatagtcc gtgaagccat aaaaacaaga ctccgtactg tgatcttagc  5280
tccaaccagg gttgtcgctg ctgaaatgga ggaggcccgtt agagggcttc cagtgcgtta  5340
tatgacaaca gcagtcaatg tcacccactc tggaacagaa atcgtcgact taatgtgcca  5400
tgccaccttc acttcacgtc tactacagcc aatcagagtc cccaactata atctgtatat  5460
tatggatgag gcccacttca cagatccctc aagtatagca gcaagaggat acatttcaac  5520
aagggttgag atgggcgagg cggctgccat cttcatgact gccacgccac caggaaccccg  5580
tgacgcattt ccggactcca actcaccaat tatggacacc gaagtggaag tcccagagag  5640
agcctggagc tcaggctttg attgggtgac ggatcattct ggaaaaacag tttggttttgt  5700
tccaagcgtg aggaacggca atgagatcgc agcttgtctg acaaaggctg aaaacgggt  5760
catacagctc agcagaaaga cttttgagac agagttccag aaaacaaaac atcaagagtg  5820
ggacttttgtc gtgacaactg acatttcaga gatgggcgcc aactttaaag ctgaccgtgt  5880
catagattcc aggagatgcc taaagccggt catacttgat ggcgagagag tcattctggc  5940
tggacccatg cctgtcacac atgccagcgc tgcccagagg aggggcgca taggcaggaa  6000
tcccaacaaa cctggagatg agtatctgta tggaggtggg tgcgcagaga ctgacgagga  6060
ccatgcacac tggcttgaag caagaatgct ccttgacaat atttacctcc aagatggcct  6120
catagcctcg ctctatcgac ctgaggccga caagtagca gccattgagg gagagttcaa  6180
gcttaggacg gagcaaagga agacctttgt ggaactcatg aaaagaggag atcttcctgt  6240
ttggctggcc tatcaggttg catctgccgg aataacctac acagatagaa gatggtgctt  6300
tgatgccacg accaacaaca ccataatgga agacagtgtg ccggcagagg tgtgaccag  6360
acacggagag aaaagagtgc tcaaaccgag gtggatggac gccagagttt gttcagatca  6420
tgcggccctg aagtcattca aggagtttgc cgctgggaaa agaggagcgg cttttggagt  6480
gatggaagcc ctgggaacac tgccaggaca catgacagag agattccagg aagccattga  6540
caacctcgct gtgctcatgc gggcagagac tggaagcagg ccttacaaag ccgcggccgg  6600
ccaattgccg gagaccctag agaccataat gcttttgggg ttgctgggaa cagtctcgct  6660
gggaatcttc ttcgtcttga tgaggaacaa gggcataggg aagatgggct ttggaatggt  6720
gactcttggg gccagcgcat ggctcatgtg gctctcggaa attgagccag ccagaattgc  6780
atgtgtcctc attgttgtgt tcctattgct ggtggtctc atacctgagc cagaaaagca  6840
aagatctccc caggacaacc aaatggcaat catcatcatg gtagcagtag gtcttctggg  6900
cttgattacc gccaatgaac tcggatggtt ggagagaaca aagagtgacc taagccatct  6960
aatgggaagg agagaggagg gggcaaccat aggattctca atggacattg acctgcggcc  7020
agcctcagct tgggccatct atgctgcctt gacaactttc attaccccag ccgtccaaca  7080
tgcagtgacc acctcataca acaactactc cttaatggcg atggccacgc aagctggagt  7140
gttgtttggc atgggcaaag ggatgccatt ctacgcatgg gactttggag tcccgctgct  7200
aatgataggt tgctactcac aattaacacc cctgaccca atagtggcca tcattttgct  7260
cgtggcgcac tacatgtact tgatcccgag gctgcaggca cagcggcga gctgctgccca  7320
gaagagaacg gcagctggca tcatgaagaa ccctgttgtg gatggaatag tggtgactga  7380
cattgacaca atgacaattg accccaagt ggagaaaaag atgggacagg tgctactcat  7440
agcagtagcc gtctccagcg ccatactgtc gcggaccgcc tggggtggg gggaggctgg  7500
ggctctgatc acagccgcaa cttccactt gtgggaaggc tctccgaaca agtactggaa  7560
ctcctctaca gccacttcac tgtgtaacat agttacttgg ctggagcttc  7620
tctaatctac acagtaacaa gaaacgctgg cttggtcaag agacgtgggg gtgaacagg  7680
agagaccctg gagagaaat ggaaggcccg cttgaaccag atgtcggccc tggagttcta  7740
ctcctacaaa aagtcaggca tcaccgaggt gtgcagaaga gaggcccgcc gcgccctcaa  7800
ggacggtgtg caacgggag gccatgctgt gtcccgagga acgtgcaaagc tgagatggtt  7860
ggtgagcgg ggataccgtc agccctatg aaaggtcatt gatcttggat gtggcagagg  7920
gggctggagt tactacgtcg ccaccatccg caaagttcaa gaagtgaaag atacacaaa  7980
aggaggcccc ggtcatgaag aacccgtgtt ggtgcaaagc tatgggtgga acatagtccg  8040
tcttaagagt ggggtggacg tcttttcatat ggcggctgag ccgtgtgaca cgttgctgtg  8100
tgacataggt gagtcatcat ctagtcctga agtggaagaa gcacgacgc tcagagtcct  8160
ctccatggtg ggggattggc ttgaaaaaag accaggagcc ttttgtataa agtgttgtg  8220
cccatacacc agcactatga tggaaaccct ggagcgactg cagcgtaggt atgggggagg  8280
actggtcaga gtgccactct cccgcaactc tacacatgag atgtactggg tctctggagc  8340
gaaaagcaac accataaaaa gtgtgtccac cacgagccag ctcctcttgg ggcgcatgga  8400
ccctagg aggccagtga aatatgagga ggatgtaat ctcggctctg gcacgcgggc  8460
tgtggtaagc tgcgctgaag ctcccaacat gaagatcatt ggtaaccgca ttgaaaggat  8520
ccgcagtgag cacgcggaaa cgtggttctt tgacgagaac caccatata ggacatgggc  8580
ttaccatgga agctatgagg cccccacaca agggtcagcg tcctctctaa taaacggggt  8640
tgtcaggctc ctgtcaaaac cctgggatgt ggtgactgga gtcacaggaa tagccatgac  8700
cgacaccaca ccgtatggtc agcaaagagt tttcaaggaa aaagtggaca ctagggtgcc  8760
```

```
agaccccaa gaaggcactc gtcaggttat gagcatggtc tcttcctggt tgtggaaaga   8820
gctaggcaaa cacaaacggc cacgagtctg caccaaagaa gagttcatca acaaggttcg   8880
tagcaatgca gcattagggg caatatttga agaggaaaaa gagtggaaga ctgcagtgga   8940
agctgtgaac gatccaaggt tctgggctct agtggacaag gaaagagagc accacctgag   9000
aggagagtgc cagagctgtg tgtacaacat gatgggaaaa agagaaaaga aacaagggga   9060
atttggaaag gccaagggca gccgcgccat ctggtatatg tggctagggg ctagatttct   9120
agagttcgaa gcccttggat tcttgaacga ggatcactgg atgggagag agaactcagg    9180
aggtggtgtt gaagggctgg gattacaaag actcggatat gtcctagaag agatgagtcg   9240
tataccagga ggaaggatgt atgcagatga cactgctggc tgggacaccc gcattagcag   9300
gtttgatctg gagaatgaag ctctaatcac caaccaaatg gagaaagggc acagggcctt   9360
ggcattggcc ataatcaagt acacatacca aaccaaagtg gtaaaggtcc ttagaccagc   9420
tgaaaaaggg aaaacagtta tggacattat ttcgagacaa gaccaaaggg ggagcggaca   9480
agttgtcact tacgctctta acacatttac caacctagtg gtgcaactca ttcggaatat   9540
ggaggctgag gaagttctag agatgcaaga cttgtgctg ctgcgggaca cagagaaagt    9600
gaccaactgg ttgcagagca acggatggga taggctcaaa cgaatggcag tcagtggaga   9660
tgattgcgtt gtgaagccaa ttgatgatag gttttgcaca tgccctcaggt tcttgaatga   9720
tatgggaaaa gttaggaagg acacacaaga gtggaaaccc tcaactggat gggacaactg   9780
ggaagaagtt ccgttttgct cccaccactt caacaagctc catctcaagg acgggaggtc   9840
cattgtggtt ccctgccgcc accaagatga actgattggc cgggcccgcg tctctccagg   9900
ggcgggatgg agcatccggg agactgcttc cctagcaaaa tcatatgcgc aaatgtggca   9960
gctcctttat ttccacagaa gggacctccg actgatggcc aatgccattt gttcatctgt  10020
gccagttgac tgggttccaa ctgggagaac tacctggtca atccatgaca agggagaatg  10080
gatgaccact gaagacatgc ttgtggtgtg aacagagtg tggattgagg agaacgacca   10140
catgaagac aagaccccag ttacgaaatg gacagacatt ccctatttgg gaaaaaggga    10200
agacttgtgt gtgtggatctc tcataggcca cagaccgcgc accacctggg ctgagaacat  10260
taaaaacaca gtcaacatgg tgcgcaggat cataggtgat gaagaaaagt acatggacta  10320
cctatccacc caagttcgct acttgggtga agaagggtct acacctggag tgctgtaagc  10380
accaatctta atgttgtcag gcctgctagt cagccacagc ttggggaaag ctgtgcagcc  10440
tgtgaccccc caggagaag ctgggaaacc aagcctatag tcaggccgag aacgccatgg    10500
cacggaagaa gccatgctgc ctgtgagccc ctcagagac actgagtcaa aaaacccac    10560
gcgcttggag gcgcaggatg ggaaaagaag gtggcgacct tccccaccct tcaatctggg  10620
gcctgaactg gagatcagct gtggatctcc agaagaggga ctagtggtta gagga       10675

SEQ ID NO: 5        moltype = DNA   length = 10676
FEATURE             Location/Qualifiers
source              1..10676
                    mol_type = genomic DNA
                    organism = Zika virus
SEQUENCE: 5
gttgttactg ttgctgactc agactgcgac agttcgagtt tgaagcgaaa gctagcaaca     60
gtatcaacag gttttatttg gatttggaaa cgagagtttc tggtcatgaa aaacccaaaa    120
aagaaatccg gaggattccg gattgtcaat atgctaaaac gcggagtagc ccgtgtgagc    180
ccctttgggg gcttgaagag gctgccagcc ggacttctgc tgggtcatgg gcccatcagg    240
atggtcttgg caattctagc ctttttgaga ttcacggcaa tcaagccatc actgggtctc    300
atcaatagat ggggttcagt ggggaaaaaa gaggctatgg aaataataaa gaagttcaag    360
aaagatctgc tgccatgct gagaataatc aatgctagga aggagaagaa gagacgaggc     420
gcagatacta gtgtcggaat tgttggcctc ctgctatgca gctatggc agcggaggtc      480
actagacgtg ggagtgcata ctatatgtac ttggacagaa acgatgctgg ggaggccata    540
tcttttccaa ccacattggg gatgaataag tgttatatac agatcatgga tcttggacac    600
atgtgtgatg ccaccatgag ctatgaatgc cctatgctgg atgaggggt ggaaccagat     660
gacgtcgatt gttggtgcaa cacgacgtca acttgggttg tgtacggaac ctgccatcac    720
aaaaaggtg aagcacggag atctagaaga gctgtgacgc tcccctccca ttccactagg    780
aagctgcaaa cgcggtcgca aacctggttg aatcaagag aatacacaaa gcacttgatt     840
agagtcgaaa attggatatt caggaaccct ggcttcgcgt tagcagcagc tgccatcgct    900
tggcttttgg gaagctcaac gagccaaaaa gtcatatact tggtcatgat actgctgatt    960
gccccggcat acagcatcag gtgcatagga gtcagcaata gggactttgt ggaaggtatg   1020
tcaggtggga cttgggttga tgttgtcttg aacatggagg ttgtgtcac cgtaatggca    1080
caggacaaac cgactgtcga catagagctg gttacaacaa cagtcagcaa catggcggag   1140
gtaagatcct actgctatga ggcatcaata tcagacatca cttcggacac ccgctgccca   1200
acacaaggtg aagcctacct tgacaagcaa tcagacactc aatatgtctg caaaagaacg   1260
ttagtggaca gaggctgggg aaatggatgt ggacttttg gcaaagggag tctggtgaca    1320
tgcgctaagt tgcatgctc caagaaaatg accgggaaga gcatccagcc agaaaatctg   1380
gagtaccgga taatgctgtc agttcatggc tcccagcaca gtgggatgat cgttaatgac   1440
acaggacatg aaactgatga gaatagagcg aaggtttaga taacgcccaa ttcaccaaga   1500
gccgaagcca ccctgggggg ttttggaagc ctaggacttg attgtgaacc gaggacaggc   1560
cttgactttt cagatttgta ttacttgact atgaataaca agcactggtt ggttcacaag   1620
gagtggttcc acgacattcc attaccttgg cacgctgggg cagacaccgg aactccacac   1680
tggaacaaca aagaagcact ggtagagttc aaggacgcac atgccaaaag gcaaactgtc   1740
gtggttctag ggagtcaaga aggagcagtt cacacgcgcc ttgctggagc tctgaggct   1800
gagatggatg tgcaaaggga aaggctgtcc tctggccact gaaatgtcg cctgaaaatg    1860
gataaactta gattgaaggg cgtgtcatac tccttgtgta ccgcagcgtt cacattcacc   1920
aagatcccgc tgaaacact gcagggaca gtcacagtgg aggtacagta cgcagggaca    1980
gatggacctt gcaaggttcc agctcagatg gcggtgaca tgcaaactct gaccccagtt     2040
gggaggttga taccgctaa ccccgtaatc actgaaagcg ctgagaactc taagatgatg    2100
ctggaacttg atccaccatt tggggactct tacattgtca taggagtcgg ggagaagaag   2160
atcacccacc actgcacag gagtggcagc accattggaa aagcattga gccactgtg     2220
agaggtgcca gagaatggc agtcttggga cacagcct gggctttgg atcagttgga       2280
ggcgctctca actcattggg caaggcatc catcaaattt ttgagcagc tttcaaatca    2340
ttgtttggag gaatgtcctg gttctcacaa attctcattg gaacgttgct gatgtggttg   2400
```

```
ggtctgaaca caaagaatgg atctatttcc cttatgtgct tggccttagg gggagtgttg    2460
atcttcttat ccacagccgt ctctgctgat gtggggtgct cggtggactt ctcaaagaag    2520
gagacgagat gcggtacagg ggtgttcgtc tataacgacg ttgaagcctg gagggacagg    2580
tacaagtacc atcctgactc cccccgtaga ttggcagcag cagtcaagca agcctgggaa    2640
gatggtatct gcgggatctc ctctgtttca agaatggaaa acatcatgtg gagatcagta    2700
gaaggggagc tcaacgcaat cctggaagag aatggagttc aactgacggt cgttgtggga    2760
tctgtaaaaa accccatgtg gagaggtcca cagagattgc ccgtgcctgt gaacgagctg    2820
ccccacggct ggaaggcttg ggggaaatcg cacttcgtca gagcagcaaa gacaaataac    2880
agctttgtcg tggatggtga cacactgaag gaatgcccac tcaaacatag agcatggaac    2940
agcttccttg tggaggatca tgggttcggg gtatttcaca ctagtgtctg gctcaaggtt    3000
agagaagatt attcattaga gtgtgatcca gccgttattg gaacagctgt taagggaaag    3060
gaggctgtac acagtgatct aggctactgg attgagagtg agaagaatga cacatggagg    3120
ctgaagaggg cccatctgat cgagatgaaa acatgtgaat ggccaaagtc ccacacattg    3180
tggacagatg gaatagaaga gagtgatctg atcatacccc agtcttttagc tgggccactc    3240
agccatcaca ataccagaga gggctacagg acccaaatga aagggccatg gcacagtgaa    3300
gagcttgaaa ttcggtttga ggaatgccca ggcactaagg tccacgtgga ggaaacatgt    3360
ggaacaagag gaccatctct gagatcaacc actgcaagcg gaagggtgat cgaggaatgg    3420
tgctgcaggg agtgcacaat gccccccactg tcgttccggg ctaaagatgg ctgttggtat    3480
ggaatggaga taaggcccag gaaagaacca gaaagcaact tagtaaggtc aatggtgact    3540
gcaggatcaa ctgatcacat ggatcacttc tcccttggag tgcttgtgat tctgctcatg    3600
gtgcaggaag ggctgaagaa gagaatgacc acaaagatca tcataagcac atcaatggca    3660
gtgctggtag ctatgatcct gggaggattt tcaatgagtg acctggctaa gcttgcaatt    3720
ttgatgggtg ccaccttcgc ggaaatgaac actggaggag atgtagctca tctggcgctg    3780
atagcggcat tcaaagtcag accagcgttg ctggtatctt tcatcttcag agctaattgg    3840
acaccccgtg aaagcatgct gctggccttg gcctcgtgtc ttttgcaaac tgcgatctcc    3900
gccttggaag gcgacctgat ggttctcatc aatggttttg ctttggcctg gttggcaata    3960
cgagcgatgg ttgttccacg cactgataac atccaccttg gcaatcctgg ctgctctgaca   4020
ccactggccc ggggcacact gcttgtggcg tggagagcag gccttgctac ttgcggggga   4080
tttatgctcc tctctctgaa gggaaaaggc agtgtgaaga agaacttacc atttgtcatg   4140
gccctgggac taaccgctgt gaggctggtc gacccatca acgtggtggg gctgctgttg   4200
ctcacaagga gtgggaagcg gagctggccc cctagcgaag tactcacaga tgttggcctg   4260
atatgcgcat tggctggagg gttcgccaag gcagatatag agatggctgg gcccatggcc   4320
gcggtcggtc tgctaattgt cagttacgtg gtctcaggaa agagtgtgga catgtacatt   4380
gaaagagcag gtgacatcac atgggaaaaa gatgcggaaa tcactggaaa cagtcccccgg   4440
ctcgatgtgg cgctagatga gagtggtgat ttctccctgg tggaggatga cggtccccca   4500
atgagagaga tcatactcaa ggtggtcctg atgaccatct gtggcatgaa cccaatagcc   4560
ataccctttg cagctggagc gtggtacgta tacgtgaaga ctggaaaaag gagtggtgct   4620
ctatgggatg tgcctgctcc caaggaagta aaaaaggggg agaccacaga tggagtgtac   4680
agagtaatga ctcgtagact gctaggttca acacaagttg gatgggagct tatgcaagag   4740
ggggtctttc acactatgtg gcacgtcaca aaaggatccg cgctgagaag cggtgaaggg   4800
agacttgatc catactgggg agatgtcaag caggatctgg tgtcatactg tggtccatgg   4860
aagctagatg ccgcctggga cgggcacagc gaggtgcagc tcttggccgt gccccccgga   4920
gagagcagga ggaacatcca gactctgccc ggaatattta agcaaaggta tggggacatt   4980
ggagcggttg cgctggatta cccagcagga acttcaggat ctccaatcct agacaagtgt   5040
gggagagtga taggactttta tggcaatggg gtcgtgatca aaaatgggag ttatgttagt   5100
gccatcaccc aagggaggag gggaggaagag actcctgttg agtgcttcga gccttcgatg   5160
ctgaagaaga agcagctaac tgtcttagac ttgcatcctg gagctgggaa aaccaggaga   5220
gttcttcctg aaatagtccg tgaagccata aaaacaagac tccgtactgt gatcttagct   5280
ccaaccaggg ttgtcgctgc tgaaatggag gaagcccta gagggcttcc agtgcgttat   5340
atgacaacag cagtcaatgt cacccactct ggaacagaaa tcgtcgactt aatgtgccat   5400
gccaccttca cttcacgtct actacagcca atcagagtcc ccaactataa tctgtatatt   5460
atggatgagg cccacttcac agatccctca agtatagcag caagaggata catttcaaca   5520
agggttgaga tgggcgaggc ggctgccatc ttcatgaccg ccacgccacc aggaaccgt   5580
gacgcatttc cggactccaa ctcaccaatt atggacaccg aagtggaagt cccagagaga   5640
gcctggagct caggcttga ttgggtgacg gattattctg gaaaaacagt ttggtttgtt   5700
ccaagcgtga ggaacggcaa tgagatcgca gcttgtctga caaaggctgg aaaacgggtc   5760
atacagctca gcagaaagac ttttgagaca gagttccaga aaacaaaaca tcaagagtgg   5820
gactttgtcg tgacaactga catttcagag atgggcgcca actttaaagc tgaccgtgtc   5880
atagattcca ggagatgcct aaagccggtc atacttgatg gcgagagagt cattctggct   5940
ggacccatgc ctgtcacaca tgccagcgct gcccagagga ggggcgcat aggcaggaat   6000
cccaacaaac ctgagatgaa gtatctgtat gaggtgggt gcgcagagac tgacgaagac   6060
catgcacact ggcttgaagc aagaatgctc cttgacaata tttacctcca agatggcctc   6120
atagcctcgc tctatcgacc tgaggccgac aaagtagcag ccattgaggg agagttcaag   6180
cttaggacgg agcaaaggaa gaccttgtg gaactcatga aaagaggaga tcttcctgtt   6240
tggctggcct atcaggttgc atctgccgga ataacctaca gatagaag atggctcttt   6300
gatgctggacga ccaacaacac cataatggaa gacagtgtgc cggcagaggt gtggaccaga   6360
cacggagaga aaagagtgct caaaccgagg tggatgacg ccagagtttg ttcagatcat   6420
gcggccctga agtcattcaa ggagtttgcc gctgggaaaa gaggagcggc ttttggagtg   6480
atggaagccc tgggaacact gccaggacac atgacagagc gattccagga agccattgac   6540
aacctcgctg tgctcatgcg ggcagagact ggaagcaggc cttacaaagc cgcggcggcc   6600
caattgccgg agaccctaga gaccattatg cttttgggt tgctgggaac agtctcgctg   6660
ggaatctttt tcgtcttgat gaggaacaag gcatagga gatgggctt tggaatggtg   6720
actcttgggg ccagcgcatg gctcatgtgg ctctcggaaa ttgagccagc cagaattgca   6780
tgtgtcctca ttgttgtgtt cctattgctg gtggtgctca tacctgagcc agaaaagcaa   6840
agatctcccc aggacaacca aatggcaatc atcatcatgg tagcagtagg tcttctgggc   6900
ttgattaccg ccaatgaact cggatggttg gagagaacaa agagtgacct aagccatcta   6960
atgggaagga gagaggaggg ggcaaccatg ggattctcaa tggacattga cctgcggcca   7020
gcctcagctt gggccatcta tgctgccttg acaactttca ttaccccagc cgtccaacat   7080
gcagtgacca cttcatacaa caactactcc ttaatgcgca tggccacgca agctggagtg   7140
```

```
ttgtttggta tgggcaaagg gatgccattc tacgcatggg actttggagt cccgctgcta   7200
atgataggtt gctactcaca attaacgccc ctgaccctaa tagtggccat cattttgctc   7260
gtggcgcact acatgtactt gatcccaggg ctgcaggcag cagctgcgcg tgctgcccag   7320
aagagaacgg cagctggcat catgaagaac cctgttgtgg atggaatagt ggtgactgac   7380
attgacacaa tgcaattgac cccccaagtg gagaaaaaga ggacacaggt gctactcatg   7440
gcagtagccg tctccagcgc catactgtcg cggaccgcct gggggtgggg ggaggctggg   7500
gccctgatca cagccgcaac ttccactttg tgggaaggct ctccgaacaa gtactggaac   7560
tcctctacag ccacttcact gtgtaacatt tttaggggaa gttacttggc tggagcttct   7620
ctaatctaca cagtaacaag aaacgctggc ttggtcaaga gacgtggggg tggaacagga   7680
gagaccctgg gagagaaatg gaaggcccgc ttgaaccaga tgtcggccct ggagttctac   7740
tcctacaaaa agtcaggcat caccgaggtg tgcagagaag aggcccgccg cgccctcaag   7800
gacggtgtgg caacggggag ccatgctgtg tcccgaggaa gtgcaaagct gagatggttg   7860
gtggagcggg gatacctgca gccctatgga aaggtcattg atcttggatg tggcagaggg   7920
ggctggagtt actacgccgc caccatccgc aaagttcaag aagtgaaagg atacacaaaa   7980
ggaggccctg gtcatgaaga acccgtgttg gtgcaaagct atgggtggaa catagtccgt   8040
cttaagagtg gggtgacgt cttttcatatg gcggctgagc cgtgtgacac gttgctgtgt   8100
gacataggtg agtcatcatc tagtcctgaa gtggaagaag cacggacgct cagagtcctc   8160
tccatggtgg gggattggct tgaaaaaaga ccaggagcct tttgtataaa agtgttgtgc   8220
ccatacacca gcactatgat ggaaaccctg gagcgactgc agcgtaggta tgggggagga   8280
ctggtcagag tgccactctc ccgcaactct acacatgaga tgtactgggt ctctggagcg   8340
aaaagcaaca ccataaaaag tgtgtccacc acgagccagc tcctcttggg gcgcatggac   8400
gggcctagga ggcagtgaa atatgaggag gatgtgaatc tcggctctgg cacgcgggct   8460
gtggtaagct cgcgctgaagc tcccaacatg aagatcattg gtaaccgcat tgaaaggatc   8520
cgcagtgagc acgcggaaac gtggttcttt gacgagaacc cccatatag gacatgggct   8580
taccatggaa gctatgaggc ccccacacaa gggtcagcgt cctctctaat aaacgggttt   8640
gtcaggctcc tgtcaaaacc ctgggatgtg gtgactggaa tcacaggaat agccatgacc   8700
gacaccacac cgtatggtca gcaaagagtt ttcaaggaaa aagtggacac tagggtgcca   8760
gaccccccaag aaggcactcg tcaggttatg agcatggtct cttcctggtt gtggaaagag   8820
ctaggcaaac acaaacggcc acgagtctgt accaaagaag agttcatcaa caaggttcgt   8880
agcaatgcag cattagggc aatatttgaa gaggaaaaag agtggaagac tgcagtggaa   8940
gctgtgaacg atccaaggtt ctgggctcta gtggacaagg aaagagagca ccacctgaga   9000
ggagagtgcc agagttgtgt gtacaacatg atgggaaaaa gagaaaagaa acaaggggaa   9060
tttgaaaggg ccaagggcag ccgcgccatc tggtatatgt ggctaggggc tagatttcta   9120
gagttcgaag cccttggatt cttgaacgag gatcactgga tgggggagaga gaactcagga   9180
ggtggtgttg aagggctggg attacaaaga ctcggatatg tcctagaaga gatgagtcgc   9240
ataccaggag gaaggatgta tgcagatgac actgctggct gggacacccg catcagcagg   9300
tttgatctgg agaatgaagc tctaatcacc aaccaaatgg agaaaggca cagggccttg   9360
gcattggcca taatcaagta cacataccaa aacaaagtgg taaaggtcct tagaccagct   9420
gaaaagggta agacagttat ggacattatt cgagacaaga cccaagggg gagcggacca   9480
gttgtcactt acgctcttaa cacatttacc aacctagtgg tgcaactcat tcggaatatg   9540
gaggctgagg aagttctaga gatgcaagac ttgtggctgc tgcggaggtc agagaaagtg   9600
accaactggt tgcagagcaa cggatgggat aggctcaaac gaatggcagt cagtggagat   9660
gattggttg tgaagccaat tgatgataggg tttgcacatg ccctcagttt cttgaatgat   9720
atgggaaaag ttaggaagga cacacaagag tggaaaccct caactggatg ggacaactgg   9780
gaagaagttc cgttttgctc ccaccacttc aacaagctcc atctcaagga cgggaggtcc   9840
attgtggttc cctgccgcca ccaagatgaa ctgattggcc gggcccgcgt ctctccaggg   9900
gcgggatgga gcatccggga gactgcttgc ctagcaaaat catatgccga aatgtggcag   9960
ctcctttatt tccacagaag ggacctccga ctgatggcca atgccatttg ttcatctgtg  10020
ccagttgact gggttccaac tgggagaact acctggtcaa tccatggaaa gggagaatgg  10080
atgaccactg aagacatgct tgtggtgtgg aacagagtgt ggattgagga gaacgaccac  10140
atggaagaca agacccagt tacgaaatgg acagacattc cctatttggg aaaaagggaa  10200
gacttgtggt gtgatctct catagggcac agaccgcgca ccacctgggc tgagaacatt  10260
aaaaacacag tcaacatggt gcgcaggatc ataggtgatg aagaaagta catggactac  10320
ctatccaccc aagttcgcta cttgggtgaa gagggtctca caggctgagt gctgtaagca  10380
ccaatcttaa tgttgtcagg cctgctagtc agccacagct tgggaaagc tgtgcagcct  10440
gtgacccccc caggagaagc tgggaaacca agcctatagt caggccgaga acgccatggc  10500
acggaagaag ccatgctgcc tgtgagcccc tcagaggaca ctgagtcaaa aaccccacg  10560
cgcttggagg cgcaggatgg gaaaagaagg tggcgacctt ccccacccctt caatctgggg  10620
cctgaactgg agatcagctg tggatctcca gaagagggac tagtggttag aggaga      10676

SEQ ID NO: 6              moltype = DNA   length = 10808
FEATURE                   Location/Qualifiers
source                    1..10808
                          mol_type = genomic DNA
                          organism = Zika virus
SEQUENCE: 6
agttgttgat ctgtgtgaat cagactgcga cagttcgagt ttgaagcgaa agctagcaac     60
agtatcaaca ggttttattt tggatttgga aacgagagtt tctggtcatg aaaaacccaa    120
aaaagaaatc cggaggattc cggattgtca atatgctaaa acgcggagta gcccgtgtga    180
gcccctttgg gggcttgaag aggctgccag ccggacttct gctgggtcat gggcccatca    240
ggatggtctt ggcaattcta gcctttttga gattcacggc aatcaagcca tcactgggtc    300
tcatcaatag atggggttca gtggggaaaa agaggctat ggaaataata agaagttca    360
agaaagatct ggctgccatg ctgagaataa tcaatgctag gaaggagaag aagagacgag    420
gcgcagatac tagtgtcgga attgttggcc tcctgctcac cacagctatg gcagcggaag    480
tcactagacg tgggagtgca tactatatgt acttggacaa aaacgatgct ggggaggcca    540
tatcttttcc aaccacattg gggatgaata gtgttatat acagatcatg gatcttggac    600
acatgtgtga tgccaccatg agctatgaat gccctatgct ggatgagggg gtggaaccag    660
atgacgtcga ttgttggtgc aacacgacgt caacttgggt tgtgtacgga acctgccatc    720
acaaaaaagg tgaagcacgg agatctagaa gagctgtgac gctcccctcc cattccacta    780
```

```
ggaagctgca aacgcggtcg caaacctggt tggaatcaag agaatacaca aagcacttga  840
ttagagtcga aaattggata ttcaggaacc ctggcttcgc gttagcagca gctgccatcg  900
cttggctttt gggaagctca acgagccaaa aagtcatata cttggtcatg atactgctga  960
ttgccccggc atacagcatc aggtgcatag gagtcagcaa tagggacttt gtggaaggta 1020
tgtcaggtgg gacttgggtt gatgttgtct tggaacatgg aggttgtgtc accgtaatgg 1080
cacaggacaa accgactgtc gacatagagc tggttacaac aacagtcagc aacatggcgg 1140
aggtaagatc ctactgctat gaggcatcaa tatcagacat ggcttcggac agccgctgcc 1200
caacacaagg tgaagcctac cttgacaagc aatcagacac tcaatatgtc tgcaaaagaa 1260
cgttagtgga cagaggctgg ggaaatggat gtggacttttt tggcaaaggg agcctggtga 1320
catgcgctaa gtttgcatgc tccaagaaaa tgaccgggaa gagcatccag ccagagaatc 1380
tggagtaccg gataatgctg tcagttcatg gctcccagca cagtgggatg atcgttaatg 1440
acacaggaca tgaaactgat gagaatagag cgaaggttga gataacgccc aattcaccaa 1500
gagccgaagc caccctgggg ggttttggaa gcctaggact tgattgtgaa ccgaggacag 1560
gccttgactt ttcagatttg tattacttga ctatgaataa caagcactgg ttggtccaca 1620
aggagtggtt ccacgacatt ccattacctt ggcacgctgg ggcagacacc ggaactccac 1680
actgaacaa caaagaagca ctggtagagt tcaaggacgc acatgccaaa aggcaaactg 1740
tcgtggttct agggagtcaa gaaggagcag ttcacacggc ccttgctgga gctctggagg 1800
ctgagatgga tggtgcaaag ggaaggctgt cctctgtgcca cttgaaatgt cgcctgaaaa 1860
tggataaact tagattgaag ggcgtgtcat actccttgtg taccgcagcg ttcacattca 1920
ccaagatccc ggctgaaaca ctgcacggga cagtcacagt ggaggtacag tacgcaggga 1980
cagatggacc ttgcaaggtt ccagctcaga tggcggtgga catgcaaact ctgaccccag 2040
tgggaggtt gataaccgct aaccccgtaa tcactgaaag cactgagaac tctaagatga 2100
tgctgaaact tgatccacca tttgggact cttacattgt cataggagtc ggggagaaga 2160
agatcaccca ccactggcac aggagtggca gcaccattgg aaaagcattt gaagccactg 2220
tgagaggtgc caagagaatg gcagtcttgg gagacacagc ctgggactttt ggatcagttg 2280
gaggcgctct caactcattg ggcaagggca tccatcaaat ttttgagca gctttcaaat 2340
cattgtttgg aggaatgtcc tggttctcac aaatcctcat tggaacgttg ctgatgtggt 2400
tgggtctgaa cacaaagaat ggatctattt cccttatgtg cttggcctta ggggagtgt 2460
tgatcttctt atccacagcc gtctctgctg atgtggggtg ctcggtggac ttctcaaaga 2520
aggagacgag atgcggtaca ggggtgttcg tctataacga cgttgaagcc tggagggaca 2580
ggtacaagta ccatcctgac tcccccgta gattggcagc agcagtcaag caagcctggg 2640
aagatggtat ctgcgggatc tcctctgtttt caagaatgga gaacatcatg tggagatcag 2700
tagaagggga gctcaacgca atcttggaag agaatggagt tcaactgacg gtcgttgtgg 2760
gatctgtaaa aaaccccatg tggagaggtc cacagagatt gcccgtgcct gtgaacagc 2820
tgcccacgg ctggaaggct tgggggaaat cgtacttcgt cagagcagca aagacaaata 2880
acagctttgt cgtggatggt gacacactga aggaatgccc actcgaacat agagcatgga 2940
acagctttct tgtggaggat catgggttcg gggtatttca cactagtgtc tggctcaagg 3000
ttagagaaga ttattcatta gagtgtgatc cagccgttat tggaacagct gttaagggaa 3060
aggaggctgt acacagtgat ctaggctact ggattgagag tgagaagaat gacacatgga 3120
ggctgaagag ggcccatcta atcgagatga aaacatgtga atggccaaag tcccacacat 3180
tgtgggcaga tggaatagaa gagagtgatc tgatcattcc caagtctta gctgggccac 3240
tcagccatca caataccaga gagggctaca ggacccaaat gaaagggcca tggcacagtg 3300
aagagcttga aattcggttt gaggaatgcc cgggcactaa ggtccacgtg gaggaaacat 3360
gtggaacaag aggaccatct ctgagatcaa ccactgcaag cggaagggtg atcgaggaat 3420
ggtgctgcag ggagtgcaca atgcccccac tgtcgttccg ggctaaagat ggctgttggt 3480
atggaatgga gataaggccc aggaaagaac cagaaagcaa cttagtaagg tcagtggtga 3540
ctgcaggatc aactgatcac atggatcact tctcccttgg agtgcttgtg attctgctca 3600
tggtgcagga agggctgaag aagagaatga ccacaaagat catcataagc acatcaatgg 3660
cagtgctggt agctatgatc ctgggaggat tttcaatgag tgacctggct aagcttgcaa 3720
ttttgatggg cgccaccttc gcggaaatga acactggagg agatgtagct catctggcgc 3780
tgatacggc attcaaagtc agaccagcgt tgctggtatc tttcatcttc agagctaattt 3840
ggacaccccg tgaaagcatg ctgctggcct tggcctcgtg tcttttgcaa actgcgatct 3900
ccgccttgga aggcgacctg atggttctca tcaatggttt tgctttggcc tggttggcaa 3960
tacgagcgat ggttgttcca cgcactgata acatcaccct tgcaatcctg gctgctctga 4020
caccactggc ccggggcaca ctgcttgtgg cgtgggagac aggcctttgt acttgcgggg 4080
ggtttatgct cctctctctg aagggaaaag gcagtgtgaa gaagaactta ccatttgtca 4140
tggcctggg actaaccgct gtgaggctgg tcgaccccat caacgtggtg ggactgctgt 4200
tgctcacaag gagtgggaag cggagctggc ccctagcga agtactcaca gctgttggcc 4260
tgatatgcgc attggctgga gggttcgcca aggcagatat agagatggct gggcccatgg 4320
ccgcggtcgg tctgctaatt gtcagttacg tggtctcagg aaagagtgtg gacatgtaca 4380
ttgaaagagc aggtgacatc acatgggaaa aagatgcgga agtcactgga aacagtcccc 4440
ggctcgatgt ggcgctagat gagagtgtg atttctccct ggtggaggat gacggtcccc 4500
ccatgagaga gatcatactc aaggtggtcc tgatgaccat ctgtggcatg aacccaatag 4560
ccatacccttt tgcagctgga gcgtggtacg tatacgtgaa gactggaaaa aggagtggtg 4620
ctctatggga tgtgcctgct cccaaggaag taaaaagggg ggagaccaca gatgagtgt 4680
acagagtaat gactcgtaga ctgctaggtt caacacaagt tggagtggga ttatgcaag 4740
agggggtctt tcacactatg tggcacgtca caaaggatc cgcgctgaga agcggtgaag 4800
ggagacttga tccatactgg ggagatgtca agcaggatct ggtgtcatac tgtggtccat 4860
ggaagctaga tgccgcctgg gacgggcaca gcgaggtgca gctcttggcc gtgccccgg 4920
gagagagagc gaggaacatc cagactctgc ccggaatatt taagacaaag gatgggaca 4980
ttggagcggt tgcgctggat tacccagcag gaacttcagg atctccaatc ctagacaagt 5040
gtgggagagt gataggactt tatggcaatg ggtcgtgat caaaaatggg agttatgtta 5100
gtgccatcac ccaagggagg agggaggaag agactcctgt tgagtgcttc gagccttcga 5160
tgctgaagaa gaagcagcta actgtcttag acttgcatcc tgggagctggg aaaaccagga 5220
gagttcttcc tgaaatagtc cgtgaagcca taaaacaag actccgtact gtgatcttag 5280
ctccaaccag ggttgtcgct gctgaaatgg aggaagccct tagagggctt ccagtgcgtt 5340
atatgacaac agcagtcaat gtcacccact ctggaacaga aatcgtcgac ttaatgtgcc 5400
atgccacctt cacttcacgt ctactacagc caatcagagt ccccaactat aatctgtata 5460
ttatggatga ggcccacttc acagatccct caagtatagc agcaagagga tacatttcaa 5520
```

```
caagggttga gatgggcgag gcggctgcca tcttcatgac cgccacgcca ccaggaaccc   5580
gtgacgcatt tccggactcc aactcaccaa ttatggacac cgaagtggaa gtcccagaga   5640
gagcctggag ctcaggcttt gattgggtga cggatcattc tggaaaaaca gtttggtttg   5700
ttccaagcgt gaggaacggc aatgagatcg cagcttgtct gacaaaggct ggaaaacggg   5760
tcatacagct cagcagaaag acttttgaga cagagttcca gaaaacaaaa catcaagagt   5820
gggactttgt cgtgacaact gacatttcag agatgggcgc caactttaaa gctgaccgtg   5880
tcatagattc caggagatgc ctaaagccgg tcatacttga tggcgagaga gtcattttgg   5940
ctggacccat gcctgtcaca catgccagcg ctcccagag gaggggggcgc ataggcagga   6000
atcccaacaa acctggagat gagtatctgt atggaggtgg gtgcgcagag actgacgaag   6060
accatgcaca ctggcttgaa gcaagaatgc tccttgacaa tatttacctc caagatggcc   6120
tcatagcctc gctctatcga cctgaggccg acaaagtagc agccattgag ggagagttca   6180
agcttaggac ggagcaaagg aagacctttg tggaactcat gaaaagagga gatcttcctg   6240
tttggctggc ctatcaggtt gcatctgccg gaataaccta cacagataga agatggtgct   6300
ttgatggcac gaccaacaac accataatgg aagacagtgt gccggcagag gtgtggacca   6360
gacacggaga gaaaagagtg ctcaaaccga ggtggatgga cgccagagtt tgttcagatc   6420
atgcggccct gaagtcattc aaggagtttg ccgctgggaa aagaggagcg gcttttggag   6480
tgatggaagc cctgggaaca ctgccaggac acatgacaga gagattccag gaagccattg   6540
acaacctcgc tgtgctcatg cgggcagaga ctggaagcag gccttacaaa gccgcggcgg   6600
cccaattgcc ggagacccta gagaccatta tgcttttggg gttgctggga acagtctcgc   6660
tgggaatctt tttcgtcttg atgaggaaca agggcatagg gaagatgggc tttgaaatgg   6720
tgactcttgg ggccagcgca tggctcatgt ggctctcgga aattgagcca gccagaattg   6780
catgtgtcct cattgttgtg ttcctattgc tggtggtgct catacctgag ccagaaaagc   6840
aaagatctcc ccaggacaac caaatggcaa tcatcatcat ggtagcagta ggtcttctgt   6900
gcttgattac cgccaatgaa ctcggatggt tggagagaac aaaagagtga ctaagccatc   6960
taatgggaag gagagaggag ggagcaacca taggattctc aatggacatt gacctgcggc   7020
cagcctcagc ttgggccatc tatgctgcct tgacaacttt cattaccccca gccgtccaac   7080
atgcagtgac cacttcatac aacaactact ccttaatggc gatggccacg caagctggag   7140
tgttgtttgg tatgggcaaa gggatgccat tctacgcatg ggactttgga gtcccgctgc   7200
taatgatagg ttgctactca caattaacac ccctgacccct aatagtggcc atcatttgc    7260
tcgtgcgca ctacatgtac ttgatcccag ggctgcgtga agcagctgcg cgtgctgccc    7320
agaagagaac ggcagctggc atcatgaaga accctgttgt ggatggaata gtggtgactg    7380
acattgacac aatgacaatt gacccccaag tggagaaaaa gatgggacag gtgctactca    7440
tagcagtagc agtctccagc gccatactgt cgcggaccgc ctgggggtgg ggaggctga    7500
gggccctgat cacagccgca acttccactt tgtgggaagg ctctccgaac aagtactgga    7560
actcctctac agccacttca ctgtgtaaca tttttagggg aagttacttg gctggagctt    7620
ctctaatcta catagtaaca agaaacgctg gcttggtcaa gagacgtggg ggtggaacag    7680
gagagaccct gggagagaaa tggaaggccc gcttgaacca gatgtcggcc ctggagttct    7740
actcctacaa aaagtcaggc atcaccgagg tgtgcagaga gaggcccgc cgcgccctca    7800
aggatgtgtg ggcaacggga ggccatgctg tgtcccgagg aagtcaaag ctgagatggt    7860
tggtggagcg gggatacctg cagccctatg gaaaggtcat tgatcttgga tgtggcagag    7920
ggggctggag ttactacgcc gccaccatcc gcaaagttca agaagtgaaa ggatacacaa    7980
aaggaggccc tggtcatgaa gaacccgtgt tggtgcaaag ctatgggtgg aacatagtcc    8040
gtcttaagag tggggtggac gtcttttcata tggcggctga gccgtgtgac acgttgctgt    8100
gtgacatagg tgagtcatca tctagtcctg aagtggaaga agcacggacg ctcagagtcc    8160
tctccatggt gggggattgg cttgaaaaaa gaccaggagc cttttgtata aaagtgttgt    8220
gcccatacac cagcactatg atggaaaccc tggagcgact gcagcgtagg tatgggggag    8280
gactggtcag agtgccactc tcccgcaact ctacacatga gatgtactgg gtctctggag    8340
cgaaaagcaa caccataaaa agtgtgtcca ccacgagcca gctcctcttg ggggcgcatgg    8400
acgggcctag gaggccagtg aaatatgagg aggatgtgaa tctcggctct ggcacgcggg    8460
ctgtggtaag ctgcgctgaa gctcccaaca tgaagatcat tggtaaccgc attgaaagga    8520
tccgcagtga gcacgcggaa acgtggttct ttgacgagaa ccacccatat aggacatggg    8580
cttaccatgg aagctatgag gcccccacac aagggtcagc gtcctctcta ataaacgggg    8640
ttgtcaggct cctgtcaaaa ccctgggatg tggtgactgg agtcacagga atagccatga    8700
ccgacaccac accgtatggt cagcaaagag ttttcaagga aaaagtggac actagggtgc    8760
cagacccca agaaggcact cgtcaggtta tgagcatggt ctcttcctgg ttgtggaaag    8820
agctaggcaa acacaaacgg ccacgagtct gtaccaaaga agagttcatc aacaaggttc    8880
gtagcaatgc agcattaggg gcaatatttt aagaggaaaa agagtggaag actgcagtgg    8940
aagctgtgaa cgatccaagg ttctgggctc tagtggacaa ggaaagagag caccacctga    9000
gaggagagtg ccagagttgt gtgtacaaca tgatgggaaa aagaaaaag aaacaagggg    9060
aatttggaaa ggccaagggc agccgcgcca tctggtatat gtggctaggg gctagatttc    9120
tagagttcga agcccttgga ttcttgaacg aggatcactg gatggggaga gagaactcag    9180
gaggtggtgt tgaagggctg ggattacaaa gactcggata tgtcctagaa gagatgagtc    9240
gcataccagg aggaaggatg tatgcagatg acactgctgg ctgggacacc cgcatcagca    9300
ggttcgatct ggagaatgaa gctctaatca ccaaccaaat ggaaaaggtg catagggtca    9360
tggcattggc cataatcaag tacacatacc aaaacaaagt ggtaaaggtc cttagaccag    9420
ctgaaaaagg gaaaacagtt atggacatta tttcgagaca agaccaaagg gggagcggac    9480
aagttgtcac ttacgctctt aacacattta ccaacctagt ggtgcaactc attcggaata    9540
tggaggctga ggaagttcta gagatgcaag acttgtggct gctgcggagg tcagagaaag    9600
tgaccaactg gttgcagagc aacggatggg ataggctcgca gtcagtgtgg aacatgatcg    9660
atgattcgt tgtgaagcca attgatgata ggtttgcaca tgccctcagg ttcttgaatg    9720
atatgggaaa agttaggaag gacacacaag agtggaaacc ctcaactgga tgggacaact    9780
gggaagaagt tccgttttgc tcccaccact tcaacaagct ccatctcaag gacgggaggt    9840
ccattgtggt tccctgccgc caccaagatg aactgattgg ccgggcccgc gtctctccag    9900
gggcggatgg gagcatccgg gagactgctt gcctagcaaa atcatatgcg caaatgtggc    9960
agctcctta tttccacaga agggacctcc gactgatggc caatgccatt tgttcatctg   10020
tgccagttga ctgggttcca actgggagaa ctacctggtc aatccatgga aagggagaat   10080
ggatgaccac tgaagacatg cttgtggtgt ggaacagagt gtggattgag agaacgacc    10140
acatggaaga caagacccca gttacgaaat ggacagacat tccctatttg ggaaaaaggg   10200
aagacttgtg tgtggatctc tcataggggc acagaccgcg caccacctgg gctgagaaca   10260
```

```
ttaaaaacac agtcaacatg gtgcgcagga tcataggtga tgaagaaaag tacatggact   10320
acctatccac ccaagttcgc tacttgggtg aagaagggtc tacacctgga gtgctgtaag   10380
caccaatctt aatgttgtca ggcctgctag tcagccacag cttggggaaa gctgtgcagc   10440
ctgtgacccc cccaggagaa gctgggaaac caagcctata gtcaggccga aacgccatg    10500
gcacggaaga agccatgctg cctgtgagcc cctcagagga cactgagtca aaaaacccca   10560
tgcgcttgga ggcgcaggat gggaaaagaa ggtggcgacc ttccccaccc ttcaatctgg   10620
ggcctgaact ggagatcagc tgtggatctc cagaagaggg actagtggtt agaggagacc   10680
ccccggaaaa cgcaaaacag catattgacg ctgggaaaga ccagagactc catgagtttc   10740
caccacgctg gccgccaggc acagatcgcc gaatagcggc ggccggtgtg gggaaatcca   10800
tgggtctt                                                            10808

SEQ ID NO: 7            moltype = DNA   length = 10807
FEATURE                 Location/Qualifiers
source                  1..10807
                        mol_type = genomic DNA
                        organism = Zika virus
SEQUENCE: 7
agttgttgat ctgtgtgaat cagactgcga cagttcgagt ttgaagcgaa agctagcaac     60
agtatcaaca ggttttattt tggatttgga acgagagtt tctggtcatg aaaaacccaa    120
aaaagaaatc cggaggattc cggattgtca atatgctaaa acgcggagta gcccgtgtga    180
gccccttttgg gggcttgaag aggctgccag ccggacttct gctgggtcat gggcccatca    240
ggatggtctt ggcgattcta gccttttttga gattcacgac aatcaagcca tcactgggtc    300
tcatcaatag atggggttca gtgggaaaaa aagaggctat ggaataata aagaagttca    360
agaaagatct ggctgccatg ctgagaataa tcaatgctag gaaggagaag aagagacgag    420
gcacagatac tagtgtcgga attgttgcc tcctgctgac cacagctatg gcagcggagg    480
tcactagacg tgggagtgca tactatatgt acttggaaga aagcgatgct ggggaggcca    540
tatcttttcc aaccacactg gggatgaata agtgttatat acagatcatg gatcttggac    600
acatgtgtga tgccaccatg agctatgaat gccctatgct ggatgagggg gtagaaccag    660
atgacgtcga ttgttggtgc aacacgacgt caacttgggt tgtgtacgga acctgccatc    720
acaaaaaagg tgaagcacgg agatccagaa gagctgtgac gctccccctcc cattccacta    780
ggaagctgca aacgcggtcg cagacctggt tggaatcaag agaatacaca aagcacttga    840
ttagagtcga aaattggata ttcaggaacc ctggcttcgc gttagcagca gctgccatcg    900
cttggctttt gggaagctca acgagccaaa aagtcatata cttggtcatg atactgctga    960
ttgccccggc atacagcatc aggtgcatag gagtcagtaa tagggacttt gtggaaggta   1020
tgtcaggtgg gacttgggtt gatgttgtct tggaacatgg aggttgtgtc accgtaatgg   1080
cacaggacaa accgactgtc gacatagagc tggttacaac aacagtcagc aacatggcgg   1140
aggtaagatc ctactgctat gaggcatcaa tatcggacat ggcttcggac agccgctgcc   1200
caacacaagg tgaagcctac cttgacaagc aatcagacac tcaatatgtc tgcaaaagaa   1260
cgttagtgga cagggcctgg ggaaatggat gtggacttttt tggcaagggg agcctggtga   1320
catgcgctaa gtttgcatgc tccaagaaaa tgaccgggaa gagcatccag ccagagaatc   1380
tggagtaccg gataatgctg tcagttcatg gctcccagca cagtgggatg atcgttaatg   1440
acacaggaca tgaaactgat gagaatagag cgaaggttga taacgccc aattcaccaa      1500
gagccgaagc caccctgggg ggttttgaa gcctaggact tgattgtgaa ccgaggacag   1560
gccttgactt ttcagatttg tattacttga ctatgaacaa caagcactgg ttggttcaca   1620
aggagtggtt ccacgacatt ccattacctt ggcacactgg ggcagacacc ggaactccac   1680
actgaacaa caaagaagca ctggtagagt tcaaggacgc acatgccaaa aggcaaactg   1740
tcgtggttct agggagtcaa gaaggagcag ttcacacggc ccttgctggg gctctggagg   1800
ctgagatgga tggtgcaaag ggaaggctgt cctctggcca cttgaaatgt cgcctgaaaa   1860
tggataaaact tagattgaag ggcgtgtcat actccttgtg taccgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga catgcaaact ctgacccccag   2040
ttgggaggtt gataaccgct aaccccgtaa tcactgaagg cactgagaac ctcaagatga   2100
tgctggaact tgatccacca tttggggact cttacattgt cataggagtc ggggagaaga   2160
agatcacca ccactggcac aggagtggca gcaccattgg aaaagcattt gaagccactg   2220
tgagaggtgc caagagaatg gcagtcttgg gagacacagc ctgggacttt ggatcagttg   2280
gaggcgttct taactcattg ggcaagggca tccatcaaat tttttggagca gctttcaaat   2340
cattgttgg aggaatgtcc tggttctcac aaattctcat tggaacgttg ctgatgtggt   2400
tgggtctgaa tacaaagaat ggatctattt cccttatgtg cttggcctta ggggagtgt    2460
tgatcttctt atccacagcc gtctccgctg atgtggggtg ctcggtggac ttctcaaaga   2520
aggaaacgag atgcggtaca ggggtgttcg tctataacga cgttgaagcc tggagggaca   2580
ggtacaagta ccatcctgac tcccctcgta gattggcagc agtagtcaag caagcctggg   2640
aagatgtat ctgtgggatc tcctctgttt caagaatgga aaacatcatg tggagatcag    2700
tagaagggga gctcaacgca atcctggaag agaatgagt tcaactgacg gtcgttgtg    2760
gatctgtaaa aaacccccatg tggagaggtc cacagagatt ccgtcgtgaa ccgtgaacgagc   2820
tgccccacgg ctgaaggct tgggggaaat cgtacttcgt cagagcagca aagacaaata   2880
acagctttgt cgtggatggt gacacactga aggaatgccc actcaaacat agagcatgga   2940
acagctttct tgtggaggat catggggtcg gggtatttca cactagtgtc tggctcaagg   3000
ttagagaaga ttattcacta gagtgtgatc agccgtgcat tggaacagct gttaaggaa    3060
aggaggctgt acacagtgat ctaggctact ggattgagaa tgagaagaac agacatgga   3120
ggctgaggag ggcccacctg atcgagatga aacatgtga atggccaaag tcccacacat   3180
tgtgacagga tggaatagaa gagagtgatc tgatcatacc caagtcttta gctgggccac   3240
tcagccatca caacaccaga gagggctaca ggacccaaat gaaagggcca tggcacagtg   3300
aagagcttga aattcggttt gaggaatgcc caggcactaa ggtccacgtg gagaaaacat   3360
gtggaacaag gggaccatct ctgagatcaa ccactgaaag tgggaagggtg atcgaggaat   3420
ggtgctgcag ggagtgcaca atgccccac tgtcgttccg ggctaaagat ggctgttggt   3480
atggaatgga gataaggccc aggaaagaac cagaaagtaa cttagtaagg tcaatggtga   3540
ctgcaggatc aactgatcac atggatcact tttcccttgg agtgcttgtg attctgctca   3600
tggtgcagga agggcctgaag aagagaatga ccacaaagat catcataagc acatcaatgg   3660
cagtgctggt agctatgatc ctgggaggat tttcaatgag tgatctggct aagcttgcaa   3720
```

```
ttttgatggg tgccacctttt gcggaaatga acactggagg agatgtagct catctggcgc    3780
tggtagcggc attcaaagtc agaccagcgt tgctggtatc tttcatcttc agagctaatt    3840
ggacaccccg tgaaagcatg ctgctggcct tggcctcgtg tcttttgcaa actgcgatct    3900
ccgccttgga aggcgacctg atggttctca tcaatggttt tgctttggcc tggttggcaa    3960
tacgagcgat ggttgttcca cgcactgaca atatcacctt ggcaatcctg gctgctctga    4020
caccactggc ccggggcaca ctgcttgtgg cgtggagagc aggccttgct acttgcgggg    4080
ggttcatgct cctctctctg aaggggaaag gcagtgtgaa gaagaactta ccatttgtca    4140
tggccctggg actaaccgct gtgaggctgg tcgaccccat caacgtggtg ggactgctgt    4200
tgctcacaag gagtgggaag cggagctggc cccctagcga agtactcaca gctgttggcc    4260
tgatatgcgc attggctgga gggttcgcca aggcagatat agagatggct gggcccatgg    4320
ccgcggtcgg tctgctaatt gtcagttacg tggtctcagg aaaagagtgtg gacatgtaca    4380
ttgaaagagc aggtgacatc acatgggaaa aagatgcgga agttactgga aacagtcccc    4440
ggctcgatgt ggcactagat gagagtggtg atttctccct ggtggaggat gacggtcccc    4500
ccatgagaga gatcatactc aaagtgtcc tgatgaccat ctgtggcatg aacccaatag    4560
ccataccctt tgcagctgga gcgtggtacg tatacgtgaa aactggaaaa aggagtggtg    4620
ctctatggga tgtgcctgct cccaaggaag taaaaaaggg ggagaccaca gatggagtgt    4680
acagagtaat gactcgtaga ctgctaggtt caacacaagt tggagtggga gttatgcaag    4740
aggggggtctt tcacactatg tggcatgtca caaaggatc cgcgctgaga agcggtgaag    4800
ggagacttga tccatactgg ggagatgtca agcaggatcc ggtgtcatac tgtggtccat    4860
ggaagctaga tgccgcctgg gacgggcaca gcgaggtgca gctcttggcc gtgcccccg     4920
gagagagagc gaggaacatc cagactctgc ccggaatatt taagacaaag gatgggggaca    4980
ttggagcggt tgcgctggac tatccagcag gaacttcagg atctccaatc ctagacaagt    5040
gtgggagagt gataggactc tatggcaatg gggtcgtgat caagaatggg agttatgtca    5100
gtgccatcac ccaagggagg agggaggaag agactcctgt tgagtgcttc gagccttcga    5160
tgctgaagaa aagcagcta actgtcttag acttgcatcc tggagctggg aaaaccagga    5220
gagttcttcc tgaaatagtc cgtgaagcca taaaaacgag actccgtact gtgatcttag    5280
ctccaaccag ggttgtcgct gctgaaatgg aggaagccct tagagggctt ccagtgcgtt    5340
atatgacaac agcagtcaat gtcacccatt ctgggacaga aatcgttgac ttaatgtgcc    5400
atgccacctt cacttcacgt ctactacagc caatcagagt ccccaactat aatctgtata    5460
tatgatgga ggcccacttc acagatccct caagtatagc agcaaggtac tacatttcaa    5520
caagggttga gatgggcgag gcagctgcca tcttcatgac cgccacgcca ccaggaaccc    5580
gtgacgcatt cccggactcc aactcaccaa ttatggacac cgaagtggaa gtcccagaga    5640
gagcctggag ctcaggcttt gattgggtga cggatcattc tggaaaaaca gtttggtttg    5700
tcccaagcgt gaggaacggc aatgagatcg cagcttgtct gacaaaggct ggaaaacggg    5760
tcatacagct cagcagaaag acttttgaga cagagttcca gaaaacaaaa catcaagagt    5820
gggacttcgt cgtgacaact gacatttcag agatgggcgc caactttaaa gctgaccgtg    5880
tcatagattc caggagatgc ctaaagccgg tcatacttga tggcgagaga gtcattctgg    5940
ctggacccat gcctgtcaca catgccagcg ctgcccagag gaggggcgc ataggcagga    6000
atcccaacaa acctggagat gagtatctgt atggaggtgg gtgcgcagag actgatgaag    6060
accatgcaca ctggcttgaa gcaagaatgc tccttgacaa tatttacctc caagatggcc    6120
tcatagcctc gctctatcga cctgaggccg acaaagtagc agccattgag ggagagttca    6180
agcttaggac ggagcaaagg aagacctttg tggaactcat gaaaagagga gatcttcctg    6240
tttggctggc ctatcaggtt gcatctgccg gaataaccta cacagataga agtggtgct     6300
ttgatggcat gaccaacaac accataatgg aagacagttg gccggcagag gtgtggacca    6360
gacacgagga gaaagagtg ctcaaaccga ggtggatgga cgccagagtt tgttcagatc     6420
atgcggccct gaagtcattc aaggagtttg ccgctgggaa aagaggagcg gcttttgag    6480
tgatgaagaa cctgggaaca ctgccaggac acatgacgga gagattccag gaagccattg    6540
acaacctcgc tgtgctcatg cgggcagaga ctgaagcag gccttacaaa gccgcggcgg    6600
cccaattgcc ggagaccta gagaccatta tgctttggg gttgctggga acagtctcgc     6660
tgggaatctt tttcgtcttg atgcggaaca agggcatagg gaagatgggc tttggaatgg    6720
tgactcttgg ggccagcgca tggctcatgt ggctctcgga aattgagcca gccagaattg    6780
catgcgtcct cattgttgtg ttcctattgc tggtggtgct catacctgag ccagaaagc     6840
aaagatcccc caggacaac caaatggcaa tcatcatcat ggtagcagta ggtcttctgg    6900
gcttgattac cgccaatgaa ctcggatggt tggagagaac aaagagtgac ctaagccatc    6960
taatggaag gagagaggag ggggcaacca taggattctc aatggacatt gacctgcgc   7020
cagcctcggc ctgggccatc tatgctgccc tgacaacttt cattacccca gccgtccaac    7080
atgcagtgac cacttcatac aacaactact ccttaatggc gatggccacg caagctggag    7140
tgttgtttgg tatgggcaaa gggatgccat tctacgcatg gactttgga gtcccgctgc    7200
taatgatagg ttgctactca caattaacac ccctgacct aatatggct atcattttgc    7260
tcgtggcgca ctacatgtac ttgatccag gctgcaggc agcagctgcg cgtgctgccc    7320
agaagagaac ggcagctggc atcatgaaga accctgttgt ggatggaata gtgtgactg     7380
acattgacac aatgactatt gacccccaag tggagaaaaa gatgggacag gtgctactca    7440
tagcagtagc cgtctccagc gccatactgt cgcggaccgc ctgggggtgg ggggaagctg    7500
gggccctgat cacagctgca acttccactt tgtgggaagg ctctccgaac aagtactgga    7560
actcctctac agccacttca ctgtgcaaca ttttttaggg aagttacttg ctggagctt      7620
ctctaatcta cacagtaaca agaaacgctg cttggtggcaa gagacgtggg ggtggaacag    7680
gagagaccct gggagagaaa tggaaggccc gcttgaacca gatgtcggcc ctggagttct    7740
actcctacaa aaagtcaggc atcaccgagg tgtgcagaga agaggcccgc cgcgccctca    7800
aggacggtgt ggcaacggga gccatgctgt gtcccggaa aagtcaaag ctgagatggt      7860
tggtggagcg gggatacctg cagccctatg gaaaggtcat tgatcttgga tgtggcagag    7920
ggggctggag ttactacgcc gccaccatcc gcaaagttca agaagtgaaa ggatacacaa    7980
aaggaggcc tggtcatgaa gaaccatgt tggtgcaaag ctatgggtgg aacatagtcc      8040
gtcttaagag tggggtggac gtctttcata tggcggctga gccgtgtgac acgttgctgt    8100
gtgacatagg tgagtcatca tctagtcctg aagtggaaga agcacggacg ctcagagtcc    8160
tctccatggt gggggattgg cttgaaaaaa gaccaggagc cttttgtgta aaagtgttgt    8220
gcccatacac cagcactatg atggaaaccc tggagcgact gcagcgtagg tatgggggag    8280
gactggtcag agtgccactc tcccgcaact ctacacatga gatgtactgg gtctctggag    8340
cgaaagcaa caccataaaa agtgtgtcca ccacgagcca gctcctcttg gggcgcatgg    8400
acgggcccag gaggccagtg aaatatgagg aggatgtgaa tctcggctct ggcacgcggg    8460
```

```
ctgtggtaag ctcgctgaa gctcccaaca tgaagatcat tggtaaccgc attgaaagga    8520
tccgcagtga gcacgcggaa acgtggttct tgacgagaa ccaccctat aggacatggg    8580
cttaccatgg aagctatgag gcccctacac aagggtcagc gtcctctcta ataaacgggg    8640
ttgtcaggct cctgtcaaaa ccctgggatg tggtgactgg agtcacagga atagccatga    8700
ccgacaccac accgtatggt cagcaaagag ttttcaagga aaaagtggac accagggtgc    8760
cagaccccca agaaggcact cgtcaggtta tgagcatggt ctcttcctgg ttgtgggaaag   8820
agctaggcaa acacaaacgg ccacgagtct gtaccaaaga agagttcatc aacaaggttc    8880
gtagcaatgc agcattaggg gcaatatttg aagaggaaaa agagtggaag accgcagtgg    8940
aagctgtgaa cgatccaagg ttctgggctc tagtggacaa ggaaagagag caccacctga    9000
gaggagagtg ccagagctgt gtgtacaaca tgatgggaaa aagagaaaag aaacaagggg    9060
aatttggaaa ggccaagggc agccgcgcca tctggtatat gtggctaggg gctagatttc    9120
tagagttcga agcccttgga ttcttaaatg aggatcactg gatggggaga gagaactcag    9180
gaggtggtgt tgaagggctg ggattacaaa gactcggata tgtcctagaa gagatgagtc    9240
gcataccagg aggaaggatg tatgcagatg acactcggga caccc cgcatcagca    9300
ggtttgatct ggagaatgaa gctttaatca ccaaccaaat ggagaaaggg cacagggcct    9360
tagcattggc cataatcaag tacacatacc aaaacaaagt ggtaaggtc cttagaccag    9420
ctgaaaaagg gaagacagtt atggacatta tttcaagaca agaccaaagg gggagcggac    9480
aagttgtcac ttacgctctt aacacattta ccaacctagt ggtgcaactc attcggaata    9540
tggaggctga ggaagttcta gagatgcaag acttgtggct gctgcggagg tcagagaaag    9600
tgaccaactg gttgcagagc aacgatgggg ataggctcaa acgaatggca gtcagtggag    9660
atgattgcgt tgtgaagcca attgatgata ggtttgcaca tgccctcagg ttcttgaatg    9720
atatgggaaa agttaggaag gacacacaag aatggaaacc ctcaactgta tgggacaact    9780
gggaagaagt tccgttttgt tcccaccact tcaacaagcc ccatctcaag gacgggaggt    9840
ccattgtggt tccctgccgc caccaagatg aactgattgg ccgggccgt gtctctccag    9900
gggcgggatg gagcatccgg gagactgctt gcctagcaaa gtcatatgcg caaatgtggc    9960
agctccttta tttccacaga caagggacct cc gactgatgac caatgccatc tgttcatctg   10020
tgccagttga ctgggttcca actgggagaa ctacctggtc aatccatgaa agggagaat   10080
ggatgaccac tgaagacatg cttgtggtgt ggaacagagt gtggattgag agaacgacc   10140
acatggaaga caagacccca gttacgaaat ggacagacat tcctatctg ggaaaagggg   10200
aagacttgtg gtgtggatct ctcatagggc acagaccgcc caccacctgg gctgagaaca   10260
ttaaaaacac agtcaacatg gtgcgcagga tcataggtga tgaagaaaag tacatggact   10320
acctatccac ccaagttcgc tacttgggtg aagaagggtc tacacctgga gtgctataag   10380
caccaatctt agtgttgtca ggcctgctag tcagccacag cttggggaaa gctgtgcagc   10440
ctgtgacccc cccaggagag gctgggaaac caagcccata gtcaggccga aacgccatg   10500
gcacggaaga agccatgctg cctgtgagcc cctcagagga cactgagtca aaaaacccca   10560
cgcgcttgga ggcgcaggat gggaaaagaa ggtggcgacc ttcccacccc ttcaatctgg   10620
ggcctgaact ggagatcagc tgtggatctc cagaagaggg actagtggtt agaggagacc   10680
ccccggaaaa cgcaaaacag catattgacg ctgggaaaga ccagagactc catgagtttc   10740
caccacgctg gccgccaggc acagatcgcc gaatagcggc ggccggtgtg gggaaatcca   10800
tgggtct                                                            10807

SEQ ID NO: 8        moltype = DNA  length = 10807
FEATURE             Location/Qualifiers
source              1..10807
                    mol_type = genomic DNA
                    organism = Zika virus
SEQUENCE: 8
agttgttgat ctgtgtgaat cagactgcga cagttcgagt ttgaagcgaa agctagcaac      60
agtatcaaca ggtttatttt tggatttgga aacgagagtt tctggtcatg aaaaacccaa     120
aaaagaaatc cggaggattc cggattgtca atatgctaaa acgcggagta gcccgtgtga     180
gccccttttgg gggcttgaag aggctgccag ccggacttct gctgggccat gggcccatca     240
ggatggtctt ggcgatacta gccttttga gattcacggc aatcaagcca tcactgggtc     300
tcatcaatag atgggggttca gtggggaaaa aagaggctat ggaaataata aagaagttca     360
agaaagatct ggctgccatg ctgagaataa tcaatgctag gaaggagaag aagagacgag     420
gcgcagatac tagcgtcgga attgttggcc tcctcctgac cacagccatg gcagtagagg     480
tcactagacg tgggagtgca tactatatgt acttggacag aagcgatgct ggggaggcca     540
tatcttttcc aacccactg gggatgaata agtgttacat acaaatcatg gatcttggac     600
acatgtgtga tgccaccatg agctatgaat gccctatgtt ggatgagggg gtagaaccag     660
atgacgtcga ttgctggtgc aacacgacat caacttgggt tgtgtatgga acctgccaaa     720
acaaaaaagg tgaagcacgg agatctagaa gagctgtgac gctcccctcc cattccacta     780
ggaagctgca aacgcggtcg cagacctggt tggaatcaag agaatacaca aagcacctga     840
ttagagttga aaattggata ttcaggaacc ctggcttcgc gttagcagca gctgtcatcg     900
cttggctttt gggaagttca acgagccaaa aagtcatata tctggtcatg atactgctga     960
ttgccccggc atacagcatc aggtgtatag gagtcagcaa taggactttt gtggaaggta    1020
tgtcaggtgg gacttgggtt gatgttgtct tggaacatgg aggttgtgtt accgtaatgg    1080
cacaggacaa accgactgtc gacatagagc tggttacaac aacagtcagc aacatggcgg    1140
aggtaagatc ctactgctat gaggcatcaa tatcggatat ggcttcggac agccgctgcc    1200
caacacaagg tgaggcctac cttgacaagc agtcagacac tcaatatgtc tgcaaaagaa    1260
cgttagtgga cagaggctgg ggaaatgat gtggactttt tggcaaaggg agctggtga    1320
catgcgctaa gtttgcatgc tccaagaaaa tgaccgggaa gagcatccag ccagagaatc    1380
tggagtaccg gataatgctg tcagttcatg gctcccagca cagtgggatg atcgttaatg    1440
acacaggaca tgaaactgat gagaatagag cgaaggttga gataacgccc aattcaccaa    1500
gagccgaagc caccctgggg ggttttggga gcctaggact tgattgtgaa ccgaggacag    1560
gccttgactt ttcagatttg tattacctga ctatgaataa caagcactgg ttggttcaca    1620
aggagtggtt ccacgacatt ccattacctt ggcatgctgg ggcagacact ggaactccac    1680
attggaacaa caaagaagca ctggtagagt tcaaggacgc acatgcaaaa aggcaaactg    1740
tcgtggttct agggagtcaa gaaggagcag ttcacacggc ccttgctgga gctctggagg    1800
ctgagatgga tggagccaag ggaaggctgt cctctgccca cttgaaatgt cgcctgaaaa    1860
tggataaact tagattgaag ggcgtgtcat actccttgtg cactgcagcg ttcacattca    1920
```

```
ccaagatccc ggctgaaaca ctgcacggga cagtcacagt ggaggtacag tacgcaggga  1980
cagatggacc ttgcaaggtt ccagctcaga tggcggtgga tatgcaaact ctgaccccag  2040
ttgggaggtt gataaccgct aaccctgtaa tcactgaaag caccgagaac tctaagatga  2100
tgctggaact tgatccacca tttgggact cttacattgt cataggagtc ggggagaaga  2160
agatcaccca tcactggcac aggagtggca gcaccattgg aaaagcattt gaagccactg  2220
tgagaggtgc caagagaatg gcagtcttgg gagacacagc ctgggacttt ggatcagttg  2280
ggggtgctct caactcattg gcaagggca tccatcaaat ttttggagca gctttcaaat  2340
cattgttcgg aggaatgtcc tggttctcac aaattctcat tggaacgttg ctggtgtggt  2400
tgggtctgaa tacaaagaat ggatctattt cccttacgtg cttggcctta ggggagtgt  2460
tgatcttctt atccacagcc gtttctgctg atgtggggtg ctcggtggac ttctcaaaga  2520
aggaaacgag atgcggtaca ggggtgttcg tctataacga cgttgaagcc tgagggggaca  2580
ggtacaagta ccatcctgac tcccctcgta gattggcagc agcagtcaag caagcctggg  2640
aagatgggat ctgtgggatc tcctctgtct caagaatgga aaacatcatg tggagatcag  2700
tagaagggga gctcaacgca atcctggaag agaatggagt tcaactgacg tcgttgttga  2760
gatctgtaaa aaaccccatg tggagaggtc cacagagatt gcccgtgcct gtgaacgagc  2820
tgccccacgg ctggaaggct tgggggaaat cgtacttcgt cagagcagca aagacaaata  2880
acagctttgt cgtggatggt gacacactga aggaatgccc actcaaacat agagcatgga  2940
acagcttttct tgtggaggat catgggtttg gggtatttca cactagtgtc tggctcaagg  3000
ttagagaaga ttattcatta gagtgtgatc cagccgtcat tggaacagct gctaagggaa  3060
aggaggctgt gcacagcgat ctaggctact ggattgagag tgagaagaac gacacatgga  3120
ggctgaagag ggcccacctg atcgagatga aaacatgtga atggccaaag tcccacacat  3180
tgtggacaga tggagtagaa gaaagtgatc tgatcatacc caagtcttta gctgggccac  3240
tcagccatca caacaccaga gagggctaca ggactcaaat gaaagggcca tggcacagtg  3300
aagagcttga aattcggttt gaggaatgcc caggcactaa ggtccacgtg gaggaaacat  3360
gtgggacaag aggaccatcc ctgagatcaa ccactgcaag cggaagggtg atcgaggaat  3420
ggtgctgcag ggaatgcaca atgccccac tgtcgttccg agctaaagat ggctgttggt  3480
atggaatgga gataaggccc aggaaagaac cagaaagtaa cttagtaagg tcaatggtga  3540
ctgcaggatc aactgatcac atggatcact tctctcttgg agtgcttgtg attttgctca  3600
tggtgcagga agggctgaag aagagaatga ccacaaagat catcataagc acatcaatgg  3660
cagtgctggt agccatgatc ctggaggat tttcaatgag tgacctggct aagcttgcaa  3720
ttttgatggg tgccaccttc gcggaaatga acactggagg agatgtagct catttggcgc  3780
tgatagcggc attcaaagtc agacctgcgt tgctggtatc tttcatcttc agagctaatt  3840
ggacacccccg tgagagcatg ctgctggcct tggcctcgtg tcttctgcaa actgcgatct  3900
ccgccttgga aggcgacctg atggttctca tcaatggttt tgctttggcc tggttggcaa  3960
tacgagcgat ggttgttcca cgcactgaca acatcaccct ggcaatcctg gctgctctga  4020
caccactggc ccggggcaca ctgcttgtgg cgtggagagc aggccttgct acttgcgggg  4080
ggttcatgct cctctctctg aaggggaaag gcagtgtgaa gaagaaccta ccatttgtca  4140
tggccttggg actaactgct gtgaggctgg tcgacccat caacgtggtg ggactgctgt  4200
tgctcacaag gagtgggaag cggagctggc cccctagtga agtactcaca gctgttggcc  4260
tgatatgcgc attggctgga gggttcgcca aggcggatat agagatggct gggcccatgg  4320
ccgcggtcgg tctgctaatt gtcagttacg tggtctcagg aaaagagtgtg gacatgtaca  4380
ttgaaagagc aggtgacatc acatgggaaa agatgcggaa aatcactgga aacagtcccc  4440
ggctcgatgt ggcactagat gagagtggtg atttctcctg gaaggaggat gatggtccac  4500
ccatgagaga gatcatactc aaagtggtcc tgatgaccat ctgcggcatg aacccaatag  4560
ccataccctt tgcagctgga gcgtggtacg tgtatgtgaa gactggaaaa aggagtggtg  4620
ctctatggga tgtgcctgct cccaaggaag taaaaagggg ggagaccaca gatggagtgt  4680
acagagtaat gactcgtaga ctgcttggtt caacacaagt tggagtggga gtcatgcaag  4740
aggggggtctt ccacactatg tggcacgtca caaaaggatc cgcgctgaga gcggtgaag  4800
ggagacttga tccatactgg ggagatgtca agcaggatct ggtgtcatac tgtggtccgt  4860
ggaagctaga cgccgcctgg gacgggcaca gcgaggtgca gctcttggcc gtgccccccg  4920
gagagagagc gaggaacatc cagactctgc ccggaacatt taagacaaag gatgggggaca  4980
ttggagcagt tgcgctggac tacccagcag gaacttcagg atctccaatc ctagacaagt  5040
gtgggagagt gataggactc tatggtaatg gggtcgtgat aaaaaatggg agttatgtta  5100
gtgccatcac ccaagggagg agggaggaag agactcctgt tgagtgcttc gagccttcga  5160
tgctgaagaa gaagcagcta actgtgctta gacctgcatc tgggagccgg aaaaccagga  5220
gagttcttcc tgaaatagtc cgtgaagcca taaaaacaag actccgtact gtgatcttag  5280
ctccaaccag ggtcgtcgct gctgaaatgg aggaagccct tagagggctt ccagttcgtt  5340
atatgacaac agcagtcaat gtcacccatt ctgggacaga aatcgttgac ttaatgtgcc  5400
atgctacctt cacttcacgc ctactacaac caatcagagt cccaactat aatttgtata  5460
ttatggatga ggccccactt cacagatccc caagtatagc agcaagagga tacattcaa  5520
caagggttga gatgggcgag gcggctgcca tctcatgac cgccacgcca ccaggaaccc  5580
gtgacgcatt cccggactcc aactcaccaa ttatggacac cgaggtggaa gtcccagaga  5640
gagcctggag cacaggcttt gattgggtga cggatcattc tgggaaaaca gtctggtttg  5700
ttccaagcgt gaggaacggc aatgaacg cagcttgtct gacaaaggct ggaaaacggg  5760
tcatacagct cagcagaaag acttttgaga cagagttcca gaaaaacgaaa atcaagagt  5820
gggacttcgt cgtgacaacc gacatttcag agatgggcgc caactttaaa gctgaccgtg  5880
tcatagattc caggagatgc ttaaagccgg tcatacttga tggcgagaga gtcatttgg  5940
ctggacccat gcctgtcaca catgccagcg ctgctcagag gagggggcgc ataggcagga  6000
atcccaacaa acctggagat gagtatctgt atggaggtgg gtgcgcagag actgatgaag  6060
atcacgcaca ctggcttgaa gcaagaatgc ttcttgacaa catttacctc caagatggcc  6120
tcatagcttc gctctatcga cctgaggccg acaaagtagc agctattgag ggagagttca  6180
agcttaggac ggagcaaagg aagacctttg tggaactcat gaaagaggga gatcttccgg  6240
tttggttggc ctatcaggtt gcatctgccg gaataaccta cacagataga agatggtgct  6300
ttgatggcat gaccaacaac accataatgg aagacactgt gccggcagga gtgtggaacca  6360
gatacgagaa gaaaagagtg ctcaaaccga ggtggatgga cgccagagtt tgttcagatc  6420
atgcggccct gaagtcattc aaagagtttg ccgctgggaa aagaggagcg gccttttgag  6480
tgatagaagc cctgggaaca ctgccaggac acatgcagagag agattccag gaagccattg  6540
acaacctcgc tgtgctcatg cgggcagaga ctggaagcag gccttacaaa gccgcggcgg  6600
cccaattgcc ggagaccta gagaccatta tgctttggg gttgctggga acagtctcgc  6660
```

```
tgggaatctt tttcgtcttg atgcggaaca agggcatggg gaagatgggc tttggaatgg    6720
tgactcttgg ggccagcgca tggcttatgt ggctctcgga aattgagcca gccagaattg    6780
catgtgtcct cattgtcgtg ttcctattgc tggtggtgct catacctgag ccagaaaagc    6840
aaagatctcc tcaggacaac caaatggcaa tcatcatcat ggtagcagtg ggtcttctgg    6900
gcttgattac cgccaatgaa ctcggatggt tggagagaac aaaaagtgac ctaagccatc    6960
taatgggaag gagagaggag ggggcaacca caggattctc aatggacatt gacctgcgc    7020
cagcctcagc ttgggctatc tatgctgctc tgcaactttt catcaccca gccgtccaac    7080
atgcggtgac cacttcatac aacaactact ccttaatggc gatggccacg caagctgggg    7140
tgttgtttgg tatgggcaaa gggatgccat tctacgcatg ggactttgga gtcccgctgc    7200
taatgatggg ttgctactca caattaacac ctctgacact aatagtggcc atcattttgc    7260
tcgtggcgca ctacatgtac ttgatcccag ggctgcaggc agcagctgcg cgggctgccc    7320
agaagagaac ggcagctggc atcatgaaga accctgttgt ggatggaata gtggtgactg    7380
acattgacac aatgacaatt gaccccccaa gtggaaaaaa gatggggcag gtgctactca    7440
tagcagtagc cgtctccagc gccatactgt cgcggaccac ctgggggtgg ggggaggctg    7500
gggccctgat cacagctgca acttccacct tgtgggaagg ctctccgaac aagtactgga    7560
actcctccac agccacttca ctgtgtaaca ttttaggg aagttacttg gctggagctt    7620
ctcaatccta cacagtaaca agaaacgctg gcttggtcaa gagacgtggg ggtggaacgg    7680
gagagaccct gggagagaaa tggaaagccc gcctgaacca gatgtcggcc ctggagttct    7740
actcctacaa aaagtcaggc atcaccgagg tgtgcagaga gaggccccgc cgtgccctca    7800
aggacggtgt ggcaacagga ggccatgctg tgtcccgagg aagtgcaaag cttagatggc    7860
tggtggagag aggataccctg cagccctatg gaaaggtcat tgatcttgga tgtggcagag    7920
ggggctggag ttactatgcc gccaccatcc gcaaagttca ggaagtgaaa ggatacacaa    7980
aaggaggccc tgggtcatgaa gaacccatgt tggtgcaaag ctatgggtgg aacatagtcc    8040
gtcttaagag tggggtggac gtctttcaca tggcggctga gccgtgtgac actttgctgt    8100
gtgatatagg tgagtcatca tctagtcctg aagtggaaga agcacggacg ctcagagtcc    8160
tctccagtgg ggggattgg cttgaaaaaa gaccaggagc cttttgtata aaagtgttgt    8220
gcccatacac cagcactatg atggaaaccc tggagcgact gcagcgtagg tatgggggag    8280
gactggtcag ggtgccactc tcccgcaact ctacacatga gatgtactgg gtctctggag    8340
cgaaaagcaa caccataaaa agtgtgtcca ccacgagcca gctcctcttg gggcgcatgg    8400
acggggccag gaggccagtg aaatatgagg aggatgtgaa tctcggctct ggcacgcggg    8460
ctgtggtaag ctgcgctgaa gctcccaaca tgaagatcat tggtaaccgc attgagagga    8520
tccgcagtga gcacgcggaa acgtggttct ttgacgagaa ccacccatat aggacatggg    8580
cttaccatga agctatgag gcccctacac aagggtcagc gtcctctcta ataaacgggg    8640
ttgtcaggct cctgtcaaaa cccgggatg tggtgactgg agtcacagga atagccatga    8700
ctgacaccac accgtatggt cagcaaagag ttttcaagga aaaagtggac actagggtgc    8760
cagacccca agaaggcact cgtcaggtta tgagcatggt ctcttcctgg ttatggaagg    8820
agctaggcaa acacaaacgg ccacgagtct gtaccaaaga agagttcatc aacaaggttc    8880
gtagcaatgc agcattaggg gcaatatttg aagaggaaaa agagtggaag actgcagtgg    8940
aagctgtgaa tgatccaagg ttctgggctc tagtggacaa ggaaagagag catcacctga    9000
gaggagagtg tcagagctgt gtgtacaaca tgatggaaa aagagaaaag aaacaagggg    9060
aatttggaaa ggccaagggc agccgcgcca tctggtatat gtggctaggg ctagattcc    9120
tagagttcga agcccttgga ttcttgaatg aggatcattg gatggggaga gagaattcag    9180
gaggtggtgt tgaaggactg ggattacaaa gactcggata tgtcctagaa gagatgagtc    9240
gcataccagg aggaaggatg tatgcagatg atactgctgg ctgggacacc cgcatcagca    9300
ggtttgatct ggagaatgaa gctctaatca ccaaccaaat ggagaaaggg cacaggggcct    9360
tggcattggc cataatcaag tacacatacc aaaacaaagt ggtaaggtc cttagaccag    9420
ctgaaaaggg gaagacagtt atggacatta tttcaagaca agaccaaagg gggagcggac    9480
aagttgtcac ttacgctctt aatacattca ccaacctggt ggtgcagctc attcggaata    9540
tggaggctga ggaagttcta gagatgcaag acttgtggct gctgcggagg ccagagaaag    9600
tgaccaactg gttgcaaagc aacggatggg ataggctcaa aagaatggca gtcagtggag    9660
atgattccgt tgtgaaacca attgatgata ggttttgcaca tgccctcagg ttcttgaatg    9720
atatgggaaa agttaggaag gacacacaag agtggaaacc ctcaactgga tgggacaact    9780
gggaagaagt tccgttttgc tcccaccact tcaacaaact ccatcttaag gacgggaggt    9840
ccattgtggt tccctgccgc caccaagatg aactgattgg ccgagcccgc gtatccaag    9900
gggcggatga gagcatccgg gagactgctt gcctagcaaa atcatatgcc caaatgtggc    9960
agctcccttta tttccacaga agggacctcc gactgatggc caatgccatt tgttcatctg    10020
tgccagttga ttgggttcca actgggagaa ctacctggtc aatccatgga aagggagaat    10080
ggatgaccac tgaagacatg cttgtggtat ggaacagagt gtggattgag gaaaacgacc    10140
acatggaaga caaggcccca gttacaaaat ggacagacat tccctatttg ggaaaaagag    10200
aagacttgtg gtgtgatctc tcatagggc acagaccgcg tactacctgg gctgagaaca    10260
tcaaaaatac agtcaacatg atgcgcagga tcataggtga tgaagaaaag tacatggact    10320
acctatccac ccaggttcgc tacttgggtg aagaagggtc cacacctgga gtgctgtaag    10380
caccaatctt agtgttgtca ggcctgctag tcagccacag cttggggaaa gctgtgcagc    10440
ctgtgaccccc cccaggagaa gctgggaaac caagcctata gtcaggccga gaacgccatg    10500
gcacggaaga agccatgctg cctgtgagcc cctcaggga cactgagtca aaaaaccccca    10560
cgcgcttgga ggcgcaggat gggaaaagaa ggtggcgacc ttcccccaccc ttcaatctgg    10620
ggcctgaact ggagatcagc tgtggatctc cagaagaggg actagtggtt agaggagacc    10680
ccccggaaaa cgcaaaacag catattgacg ctgggaaaga ccagagactc catgagtttc    10740
caccacgctg gccgccaggc acagatcgcc gaatagcggc ggccggtgtg gggaaatcca    10800
tgggtct                                                              10807
```

```
SEQ ID NO: 9            moltype = DNA  length = 10648
FEATURE                 Location/Qualifiers
source                  1..10648
                        mol_type = genomic DNA
                        organism = Zika virus
SEQUENCE: 9
gacagttcga gtttgaagcg aaagctagca acagtatcaa caggttttat ttggatttgg    60
aaacgagagt ttctggtcat gaaaacccca aaaagaaat ccggaggatt ccggattgtc    120
```

```
aatatgctaa aacgcggagt agcccgtgtg agcccctttg ggggcttgaa gaggctgcca    180
gccggacttc tgctgggtca tgggcccatc aggatggtct tggcgattct agccttttg    240
agattcacgg caatcaagcc atcactgggt ctcatcaata gatggggttc agtggggaaa    300
aaagaggcta tggaaataat aaagaagttc aagaaagatc tggctgccat gctgagaata    360
atcaatgcta ggaaggagaa gaagagacga ggcgcagata ctagtgtcgg aattgttggc    420
ctcctgctga ccacagctat ggcagcggag gtcactagca gtgggagtgc atactatatg    480
tacttggaca gaaacgatgc tggggaggcc atatcttttc caaccacatt ggggatgaat    540
aagtgttata tacagatcat ggatcttgga cacatgtgtg atgccaccat gagctatgaa    600
tgccctatgc tggatgaggg ggtggaacca gatgacgtcg attgttggtg caacacgacg    660
tcaacttggg ttgtgtacgg aacctgccat cacaaaaaag gtgaagcacg gagatctaga    720
agagctgtga cgctcccctc ccattccact aggaagctgc aaacgcggtc gcaaacctgg    780
ttggaatcaa gagaatacac aaagcacttg attagagtcg aaaattggat attcaggaac    840
cctggcttcg cgttagcagc agctgccatc gcttggcttt tgggaagctc aacgagccaa    900
aaagtcatat acttggtcat gatactgctg attgccccgc catacagcat caggtgcata    960
ggagtcagca ataggacttt tgtgaaggt atgtcaggtg ggacctgggt tgatgttgtc    1020
ttggaacatg gaggttgtgt caccgtaatg gcacaggaca aaccgactgt cgacatagag    1080
ctggttacaa caacagtcag caacatggcg gaggtaagat cctactgcta tgaggcatca    1140
atatcagaca tggcttcgga cagccgctgc ccaacacaag gtgaagccta ccttgacaag    1200
caatcagaca ctcaatatgt ctgcaaagaa acgttagtgg acagaggctg gggaaatgga    1260
tgtggacttt ttggcaaagg gagcctggtg acatgcgcta agtttgcatg ctccaagaaa    1320
atgaccggga agagcatcca gccagagaat ctggagtacc ggataatgct gtcagttcat    1380
ggctcccagc acagtgggat gattgttaat gacacaggac atgaaactga tgagaataga    1440
gcgaaagttg agataacgcc caattcacca agagccgaag ccaccctggg gggttttgga    1500
agcctaggac ttgattgtga accgaggaca ggccttgact tttcagattt gtattacttg    1560
actatgaata acaagcactg gttggttcac aaggagtggt tccacgacat tccattacct    1620
tggcacgctg gggcagacac cggaactcca cactggaaca acaaagaagc actggtagag    1680
ttcaaggacg cacatgccaa aaggcaaact gtcgtggttc tagggagtca agaaggagca    1740
gttcacacgg cccttgctgg agctctggag gctgagatgg atggtgcaaa gggaaggctg    1800
tcctctggcc acttgaaatg tcgcctgaaa atggataaac ttagattgaa gggcgtgtca    1860
tactccttgt gtactgcagc gttcacattc accaagatcc cggctgaaac actgcacggg    1920
acagtcacag tggaggtaca gtacgcaggg acagatggac cttgcaaggt tccagctcag    1980
atggcggtgg acatgcaaac tctgacccca gttgggaggt tgataaccgc taaccccgta    2040
atcactgaaa gcactgagaa ctctaagatg atgctgaac ttgatccacc atttgggac    2100
tcttacattg tcataggagt cggggaggaa aagatcaccc accactggca caggagtggc    2160
agcaccattg gaaaagcatt tgaagccact gtgagaggtg ccaagagaat ggcagtcttg    2220
ggagacacag cctgggactt tggatcagtt ggaggcgctc tcaactcatt gggcaagggc    2280
atccatcaaa ttttttggagc agctttcaaa tcattgtttg gaggaatgtc ctggttctca    2340
caaattctca ttgaacgttt gctgatgtgg ttgggtctga cacaaagaa tggatctatt    2400
tccttatgt gcttggcctt aggggagtg ttgatcttct tatccacagc cgtctctgct    2460
gatgtgggt gctcggtgga cttctcaaag aaggagacga gatgcggtac aggggtgttc    2520
gtctataacg acgttgaagc ctggagggac aggtacaagt accatcctga ctcccccgt    2580
agattggcag cagcagtcaa gcaagcctgg gaagatggta tctgcgggat ctcctctgtt    2640
tcaagaatgg aaaacatcat gtggagatca gtagaagggg agctcaacgc aatcctgaa    2700
gagaatggag ttcaactgac ggtcgttgtg ggatctgtaa aaaaacccat gtggagaggt    2760
ccacagagat tgcccgtgcc tgtgaacgag ctgccccacg gctggaaggc ttgggggaaa    2820
tcgtacttc tcagagcagc aaagacaaat aacagctttg tcgtggatgg tgacacactg    2880
aaggaatgcc cactcaaaca tagagcatgg aacagcttc ttgtgaggga tcatgggttc    2940
gggtatttc acactagtgt ctggctcaag gttagagaag attattcatt agagtgtgat    3000
ccagccgtta ttggaacagc tgttaaggga aaggaggctg tacacagtga tctaggctac    3060
tggattgaga gtgagaagaa tgacacatgg aggctgaaga gggcccatct gatcgagatg    3120
aaaacatgtg aatggccaaa gtcccacaca ttgtggacag atggaataga agaagtgat    3180
ctgatcatac ccaagtcttt agctgggcca ctcagccatc acaataccag agagggctac    3240
aggacccaaa tgaaagggcc atggcacagt gaagagcttg aaattcggtt tgaggaatgc    3300
ccaggcacta aggtccacgt ggaggaaaca tgtggaacaa gaggaccatc tctgagatca    3360
accactgcaa gcgaagggt gatcgaggaa tggtgctgca gggagtgcaa aatgccccca    3420
ctgtcgttcc gggctaaaga tggctgttgg tatgaatgg agataaggcc caggaaagaa    3480
ccagaaagca acttagtaag gtcaatggt actgcaggat caactgatca catggaccac    3540
ttctcccttg gagtgcttgt gattctgctc atggtgcagg aagggctgaa gagagaatg    3600
accacaaaga tcatcataag cacatcaatg gcagtgctgg tagctatgat cctgggagga    3660
ttttcaatga gtgacctggc taagcttgca attttgatgg gtgccacctt cgcggaaatg    3720
aacactggag gagatgtagc tcatctggcg ctgatagcgg cattcaaagt cagaccagcg    3780
ttgctggtat ctttcatctt cagagctaat tggacacccc gtgaaagcat gctgctggcc    3840
ttggcctcgt gtcttttgca aactgcgatc tccgccttg aaggcgacct gatggttctc    3900
atcaatggtt ttgctttggc ctggttgca atacgagcg tggttgttcc acgcactgat    3960
aacatcacct tggcaatcct ggctgctctg acaccactgg cccggggcac actgcttgtg    4020
gcgtggagag caggccttgc tacttgcggg gggtttatgc tcctctctct gaagggaaaa    4080
ggcagtgtga agaagaactt accatttgtc atggcctgg gactaaccgc tgtgaggctg    4140
gtcgacccca tcaacgtggt gggactgctg ttgctcacaa ggagtgggaa gcggagctgg    4200
ccccctagcg aagtactcac tgctgttggc ctgatatgcg cattggctgg aggggttcgcc    4260
aaggcagata tagagatggc tgggcccatg gccgcggtcg gtctgctaat tgtcagttac    4320
gtggtctcag gaaagagtgt ggacatgtac attgaaagag caggtgacat cacatgggaa    4380
aaagatgcgg aagtcactgg aaacagtccc cggctcgatg tggcgctaga tgagagtggt    4440
gatttctccc tggtggagga tgacggtccc cccatgagag agatcatact caaggtggtc    4500
ctgatgccaa tctgtggcat gaacccaata gccataccct tgcagctgg agcgtggtac    4560
gtatacgtca agactggaaa aaggagtggt gctctatggg atgtgcctgc tcccaaggaa    4620
gtaaaaaagg gggagaccac agatggagtg tacagagtaa tgactcgtag actgctaggt    4680
tcaacacaag ttggagtggg agttatgcaa gagggggtct ttcacactat gtggcacgtc    4740
acaaaaggat ccgcgctgag aagcggtgaa gggagacttg atccatactg gggagatgtc    4800
aagcaggatc tggtgtcata ctgtggtcca tggaagctag atgccgcctg ggacgggcac    4860
```

```
agcgaggtgc agctcttggc cgtgcccccc ggagagagag cgaggaacat ccagactctg    4920
cccggaatat ttaagacaaa ggatggggac attggagcgg ttgcgctgga ttacccagca    4980
ggaacttcag gatctccaat cctagacaag tgtgggagag tgataggact ttatggcaat    5040
ggggtcgtga tcaaaaatgg gagttatgtt agtgccatca cccaagggag gagggaggaa    5100
gagactcctg ttgagtgctt cgagccttcg atgctgaaga agaagcagct aactgtctta    5160
gacttgcatc ctggagctgg gaaaaccagg agagttcttc ctgaaatagt ccgtgaagcc    5220
ataaaaacaa gactccgtac tgtgatctta gctccaacca gggttgtcgc tgctgaaatg    5280
gaggaggccc ttagagggct tccagtgcgt tatatgacaa cagcagtcaa tgtcacccac    5340
tctggaacag aaatcgtcga cttaatgtgc catgccacct tcacttcacg tctactacag    5400
ccaatcagag tccccaacta taatctgtat attatggatg aggcccactt cacagatccc    5460
tcaagtatag cagcaagagg atacatttca acaaggggttg agatgggcga ggcggctgcc    5520
atcttcatga ccgccacgcc accaggaacc cgtgacgcat ttccggactc caactcacca    5580
attatgtgaca ccgaagtgga agtcccagag agagcctgga gctcaggctt tgattgggtg    5640
acggatcatt ctggaaaaac agtttggttt gttccaagcg tgaggaacgg caatgagatc    5700
gcagcttgtc tgacaaaggc tggaaaacgg gtcatacagc tcagcagaaa gactttttgag    5760
acagagttcc agaaaacaaa acatcaagag tgggactttg tcgtgacaac tgacatttca    5820
gagatgggcg ccaactttaa agctgaccgt gtcatagatt ccaggagatg cctaaagccg    5880
gtcatacttg atggcgagag agtcattctg gctggaccca tgcctgtcac acatgccagc    5940
gctgcccaga ggaggggggcg cataggcagg aatcccaaca aacctgggaga tgagtatctg    6000
tatgagagtg ggtgcgcaga gactgacgaa gaccatgcac actggcttga agcaagaatg    6060
ctccttgaca atatttacct ccaagatggc ctcatagcct cgctctatcg acctgaggcc    6120
gacaaagtag cagccattga gggagagttc aagcttagga tgaggacaaag gaagacctttt    6180
gtggaactca tgaaagagg agatcttcct gtttggctgg cctatcaggt tgcatctgcc    6240
ggaataacct acacagatag aagatggtgc tttgatggca cgaccaacaa caccataatg    6300
gaagacagtg tgccggcaga ggtgtggacc agacacggag agaaaagagt gctcaaaccg    6360
aggtggatgg acgccagagt ttgttcagat catgcggccc tgaagtcatt caaggagttt    6420
gccgctggga aaagaggagc ggcttttttga gtgatgaaag ccctgggaac actgccagga    6480
cacatgacag agagattcca ggaagccatt gacaacctcg ctgtgctcat gcgggcagag    6540
actgaagca ggccttacaa agccgcgcg gcccaattgc cggagaccct agagaccatt    6600
atgcttttgg ggttgctggg aacagtctcg ctgggaatct tcttcgtctt gatgaggaac    6660
aagggcatag ggaagatggg ctttggaatg gtgactcttg gggccagcgc atggctcatg    6720
tggctctcgg aaattgagcc agcagaatt gcatgtgtcc tcattgttgt gtttctattg    6780
ctggtggtgc tcatacctga gccagaaaag caaagatctc cccaggacaa ccaaatggca    6840
atcatcatca tggtagcagt aggtcttctg ggcttgatta ccgccaatga actcggatgg    6900
ttggagagaa caaagagtga cctaagccat ctaatgggaa ggagagagga ggggcaacc    6960
ataggattct caatggacat tgacctgcgg ccagcctcag cttgggccat ctatgctgcc    7020
ttgacaactt tcattacccc agccgtccaa catgcagtga ccacttcata caacaactac    7080
tccttaatgg cgatggccac gcaagctgga gtgttgtttg gtatgggcaa agggatgcca    7140
ttctacgcat gggactttgg agtccgctg ctaatgatag gttgctactc acaattaaca    7200
cccctgaccc taatagtggc catcattttg ctcgtggcgc actacatgta cttgatccca    7260
gggctgcagg cagcagctgc gcgtgctgcc cagaagagaa cggcagctgg catcatgaag    7320
aaccctgttg tggatggaat agtggtgact gacattgaca caatgacaat tgaccccaa    7380
gtggagaaaa agatgggaca ggtgctactc atagcagtag ccgtctccag cgccatactg    7440
tcgcggaccg cctgggggtg gggggaggct ggggcccctga tcacagccgc aacttccact    7500
ttgtgggaag gctctccgaa caagtactgg aactcctcta cagccacttc actgtgtaac    7560
attttttaggg gaagttactt ggctggagct tctctaatct acacagtaac aagaaacgct    7620
ggcttggtca agagacgtgg gggtggaaca ggagagaccc tgggagaga atggaaggcc    7680
cgcttgaacc agatgtcggc cctggagttc tactcctaca aaaagtcagg catcaccgag    7740
gtgtgcagag aagaggcccg ccgcgccctc aaggacggtg tggcaacggg aggccatgct    7800
gtgtcccgag gaagtcaaa gctgagatgg ttggtggagc ggggatacct gcagccctat    7860
ggaaaggtca ttgatcttgg atgtggcaga ggggccggga gttactacgc cgccaccatc    7920
cgcaaagttc aagaagtgaa aggatacaca aaaggaggcc ctggtcatga agaacccgtg    7980
ttggtgcaaa gctatgggtg gaacatagtc cgtcttaaga gtgggtggga cgtctttcat    8040
atggcggctg agccgtgtga cacgttgctg tgtgacatag gtgagtcatc atctagtcct    8100
gaagtggaag aagcacggac gctcagagtc ctctccagtg tggggaattg gcttgaaaaa    8160
agaccaggag cctttttgtat aaaggtgttg tgcccataca ccagcactat gatggaaacc    8220
ctggagcgac tgcagcgtag gtatgggga ggactggtca gagtgccact ctcccgcaac    8280
tctacacatg agatgtattg ggtctctgga gcgaaaagca acaccataaa aagtgtgtcc    8340
accacgagcc agctcctctt gggcgcatg gacggggccta ggaggccagt gaaatatgag    8400
gaggatgtga atctcggctc tggcacgcgg gctgtggtaa gctgcgctga agctcccaac    8460
atgaagatca ttggtaaccg cattgaaagg atccgcagtg agcacgcgga aacgtggttc    8520
tttgacgaga accacccata taggacatgg gcttaccatg gaagctatga ggccccacac    8580
caagggtcag cgtcctctct aataaacggg gttgtcaggc tcctgtcaaa acctgggat    8640
gtggtgactg gagtcacagg aatagccatg accgacacca caccgtatgg tcagcaaaga    8700
gttttcaagg aaaagtgga cactagggtg ccagaccccc aagaaggcac tcgtcaggtt    8760
atgagcatgg tctcttcctg gttgtggaaa gagctaggca aacacaaacg gccacgagtc    8820
tgtaccaaag aagagttcat caacaaggtt cgtagcaatg cagcattagg ggcaatatt    8880
gaagaggaaa aagagtggaa gactgcagtg gaagctgtga acgatccaag gttctgggct    8940
ctagtggata aggaaagaga gcaccacctg gagggaggt ccagagttg tgtgtacaac    9000
atgatgggaa aaagagaaaa gaaacaaggg gaatttggaa aggccaaggg cagccgcgcc    9060
atctggtata tgtgctagg ggctagattt ctagagttcg aagcccttgg attcttgaac    9120
gaggatcact ggatggggag agaaactca ggaggtggtg ttgaagggct gggattacaa    9180
agactcggat atgtcctaga agagatgagt cgtatccag aggaaggat gtatgcagat    9240
gacactgctg gctgggacac ccgcatcagc aggtttgatc tggagaatga agctctaatc    9300
accaaccaaa tggaaaaagg gcacagggcc ttggcattgg ccataatcaa gtacacatac    9360
caaaacaaag tggtaaaggt ccttagacca gctgaaaaag ggaaaacagt tatggacatt    9420
atttcgagac aagaccaaag ggggagcgga caagttgtca cttacgctct taacacattt    9480
accaacctag tggtgcaact cattcggaat atggaggctg aggaagttct agagatgcaa    9540
gacttgtggc tgctgcggag gtcagagaaa gtgaccaact ggttgcagag caacggatgg    9600
```

-continued

```
gataggctca aacgaatggc agtcagtgga gatgattgcg ttgtgaagcc aattgatgat  9660
aggtttgcac atgccctcag gttcttgaat gatatgggaa aagttaggaa ggacacacaa  9720
gagtggaaac cctcaactgg atgggacaac tggaagaag ttccgttttg ctcccaccac   9780
ttcaacaagc tccatctcaa ggacgggagg tccattgtgg ttccctgccg ccaccaagat  9840
gaactgattg gccggggccg cgtctctcca ggggcggatt ggagcatccg ggagactgct  9900
tgcctagcaa aatcatatgc gcaaatgtgg cagctccttt atttccacag aagggacctc  9960
cgactgatgg ccaatgccat ttgttcatct gtgccagttg actgggttcc aactgggaga  10020
actacctggt caatccatgg aaagggagaa tggatgacca ctgaagacat gcttgtggtg  10080
tggaacagag tgtggattga ggagaacgac cacatggaag acaagacccc agttacgaaa  10140
tggacagaca tcccctattt ggggaaaagg gaagacttgt ggtgtggatc tctcataggg  10200
cacagaccgc gcaccacctg ggctgagaac attaaaaaca cagtcaacat ggtgcgcagg  10260
atcataggtg atgaagaaaa gtacatggac tacctatcca cccaagttcg ctacttgggt  10320
gaagaagggt ctacacctgg agtgctgtaa gcaccagtct taatgttgtc aggcctgcta  10380
gtcagccaca gcttgggaa agctgtgcag cctgtgaccc cccaggaga agctgggaa   10440
ccaagcctat agtcaggccg agaacgccat ggcacggaag aagccatgct gcctgtgagc  10500
ccctcagagg acactgagtc aaaaaacccc acgcgcttgg aggcgcagga tgggaaagga  10560
aggtggcgac cttccccacc cttcaatctg gggcctgaac tggagatcag ctgtggatct  10620
ccagaagagg gactagtggt tagaggag                                     10648
```

```
SEQ ID NO: 10          moltype = DNA   length = 10676
FEATURE                Location/Qualifiers
source                 1..10676
                       mol_type = genomic DNA
                       organism = Zika virus
SEQUENCE: 10
gttgttactg ttgctgactc agactgcgac agttcgagtt tgaagcgaaa gctagcaaca  60
gtatcaacag gttttatttg gatttggaaa cgagagtttc tggtcatgaa aaacccaaaa  120
aagaaatccg gaggattccg gattgtcaat atgctaaaac gcggagtagc ccgtgtgagc  180
cccctttggg gcttgaagag gctgccagcc ggacttctgc tgggtcatgg gcccatcagg  240
atggtcttgg caattctagc ctttttgaga ttcacggcaa tcaagccatc actgggtctc  300
atcaatagat ggggttcagt ggggaaaaaa gatgctatgg aaataataaa gaagttcaag  360
aaagatctgc tgccatgcct gagaataatc aatgctagga aggagaagaa gacgaggc   420
gcagatacta gtgtcggaat tgttggcctc tgctgacca cagctatggc agcggaggtc  480
actagacgtg ggagtgcata ctatatgtac ttggacagaa acgatgctgg ggaggccata  540
tcttttccaa ccacattggg gatgaataag tgttatatac agatcatgga tcttggacac  600
atgtgtgatg ccaccatgag ctatgaatgc cctatgctgg atgaggggt ggaaccagat   660
gacgtcgatt gttggtgcaa cacgacgtca acttgggttg tgtacggaac ctgccatcac  720
aaaaaaggtg aagcacggag atctagaaga gctgtgacgc tccctcccca ttccactagg  780
aagctgcaaa cgcggtcgca aacctggttg gaatcaagag aatacacaaa gcacttgatt  840
agagtcgaaa attggatatt caggaaccct ggcttcgcgt tagcagcagc tgccatcgct  900
tggcttttgg gaagctcaac gagccaaaaa gtcatatact tggtcatgat actgctgatt  960
gccccggcat acagcatcag tgtcatagga gtcagcaata gggactttgt ggaaggtatg  1020
tcaggtggga cttgggttga tgttgtcttg gaacatggag gttgtgtcac cgcaatgctc  1080
caggacaaac cgactgtcga catagagctg gttacaacaa cagtcagcaa catggcggag  1140
gtaagatcct actgctatga ggcatcaata tcagacatgg cttcggacag ccgctgccca  1200
acacaaggtg aagcctacct tgacaagcaa tcagacactc aatatgtttg caaaagaacg  1260
ttagtgacca gaggctgggg aaatggatgt ggacttttg gcaaagggag tctggtgaca  1320
tgcgctaagt ttgcatgctc caagaaaatg accgggaaga gcatccagcc agagaatctg  1380
gagtaccgga taatgctgtc agttcatgc tcccagcaca gtgggatgct cgttaatgac  1440
acaggacatg aaactgatga aatagagcg aaggttgaga taacgcccaa ttcaccaaga  1500
gccgaagcca cctgggggg ttttgaagcc ctaggacttg attgtgaacc gaggacaggc  1560
cttgactttt cagatttgta ttacttgact atgaataaca agcactggtt ggctcacaag  1620
gagtggttcc acgacattcc attaccttgg cacgctgggg cagccaccgg aactccacac  1680
tggaacaaca agaagcact ggtagagttc aaggacgcac atgccaaaag gcaaactgtc  1740
gtggttctag ggagtcaaga aggagcagtt cacacgcgcc ttgctggagc tctgaggct  1800
gagatggatg gtgcaaaggg aaggctgtcc tctggccact gaaatgtcg cctgaaaatg  1860
gataaactta gattgaaggg cgtgtcatac tccttgtgta ccgcagcgtt cacattcacc  1920
aagatcccgg ctgaaacagt ggacgggaca gtcacagtgg agggacagta cggagggaca  1980
gatggccctt gcaaggttcc agctcagatg gcggtgacac tgcagactct gacccccagt  2040
gggaggttga taaccgctaa ccccgtaatc actgaaagca ctgagaactc taagatgatg  2100
ctggaacttg atccaccatt tggggactct tacattgtca taggagtcgg ggagaagaag  2160
atcacccacc actggcacag gagtggcagc accattggaa aagcatttga agccactgtg  2220
agaggtgcca gagaatggc agtcttggga gacacagcc gggactttgg atcagttgga  2280
ggcgctctca actcattggg caagggcatc catcaaatta ttggagcagc tttcaaatca  2340
ttgtttggag gaatgtcctg gttctcacaa attctcattg gacgttgct gatgtggttg  2400
ggtctgaaca caaagaatgg atctatttcc cttatgtgct tggccttagg ggagtgttg   2460
atcttcttat ccacagccgt tcaggtggt gtggggtgct cggtggactt ctcaagaag   2520
gagacgagat gcggtacagg ggtgttcgtc tataacgatg ttgaagcctg gagggacagg  2580
tacaagtacc atcctgactc cccccgtaga ttggcagcag cagtcaagca agctgtggaa  2640
gatggtatct gcgggatctc ctctgtttca agaatggaaa acatcatgtg gagatcagta  2700
gaaggggagc tcaacgcaat cctggaagag aatggagttc aactgacggt cgttgtggga  2760
tctgtaaaaa accccatgtg gagaggtcca cagagattgc ccgtgcctgt gaacgagctg  2820
ccccacggct ggaaggcttg ggggaaatcg tacttcgtca gcagcaaa gacaaataac   2880
agctttgtcg tggatggtga cacactgaag gaatgcccac tcaaacatag agcatggaat  2940
agctttcttg tggaggatca tgggttcggg gtatttcaca ctagtgtctg gctcaaggtt  3000
agagaagact attggttaga gtgtgatcca gccgttattg gaacagcgt taagggaaag  3060
gaggctgtac acagtgatct aggctactgg attgagagtg agaagaatga cacatggtgg  3120
ctgaagaggg cccatctgat cgagatgaaa acatgtgaat ggcaaagtc ccacacattg  3180
tggacagatg gaatagaaga gagtgatctg atcatacca agtctttagc tgggccactc  3240
```

```
agccatcaca atgccagaga gggctacagg acccaaatga aagggccatg gcacagtgaa   3300
gagcttgaaa ttcggtttga ggaatgccca ggcactaagg tccacgtgga ggaaacatgt   3360
ggaacaagag gaccatctct gagatcaacc actgcaagcg gaagggtgat cgaggaatgg   3420
tgctccaggg agtgcacaat gcccccactg tccttccagg ctaaagatgg ctgttggtat   3480
ggaatggaga taaggcccag gaaagaacca gaaagcaact tagtaaggtc aatggtgact   3540
gcaggatcaa ctgatcacat ggatcacttc tcccttggag tgcttgtgat tctgctcatg   3600
gtgcaggaag ggctgaagaa gagaatgacc acaaagatca tcataagcac atcaatggca   3660
gtgctggtag ctatgatcct gggaggattt tcaatgagtg acctggctaa gcttgcaatt   3720
ttgatgggtg ccaccttcgc ggaaatgaac actggaggag atgtagctca tctggcgctg   3780
atagcggcat tcaaagtcag accagcgttg ctggtatctt tcatcttcag agctaattgg   3840
acaccccgtg aaagcatgct gctggccttg gcctcgtgtc ttttgcaaac tgcgatctcc   3900
gccttggaag gcgacctgat ggttctcatc aatggttttg cttggcctg gttggcaata   3960
cgagcgatgg ttgttccacg cactgataac atcaccttag caatcctggc tgctctgaca   4020
ccactggccc ggggcacact gcttgtggcg tggagagcag gccttgctac ttgcgggggg   4080
tttatgctcc tctctctgaa gggaaaaggc agtgtgaaga agaacttacc atttgtcatg   4140
gccctggac taaccgctgt gaggctggtc gaccccatca acgtggtggg actgctgttg   4200
ctcacaagga gtgggaagcg gagctggccc cctagcgaag tactcacagc tgttggcctg   4260
atatgcgcat tggctggagg gttcgccaag gcagatatag agatggctgg gcccatggcc   4320
gcggtcggtc tgctaattgt cagttacgtg gtctcaggag agagtgtgga catgtacatt   4380
gaaagagcag gtgacatcac atgggaaaaa gatgcggaag tcactggaaa cagtcccgg   4440
ctcgatgtgc cgctagatga gagtggtgat ttctccctgg tggaggatga cggtcccccc   4500
atgagagaga tcatactcaa ggtggtcctg atgaccctg gtgcatgaa cccaatagcc   4560
atacccttg cagctggagc gtggtacgta tacgtgaaga ctggaaaaag gagtggtgct   4620
ctatgggatg tgcctgctcc caaggaagta aaaaagggg agaccacaga tggagtgtac   4680
agagtaatga ctcgcagact gctaggttca acacaagttg gagtgggagt tatgcaagag   4740
ggggtctttc acactatgtg gcacgtcaca aaaggatccg cgctgagaag cggtgaaggg   4800
agacttgatc catactgggg agatgtcaag caggatctgg tgtcatactg tggtccatgg   4860
aagctagatg ccgcctggga cgggcacagc gaggtgcagc tcttggccgt gcccccggga   4920
gagagagcga ggaacatcca gactctgccc ggaatattta gacaaagga tggggacatt   4980
ggagcggttg cactggatta cccagcagga acttcaggat ctccaatcct agacaagtgt   5040
gggagagtga taggacttta tggcaatggg gtcgtgatca aaaatgggag ttatgttagt   5100
gccatcaccc aagggaggag ggaggaagag actcctgttg agtgcttcga gccttcgatg   5160
ctgaagaaga agcagctaac tgtcttagac ttgcatcctg gagctgggaa aaccaggaga   5220
gttcttcctg aaatagtccg tgaagccata aaaacaagac tccgtactgt gatcttggct   5280
ccaaccaggg ttgtcgctgc tgaaatggag gaggcccta gagggcttcc agtgcgttat   5340
atgacaacag cagtcaatgt cacccactct ggaacagaaa tcgtcgactt aatgtgccat   5400
gccaccttca cttcacgtct actacagcca attagagtcc ccaactataa tctgtatatt   5460
atggatgagg cccacttcac agatcccta agtatacag caaggata cattttcaaca   5520
agggttgaga tgggcgaggc ggctgccatc ttcatgaccg ccacgccacc aggaaccgt   5580
gacgcatttc cggactccaa ctcaccaatt atggacaccg aagtggaagt cccagagaga   5640
gcctggagct caggctttga ttgggtgacg gagtattctg gaaaaacagt ttggtttgtt   5700
ccacgcgtga ggaacggcaa tgagatcgca gcttgtctga caaaggctgg aaaacgggtc   5760
atacagctca gcagaaagac ttttgagaca gagttccaga aaacaaaca tcaagagtgg   5820
gactttgtcg tgacaactga catttcagag atgggcgcca actttaaagc tgaccgtgtc   5880
atagattcca gagatgcct aaagccggtc tacttggtg cgagagagt cattctgggct   5940
ggacccatgc ctgtcacaca tgccagcgct gcccagagga ggggcgcat aggcaggaat   6000
cccaacaaac ctgagatga gtatctgtat ggaggtggt gcgcagac tgacgaagac   6060
catgcacact ggcttgaagc aagaatgctc cttgacaata tttacctcca agatggcctc   6120
atagcctcgc tctatcgacc tgaggccgac aaagtagcag ccattgaggg agagttcaag   6180
cttaggacg agcaaaggaa gacctttgtg gaactcatga aagaggaga tcttcctgtt   6240
tggctggcct atcaggttgc atctgccgga ataacctaca cagatagaag atggtgtttc   6300
gatggcacga ccaacaacac cataatgaa gacagtgtgc cggcagaggt gtggaccaga   6360
cacgagaga aaagagtgct caaaccgagg tggatgacg ccagagtttg ttcagatcat   6420
gcggccctga gtcattcaa ggagtttgcc gctgggaaaa gaggagcgc ttttggagtg   6480
atggaagccc tgggaaacact gccaggacac atgcagaga gattccagga agccattgac   6540
aacctcgctg tgctcatgcg ggcagagact ggaagcagge cttacaaagc cgcggcggcc   6600
caattgccgg agaccctaga gaccattatg ctttgggt tgctgggaac agtctcgctg   6660
ggaatctttt tcgtcttgat gaggaacaag ggcataggga agatgggctt ggaatggtg   6720
actcttgggg ccagcgcatg gctcatgtgg ctctcggaga ttgagccagc cagaattgca   6780
tgtgtcctca ttgttgtgtt cctattgctg gtggtgctca tacctgagcc agaaaagcaa   6840
agatctcccc aggacaacca aatggccatc atcatcatgg tagcagtagg tcttctgggc   6900
ttgattaccg ccaatgaact cggatggttg gagagaacaa agagtgacct aagccatcta   6960
atgggaagga gagaggaggg ggcaaccatg ggattctcaa tggacattga cctgcggcca   7020
gcctcagctt gggccatcta tcctgccttg acatcttca ttaccccagc cgtccaacat   7080
gcagtgacca cttcatacaa caactactcc ttaatgcga tggccacgca agctggagtg   7140
ttgtttggta tgggcaaagg gatgccattc tacgcatggg actttggagt cccgctgcta   7200
atgataggtt gctactcaca attaacgccc ctgaccctaa tagtggccat cattttgctc   7260
gtggcgcact acatgtactt gatcccaggg ctgcaggcag cagctcgcgc tgctcgccag   7320
aagagaacgg cagctggcat catgaagaac cctgttgtgc agggaatagt ggtgactgac   7380
attgacacaa tgacaattga cccccaagtg gagaaaaaga tgggacaggt gctactcatg   7440
gcagtagccg tctccagcgc catactgcg aggaccgcct gggggtggg ggaggctggg   7500
gccctgatca cagccgcaac ttccactttg tgggaaggct ctcgaacaa gtactggaac   7560
tcctctcag ccacctcact gtgtaacatt ttagggggaa gttacttggc tggagcttct   7620
ctaatctaca cagtcaaag aaacgctggc ttggtcaaga gcgggtggg tggaacagga   7680
gagaccctgg gagagaaatg gaaggccgc ttgaaccaga tgtcggccct ggagttctac   7740
tcctacaaaa agtcaggcat caccgaggtg tgcagagaag aggcccgccg cgccctcaag   7800
gacggtgtgt caacgggagg ccatgctgtg tcccgaggaa gtgcaaagct gagatggttg   7860
gtggagcggg gatacctgca gccctatgga aaggtcattg atcttggatg tggcagaggg   7920
ggctggagtt actacgccgc caccatccgc aaagttcaag aagtgaaagg atacacaaaa   7980
```

```
ggaggccctg gtcatgaaga acccgtgttg gtgcaaagct atgggtgaaa catagtccgt   8040
cttaagagtg gggtggacgt ctttcatatg gcggctgagc cgtgtgacac gttgctgtgt   8100
gacataggtg agtcatcatc tagtcctgaa gtggaagaag cacggacgct cagagtcctc   8160
tccatggtgg gggattggct tgaaaaagaa ccaggagcct tttgtataaa agtgttgtgc   8220
ccatacacca gcactatgat ggaaaccctg gagcgactgc agcgtaggta tggggaggga   8280
ctggtcagag tgccactctc ccgcaactct acacatgaga tgtactgggg ctctggagcg   8340
aaaagcaaca ccataaaaag tgtgtccacc acgagccagc tcctcttggg gcgcatggac   8400
gggcctagga ggccagtgaa atatgaggag gatgtgaatc tcggctctgg cacgcgggct   8460
gtggtaagct gcgctgaagc tcccaacatg aagatcattg gtaaccgcat tgaaaggatc   8520
cgcgctgaga aagcggaaac gtggttcttt gacgagaacc acccatatag gacatgggct   8580
taccatggaa gctatgatgc cgccacacaa gggtcagcgt cctctctaat aaacggggtt   8640
gtcaggctcc tgtcaaaacc ctgggatgtg tgactggagt cacaggaat agccatgacc   8700
gacaccacac cgtatggtca gcaaagagtt ttcaaggaaa aagttggacac tagggtgcca   8760
gaccccaag aaggcactcg tcaggttatg agcatggtct cttcctggtt gtggaaagag   8820
ctaggcaaac acaaacggcc acgagtctgt accaaagaca agttcatcaa caaggttcgt   8880
agcaatgcag cattagggc aatatttgaa gaggaaaaag agtggaagac tgcagtggaa   8940
gctgtgaacg atccaaggtt ctgggctcta gtggacaagg aaagagagca ccacctgaga   9000
ggagagtgcc agagttgtgt gtacatcaca atgggaaaaa gagaaaagaa acaagggaa   9060
tttggaaagg ccaagggcag ccgcgccatc tggtatatgt ggctaggggc tagatttcta   9120
gagttcgaag cccttggatt cttgaacgag gatcactgga tggggagaga gaactcagga   9180
ggtggtgttg aagggctggg attacaaaga ctcggatatg tcctagaaga gatgagtcgc   9240
ataccaggag gaaggatgta tgcagatgac actgctggct ggacgacccg catcagcagg   9300
tttgatctgg agaatgaagc tctaatcacc aaccaaatgg agaaagggca cagggccttg   9360
gcattggcca taatcaagta cacataccaa aacaaagtgg taaaggtcct tagaccagct   9420
gaaaaaggga agacagttat ggacattatt tcgagacaag accaaagggg gagcggacaa   9480
gttgtcactt acgctctcaa cacatttacc aacctagtgg tgcaactcat tcggaatatg   9540
gaggctgagg aagttctaga gatgcaagac ttgtggctgc tgcggaggtc agagaaagtg   9600
accaactggt tgcagagcaa cggatgggat aggctcaaac gaatggccgt cagtggagat   9660
gattgcgttg tgaaaccaat tgatgatagg tttgcacatg ccctcaggtt cttgaatgat   9720
atgggaaaag ttaggaagga cacacaagag tggaaaccct tgggagggca ggacaactgg   9780
gaagaagttc ccttctgctc ccaccacttc aacaagctcc atctcaagga cgggaggtcc   9840
attgtggttc cctgccgcca ccaagatgaa ctgattggcc gggcccgcgt ctctccaggg   9900
gcgggatgga gcatccggga gactgcttgc ctagcaaaat catatgcgca aatgtggcag   9960
ctcctttatt tccacagaag ggacctccga ctgatggcca atgccatttg ttcatctgtg   10020
ccagttgact gggttccaac tgggagaact acctggtcaa tccatggaaa gggagaatgt   10080
atgaccactg aagacatgct tgtggcgtgg aacagagtgt ggattgagga aacgaccac   10140
atggaagaca gaccccagt cacgaaatgg acagacattc cctatttggg aaaagggaa   10200
gacttgtggt gtggatctct cataggggcac agaccgcgca ccacctgggc tgagaacatt   10260
aaaaacacag tcaacatggt gcgcaggatc ataggtggag aagaaagta catggactac   10320
ctatccaccc aagttcgcta cttgggtgaa aagggtcta cacctggagt gctgtaagca   10380
ccaatcttaa tgttgtcagg cctgctagtc agccacagct tggggaaagc tgtgcagcct   10440
gtgacccccc caggagaagc tgggaaacca agcctatagt caggccgaga acgccatggc   10500
acggaagaag ccatgctgcc tgtgagcccc tcagaggaca ctgagtcaaa aaaccccacg   10560
cgcttggagg cgcaggatgg gaaaagaagg tggcgacctt ccccacccct caatctgggg   10620
cctgaactgg agatcagctg tggatctcca gaagagggac tagtggttag aggaga        10676
```

SEQ ID NO: 11         moltype = DNA   length = 10807
FEATURE                Location/Qualifiers
source                 1..10807
                        mol_type = genomic DNA
                        organism = Zika virus
SEQUENCE: 11

```
agttgttgat ctgtgtgagt cagactgcga cagttcgagt ctgaagcgag agctaacaac   60
agtatcaaca ggtttaattt ggatttggaa acgagagttt ctggtcatga aaacccaaa    120
gaagaaatcc ggaggattcc ggattgtcaa tatgctaaaa cgcggagtag cccgtgtaaa   180
cccccttggg ggtttgaaga ggttgccagc cggacttctg ctgggtcatg gacccatcag   240
aatggttttg cgatactagc cttttttgag atttacagca atcaagccat cactgggcct   300
tatcaacaga tggggttccg tggggaaaaa agaggctatg gaataataaa gaagttcaa    360
gaaagatctt gctgccatgt tgagaataat caatgctagg aaagagagga agacgttgg    420
cgcagacacc agcatcggaa tcattgcct cctgctgact acagccatgg cagcagagat   480
cactagacgc gggagtgcat actacatgta cttggatagc gatgccgcc gaaggccat    540
ttcgtttgct accacattgg gagtgaacaa gtgccacgta cagatcatgg acctcgggca   600
catgtgtgac gccaccatga gttatgagtg ccctatgctg gatgagggag tggaaccaga   660
tgatgtcgat tgctggtgca acacgacatc aacttggtgt gtacggaa cctgtcatca   720
caaaaaggt gaggcacggc gatctagaag agcgtgacg ctcccttctc actctacaag   780
gaagttgcaa acgcggtcgc agacctggtt agaatcaaga aatacacga agcacttgat   840
caaggttgaa aactggatat tcaggaaccc cgggttgcg ctagtggccg ttgccattgc   900
ctggcttttg ggaagtctcga cgagccaaaa agtcatatac ttggtcatga tactgctgat   960
tgccccggca tacagtatca ggtcatagc gtcagcgaat agagactttcg tggagggcat   1020
gtcaggtggg acctggggttg atgttgtctt ggaactgatgga ggctgcgtta ccgtgatggc   1080
acaggacaag ccaacagttg acatagagtt ggtcacgacg acggttagta catggcgaa   1140
ggtaagatcc tattgctacg aggcatcgat atcgacatg gcttcggaca gtcgttgccc   1200
aacacaaggt gaagcctacc ttgacaagca atcagacact caatatgtct gcaaaagaac   1260
attagtgaca gaaggttggg gaaacggttg tggactttt ggcaaagga gcttggtgac   1320
atgtgccaag tttacgtgt ctaagaagat gaccggaaag agcattcaac cggaaaatct   1380
ggagtatcgg ataatgctat cagtgcatgg ctcccagcat agcgggatga ctgtcaatga   1440
tataggatat gaaactgacg aaaatagagc gaaagtcgag gttacgccta attccaccaag   1500
agcggaagca accttgggag cttggaag ttaggactt gactgtgaac caaggacagg   1560
ccttgacttt tcagatctgt attacctgac catgaacaat aagcattggt tggtgcacaa   1620
```

```
agagtggttt catgacatcc cattgccttg gcatgctggg gcagacactg gaactccaca   1680
ctggaacaac aaagaggcat tggtagaatt caaggatgcc cacgccaaga ggcaaaccgt   1740
cgtcgttctg gggagccagg aaggagccgt tcacacggct ctcgctggag ctctagaggc   1800
tgagatggat ggtgcaaagg gaaagctgtt ctctggccat ttgaaatgcc gcctaaaaat   1860
ggacaagctt agattgaagg gcgtgtcata ttccttgtgc actgcggcat tcacattcac   1920
caaggtccca gctgaaacac tgcatggaac agtcacagtg gaggtgcagt atgcagggac   1980
agatggaccc tgcaagatcc cagtccagat ggcggtggac atgcagaccc tgaccccagt   2040
tggaaggctg ataaccgcca accccgtgat tactgaaagc actgagaact caaagatgat   2100
gttggagctt gacccaccat ttggggattc ttacattgtc ataggagttg gggacaagaa   2160
aatcacccac cactgggcata ggagtggtag caccatcgga aaggcatttg aggccactgt   2220
gagaggcgcc aagagaatgg cagtcctggg ggatacagcc tgggacttcg gatcagtcgg   2280
gggtgtgttc aactcactgg gtaagggcat tcaccagatt tttggagcag ccttcaaatc   2340
actgtttgga ggaatgtcct ggttctcaca gatcctcata ggcacgctgc tagtgtggtt   2400
aggtttgaac acaaagaatg gatctatctc cctcacatgc ttgggcctgg ggggagtgat   2460
gatcttcctc tccacggctg tttctgctga cgtggggtgc tcagtggact tctcaaaaaa   2520
ggaaacgaga tgtggcacgg gggtattcat ctataatgat gttgaagcct ggagggaccg   2580
gtacaagtac catcctgact ccccccgcag attggcagca gcagtcaagc aggcctggga   2640
agaggggatc tgtgggatcc catccgtttc aagaatggaa aacatcatgt ggaaatcagt   2700
agaaggggag ctcaatgcta tcctagagga gaatggagtt caactgacag ttgttgtggg   2760
atctgtaaaa aaccccatgt ggagaggtcc acaaagattg ccagtgcctg tgaatgagct   2820
gcccccatgg ctggaaagcct ggggggaaatc gtattttgtt agggcggcaa agaccaacaa   2880
cagttttgtt gtcgacggtg acacactgaa ggaatgtccg cttgagcaga gagcatggaa   2940
tagttttctt gtggaggatc acgggttttgg agtcttccac accagtgtct ggcttaaggt   3000
cagagaagat tactcattag aatgtgaccc agccgtcata ggaacagctg ttaagggaag   3060
ggaggccgcg cacagtgatc tgggctattg gattgaaagt gaaaagaatg acacatggag   3120
gctgaagagg gcccacctga ttgagatgaa aacatgtgag tggccaaagt ctcacacatt   3180
gtggacagat ggagtagaag aaagtgatct tatcataccc aagtctttag ctggtccact   3240
cagccaccac aacaccagag agggttacag aacccaagtg aaaggggccat ggcacagtga   3300
agagcttgaa atccggtttg aggaatgtcc aggcaccaag gttacgtggg aggagacatg   3360
cggaactaga ggaccatctc tgagatcaac tactgcaagt ggagggtca ttgaggaatg   3420
gtgctgtagg gaatgcacaa tgccccccact atcgtttcga gcaaaagacg gctgctggta   3480
tggaatggag ataaggccca ggaaagaacc agagagcaac ttagtgaggt caatggtgac   3540
agcggggtca accgatcata tggaccactt ctctcttgga gtgcttgtga ttctactcat   3600
ggtgcaggag gggttgaaga agagaatgac acaaaagatc atcatgagca catcaatggc   3660
agtgctggta gtcatgatct tgggaggatt ttcaatgagt gacctgggcca agcttgtgat   3720
cctgatgggt gctactttcg cagaaatgaa cactggagga gatgtagctc acttggcatt   3780
ggtagcggca tttaaagtca gaccagcctt gctggtctcc ttcattttca gagccaattg   3840
gacacccgt gagagcatgc tgctagccct ggcttcgtgt cttctgcaaa ctgcgatctc   3900
tgctcttgaa ggtgacttga tggtcctcat taatggattt gctttggcct ggttggcaac   3960
tcgagcaatg gccgtgccac gcactgacaa catcgctcta ccaatcttgg ctgctctaac   4020
accactagct cgaggcacac tgctcgtggc atggagagcg ggcctggcta cttgtggagg   4080
gatcatgctc ctctccctga agggaaagg tagtgtgaag aagaacctgc catttgtcat   4140
ggcctgggca ttgacagctg tgagggtagt agacccatatt aatggtggtag gactactgtt   4200
actcacaagg agtgggaagc ggagctggcc ccctagtgaa gttctcacag ccgttggcct   4260
gatatgtgca ctgccggag ggtttgccaa ggcagacatt gagatgctg gacccatggc   4320
tgcagtaggc ttgctaattg tcagctatgt ggtctcggga aagagtgtgg acatgtacat   4380
tgaaagagca ggtgacatca catggaaaa ggacgcggaa gtcactggaa acagtcctcg   4440
gcttgacgtg gcactggatg agagtggtga tttctcctig gtagaggaag atggtccacc   4500
catgagagag atcatactta aggtggtcct gatggccatc tgtggcatga cccaatagc   4560
tatacctttt gctgcaggag cgtggtatgt gtatgtgaag actgggaaaa ggagtggcgc   4620
cctctgggac gtgcctgctc ccaaagaagt gaagaaagga gagaccacag atggagtgta   4680
cagagtgatg actcgcagac tgctaggttc aacacaggtt ggagtgggag tcatgcaaga   4740
gggagtcttc cacaccatgt ggcacgttac aaaaggagcc gcactgagga gcggtgaggg   4800
aagacttgat ccatactggg gggatgtcaa gcaggacttg gtgtcatact gtgggccttg   4860
gaagttggat gcagcttggg atggactcag cgaggtacag ctttttggcg tacctcccgg   4920
agagagggcc agaaacattc agaccctgcc tggaatattc aagacaaagg acgggacat   4980
cggagcagtt gctctggact accctgcagg gacctcagga tctccgatcc tagacaaatg   5040
tggaagagtg ataggactct atggcaatgg ggttgtgatc aagaatggaa gctatgttag   5100
tgctataacc caggggaaga gggaggagga gactccggtt gaatgtttcg aaccctcgat   5160
gctgaagaag aagcagctaa ctgtcttgga tctgcatcca ggagccggaa aaaccaggag   5220
agttcttcct gaaatagtcc gtgaagccta aaaaaagaga ctccggacag tgatcttggc   5280
accaactagg gttgtcgctg ctgagatgga ggaggcttg agaggacttc cggtgcgtta   5340
catgacaaca gcagtcaacg tcacccattc tgggacagaa atcgttgatt tgatgtgcca   5400
tgccactttc acttcacgct tactacaacc catcagatcc cctaattaca atctctacat   5460
catggatgaa gcccacttca cagacccctc aagtatagct gcaagaggat atatatcaac   5520
aagggttgaa atgggcgagg cggctgccat tttatgact gccacaccac caggaacccg   5580
tgatgcgttt cctgactcta actcaccaat catggacaca gaagtggaag tcccagagag   5640
agcctggagc tcaggctttg attgggtgac agaccattct gggaaaacag tttggttcgt   5700
tccaagcgtg agaaacggaa atgaaatcgc agcctgtctg acaaaggctg gaaagcgtgt   5760
catacagctc agcaggaaga cttttgagac agaatttcag aaaacaaaaa atcaagagtg   5820
ggacttttgtc ataacaactg acatctcaga gatgggcgcc aacttcaagg ctgaccgggt   5880
catagactct aggagatgcc taaaaccagt catacttgat ggtgagagag tcatcttggc   5940
tgggcccatg cctgtcacgc atgctagtgc tgctcagagag aggacgta taggcaggaa   6000
ccctaacaaa cctggagatg agtacatgta tggaggtggg ctgatgaagg ccatgcacac   6060
tggcttgaag caagaatgct tcttgacaac atctaactcc aggatggcct   6120
catagcctcg ctctatcggc ctgaggccga taagtagcc gccattgagg gagagttttaa   6180
gctgaggaca gagcaaagga agaccttcgt ggaactcatg aagagaggag accttcccgt   6240
ctggctagcc tatcaggttg catctgccgg aataacttac acagacagaa gatggtgctt   6300
tgatggcaca accaacaaca ccataatgga agacagcgta ccagcagagg tgtggacaaa   6360
```

```
gtatggagag aagagagtgc tcaaaccgag atggatggat gctagggtct gttcagacca   6420
tgcggccctg aagtcgttca aagaattcgc cgctggaaaa agaggagcgg ctttgggagt   6480
aatggaggcc ctgggaacac tgccaggaca catgacagag aggtttcagg aagccattga   6540
caacctcgcc gtgctcatgc gagcagagac tggaagcagg ccttataagg cagcggcagc   6600
ccaactgccg gagaccctag agaccattat gctcttaggt ttgctgggaa cagtttcact   6660
ggggatcttc ttcgtcttga tgcggaataa gggcatcggg aagatgggct ttggaatggt   6720
aaccccttggg gccagtgcat ggctcatgtg gctttcggaa attgaaccag ccagaattgc   6780
atgtgtcctc attgttgtgt ttttattact ggtggtgctc atacccgagc agagaagca    6840
aagatctccc caagataacc agatggcaat tatcatcatg gtggcagtgg gcctttctagg   6900
tttgataact gcaaacgaac ttggatggct ggaaagaaca aaaaatgaca tagctcatct    6960
aatgggaagg agaagaagg  gagcaaccat gggattctca atggacattg atctgcggcc    7020
agcctccgcc tgggctatct atgccgcatt gacaactctc atcacccag  ctgtccaaca    7080
tgcggtaacc acttcataca caactactc  cttaatggcg atgccacac  aagctggagt    7140
gctgtttggc atgggcaaag ggatgccatt ttatgcaggt gaccttggag tcccgctgct   7200
aatgatgggt tgctattcac aattaacacc cctgactctg atagtagcta tcattctgct   7260
tgtggcgcac tacatgtact tgatcccagg cctacaagcg gcagcagcgc gtgctgccca   7320
gaaaaggaca gcagctggca tcatgaagaa tcccgttgtg gatggaatag tggtaactga   7380
cattgacaca atgacaatag acccccaggt ggagaagaaa atgggacagg tgttactcat    7440
agcagtagcc atctccagtg ctgtgctgct gcggaccgcc tggggatggg gggaggctgg   7500
agctctgatc acagcagcga cctccacctt gtgggaaggc tctccaaaca atactggaa    7560
ctcctctaca gccacctcac tgtgcaacat cttcagagga agctatctgg caggagcttc   7620
ccttatctat acagtgacga gaaacgctgg cctggttaag acagctggag gtgggacggg   7680
agagactctg ggagagaagt ggaaagctcg tctgaatcag atgtcggccc tggagttcta    7740
ctcttataaa aagtcaggta tcactgaagt gtgtagagag gaggctcgcc gtgccctcaa    7800
ggatggagtg gccacaggag gacatgccgt atcccgggga agtgcaaagc tcagatggtt    7860
ggtgagagag ggatatctgc agccctatgg gaaggttgtt gacctcggat gtggcagagg   7920
gggctggagc tattatgccg ccaccatccg caaagtgcag gaggtgagag gatacacaaa   7980
ggaggtccc ggtcatgaag aacccatgct ggtgcaaagc tatgggtgga acatagttcg   8040
tctcaagagt ggagtggacg tcttccacat ggcggctgag ccgtgtgaca ctctgctgtg   8100
tgacataggt gagtcatcat ctagtcctga agtggaagag acacgaacac tcagagtgct    8160
ctctatggtg ggggactggc ttgaaaaaag accaggggcc ttctgtataa aggtgctgtg    8220
cccatacacc agcactatga tggaaaccat ggagcgactg caacgtaggc atggggggagg   8280
attagtcaga gtgccattgt ctcgcaactc cacacatgga atgtactggg tctctggggc    8340
aaagagcaac atcataaaaa gtgtgtccac cacaagtcag ctcctcctgg gacgcatgga   8400
tggccccagg aggccagtga aatatgagga ggatgtgaac ctcggctcgg gtacacgaga   8460
tgtggcaagc tgtgctgagg ctcctaacat gaaaatcatc ggcaggcgca ttgagagaat   8520
ccgcaatgaa catgcagaaa catggttttct tgatgaaaac cacccataca ggacatgggc   8580
ctaccatggg agctacgaag cccccacgca aggatcagcc tcttccctcg tgaacggggt    8640
tgttagactc ctgtcaaagc cttgggacgt ggtgactgga gttacaggaa tagccatgac   8700
tgacaccaca ccatacgcc  aacaaagagt cttcaaagaa aaagtggaca ccagggtgcc   8760
agatccccaa gaaggcactc gccaggtaat gaacatagtc tcttcctggc tgtgaagga    8820
gctggggaaa cgcaagcggc cacgcgtctg caccaaagaa gagtttatca acaaggtgcg   8880
cagcaatgca gcactgggag caatatttga agaggaaaga cggctgtgga agctgtgaat   8940
gatccaaggt tttgggcccct agtggatagg gagagagaac accacctgag                9000
aggagagtgt cacagctgtg tgtacaacat gatgggaaaa agagaaaaga agcaaggaga   9060
gttcgggaaa gcaaaaggta gccgcgccat ctggtacatg tggttgggag ccagattctt    9120
ggagtttgaa gcccttggat tcttgaacga ggaccattgg atgggaaagg aaaactcagg   9180
aggtggagtc gaagggttag gattgcaaag acttggatac attctagaag aaatgaatcg    9240
ggcaccagga ggaaagatgt acgcagatga cactgctggc tgggacaccc gcattagtaa    9300
gtttgatctg gagaatgaag ctctgattac caaccaaatg gaggaagggc acagaactct   9360
ggcgttggcc gtgattaaat acacatacca aaacaaagtg gtgaaggttc tcagaccagc   9420
tgaaggagga aaaacagtta tggacatcat ttcaagacaa gaccagagag ggagtggaca    9480
agttgtcact tatgctctca acacattcac caacttggtg gtgcagctta tccgaacat    9540
ggaagctgag gaagtgttag agatgcaaga cttatggttg ttgaggaagc cagagaaagt   9600
gaccagatgg ttgcagagca atggatggga tagactcaaa cgaatggccg tcagtggaa    9660
tgactgcgtt gtgaagccaa tcgatgatag gttgcacat  gccctcaggt tcttgaatga    9720
catgggaaaa gttaggaaag acacacagga gtggaaccc tcgactggat ggagcaattg   9780
ggaagaagtc ccgttctgct cccaccacttt caacaagctg tacctcaagg atgggagatc    9840
cattgtggtc ccttgccgcc accaagatga actgattggc cgagctcgcg tctccaccagg   9900
ggcaggatgg agcatccggg agactgcctg tcttgcaaaa tcatatgcgc agatgtggca    9960
gctcctttat ttccacagaa gagaccttcg actgatggct aatgccattt gctcggctgt    10020
gccagttgac tgggtaccaa ctgggagaac cacctggtca atccatggaa agggagaatg   10080
gatgaccact gaggacatgc tcatggtgtg gaatagagtg tggattgagg agaacgacca   10140
tatggaggac aagactcctg taacaaaatg gacagacatt ccctatctag gaaaagggga   10200
ggacttatgg tgtggatccc ttataggca  cagaccccgc accttgggg  ctgaaaacat    10260
caaagacaca gtcaacatgg tgcgcaggat cataggtgat gaagaaagt  acatggacta    10320
tctatccacc caagtccgct acttgggtga ggaagggtcc acaccggag  gttgtaagc    10380
accaattta  gtgttgtcag gcctgctagt cagccacagt ttggggaaag ctgtgcagcc   10440
tgtaaccccc ccaggagaag ctgggaaacc aagctcatag tcaggccgag aacgccatgc   10500
cacggaagaa gccatgctgc ctgtgagccc ctcagaggac actgagtcaa aaaccccac    10560
gcgcttggaa gcgcaggatg ggaaagaag gtggcgacct tccccaccct tcaatctggg   10620
gcctgaactg gagactagct gtgaatctcc agcagggga  ctagtggtta gaggagaccc   10680
cccggaaaac gcaaaacagc atattgacgc tgggaaagac cagagactcc atgagtttcc   10740
accacgctgg ccgccaggca cagatcgccg aacagcggcg gccggtgtgg ggaaatccat   10800
ggtttct                                                              10807

SEQ ID NO: 12          moltype = DNA  length = 10794
FEATURE                Location/Qualifiers
source                 1..10794
```

-continued

```
                         mol_type = genomic DNA
                         organism = Zika virus
SEQUENCE: 12
agttgttgat ctgtgtgagt cagactgcga cagttcgagt ctgaagcgag agctaacaac  60
agtatcaaca ggtttaattt ggatttggaa acgagagttt ctggtcatga aaaaccccaa  120
agaagaaatc cggaggatcc ggattgtcaa tatgctaaaa cgcggagtag cccgtgtaaa  180
ccccttggga ggtttgaaga ggttgccagc cggacttctg ctgggtcatg gacccatcag  240
aatggttttg gcgatactag cctttttgag atttacagca atcaagccat cactgggcct  300
tatcaacaga tggggttccg tggggaaaaa agaggctatg gaaataataa agaagttcaa  360
gaaagatctt gctgccatgt tgagaataat caatgctagg aaagagagga agagacgtgg  420
cgcagacacc agcatcggaa tcattggcct cctgctgact acagccatgg cagcagagat  480
cactagacgc gggagtgcat actacatgta cttggatagg agcgatgccg ggaaggccat  540
ttcgtttgct accacattgg gagtgaacaa gtgccacgta cagatcatgg acctcgggca  600
catgtgtgac gccaccatga gttatgagtg ccctatgctg gatgagggag tggaaccaga  660
tgatgtcgat tgctggtgca acacgacatc aacttgggtt gtgtacggaa cctgtcatca  720
caaaaaaggt gaggcacggc gatctagaag agccgtgacg ctcccttctc actctacaag  780
gaagttgcaa acgcggtcgc agacctggtt agaatcaaga gaatacacga agcacttgat  840
caaggttgaa aactggatat tcaggaaccc cgggtttgcg ctagtggccg ttgccattgc  900
ctggcttttg ggaagctcga cgagccaaaa agtcatatac ttggtcatga tactgctgat  960
tgccccggca tacagtatca ggtgcattgg agtcagcaat agagacttcg tggagggcat  1020
gtcaggtggg acctgggttg atgttgtctt ggaacatgga ggctgcgtta ccgtgatggc  1080
acaggacaag ccaacagtcg acatagagtt ggtcacgacg acggttagta acatggccga  1140
ggtaagatcc tattgctacg aggcatcgat atcggacatg gcttcggaca gtcgttgccc  1200
aacacaaggt gaagcctacc ttgacaagca atcagacact caatatgtct gcaaaagaac  1260
attagtggac agaggttggg gaaacggttg tggacttttt ggcaaaggga gcttggtgac  1320
atgtgccaag tttacgtgtt ctaagaagat gaccgggaag agcattcaac cggaaaatct  1380
ggagtatcgg ataatgctat cagtgcatgg ctcccagcat agcgggatga ttggatatga  1440
aactgacgaa gatagagcga aagtcgaggt tacgcctaat tcaccaagag cggaagcaac  1500
cttgggaggc tttggaagct taggacttga ctgtgaacca aggacaggcc ttgacttttc  1560
agatctgtat tacctgacca tgaacaataa gcattggttg gtgcacaaag agtggtttca  1620
tgacatccca ttgccttggc atgctggggc agacaccgga actccacact ggaacaacaa  1680
agaggcattg gtagaattca aggatgccca cgccaagagg caaaccgtcg tcgttctggg  1740
gagccaggaa ggagccgttc acacggctct cgctggagct ctagaggctg agatggatgg  1800
tgcaaaggga aggctgttct ctggccattt gaaatgccgc ctaaaaatgg acaagcttag  1860
attgaagggc gtgtcatatt ccttgtgcac tgcggcattc acattcacca aggtcccagc  1920
tgaaacactg catggaacag tcacagtgga ggtgcagtat gcagggacag atggaccctg  1980
caagatccca gtccagatgg cggtggacat gcagaccctg accccagttg gaaggctgat  2040
aaccgccaac cccgtgatta ctgaaagcac tgagaactca aagatgatgt tggagcttga  2100
cccaccattt ggggattctt acattgtcat aggagttggg gacaagaaaa tcacccacca  2160
ctggcatagg agtggtagca ccatcggaaa ggcatttgag gccactgtga gaggcgccaa  2220
gagaatggca gtcctggggg atacagcctg ggacttcgga tcagtcgggg gtgtgttcaa  2280
ctcactgggt aagggcattc accagatttt tggagcagcc ttcaaatcac tgtttggagg  2340
aatgtcctgg ttctcacaga tcctcatagg cacgctgcta gtgtggttag gtttgaacac  2400
aaagaatgga tctatctccc tcacatgctt ggccctgggg ggagtgatga tcttcctctc  2460
cacggctgtt tctgctgacg tggggtgctc agtggacttc tcaaaaaagg aaacgagatg  2520
tggcacgggg gtattcatct ataatgatgt tgaagcctgg agggaccggt acaagtacca  2580
tcctgactcc ccccgcagat tggcagcagc agtcaagcag gcctgggaag aggggatctg  2640
tgggatctca tccgtttcaa gaatggaaaa catcatgtgg aaatcagtag aaggggagct  2700
caatgctatc ctagaggaga atggagttca actgacagtt gttgtgggat ctgtaaaaaa  2760
ccccatgtgg agaggtccac aaagattgcc agtgcctgtg aatgagctgc cccatggctg  2820
gaaagcctgg gggaaatcgt attttgttag ggcggcaaag accaacaaca gttttgttgt  2880
cgacggtgac acactgaagg aatgtccgct tgagcacaga gcatggaata gttttcttgt  2940
ggaggatcac gggtttggag tcttccacac cagtgtctgg cttaaggtca gagaagatta  3000
ctcattagaa tgtgacccag ccgtcatagg aacagctgtt aagggaaggg aggccgcgca  3060
cagtgatctg ggctattgga ttgaaagtga aaagaatgac acatggaggc tgaagagggc  3120
ccacctgatt gagatgaaaa catgtgaatg gccaaagtct cacacattgt ggacagatgg  3180
agtagaagaa agtgatctta tcatacccaa gtctttagct ggtccactca gccaccacaa  3240
caccagagag ggttacagaa cccaagtgaa agggccatgg cacagtgaag agcttgaaat  3300
ccggtttgag gaatgtccag gcaccaaggt ttacgtggag gagacatgcg gaactagagg  3360
accatctctg agatcaacta ctgcaagtgg aagggtcatt gaggaatggt gctgtaggga  3420
atgcacaatg cccccactat cgtttcgagc aaaagacggc tgctggtatg gaatggagat  3480
aaggcccagg aaagaaccag agagcaactt agtgaggtca atggtgacag cggggtcaac  3540
cgatcatatg gaccacttct ctcttggagt gcttgtgatt ctactcatgg tgcaggaggg  3600
gttgaagaag agaatgacca caaagatcat catgagcaca tcaatggcag tgctggtagt  3660
catgatcttg ggaggatttt caatgagtga cctggccaag cttgtgatcc tgatgggtgc  3720
tactttcgca gaaatgaaca ctggaggaga tgtagctcac ttggcattgg tagcggcatt  3780
taaagtcaga ccagccttgc tggtctcctt cattttcaga gccaattgga caccccgtga  3840
gagcatgctg ctagccctgg cttcgtgtct tctgcaaact gcgatctctg ctcttgaagg  3900
tgacttgatg gtcctcatta atggatttgc tttggcctgg ttggcaattc gagcaatggc  3960
cgtgccacgc actgacaaca tcgctctacc aatcttggct gctctaacac cactagctcg  4020
aggcacactg ctcgtggcat ggagagcggg cctggctact tgtggaggga tcatgctcct  4080
ctccctgaaa gggaaaggta gtgtgaagaa gaacctgcca tttgtcatgg ccctgggatt  4140
gacagctgtg agggtagtag accctattaa tgtggtagga ctactgttac tcacaaggag  4200
tgggaagcgg agctggcccc ctagtgaagt tctcacagcc gttggcctga tatgtgcact  4260
ggccggaggg tttgccaagg cagacattga gatggctgga cccatggctg cagtaggctt  4320
gctaattgtc agctatgtgg tctcgggaaa gagtgtggac atgtacattg aaagagcagg  4380
tgacatcaca tgggaaaagg acgcggaagt cactggaaac agtcctcggc ttgacgtggc  4440
actggatgag agtggtgact tctccttggt agaggaagat ggtccaccca tgagagagat  4500
catactcaag gtggtcctga tggccatctg tggcatgaac ccaatagcta taccttttgc  4560

```
tgcaggagcg tggtatgtgt atgtgaagac tgggaaaagg agtggcgccc tctgggacgt  4620
gcctgctccc aaagaagtga agaaaggaga gaccacagat ggagtgtaca gagtgatgac  4680
tcgcagactg ctaggttcaa cacaggttgg agtgggagtc atgcaagagg gagtctttcca 4740
caccatgtgg cacgttacaa aaggagccgc actgaggagc ggtgagggaa gacttgatcc  4800
atactggggg gatgtcaagc aggacttggt gtcatactgt gggccttgga agttggatgc  4860
agcttgggat ggactcagcg aggtacagct tttggccgta cctcccggag agagggccag  4920
aaacattcag accctgcctg gaatattcaa gacaaaggac ggggacatcg gagcagttgc  4980
tctggactac cctgcaggga cctcaggatc tccgatccta gacaaatgtg gaagagtgat  5040
aggactctat ggcaatgggg ttgtgatcaa gaatggaagc tatgttagtg ctataaccca  5100
gggaaagagg gaggaggaga ctccggttga atgtttcgaa ccctcgatgc tgaagaagaa  5160
gcagctaact gtcttggatc tgcatccagg agccggaaaa accaggagag ttcttcctga  5220
aatagtccgt gaagccataa aaagagact ccggacagtg atcttggcac caactagggt   5280
tgtcgctgct gagatggagg aggccttgag aggacttccg gtgcgttaca tgacaacagc  5340
agtcaacgtc acccattctg ggacagaaat cgttgatttg atgtgccatg ccactttcac  5400
ttcacgctta ctacaaccca tcagagtccc taattacaat ctcaacatca tggatgaagc  5460
ccacttcaca gaccccctcaa gtatagctgc aagaggatac atatcaacaa gggttgaaat 5520
gggcgaggcg gctgccattt tatgactgc cacaccacca ggaacccgtg atgcgtttcc   5580
tgactctaac tcaccaatca tggacacaga agtggaagtc ccagagagag cctggagctc  5640
aggctttgat tgggtgacag accattctgg gaaaacagtt tggttcgttc caagcgtgag  5700
aaacggaaat gaaatcgcag cctgtctgac aaaggctgga aagcgggtca tacagctcag  5760
caggaagact tttgagacag aatttcagaa aacaaaaaat caagagtggg actttgtcat  5820
aacaactgac atctcagaga tgggcgccaa cttcaaggct gaccgggtca tagactctag  5880
gagatgccta aaaccagtca tacttgatgg tgagagagtc atcttggctg ggcccatgcc  5940
tgtcacgcat gctagtgctg ctcagaggag aggacgtata ggcaggaacc ctaacaaacc  6000
tggagatgag tacatgtatg gaggtgggtg tgcagagact gatgaaggcc atgcacactg  6060
gcttgaagca agaatgcttc ttgacaacat ctacctccag gatggcctca tagcctcgct  6120
ctatcggcct gaggccgata aggtagccgc cattgaggga gagtttaagc tgaggacaga  6180
gcaaaggaag accttcgtgg aactcatgaa gagaggagac cttcccgtct ggctagccta  6240
tcaggttgca tctgccggaa taacttacac agacagaaga tggtgctttg atggcacaac  6300
caacaacacc ataatggaag acagtgtacc agcagaggtc tgcaaagt atggagagaa   6360
gagagtgctc aaaccgagat ggatggatgc tagggtctgt tcagaccatg cggccctgaa  6420
gtcgttcaaa gaattcgccg ctggaaaaag aggagcggct ttgggagtaa tggaggccct  6480
gggaacactg ccaggacaca tgacagagag gtttcaggaa gccattgaca acctcgccgt  6540
gctcatgcga gcagagactg aagcaggcc ttataaggca gcggcagccc aactgccgga  6600
gaccctagag accattatgc tcttaggttt gctgggaaca gtttcactgg ggatcttcct  6660
cgtcttgatg cggaataagg gcatcggaaa gatgggcttt ggaatggtaa cccttgggc   6720
cagtgcatgg ctcatgtggc tttcggaaat tgaaccagcc agaattgcat gtgtcctcat  6780
tgttgtgttt ttattactgg tggtgctcat acccgagcca gagaagcaaa gatctcccca  6840
agataaccag atggcaatta tcatcatggt ggcagtgggc cttctaggtt tgataactgc  6900
aaacgaactt ggatggctgg aaagaacaaa aaatgacata gctcatctaa tgggaaggag  6960
agaagaagga gcaaccatgg gattctcaat ggacattgat ctgcggccag cctccgcctg  7020
ggctatctat gccgcattga caactctcat caccccagct gtccaacatg cggtaaccac  7080
ttcatacaac aactactcct taatgcgat ggccacacaa gctggaggtc tgttttggca   7140
gggcaaaggg atgccattta tgcatgggga ccttggagtc ccgctgctaa tgatgggttg  7200
ctattcacaa ttaacacccc tgactctgat agtagctatc attctgcttg tggcgcacta  7260
catgtacttg atcccaggcc tacaagcggc agcagcgcgt gctgcccaga aaggacagc   7320
agctggcatc atgaagaatc ccgttgtgga tggaatagtg gtaactgaca ttgacacaat  7380
gacaatagac ccccaggtgg agaagaagat gggacaagtg ttactcatag cagtagccat  7440
ctccagtgct gtgctgctgc ggaccgcctg gggatggggg gaggctggag ctctgatcac  7500
agcagcgacc tccaccttgt gggaaggctc tccaaacaaa tactgaact cctctacagc   7560
cacctcactg tgcaacatct tcagaggaag ctatctatgc ggagcttcc ttatctatac   7620
agtgacgaga aacgctggcc tggttaagag acgtggaggt gggacgggga gactctgggg  7680
agagaagtgg aaagctcgtc tgaatcagat gtcggccctg gagttctact cttataaaaa  7740
gtcaggtatc actgaagtgt gtagagagga ggctcgccgt gccctcaagg atggagtggc  7800
cacaggagga catgccgtat cccggggaag tgcaaagatc agatggttgg aggagagagg  7860
atatctgcag ccctatggga aggttgttga cctcggatgt ggcagagggg gctggagcta  7920
ttatgccgcc accatccgca aagtgcagga ggtgagagga tacacaaagg gaggtcccgg  7980
tcatgaagaa cccatgctgg tgcaaagcta tgggtggaac atagttcgtc tcaagagtgg  8040
agtggacgtc ttccacatgg cggctgagcc gtgtgacact ctgctgtgtg acataggtga  8100
gtcatcatct agtcctgaag tggaagagac acgaacactc agatgtctct ctatggtgga  8160
ggactggctt gaaaaaagac caggggcctt ctgtataaag gtgctgtgcc catacaccag  8220
cactatgatg gaaccatggg agcgactgca acgtaggcat gggggaggat tagtcagagt  8280
gccattgtgt cgcaactcca cacatgagat gtactggtc tctggggcaa agagcaacat   8340
cataaaaagt gtgtccacca agtcagct cctcctggga cgcatgggtg gcccaggga   8400
gccagtgaaa tatgaggagg atgtgaacct cggctcgggt acacgagctg tgcaagctg   8460
tgctgaggct cctaacatga aaatcatcgg caggcgcatt gagagaatcc gcaatgaaca  8520
tgcagaaaca tggtttcttg atgaaaacca cccatacagg acatgggcct accatggag   8580
ctacgaagcc cccacgcaag gatcagcgtc ttccctcgtg aacggggttg ttagactcct  8640
gtcaaagcct tgggacgtgg tgactggagt tacaggaata gccatgactg acaccacacc  8700
atacggccaa caaagagtct tcaaagaaaa agtggacacc agggtgccag atccccaaga  8760
aggcactcgc caggtaatga caatagtctc ttcctggctg tggaaggagc tggggaaacg  8820
caagcggcca cgcgtctgca ccaaagaaga gtttatcaac aaggtgcgca gcaatgcagc  8880
actgggagca atatttgaag aggaaaagaa atggaagacg gctgtggaag ctgtgaatga  8940
tccaaggttt tgggcctag tggataggga gagagaacac catagggagt tcggaaagc   9000
cagctgtgtg tacaacatga tgggaaaaag agaaaagaaa caagagagt tcggaaagc   9060
aaaaggtagc cgcgccatct ggtacatgtg gttgggagcc agattcttgg agtttgaagc  9120
ccttggattc ttgaacgagg accattggat gggaagagaa aactcaggag gtggagtcga  9180
agggttagga ttgcaaagac ttggatacat tctagaagaa atgaatcggg caccaggagg  9240
aaagatgtac gcagatgaca ctgctggctg ggacaccgc attagtaagt ttgatctgga  9300
```

```
gaatgaagct ctgattacca accaaatgga ggaagggcac agaactctgg cgttggccgt   9360
gattaaatac acataccaaa acaaagtggg gaaggttctc agaccagctg aaggaggaaa   9420
aacagttatg gacatcattt caagacaaga ccagagaggg agtggacaag ttgtcactta   9480
tgctctcaac acattcacca acttggtggt gcagcttatc cggaacatgg aagctgagga   9540
agtgttagag atgcaagact tatggttgtt gaggaagcca gagaaagtga ccagatggtt   9600
gcagagcaat ggatgggata gactcaaacg aatggcggtc agtggagatg actgcgttgt   9660
gaagccaatc gatgataggt ttgcacatgc cctcaggttc ttgaatgaca tgggaaaagt   9720
taggaaagac acacaggagt ggaaaccctc gactggatgg agcaattggg aagaagtccc   9780
gttctgctcc caccacttca acaagctgta cctcaaggat gggagatcca ttgtggtctg   9840
ttgccgccac caagatgaac tgattggccg agctcgcgtc tcaccagggg caggatggag   9900
catccgggag actgcctgtc ttgcaaaatc atatgcgcag atgtggcagc tcctttattt   9960
ccacagaaga gaccttcgac tgatggctaa tgccatttgc tcggctgtgc cagttgactg  10020
ggtaccaact gggagaacca cctggtcaat ccatggaaag ggagaatgga tgaccactga  10080
ggacatgctc atggtgtgga atagagtgtg gattgaggag aacgaccata tggaggacaa  10140
gactcctgta acaaaatgga cagacattcc ctatctagga aaagggagg acttatggtg  10200
tggatccctt atagggcaca gaccccgcac cacttgggct gaaaacatca agacacagt   10260
caacatggtg cgcaggatca taggtgatga agaaaagtac atggactatc tatccaccca  10320
agtccgctac ttgggtgagg aagggtccac acccggagtc ttgtaagcac caattttagt  10380
gttgtcaggc ctgctagtca gccacagttt ggggaaagct gtgcagcctg taacccccc   10440
aggagaagct gggaaaccaa gctcatagtc aggccgagaa cgccatggca cggaagaagc  10500
catgctgcct gtgagcccct cagaggacac tgagtcaaaa accccacgc gcttggaagc   10560
gcaggatggg aaaagaaggt ggcgaccttc cccaccttc aatctggggc ctgaactgga  10620
gactagctgt gaatctccag cagagggact agtggttaga ggagacccc cggaaaacgc   10680
aaaacagcat attgacgtgg gaaagaccag agactccatg agtttccacc acgctggccg  10740
ccaggcacag atcgccgaac ttcggcggcc ggtgtgggga aatccatggt ttct          10794

SEQ ID NO: 13          moltype = DNA  length = 10617
FEATURE                Location/Qualifiers
source                 1..10617
                       mol_type = genomic DNA
                       organism = Zika virus
SEQUENCE: 13
agtatcaaca ggttttattt tggatttgga aacgagagtt tctggtcatg aaaaacccaa     60
aaaagaaatc cggaggattc cggattgtca atatgctaaa acgcggagta gcccgtgtga    120
gccccttttgg gggcttgaag aggctgccga ccgggacttct gctgggtcat gggcccatca    180
ggatggtctt ggcgattcta gccttttttga gattcacggc aatcaagcca tcactgggtc    240
tcatcaatag atggggttca gtggggaaaa aagaggctat ggaataata aagaagttca    300
agaaagatct ggctgccatg ctgagaataa tcaatgctag gaaggagaag aagagacgag    360
gcgcagatac tagtgtcgga attgttggcc tcctgctgac cacagctatg gcagcggagg    420
tcactagacg tgggagtgca tactatatgt acttggacag aaacgacgct ggggaggcca    480
tatcttttcc aaccacattg gggatgaata agtgttatat acagatcatg gatcttggac    540
acatgtgtga tgccaccatg agctatgaat gccctatgct ggatgagggg gtggaaccag    600
atgacgtcga ttgttggtgc aacacgacgt caacttggtg tgtgtacgga acctgccatc    660
acaaaaaagg tgaagcacgg agatctagaa gagctgtgac gctccctcc cattccacta    720
ggaagctgca aacgcggtcg caaacctggt tggaatcaag agaatacaca aagcacttga    780
ttagagtcga aaattggata ttcaggaacc ctggcttcgc gttagcagca gctgccatcg    840
cttggcttt gggaagctca acgagccaaa aagtcatata cttggtcatg atactgctga    900
ttgccccggc atacagcatc aggtgcatag gagtcagcaa taggactttt gtggaagtta    960
tgtcaggtgg gacttgggtt gatgttgtct tggaacatgg aggttgtgtc accgtaatgg   1020
cacaggacaa accgactgtc gacatagagc tggttacaac aacagtcagc aacatggcgg   1080
aggtaagatc ctactgctat gaggcatcaa tatcggacat ggcttcggac agccgctgcc   1140
caacacaagg tgaagcctac cttgacaagc aatcagacac tcaatatgtc tgcaaaagaa   1200
cgttagtgga cagaggctgg ggaaatggat gtggactttt tggcaaaggg agcctggtga   1260
catgcgctaa gtttgcatgc tccaagaaaa tgaccgggaa gagcatccag ccagagaatc   1320
tggagtaccg gataatgctg tcagttcatg gctcccagca cagtgggatg atcgttaatg   1380
acacaggaca tgaaactgat gagaatagag caaggttga gataacgccc aattcaccaa   1440
gagccgaagc caccctgggg ggttttgaa gcctaggact tgattgtgaa ccgaggacag   1500
gccttgactt tcagatttg tattacttga ctatgaataa caagcactgg ttggttcaca   1560
aggagtggtt ccacgacatt ccattacctt ggcacgctgg ggcagacacc ggaactcac   1620
actgaacaa caaagaagca ctggtagagt tcaaggacgc acatgccaaa aggcaaactg   1680
tcgtggttct agggagtcaa gaaggagcag ttcacacggc ccttgctgga gctctgagg   1740
ctgagatgga tggtgcaaag ggaaggctgt cctctggcca cttgaaatgt cgcctgaaaa   1800
tggataaact tagattgaag ggcgtgtcat actccttgtg taccgcagcg ttcacattca   1860
ccaagatccc ggctgaaaca ctgcacggga cagtcacagt ggaggtacag tacgcaggga   1920
cagatggacc ttgcaaggtt ccagctcaga tggcggtgga catgcaaact ctgacccag   1980
ttgggaggtt gataaccgct aacccgtaa tcactgaaag cactgagaac tctaagatga   2040
tgctggaact tgatccacca tttggggact cttacattgt cataggagtc ggggagaaga   2100
agatcaccca ccactggcac aggagtggca gcaccattg aaaagcatt gaagccactg   2160
tgagaggtgc caagagaatg gcagtcttgg gagacacagc ctgggacttt ggatcagttg   2220
gaggcgctct caactcattg ggcaagggca tccatcaaat ttttggagca gctttcaaat   2280
cattgtttgg aggaatgtcc tggttctcac aaattctcat tggaacgttg ctgatgtggt   2340
tgggtctgaa cacaaagaat ggatctattt cccttatgtg cttggctta ggggagtgt   2400
tgatcttctt atccacagct gtctctgctg atgtggggtg ctcggtggac ttctcaaaga   2460
aggagagtga atgcggtaca ggggtgttcg tctataacga cgttgaagcc tggagggaca   2520
ggtacaagta ccatcctgac tccccccgta gattggcagc agcagtcaag caagcctggg   2580
aagatggtat ctgtgggatc tcctctgttt caagaatgga aaacatcatg tggagatcag   2640
tagaagggga gctcaacgca atcctggaag agaatgagt caactgacg gtcgttgtgg   2700
gatctgtaaa aaaccccatg tggagaggtc acagagatt gccccgtgcct gtgaacgagc   2760
tgccccacgg ctgaaaggct tggggggaaat cgtacttcgt cagagcagca aagacaaata   2820
```

```
acagctttgt cgtggatggt gacacactga aggaatgccc actcaaacat agagcatgga 2880
acagctttct tgtggaggat catgggttcg gggtatttca cactagtgtc tggctcaagg 2940
ttagagaaga ttattcatta gagtgtgatc cagccgttat tggaacagct gttaagggaa 3000
aggaggctgt acacagtgat ctaggctact ggattgagag tgagaagaat gacacatgga 3060
ggctgaagag ggcccatctg atcgagatga aaacatgtga atggccaaag tcccacacat 3120
tgtggacaga tggaatagaa gagagtgatc tgatcatacc caagtcttta gctgggccac 3180
tcagccatca caataccaga gagggctaca ggacccaaat gaaagggcca tggcacagtg 3240
aagagcttga aattcggttt gaggaatgcc caggcactaa ggtccacgtg gaggaaacat 3300
gtggaacaag aggaccatct ctgagatcaa ccactgcaag cggaagggtg atcgaggaat 3360
ggtgctgcag ggagtgcaca atgcccccac tgtcgttccg ggctaaagat ggctgttggt 3420
atggaatgga gataaggccc aggaaagaac cagaaagtaa cttagtaagg tcaatggtga 3480
ctgcaggatc aactgatcac atggatcact tctcccttgg agtgcttgtg attctgctca 3540
tggtgcagga agggctgaag aagagaatga ccacaaagat catcataagc acatcgatgg 3600
cagtgctggt agctatgatc ctgggaggat tttcaatgag tgacctggct aagcttgcaa 3660
ttttgatggg tgccaccttc gcggaaatga acactggagg agatgtagct catctggcgc 3720
tgatagcggc attcaaagtc agaccagcgt tgctggtatc tttcatcttc agagctaatt 3780
ggacaccccg tgaaagcatg ctgctggcct tggcctcgtg tcttttgcaa actgcgatct 3840
ccgccttgga aggcgacctg atggttctca tcaatggttt tgcttttggcc tggttggcaa 3900
tacgagcgat ggttgttcca cgcactgata acatccacctt ggcaatcctg gctgctctga 3960
caccactggc ccgggcaca ctgctcgtgt gt cgtggagagc aggccttgct acttgcgggg 4020
ggtttatgct cctctctctg aagggaaag gcagtgtgaa aagaacatta ccatttgtca 4080
tggccctggg actaaccgct gtgaggcctg tcgaccccat caacgtggtg ggactgctgg 4140
tgctcacaag gagtgggaag cggagctggc cccctagcga agtactcaca gctgttggcc 4200
tgatatgcgc attggctgga gggttcgcca aggcagatat agagatggct gggcccatgg 4260
ccgcggtcgg tctgctaatt gtcagttacg tggtctcagg aaagagtgtg gacatgtaca 4320
ttgaaagagc aggtgacatc acatggggaaa aagatgcgga gtcactgga agcagtcccc 4380
ggctcgatgt ggcgctagat gagagtgtg atttctccct ggtggaggat gacggtcccc 4440
ccatgagaga gatcatactc aaggtggtcc tgatgaccat ctgtggcatg aacccaatag 4500
ccataccctt tgcagctgga gcgtggtacg tatacgtgaa gactgaaaaa aggagtggtg 4560
ctctatggga tgtgcctgct cccaaggaag taaaaaaggg aggagaccaca gatgagtgt 4620
acagagtaat gactcgtaga ctgctaggtt caacacaagt tggagtggga gttatgcaag 4680
aggggggtctt tcacactatg tggcacgtca caaaaggatc cgcgctgaga agcggtgaag 4740
ggagacttga tccatactgg ggagatgtca agcaggatct ggtgtcatac tgtggtccat 4800
ggaagctaga tgccgcctgg gacgggcaca gcgaggtgca gctcttggcc gtgccccccg 4860
gagagagagc gaggaacatc cagactctgc ccggaatatt taagacaaag gatggggaca 4920
ttggagcggt tgcgctggat tacccagcag gaacttcagg atctccaatc ctagacaagt 4980
gtgggagagt gataggactt tatggcaatg gggtcgtgat caaaaatggg agttatgtta 5040
gtgccatcac ccaaggagg agggaggaag agacttcctgt tgagtgcttc gagccttcga 5100
tgctgaagaa gaagcagcta actgtgcttаg acttgcatcc tggagctgga aaaaccagga 5160
gagttcttcc tgaaatagtc cgtgaagcca taaaaacaag actccgtact gtgatcttag 5220
ctccaaccag ggttgtcgct gctgaaatgg aggaagccct tagagggctt ccagtgcgtt 5280
atatgacaac agcagtcaat gtcacccact ctggaacaga aatcgtcgac ttaatgtgcc 5340
atgccacctt cacttcacgt ctactacagc caatcagagt cccaaactat aatctgtata 5400
ttatggatga ggcccacttc acagatccct caagtatagc agcaaggagga tacatttcaa 5460
caagggttga gatgggcgag gcggctgcca tcttcatgac cgccacgcca ccaggaaccc 5520
gtgacgcatt tccggactcc aactcaccaa ttatggacac cgaagtggaa gtcccagaga 5580
gagccggag ctcaggctttt gattgggtga cggatcattc tggaaaaaca gtttggtttg 5640
ttccaagcgt gaggaacggc aatgagatcg cagcttgtct gacaaaggct ggaaaacggg 5700
tcatacagct cagcagaaag acttttgaga cagattcca gaaaacaaaa catcaagagt 5760
gggacttгtgt cgtgacaact gacatttcag agatgggcgc caactttaaa gctgaccgtg 5820
tcatagattc caggagatgc ctaaagccgg tcatacttga tggcgagaga gtcattctgg 5880
ctggacccat gcctgtcaca catgccagcg ctgcccagag gaggggggcgc ataggcagga 5940
atccaacaa acctggagat gagtatctgt atgaggtgg gtgcgcagag actgacgaag 6000
accatgcaca ctggcttgaa gcaagaatgc tccttgacaa tatttacctc caagatggcc 6060
tcatagcctc gctctatcga cctgaggccg acaaagtagc agccattgag ggagagttca 6120
agcttaggac ggagcaaagg aagacctttg tggaactcat gaaaagagga gatcttcctg 6180
tttggctggc ctatcaggtt gcatctgccg gaataaccta cacagataga gatggtgct 6240
ttgatggcac gaccaacaac accataatgg aagacagtgt gccggcagag gtgtggacca 6300
gacacgaga gaaaagtga tcaaaccga ggtggatgga cgccagagtt tgttcagatc 6360
atgcggccct gaagtcattc aaggagtttg ccgctgggaa aagaggagcg gcttttggag 6420
tgatggaagc cctgggaaca ctgccaggac acatgacaga gagattccag gaagccattg 6480
acaacctcgc tgtgctcatg cgggcagaga ctggaagcag gccttacaaa gccgcggcgg 6540
cccaattgcc ggagacccta gagaccatta tgcttttggg gttgctggga acagtctcgc 6600
tgggaatctt tttcgtcttg atgaggaaca agggcatagg gaagatgggt tttggaatgg 6660
tgactcttgg ggccagcgca tggctcatgt ggctctcgga aattgagcca gccagaattg 6720
catgtgtcct cattgttgtg ttcctattgc tggtggtgct catacctgag ccagaaaagc 6780
aaagatctcc ccaggacaac caaatggcaa tcatcatcat ggtagcagta ggtcttctgg 6840
gcttgattac cgccaatgaa ctcggatggt tggagagaac aaagagtgac ctaagccatc 6900
taatgggaag gagagaggag ggggcaacca taggattctc aatggacatt gacctgcggc 6960
cagcctcagc ttgggccatc tatgctgcct tgacaacttt cattacccca gccgtccaac 7020
atgcagtgac cacttcatac aacaactact ccttaatggc gatggccacg caagctggag 7080
tgttgtttgg tatgggcaaa gggatgccat tctacgcatg gactttgga gtcccgctgc 7140
taatgatagg ttgctactca caattaacac ccctgacccd aatagtggcc atcatttgc 7200
tcgtgggca ctacatgac ttgatcccaa ggctgcgaag cggctgcgcg cgtgctgccg 7260
agaagagaac ggcagctggc atcatgaaga accctgttgt ggatggaata gtggtgactg 7320
acattgacac aatgacaatt gacccccaag tggagaaaaa gatgggacag gtgctactca 7380
tagcagtagc cgtctccagc gccatactgt cgcggaccgc ctgggggtgg ggggaggctg 7440
gggccctgat cacagcggca acttccactt tgtgggaagg ctctccgaac aagtactgga 7500
actcctctac agccacttca ctgtgtaaca ttttttaggg aagttacttg gctggagctt 7560
```

-continued

```
ctctaatcta cacagtaaca agaaacgctg gcttggtcaa gagacgtggg ggtggaacag  7620
gagagaccct gggagagaaa tggaaggccc gcttgaacca gatgtcggcc ctggagttct  7680
actcctacaa aaagtcaggc atcaccgagt gtgcagaga agaggcccgc cgcgccctca   7740
aggacggtgt ggcaacggga ggccatgctg tgtcccgagg aagtgcaaag ctgagatggt  7800
tggtggagcg gggatacctg cagccctatg gaaaggtcat tgatcttgga tgtggcagag  7860
ggggctggag ttactacgcc gccaccatcc gcaaagttca agaagtgaaa ggatacacaa  7920
aaggaggccc tggtcatgaa gaacccatgt tggtgcaaag ctatgggtgg aacatagtcc  7980
gtcttaagag tgggtggac gtctttcata tggcggctga gccgtgtgac acgttgctgt   8040
gtgacatagg tgagtcatca tctagtcctg aagtggaaga agcacggacg ctcagagtcg  8100
tctccatggt gggggattgg cttgaaaaaa gaccaggagc cttttgtata aaagtgttgt  8160
gcccatacac cagcactatg atggaaaccc tggagcgact gcagcgtagg tatgggggag  8220
gactggtcag agtgccactc tcccgcaact ctacacatga gatgtactgg gtctctggag  8280
cgaaaagcaa caccataaaa agtgtgtcca ccacgagcca gctcctcttg gggcgcatgg  8340
acgggccagg gaggccagtg aaatatgagg aggatgtgaa tctcggctct ggcacgcatg  8400
ctgtggtaag ctgcgctgaa gctcccaaca tgaagatcat tggtaaccgc attgaaagga  8460
tccgcagtga gcacgcggaa acgtggttct ttgacgagaa ccacccatat aggacatggg  8520
cttaccatgg aagctatgag gccccccacac aagggtcagc gtcctctcta ataaacgggg  8580
ttgtcaggct cctgtcaaaa ccctgggatg tggtgactga agtcacagga atagccatga  8640
ccgacaccac accgtatggt cagcaaagag ttttcaagga aaaagtggac actagggtgc  8700
cagacccca agaaggcact cgtcaggtta tgagcatggt ctcttcctgg ttgtggaaag  8760
agctaggcaa acacaaacgg ccacgagtct gtaccaaaga agagttcatc aacaaggttc  8820
gtagcaatgc agcattaggg gcaatatttg aagaggaaaa agagtcagtgg  8880
aagctgtgaa cgatccaagg ttctgggctc tagtggacaa ggaaagagag caccacctga  8940
gaggagagtg ccagagttgt gtgtacaaca tgatgggaaa aagagaaaag aaacaagggg  9000
aatttggaaa ggccaagggc agccgcgcca tctggtatat gtggctaggg gctagatttc  9060
tagagttcga agccctggtga ttcttgaacg aggatcactg gatggggaga gagaactcag  9120
gaggtggtgt tgaagggctg ggattacaaa gactcggata tgtcctagaa gagatgagtc  9180
gcataccagg aggaaggatg tatgcagatg acactgctgg ctgggacacc cgcatcagca  9240
ggtttgatct ggagaatgaa gctctaatca ccaaccaaat ggagaaaggg cacagggcct  9300
tggcattgga cataatcaag tacacatacc aaaacaaagt ggtaaaggtc cttagacgag  9360
ctgaaaaagg gaagacagtt atggacatta tttcgagaca agaccaaagg gggagcggac  9420
aagttgtcac ttacgctctt aacacattta ccaacctagt ggtgcaactc attcggaata  9480
tggaggctga ggaagttcta gagatgcaag acttgtggct gctgcggagg tcagagaaag  9540
tgaccaactg gttgcagagc aacggatggg ataggctcaa acgaatggca gtcagtggag  9600
atgattgcgt tgtgaagcca attgatgata ggtttgcaca tgccctcagg ttcttgaatg  9660
atatgggaaa agttaggaag gacacacaag agtggaaacc ctcaactgga tgggacaact  9720
gggaagaagt tccgttttgc tcccaccact tcaacaagct ccatctcaag gacgggaggt  9780
ccattgtggt tccctgccgc caccaagatg aactgattgg ccgggcccgc gtctctccag  9840
gggcgggatg gagcatccgg gagactgctt gcctagcaaa atcatatgcg caaatgtgcc  9900
agctccttta tttccacaga agggacctcc gactgatggc caatgccatt tgttcatctg  9960
tgccagttga ctgggttcca actgggagaa ctacctggtc aatccatgga aagggagaat 10020
ggatgaccac tgaagacatg cttgtggtgt ggaacagagt gtggattgag agaacgacc  10080
acatggaaca caagcccca gttacgaaat ggacagacat tccctatttg ggaaaagagg 10140
aagacttgtg gtgtgatctc tcatagggc acagaccgcg caccacctgg gctgagaaca 10200
ttaaaaacac agtcaacatg gtgcgcagga tcataggtga tgaagaaaag tacatggact 10260
acctatccca ccaagttcgc tacttgggtg aagaagggtc tacacctgga gtgctgtaag 10320
caccaatctt agtgttgtca ggcctgctag tcagccacag cttggggaaa gctgtgcagc 10380
ctgtgacccc cccaggagaa gctgggaaac caagcctata gtcaggccga gaacgccatg 10440
gcacggaaga agccatgctg cctgtgagcc cctcagagga cactgagtca aaaaacccca 10500
cgcgcttgga ggcgcaggat gggaaaagaa ggtggcgacc ttccccaccc ttcaatctgg 10560
ggcctgaact ggagatcagc tgtggatctc agaagaggg actagtggtt agaggag     10617
```

```
SEQ ID NO: 14           moltype = AA   length = 498
FEATURE                 Location/Qualifiers
source                  1..498
                        mol_type = protein
                        organism = Zika virus
SEQUENCE: 14
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MIVNDENRAK VEVTPNSPRA EATLGGFGSL  180
GLDCEPRTGL DFSDLYYLTM NNKHWLVHKE WFHDIPLPWH AGADTGTPHW NNKEALVEFK  240
DAHAKRQTVV VLGSQEGAVH TALAGALEAE MDGAKGRLFS GHLKCRLKMD KLRLKGVSYS  300
LCTAAFTFTK VPAETLHGTV TVEVQYAGTD GPCKVPAQMA VDMQTLTPVG RLITANPVIT  360
ESTENSKMML ELDPPFGDSY IVIGVGDKKI THHWHRSGST IGKAFEATVR GAKRMAVLGD  420
TAWDFGSVGG VFNSLGKGIH QIFGAAFKSL FGGMSWFSQI LIGTLLVWLG LNTKNGSISL  480
TCLALGGVMI FLSTAVSA                                                498

SEQ ID NO: 15           moltype = AA   length = 498
FEATURE                 Location/Qualifiers
source                  1..498
                        mol_type = protein
                        organism = Zika virus
SEQUENCE: 15
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MIVNDENRAK VEVTPNSPRA EATLGGFGSL  180
GLDCEPRTGL DFSDLYYLTM NNKHWLVHKE WFHDIPLPWH SGADTETPHW NNKEALVEFK  240
DAHAKRQTVV VLGSQEGAVH TALAGALEAE MDGAKGRLSS GHLKCRLKMD KLRLKGVSYS  300
```

```
LCTAAFTFTK VPAETLHGTV TVEVQYAGRD GPCKVPAQMA VDMQTLTPVG RLITANPVIT    360
ESTENSKMML ELDPPFGDSY IVIGVGDKKI THHWHRSGSI IGKAFEATVR GAKRMAVLGD    420
TAWDFGSVGG VFNSLGKGIH QIFGAAFKSL FGGMSWFSQI LIGTLLVWLG LNTKNGSISL    480
TCLALGGVMI FLSTAVSA                                                 498

SEQ ID NO: 16           moltype = AA   length = 504
FEATURE                 Location/Qualifiers
VARIANT                 156..162
                        note = X can be any amino acid
source                  1..504
                        mol_type = protein
                        organism = Zika virus
SEQUENCE: 16
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFT    120
CSKKMTGKSI QPENLEYRIM LSVHGSQHSG MIVNDXXXXX XXNRAEVEVT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLFSGHLK CRLKMDKLRL    300
KGVSYSLCTA AFTFTKVPAE TLHGTVTVEV QYAGTDGPCK VPAQMAVDMQ TLTPVGRLIT    360
ANPVITESTE NSKMMLELDP PFGDSYIVIG VGDKKITHHW HRSGSTIGKA FEATVRGAKR    420
MAVLGDTAWD FGSVGGVFNS LGKGIHQIFG AAFKSLFGGM SWFSQILIGT LLVWLGLNTK    480
NGSISLTCLA LGGVMIFLST AVSA                                          504

SEQ ID NO: 17           moltype = AA   length = 504
FEATURE                 Location/Qualifiers
VARIANT                 152..156
                        note = X can be any amino acid
source                  1..504
                        mol_type = protein
                        organism = Zika virus
SEQUENCE: 17
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFT    120
CSKKMTGKSI QPENLEYRIM LSVHGSQHSG MXXXXXGHET DENRAKVEVT PNSPRAEATL    180
GGFGSLGLDC EPRTGLDFSD LYYLTMNNKH RLVRKEWFHD IPLPWHAGAD TGTPHWNNKE    240
ALVEFKDAHA KRQTVVVLGS QEGAVHTALA GALEAEMDGA KGRLFSGHLK CRLKMDKLRL    300
KGVSYSLCTA AFTFTKVPAE TLHGTVTVEV QYAGTDGPCK VPAQMAVDMQ TLTPVGRLIT    360
ANPVITESTE NSKMMLELDP PFGDSYIVIG VGDKKITHHW LKKGSSIGKA FEATVRGAKR    420
MAVLGDTAWD FGSVGGVFNS LGKGVHQIFG AAFKSLFGGM SWFSQILIGT LLVWLGLNTK    480
NGSISLTCLA LGGVMIFLST AVSA                                          504

SEQ ID NO: 18           moltype = AA   length = 504
FEATURE                 Location/Qualifiers
source                  1..504
                        mol_type = protein
                        organism = Zika virus
SEQUENCE: 18
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFT    120
CSKKMTGKSI QPENLEYRIM LSVHGSQHSG MIVNDIGHET DENRAKVEVT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLFSGHLK CRLKMDKLRL    300
KGVSYSLCTA AFTFTKVPAE TLHGTVTVEV QYAGTDGPCK VPAQMAVDMQ TLTPVGRLIT    360
ANPVITESTE NSKMMLELDP PFGDSYIVIG VGDKKITHHW HRSGSTIGKA FEATVRGAKR    420
MAVLGDTAWD FGSVGGVFNS LGKGIHQIFG AAFKSLFGGM SWFSQILIGT LLVWLGLNTK    480
NGSISLTCLA LGGVMIFLST AVSA                                          504

SEQ ID NO: 19           moltype = AA   length = 504
FEATURE                 Location/Qualifiers
source                  1..504
                        mol_type = protein
                        organism = Zika virus
SEQUENCE: 19
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFT    120
CSKKMTGKSI QPENLEYRIM LSVHGSQHSG MIVNDIGHET DENRAKVEVT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLFSGHLK CRLKMDKLRL    300
KGVSYSLCTA AFTFTKVPAE TLHGTVTVEV QYAGTDGPCK VPAQMAVDMQ TLTPVGRLIT    360
ANPVITESTE NSKMMLELDP PFGDSYIVIG VGDKKITHHW HRSGSTIGKA FEATVRGAKR    420
MAVLGDTAWD FGSVGGVFNS LGKGIHQIFG AAFKSLFGGM SWFSQILIGT LLVWLGLNTK    480
NGSISLTCLA LGGVMIFLST AVSA                                          504

SEQ ID NO: 20           moltype = AA   length = 504
FEATURE                 Location/Qualifiers
source                  1..504
                        mol_type = protein
                        organism = Zika virus
SEQUENCE: 20
```

```
IRCIGVSNRD FVEGMSGGTW VDVVLEHGGC TVMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIVNDIGHET DENRAKVEVT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLFSGHLK CRLKMDKLRL   300
KGVSYSLCTA AFTFTKVPAE TLHGTVTVEV QYAGTDGPCK VPAQMAVDMQ TLTPVGRLIT   360
ANPVITESTE NSKMMLELDP PFGDSYIVIG VGDKKITHHW HRSGSTIGKA FEATVRGAKR   420
MAVLGDTAWD FGSVGGVFNS LGKGVHQIFG AAFKSLFGGM SWFSQILIGT LLVWLGLNTK   480
NGSISLTCLA LGGVMIFLST AVSA                                         504

SEQ ID NO: 21            moltype = AA  length = 504
FEATURE                  Location/Qualifiers
source                   1..504
                         mol_type = protein
                         organism = Zika virus
SEQUENCE: 21
IRCIGVSNRD FVEGMSGGTW VDVVLEHGGC TVMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIVNDIGHET DENRAKVEVT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLFSGHLK CRLKMDKLRL   300
KGVSYSLCTA AFTFTKVPAE TLHGTVTVEV QYAGTDGPCK VPAQMAVDMQ TLTPVGRLIT   360
ANPVITESTE NSKMMLELDP PFGDSYIVIG VGDKKITHHW HRSGSTIGKA FEATVRGAKR   420
MAVLGDTAWD FGSVGGVFNS LGKGVHQIFG AAFKSLFGGM SWFSQILIGT LLVWLGLNTK   480
NGSISLTCLA LGGVMIFLST AVSA                                         504

SEQ ID NO: 22            moltype = AA  length = 504
FEATURE                  Location/Qualifiers
source                   1..504
                         mol_type = protein
                         organism = Zika virus
SEQUENCE: 22
IRCIGVSNRD FVEGMSGGTW VDVVLEHGGC TVMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIVNDTGHET DENRAKVEVT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLFSGHLK CRLKMDKLRL   300
KGVSYSLCTA AFTFTKVPAE TLHGTVTVEV QYAGTDGPCK VPAQMAVDMQ TLTPVGRLIT   360
ANPVITESTE NSKMMLELDP PFGDSYIVIG VGDKKITHHW HRSGSTIGKA FEATVRGAKR   420
MAVLGDTAWD FGSVGGVFNS LGKGIHQIFG AAFKSLFGGM SWFSQILIGT LLVWLGLNTK   480
NGSISLTCLA LGGVMIFLST AVSA                                         504

SEQ ID NO: 23            moltype = AA  length = 504
FEATURE                  Location/Qualifiers
source                   1..504
                         mol_type = protein
                         organism = Zika virus
SEQUENCE: 23
IRCIGVSNRD FVEGMSGGTW VDVVLEHGGC TVMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MTVNDIGYET DENRAKVEVT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGKLFSGHLK CRLKMDKLRL   300
KGVSYSLCTA AFTFTKVPAE TLHGTVTVEV QYAGTDGPCK IPVQMAVDMQ TLTPVGRLIT   360
ANPVITESTE NSKMMLELDP PFGDSYIVIG VGDKKITHHW HRSGSTIGKA FEATVRGAKR   420
MAVLGDTAWD FGSVGGVFNS LGKGIHQIFG AAFKSLFGGM SWFSQILIGT LLVWLGLNTK   480
NGSISLTCLA LGGVMIFLST AVSA                                         504

SEQ ID NO: 24            moltype = AA  length = 504
FEATURE                  Location/Qualifiers
source                   1..504
                         mol_type = protein
                         organism = Zika virus
SEQUENCE: 24
IRCIGVSNRD FVEGMSGGTW VDVVLEHGGC TVMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MTVNDIGYET DENRAKVEVT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGKLFSGHLK CRLKMDKLRL   300
KGVSYSLCTA AFTFTKVPAE TLHGTVTVEV QYAGTDGPCK IPVQMAVDMQ TLTPVGRLIT   360
ANPVITESTE NSKMMLELDP PFGDSYIVIG VGDKKITHHW HRSGSTIGKA FEATVRGAKR   420
MAVLGDTAWD FGSVGGVFNS LGKGIHQIFG AAFKSLFGGM SWFSQILIGT LLVWLGLNTK   480
NGSISLTCLA LGGVMIFLST AVSA                                         504

SEQ ID NO: 25            moltype = AA  length = 504
FEATURE                  Location/Qualifiers
source                   1..504
                         mol_type = protein
                         organism = Zika virus
```

```
SEQUENCE: 25
IRCIGVSNRD FVEGMSGGTW VDVVLEHGGC TVTMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIVNDTGYET DENRAKVEVT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGKLFSGHLK CRLKMDKLRL   300
KGVSYSLCTA AFTFTKVPAE TLHGTVTVEV QYAGTDGPCK IPVQMAVDMQ TLTPVGRLIT   360
ANPVITESTE NSKMMLELDP PFGDSYIVIG VGDKKITHHW HRSGSTIGKA FEATVRGAKR   420
MAVLGDTAWD FGSVGGVFNS LGKGIHQIFG AAFKSLFGGM SWFSQILIGT LLVWLGLNTK   480
NGSISLTCLA LGGVMIFLST AVSA                                         504

SEQ ID NO: 26           moltype = AA  length = 504
FEATURE                 Location/Qualifiers
source                  1..504
                        mol_type = protein
                        organism = Zika virus
SEQUENCE: 26
IRCIGVSNRD FVEGMSGGTW VDVVLEHGGC TVTMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIVNDIGHET DENRAKVEVT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLFSGHLK CRLKMDKLRL   300
KGVSYSLCTA VCTAAKVPAE TLHGTVTVEV QYAGTDGPCK VPAQMAVDMQ TLTPVGRLIT   360
ANPVITESTE NSKMMLELDP PFGDSYIVIG VGDKKITHHW HRSGSTIGKA FEATVRGAKR   420
MAVLGDTAWD FGSVGGVFNS LGKGIHQIFG AAFKSLFGGM SWFSQILIGT LLVWLGLNTK   480
NGSISLTCLA LGGVMIFLST AVSA                                         504

SEQ ID NO: 27           moltype = AA  length = 500
FEATURE                 Location/Qualifiers
source                  1..500
                        mol_type = protein
                        organism = Zika virus
SEQUENCE: 27
IRCIGVSNRD FVEGMSGGTW VDVVLEHGGC TVTMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIGYETDEDR AKVEVTPNSP RAEATLGGFG   180
SLGLDCEPRT GLDFSDLYYL TMNNKHWLVH KEWFHDIPLP WHAGADTGTP HWNNKEALVE   240
FKDAHAKRQT VVVLGSQEGA VHTALAGALE AEMDGAKGRL FSGHLKCRLK MDKLRLKGVS   300
YSLCTAAFTF TKVPAETLHG TVTVEVQYAG TDGPCKIPVQ MAVDMQTLTP VGRLITANPV   360
ITESTENSKM MLELDPPFGD SYIVIGVGDK KITHHWHRSG STIGKAFEAT VRGAKRMAVL   420
GDTAWDFGSV GGVFNSLGKG IHQIFGAAFK SLFGGMSWFS QILIGTLLVW LGLNTKNGSI   480
SLTCLALGGV MIFLSTAVSA                                              500

SEQ ID NO: 28           moltype = AA  length = 500
FEATURE                 Location/Qualifiers
source                  1..500
                        mol_type = protein
                        organism = Zika virus
SEQUENCE: 28
IRCIGVSNRD FVEGMSGGTW VDVVLEHGGC TVTMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIGYETDEDR AKVEVTPNSP RAEATLGGFG   180
SLGLDCEPRT GLDFSDLYYL TMNNKHWLVH KEWFHDIPLP WHAGADTGTP HWNNKEALVE   240
FKDAHAKRQT VVVLGSQEGA VHTALAGALE AEMDGAKGRL FSGHLKCRLK MDKLRLKGVS   300
YSLCTAAFTF TKVPAETLHG TVTVEVQYAG TDGPCKIPVQ MAVDMQTLTP VGRLITANPV   360
ITESTENSKM MLELDPPFGD SYIVIGVGDK KITHHWHRSG STIGKAFEAT VRGAKRMAVL   420
GDTAWDFGSV GGVFNSLGKG IHQIFGAAFK SLFGGMSWFS QILIGTLLVW LGLNTKNGSI   480
SLTCLALGGV MIFLSTAVSA                                              500

SEQ ID NO: 29           moltype = AA  length = 500
FEATURE                 Location/Qualifiers
source                  1..500
                        mol_type = protein
                        organism = Zika virus
SEQUENCE: 29
IRCIGVSNRD FVEGMSGGTW VDVVLEHGGC TVTMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIGYETDEDR AKVEVTPNSP RAEATLGGFG   180
SLGLDCEPRT GLDFSDLYYL TMNNKHWLVH KEWFHDIPLP WHAGADTGTP HWNNKEALVE   240
FKDAHAKRQT VVVLGSQEGA VHTALAGALE AEMDGAKGRL FSGHLKCRLK MDKLRLKGVS   300
YSLCTAAFTF TKVPAETLHG TVTVEVQYAG TDGPCKIPVQ MAVDMQTLTP VGRLITANPV   360
ITESTENSKM MLELDPPFGD SYIVIGVGDK KITHHWHRSG STIGKAFEAT VRGAKRMAVL   420
GDTAWDFGSV GGVFNSLGKG IHQIFGAAFK SLFGGMSWFS QILIGTLLVW LGLNTKNGSI   480
SLTCLALGGV MIFLSTAVSA                                              500

SEQ ID NO: 30           moltype = AA  length = 504
FEATURE                 Location/Qualifiers
source                  1..504
                        mol_type = protein
```

```
                              organism = Zika virus
SEQUENCE: 30
IRCIGVSNRD FVEGMSGGTW VDVVLEHGGC VTVMAQDKPT VDIELVTTTV SNMAEVRSYC    60
YE

```
                        mol_type = protein
                        organism = Zika virus
SEQUENCE: 35
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 36           moltype = AA   length = 504
FEATURE                 Location/Qualifiers
source                  1..504
                        mol_type = protein
                        organism = Zika virus
SEQUENCE: 36
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 37           moltype = AA   length = 504
FEATURE                 Location/Qualifiers
source                  1..504
                        mol_type = protein
                        organism = Zika virus
SEQUENCE: 37
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 38           moltype = AA   length = 504
FEATURE                 Location/Qualifiers
source                  1..504
                        mol_type = protein
                        organism = Zika virus
SEQUENCE: 38
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 39           moltype = AA   length = 504
FEATURE                 Location/Qualifiers
source                  1..504
                        mol_type = protein
                        organism = Zika virus
SEQUENCE: 39
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 40           moltype = AA   length = 504
FEATURE                 Location/Qualifiers
```

```
source                   1..504
                         mol_type = protein
                         organism = Zika virus
SEQUENCE: 40
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 41            moltype = AA  length = 504
FEATURE                  Location/Qualifiers
source                   1..504
                         mol_type = protein
                         organism = Zika virus
SEQUENCE: 41
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 42            moltype = AA  length = 504
FEATURE                  Location/Qualifiers
source                   1..504
                         mol_type = protein
                         organism = Zika virus
SEQUENCE: 42
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 43            moltype = AA  length = 504
FEATURE                  Location/Qualifiers
source                   1..504
                         mol_type = protein
                         organism = Zika virus
SEQUENCE: 43
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 44            moltype = AA  length = 504
FEATURE                  Location/Qualifiers
source                   1..504
                         mol_type = protein
                         organism = Zika virus
SEQUENCE: 44
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 45            moltype = AA  length = 504
```

```
FEATURE                 Location/Qualifiers
source                  1..504
                        mol_type = protein
                        organism = Zika virus
SEQUENCE: 45
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 46           moltype = AA  length = 504
FEATURE                 Location/Qualifiers
source                  1..504
                        mol_type = protein
                        organism = Zika virus
SEQUENCE: 46
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 47           moltype = AA  length = 504
FEATURE                 Location/Qualifiers
source                  1..504
                        mol_type = protein
                        organism = Zika virus
SEQUENCE: 47
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 48           moltype = AA  length = 504
FEATURE                 Location/Qualifiers
source                  1..504
                        mol_type = protein
                        organism = Zika virus
SEQUENCE: 48
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 49           moltype = AA  length = 504
FEATURE                 Location/Qualifiers
source                  1..504
                        mol_type = protein
                        organism = Zika virus
SEQUENCE: 49
IRCIGVSNRD FVEGMSGGTW VDIVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504
```

```
SEQ ID NO: 50            moltype = AA  length = 504
FEATURE                  Location/Qualifiers
source                   1..504
                         mol_type = protein
                         organism = Zika virus
SEQUENCE: 50
IRCIGVSNRD FVEGMSGGTW VDIVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 51            moltype = AA  length = 504
FEATURE                  Location/Qualifiers
source                   1..504
                         mol_type = protein
                         organism = Zika virus
SEQUENCE: 51
IRCIGVSNRD FVEGMSGGTW VDVVLEHGGC VTVMAQDKPT VDIELVTTTV SNMAEIRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 52            moltype = AA  length = 504
FEATURE                  Location/Qualifiers
source                   1..504
                         mol_type = protein
                         organism = Zika virus
SEQUENCE: 52
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGT QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 53            moltype = AA  length = 504
FEATURE                  Location/Qualifiers
source                   1..504
                         mol_type = protein
                         organism = Zika virus
SEQUENCE: 53
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGT QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 54            moltype = AA  length = 504
FEATURE                  Location/Qualifiers
source                   1..504
                         mol_type = protein
                         organism = Zika virus
SEQUENCE: 54
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGARR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504
```

```
SEQ ID NO: 55            moltype = AA  length = 504
FEATURE                  Location/Qualifiers
source                   1..504
                         mol_type = protein
                         organism = Zika virus
SEQUENCE: 55
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFA 120
CSKKMTGKSI QPENLEYRIM LSVHGSQHSG MIVNDTGHET DENRAKVEIT PNSPRAEATL 180
GGFGSLGLDC EPRTGLDFSD LYYLTMNNKH WLVHKEWFHD IPLPWHAGAD TGTPHWNNKE 240
ALVEFKDAHA KRQTVVVLGS QEGAVHTALA GALEAEMDGA KGRLSSGHLK CRLKMDKLRL 300
KGVSYSLCTA AFTFTKIPAE TLHGTVTVEV QYAGTDGPCK VPAQMAVDMQ TLTPVGRLIT 360
ANPVITESTE NSKMMLELDP PFGDSYIVIG VGEKKITHHW HRSGSTIGKA FEATVRGAKR 420
MAVLGDTAWD FGSVGGALNS LGKGIHQIFG AAFKSLFGGM SWFSQILIGT LLVWLGLNTK 480
NGSISLMCLA LGGVLIFLST AVSA                                       504

SEQ ID NO: 56            moltype = AA  length = 504
FEATURE                  Location/Qualifiers
source                   1..504
                         mol_type = protein
                         organism = Zika virus
SEQUENCE: 56
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFA 120
CSKKMTGKSI QPENLEYRIM LSVHGSQHSG MIVNDTGHET DENRAKVEIT PNSPRAEATL 180
GGFGSLGLDC EPRTGLDFSD LYYLTMNNKH WLVHKEWFHD IPLPWHAGAD TGTPHWNNKE 240
ALVEFKDAHA KRQTVVVLGS QEGAVHTALA GALEAEMDGA KGRLSSGHLK CRLKMDKLRL 300
KGVSYSLCTA AFTFTKIPAE TLHGTVTVEV QYAGTDGPCK VPAQMAVDMQ TLTPVGRLIT 360
ANPVITESTE NSKMMLELDP PFGDSYIVIG VGEKKITHHW HRSGSTIGKA FEATVRGAKR 420
MAVLGDTAWD FGSVGGALNS LGKGIHQIFG AAFKSLFGGM SWFSQILIGT LLMWLGLNAK 480
NGSISLMCLA LGGVLIFLST AVSA                                       504

SEQ ID NO: 57            moltype = AA  length = 504
FEATURE                  Location/Qualifiers
source                   1..504
                         mol_type = protein
                         organism = Zika virus
SEQUENCE: 57
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFA 120
CSKKMTGKSI QPENLEYRIM LSVHGSQHSG MIVNDTGHET DENRAKVEIT PNSPRAEATL 180
GGFGSLGLDC EPRTGLDFSD LYYLTMNNKH WLVHKEWFHD IPLPWHAGAD TGTPHWNNKE 240
ALVEFKDAHA KRQTVVVLGS QEGAVHTALA GALEAEMDGA KGRLSSGHLK CRLKMDKLRL 300
KGVSYSLCTA AFTFTKIPAE TLHGTVTVEV QYAGTDGPCK VPAQMAVDMQ TLTPVGRLIT 360
ANPVITESTE NSKMMLELDP PFGDSYIVIG VGEKKITHHW HRSGSTIGKA FEATVRGAKR 420
MAVLGDTAWD FGSVGGALNS LGKGIHQIFG AAFKSLFGGM SWFSQILIGT LLMWLGLNAK 480
NGSISLMCLA LGGVLIFLST AVSA                                       504

SEQ ID NO: 58            moltype = AA  length = 504
FEATURE                  Location/Qualifiers
source                   1..504
                         mol_type = protein
                         organism = Zika virus
SEQUENCE: 58
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFA 120
CSKKMTGKSI QPENLEYRIM LSVHGSQHSG MIVNDTGHET DENRAKVEIT PNSPRAEATL 180
GGFGSLGLDC EPRTGLDFSD LYYLTMNNKH WLVHKEWFHD IPLPWHAGAD TGTPHWNNKE 240
ALVEFKDAHA KRQTVVVLGS QEGAVHTALA GALEAEMDGA KGRLSSGHLK CRLKMDKLRL 300
KGVSYSLCTA AFTFTKIPAE TLHGTVTVEV QYAGTDGPCK VPAQMAVDTQ TLTPVGRLIT 360
ANPVITESTE NSKMMLELDP PFGDSYIVIG VGEKKITHHW HRSGSTIGKA FEATVRGAKR 420
MAVLGDTAWD FGSVGGALNS LGKGIHQIFG AAFKSLFGGM SWFSQILIGT LLMWLGLNTK 480
NGSISLMCLA LGGVLIFLST AVSA                                       504

SEQ ID NO: 59            moltype = AA  length = 504
FEATURE                  Location/Qualifiers
source                   1..504
                         mol_type = protein
                         organism = Zika virus
SEQUENCE: 59
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFA 120
CSKKMTGKSI QPENLEYRIM LSVHGSQHSG MIVNGTGHET DENRAKVEIT PNSPRAEATL 180
GGFGSLGLDC EPRTGLDFSD LYYLTMNNKH WLVHKEWFHD IPLPWHAGAD TGTPHWNNKE 240
ALVEFKDAHA KRQTVVVLGS QEGAVHTALA GALEAEMDGA KGRLSSGHLK CRLKMDKLRL 300
KGVSYSLCTA AFTFTKIPAE TLHGTVTVEV QYAGTDGPCK VPAQMAVDMQ TLTPVGRLIT 360
ANPVITESTE NSKMMLELDP PFGDSYIVIG VGEKKITHHW HRSGSTIGKA FEATVRGAKR 420
MAVLGDTAWD FGSVGGALNS LGKGIHQIFG AAFKSLFGGM SWFSQILIGT LLMWLGLNTK 480
```

```
NGSISLMCLA LGGVLIFLST AVSA                                              504

SEQ ID NO: 60           moltype = AA  length = 504
FEATURE                 Location/Qualifiers
source                  1..504
                        mol_type = protein
                        organism = Zika virus
SEQUENCE: 60
IRCIGVSNRD FVEGMSGGTW VDVVLEHGGC VTVMAQDKPT VDIELVTTTV SNMAEVRSYC      60
YEASISDMAS DSRCPTQGEA YLDKQSDTQY VCKRTLVDRG WGNGCGLFGK GSLVTCAKFA      120
CSKKMTGKSI QPENLEYRIM LSVHGSQHSG MIVNDTGHET DENRAKVEIT PNSPRAEATL      180
GGFGSLGLDC EPRTGLDFSD LYYLTMNNKH WLVHKEWFHD IPLPWHAGAD TGTPHWNNKE      240
ALVEFKDAHA KRQTVVVLGS QEGAVHTALA GALEAEMDGA KGRLSSGHLK CRLKMDKLRL      300
KGVSYSLCTA AFTFTKIPAE TLHGTVTVEV QYAGTDGPCK VLAQMAVDMQ TLTPVGRLIT      360
ANPVITESTE NSKMMLELDP PFGDSYIVIG VGEKKITHHW HRSGSTIGKA FEATVRGAKR      420
MAVLGDTAWD FGSVGGALNS LGKGIHQIFG AAFKSLFGGM SWFSQILIGT LLMWLGLNTK      480
NGSISLMCLA LGGVLIFLST AVSA                                              504

SEQ ID NO: 61           moltype = AA  length = 504
FEATURE                 Location/Qualifiers
source                  1..504
                        mol_type = protein
                        organism = Zika virus
SEQUENCE: 61
IRCIGVSNRD FVEGMSGGTW VDVVLEHGGC VTVMAQDKPA VDIELVTTTV SNMAEVRSYC      60
YEASISDMAS DSRCPTQGEA YLDKQSDTQY VCKRTLVDRG WGNGCGLFGK GSLVTCAKFA      120
CSKKMTGKSI QPENLEYRIM LSVHGSQHSG MIVNDTGHET DENRAKVEIT PNSPRAEATL      180
GGFGSLGLDC EPRTGLDFSD LYYLTMNNKH WLVHKEWFHD IPLPWHAGAD TGTPHWNNKE      240
ALVEFKDAHA KRQTVVVLGS QEGAVHTALA GALEAEMDGA KGRLSSGHLK CRLKMDKLRL      300
KGVSYSLCTA AFTFTKIPAE TLHGTVTVEV QYAGTDGPCK VPAQMAVDMQ TLTPVGRLIT      360
ANPVITESTE NSKMMLELDP PFGDSYIVIG VGEKKITHHW HRSGSTIGKA FEATVRGAKR      420
MAVLGDTAWD FGSVGGALNS LGKGIHQIFG AAFKSLFGGM SWFSQILIGT LLVWLGLNTK      480
NGSISLTCLA LGGVLIFLST AVSA                                              504

SEQ ID NO: 62           moltype = AA  length = 504
FEATURE                 Location/Qualifiers
source                  1..504
                        mol_type = protein
                        organism = Zika virus
SEQUENCE: 62
IRCIGVSNRD FVEGMSGGTW VDVVLEHGGC VTVMAQDKPT VDIELVTTTV SNMAEVRSYC      60
YEASISDMAS DSRCPTQGEA YLDKQSDTQY VCKRTLVDRG WGNGCGLFGK GSLVTCAKFA      120
CSKKMTGKSI QPENLEYRIM LSVHGSQHSG MIVNDTGHET DENRAKVEIT PNSPRAEATL      180
GGFGSLGLDC EPRTGLDFSD LYYLTMNNKH WLVHKEWFHD IPLPWHAGAD TGTPHWNNKE      240
ALVEFKDAHA KRQTVVVLGS QEGAVHTALA GALEAEMDGA KGRLSSGHLK CRLKMDKLRL      300
KGVSYSLCTA AFTFTKIPAE TLHGTVTVEV QYAGTDGPCK VPAQMAVDMQ TLTPVGRLIT      360
ANPVITESTE NSKMMLELDP PFGDSYIVIG VGEKKITHHW HRSGSTIGKA FEATVRGAKR      420
MAVLGDTAWD FGSVGGALNS LGKGIHQIFG AAFKSLFGGM SWFSQILIGT LLVWLGLNTK      480
NGSISLTCLA LGGVLIFLST AVSA                                              504

SEQ ID NO: 63           moltype = AA  length = 504
FEATURE                 Location/Qualifiers
source                  1..504
                        mol_type = protein
                        organism = Zika virus
SEQUENCE: 63
IRCIGVSNRD FVEGMSGGTW VDVVLEHGGC VTVMAQDKPT VDIELVTTTV SNMAEVRSYC      60
YEASISDMAS DSRCPTQGEA YLDKQSDTQY VCKRTLVDRG WGNGCGLFGK GSLVTCAKFA      120
CSKKMTGKSI QPENLEYRIM LSVHGSQHSG MIVNDTGHET DENRAKVEIT PNSPRAEATL      180
GGFGSLGLDC EPRTGLDFSD LYYLTMNNKH WLVHKEWFHD IPLPWHAGAD TGTPHWNNKE      240
ALVEFKDAHA KRQTVVVLGS QEGAVHTALA GALEAEMDGA KGRLSSGHLK CRLKMDKLRL      300
KGVSYSLCTA AFTFTKIPAE TLHGTVTVEV QYAGTDGPCK VPAQMAVDMQ TLTPVGRLIT      360
ANPVITESTE NSKMMLELDP PFGDSYIVIG VGEKKITHHW HRSGSTIGKA FEATVRGAKR      420
MAVLGDTAWD FGSVGGALNS LGKGIHQIFG AAFKSLFGGM SWFSQILIGT LLVWLGLNTK      480
NGSISLTCLA LGGVLIFLST AVSA                                              504

SEQ ID NO: 64           moltype = AA  length = 504
FEATURE                 Location/Qualifiers
source                  1..504
                        mol_type = protein
                        organism = Zika virus
SEQUENCE: 64
IRCIGVSNRD FVEGMSGGTW VDVVLEHGGC VTVMAQDKPT VDIELVSTTV SNMAEVRSYC      60
YEATISDIAS DSRCPTQGEA YLDKQSDTQY VCKRTLVDRG WGNGCGLFGK GSLVTCAKFA      120
CSKKMTGKSI QPENLEYRIM LSVHGSQHSG MIVNDTGHET DENRAKVEIT PNSPRAEATL      180
GGFGSLGLDC EPRTGLDFSD LYYLTMNNKH WLVHKEWFHD IPLPWHAGAD TGTPHWNNKE      240
ALVEFKDAHA KRQTAVVLGS QEGAVHTALA GALEAEMDGA KGRLSSGHLK CRLKMDKLRL      300
KGVSYSLCTA AFTFTKIPAE TLHGTVTVEV QYAGTDGPCK VPAQMAVDMQ TLTPVGRLIT      360
ANPVITESTE NSKMMLELDP PFGDSYIVIG VGEKKITHHW HRSGSTIGKA FEATVRGAKR      420
```

```
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 65           moltype = AA  length = 504
FEATURE                 Location/Qualifiers
VARIANT                 156
                        note = X can be any amino acid
source                  1..504
                        mol_type = protein
                        organism = Zika virus
VARIANT                 401
                        note = X can be any amino acid
SEQUENCE: 65
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDXGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGDKKITHHW XRSGSTIGKA FEATVRGAKR  420
MAVLGDTAWD FGSVGGALNS LGKGIHQIFG AAFKSLFGGM SWFSQILIGT LLVWLGLNTK  480
NGSISLTCLA LGGVLIFLST AVSA                                        504

SEQ ID NO: 66           moltype = AA  length = 504
FEATURE                 Location/Qualifiers
source                  1..504
                        mol_type = protein
                        organism = Zika virus
SEQUENCE: 66
IRCIGVSNRD FVEGMSGGTW VDVVLEHGGC VTAMAQDKPT VDIELVTTTV SNMAEVRSYC  60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MLVNDTGHET DENRAKVEIT PNSPRAEATL  180
GGFGSLGLDC EPRTGLDFSD LYYLTMNNKH WLAHKEWFHD IPLPWHAGAA TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TVDGTVTVEG QYGGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIIG AAFKSLFGGM SWFSQILIGT LLMWLGLNTK  480
NGSISLMCLA LGGVLIFLST AVSG                                        504

SEQ ID NO: 67           moltype = AA  length = 504
FEATURE                 Location/Qualifiers
source                  1..504
                        mol_type = protein
                        organism = Zika virus
SEQUENCE: 67
IRCIGVSNRD FVEGMSGGTW VDVVLEHGGC VTAMAQDKPT VDIELVTTTV SNMAEVRSYC  60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MLVNDTGHET DENRAKVEIT PNSPRAEATL  180
GGFGSLGLDC EPRTGLDFSD LYYLTMNNKH WLAHKEWFHD IPLPWHAGAA TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TVDGTVTVEG QYGGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIIG AAFKSLFGGM SWFSQILIGT LLMWLGLNTK  480
NGSISLMCLA LGGVLIFLST AVSG                                        504

SEQ ID NO: 68           moltype = AA  length = 504
FEATURE                 Location/Qualifiers
source                  1..504
                        mol_type = protein
                        organism = Zika virus
SEQUENCE: 68
ISCIGVSNRD LVEGMSGGTW VDVVLEHGGC VTEMAQDKPT VDIELVTMTV SNMAEVRSYC  60
YEASLSDMAS ASRCPTQGEP SLDKQSDTQS VCKRTLGDRG WGNGCGIFGK GSLVTCSKFT  120
CCKKMPGKSI QPENLEYRIM LPVHGSQHSG MIVNDIGHET DENRAKVEVT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLFSGHLK CRLKMDKLRL  300
KGVSYSLCTA AFTFTKVPAE TLHGTVTVEV QSAGTDGPCK VPAQMAVDMQ TLTPVGRLIT  360
ANPVITESTE NSKMMLELDP PFGDSYIVIG VGDKKITHHW HRSGSTIGKA FEATVRGAKR  420
MAVLGDTAWD FGSVGGVFNS LGKGIHQIFG AAFKSLFGGM SWFSQILIGT LLVWLGLNTK  480
NGSISLTCLA LGGVMIFLST AVSA                                        504

SEQ ID NO: 69           moltype = AA  length = 498
FEATURE                 Location/Qualifiers
source                  1..498
                        mol_type = protein
                        organism = Zika virus
SEQUENCE: 69
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFT  120
```

```
CSKKMTGKSI QPENLEYRIM LSVHGSQHSG MIVNDENRAK VEVTPNSPRA EATLGGFGSL    180
GLDCEPRTGL DFSDLYYLTM NNKHWLVHKE WFHDIPLPWH AGADTGTPHW NNKEALVEFK    240
DAHAKRQTVV VLGSQEGAVH TALAGALEAE MDGAKGRLFS GHLKCRLKMD KLRLKGVSYS    300
LCTAAFTFTK VPAETLHGTV TVEVQYAGTD GPCKVPAQMA VDMQTLTPVG RLITANPVIT    360
ESTENSKMML ELDPPFGDSY IVIGVGDKKI THHWHRSGST IGKAFEATVR GAKRMAVLGD    420
TAWDFGSVGG VFNSLGKGIH QIFGAAFKSL FGGMSWFSQI LIGTLLVWLG LNTKNGSISL    480
TCLALGGVMI FLSTAVSA                                                 498

SEQ ID NO: 70            moltype = DNA   length = 26
FEATURE                  Location/Qualifiers
misc_feature             1..26
                         note = synthetic polynucleotide
modified_base            1
                         mod_base = i
source                   1..26
                         mol_type = other DNA
                         organism = synthetic construct
modified_base            3
                         mod_base = i
modified_base            5
                         mod_base = i
modified_base            7
                         mod_base = i
modified_base            9
                         mod_base = i
modified_base            11
                         mod_base = i
modified_base            13
                         mod_base = i
modified_base            15
                         mod_base = i
modified_base            17
                         mod_base = i
modified_base            19
                         mod_base = i
modified_base            21
                         mod_base = i
modified_base            23
                         mod_base = i
modified_base            25
                         mod_base = i
SEQUENCE: 70
ncncncnc ncncncncnc ncncnc                                           26

SEQ ID NO: 71            moltype = AA   length = 11
FEATURE                  Location/Qualifiers
REGION                   1..11
                         note = synthetic peptide
source                   1..11
                         mol_type = protein
                         organism = synthetic construct
SEQUENCE: 71
KLKLLLLLKL K                                                         11

SEQ ID NO: 72            moltype = DNA   length = 10773
FEATURE                  Location/Qualifiers
source                   1..10773
                         mol_type = genomic DNA
                         organism = Zika virus
SEQUENCE: 72
cagactgcga cagttcgagt ttgaagcgaa agctagcaac agtatcaaca ggttttattt     60
tggatttgga aacgagagtt tctggtcatg aaaaacccaa aaaagaaatc cggaggattc    120
cggattgtca atatgctaaa acgcggagta gcccgtgtga gccccttttgg gggcttgaag   180
aggctgccag ccggacttct gctgggtcat gggcccatca ggatggtctt ggcgattcta    240
gcctttttga gattcacggc aatcaagcca tcactgggtc tcatcaatag atggggttca    300
gtggggaaaa aagaggctat ggaaataata aagaagttca gaaagatct ggctgccatg     360
ctgagaataa tcaatgctag gaaggagaag aagagacgag gcgcagatac tagtgtcgga    420
attgttggcc tcctgctgac cacagctatg gcagcggagg tcactagacg tgggagtgca    480
tactatatgt acttggacag aaacgacgct ggggaggccc tatcttttcc aaccacattg    540
gggatgaata agtgttatat acagatcatg gatcttggac acatgtgtga tgccaccatg    600
agctatgaat gccctatgct ggatgagggg gtggaaccag atgacgtcga ttgttggtgc    660
aacacgacgt caacttgggt tgtgtacgga acctgccatc acaaaaaagg tgaagcacgg    720
agatctagaa gagctgtgac gctccctcc cattccacta ggaagctgca aacgcggtcg     780
caaacctggt tggaatcaag agaatacaca aagcacttga ttagagtcga aaattggata    840
ttcaggaacc ctggcttcgc gttagcagca gctgccatcg cttggcttttt gggaagctca   900
acgagccaaa aagtcatata cttggtcatg atactgctga ttgccccggc atacagcatc    960
aggtgcatag gagtcagcaa tagggacttt gtggaaggta tgtcaggtgg acttggggtt   1020
gatgttgtct tggaacatgg aggttgtgtc accgtaatgg cacaggacaa accgactgtc   1080
gacatagagc tggttacaac aacagtcagc aacatgcgcg aggtaagatc ctactgctat   1140
```

```
gaggcatcaa tatcggacat ggcttcggac agccgctgcc caacacaagg tgaagcctac  1200
cttgacaagc aatcagacac tcaatatgtc tgcaaaagaa cgttagtgga cagaggctgg  1260
ggaaatggat gtggactttt tggcaaaggg agcctggtga catgcgctaa gtttgcatgc  1320
tccaagaaaa tgaccgggaa gagcatccag ccagagaatc tggagtaccg gataatgctg  1380
tcagttcatg gctcccagca cagtgggatg atcgttaatg acacaggaca tgaaactgat  1440
gagaatagag cgaaggttga gataacgccc aattcaccaa gagccgaagc caccctgggg  1500
ggttttggaa gcctaggact tgattgtgaa ccgaggacag gccttgactt ttcagatttg  1560
tattacttga ctatgaataa caagcactgg ttggttcaca aggagtggtt ccacgacatt  1620
ccattacctt ggcacgctgg ggcagacacc ggaactccac actggaacaa caaagaagca  1680
ctggtagagt tcaaggacgc acatgccaaa aggcaaactg tcgtggttct agggagtcaa  1740
gaaggagcag ttcacacggc ccttgctgga gctctggagg ctgagatgga tggtgcaaag  1800
ggaaggctgt cctctggcca cttgaaatgt cgcctgaaaa tggataaact tagattgaag  1860
ggcgtgtcat actccttgtg taccgcagcg ttcacattca ccaagatccc ggctgaaaca  1920
ctgcacggga cagtcacagt ggaggtacag tacgcaggga cagatggacc ttgcaaggtt  1980
ccagctcaga tggcggtgga catgcaaact ctgaccccag ttgggaggtt gataaccgct  2040
aaccccgtaa tcactgaaag cactgagaac tctaagatga tgctggaact tgatccacca  2100
tttgggggact cttacattgt cataggagtc ggggagaaga agatcaccca ccactggcac  2160
aggagtggca gcaccattgg aaaagcattt gaagccactg tgagaggtgc caagagaatg  2220
gcagtcttgg gagacacagc ctgggacttt ggatcagttg gaggcgctct caactcattg  2280
ggcaagggca tccatcaaat ttttggagca gctttcaaat cattgtttgg aggaatgtcc  2340
tggttctcac aaattctcat tggaacgttg ctgatgtggt tgggtctgaa cacaaagaat  2400
ggatctatt ccctt atgtg cttggcttta ggggagttgt tgatcttctt atccacagct  2460
gtctctgctg atgtggggtg ctcggtggac ttctcaaaga aggagacgag atgcggtaca  2520
ggggtgttcg tctataacga cgttgaagcc tggagggaca ggtacaagta ccatcctgac  2580
tcccccgta gattggcagc agcagtcaag caagcctggg aagatggtat ctgtgggatc  2640
tcctctgttt caagaatgga aaacatcatg tggagatcga tagaagggaa gctcaacgca  2700
atcctggaag agaatggagt tcaactgacg gtcgttgtgg gatctgtaaa aaaccccatg  2760
tggagaggtc cacagagatt gcccgtgcct gtgaacgagc tgccccacgg ctggaaggct  2820
tgggggaaat cgtacttcgt cagagcagca aagacaaata acagctttgt cgtggatggt  2880
gacacactga aggaatgccc actcaaacat agagcatggc actttcct tgtggaggat  2940
catgggttcg gggtatttca cactagtgtc tggctcaagg ttagagaaga ttattcatta  3000
gagtgtgatc cagccgttat tggaacagct gttaagggaa aggaggctgt acacagtgat  3060
ctaggctact ggattgagag tgagaagaat gacacatgga ggctgaagag ggcccatctg  3120
atcgagatga aaacatgga atggccaaag tcccacacat tgtggacaga tggaataga   3180
gagagtgatc tgatcatacc caagtcttta gctgggccac tcagccatca caataccaga  3240
gagggctaca ggacccaaat gaaagggcca tggcacagtg aagagcttga aattcggttt  3300
gaggaatgcc caggcactaa ggtccacgtg gaggaaacat gtggaacaag aggaccatct  3360
ctgagatcaa ccactgcaag cggaaggtg atcgaggaat ggtgctgcag ggagtgcaca  3420
atgcccccac tgtcgttccg ggctaaagat ggctgttgt atggaatgga gataaggccc  3480
aggaaagaac cagaaagtaa cttagtaagg tcaatggtga ctgcaggatc aactgatcac  3540
atggatcact tctcccttgg agtgcttgtg attctgctca tggtgcagga agggctgaag  3600
aagagaatga ccacaaagat catcataagc acatcgatgg cagtgctggt agctatgatc  3660
ctgggggat tttcaatgag tgacctggct aagcttgcaa ttttgatggg tgccaccttc  3720
gcggaaatga acactggagg agatgtagct catctggcgc tgatagcggc attcaaagtc  3780
agaccagcgt tgctggtatc tttcatcttc agagctaatt ggacaccccg tgaaagcatg  3840
ctgctggcct tggcctcgtg tctttttgcaa actgcgatct ccgccttgga aggcgacctg  3900
atggttctca tcaatggtttt tgctttggcc tggttggcaa tacgagcgat ggttgttcca  3960
cgcactgata acatcacctt ggcaatcctg gctgctctga caccactggc ccggggcaca  4020
ctgcttgtgg cgtggagagc aggccttgct acttgcgggg ggtttatgct cctctctctg  4080
aagggaaaag gcagtgtgaa gaagaactta ccatttgtca tggcccctggg actaaccgct  4140
gtgaggctgg tcgaccccat caacgtgtgg ggactgctgt tgctcacaag gagtgggaag  4200
cggagctggc cccctagcga agtactcaca gctgttggcc tgatatgcgc attggctgga  4260
gggttcgcca aggcagatat agagatggct gggcccatgg ccgcggtcgg tctgctaatt  4320
gtcagttacg tggtctcagg aaagagtgtg gacatgtaca ttgaaagagc aggtgacatc  4380
acatgggaaa aagatgcgga agtcactgga aacagtcccc ggctcgatgt ggcgctagat  4440
gagagtggtg attctcccct ggtggaggat gacggtcccc ccatgagaga gatcatactc  4500
aaggtggtcc tgatgaccat ctgtggcatg aacccaatag ccataccctt tgcagctgga  4560
gcgtggtacg tatacgtgaa gactggaaaa aggagtggtg ctctatggga tgtgcctgct  4620
cccaaggaag taaaaaaggg gagaccacca gatggagtgt acagagtaat gactcgtaga  4680
ctgctaggtt caacacaagt tggagtggga gttatgcaag aggggtcctt tcacactatg  4740
tggcacgtca caaaaggatc cgcgctgaga agcggtgaag ggagacttga tccatactgg  4800
ggagatgtca gcaggatct ggtgtcatac tgtggtccat ggaagctaga tgccgcctgg  4860
gacgggcaca gcgaggtgca gctcttggcc gtgcccccg agagagagc gaggaacatc  4920
cagactctgc ccggaatatt taagacaaag gatgggggat ttggggactt tgcgctgact  4980
tacccagcag gaacttcagg atctccaatc ctagacaagt gtgggagagt gataggactt  5040
tatggcaatg gggtcgtgat caaaaatggg agttatgtta gtgccatcac ccaagggagg  5100
agggaggaag agactcctgt tgagtgcttc gagccttcga tgctgaagaa gaagcagcta  5160
actgtcttag acttgcatcc tggagctggg aaaaccagga gagttcttcc tgaaatagtc  5220
cgtgaagcca taaaacaag actccgtact gtgatccttag ctccaaccag ggttgtcgct  5280
gctgaaatgg aggaagccct tagagggctt ccagtgcgtt atatgacaac agcagtcaat  5340
gtcacccact ctgaaacaga aatcgtcgac ttaatgtgcc atgccacctt cacttcacgt  5400
ctactacagc caatcagagt cccccaactat aatctgtata ttatggatga ggcccacttc  5460
acagatcccg caagtatagc agcaagagga tacatttcaa caagggttga gatggcgag  5520
gcggctgcca tcttcatgac cgccacgcca ccaggaaccg atgacgcatt tccggactcc  5580
aactcaccaa ttatggacac cgaagtggaa gtcccagaga gagcctggag ctcaggcttt  5640
gattgggtga cggatcattc tggaaaaaca gtttggtttg ttccaagcgt gaagaacggc  5700
aatgagatcg cagcttgtct gacaaaggct ggaaaacggg tcatacagct cagcagaaag  5760
acttttgaga cagagttcca gaaaacaaaa catcaagagt gggactttgt cgtgacaact  5820
gacatttcag agatgggcgc caactttaaa gctgaccgtg tcatagatcc aggagatgc   5880
```

```
ctaaagccgg tcatacttga tggcgagaga gtcattctgg ctggacccat gcctgtcaca    5940
catgccagcg ctgcccagag gaggggcgc ataggcagga atcccaacaa acctggagat    6000
gagtatctgt atggaggtgg gtgcgcagag actgacgaag accatgcaca ctggcttgaa    6060
gcaagaatgc tccttgacaa tatttacctc caagatggcc tcatagcctc gctctatcga    6120
cctgaggccg acaaagtagc agccattgag ggagagttca agcttaggac ggacaaagg    6180
aagacctttg tggaactcat gaaaagagga gatcttcctg tttggctggc ctatcaggtt    6240
gcatctgccg gaataaccta cacagataga agatggtgct ttgatggcac gaccaacaac    6300
accataatgg aagacagtgt gccggcagag gtgtggacca gacacggaga gaaagagtg    6360
ctcaaaccga ggtggatgga cgccagagtt tgttcagatc atgcggccct gaagtcattc    6420
aaggagtttg ccgctgggaa aagaggagcg gcttttggag tgatggaagc cctgggaaca    6480
ctgccaggac acatgacaga gagattccag gaagccattg acaacctcgc tgtgctcatg    6540
cgggcagaga ctggaagcag gccttacaaa gccgcggcgg cccaattgcc ggagaccta    6600
gagaccatta tgcttttggg gttgctggaa acagtctcgc tggaatctt tttcgtcttg    6660
atgaggaaca agggcatagg gaagatgggc tttggaagtg tgactcttgg ggccagcgca    6720
tggctcatgt ggctctcgga aattgagcca gccagaattg catgtgtcct cattgttgtg    6780
ttcctattgc tggtggtgct cataccgagg ccagaaaagc aaagatctcc ccaggacaac    6840
caaatggcaa tcatcatcat ggtagcagta ggtcttctgg gcttgattac cgccaatgaa    6900
ctcggatggt tggagagaac aaaagtgac ctaagccatc taatgggaag gagagaggag    6960
ggggcaacca taggattctc aatggacatt gacctgcggc cagcctcagc ttgggccatc    7020
tatgctgcct tgacaacttt cattacccca gccgtccaac atgcagtgac cacttcatac    7080
aacaactact cccttaatgg cgatggccacg caagctgagg tgttgtttgg tatgggcaaa    7140
gggatgccat tctacgcatg ggactttgga tcccgctgc taatgatagg ttgctactca    7200
caattaacac ccctgacct aatagtggcc atcattttgc tcgtggcgca ctacatgtac    7260
ttgatcccag ggctgcaggc agcagctgcg cgtgctgccc agaagagaac ggcagctggc    7320
atcatgaaga accctgttgt ggatggaata gtggtgactg acattgacac aatgacaatt    7380
gacccccaag tggagaaaaa gatgggacag gtgctactca tagcagtagc cgtctccaag    7440
gccatactgt cgcggaccgc ctgggggtgg ggggaggctg gggccctgat cacagcggca    7500
acttccactt tgtgggaagg ctctccgaac aagtactgga actcctctac agccacttca    7560
ctgtgtaaca ttttaggg aagttacttg gctggagctt ctctaatcta cacagtaaca    7620
agaaacgctg gcttggtcaa gagacgtggg ggtggaacag gagagaccct gggagagaaa    7680
tggaaggccc gcttgaacca gatgtcggcc ctggagttct actcctacaa aaagtcaggc    7740
atcaccgagg tgtgcagaga agaggcccgc gcgccctca aggacggtgt ggcaacggga    7800
ggccatgctg tgtcccgagg aagtgcaaag ctgagatggt tggtggagcg gggatacctg    7860
cagcccctatg gaaaggtcat tgatcttgga tgtgggcagag ggggctggag ttactacgcc    7920
gccaccatcc gcaaagttca gaagtgaaa ggatacacaa aaggaggccc tggtcatgaa    7980
gaacccatgt tggtgcaaag ctatgggtgg aacatagtcc gtcttaagag tggggtggac    8040
gtctttcata tggcggctga gccgtgtgac acgttgctgt gtgacatagg tgagtcatca    8100
tctagtcctg aagtggaaga agcacggacg ctcagagtcc tctccatggt gggggattgg    8160
cttgaaaaaa gaccaggagc cttttgtata aagtgttgt gcccatacac tggcactatg    8220
atggaaaccc tggagcgact gcagcgtagg tatgggggag gactggtcag agtgccactc    8280
tcccgcaact ctacacatga gatgtactgg gtctctggga cgaaaagcaa caccataaaa    8340
agtgtgtcca ccacgagcca gctcctcttg gggcgcatgg acgggccag gaggccagtg    8400
aaatatgagg aggatgtgaa tctctgtct ggcacgcggg ctgtggtaag ctgcgctgaa    8460
gctcccaaca tgaagatcat tggtaaccgc attgaaagga tccgcagtga gcacgcggaa    8520
acgtggttct tgacgagaa ccacccatat aggacatggg cttaccatgg aagctatgag    8580
gcccccacac aagggtcagc gtcctctcta ataaacgggg ttgtcaggct cctgtcaaaa    8640
ccctggatg tggtgactgg agtcacagga atagccgtag ccgacaccac accgtatggt    8700
cagcaaagag ttttcaagga aaaagtggac actagggtgc cagacccca agaaggcact    8760
cgtcaggtta tgagcatggt ctcttcctgg ttgtggaaag agctaggcaa acacaaacgg    8820
ccacgagtct gtaccaaaga gagttcatc aacaaggttc gtagcaatgc agcattaggg    8880
gcaatatttg aagaggaaaa agagtggaag actgcagttg aagctgtgaa cgatccaaagg    8940
ttctgggctc tagtgacaa ggaaagagag caccacctga gggagagtg ccagagttgt    9000
gtgtacaaca tgatgggaaa aagagaaag aaacaagggg aatttggaaa ggccaagggc    9060
agccgcgcca tctggtata tgtggctaggg gctagatttc tagagttcga agcccttgga    9120
ttcttgaacg aggatcactg gatggggaga gagaactcag gaggtggtgt tgaagggctg    9180
ggattacaaa gactcggata tgtcctagaa gagatgagtc gcataccagg aggaaggatg    9240
tatgcagatg acactgctgg ctgggacacc cgcatcagca ggtttgatct ggagaatgaa    9300
gctctaatca ccaaccaaat ggagaaaggg cacagggcct tggcattggc cataatcaag    9360
tacacatacc aaaacaaagt ggtaaaggtc cttagaccag ctgaaaaagg gaagacagtt    9420
atggacatta tttcgagaca agaccaaagg gggagcggaa agttgtcac ttacgctctt    9480
aacacattta ccaacctagt ggtgcaactc attcggaata tggaggctga ggaagttcta    9540
gagatgcaag acttgtggct gctgcggagg tcagagaaag tgaccaactg gttgcagagc    9600
aacggatggg ataggctcaa acgaatggca gtcagtggag atgattgcgt tgtgaagcca    9660
attgatgata ggtttgcaca tgccctcagg ttcttgaata atatggggaaa agttaggaag    9720
gacacacaag agtggaaacc ctcaactgga tgggacaact gggaagaagt tccgttttgc    9780
tcccaccact tcaacaagct ccatctcaag gacgggaggt ccattgtggt tccctgccgc    9840
caccaagatg aactgattgg ccgggcccgc gtctctccag gggcgggatg gagcatccgg    9900
gagactgctt gcctagcaaa atcatatgcg caaatgtggc agctcttta tttccacaga    9960
agggaccctcc gactgatggc caatgccatt tgttcatctg tgccagttga ctgggttcca   10020
actgggagaa ctacctggtc aatccatgga aagggagaat ggatgaccac tgaagacatg   10080
cttgtggtgt ggaacagagt gtggattgag gagaacgacc acatggaaga caagcccca   10140
gttacgaaat ggacagacat tccctatttg ggaaaaaggg aagacttgtg tgtggatcct   10200
ctcataggc acagaccgcg caccacctgg gctgagaaca ttaaaaacac agtcaacatg   10260
gtgcgaggtc tcataggtga tgaagaaaag tacatggact ccaagttcga   10320
tacttgggtg aagaagggtc tacacctgga gtgctgtaag caccaatctt agtgttgtca   10380
ggcctgctag tcagccacag cttgggaaa gctgtgcagc ctgtgacccc ccaggagaa   10440
gctgggaaac aagcctata gtcaggccga gaacgccatg gcacggaaga agccatgctg   10500
cctgtgagcc cctcagagga cactgagtca aaaaacccca cgcgcttgga ggcgcaggat   10560
ggggaaaagaa ggtggcgacc ttccccaccc ttcaatctgg ggcctgaact ggagatcagc   10620
```

-continued

```
tgtggatctc cagaagaggg actagtggtt agaggagacc ccccggaaaa cgcaaaacag   10680
catattgacg ctgggaaaga ccagagactc catgagtttc caccacgctg gccgccaggc   10740
acagatcgcc gaatagcggc ggccggtgtg ggg                                10773

SEQ ID NO: 73          moltype = AA   length = 3423
FEATURE                Location/Qualifiers
source                 1..3423
                       mol_type = protein
                       organism = Zika virus
SEQUENCE: 73
MKNPKKKSGG FRIVNMLKRG VARVSPFGGL KRLPAGLLLG HGPIRMVLAI LAFLRFTAIK    60
PSLGLINRWG SVGKKEAMEI IKKFKKDLAA MLRIINARKE KKRRGADTSV GIVGLLLTTA   120
MAAEVTRRGS AYYMYLDRND AGEAISFPTT LGMNKCYIQI MDLGHMCDAT MSYECPMLDE   180
GVEPDDVDCW CNTTSTWVVY GTCHHKKGEA RRSRRAVTLP SHSTRKLQTR SQTWLESREY   240
TKHLIRVENW IFRNPGFALA AAAIAWLLGS STSQKVIYLV MILLIAPAYS IRCIGVSNRD   300
FVEGMSGGTW VDVVLEHGGC VTVMAQDKPT VDIELVTTTV SNMAEVRSYC YEASISDMAS   360
DSRCPTQGEA YLDKQSDTQY VCKRTLVDRG WGNGCGLFGK GSLVTCAKFA CSKKMTGKSI   420
QPENLEYRIM LSVHGSQHSG MIVNDTGHET DENRAKVEIT PNSPRAEATL GGFGSLGLDC   480
EPRTGLDFSD LYYLTMNNKH WLVHKEWFHD IPLPWHAGAD TGTPHWNNKE ALVEFKDAHA   540
KRQTVVVLGS QEGAVHTALA GALEAEMDGA KGRLSSGHLK CRLKMDKLRL KGVSYSLCTA   600
AFTFTKIPAE TLHGTVTVEV QYAGTDGPCK VPAQMAVDMQ TLTPVGRLIT ANPVITESTE   660
NSKMMLELDP PFGDSYIVIG VGEKKITHHW HRSGSTIGKA FEATVRGAKR MAVLGDTAWD   720
FGSVGGALNS LGKGIHQIFG AAFKSLFGGM SWFSQILIGT LLMWLGLNTK NGSISLMCLA   780
LGGVLIFLST AVSADVGCSV DFSKKETRCG TGVFVYNDVE AWRDRYKYHP DSPRRLAAAV   840
KQAWEDGICG ISSVSRMENI MWRSVEGELN AILEENGVQL TVVVGSVKNP MWRGPQRLPV   900
PVNELPHGWK AWGKSYFVRA AKTNNSFVVD GDTLKECPLK HRAWNSFLVE DHGFGVFHTS   960
VWLKVREDYS LECDPAVIGT AVKGKEAVHS DLGYWIESEK NDTWRLKRAH LIEMKTCEWP  1020
KSHTLWTDGI EESDLIIPKS LAGPLSHHNT REGYRTQMKG PWHSEELEIR FEECPGTKVH  1080
VEETCGTRGP SLRSTTASGR VIEEWCCREC TMPPLSFRAK DGCWYGMEIR PRKEPESNLV  1140
RSMVTAGSTD HMDHFSLGVL VILLMVQEGL KKRMTTKIII ILGGFSMSDL              1200
AKLAILMGAT FAEMNTGGDV AHLALIAAFK VRPALLVSFI FRANWTPRES MLLLASCLL   1260
QTAISALEGD LMVLINGFAL AWLAIRAMVV PRTDNITLAI LAALTPLARG TLLVAWRAGL  1320
ATCGGFMLLS LKGKGSVKKN LPFVMALGLT AVRLVDPINV VGLLLLTRSG KRSWPPSEVL  1380
TAVGLICALA GGFAKADIEM AGPMAAVGLL IVSYVVSGKS VDMYIERAGD ITWEKDAEVT  1440
GNSPRLDVAL DESGDFSLVE DDGPPMREII LKVVLMTICG MNPIAIPFAA GAWYVYVKTG  1500
KRSGALWDVP APKEVKKGET TDGVYRVMTR RLLGSTQVGV GVMQEGVFHT MWHVTKGSAL  1560
RSGEGRLDPY WGDVKQDLVS YCGPWKLDAA WDGHSEVQLL AVPPGERARN IQTLPGIFKT  1620
KDGDIGAVAL DYPAGTSGSP ILDKCGRVIG LYGNGVVIKN GSYVSAITQG RREEETPVEC  1680
FEPSMLKKKQ LTVLDLHPGA GKTRRVLPEI VREAIKTRLR TVILAPTRVV AAEMEEALRG  1740
LPVRYMTTAV NVTHSGTEIV DLMCHATFTS RLLQPIRVPN YNLYIMDEAH FTDPSSIAAR  1800
GYISTRVEMG EAAAIFMTAT PPGTRDAFPD SNSPIMDTEV EVPERAWSSG FDWVTDHSGK  1860
TVWFVPSVRN GNEIAACLTK AGKRVIQLSR KTFETEFQKT KHQEWDFVVT TDISEMGANF  1920
KADRVIDSRR CLKPVILDGE RVILAGPMPV THASAAQPRG DEYLYGGGCA ETDEDHAHWL  1980
ETDEDHAHWL EARMLLDNIY LQDGLIASLY RPEADKVAAI EGEFKLRTEQ RKTFVELMKR  2040
GDLPVWLAYQ VASAGITYTD RRWCFDGTTN NTIMEDSVPA EVWTRHGEKR VLKPRWMDAR  2100
VCSDHAALKS FKEFAAGKRG AAFGVMEALG TLPGHMTERF QEAIDNLAVL MRAETGSRPY  2160
KAAAAQLPET LETIMLLGLL GTVSLGIFFV LMRNKGIGKM GFGMVTLGAS AWLMWLSEIE  2220
PARIACVLIV VFLLLVVLIP EPEKQRSPQD NQMAIIIMVA VGLLGLITAN ELGWLERTKS  2280
DLSHLMGRRE EGATIGFSMD IDLRPASAWA IYAALTTFIT PAVQHAVTTS YNNYSLMAMA  2340
TQAGVLFGMG KGMPFYAWDF GVPLLMIGCY SQLTPLTLIV AIILLVAHYM YLIPGLQAAA  2400
ARAAQKRTAA GIMKNPVVDG IVVTDIDTMT IDPQVEKMEG QVLLIAVAVS SAILSRTAWG  2460
WGEAGALITA ATSTLWEGSP NKYWNSSTAT SLCNIFRGSY LAGASLIYTV TRNAGLVKRR  2520
GGGTGETLGE KWKARLNQMS ALEFYSYKKS GITEVCREEA RRALKDGVAT GGHAVSRGSA  2580
KLRWLVERGY LQPYGKVIDL GCGRGGWSYY AATIRKVQEV KGYTKGGPGH EEPMLVQSYG  2640
WNIVRLKSGV DVFHMAAEPC DTLLCDIGES SSPEVEEAR TLRVLSMVGD WLEKRPGAEC  2700
IKVLCPYTST MMETLERLQR RYGGGLVRVP LSRNSTHEMY WVSGAKSNTI KSVSTTSQLL  2760
LGRMDGPRRP VKYEEDVNLG SGTRAVVSCA EAPNMKIIGN RIERIRSEHA ETWFFDENHP  2820
YRTWAYHGSY EAPTQGSASS LINGVVRLLS KPWDVVTGVT GIAMTDTTPY GQQRVFKEKV  2880
DTRVPDPQEG TRQVMSMVSS WLWKELGKHK RPRVCTKEEF INKVRSNAAL GAIFEEEKEW  2940
KTAVEAVNDP RFWALVDKER EHHLRGECQS CVYNMMGKRE KKQGEFGKAK GSRAIWYMWL  3000
GARFLEFEAL GFLNEDHWMG RENSGGGVEG LGLQRLGYVL EEMSRIPGGR MYADDTAGWD  3060
TRISRFDLEN EALITNQMEK GHRALALAII KYTYQNKVVK VLRPAEKGKT VMDIISRQDQ  3120
RGSGQVVTYA LNTFTNLVVQ LIRNMEAEEV LEMQDLWLLR RSEKVTNWLQ SNGWDRLKRM  3180
AVSGDDCVVK PIDDRFAHAL RFLNDMGKVR KDTQEWKPST GWDNWEEVPF CSHHFNKLHL  3240
KDGRSIVVPC RHQDELIGRA RVSPGAGWSI RETACLAKSY AQMWQLLYFH RRDLRLMANA  3300
ICSSVPVDWV PTGRTTWSIH GKGEWMTTED MLVVWNRVWI EENDHMEDKT PVTKWTDIPY  3360
LGKREDLWCG SLIGHRPRTT WAENIKNTVN MVRRIIGDEE KYMDYLSTQV RYLGEEGSTP  3420
GVL                                                                3423

SEQ ID NO: 74          moltype = DNA   length = 28
FEATURE                Location/Qualifiers
source                 1..28
                       mol_type = other DNA
                       organism = synthetic construct
SEQUENCE: 74
ttaggatccg ttgttgatct gtgtgaat                                       28

SEQ ID NO: 75          moltype = DNA   length = 26
FEATURE                Location/Qualifiers
```

```
source                  1..26
                        mol_type = other DNA
                        organism = synthetic construct
SEQUENCE: 75
taactcgagc gtacacaacc caagtt                                              26

SEQ ID NO: 76           moltype = DNA   length = 27
FEATURE                 Location/Qualifiers
source                  1..27
                        mol_type = other DNA
                        organism = synthetic construct
SEQUENCE: 76
ttaggatcct cactagacgt gggagtg                                             27

SEQ ID NO: 77           moltype = DNA   length = 29
FEATURE                 Location/Qualifiers
source                  1..29
                        mol_type = other DNA
                        organism = synthetic construct
SEQUENCE: 77
taactcgaga agccatgtcy gatattgat                                           29

SEQ ID NO: 78           moltype = DNA   length = 26
FEATURE                 Location/Qualifiers
source                  1..26
                        mol_type = other DNA
                        organism = synthetic construct
SEQUENCE: 78
ttaggatccg catacagcat caggtg                                              26

SEQ ID NO: 79           moltype = DNA   length = 27
FEATURE                 Location/Qualifiers
source                  1..27
                        mol_type = other DNA
                        organism = synthetic construct
SEQUENCE: 79
taactcgagt gtggagttcc ggtgtct                                             27

SEQ ID NO: 80           moltype = DNA   length = 31
FEATURE                 Location/Qualifiers
source                  1..31
                        mol_type = other DNA
                        organism = synthetic construct
SEQUENCE: 80
ttaggatccg aatagagcga argttgagat a                                        31

SEQ ID NO: 81           moltype = DNA   length = 28
FEATURE                 Location/Qualifiers
source                  1..28
                        mol_type = other DNA
                        organism = synthetic construct
SEQUENCE: 81
taactcgagt ggtgggtgat cttcttct                                            28

SEQ ID NO: 82           moltype = DNA   length = 31
FEATURE                 Location/Qualifiers
source                  1..31
                        mol_type = other DNA
                        organism = synthetic construct
SEQUENCE: 82
ttaggatcca gtcacagtgg aggtacagta c                                        31

SEQ ID NO: 83           moltype = DNA   length = 27
FEATURE                 Location/Qualifiers
source                  1..27
                        mol_type = other DNA
                        organism = synthetic construct
SEQUENCE: 83
taactcgagc rcagatacca tcttccc                                             27

SEQ ID NO: 84           moltype = DNA   length = 28
FEATURE                 Location/Qualifiers
source                  1..28
                        mol_type = other DNA
                        organism = synthetic construct
SEQUENCE: 84
ttaggatccc ttatgtgctt ggccttag                                            28

SEQ ID NO: 85           moltype = DNA   length = 26
```

```
FEATURE                 Location/Qualifiers
source                  1..26
                        mol_type = other DNA
                        organism = synthetic construct
SEQUENCE: 85
taactcgagt cttcagcctc catgtg                                        26

SEQ ID NO: 86           moltype = DNA   length = 29
FEATURE                 Location/Qualifiers
source                  1..29
                        mol_type = other DNA
                        organism = synthetic construct
SEQUENCE: 86
ttaggatcca atgcccactc aaacataga                                     29

SEQ ID NO: 87           moltype = DNA   length = 30
FEATURE                 Location/Qualifiers
source                  1..30
                        mol_type = other DNA
                        organism = synthetic construct
SEQUENCE: 87
taactcgagt cattctcttc ttcagcccctt                                   30

SEQ ID NO: 88           moltype = DNA   length = 26
FEATURE                 Location/Qualifiers
source                  1..26
                        mol_type = other DNA
                        organism = synthetic construct
SEQUENCE: 88
ttaggatcca agggtgatcg aggaat                                        26

SEQ ID NO: 89           moltype = DNA   length = 29
FEATURE                 Location/Qualifiers
source                  1..29
                        mol_type = other DNA
                        organism = synthetic construct
SEQUENCE: 89
taactcgagt tcccttcaga gagaggagc                                     29

SEQ ID NO: 90           moltype = DNA   length = 28
FEATURE                 Location/Qualifiers
source                  1..28
                        mol_type = other DNA
                        organism = synthetic construct
SEQUENCE: 90
ttaggatcct cttttgcaaa ctgcgatc                                      28

SEQ ID NO: 91           moltype = DNA   length = 27
FEATURE                 Location/Qualifiers
source                  1..27
                        mol_type = other DNA
                        organism = synthetic construct
SEQUENCE: 91
taactcgagt ccagctgcaa agggtat                                       27

SEQ ID NO: 92           moltype = DNA   length = 28
FEATURE                 Location/Qualifiers
source                  1..28
                        mol_type = other DNA
                        organism = synthetic construct
SEQUENCE: 92
ttaggatccg tgtggacatg tacattga                                      28

SEQ ID NO: 93           moltype = DNA   length = 26
FEATURE                 Location/Qualifiers
source                  1..26
                        mol_type = other DNA
                        organism = synthetic construct
SEQUENCE: 93
taactcgagc ccattgccat aaagtc                                        26

SEQ ID NO: 94           moltype = DNA   length = 28
FEATURE                 Location/Qualifiers
source                  1..28
                        mol_type = other DNA
                        organism = synthetic construct
SEQUENCE: 94
ttaggatcct catactgtgg tccatgga                                      28
```

```
SEQ ID NO: 95          moltype = DNA   length = 26
FEATURE                Location/Qualifiers
source                 1..26
                       mol_type = other DNA
                       organism = synthetic construct
SEQUENCE: 95
taactcgagg cccatctcaa cccttg                                              26

SEQ ID NO: 96          moltype = DNA   length = 26
FEATURE                Location/Qualifiers
source                 1..26
                       mol_type = other DNA
                       organism = synthetic construct
SEQUENCE: 96
ttaggatcct agagggcttc cagtgc                                              26

SEQ ID NO: 97          moltype = DNA   length = 31
FEATURE                Location/Qualifiers
source                 1..31
                       mol_type = other DNA
                       organism = synthetic construct
SEQUENCE: 97
taactcgaga tactcatctc caggtttgtt g                                        31

SEQ ID NO: 98          moltype = DNA   length = 30
FEATURE                Location/Qualifiers
source                 1..30
                       mol_type = other DNA
                       organism = synthetic construct
SEQUENCE: 98
ttaggatccg aaaacaaaac atcaagagtg                                          30

SEQ ID NO: 99          moltype = DNA   length = 31
FEATURE                Location/Qualifiers
source                 1..31
                       mol_type = other DNA
                       organism = synthetic construct
SEQUENCE: 99
taactcgagg aatctctctg tcatgtgtcc t                                        31

SEQ ID NO: 100         moltype = DNA   length = 26
FEATURE                Location/Qualifiers
source                 1..26
                       mol_type = other DNA
                       organism = synthetic construct
SEQUENCE: 100
ttaggatcct tgatggcacg accaac                                              26

SEQ ID NO: 101         moltype = DNA   length = 28
FEATURE                Location/Qualifiers
source                 1..28
                       mol_type = other DNA
                       organism = synthetic construct
SEQUENCE: 101
ttaggatccg ttgttgatct gtgtgaat                                            28

SEQ ID NO: 102         moltype = DNA   length = 26
FEATURE                Location/Qualifiers
source                 1..26
                       mol_type = other DNA
                       organism = synthetic construct
SEQUENCE: 102
taactcgagc aggtcaatgt ccattg                                              26

SEQ ID NO: 103         moltype = DNA   length = 30
FEATURE                Location/Qualifiers
source                 1..30
                       mol_type = other DNA
                       organism = synthetic construct
SEQUENCE: 103
ttaggatcct gttgtgttcc tattgctggt                                          30

SEQ ID NO: 104         moltype = DNA   length = 25
FEATURE                Location/Qualifiers
source                 1..25
                       mol_type = other DNA
                       organism = synthetic construct
SEQUENCE: 104
taactcgagt gatcagrgcc ccagc                                               25
```

```
SEQ ID NO: 105          moltype = DNA  length = 26
FEATURE                 Location/Qualifiers
source                  1..26
                        mol_type = other DNA
                        organism = synthetic construct
SEQUENCE: 105
ttaggatcct gctgcccaga agagaa                                          26

SEQ ID NO: 106          moltype = DNA  length = 26
FEATURE                 Location/Qualifiers
source                  1..26
                        mol_type = other DNA
                        organism = synthetic construct
SEQUENCE: 106
taactcgagc accaacaygg gttctt                                          26

SEQ ID NO: 107          moltype = DNA  length = 25
FEATURE                 Location/Qualifiers
source                  1..25
                        mol_type = other DNA
                        organism = synthetic construct
SEQUENCE: 107
ttaggatcct caaggacggt gtggc                                           25

SEQ ID NO: 108          moltype = DNA  length = 28
FEATURE                 Location/Qualifiers
source                  1..28
                        mol_type = other DNA
                        organism = synthetic construct
SEQUENCE: 108
taactcgagc aatgatcttc atgttggg                                        28

SEQ ID NO: 109          moltype = DNA  length = 26
FEATURE                 Location/Qualifiers
source                  1..26
                        mol_type = other DNA
                        organism = synthetic construct
SEQUENCE: 109
ttaggatcct atggggagg actggt                                           26

SEQ ID NO: 110          moltype = DNA  length = 25
FEATURE                 Location/Qualifiers
source                  1..25
                        mol_type = other DNA
                        organism = synthetic construct
SEQUENCE: 110
taactcgagc ccagaacctt ggatc                                           25

SEQ ID NO: 111          moltype = DNA  length = 25
FEATURE                 Location/Qualifiers
source                  1..25
                        mol_type = other DNA
                        organism = synthetic construct
SEQUENCE: 111
ttaggatcca gacccccaag aaggc                                           25

SEQ ID NO: 112          moltype = DNA  length = 26
FEATURE                 Location/Qualifiers
source                  1..26
                        mol_type = other DNA
                        organism = synthetic construct
SEQUENCE: 112
taactcgagc ccctttggtc ttgtct                                          26

SEQ ID NO: 113          moltype = DNA  length = 29
FEATURE                 Location/Qualifiers
source                  1..29
                        mol_type = other DNA
                        organism = synthetic construct
SEQUENCE: 113
ttaggatcca ggaaggatgt atgcagatg                                       29

SEQ ID NO: 114          moltype = DNA  length = 30
FEATURE                 Location/Qualifiers
source                  1..30
                        mol_type = other DNA
                        organism = synthetic construct
SEQUENCE: 114
```

```
taactcgaga catttgcgca tatgattttg                                        30

SEQ ID NO: 115          moltype = DNA  length = 28
FEATURE                 Location/Qualifiers
source                  1..28
                        mol_type = other DNA
                        organism = synthetic construct
SEQUENCE: 115
ttaggatcca ggaaggacac acaagagt                                          28

SEQ ID NO: 116          moltype = DNA  length = 26
FEATURE                 Location/Qualifiers
source                  1..26
                        mol_type = other DNA
                        organism = synthetic construct
SEQUENCE: 116
taactcgaga caggctgcac agcttt                                            26

SEQ ID NO: 117          moltype = DNA  length = 28
FEATURE                 Location/Qualifiers
source                  1..28
                        mol_type = other DNA
                        organism = synthetic construct
SEQUENCE: 117
ttaggatcct ctctcatagg gcacagac                                          28
```